US010647946B2

(12) United States Patent
Andersen et al.

(10) Patent No.: US 10,647,946 B2
(45) **Date of Patent: *May 12, 2020**

(54) ALPHA-AMYLASE VARIANTS AND POLYNUCLEOTIDES ENCODING SAME

(71) Applicant: NOVOZYMES A/S, Bagsvaerd (DK)

(72) Inventors: Carsten Andersen, Vaerloese (DK); Chakshusmathi Ghadiyaram, Bangalore (IN); Rajendra Kulothungan Sainathan, Bangalore (IN); Padmavathi Balumuri, Chennai (IN); Padma Venkatachalam Iyer, Mumbai (IN); Iben Damager, Valby (DK); Astrid Munch, Frederiksberg (DK); Sohel Dalal, Ahmedabad (IN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/571,219

(22) PCT Filed: May 9, 2016

(86) PCT No.: PCT/EP2016/060266

§ 371 (c)(1),
(2) Date: Nov. 1, 2017

(87) PCT Pub. No.: WO2016/180748

PCT Pub. Date: Nov. 17, 2016

(65) Prior Publication Data

US 2019/0085268 A1 Mar. 21, 2019

(30) Foreign Application Priority Data

May 8, 2015 (IN) .......................... 2335/CHE/2015

(51) Int. Cl.

| | |
|---|---|
| ***C11D 3/386*** | (2006.01) |
| ***C12N 9/26*** | (2006.01) |
| ***C12N 9/28*** | (2006.01) |

(52) U.S. Cl.

CPC ............ *C11D 3/386* (2013.01); *C12N 9/2414* (2013.01); *C12N 9/2417* (2013.01); *C12Y 302/01001* (2013.01)

(58) Field of Classification Search

None

See application file for complete search history.

(56) References Cited

U.S. PATENT DOCUMENTS

| | | | |
|---|---|---|---|
| 3,642,582 | A | 2/1972 | McClary |
| 5,824,531 | A | 10/1998 | Outtrup |
| 5,856,164 | A | 1/1999 | Outtrup |
| 6,093,562 | A | 7/2000 | Bisgaard-Frantzen |
| 6,187,576 | B1 | 2/2001 | Svendsen |
| 6,197,565 | B1 | 3/2001 | Svendsen |
| 6,204,232 | B1 | 3/2001 | Borchert |
| 6,297,038 | B1 | 10/2001 | Bisgaard-Frantzen |
| 6,309,871 | B1 * | 10/2001 | Outtrup ................. C11D 3/386 435/202 |
| 6,361,989 | B1 | 3/2002 | Svendsen |
| 6,623,948 | B1 | 9/2003 | Outtrup |
| 2004/0096952 | A1 | 5/2004 | Svendsen |
| 2009/0104681 | A1 | 4/2009 | Bower |
| 2010/0112637 | A1 | 5/2010 | Borchert |
| 2015/0031091 | A1 | 1/2015 | Li |
| 2015/0044754 | A1 | 2/2015 | Sun |

FOREIGN PATENT DOCUMENTS

| | | | |
|---|---|---|---|
| JP | 08-336392 | A | 12/1996 |
| JP | 11-503003 | A | 3/1999 |
| WO | 94/018314 | A1 | 8/1994 |
| WO | 95/026397 | A1 | 10/1995 |
| WO | 96/023873 | A1 | 8/1996 |
| WO | 97/00324 | A1 | 1/1997 |
| WO | 97/32961 | A2 | 9/1997 |
| WO | 98/05748 | A1 | 2/1998 |
| WO | 00/060058 | A2 | 10/2000 |
| WO | 00/060060 | A2 | 10/2000 |
| WO | 01/18180 | A2 | 3/2001 |
| WO | 01/64852 | A1 | 9/2001 |
| WO | 01/066712 | A2 | 9/2001 |
| WO | 02/042740 | A1 | 5/2002 |
| WO | 2006/002643 | A2 | 1/2006 |
| WO | 2009/102854 | A1 | 8/2009 |
| WO | 2011/098531 | A1 | 8/2011 |
| WO | 2013/001087 | A2 | 1/2013 |
| WO | 2014/106593 | A1 | 7/2014 |
| WO | 2014/162001 | A1 | 10/2014 |
| WO | 2014/183920 | A1 | 11/2014 |
| WO | 2014/183921 | A1 | 11/2014 |
| WO | 2015/044448 | A1 | 4/2015 |

(Continued)

OTHER PUBLICATIONS

EBI Accession No. GM992869—linear protein—Sequence 40 from Patent WO2008153805 (2009).
EBI Accession No. BBK44028—*Bacillus* sp. mature alpha-amylase variant W140Y/N260P #2. (2014).
Broun et al, 1998, Science 282, 1315-1317.
Davail et al, 1994, The J of Biological Chem 269(26), 17448-17453.
Devos et al, 2000, Proteins Struc, Func, Genet 41, 98-107.
Igarashi et al, 1998, Biochem Biophysic Res Commun, 248 (2), 372-377.
Narinx et al, 1997, Protein Engineering 10(11), 1271-1279.
Seffernick et al, 2001, J Bacteriol 183(8), 2405-2410.
Tsukamoto et al, 1988, Biochem Biophysic Res Commun 151 (1), 25-31.

(Continued)

*Primary Examiner* — Suzanne M Noakes
*Assistant Examiner* — Jae W Lee
(74) *Attorney, Agent, or Firm* — David Fazzolare

(57) ABSTRACT

The present invention relates to alpha-amylase variants. The present invention also relates to polynucleotides encoding the variants; nucleic acid constructs, vectors, and host cells comprising the polynucleotides; and methods of using the variants.

13 Claims, No Drawings

Specification includes a Sequence Listing.

(56) References Cited

FOREIGN PATENT DOCUMENTS

| | | | |
|---|---|---|---|
| WO | 2015/144782 | A1 | 10/2015 |
| WO | 2015/149641 | A1 | 10/2015 |
| WO | 2015/189370 | A1 | 12/2015 |
| WO | 2015/189371 | A1 | 12/2015 |

OTHER PUBLICATIONS

Siezen et al, 1997, Protein Sci 6, 501-523.
Witkowski et al, 1999, Biochemistry 38, 11643-11650.
Whisstock et al, 2003, Quart Rev Biophys 36(3), 307-340.
U.S. Pat. No. 7,378,264—EBI Accession No. ACE45183.
U.S. Pat. No. 8,263,368—EBI Accession No. AFS96539.
WO 2014-183921 A1—EBI Accession No. BBQ10961.
WO 2014-183921 A1—EBI Accession No. BBQ10987.

* cited by examiner

SEQUENCE LISTING

<160> NUMBER OF SEQ ID NOS: 17

<210> SEQ ID NO 1
<211> LENGTH: 1458
<212> TYPE: DNA
<213> ORGANISM: Bacillus sp.

<400> SEQUENCE: 1

```
catcacgatg ggacgaacgg aacgattatg cagtattttg aatggaacgt tccgaatgat     60

ggacaacatt ggaaccgctt acacaacaac gctcaaaatt taaaaaatgc cggaattaca    120

gcaatctgga ttccacctgc gtggaaagga acgagccaaa atgatgtagg ctacggtgcg    180

tatgaccttt atgaccttgg tgaatttaac caaaaaggaa cggtccgtac gaaatatgga    240

acaaaagcag aattagaacg agcgattcgt tcgttaaagg cgaacgggat tcaagtgtat    300

ggcgatgttg ttatgaacca taaaggcgga gctgatttca ccgagcgtgt tcaagcggtt    360

gaagtgaacc cgcaaaaccg aaaccaagaa gtgtctggca cttatcaaat cgaagcatgg    420

acagggttca attttcctgg acgtggcaat caacattctt cgtttaaatg gcgctggtat    480

catttcgatg ggacggattg ggaccagtct cgccaactcg caaatcgtat ttataagttt    540

agaggagacg gaaaagcatg ggactgggaa gttgacactg aaaatgggaa ctatgattac    600

ttaatgtatg cagacgttga catggatcat ccagaagtga ttaacgaact aaaccgttgg    660

ggcgtctggt acgcgaatac ccttaattta gacggcttcc gactggatgc agtgaaacat    720

attaaattta gcttcatgcg tgattggtta gggcatgttc gcgggcaaac gggcaagaat    780

ctttttgccg ttgcagagta ttggaagaat gacctagggg ctttagaaaa ttatttaagc    840

aaaacaaatt ggacgatgag cgcctttgat gttccgcttc attacaacct ttatcaagcg    900

tcaaatagta gcggaaatta cgacatgaga aacttgttaa atggaacact cgttcaacgt    960

catccgagcc atgcggttac gtttgtcgat aaccacgaca cacagcctgg agaagccctc   1020

gaatcgttcg ttcaaggctg gtttaaacca ctagcttatg caacgattct tacgagagag   1080

caaggctacc cacaagtgtt ttacggcgat tattatggca tcccaagtga cggtgttcca   1140

agctaccgtc aacagatcga cccactttta aaagctcgtc aacaatatgc ttatggtaga   1200

cagcacgatt actttgatca ttgggatgta attggctgga cacgtgaagg aaacgcatct   1260

cacccgaact caggacttgc aaccattatg tctgatggtc caggtggatc aaaatggatg   1320

tatgttggcc gtcagaaagc tggcgaagtg tggcatgaca tgactggaaa ccgcagtggc   1380

actgtgacaa ttaatcaaga cggctgggga cactttttg tcaacggcgg ctctgtctcc   1440

gtatgggtga aacgataa                                                 1458
```

<210> SEQ ID NO 2
<211> LENGTH: 1539
<212> TYPE: DNA
<213> ORGANISM: Alicyclobacillus sp.

<400> SEQUENCE: 2

```
atgaaaatcc gcaacggttg gaaaaaaacc ttgacgctgt tatttgcgct catcttcttg     60

ctgcctcatt ctgcagccgc gacctttgcc ggggacaacg gcacgatgat gcaatacttt    120

gaatggtatc tgcccaacga cgggacgctt tggaccaaga tgggcagcga cgcgtcgcac    180

ctgaagtcga tcgggatcac cggcgtctgg ttcccgccgg cgtacaaagg ccaatcgcag    240

tcggacgtcg gctacggcgt atacgacatg tacgacctcg gcgaattcaa ccaaaaagga    300

accgtccgca ccaagtacgg caccaaagcc cagctccaat cggcgatcac ctccctgcac    360
```

-continued aacaacggca tccaagccta cggggacgtc gtcctcaacc accgcatggg cgccgatgcg 420
acggagacga tctccgccgt ggaagtcaac ccgtccaacc gcaaccaagt cacctccggg 480
gcttacaaca tctccgcttg gaccgacttc gaattcccgg gccgcggcaa cacctactcc 540
tcgtttaagt ggcactccta ctactttgac ggcgtggact gggaccaatc ccgccagctg 600
agcggcaaga tctaccagat ccaaggcacc ggcaaagcgt gggactggga agtcgattcc 660
gaaaacggca actacgacta cctgatgggc gcggacatcg actacgacca cccggacgtg 720
caaacggaag tgaagaactg ggcaagtgg ttcgtcaaca ccctcaacct cgacggcgtg 780
cgcctcgacg cggtcaagca catcaagttc gactacatgt cttcctggct gtccagcgtc 840
aaatccacga ccggcaagtc caacctgttc gccgtcggcg aatactggaa cacctcgctc 900
ggagcgctgg agaactacga gaacaaaacc aactggagca tgtcgctgtt cgacgtgccg 960
ctgcacatga acttccaagc ggcagcgaac ggcggcggct actatgatat gcgcaacctg 1020
ctcaacaaca cgatgatgaa aaatcacccg atccaagcgg tcaccttcgt cgacaaccac 1080
gacaccgagc cgggccaagc cctgcaatcg tgggtatccg actggttcaa accgctggcc 1140
tacgcgacga tcctgacccg tcaagaaggc tacccgtgcg tgttctacgg cgactactac 1200
ggcatcccgt cgcaaagcgt ctccgcgaaa tccacctggt tggacaagca gctttccgca 1260
cgcaaatcct acgcgtacgg cacccagcac gactacttgg acaaccaaga cgtgatcggc 1320
tggacgcgcg aaggcgattc cgcgcacgcg ggctcgggtc ttgccaccgt catgtcggac 1380
ggccctggcg gctccaagac gatgtacgtc ggcaccgccc atgccggcca agtcttcaag 1440
gacatcaccg gcaaccgcac cgacaccgtc acgatcaact ccgcaggcaa cggcaccttc 1500
ccctgcaacg gcggctccgt ctcgatctgg gtcaaacaa 1539

<210> SEQ ID NO 3
<211> LENGTH: 1560
<212> TYPE: DNA
<213> ORGANISM: Bacillus amyloliquefaciens

<400> SEQUENCE: 3
atgagaggga gaggaaacat gattcaaaaa cgaaagcgga cagtttcgtt cagacttgtg 60
cttatgtgca cgctgttatt tgtcagtttg ccgattacaa aaacatcagc cgtaaatggc 120
acgctgatgc agtattttga atggtatacg ccgaacgacg gccagcattg gaaacgattg 180
cagaatgatg cggaacattt atcggatatc ggaatcactg ccgtctggat tcctcccgca 240
tacaaaggat tgagccaatc cgataacgga tacggacctt atgatttgta tgatttagga 300
gaattccagc aaaaagggac ggtcagaacg aaatacggca caaaatcaga gcttcaagat 360
gcgatcggct cactgcattc ccggaacgtc caagtatacg gagatgtggt tttgaatcat 420
aaggctggtg ctgatgcaac agaagatgta actgccgtcg aagtcaatcc ggccaataga 480
aatcaggaaa cttcggagga atatcaaatc aaagcgtgga cggattttcg ttttccgggc 540
cgtggaaaca cgtacagtga ttttaaatgg cattggtatc atttcgacgg agcggactgg 600
gatgaatccc ggaagatcag ccgcatcttt aagtttcgtg gggaaggaaa agcgtgggat 660
tgggaagtat caagtgaaaa cggcaactat gactatttaa tgtatgctga tgttgactac 720
gaccaccctg atgtcgtggc agagacaaaa aaatggggta tctggtatgc gaatgaactg 780
tcattagacg gcttccgtat tgatgccgcc aaacatatta aattttcatt tctgcgtgat 840
tgggttcagg cggtcagaca ggcgacggga aaagaaatgt ttacggttgc ggagtattgg 900

```
cagaataatg ccgggaaact cgaaaactac ttgaataaaa caagctttaa tcaatccgtg    960

tttgatgttc cgcttcattt caatttacag gcggcttcct cacaaggagg cggatatgat   1020

atgaggcgtt tgctggacgg taccgttgtg tccaggcatc cggaaaaggc ggttacattt   1080

gttgaaaatc atgacacaca gccgggacag tcattggaat cgacagtcca aacttggttt   1140

aaaccgcttg catacgcctt tattttgaca agagaatccg gttatcctca ggtgttctat   1200

ggggatatgt acgggacaaa agggacatcg ccaaaggaaa ttccctcact gaaagataat   1260

atagagccga ttttaaaagc gcgtaaggag tacgcatacg ggccccagca cgattatatt   1320

gaccacccgg atgtgatcgg atggacgagg gaaggtgaca gctccgccgc caaatcaggt   1380

ttggccgctt taatcacgga cggacccggc ggatcaaagc ggatgtatgc cggcctgaaa   1440

aatgccggcg agacatggta tgacataacg ggcaaccgtt cagatactgt aaaaatcgga   1500

tctgacggct ggggagagtt tcatgtaaac gatgggtccg tctccattta tgttcagaaa   1560
```

```
<210> SEQ ID NO 4
<211> LENGTH: 514
<212> TYPE: PRT
<213> ORGANISM: Bacillus sp.
<220> FEATURE:
<221> NAME/KEY: mat_peptide
<222> LOCATION: (30)..(514)

<400> SEQUENCE: 4

Met Asn Arg Trp Lys Ala Ala Phe Ser Trp Met Leu Ser Leu Ala Leu
                -25                 -20                 -15

Val Phe Thr Leu Phe Tyr Thr Pro Ser Ser Ala Ser Ala His His Asp
            -10                 -5              -1  1

Gly Thr Asn Gly Thr Ile Met Gln Tyr Phe Glu Trp Asn Val Pro Asn
    5                   10                  15

Asp Gly Gln His Trp Asn Arg Leu His Asn Asn Ala Gln Asn Leu Lys
20                  25                  30                  35

Asn Ala Gly Ile Thr Ala Ile Trp Ile Pro Pro Ala Trp Lys Gly Thr
                40                  45                  50

Ser Gln Asn Asp Val Gly Tyr Gly Ala Tyr Asp Leu Tyr Asp Leu Gly
            55                  60                  65

Glu Phe Asn Gln Lys Gly Thr Val Arg Thr Lys Tyr Gly Thr Lys Ala
        70                  75                  80

Glu Leu Glu Arg Ala Ile Arg Ser Leu Lys Ala Asn Gly Ile Gln Val
    85                  90                  95

Tyr Gly Asp Val Val Met Asn His Lys Gly Gly Ala Asp Phe Thr Glu
100                 105                 110                 115

Arg Val Gln Ala Val Glu Val Asn Pro Gln Asn Arg Asn Gln Glu Val
                120                 125                 130

Ser Gly Thr Tyr Gln Ile Glu Ala Trp Thr Gly Phe Asn Phe Pro Gly
            135                 140                 145

Arg Gly Asn Gln His Ser Ser Phe Lys Trp Arg Trp Tyr His Phe Asp
        150                 155                 160

Gly Thr Asp Trp Asp Gln Ser Arg Gln Leu Ala Asn Arg Ile Tyr Lys
    165                 170                 175

Phe Arg Gly Asp Gly Lys Ala Trp Asp Trp Glu Val Asp Thr Glu Asn
180                 185                 190                 195

Gly Asn Tyr Asp Tyr Leu Met Tyr Ala Asp Val Asp Met Asp His Pro
                200                 205                 210

Glu Val Ile Asn Glu Leu Asn Arg Trp Gly Val Trp Tyr Ala Asn Thr
```

-continued

```
            215                 220                 225

Leu Asn Leu Asp Gly Phe Arg Leu Asp Ala Val Lys His Ile Lys Phe
        230                 235                 240

Ser Phe Met Arg Asp Trp Leu Gly His Val Arg Gly Gln Thr Gly Lys
    245                 250                 255

Asn Leu Phe Ala Val Ala Glu Tyr Trp Lys Asn Asp Leu Gly Ala Leu
260                 265                 270                 275

Glu Asn Tyr Leu Ser Lys Thr Asn Trp Thr Met Ser Ala Phe Asp Val
                280                 285                 290

Pro Leu His Tyr Asn Leu Tyr Gln Ala Ser Asn Ser Ser Gly Asn Tyr
            295                 300                 305

Asp Met Arg Asn Leu Leu Asn Gly Thr Leu Val Gln Arg His Pro Ser
        310                 315                 320

His Ala Val Thr Phe Val Asp Asn His Asp Thr Gln Pro Gly Glu Ala
    325                 330                 335

Leu Glu Ser Phe Val Gln Gly Trp Phe Lys Pro Leu Ala Tyr Ala Thr
340                 345                 350                 355

Ile Leu Thr Arg Glu Gln Gly Tyr Pro Gln Val Phe Tyr Gly Asp Tyr
                360                 365                 370

Tyr Gly Ile Pro Ser Asp Gly Val Pro Ser Tyr Arg Gln Gln Ile Asp
            375                 380                 385

Pro Leu Leu Lys Ala Arg Gln Gln Tyr Ala Tyr Gly Arg Gln His Asp
        390                 395                 400

Tyr Phe Asp His Trp Asp Val Ile Gly Trp Thr Arg Glu Gly Asn Ala
    405                 410                 415

Ser His Pro Asn Ser Gly Leu Ala Thr Ile Met Ser Asp Gly Pro Gly
420                 425                 430                 435

Gly Ser Lys Trp Met Tyr Val Gly Arg Gln Lys Ala Gly Glu Val Trp
                440                 445                 450

His Asp Met Thr Gly Asn Arg Ser Gly Thr Val Thr Ile Asn Gln Asp
            455                 460                 465

Gly Trp Gly His Phe Phe Val Asn Gly Gly Ser Val Ser Val Trp Val
        470                 475                 480

Lys Arg
    485


<210> SEQ ID NO 5
<211> LENGTH: 513
<212> TYPE: PRT
<213> ORGANISM: Alicyclobacillus sp.
<220> FEATURE:
<221> NAME/KEY: mat_peptide
<222> LOCATION: (28)..(513)

<400> SEQUENCE: 5

Met Lys Ile Arg Asn Gly Trp Lys Lys Thr Leu Thr Leu Leu Phe Ala
        -25                 -20                 -15

Leu Ile Phe Leu Leu Pro His Ser Ala Ala Ala Thr Phe Ala Gly Asp
    -10                 -5              -1  1               5

Asn Gly Thr Met Met Gln Tyr Phe Glu Trp Tyr Leu Pro Asn Asp Gly
                10                  15                  20

Thr Leu Trp Thr Lys Met Gly Ser Asp Ala Ser His Leu Lys Ser Ile
            25                  30                  35

Gly Ile Thr Gly Val Trp Phe Pro Pro Ala Tyr Lys Gly Gln Ser Gln
        40                  45                  50
```

-continued

```
Ser Asp Val Gly Tyr Gly Val Tyr Asp Met Tyr Asp Leu Gly Glu Phe
    55                  60                  65

Asn Gln Lys Gly Thr Val Arg Thr Lys Tyr Gly Thr Lys Ala Gln Leu
70                  75                  80                  85

Gln Ser Ala Ile Thr Ser Leu His Asn Asn Gly Ile Gln Ala Tyr Gly
                90                  95                  100

Asp Val Val Leu Asn His Arg Met Gly Ala Asp Ala Thr Glu Thr Ile
            105                 110                 115

Ser Ala Val Glu Val Asn Pro Ser Asn Arg Asn Gln Val Thr Ser Gly
        120                 125                 130

Ala Tyr Asn Ile Ser Ala Trp Thr Asp Phe Glu Phe Pro Gly Arg Gly
    135                 140                 145

Asn Thr Tyr Ser Ser Phe Lys Trp His Ser Tyr Tyr Phe Asp Gly Val
150                 155                 160                 165

Asp Trp Asp Gln Ser Arg Gln Leu Ser Gly Lys Ile Tyr Gln Ile Gln
                170                 175                 180

Gly Thr Gly Lys Ala Trp Asp Trp Glu Val Asp Ser Glu Asn Gly Asn
            185                 190                 195

Tyr Asp Tyr Leu Met Gly Ala Asp Ile Asp Tyr Asp His Pro Asp Val
        200                 205                 210

Gln Thr Glu Val Lys Asn Trp Gly Lys Trp Phe Val Asn Thr Leu Asn
    215                 220                 225

Leu Asp Gly Val Arg Leu Asp Ala Val Lys His Ile Lys Phe Asp Tyr
230                 235                 240                 245

Met Ser Ser Trp Leu Ser Ser Val Lys Ser Thr Thr Gly Lys Ser Asn
                250                 255                 260

Leu Phe Ala Val Gly Glu Tyr Trp Asn Thr Ser Leu Gly Ala Leu Glu
            265                 270                 275

Asn Tyr Glu Asn Lys Thr Asn Trp Ser Met Ser Leu Phe Asp Val Pro
        280                 285                 290

Leu His Met Asn Phe Gln Ala Ala Ala Asn Gly Gly Gly Tyr Tyr Asp
    295                 300                 305

Met Arg Asn Leu Leu Asn Asn Thr Met Met Lys Asn His Pro Ile Gln
310                 315                 320                 325

Ala Val Thr Phe Val Asp Asn His Asp Thr Glu Pro Gly Gln Ala Leu
                330                 335                 340

Gln Ser Trp Val Ser Asp Trp Phe Lys Pro Leu Ala Tyr Ala Thr Ile
            345                 350                 355

Leu Thr Arg Gln Glu Gly Tyr Pro Cys Val Phe Tyr Gly Asp Tyr Tyr
        360                 365                 370

Gly Ile Pro Ser Gln Ser Val Ser Ala Lys Ser Thr Trp Leu Asp Lys
    375                 380                 385

Gln Leu Ser Ala Arg Lys Ser Tyr Ala Tyr Gly Thr Gln His Asp Tyr
390                 395                 400                 405

Leu Asp Asn Gln Asp Val Ile Gly Trp Thr Arg Glu Gly Asp Ser Ala
                410                 415                 420

His Ala Gly Ser Gly Leu Ala Thr Val Met Ser Asp Gly Pro Gly Gly
            425                 430                 435

Ser Lys Thr Met Tyr Val Gly Thr Ala His Ala Gly Gln Val Phe Lys
        440                 445                 450

Asp Ile Thr Gly Asn Arg Thr Asp Thr Val Thr Ile Asn Ser Ala Gly
    455                 460                 465

Asn Gly Thr Phe Pro Cys Asn Gly Gly Ser Val Ser Ile Trp Val Lys
```

```
470                 475                 480                 485

Gln


<210> SEQ ID NO 6
<211> LENGTH: 514
<212> TYPE: PRT
<213> ORGANISM: Bacillus amyloliquefaciens
<220> FEATURE:
<221> NAME/KEY: mat_peptide
<222> LOCATION: (32)..(514)

<400> SEQUENCE: 6

Met Ile Gln Lys Arg Lys Arg Thr Val Ser Phe Arg Leu Val Leu Met
    -30                 -25                 -20

Cys Thr Leu Leu Phe Val Ser Leu Pro Ile Thr Lys Thr Ser Ala Val
-15                 -10                 -5                  -1  1

Asn Gly Thr Leu Met Gln Tyr Phe Glu Trp Tyr Thr Pro Asn Asp Gly
            5                   10                  15

Gln His Trp Lys Arg Leu Gln Asn Asp Ala Glu His Leu Ser Asp Ile
        20                  25                  30

Gly Ile Thr Ala Val Trp Ile Pro Pro Ala Tyr Lys Gly Leu Ser Gln
    35                  40                  45

Ser Asp Asn Gly Tyr Gly Pro Tyr Asp Leu Tyr Asp Leu Gly Glu Phe
50                  55                  60                  65

Gln Gln Lys Gly Thr Val Arg Thr Lys Tyr Gly Thr Lys Ser Glu Leu
                70                  75                  80

Gln Asp Ala Ile Gly Ser Leu His Ser Arg Asn Val Gln Val Tyr Gly
            85                  90                  95

Asp Val Val Leu Asn His Lys Ala Gly Ala Asp Ala Thr Glu Asp Val
        100                 105                 110

Thr Ala Val Glu Val Asn Pro Ala Asn Arg Asn Gln Glu Thr Ser Glu
    115                 120                 125

Glu Tyr Gln Ile Lys Ala Trp Thr Asp Phe Arg Phe Pro Gly Arg Gly
130                 135                 140                 145

Asn Thr Tyr Ser Asp Phe Lys Trp His Trp Tyr His Phe Asp Gly Ala
                150                 155                 160

Asp Trp Asp Glu Ser Arg Lys Ile Ser Arg Ile Phe Lys Phe Arg Gly
            165                 170                 175

Glu Gly Lys Ala Trp Asp Trp Glu Val Ser Ser Glu Asn Gly Asn Tyr
        180                 185                 190

Asp Tyr Leu Met Tyr Ala Asp Val Asp Tyr Asp His Pro Asp Val Val
    195                 200                 205

Ala Glu Thr Lys Lys Trp Gly Ile Trp Tyr Ala Asn Glu Leu Ser Leu
210                 215                 220                 225

Asp Gly Phe Arg Ile Asp Ala Ala Lys His Ile Lys Phe Ser Phe Leu
                230                 235                 240

Arg Asp Trp Val Gln Ala Val Arg Gln Ala Thr Gly Lys Glu Met Phe
            245                 250                 255

Thr Val Ala Glu Tyr Trp Gln Asn Asn Ala Gly Lys Leu Glu Asn Tyr
        260                 265                 270

Leu Asn Lys Thr Ser Phe Asn Gln Ser Val Phe Asp Val Pro Leu His
    275                 280                 285

Phe Asn Leu Gln Ala Ala Ser Ser Gln Gly Gly Gly Tyr Asp Met Arg
290                 295                 300                 305

Arg Leu Leu Asp Gly Thr Val Val Ser Arg His Pro Glu Lys Ala Val
```

310 315 320

Thr Phe Val Glu Asn His Asp Thr Gln Pro Gly Gln Ser Leu Glu Ser
325 330 335

Thr Val Gln Thr Trp Phe Lys Pro Leu Ala Tyr Ala Phe Ile Leu Thr
340 345 350

Arg Glu Ser Gly Tyr Pro Gln Val Phe Tyr Gly Asp Met Tyr Gly Thr
355 360 365

Lys Gly Thr Ser Pro Lys Glu Ile Pro Ser Leu Lys Asp Asn Ile Glu
370 375 380 385

Pro Ile Leu Lys Ala Arg Lys Glu Tyr Ala Tyr Gly Pro Gln His Asp
390 395 400

Tyr Ile Asp His Pro Asp Val Ile Gly Trp Thr Arg Glu Gly Asp Ser
405 410 415

Ser Ala Ala Lys Ser Gly Leu Ala Ala Leu Ile Thr Asp Gly Pro Gly
420 425 430

Gly Ser Lys Arg Met Tyr Ala Gly Leu Lys Asn Ala Gly Glu Thr Trp
435 440 445

Tyr Asp Ile Thr Gly Asn Arg Ser Asp Thr Val Lys Ile Gly Ser Asp
450 455 460 465

Gly Trp Gly Glu Phe His Val Asn Asp Gly Ser Val Ser Ile Tyr Val
470 475 480

Gln Lys

<210> SEQ ID NO 7
<211> LENGTH: 485
<212> TYPE: PRT
<213> ORGANISM: Bacillus sp.

<400> SEQUENCE: 7

His His Asp Gly Thr Asn Gly Thr Ile Met Gln Tyr Phe Glu Trp Asn
1 5 10 15

Val Pro Asn Asp Gly Gln His Trp Asn Arg Leu His Asn Asn Ala Gln
20 25 30

Asn Leu Lys Asn Ala Gly Ile Thr Ala Ile Trp Ile Pro Pro Ala Trp
35 40 45

Lys Gly Thr Ser Gln Asn Asp Val Gly Tyr Gly Ala Tyr Asp Leu Tyr
50 55 60

Asp Leu Gly Glu Phe Asn Gln Lys Gly Thr Val Arg Thr Lys Tyr Gly
65 70 75 80

Thr Lys Ala Glu Leu Glu Arg Ala Ile Arg Ser Leu Lys Ala Asn Gly
85 90 95

Ile Gln Val Tyr Gly Asp Val Val Met Asn His Lys Gly Gly Ala Asp
100 105 110

Phe Thr Glu Arg Val Gln Ala Val Glu Val Asn Pro Gln Asn Arg Asn
115 120 125

Gln Glu Val Ser Gly Thr Tyr Gln Ile Glu Ala Trp Thr Gly Phe Asn
130 135 140

Phe Pro Gly Arg Gly Asn Gln His Ser Ser Phe Lys Trp Arg Trp Tyr
145 150 155 160

His Phe Asp Gly Thr Asp Trp Asp Gln Ser Arg Gln Leu Ala Asn Arg
165 170 175

Ile Tyr Lys Phe Arg Gly Asp Gly Lys Ala Trp Asp Trp Glu Val Asp
180 185 190

Thr Glu Asn Gly Asn Tyr Asp Tyr Leu Met Tyr Ala Asp Val Asp Met

```
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Met Thr Gly Asn Arg Ser Gly Thr Val Thr Ile
    450                 455                 460

Asn Gln Asp Gly Trp Gly His Phe Phe Val Asn Gly Gly Ser Val Ser
465                 470                 475                 480

Val Trp Val Lys Arg
                485


<210> SEQ ID NO 8
<211> LENGTH: 486
<212> TYPE: PRT
<213> ORGANISM: Alicyclobacillus sp.

<400> SEQUENCE: 8

Thr Phe Ala Gly Asp Asn Gly Thr Met Met Gln Tyr Phe Glu Trp Tyr
1               5                   10                  15

Leu Pro Asn Asp Gly Thr Leu Trp Thr Lys Met Gly Ser Asp Ala Ser
            20                  25                  30

His Leu Lys Ser Ile Gly Ile Thr Gly Val Trp Phe Pro Pro Ala Tyr
        35                  40                  45

Lys Gly Gln Ser Gln Ser Asp Val Gly Tyr Gly Val Tyr Asp Met Tyr
    50                  55                  60

Asp Leu Gly Glu Phe Asn Gln Lys Gly Thr Val Arg Thr Lys Tyr Gly
65                  70                  75                  80
```

-continued

```
Thr Lys Ala Gln Leu Gln Ser Ala Ile Thr Ser Leu His Asn Asn Gly
                85                  90                  95

Ile Gln Ala Tyr Gly Asp Val Val Leu Asn His Arg Met Gly Ala Asp
            100                 105                 110

Ala Thr Glu Thr Ile Ser Ala Val Glu Val Asn Pro Ser Asn Arg Asn
        115                 120                 125

Gln Val Thr Ser Gly Ala Tyr Asn Ile Ser Ala Trp Thr Asp Phe Glu
    130                 135                 140

Phe Pro Gly Arg Gly Asn Thr Tyr Ser Ser Phe Lys Trp His Ser Tyr
145                 150                 155                 160

Tyr Phe Asp Gly Val Asp Trp Asp Gln Ser Arg Gln Leu Ser Gly Lys
                165                 170                 175

Ile Tyr Gln Ile Gln Gly Thr Gly Lys Ala Trp Asp Trp Glu Val Asp
            180                 185                 190

Ser Glu Asn Gly Asn Tyr Asp Tyr Leu Met Gly Ala Asp Ile Asp Tyr
        195                 200                 205

Asp His Pro Asp Val Gln Thr Glu Val Lys Asn Trp Gly Lys Trp Phe
    210                 215                 220

Val Asn Thr Leu Asn Leu Asp Gly Val Arg Leu Asp Ala Val Lys His
225                 230                 235                 240

Ile Lys Phe Asp Tyr Met Ser Ser Trp Leu Ser Ser Val Lys Ser Thr
                245                 250                 255

Thr Gly Lys Ser Asn Leu Phe Ala Val Gly Glu Tyr Trp Asn Thr Ser
            260                 265                 270

Leu Gly Ala Leu Glu Asn Tyr Glu Asn Lys Thr Asn Trp Ser Met Ser
        275                 280                 285

Leu Phe Asp Val Pro Leu His Met Asn Phe Gln Ala Ala Ala Asn Gly
    290                 295                 300

Gly Gly Tyr Tyr Asp Met Arg Asn Leu Leu Asn Asn Thr Met Met Lys
305                 310                 315                 320

Asn His Pro Ile Gln Ala Val Thr Phe Val Asp Asn His Asp Thr Glu
                325                 330                 335

Pro Gly Gln Ala Leu Gln Ser Trp Val Ser Asp Trp Phe Lys Pro Leu
            340                 345                 350

Ala Tyr Ala Thr Ile Leu Thr Arg Gln Glu Gly Tyr Pro Cys Val Phe
        355                 360                 365

Tyr Gly Asp Tyr Tyr Gly Ile Pro Ser Gln Ser Val Ser Ala Lys Ser
    370                 375                 380

Thr Trp Leu Asp Lys Gln Leu Ser Ala Arg Lys Ser Tyr Ala Tyr Gly
385                 390                 395                 400

Thr Gln His Asp Tyr Leu Asp Asn Gln Asp Val Ile Gly Trp Thr Arg
                405                 410                 415

Glu Gly Asp Ser Ala His Ala Gly Ser Gly Leu Ala Thr Val Met Ser
            420                 425                 430

Asp Gly Pro Gly Gly Ser Lys Thr Met Tyr Val Gly Thr Ala His Ala
        435                 440                 445

Gly Gln Val Phe Lys Asp Ile Thr Gly Asn Arg Thr Asp Thr Val Thr
    450                 455                 460

Ile Asn Ser Ala Gly Asn Gly Thr Phe Pro Cys Asn Gly Gly Ser Val
465                 470                 475                 480

Ser Ile Trp Val Lys Gln
                485
```

-continued

<210> SEQ ID NO 9
<211> LENGTH: 483
<212> TYPE: PRT
<213> ORGANISM: Bacillus amyloliquefaciens

<400> SEQUENCE: 9

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380
```

-continued

```
Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys


<210> SEQ ID NO 10
<211> LENGTH: 399
<212> TYPE: PRT
<213> ORGANISM: Bacillus sp.

<400> SEQUENCE: 10

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270
```

```
Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly
385                 390                 395


<210> SEQ ID NO 11
<211> LENGTH: 86
<212> TYPE: PRT
<213> ORGANISM: Alicyclobacillus sp.

<400> SEQUENCE: 11

Thr Gln His Asp Tyr Leu Asp Asn Gln Asp Val Ile Gly Trp Thr Arg
1               5                   10                  15

Glu Gly Asp Ser Ala His Ala Gly Ser Gly Leu Ala Thr Val Met Ser
            20                  25                  30

Asp Gly Pro Gly Gly Ser Lys Thr Met Tyr Val Gly Thr Ala His Ala
        35                  40                  45

Gly Gln Val Phe Lys Asp Ile Thr Gly Asn Arg Thr Asp Thr Val Thr
    50                  55                  60

Ile Asn Ser Ala Gly Asn Gly Thr Phe Pro Cys Asn Gly Gly Ser Val
65                  70                  75                  80

Ser Ile Trp Val Lys Gln
                85


<210> SEQ ID NO 12
<211> LENGTH: 86
<212> TYPE: PRT
<213> ORGANISM: Bacillus amyloliquefaciens

<400> SEQUENCE: 12

Pro Gln His Asp Tyr Ile Asp His Pro Asp Val Ile Gly Trp Thr Arg
1               5                   10                  15

Glu Gly Asp Ser Ser Ala Ala Lys Ser Gly Leu Ala Ala Leu Ile Thr
            20                  25                  30

Asp Gly Pro Gly Gly Ser Lys Arg Met Tyr Ala Gly Leu Lys Asn Ala
        35                  40                  45

Gly Glu Thr Trp Tyr Asp Ile Thr Gly Asn Arg Ser Asp Thr Val Lys
    50                  55                  60

Ile Gly Ser Asp Gly Trp Gly Glu Phe His Val Asn Asp Gly Ser Val
65                  70                  75                  80

Ser Ile Tyr Val Gln Lys
                85


<210> SEQ ID NO 13
<211> LENGTH: 485
```

<212> TYPE: PRT
<213> ORGANISM: Artificial sequence
<220> FEATURE:
<223> OTHER INFORMATION: Fusion protein 1

<400> SEQUENCE: 13

```
His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380
```

```
Gln Ile Asp Pro Leu Leu Lys Ala Arg Gln Gln Tyr Ala Tyr Gly Thr
385                 390                 395                 400

Gln His Asp Tyr Leu Asp Asn Gln Asp Val Ile Gly Trp Thr Arg Glu
                405                 410                 415

Gly Asp Ser Ala His Ala Gly Ser Gly Leu Ala Thr Val Met Ser Asp
            420                 425                 430

Gly Pro Gly Gly Ser Lys Thr Met Tyr Val Gly Thr Ala His Ala Gly
        435                 440                 445

Gln Val Phe Lys Asp Ile Thr Gly Asn Arg Thr Asp Thr Val Thr Ile
    450                 455                 460

Asn Ser Ala Gly Asn Gly Thr Phe Pro Cys Asn Gly Gly Ser Val Ser
465                 470                 475                 480

Ile Trp Val Lys Gln
                485


<210> SEQ ID NO 14
<211> LENGTH: 485
<212> TYPE: PRT
<213> ORGANISM: Artificial sequence
<220> FEATURE:
<223> OTHER INFORMATION: Fusion protein 2

<400> SEQUENCE: 14

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255
```

```
Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Pro
385                 390                 395                 400

Gln His Asp Tyr Ile Asp His Pro Asp Val Ile Gly Trp Thr Arg Glu
                405                 410                 415

Gly Asp Ser Ser Ala Ala Lys Ser Gly Leu Ala Ala Leu Ile Thr Asp
            420                 425                 430

Gly Pro Gly Gly Ser Lys Arg Met Tyr Ala Gly Leu Lys Asn Ala Gly
        435                 440                 445

Glu Thr Trp Tyr Asp Ile Thr Gly Asn Arg Ser Asp Thr Val Lys Ile
    450                 455                 460

Gly Ser Asp Gly Trp Gly Glu Phe His Val Asn Asp Gly Ser Val Ser
465                 470                 475                 480

Ile Tyr Val Gln Lys
                485


<210> SEQ ID NO 15
<211> LENGTH: 483
<212> TYPE: PRT
<213> ORGANISM: Bacillus sp.

<400> SEQUENCE: 15

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140
```

```
Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Val Asp Met Asp His
        195                 200                 205

Pro Glu Val Ile Asn Glu Leu Asn Arg Trp Gly Val Trp Tyr Ala Asn
    210                 215                 220

Thr Leu Asn Leu Asp Gly Phe Arg Leu Asp Ala Val Lys His Ile Lys
225                 230                 235                 240

Phe Ser Phe Met Arg Asp Trp Leu Gly His Val Arg Gly Gln Thr Gly
                245                 250                 255

Lys Asn Leu Phe Ala Val Ala Glu Tyr Trp Lys Asn Asp Leu Gly Ala
            260                 265                 270

Leu Glu Asn Tyr Leu Ser Lys Thr Asn Trp Thr Met Ser Ala Phe Asp
        275                 280                 285

Val Pro Leu His Tyr Asn Leu Tyr Gln Ala Ser Asn Ser Ser Gly Asn
    290                 295                 300

Tyr Asp Met Arg Asn Leu Leu Asn Gly Thr Leu Val Gln Arg His Pro
305                 310                 315                 320

Ser His Ala Val Thr Phe Val Asp Asn His Asp Thr Gln Pro Gly Glu
                325                 330                 335

Ala Leu Glu Ser Phe Val Gln Gly Trp Phe Lys Pro Leu Ala Tyr Ala
            340                 345                 350

Thr Ile Leu Thr Arg Glu Gln Gly Tyr Pro Gln Val Phe Tyr Gly Asp
        355                 360                 365

Tyr Tyr Gly Ile Pro Ser Asp Gly Val Pro Ser Tyr Arg Gln Gln Ile
    370                 375                 380

Asp Pro Leu Leu Lys Ala Arg Gln Gln Tyr Ala Tyr Gly Arg Gln His
385                 390                 395                 400

Asp Tyr Phe Asp His Trp Asp Val Ile Gly Trp Thr Arg Glu Gly Asn
                405                 410                 415

Ala Ser His Pro Asn Ser Gly Leu Ala Thr Ile Met Ser Asp Gly Pro
            420                 425                 430

Gly Gly Ser Lys Trp Met Tyr Val Gly Arg Gln Lys Ala Gly Glu Val
        435                 440                 445

Trp His Asp Met Thr Gly Asn Arg Ser Gly Thr Val Thr Ile Asn Gln
    450                 455                 460

Asp Gly Trp Gly His Phe Phe Val Asn Gly Gly Ser Val Ser Val Trp
465                 470                 475                 480

Val Lys Arg
```

<210> SEQ ID NO 16
<211> LENGTH: 27
<212> TYPE: DNA
<213> ORGANISM: Artificial sequence
<220> FEATURE:
<223> OTHER INFORMATION: Synthetic construct

<400> SEQUENCE: 16
caatccaaga gaaccctgat acggatg 27

-continued

```
<210> SEQ ID NO 17
<211> LENGTH: 23
<212> TYPE: DNA
<213> ORGANISM: Artificial sequence
<220> FEATURE:
<223> OTHER INFORMATION: Synthetic construct

<400> SEQUENCE: 17

cggaacgcct ggctgacaac acg                                              23
```

ALPHA-AMYLASE VARIANTS AND POLYNUCLEOTIDES ENCODING SAME

CROSS-REFERENCE TO RELATED APPLICATIONS

This application is a 35 U.S.C. 371 national application of PCT/EP2016/060266 filed May 9, 2016, which claims priority or the benefit under 35 U.S.C. 119 of Indian application no. 2335/CHE/2015 filed May 8, 2015, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases have for many years been used in laundry where is it well-known that alpha-amylases have a beneficial effect in removal of starch containing, or starch-based, stains.

WO95/26397 discloses alkaline *Bacillus* amylases having good wash performance measured at temperatures in the range of 30-60° C.

WO00/60060 and WO00/60058 discloses further bacterial alpha-amylases having good wash performance.

In recent years there has been a desire to reduce the temperature of the laundry in order to reduce the energy consumption. Lowering the temperature in laundry often means that the performance of the detergent composition and the enzyme is reduced and a lower wash performance is therefore obtained at low temperature. It is therefore desired to find new alpha-amylases having good wash performance at low temperature. Accordingly, it is an object of the present invention to provide alpha-amylases which have good wash performance at low temperature, such as at 15° C. Thus, the present invention provides such further improved alpha-amylse variants with improved properties compared to its parent.

SUMMARY OF THE INVENTION

The present invention relates to an alpha-amylase variant of a parent polypeptide having alpha-amylase activity, wherein the variant is a fusion polypeptide which has an improved wash performance at low temperature, and wherein said variant has alpha-amylase activity.

The present invention also relates to polynucleotides encoding the variants; nucleic acid constructs, vectors, and host cells comprising the polynucleotides; and methods of producing the variants.

The present invention also relates to methods of improving wash performance of a parent alpha-amylase.

Conventions for Designation of Variants

For purposes of the present invention, the mature polypeptide disclosed in SEQ ID NO: 7 is used to determine the corresponding amino acid residue in another alpha-amylase.

Alternatively, the mature polypeptide disclosed in SEQ ID NO: 13 and 14 may be used to determine the corresponding amino acid residue in another alpha-amylase. The amino acid sequence of another alpha-amylase is aligned with the mature polypeptide disclosed in SEQ ID NO: 7, and based on the alignment, the amino acid position number corresponding to any amino acid residue in the mature polypeptide disclosed in any of SEQ ID NOs: 13 and 14 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 7 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions:

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions:

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Multiple Modifications:

Variants comprising multiple modifications are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Modifications:

Where different modifications can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to a set of sequences. For ease, these are listed below;

SEQ ID NO: 1 is the nucleotide sequence of an alpha-amylase (AAI10)

SEQ ID NO: 2 is the nucleotide sequence of an alpha-amylase originating from *Alicyclobacillus* sp.

SEQ ID NO: 3 is the nucleotide sequence of an alpha-amylase originating from *Bacillus amyloliquefaciens.*

SEQ ID NO: 4 is the amino acid sequence of AAI10 including the signal peptide.

SEQ ID NO: 5 is the amino acid sequence of *Alicyclobacillus* sp. including the signal peptide.

SEQ ID NO: 6 is the amino acid sequence of *Bacillus amyloliquefaciens* including the signal peptide.

SEQ ID NO: 7 is the amino acid sequence of the mature AAI10

SEQ ID NO: 8 is the amino acid sequence of the mature *Alicyclobacillus* sp.

SEQ ID NO: 9 is the amino acid sequence of the mature *Bacillus amyloliquefaciens*

SEQ ID NO: 10 is the amino acid sequence corresponding the A and B domains of AAI10.

SEQ ID NO: 11 is the amino acid sequence corresponding to the C domain of *Alicyclobacillus* sp.

SEQ ID NO: 12 is the amino acid sequence corresponding to the C domain of *Bacillus amyloliquefaciens*

SEQ ID NO: 13 is the amino acid sequence of the fusion polypeptide consisting of the A and B domain of AAI10 and the C domain of *Alicyclobacillus* sp.

SEQ ID NO: 14 is the amino acid sequence of the fusion polypeptide consisting of the A and the B domains of AAI10 and the C domain of *Bacillus amyloliquefaciens*

SEQ ID NO: 15 is the amino acid sequence of the mature AAI10 alpha-amylase comprising a double deletion at positions corresponding to positions 182 and 183 of SEQ ID NO. 7

Variants of the Invention

In one aspect, the present invention relates to variants of a parent polypeptide having alpha-amylase activity. Thus, in particular aspect, the present invention relates to variant of a parent polypeptide having alpha-amylase activity, wherein said variant is a fusion polypeptide which has an improved wash performance at low temperature, and wherein said variant has alpha-amylase activity.

It has been shown that variants according to the present invention have improved performance, such as wash performance, at a low temperature, in particular at 15° C., in liquid detergent compositions.

The term "variant" as used herein, refers to a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position, all as defined above. The variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NOs: 7, 13, 14, 15, or the mature polypeptide of SEQ ID NO: 4. The variants of the present invention have at least 65%, such as at least 70%, such as at least 75%, such as at least 80%, such as at least 85%, such at least 90%, such as at least 95%, such as at least 97%, such as at least 99%, but less than 100% sequence identity to any one of SEQ ID NOs: 4, 7, 13, 14, or 15

The term "parent polypeptide" as used herein, refers to a polypeptide to which an alteration is made to produce enzyme variants. The polypeptide having any of SEQ ID NOs: 4, 7, 13, 14, and 15 may e.g. be a parent for the variants of the present invention. Any polypeptide having at least 65%, such as at least 70%, such as at least 75%, such as at least 80%, such as at least 85%, such at least 90%, such as at least 95%, such as at least 97%, such as at least 99%, sequence identity to any one of SEQ ID NOs: 4, 7, 13, 14, or 15 may also be a parent polypeptide for the variants of the present invention.

The parent polypeptide may be a fusion polypeptide or cleavable fusion polypeptide. Such fusion polypeptide may consist of a subsequence of one parent polypeptide and a subsequence of second parent polypeptide. In particular, a fusion polypeptide may consist of an A and B domain of one species of alpha-amylase and a C domain of another species of alpha-amylase, and thereby providing a parent polypeptide to generate a variant of the present invention. Techniques for producing fusion polypeptides are known in the art, and include ligating the coding sequences encoding the polypeptides so that they are in frame and that expression of the fusion polypeptide is under control of the same promoter (s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide may further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent polypeptide may be obtained from microorganisms of any genus. For purposes of the present invention, the term "obtained from" as used herein in connection with a given source shall mean that the parent polypeptide encoded by a polynucleotide is produced by the source or by a strain in which the polynucleotide from the source has been inserted.

In some aspects of the present invention, the parent polypeptide is *Bacillus* sp. alpha-amylase, e.g., the alpha-amylase of SEQ ID NOs: 4, the mature polypeptide thereof, i.e. SEQ ID NO: 7. In particular aspects, the parent polypeptide is a fusion protein, and originates from both a *Bacillus* sp and a *Alicyclobacillus* sp., e.g. the alpha-amylase of SEQ ID NO: 13. In other aspects, the parent polypeptide is a fusion protein and originates from two different *Bacillus* sps., e.g. resulting in the alpha-amylase of SEQ ID NO: 14.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent polypeptide may then be obtained by similarly screening a genomic DNA or cDNA library of another microorganism or mixed DNA sample. Once a polynucleotide encoding a parent polypeptide has been detected with the probe(s), the polynucleotide can be isolated or cloned by utilizing techniques that are known to those of ordinary skill in the art (see, e.g., Sambrook et al., 1989, supra).

In one embodiment, the parent polypeptide comprises or consists of the amino acid sequence set forth in SEQ ID NO: 7, 13, or 15. In another embodiment, the parent polypeptide comprises or consists of the mature polypeptide of SEQ ID NO: 4. In particular, the parent polypeptide may comprise or consist of amino acids 1 to 485 of SEQ ID NO: 4.

In another embodiment, the parent polypeptide is a fragment of the mature polypeptide of SEQ ID NO: 4 containing at least 350, such as at least 390 amino acid residues, e.g., at least 395 and at least 397 amino acid residues of SEQ ID NO: 4.

In another embodiment, the parent polypeptide is an allelic variant of the mature polypeptide of SEQ ID NO: 4.

The term "sequence identity" as used herein, refers to the relatedness between two amino acid sequences or between two nucleotide sequences. For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

$$(\text{Identical Deoxyribonucleotides} \times 100)/(\text{Length of Alignment} - \text{Total Number of Gaps in Alignment})$$

The term "alpha-amylase activity" as used herein, refers to the activity of alpha-1,4-glucan-4-glucanohydrolases, E.C. 3.2.1.1, which constitute a group of enzymes, catalyzing hydrolysis of starch and other linear and branched 1,4-glucosidic oligo- and polysaccharides. Thus, the term "alpha-amylase" as used herein, refers to an enzyme that has alpha-amylase activity (Enzyme Class; EC 3.2.1.1) that hydrolyses alpha bonds of large, alpha-linked polysaccharides, such as starch and glycogen, yielding glucose and maltose. The terms "alpha-amylase" and "amylase" may be used interchangeably and constitute the same meaning and purpose within the scope of the present invention. For purposes of the present invention, alpha-amylase activity is determined according to the procedure described in the Examples. In one embodiment, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NOs: 7, 13, 14, or 15; or the mature polypeptide of SEQ ID NO: 4.

The term "fusion polypeptide" as used herein, refers to a polypeptide which comprises amino acid sequences originating from more than one, such as two, three, or four, species. Such a fusion polypeptide may have been generated by molecular techniques well-known to the skilled person. A fusion polypeptide of the present invention has alpha-amylase activity. In particular, a fusion polypeptide of the present invention, comprises e.g. an A and B domain of one alpha-amylase and a C domain from another alpha-amylase.

The term "wash performance" as used herein, refers to an enzyme's ability to remove starch or starch-containing stains present on the object to be cleaned during e.g. laundry or hard surface cleaning, such as dish wash. The term "wash performance" includes cleaning in general e.g. hard surface cleaning as in dish wash, but also wash performance on textiles such as laundry, and also industrial and institutional cleaning. The wash performance may be quantified by calculating the so-called Intensity value, and results may be displayed as "Improvement Factor" (IF). Wash performance may be determined as in described in the Examples herein.

The term "Intensity value" as used herein, refers to the wash performance measured as the brightness expressed as the intensity of the light reflected from the sample when illuminated with white light. When the sample is stained the intensity of the reflected light is lower, than that of a clean sample. Therefore the intensity of the reflected light can be used to measure wash performance, where a higher intensity value correlates with higher wash performance.

Color measurements are made with a professional flatbed scanner (Kodak iQsmart, Kodak) used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$\text{Int}=\sqrt{r^2+g^2+b^2}$$

The term "improved wash performance" as used herein, refers to an improvement of the wash performance of an alpha-amylase of the present invention relative to the wash performance of the parent polypeptide. Improved wash performance may be measured by comparing of the so-called Intensity value and calculating the Improvement Factor (IF). The improved wash performance is determined according to the section "Wash performance of alpha-amylases using Automatic Mechanical Stress Assay" and using model detergent J at 15° C., 30° C. or 40° C. Other model detergents may be used, such as Model detergent A.

Thus, in one embodiment, the improved wash performance is determined by a method comprising the steps of;

a) washing a fabric stained with starch with an alpha-amylase variant and a parent polypeptide sample added, respectively, to a model detergent composition, such as Model A or Model J;
b) measuring the intensity of light reflected from the sample when illuminated with white light; and
c) optionally, calculating the improvement factor (IF) as the ratio of delta intensity of the alpha-amylase sample over the delta intensity of the parent polypeptide sample.

In one embodiment, the improved wash performance is determined by a method comprising the steps of;

a) washing a fabric stained with starch with an alpha-amylase variant and a parent polypeptide sample added, respectively, to a model detergent composition, such as Model A or Model J for 20 minutes at 15° C., 30° C., and 40° C.;
b) measuring the intensity of light reflected from the sample when illuminated with white light; and
c) optionally, calculating the improvement factor (IF) as the ration of delta intensity of the alpha-amylase sample over the delta intensity of the parent polypeptide sample.

The term "low temperature" as used herein, refers to is a temperature of 5-40° C., such as 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C. Most preferred, low temperature means 15° C.

Thus, in one embodiment, the low temperature is 5° C. to 40° C., preferably 10° C. to 30°, event more preferred 15° C. to 20° C.

In one embodiment, the improved wash performance has an Improvement Factor (IF) of ≥1 when compared to said parent polypeptide having alpha-amylase activity.

The term "Improvement Factor" as used herein, refers to a quantitative way of calculating the improvement of a particular property of a variant according to the present invention. Determination of the Improvement Factor may be according to the following formula:

$$\frac{\text{Intensity value of variant} - \text{Intensity value of blank}}{\text{Intensity value of parent} - \text{Intensity value of blank}}$$

Other formulas may be used to determine the Improvement Factor. The skilled person knows the presently presented formula as well as alternative ways of calculating the Improvement Factor.

According to the present invention, a value of 1.0 corresponds to the performance observed for the parent polypeptide. A value above 1.0 indicates an improvement of performance of the variant tested compared to the parent polypeptide. Accordingly, any value of ≥1.0 is indicative for improvement of property, such as performance, of the variant compared to the parent polypeptide.

According to the present invention, a variant showing improvement of property under at least one condition tested, is considered a variant having improved property as compared to the parent polypeptide.

In one embodiment, said parent polypeptide comprises an A and a B domain comprising the amino acid sequence of SEQ ID NO: 10, or an A and a B domain having at least 80%, such as 85%, such as 90%, such as 95%, such as 97% sequence identity to SEQ ID NO: 10, and a C domain of a low temperature alpha-amylase.

The terms "A domain", "B domain" and "C domain" as used herein, refers to three distinct domains A, B and C, all part of the alpha-amylase structure, see, e.g., Machius et al., 1995, *J. Mol. Biol.* 246: 545-559. Thus, an alpha-amylase, such as a parent polypeptide and a variant according to the invention, may comprise both an A, B, and C domain. The term "domain" means a region of a polypeptide that in itself forms a distinct and independent substructure of the whole molecule. Alpha-amylases consist of a beta/alpha-8 barrel harboring the active site residues, which is denoted the A domain, a rather long loop between the beta-sheet 3 and alpha-helix 3, which is denoted the B domain (together; "A and B domain"), and a C-domain and in some cases also a carbohydrate binding domain (e.g., WO 2005/001064; Machius et al., supra).

The domains of an alpha-amylase may be determined by structure analysis such as using crystallographically techniques. An alternative method for determining the domains of an alpha-amylase is by sequence alignment of the amino acid sequence of the alpha-amylase with another alpha-amylase for which the domains have been determined. The sequence that aligns with, e.g., the C-domain sequence in the alpha-amylase for which the C-domain has been determined can be considered the C domain for the given alpha-amylase.

The term “A and B domain” as used herein, refers to two domains of an alpha-amylase taken as one unit, whereas the C domain is another unit of the alpha-amylases. Thus, the amino acid sequence of the “A and B domain” is understood as one sequence or one part of a sequence of an alpha-amylase comprising an “A and B domain” and other domains (such as the C domain). Thus, the term “the A and B domain has at least 65% sequence identity to SEQ ID NO: 10” means that the amino acid sequence that form the A and B domain has at least 65% sequence identity to SEQ ID NO: 10. As used herein, the “A and B domain” of a parent polypeptide corresponds to amino acids 1 to 399 of SEQ ID NO: 7, or to amino acids 1 to 397 of SEQ ID NO: 15. The A and B domain of a parent polypeptide may have the amino acid sequence of SEQ ID NO: 10.

The term “C domain” as used herein, refers to a domain of an alpha-amylase as one unit. The “C domain” of an alpha-amylase corresponds to amino acids 400 to 485 of SEQ ID NO: 7, or to amino acid 398 to 483 of SEQ ID NO: 15. Thus, the C domain of an alpha amylase may be found by alignment of said alpha-amylase with the polypeptide of SEQ ID NO: 7 or 15. The part of said alpha-amylase that aligns with amino acids 400 to 485 of SEQ ID NO: 7 or to amino acids 398 to 483 of SEQ ID NO: 15 is according to the present invention “the C domain” of the alpha-amylase. The C domain of a parent polypeptide may have the amino acid sequence of SEQ ID NOs: 11 or 12.

The term “C domain of a low temperature alpha-amylase” as used herein, refers to the C domain of an alpha-amylase showing particular properties at low temperatures. Non-limiting examples of such low temperature alpha-amylases are those originating from *Alicyclobacillus* sp. as well as from *Bacillus amyloliquefaciens* (BAN).

In one embodiment, the parent polypeptide comprises a C domain comprising the amino acid sequence of SEQ ID NOs: 11 or 12, or a C domain having at 80%, such as 85%, such as 90%, such as 95%, such as 97%, sequence identity to SEQ ID NO: 11 or 12.

In one embodiment, the parent polypeptide comprises the amino acid sequence of SEQ ID NOs: 13 or 14, or a sequence having at least 80%, such as 85%, such as 90%, such as 95%, such as 97% sequence identity to SEQ ID NOs: 13 or 14.

As stated elsewhere herein, the parent polypeptide may be any polypeptide having alpha-amylase activity and at least 65% sequence identity to any one of the amino acid sequences as set forth in SEQ ID NOs: 13 and 14. In certain embodiments, the parent polypeptide comprises the amino acid sequences as set forth in SEQ ID NOs: 10, 11, and 12.

In one embodiment, the parent polypeptide a sequence identity to the amino acid sequence set forth in SEQ ID NOs: 13 or 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which parent polypeptide has alpha-amylase activity. In one embodiment, the amino acid sequence of the parent polypeptide differs by up to 10 amino acids, e.g., 1, 2, 3, 4, 5, 6, 7, 8, 9, or 10, from the amino acid sequences set forth in SEQ ID NOs: 7, 13, and 14.

The present invention provides variants of such parent polypeptides.

The variants according to the present invention may advantageously comprise alterations in specific positions of the A and B domain. Thus, in a particular embodiment, the variant comprises amino acid alterations in amino acid positions corresponding the amino acid sequence set forth in SEQ ID NO: 10, or a sequence having at least 65% sequence identity to the amino acid sequence set forth in SEQ ID NO: 10.

In particular, the present invention relates to an embodiment, the A and B domains comprise a modification in one or more of the following positions corresponding to positions; H1, T5, G7, Q11, N16, V17, Q32, A37, T40, P45, W48, G50, T51, N54, V56, A60, K72, R87, Q98, M105, G109, F113, R116, Q118, Q125, G133, T134, W140, G142, G149, T165, W167, Q169, R171, Q172, L173, A174, G184, A186, E190, T193, N195, G196, A204, V206, P211, I214, V215, L217, L219, A225, L228, L235, V238, K242, S244, M246, M248, L250, G255, Q256, N260, A263, V264, A265, Y267, K269, N270, G273, S280, W284, T285, M286, F289, V291, N295, Q299, S304, R320, H321, S323, H324, V326, F328, T334, D337, Q345, G346, G348, T355, S376, D377, D379, Y382, S383, Q385, K391, K393, and Q395 of SEQ ID NOs: 7 or 10.

Such variants have shown to have improved wash performance in at least one assay wherein the temperature under which the variants have been tested was a low temperature, such as 15° C., 30° and 40° C. Specific conditions may be seen in the Examples herein.

The term “modification” as used herein, refers to both substitutions and deletions of amino acid within the amino acid sequence of a polypeptide. The terms “alteration” and “modification” may be used interchangeably herein. This should not be understood as any limitation and thus, the terms constitute the same meaning and purpose unless explicitly stated otherwise.

The term “corresponding to” as used herein, refers to way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 4, 7, or any other sequence listed herein, has been described elsewhere herein. Alternative alignment methods may be used, and are well-known for the skilled person.

In a particular embodiment, the variant comprises an alteration in two, three, four, five, six, seven, eight, nine, ten, eleven, twelf, thirteen, fourteen, fifteen, or sixteen positions corresponding to the following positions; H1, T5, G7, Q11, N16, V17, Q32, A37, T40, P45, W48, G50, T51, N54, V56, A60, K72, R87, Q98, M105, G109, F113, R116, Q118, Q125, G133, T134, W140, G142, G149, T165, W167, Q169, R171, Q172, L173, A174, G184, A186, E190, T193, N195, G196, A204, V206, P211, I214, V215, L217, L219, A225, L228, L235, V238, K242, S244, M246, M248, L250, G255, Q256, N260, A263, V264, A265, Y267, K269, N270, G273, S280, W284, T285, M286, F289, V291, Y295, Q299, S304, R320, H321, S323, H324, V326, F328, T334, D337, Q345, G346, G348, T355, S376, D377, D379, Y382, S383, Q385, K391, K393, and Q395 of SEQ ID NOs: 7 or 10.

In a particular embodiment, the variant comprises an alteration in the following positions;

| | | | | | |
|---|---|---|---|---|---|
| H1 + T5 | T40 + L217 | N54 + T285 | Q125 + G255 | G184 + P211 | M248 + Q299 |
| H1 + G7 | T40 + L219 | N54 + M286 | Q125 + Q256 | G184 + I214 | M248 + S304 |
| H1 + Q11 | T40 + L228 | N54 + F289 | Q125 + A263 | G184 + V215 | M248 + R320 |
| H1 + N16 | T40 + L235 | N54 + V291 | Q125 + V264 | G184 + L217 | M248 + H321 |
| H1 + V17 | T40 + V238 | N54 + Q299 | Q125 + A265 | G184 + L219 | M248 + S323 |
| H1 + Q32 | T40 + M246 | N54 + S304 | Q125 + Y267 | G184 + L228 | M248 + H324 |
| H1 + A37 | T40 + M248 | N54 + R320 | Q125 + N270 | G184 + L235 | M248 + F328 |
| H1 + T40 | T40 + L250 | N54 + H321 | Q125 + G273 | G184 + V238 | M248 + T334 |
| H1 + P45 | T40 + G255 | N54 + S323 | Q125 + S280 | G184 + M246 | M248 + D337 |
| H1 + W48 | T40 + Q256 | N54 + H324 | Q125 + T285 | G184 + M248 | M248 + Q345 |
| H1 + G50 | T40 + A263 | N54 + F328 | Q125 + M286 | G184 + L250 | M248 + G346 |
| H1 + T51 | T40 + V264 | N54 + T334 | Q125 + F289 | G184 + G255 | M248 + G348 |
| H1 + N54 | T40 + A265 | N54 + D337 | Q125 + V291 | G184 + Q256 | M248 + T355 |
| H1 + V56 | T40 + Y267 | N54 + Q345 | Q125 + Q299 | G184 + A263 | M248 + S376 |
| H1 + A60 | T40 + N270 | N54 + G346 | Q125 + S304 | G184 + V264 | M248 + D377 |
| H1 + K72 | T40 + G273 | N54 + G348 | Q125 + R320 | G184 + A265 | M248 + D379 |
| H1 + R87 | T40 + S280 | N54 + T355 | Q125 + H321 | G184 + Y267 | M248 + Y382 |
| H1 + Q98 | T40 + T285 | N54 + S376 | Q125 + S323 | G184 + N270 | M248 + S383 |
| H1 + M105 | T40 + M286 | N54 + D377 | Q125 + H324 | G184 + G273 | M248 + Q385 |
| H1 + G109 | T40 + F289 | N54 + D379 | Q125 + F328 | G184 + S280 | M248 + K391 |
| H1 + F113 | T40 + V291 | N54 + Y382 | Q125 + T334 | G184 + T285 | M248 + K393 |
| H1 + R116 | T40 + Q299 | N54 + S383 | Q125 + D337 | G184 + M286 | M248 + Q395 |
| H1 + Q118 | T40 + S304 | N54 + Q385 | Q125 + Q345 | G184 + F289 | L250 + G255 |
| H1 + Q125 | T40 + R320 | N54 + K391 | Q125 + G346 | G184 + V291 | L250 + Q256 |
| H1 + G133 | T40 + H321 | N54 + K393 | Q125 + G348 | G184 + Q299 | L250 + A263 |
| H1 + T134 | T40 + S323 | N54 + Q395 | Q125 + T355 | G184 + S304 | L250 + V264 |
| H1 + W140 | T40 + H324 | V56 + A60 | Q125 + S376 | G184 + R320 | L250 + A265 |
| H1 + G142 | T40 + F328 | V56 + K72 | Q125 + D377 | G184 + H321 | L250 + Y267 |
| H1 + G149 | T40 + T334 | V56 + R87 | Q125 + D379 | G184 + S323 | L250 + N270 |
| H1 + T165 | T40 + D337 | V56 + Q98 | Q125 + Y382 | G184 + H324 | L250 + G273 |
| H1 + W167 | T40 + Q345 | V56 + M105 | Q125 + S383 | G184 + F328 | L250 + S280 |
| H1 + R171 | T40 + G346 | V56 + G109 | Q125 + Q385 | G184 + T334 | L250 + T285 |
| H1 + Q172 | T40 + G348 | V56 + F113 | Q125 + K391 | G184 + D337 | L250 + M286 |
| H1 + L173 | T40 + T355 | V56 + R116 | Q125 + K393 | G184 + Q345 | L250 + F289 |
| H1 + A174 | T40 + S376 | V56 + Q118 | Q125 + Q395 | G184 + G346 | L250 + V291 |
| H1 + G184 | T40 + D377 | V56 + Q125 | G133 + T134 | G184 + G348 | L250 + Q299 |
| H1 + T193 | T40 + D379 | V56 + G133 | G133 + W140 | G184 + T355 | L250 + S304 |
| H1 + N195 | T40 + Y382 | V56 + T134 | G133 + G142 | G184 + S376 | L250 + R320 |
| H1 + G196 | T40 + S383 | V56 + W140 | G133 + G149 | G184 + D377 | L250 + H321 |
| H1 + A204 | T40 + Q385 | V56 + G142 | G133 + T165 | G184 + D379 | L250 + S323 |
| H1 + V206 | T40 + K391 | V56 + G149 | G133 + W167 | G184 + Y382 | L250 + H324 |
| H1 + P211 | T40 + K393 | V56 + T165 | G133 + R171 | G184 + S383 | L250 + F328 |
| H1 + I214 | T40 + Q395 | V56 + W167 | G133 + Q172 | G184 + Q385 | L250 + T334 |
| H1 + V215 | P45 + W48 | V56 + R171 | G133 + L173 | G184 + K391 | L250 + D337 |
| H1 + L217 | P45 + G50 | V56 + Q172 | G133 + A174 | G184 + K393 | L250 + Q345 |
| H1 + L219 | P45 + T51 | V56 + L173 | G133 + G184 | G184 + Q395 | L250 + G346 |
| H1 + L228 | P45 + N54 | V56 + A174 | G133 + T193 | T193 + N195 | L250 + G348 |
| H1 + L235 | P45 + V56 | V56 + G184 | G133 + N195 | T193 + G196 | L250 + T355 |
| H1 + V238 | P45 + A60 | V56 + T193 | G133 + G196 | T193 + A204 | L250 + S376 |
| H1 + M246 | P45 + K72 | V56 + N195 | G133 + A204 | T193 + V206 | L250 + D377 |
| H1 + M248 | P45 + R87 | V56 + G196 | G133 + V206 | T193 + P211 | L250 + D379 |
| H1 + L250 | P45 + Q98 | V56 + A204 | G133 + P211 | T193 + I214 | L250 + Y382 |
| H1 + G255 | P45 + M105 | V56 + V206 | G133 + I214 | T193 + V215 | L250 + S383 |
| H1 + Q256 | P45 + G109 | V56 + P211 | G133 + V215 | T193 + L217 | L250 + Q385 |
| H1 + A263 | P45 + F113 | V56 + I214 | G133 + L217 | T193 + L219 | L250 + K391 |
| H1 + V264 | P45 + R116 | V56 + V215 | G133 + L219 | T193 + L228 | L250 + K393 |
| H1 + A265 | P45 + Q118 | V56 + L217 | G133 + L228 | T193 + L235 | L250 + Q395 |
| H1 + Y267 | P45 + Q125 | V56 + L219 | G133 + L235 | T193 + V238 | G255 + Q256 |
| H1 + N270 | P45 + G133 | V56 + L228 | G133 + V238 | T193 + M246 | G255 + A263 |
| H1 + G273 | P45 + T134 | V56 + L235 | G133 + M246 | T193 + M248 | G255 + V264 |
| H1 + S280 | P45 + W140 | V56 + V238 | G133 + M248 | T193 + L250 | G255 + A265 |
| H1 + T285 | P45 + G142 | V56 + M246 | G133 + L250 | T193 + G255 | G255 + Y267 |
| H1 + M286 | P45 + G149 | V56 + M248 | G133 + G255 | T193 + Q256 | G255 + N270 |
| H1 + F289 | P45 + T165 | V56 + L250 | G133 + Q256 | T193 + A263 | G255 + G273 |
| H1 + V291 | P45 + W167 | V56 + G255 | G133 + A263 | T193 + V264 | G255 + S280 |
| H1 + Q299 | P45 + R171 | V56 + Q256 | G133 + V264 | T193 + A265 | G255 + T285 |
| H1 + S304 | P45 + Q172 | V56 + A263 | G133 + A265 | T193 + Y267 | G255 + M286 |
| H1 + R320 | P45 + L173 | V56 + V264 | G133 + Y267 | T193 + N270 | G255 + F289 |
| H1 + H321 | P45 + A174 | V56 + A265 | G133 + N270 | T193 + G273 | G255 + V291 |
| H1 + S323 | P45 + G184 | V56 + Y267 | G133 + G273 | T193 + S280 | G255 + Q299 |
| H1 + H324 | P45 + T193 | V56 + N270 | G133 + S280 | T193 + T285 | G255 + S304 |
| H1 + F328 | P45 + N195 | V56 + G273 | G133 + T285 | T193 + M286 | G255 + R320 |
| H1 + T334 | P45 + G196 | V56 + S280 | G133 + M286 | T193 + F289 | G255 + H321 |
| H1 + D337 | P45 + A204 | V56 + T285 | G133 + F289 | T193 + V291 | G255 + S323 |
| H1 + Q345 | P45 + V206 | V56 + M286 | G133 + V291 | T193 + Q299 | G255 + H324 |
| H1 + G346 | P45 + P211 | V56 + F289 | G133 + Q299 | T193 + S304 | G255 + F328 |
| H1 + G348 | P45 + I214 | V56 + V291 | G133 + S304 | T193 + R320 | G255 + T334 |
| H1 + T355 | P45 + V215 | V56 + Q299 | G133 + R320 | T193 + H321 | G255 + D337 |

-continued

| | | | | | |
|---|---|---|---|---|---|
| H1 + S376 | P45 + L217 | V56 + S304 | G133 + H321 | T193 + S323 | G255 + Q345 |
| H1 + D377 | P45 + L219 | V56 + R320 | G133 + S323 | T193 + H324 | G255 + G346 |
| H1 + D379 | P45 + L228 | V56 + H321 | G133 + H324 | T193 + F328 | G255 + G348 |
| H1 + Y382 | P45 + L235 | V56 + S323 | G133 + F328 | T193 + T334 | G255 + T355 |
| H1 + S383 | P45 + V238 | V56 + H324 | G133 + T334 | T193 + D337 | G255 + S376 |
| H1 + Q385 | P45 + M246 | V56 + F328 | G133 + D337 | T193 + Q345 | G255 + D377 |
| H1 + K391 | P45 + M248 | V56 + T334 | G133 + Q345 | T193 + G346 | G255 + D379 |
| H1 + K393 | P45 + L250 | V56 + D337 | G133 + G346 | T193 + G348 | G255 + Y382 |
| H1 + Q395 | P45 + G255 | V56 + Q345 | G133 + G348 | T193 + T355 | G255 + S383 |
| T5 + G7 | P45 + Q256 | V56 + G346 | G133 + T355 | T193 + S376 | G255 + Q385 |
| T5 + Q11 | P45 + A263 | V56 + G348 | G133 + S376 | T193 + D377 | G255 + K391 |
| T5 + N16 | P45 + V264 | V56 + T355 | G133 + D377 | T193 + D379 | G255 + K393 |
| T5 + V17 | P45 + A265 | V56 + S376 | G133 + D379 | T193 + Y382 | G255 + Q395 |
| T5 + Q32 | P45 + Y267 | V56 + D377 | G133 + Y382 | T193 + S383 | Q256 + A263 |
| T5 + A37 | P45 + N270 | V56 + D379 | G133 + S383 | T193 + Q385 | Q256 + V264 |
| T5 + T40 | P45 + G273 | V56 + Y382 | G133 + Q385 | T193 + K391 | Q256 + A265 |
| T5 + P45 | P45 + S280 | V56 + S383 | G133 + K391 | T193 + K393 | Q256 + Y267 |
| T5 + W48 | P45 + T285 | V56 + Q385 | G133 + K393 | T193 + Q395 | Q256 + N270 |
| T5 + G50 | P45 + M286 | V56 + K391 | G133 + Q395 | N195 + G196 | Q256 + G273 |
| T5 + T51 | P45 + F289 | V56 + K393 | T134 + W140 | N195 + A204 | Q256 + S280 |
| T5 + N54 | P45 + V291 | V56 + Q395 | T134 + G142 | N195 + V206 | Q256 + T285 |
| T5 + V56 | P45 + Q299 | A60 + K72 | T134 + G149 | N195 + P211 | Q256 + M286 |
| T5 + A60 | P45 + S304 | A60 + R87 | T134 + T165 | N195 + I214 | Q256 + F289 |
| T5 + K72 | P45 + R320 | A60 + Q98 | T134 + W167 | N195 + V215 | Q256 + V291 |
| T5 + R87 | P45 + H321 | A60 + M105 | T134 + R171 | N195 + L217 | Q256 + Q299 |
| T5 + Q98 | P45 + S323 | A60 + G109 | T134 + Q172 | N195 + L219 | Q256 + S304 |
| T5 + M105 | P45 + H324 | A60 + F113 | T134 + L173 | N195 + L228 | Q256 + R320 |
| T5 + G109 | P45 + F328 | A60 + R116 | T134 + A174 | N195 + L235 | Q256 + H321 |
| T5 + F113 | P45 + T334 | A60 + Q118 | T134 + G184 | N195 + V238 | Q256 + S323 |
| T5 + R116 | P45 + D337 | A60 + Q125 | T134 + T193 | N195 + M246 | Q256 + H324 |
| T5 + Q118 | P45 + Q345 | A60 + G133 | T134 + N195 | N195 + M248 | Q256 + F328 |
| T5 + Q125 | P45 + G346 | A60 + T134 | T134 + G196 | N195 + L250 | Q256 + T334 |
| T5 + G133 | P45 + G348 | A60 + W140 | T134 + A204 | N195 + G255 | Q256 + D337 |
| T5 + T134 | P45 + T355 | A60 + G142 | T134 + V206 | N195 + Q256 | Q256 + Q345 |
| T5 + W140 | P45 + S376 | A60 + G149 | T134 + P211 | N195 + A263 | Q256 + G346 |
| T5 + G142 | P45 + D377 | A60 + T165 | T134 + I214 | N195 + V264 | Q256 + G348 |
| T5 + G149 | P45 + D379 | A60 + W167 | T134 + V215 | N195 + A265 | Q256 + T355 |
| T5 + T165 | P45 + Y382 | A60 + R171 | T134 + L217 | N195 + Y267 | Q256 + S376 |
| T5 + W167 | P45 + S383 | A60 + Q172 | T134 + L219 | N195 + N270 | Q256 + D377 |
| T5 + R171 | P45 + Q385 | A60 + L173 | T134 + L228 | N195 + G273 | Q256 + D379 |
| T5 + Q172 | P45 + K391 | A60 + A174 | T134 + L235 | N195 + S280 | Q256 + Y382 |
| T5 + L173 | P45 + K393 | A60 + G184 | T134 + V238 | N195 + T285 | Q256 + S383 |
| T5 + A174 | P45 + Q395 | A60 + T193 | T134 + M246 | N195 + M286 | Q256 + Q385 |
| T5 + G184 | W48 + G50 | A60 + N195 | T134 + M248 | N195 + F289 | Q256 + K391 |
| T5 + T193 | W48 + T51 | A60 + G196 | T134 + L250 | N195 + V291 | Q256 + K393 |
| T5 + N195 | W48 + N54 | A60 + A204 | T134 + G255 | N195 + Q299 | Q256 + Q395 |
| T5 + G196 | W48 + V56 | A60 + V206 | T134 + Q256 | N195 + S304 | A263 + V264 |
| T5 + A204 | W48 + A60 | A60 + P211 | T134 + A263 | N195 + R320 | A263 + A265 |
| T5 + V206 | W48 + K72 | A60 + I214 | T134 + V264 | N195 + H321 | A263 + Y267 |
| T5 + P211 | W48 + R87 | A60 + V215 | T134 + A265 | N195 + S323 | A263 + N270 |
| T5 + I214 | W48 + Q98 | A60 + L217 | T134 + Y267 | N195 + H324 | A263 + G273 |
| T5 + V215 | W48 + M105 | A60 + L219 | T134 + N270 | N195 + F328 | A263 + S280 |
| T5 + L217 | W48 + G109 | A60 + L228 | T134 + G273 | N195 + T334 | A263 + T285 |
| T5 + L219 | W48 + F113 | A60 + L235 | T134 + S280 | N195 + D337 | A263 + M286 |
| T5 + L228 | W48 + R116 | A60 + V238 | T134 + T285 | N195 + Q345 | A263 + F289 |
| T5 + L235 | W48 + Q118 | A60 + M246 | T134 + M286 | N195 + G346 | A263 + V291 |
| T5 + V238 | W48 + Q125 | A60 + M248 | T134 + F289 | N195 + G348 | A263 + Q299 |
| T5 + M246 | W48 + G133 | A60 + L250 | T134 + V291 | N195 + T355 | A263 + S304 |
| T5 + M248 | W48 + T134 | A60 + G255 | T134 + Q299 | N195 + S376 | A263 + R320 |
| T5 + L250 | W48 + W140 | A60 + Q256 | T134 + S304 | N195 + D377 | A263 + H321 |
| T5 + G255 | W48 + G142 | A60 + A263 | T134 + R320 | N195 + D379 | A263 + S323 |
| T5 + Q256 | W48 + G149 | A60 + V264 | T134 + H321 | N195 + Y382 | A263 + H324 |
| T5 + A263 | W48 + T165 | A60 + A265 | T134 + S323 | N195 + S383 | A263 + F328 |
| T5 + V264 | W48 + W167 | A60 + Y267 | T134 + H324 | N195 + Q385 | A263 + T334 |
| T5 + A265 | W48 + R171 | A60 + N270 | T134 + F328 | N195 + K391 | A263 + D337 |
| T5 + Y267 | W48 + Q172 | A60 + G273 | T134 + T334 | N195 + K393 | A263 + Q345 |
| T5 + N270 | W48 + L173 | A60 + S280 | T134 + D337 | N195 + Q395 | A263 + G346 |
| T5 + G273 | W48 + A174 | A60 + T285 | T134 + Q345 | G196 + A204 | A263 + G348 |
| T5 + S280 | W48 + G184 | A60 + M286 | T134 + G346 | G196 + V206 | A263 + T355 |
| T5 + T285 | W48 + T193 | A60 + F289 | T134 + G348 | G196 + P211 | A263 + S376 |
| T5 + M286 | W48 + N195 | A60 + V291 | T134 + T355 | G196 + I214 | A263 + D377 |
| T5 + F289 | W48 + G196 | A60 + Q299 | T134 + S376 | G196 + V215 | A263 + D379 |
| T5 + V291 | W48 + A204 | A60 + S304 | T134 + D377 | G196 + L217 | A263 + Y382 |
| T5 + Q299 | W48 + V206 | A60 + R320 | T134 + D379 | G196 + L219 | A263 + S383 |
| T5 + S304 | W48 + P211 | A60 + H321 | T134 + Y382 | G196 + L228 | A263 + Q385 |
| T5 + R320 | W48 + I214 | A60 + S323 | T134 + S383 | G196 + L235 | A263 + K391 |
| T5 + H321 | W48 + V215 | A60 + H324 | T134 + Q385 | G196 + V238 | A263 + K393 |
| T5 + S323 | W48 + L217 | A60 + F328 | T134 + K391 | G196 + M246 | A263 + Q395 |
| T5 + H324 | W48 + L219 | A60 + T334 | T134 + K393 | G196 + M248 | V264 + A265 |

-continued

| | | | | | |
|---|---|---|---|---|---|
| T5 + F328 | W48 + L228 | A60 + D337 | T134 + Q395 | G196 + L250 | V264 + Y267 |
| T5 + T334 | W48 + L235 | A60 + Q345 | W140 + G142 | G196 + G255 | V264 + N270 |
| T5 + D337 | W48 + V238 | A60 + G346 | W140 + G149 | G196 + Q256 | V264 + G273 |
| T5 + Q345 | W48 + M246 | A60 + G348 | W140 + T165 | G196 + A263 | V264 + S280 |
| T5 + G346 | W48 + M248 | A60 + T355 | W140 + W167 | G196 + V264 | V264 + T285 |
| T5 + G348 | W48 + L250 | A60 + S376 | W140 + R171 | G196 + A265 | V264 + M286 |
| T5 + T355 | W48 + G255 | A60 + D377 | W140 + Q172 | G196 + Y267 | V264 + F289 |
| T5 + S376 | W48 + Q256 | A60 + D379 | W140 + L173 | G196 + N270 | V264 + V291 |
| T5 + D377 | W48 + A263 | A60 + Y382 | W140 + A174 | G196 + G273 | V264 + Q299 |
| T5 + D379 | W48 + V264 | A60 + S383 | W140 + G184 | G196 + S280 | V264 + S304 |
| T5 + Y382 | W48 + A265 | A60 + Q385 | W140 + T193 | G196 + T285 | V264 + R320 |
| T5 + S383 | W48 + Y267 | A60 + K391 | W140 + N195 | G196 + M286 | V264 + H321 |
| T5 + Q385 | W48 + N270 | A60 + K393 | W140 + G196 | G196 + F289 | V264 + S323 |
| T5 + K391 | W48 + G273 | A60 + Q395 | W140 + A204 | G196 + V291 | V264 + H324 |
| T5 + K393 | W48 + S280 | K72 + R87 | W140 + V206 | G196 + Q299 | V264 + F328 |
| T5 + Q395 | W48 + T285 | K72 + Q98 | W140 + P211 | G196 + S304 | V264 + T334 |
| G7 + Q11 | W48 + M286 | K72 + M105 | W140 + I214 | G196 + R320 | V264 + D337 |
| G7 + N16 | W48 + F289 | K72 + G109 | W140 + V215 | G196 + H321 | V264 + Q345 |
| G7 + V17 | W48 + V291 | K72 + F113 | W140 + L217 | G196 + S323 | V264 + G346 |
| G7 + Q32 | W48 + Q299 | K72 + R116 | W140 + L219 | G196 + H324 | V264 + G348 |
| G7 + A37 | W48 + S304 | K72 + Q118 | W140 + L228 | G196 + F328 | V264 + T355 |
| G7 + T40 | W48 + R320 | K72 + Q125 | W140 + L235 | G196 + T334 | V264 + S376 |
| G7 + P45 | W48 + H321 | K72 + G133 | W140 + V238 | G196 + D337 | V264 + D377 |
| G7 + W48 | W48 + S323 | K72 + T134 | W140 + M246 | G196 + Q345 | V264 + D379 |
| G7 + G50 | W48 + H324 | K72 + W140 | W140 + M248 | G196 + G346 | V264 + Y382 |
| G7 + T51 | W48 + F328 | K72 + G142 | W140 + L250 | G196 + G348 | V264 + S383 |
| G7 + N54 | W48 + T334 | K72 + G149 | W140 + G255 | G196 + T355 | V264 + Q385 |
| G7 + V56 | W48 + D337 | K72 + T165 | W140 + Q256 | G196 + S376 | V264 + K391 |
| G7 + A60 | W48 + Q345 | K72 + W167 | W140 + A263 | G196 + D377 | V264 + K393 |
| G7 + K72 | W48 + G346 | K72 + R171 | W140 + V264 | G196 + D379 | V264 + Q395 |
| G7 + R87 | W48 + G348 | K72 + Q172 | W140 + A265 | G196 + Y382 | A265 + Y267 |
| G7 + Q98 | W48 + T355 | K72 + L173 | W140 + Y267 | G196 + S383 | A265 + N270 |
| G7 + M105 | W48 + S376 | K72 + A174 | W140 + N270 | G196 + Q385 | A265 + G273 |
| G7 + G109 | W48 + D377 | K72 + G184 | W140 + G273 | G196 + K391 | A265 + S280 |
| G7 + F113 | W48 + D379 | K72 + T193 | W140 + S280 | G196 + K393 | A265 + T285 |
| G7 + R116 | W48 + Y382 | K72 + N195 | W140 + T285 | G196 + Q395 | A265 + M286 |
| G7 + Q118 | W48 + S383 | K72 + G196 | W140 + M286 | A204 + V206 | A265 + F289 |
| G7 + Q125 | W48 + Q385 | K72 + A204 | W140 + F289 | A204 + P211 | A265 + V291 |
| G7 + G133 | W48 + K391 | K72 + V206 | W140 + V291 | A204 + I214 | A265 + Q299 |
| G7 + T134 | W48 + K393 | K72 + P211 | W140 + Q299 | A204 + V215 | A265 + S304 |
| G7 + W140 | W48 + Q395 | K72 + I214 | W140 + S304 | A204 + L217 | A265 + R320 |
| G7 + G142 | G50 + T51 | K72 + V215 | W140 + R320 | A204 + L219 | A265 + H321 |
| G7 + G149 | G50 + N54 | K72 + L217 | W140 + H321 | A204 + L228 | A265 + S323 |
| G7 + T165 | G50 + V56 | K72 + L219 | W140 + S323 | A204 + L235 | A265 + H324 |
| G7 + W167 | G50 + A60 | K72 + L228 | W140 + H324 | A204 + V238 | A265 + F328 |
| G7 + R171 | G50 + K72 | K72 + L235 | W140 + F328 | A204 + M246 | A265 + T334 |
| G7 + Q172 | G50 + R87 | K72 + V238 | W140 + T334 | A204 + M248 | A265 + D337 |
| G7 + L173 | G50 + Q98 | K72 + M246 | W140 + D337 | A204 + L250 | A265 + Q345 |
| G7 + A174 | G50 + M105 | K72 + M248 | W140 + Q345 | A204 + G255 | A265 + G346 |
| G7 + G184 | G50 + G109 | K72 + L250 | W140 + G346 | A204 + Q256 | A265 + G348 |
| G7 + T193 | G50 + F113 | K72 + G255 | W140 + G348 | A204 + A263 | A265 + T355 |
| G7 + N195 | G50 + R116 | K72 + Q256 | W140 + T355 | A204 + V264 | A265 + S376 |
| G7 + G196 | G50 + Q118 | K72 + A263 | W140 + S376 | A204 + A265 | A265 + D377 |
| G7 + A204 | G50 + Q125 | K72 + V264 | W140 + D377 | A204 + Y267 | A265 + D379 |
| G7 + V206 | G50 + G133 | K72 + A265 | W140 + D379 | A204 + N270 | A265 + Y382 |
| G7 + P211 | G50 + T134 | K72 + Y267 | W140 + Y382 | A204 + G273 | A265 + S383 |
| G7 + I214 | G50 + W140 | K72 + N270 | W140 + S383 | A204 + S280 | A265 + Q385 |
| G7 + V215 | G50 + G142 | K72 + G273 | W140 + Q385 | A204 + T285 | A265 + K391 |
| G7 + L217 | G50 + G149 | K72 + S280 | W140 + K391 | A204 + M286 | A265 + K393 |
| G7 + L219 | G50 + T165 | K72 + T285 | W140 + K393 | A204 + F289 | A265 + Q395 |
| G7 + L228 | G50 + W167 | K72 + M286 | W140 + Q395 | A204 + V291 | Y267 + N270 |
| G7 + L235 | G50 + R171 | K72 + F289 | G142 + G149 | A204 + Q299 | Y267 + G273 |
| G7 + V238 | G50 + Q172 | K72 + V291 | G142 + T165 | A204 + S304 | Y267 + S280 |
| G7 + M246 | G50 + L173 | K72 + Q299 | G142 + W167 | A204 + R320 | Y267 + T285 |
| G7 + M248 | G50 + A174 | K72 + S304 | G142 + R171 | A204 + H321 | Y267 + M286 |
| G7 + L250 | G50 + G184 | K72 + R320 | G142 + Q172 | A204 + S323 | Y267 + F289 |
| G7 + G255 | G50 + T193 | K72 + H321 | G142 + L173 | A204 + H324 | Y267 + V291 |
| G7 + Q256 | G50 + N195 | K72 + S323 | G142 + A174 | A204 + F328 | Y267 + Q299 |
| G7 + A263 | G50 + G196 | K72 + H324 | G142 + G184 | A204 + T334 | Y267 + S304 |
| G7 + V264 | G50 + A204 | K72 + F328 | G142 + T193 | A204 + D337 | Y267 + R320 |
| G7 + A265 | G50 + V206 | K72 + T334 | G142 + N195 | A204 + Q345 | Y267 + H321 |
| G7 + Y267 | G50 + P211 | K72 + D337 | G142 + G196 | A204 + G346 | Y267 + S323 |
| G7 + N270 | G50 + I214 | K72 + Q345 | G142 + A204 | A204 + G348 | Y267 + H324 |
| G7 + G273 | G50 + V215 | K72 + G346 | G142 + V206 | A204 + T355 | Y267 + F328 |
| G7 + S280 | G50 + L217 | K72 + G348 | G142 + P211 | A204 + S376 | Y267 + T334 |
| G7 + T285 | G50 + L219 | K72 + T355 | G142 + I214 | A204 + D377 | Y267 + D337 |
| G7 + M286 | G50 + L228 | K72 + S376 | G142 + V215 | A204 + D379 | Y267 + Q345 |
| G7 + F289 | G50 + L235 | K72 + D377 | G142 + L217 | A204 + Y382 | Y267 + G346 |
| G7 + V291 | G50 + V238 | K72 + D379 | G142 + L219 | A204 + S383 | Y267 + G348 |

-continued

| | | | | | |
|---|---|---|---|---|---|
| G7 + Q299 | G50 + M246 | K72 + Y382 | G142 + L228 | A204 + Q385 | Y267 + T355 |
| G7 + S304 | G50 + M248 | K72 + S383 | G142 + L235 | A204 + K391 | Y267 + S376 |
| G7 + R320 | G50 + L250 | K72 + Q385 | G142 + V238 | A204 + K393 | Y267 + D377 |
| G7 + H321 | G50 + G255 | K72 + K391 | G142 + M246 | A204 + Q395 | Y267 + D379 |
| G7 + S323 | G50 + Q256 | K72 + K393 | G142 + M248 | V206 + P211 | Y267 + Y382 |
| G7 + H324 | G50 + A263 | K72 + Q395 | G142 + L250 | V206 + I214 | Y267 + S383 |
| G7 + F328 | G50 + V264 | R87 + Q98 | G142 + G255 | V206 + V215 | Y267 + Q385 |
| G7 + T334 | G50 + A265 | R87 + M105 | G142 + Q256 | V206 + L217 | Y267 + K391 |
| G7 + D337 | G50 + Y267 | R87 + G109 | G142 + A263 | V206 + L219 | Y267 + K393 |
| G7 + Q345 | G50 + N270 | R87 + F113 | G142 + V264 | V206 + L228 | Y267 + Q395 |
| G7 + G346 | G50 + G273 | R87 + R116 | G142 + A265 | V206 + L235 | N270 + G273 |
| G7 + G348 | G50 + S280 | R87 + Q118 | G142 + Y267 | V206 + V238 | N270 + S280 |
| G7 + T355 | G50 + T285 | R87 + Q125 | G142 + N270 | V206 + M246 | N270 + T285 |
| G7 + S376 | G50 + M286 | R87 + G133 | G142 + G273 | V206 + M248 | N270 + M286 |
| G7 + D377 | G50 + F289 | R87 + T134 | G142 + S280 | V206 + L250 | N270 + F289 |
| G7 + D379 | G50 + V291 | R87 + W140 | G142 + T285 | V206 + G255 | N270 + V291 |
| G7 + Y382 | G50 + Q299 | R87 + G142 | G142 + M286 | V206 + Q256 | N270 + Q299 |
| G7 + S383 | G50 + S304 | R87 + G149 | G142 + F289 | V206 + A263 | N270 + S304 |
| G7 + Q385 | G50 + R320 | R87 + T165 | G142 + V291 | V206 + V264 | N270 + R320 |
| G7 + K391 | G50 + H321 | R87 + W167 | G142 + Q299 | V206 + A265 | N270 + H321 |
| G7 + K393 | G50 + S323 | R87 + R171 | G142 + S304 | V206 + Y267 | N270 + S323 |
| G7 + Q395 | G50 + H324 | R87 + Q172 | G142 + R320 | V206 + N270 | N270 + H324 |
| Q11 + N16 | G50 + F328 | R87 + L173 | G142 + H321 | V206 + G273 | N270 + F328 |
| Q11 + V17 | G50 + T334 | R87 + A174 | G142 + S323 | V206 + S280 | N270 + T334 |
| Q11 + Q32 | G50 + D337 | R87 + G184 | G142 + H324 | V206 + T285 | N270 + D337 |
| Q11 + A37 | G50 + Q345 | R87 + T193 | G142 + F328 | V206 + M286 | N270 + Q345 |
| Q11 + T40 | G50 + G346 | R87 + N195 | G142 + T334 | V206 + F289 | N270 + G346 |
| Q11 + P45 | G50 + G348 | R87 + G196 | G142 + D337 | V206 + V291 | N270 + G348 |
| Q11 + W48 | G50 + T355 | R87 + A204 | G142 + Q345 | V206 + Q299 | N270 + T355 |
| Q11 + G50 | G50 + S376 | R87 + V206 | G142 + G346 | V206 + S304 | N270 + S376 |
| Q11 + T51 | G50 + D377 | R87 + P211 | G142 + G348 | V206 + R320 | N270 + D377 |
| Q11 + N54 | G50 + D379 | R87 + I214 | G142 + T355 | V206 + H321 | N270 + D379 |
| Q11 + V56 | G50 + Y382 | R87 + V215 | G142 + S376 | V206 + S323 | N270 + Y382 |
| Q11 + A60 | G50 + S383 | R87 + L217 | G142 + D377 | V206 + H324 | N270 + S383 |
| Q11 + K72 | G50 + Q385 | R87 + L219 | G142 + D379 | V206 + F328 | N270 + Q385 |
| Q11 + R87 | G50 + K391 | R87 + L228 | G142 + Y382 | V206 + T334 | N270 + K391 |
| Q11 + Q98 | G50 + K393 | R87 + L235 | G142 + S383 | V206 + D337 | N270 + K393 |
| Q11 + M105 | G50 + Q395 | R87 + V238 | G142 + Q385 | V206 + Q345 | N270 + Q395 |
| Q11 + G109 | T51 + N54 | R87 + M246 | G142 + K391 | V206 + G346 | G273 + S280 |
| Q11 + F113 | T51 + V56 | R87 + M248 | G142 + K393 | V206 + G348 | G273 + T285 |
| Q11 + R116 | T51 + A60 | R87 + L250 | G142 + Q395 | V206 + T355 | G273 + M286 |
| Q11 + Q118 | T51 + K72 | R87 + G255 | G149 + T165 | V206 + S376 | G273 + F289 |
| Q11 + Q125 | T51 + R87 | R87 + Q256 | G149 + W167 | V206 + D377 | G273 + V291 |
| Q11 + G133 | T51 + Q98 | R87 + A263 | G149 + R171 | V206 + D379 | G273 + Q299 |
| Q11 + T134 | T51 + M105 | R87 + V264 | G149 + Q172 | V206 + Y382 | G273 + S304 |
| Q11 + W140 | T51 + G109 | R87 + A265 | G149 + L173 | V206 + S383 | G273 + R320 |
| Q11 + G142 | T51 + F113 | R87 + Y267 | G149 + A174 | V206 + Q385 | G273 + H321 |
| Q11 + G149 | T51 + R116 | R87 + N270 | G149 + G184 | V206 + K391 | G273 + S323 |
| Q11 + T165 | T51 + Q118 | R87 + G273 | G149 + T193 | V206 + K393 | G273 + H324 |
| Q11 + W167 | T51 + Q125 | R87 + S280 | G149 + N195 | V206 + Q395 | G273 + F328 |
| Q11 + R171 | T51 + G133 | R87 + T285 | G149 + G196 | P211 + I214 | G273 + T334 |
| Q11 + Q172 | T51 + T134 | R87 + M286 | G149 + A204 | P211 + V215 | G273 + D337 |
| Q11 + L173 | T51 + W140 | R87 + F289 | G149 + V206 | P211 + L217 | G273 + Q345 |
| Q11 + A174 | T51 + G142 | R87 + V291 | G149 + P211 | P211 + L219 | G273 + G346 |
| Q11 + G184 | T51 + G149 | R87 + Q299 | G149 + I214 | P211 + L228 | G273 + G348 |
| Q11 + T193 | T51 + T165 | R87 + S304 | G149 + V215 | P211 + L235 | G273 + T355 |
| Q11 + N195 | T51 + W167 | R87 + R320 | G149 + L217 | P211 + V238 | G273 + S376 |
| Q11 + G196 | T51 + R171 | R87 + H321 | G149 + L219 | P211 + M246 | G273 + D377 |
| Q11 + A204 | T51 + Q172 | R87 + S323 | G149 + L228 | P211 + M248 | G273 + D379 |
| Q11 + V206 | T51 + L173 | R87 + H324 | G149 + L235 | P211 + L250 | G273 + Y382 |
| Q11 + P211 | T51 + A174 | R87 + F328 | G149 + V238 | P211 + G255 | G273 + S383 |
| Q11 + I214 | T51 + G184 | R87 + T334 | G149 + M246 | P211 + Q256 | G273 + Q385 |
| Q11 + V215 | T51 + T193 | R87 + D337 | G149 + M248 | P211 + A263 | G273 + K391 |
| Q11 + L217 | T51 + N195 | R87 + Q345 | G149 + L250 | P211 + V264 | G273 + K393 |
| Q11 + L219 | T51 + G196 | R87 + G346 | G149 + G255 | P211 + A265 | G273 + Q395 |
| Q11 + L228 | T51 + A204 | R87 + G348 | G149 + Q256 | P211 + Y267 | S280 + T285 |
| Q11 + L235 | T51 + V206 | R87 + T355 | G149 + A263 | P211 + N270 | S280 + M286 |
| Q11 + V238 | T51 + P211 | R87 + S376 | G149 + V264 | P211 + G273 | S280 + F289 |
| Q11 + M246 | T51 + I214 | R87 + D377 | G149 + A265 | P211 + S280 | S280 + V291 |
| Q11 + M248 | T51 + V215 | R87 + D379 | G149 + Y267 | P211 + T285 | S280 + Q299 |
| Q11 + L250 | T51 + L217 | R87 + Y382 | G149 + N270 | P211 + M286 | S280 + S304 |
| Q11 + G255 | T51 + L219 | R87 + S383 | G149 + G273 | P211 + F289 | S280 + R320 |
| Q11 + Q256 | T51 + L228 | R87 + Q385 | G149 + S280 | P211 + V291 | S280 + H321 |
| Q11 + A263 | T51 + L235 | R87 + K391 | G149 + T285 | P211 + Q299 | S280 + S323 |
| Q11 + V264 | T51 + V238 | R87 + K393 | G149 + M286 | P211 + S304 | S280 + H324 |
| Q11 + A265 | T51 + M246 | R87 + Q395 | G149 + F289 | P211 + R320 | S280 + F328 |
| Q11 + Y267 | T51 + M248 | Q98 + M105 | G149 + V291 | P211 + H321 | S280 + T334 |
| Q11 + N270 | T51 + L250 | Q98 + G109 | G149 + Q299 | P211 + S323 | S280 + D337 |
| Q11 + G273 | T51 + G255 | Q98 + F113 | G149 + S304 | P211 + H324 | S280 + Q345 |

-continued

| | | | | | |
|---|---|---|---|---|---|
| Q11 + S280 | T51 + Q256 | Q98 + R116 | G149 + R320 | P211 + F328 | S280 + G346 |
| Q11 + T285 | T51 + A263 | Q98 + Q118 | G149 + H321 | P211 + T334 | S280 + G348 |
| Q11 + M286 | T51 + V264 | Q98 + Q125 | G149 + S323 | P211 + D337 | S280 + T355 |
| Q11 + F289 | T51 + A265 | Q98 + G133 | G149 + H324 | P211 + Q345 | S280 + S376 |
| Q11 + V291 | T51 + Y267 | Q98 + T134 | G149 + F328 | P211 + G346 | S280 + D377 |
| Q11 + Q299 | T51 + N270 | Q98 + W140 | G149 + T334 | P211 + G348 | S280 + D379 |
| Q11 + S304 | T51 + G273 | Q98 + G142 | G149 + D337 | P211 + T355 | S280 + Y382 |
| Q11 + R320 | T51 + S280 | Q98 + G149 | G149 + Q345 | P211 + S376 | S280 + S383 |
| Q11 + H321 | T51 + T285 | Q98 + T165 | G149 + G346 | P211 + D377 | S280 + Q385 |
| Q11 + S323 | T51 + M286 | Q98 + W167 | G149 + G348 | P211 + D379 | S280 + K391 |
| Q11 + H324 | T51 + F289 | Q98 + R171 | G149 + T355 | P211 + Y382 | S280 + K393 |
| Q11 + F328 | T51 + V291 | Q98 + Q172 | G149 + S376 | P211 + S383 | S280 + Q395 |
| Q11 + T334 | T51 + Q299 | Q98 + L173 | G149 + D377 | P211 + Q385 | T285 + M286 |
| Q11 + D337 | T51 + S304 | Q98 + A174 | G149 + D379 | P211 + K391 | T285 + F289 |
| Q11 + Q345 | T51 + R320 | Q98 + G184 | G149 + Y382 | P211 + K393 | T285 + V291 |
| Q11 + G346 | T51 + H321 | Q98 + T193 | G149 + S383 | P211 + Q395 | T285 + Q299 |
| Q11 + G348 | T51 + S323 | Q98 + N195 | G149 + Q385 | I214 + V215 | T285 + S304 |
| Q11 + T355 | T51 + H324 | Q98 + G196 | G149 + K391 | I214 + L217 | T285 + R320 |
| Q11 + S376 | T51 + F328 | Q98 + A204 | G149 + K393 | I214 + L219 | T285 + H321 |
| Q11 + D377 | T51 + T334 | Q98 + V206 | G149 + Q395 | I214 + L228 | T285 + S323 |
| Q11 + D379 | T51 + D337 | Q98 + P211 | T165 + W167 | I214 + L235 | T285 + H324 |
| Q11 + Y382 | T51 + Q345 | Q98 + I214 | T165 + R171 | I214 + V238 | T285 + F328 |
| Q11 + S383 | T51 + G346 | Q98 + V215 | T165 + Q172 | I214 + M246 | T285 + T334 |
| Q11 + Q385 | T51 + G348 | Q98 + L217 | T165 + L173 | I214 + M248 | T285 + D337 |
| Q11 + K391 | T51 + T355 | Q98 + L219 | T165 + A174 | I214 + L250 | T285 + Q345 |
| Q11 + K393 | T51 + S376 | Q98 + L228 | T165 + G184 | I214 + G255 | T285 + G346 |
| Q11 + Q395 | T51 + D377 | Q98 + L235 | T165 + T193 | I214 + Q256 | T285 + G348 |
| N16 + V17 | T51 + D379 | Q98 + V238 | T165 + N195 | I214 + A263 | T285 + T355 |
| N16 + Q32 | T51 + Y382 | Q98 + M246 | T165 + G196 | I214 + V264 | T285 + S376 |
| N16 + A37 | T51 + S383 | Q98 + M248 | T165 + A204 | I214 + A265 | T285 + D377 |
| N16 + T40 | T51 + Q385 | Q98 + L250 | T165 + V206 | I214 + Y267 | T285 + D379 |
| N16 + P45 | T51 + K391 | Q98 + G255 | T165 + P211 | I214 + N270 | T285 + Y382 |
| N16 + W48 | T51 + K393 | Q98 + Q256 | T165 + I214 | I214 + G273 | T285 + S383 |
| N16 + G50 | T51 + Q395 | Q98 + A263 | T165 + V215 | I214 + S280 | T285 + Q385 |
| N16 + T51 | N54 + V56 | Q98 + V264 | T165 + L217 | I214 + T285 | T285 + K391 |
| N16 + N54 | N54 + A60 | Q98 + A265 | T165 + L219 | I214 + M286 | T285 + K393 |
| N16 + V56 | N54 + K72 | Q98 + Y267 | T165 + L228 | I214 + F289 | T285 + Q395 |
| N16 + A60 | N54 + R87 | Q98 + N270 | T165 + L235 | I214 + V291 | M286 + F289 |
| N16 + K72 | N54 + Q98 | Q98 + G273 | T165 + V238 | I214 + Q299 | M286 + V291 |
| N16 + R87 | N54 + M105 | Q98 + S280 | T165 + M246 | I214 + S304 | M286 + Q299 |
| N16 + Q98 | N54 + G109 | Q98 + T285 | T165 + M248 | I214 + R320 | M286 + S304 |
| N16 + M105 | N54 + F113 | Q98 + M286 | T165 + L250 | I214 + H321 | M286 + R320 |
| N16 + G109 | N54 + R116 | Q98 + F289 | T165 + G255 | I214 + S323 | M286 + H321 |
| N16 + F113 | N54 + Q118 | Q98 + V291 | T165 + Q256 | I214 + H324 | M286 + S323 |
| N16 + R116 | N54 + Q125 | Q98 + Q299 | T165 + A263 | I214 + F328 | M286 + H324 |
| N16 + Q118 | N54 + G133 | Q98 + S304 | T165 + V264 | I214 + T334 | M286 + F328 |
| N16 + Q125 | N54 + T134 | Q98 + R320 | T165 + A265 | I214 + D337 | M286 + T334 |
| N16 + G133 | N54 + W140 | Q98 + H321 | T165 + Y267 | I214 + Q345 | M286 + D337 |
| N16 + T134 | N54 + G142 | Q98 + S323 | T165 + N270 | I214 + G346 | M286 + Q345 |
| N16 + W140 | N54 + G149 | Q98 + H324 | T165 + G273 | I214 + G348 | M286 + G346 |
| N16 + G142 | N54 + T165 | Q98 + F328 | T165 + S280 | I214 + T355 | M286 + G348 |
| N16 + G149 | N54 + W167 | Q98 + T334 | T165 + T285 | I214 + S376 | M286 + T355 |
| N16 + T165 | N54 + R171 | Q98 + D337 | T165 + M286 | I214 + D377 | M286 + S376 |
| N16 + W167 | N54 + Q172 | Q98 + Q345 | T165 + F289 | I214 + D379 | M286 + D377 |
| N16 + R171 | N54 + L173 | Q98 + G346 | T165 + V291 | I214 + Y382 | M286 + D379 |
| N16 + Q172 | N54 + A174 | Q98 + G348 | T165 + Q299 | I214 + S383 | M286 + Y382 |
| N16 + L173 | N54 + G184 | Q98 + T355 | T165 + S304 | I214 + Q385 | M286 + S383 |
| N16 + A174 | N54 + T193 | Q98 + S376 | T165 + R320 | I214 + K391 | M286 + Q385 |
| N16 + G184 | N54 + N195 | Q98 + D377 | T165 + H321 | I214 + K393 | M286 + K391 |
| N16 + T193 | N54 + G196 | Q98 + D379 | T165 + S323 | I214 + Q395 | M286 + K393 |
| N16 + N195 | N54 + A204 | Q98 + Y382 | T165 + H324 | V215 + L217 | M286 + Q395 |
| N16 + G196 | N54 + V206 | Q98 + S383 | T165 + F328 | V215 + L219 | F289 + V291 |
| N16 + A204 | N54 + P211 | Q98 + Q385 | T165 + T334 | V215 + L228 | F289 + Q299 |
| N16 + V206 | N54 + I214 | Q98 + K391 | T165 + D337 | V215 + L235 | F289 + S304 |
| N16 + P211 | N54 + V215 | Q98 + K393 | T165 + Q345 | V215 + V238 | F289 + R320 |
| N16 + I214 | N54 + L217 | Q98 + Q395 | T165 + G346 | V215 + M246 | F289 + H321 |
| N16 + V215 | N54 + L219 | M105 + G109 | T165 + G348 | V215 + M248 | F289 + S323 |
| N16 + L217 | N54 + L228 | M105 + F113 | T165 + T355 | V215 + L250 | F289 + H324 |
| N16 + L219 | N54 + L235 | M105 + R116 | T165 + S376 | V215 + G255 | F289 + F328 |
| N16 + L228 | N54 + V238 | M105 + Q118 | T165 + D377 | V215 + Q256 | F289 + T334 |
| N16 + L235 | N54 + M246 | M105 + Q125 | T165 + D379 | V215 + A263 | F289 + D337 |
| N16 + V238 | N54 + M248 | M105 + G133 | T165 + Y382 | V215 + V264 | F289 + Q345 |
| N16 + M246 | N54 + L250 | M105 + T134 | T165 + S383 | V215 + A265 | F289 + G346 |
| N16 + M248 | N54 + G255 | M105 + W140 | T165 + Q385 | V215 + Y267 | F289 + G348 |
| N16 + L250 | N54 + Q256 | M105 + G142 | T165 + K391 | V215 + N270 | F289 + T355 |
| N16 + G255 | N54 + A263 | M105 + G149 | T165 + K393 | V215 + G273 | F289 + S376 |
| N16 + Q256 | N54 + V264 | M105 + T165 | T165 + Q395 | V215 + S280 | F289 + D377 |
| N16 + A263 | N54 + A265 | M105 + W167 | W167 + R171 | V215 + T285 | F289 + D379 |
| N16 + V264 | N54 + Y267 | M105 + R171 | W167 + Q172 | V215 + M286 | F289 + Y382 |

-continued

| | | | | | |
|---|---|---|---|---|---|
| N16 + A265 | N54 + N270 | M105 + Q172 | W167 + L173 | V215 + F289 | F289 + S383 |
| N16 + Y267 | N54 + G273 | M105 + L173 | W167 + A174 | V215 + V291 | F289 + Q385 |
| N16 + N270 | N54 + S280 | M105 + A174 | W167 + G184 | V215 + Q299 | F289 + K391 |
| N16 + G273 | Q118 + V215 | M105 + G184 | W167 + T193 | V215 + S304 | F289 + K393 |
| N16 + S280 | Q118 + L217 | M105 + T193 | W167 + N195 | V215 + R320 | F289 + Q395 |
| N16 + T285 | Q118 + L219 | M105 + N195 | W167 + G196 | V215 + H321 | V291 + Q299 |
| N16 + M286 | Q118 + L228 | M105 + G196 | W167 + A204 | V215 + S323 | V291 + S304 |
| N16 + F289 | Q118 + L235 | M105 + A204 | W167 + V206 | V215 + H324 | V291 + R320 |
| N16 + V291 | Q118 + V238 | M105 + V206 | W167 + P211 | V215 + F328 | V291 + H321 |
| N16 + Q299 | Q118 + M246 | M105 + P211 | W167 + I214 | V215 + T334 | V291 + S323 |
| N16 + S304 | Q118 + M248 | M105 + I214 | W167 + V215 | V215 + D337 | V291 + H324 |
| N16 + R320 | Q118 + L250 | M105 + V215 | W167 + L217 | V215 + Q345 | V291 + F328 |
| N16 + H321 | Q118 + G255 | M105 + L217 | W167 + L219 | V215 + G346 | V291 + T334 |
| N16 + S323 | Q118 + Q256 | M105 + L219 | W167 + L228 | V215 + G348 | V291 + D337 |
| N16 + H324 | Q118 + A263 | M105 + L228 | W167 + L235 | V215 + T355 | V291 + Q345 |
| N16 + F328 | Q118 + V264 | M105 + L235 | W167 + V238 | V215 + S376 | V291 + G346 |
| N16 + T334 | Q118 + A265 | M105 + V238 | W167 + M246 | V215 + D377 | V291 + G348 |
| N16 + D337 | Q118 + Y267 | M105 + M246 | W167 + M248 | V215 + D379 | V291 + T355 |
| N16 + Q345 | Q118 + N270 | M105 + M248 | W167 + L250 | V215 + Y382 | V291 + S376 |
| N16 + G346 | Q118 + G273 | M105 + L250 | W167 + G255 | V215 + S383 | V291 + D377 |
| N16 + G348 | Q118 + S280 | M105 + G255 | W167 + Q256 | V215 + Q385 | V291 + D379 |
| N16 + T355 | Q118 + T285 | M105 + Q256 | W167 + A263 | V215 + K391 | V291 + Y382 |
| N16 + S376 | Q118 + M286 | M105 + A263 | W167 + V264 | V215 + K393 | V291 + S383 |
| N16 + D377 | Q118 + F289 | M105 + V264 | W167 + A265 | V215 + Q395 | V291 + Q385 |
| N16 + D379 | Q118 + V291 | M105 + A265 | W167 + Y267 | L217 + L219 | V291 + K391 |
| N16 + Y382 | Q118 + Q299 | M105 + Y267 | W167 + N270 | L217 + L228 | V291 + K393 |
| N16 + S383 | Q118 + S304 | M105 + N270 | W167 + G273 | L217 + L235 | V291 + Q395 |
| N16 + Q385 | Q118 + R320 | M105 + G273 | W167 + S280 | L217 + V238 | Q299 + S304 |
| N16 + K391 | Q118 + H321 | M105 + S280 | W167 + T285 | L217 + M246 | Q299 + R320 |
| N16 + K393 | Q118 + S323 | M105 + T285 | W167 + M286 | L217 + M248 | Q299 + H321 |
| N16 + Q395 | Q118 + H324 | M105 + M286 | W167 + F289 | L217 + L250 | Q299 + S323 |
| V17 + Q32 | Q118 + F328 | M105 + F289 | W167 + V291 | L217 + G255 | Q299 + H324 |
| V17 + A37 | Q118 + T334 | M105 + V291 | W167 + Q299 | L217 + Q256 | Q299 + F328 |
| V17 + T40 | Q118 + D337 | M105 + Q299 | W167 + S304 | L217 + A263 | Q299 + T334 |
| V17 + P45 | Q118 + Q345 | M105 + S304 | W167 + R320 | L217 + V264 | Q299 + D337 |
| V17 + W48 | Q118 + G346 | M105 + R320 | W167 + H321 | L217 + A265 | Q299 + Q345 |
| V17 + G50 | Q118 + G348 | M105 + H321 | W167 + S323 | L217 + Y267 | Q299 + G346 |
| V17 + T51 | Q118 + T355 | M105 + S323 | W167 + H324 | L217 + N270 | Q299 + G348 |
| V17 + N54 | Q118 + S376 | M105 + H324 | W167 + F328 | L217 + G273 | Q299 + T355 |
| V17 + V56 | Q118 + D377 | M105 + F328 | W167 + T334 | L217 + S280 | Q299 + S376 |
| V17 + A60 | Q118 + D379 | M105 + T334 | W167 + D337 | L217 + T285 | Q299 + D377 |
| V17 + K72 | Q118 + Y382 | M105 + D337 | W167 + Q345 | L217 + M286 | Q299 + D379 |
| V17 + R87 | Q118 + S383 | M105 + Q345 | W167 + G346 | L217 + F289 | Q299 + Y382 |
| V17 + Q98 | Q118 + Q385 | M105 + G346 | W167 + G348 | L217 + V291 | Q299 + S383 |
| V17 + M105 | Q118 + K391 | M105 + G348 | W167 + T355 | L217 + Q299 | Q299 + Q385 |
| V17 + G109 | Q118 + K393 | M105 + T355 | W167 + S376 | L217 + S304 | Q299 + K391 |
| V17 + F113 | Q118 + Q395 | M105 + S376 | W167 + D377 | L217 + R320 | Q299 + K393 |
| V17 + R116 | Q125 + G133 | M105 + D377 | W167 + D379 | L217 + H321 | Q299 + Q395 |
| V17 + Q118 | Q125 + T134 | M105 + D379 | W167 + Y382 | L217 + S323 | S304 + R320 |
| V17 + Q125 | Q125 + W140 | M105 + Y382 | W167 + S383 | L217 + H324 | S304 + H321 |
| V17 + G133 | Q125 + G142 | M105 + S383 | W167 + Q385 | L217 + F328 | S304 + S323 |
| V17 + T134 | Q125 + G149 | M105 + Q385 | W167 + K391 | L217 + T334 | S304 + H324 |
| V17 + W140 | Q125 + T165 | M105 + K391 | W167 + K393 | L217 + D337 | S304 + F328 |
| V17 + G142 | Q125 + W167 | M105 + K393 | W167 + Q395 | L217 + Q345 | S304 + T334 |
| V17 + G149 | Q125 + R171 | M105 + Q395 | R171 + Q172 | L217 + G346 | S304 + D337 |
| V17 + T165 | Q125 + Q172 | G109 + F113 | R171 + L173 | L217 + G348 | S304 + Q345 |
| V17 + W167 | Q125 + L173 | G109 + R116 | R171 + A174 | L217 + T355 | S304 + G346 |
| V17 + R171 | Q125 + A174 | G109 + Q118 | R171 + G184 | L217 + S376 | S304 + G348 |
| V17 + Q172 | Q125 + G184 | G109 + Q125 | R171 + T193 | L217 + D377 | S304 + T355 |
| V17 + L173 | Q125 + T193 | G109 + G133 | R171 + N195 | L217 + D379 | S304 + S376 |
| V17 + A174 | Q125 + N195 | G109 + T134 | R171 + G196 | L217 + Y382 | S304 + D377 |
| V17 + G184 | Q125 + G196 | G109 + W140 | R171 + A204 | L217 + S383 | S304 + D379 |
| V17 + T193 | Q125 + A204 | G109 + G142 | R171 + V206 | L217 + Q385 | S304 + Y382 |
| V17 + N195 | Q125 + V206 | G109 + G149 | R171 + P211 | L217 + K391 | S304 + S383 |
| V17 + G196 | Q125 + P211 | G109 + T165 | R171 + I214 | L217 + K393 | S304 + Q385 |
| V17 + A204 | Q125 + I214 | G109 + W167 | R171 + V215 | L217 + Q395 | S304 + K391 |
| V17 + V206 | Q125 + V215 | G109 + R171 | R171 + L217 | L219 + L228 | S304 + K393 |
| V17 + P211 | Q125 + L217 | G109 + Q172 | R171 + L219 | L219 + L235 | S304 + Q395 |
| V17 + I214 | Q125 + L219 | G109 + L173 | R171 + L228 | L219 + V238 | R320 + H321 |
| V17 + V215 | Q125 + L228 | G109 + A174 | R171 + L235 | L219 + M246 | R320 + S323 |
| V17 + L217 | Q125 + L235 | G109 + G184 | R171 + V238 | L219 + M248 | R320 + H324 |
| V17 + L219 | Q125 + V238 | G109 + T193 | R171 + M246 | L219 + L250 | R320 + F328 |
| V17 + L228 | Q125 + M246 | G109 + N195 | R171 + M248 | L219 + G255 | R320 + T334 |
| V17 + L235 | Q125 + M248 | G109 + G196 | R171 + L250 | L219 + Q256 | R320 + D337 |
| V17 + V238 | Q125 + L250 | G109 + A204 | R171 + G255 | L219 + A263 | R320 + Q345 |
| V17 + M246 | A37 + Q395 | G109 + V206 | R171 + Q256 | L219 + V264 | R320 + G346 |
| V17 + M248 | T40 + P45 | G109 + P211 | R171 + A263 | L219 + A265 | R320 + G348 |
| V17 + L250 | T40 + W48 | G109 + I214 | R171 + V264 | L219 + Y267 | R320 + T355 |
| V17 + G255 | T40 + G50 | G109 + V215 | R171 + A265 | L219 + N270 | R320 + S376 |

-continued

| | | | | | |
|---|---|---|---|---|---|
| V17 + Q256 | T40 + T51 | G109 + L217 | R171 + Y267 | L219 + G273 | R320 + D377 |
| V17 + A263 | T40 + N54 | G109 + L219 | R171 + N270 | L219 + S280 | R320 + D379 |
| V17 + V264 | T40 + V56 | G109 + L228 | R171 + G273 | L219 + T285 | R320 + Y382 |
| V17 + A265 | T40 + A60 | G109 + L235 | R171 + S280 | L219 + M286 | R320 + S383 |
| V17 + Y267 | T40 + K72 | G109 + V238 | R171 + T285 | L219 + F289 | R320 + Q385 |
| V17 + N270 | T40 + R87 | G109 + M246 | R171 + M286 | L219 + V291 | R320 + K391 |
| V17 + G273 | T40 + Q98 | G109 + M248 | R171 + F289 | L219 + Q299 | R320 + K393 |
| V17 + S280 | T40 + M105 | G109 + L250 | R171 + V291 | L219 + S304 | R320 + Q395 |
| V17 + T285 | T40 + G109 | G109 + G255 | R171 + Q299 | L219 + R320 | H321 + S323 |
| V17 + M286 | T40 + F113 | G109 + Q256 | R171 + S304 | L219 + H321 | H321 + H324 |
| V17 + F289 | T40 + R116 | G109 + A263 | R171 + R320 | L219 + S323 | H321 + F328 |
| V17 + V291 | T40 + Q118 | G109 + V264 | R171 + H321 | L219 + H324 | H321 + T334 |
| V17 + Q299 | T40 + Q125 | G109 + A265 | R171 + S323 | L219 + F328 | H321 + D337 |
| V17 + S304 | T40 + G133 | G109 + Y267 | R171 + H324 | L219 + T334 | H321 + Q345 |
| V17 + R320 | T40 + T134 | G109 + N270 | R171 + F328 | L219 + D337 | H321 + G346 |
| V17 + H321 | T40 + W140 | G109 + G273 | R171 + T334 | L219 + Q345 | H321 + G348 |
| V17 + S323 | T40 + G142 | G109 + S280 | R171 + D337 | L219 + G346 | H321 + T355 |
| V17 + H324 | T40 + G149 | G109 + T285 | R171 + Q345 | L219 + G348 | H321 + S376 |
| V17 + F328 | T40 + T165 | G109 + M286 | R171 + G346 | L219 + T355 | H321 + D377 |
| V17 + T334 | T40 + W167 | G109 + F289 | R171 + G348 | L219 + S376 | H321 + D379 |
| V17 + D337 | T40 + R171 | G109 + V291 | R171 + T355 | L219 + D377 | H321 + Y382 |
| V17 + Q345 | T40 + Q172 | G109 + Q299 | R171 + S376 | L219 + D379 | H321 + S383 |
| V17 + G346 | T40 + L173 | G109 + S304 | R171 + D377 | L219 + Y382 | H321 + Q385 |
| V17 + G348 | T40 + A174 | G109 + R320 | R171 + D379 | L219 + S383 | H321 + K391 |
| V17 + T355 | T40 + G184 | G109 + H321 | R171 + Y382 | L219 + Q385 | H321 + K393 |
| V17 + S376 | T40 + T193 | G109 + S323 | R171 + S383 | L219 + K391 | H321 + Q395 |
| V17 + D377 | T40 + N195 | G109 + H324 | R171 + Q385 | L219 + K393 | S323 + H324 |
| V17 + D379 | T40 + G196 | G109 + F328 | R171 + K391 | L219 + Q395 | S323 + F328 |
| V17 + Y382 | T40 + A204 | G109 + T334 | R171 + K393 | L228 + L235 | S323 + T334 |
| V17 + S383 | T40 + V206 | G109 + D337 | R171 + Q395 | L228 + V238 | S323 + D337 |
| V17 + Q385 | T40 + P211 | G109 + Q345 | Q172 + L173 | L228 + M246 | S323 + Q345 |
| V17 + K391 | T40 + I214 | G109 + G346 | Q172 + A174 | L228 + M248 | S323 + G346 |
| V17 + K393 | T40 + V215 | G109 + G348 | Q172 + G184 | L228 + L250 | S323 + G348 |
| V17 + Q395 | H1 + Q169 | G109 + T355 | Q172 + T193 | L228 + G255 | S323 + T355 |
| Q32 + A37 | H1 + A186 | G109 + S376 | Q172 + N195 | L228 + Q256 | S323 + S376 |
| Q32 + T40 | H1 + E190 | G109 + D377 | Q172 + G196 | L228 + A263 | S323 + D377 |
| Q32 + P45 | H1 + A225 | G109 + D379 | Q172 + A204 | L228 + V264 | S323 + D379 |
| Q32 + W48 | H1 + K242 | G109 + Y382 | Q172 + V206 | L228 + A265 | S323 + Y382 |
| Q32 + G50 | H1 + S244 | G109 + S383 | Q172 + P211 | L228 + Y267 | S323 + S383 |
| Q32 + T51 | H1 + N260 | G109 + Q385 | Q172 + I214 | L228 + N270 | S323 + Q385 |
| Q32 + N54 | H1 + K269 | G109 + K391 | Q172 + V215 | L228 + G273 | S323 + K391 |
| Q32 + V56 | H1 + W284 | G109 + K393 | Q172 + L217 | L228 + S280 | S323 + K393 |
| Q32 + A60 | H1 + Y295 | G109 + Q395 | Q172 + L219 | L228 + T285 | S323 + Q395 |
| Q32 + K72 | H1 + V326 | F113 + R116 | Q172 + L228 | L228 + M286 | H324 + F328 |
| Q32 + R87 | T5 + Q169 | F113 + Q118 | Q172 + L235 | L228 + F289 | H324 + T334 |
| Q32 + Q98 | T5 + A186 | F113 + Q125 | Q172 + V238 | L228 + V291 | H324 + D337 |
| Q32 + M105 | T5 + E190 | F113 + G133 | Q172 + M246 | L228 + Q299 | H324 + Q345 |
| Q32 + G109 | T5 + A225 | F113 + T134 | Q172 + M248 | L228 + S304 | H324 + G346 |
| Q32 + F113 | T5 + K242 | F113 + W140 | Q172 + L250 | L228 + R320 | H324 + G348 |
| Q32 + R116 | T5 + S244 | F113 + G142 | Q172 + G255 | L228 + H321 | H324 + T355 |
| Q32 + Q118 | T5 + N260 | F113 + G149 | Q172 + Q256 | L228 + S323 | H324 + S376 |
| Q32 + Q125 | T5 + K269 | F113 + T165 | Q172 + A263 | L228 + H324 | H324 + D377 |
| Q32 + G133 | T5 + W284 | F113 + W167 | Q172 + V264 | L228 + F328 | H324 + D379 |
| Q32 + T134 | T5 + Y295 | F113 + R171 | Q172 + A265 | L228 + T334 | H324 + Y382 |
| Q32 + W140 | T5 + V326 | F113 + Q172 | Q172 + Y267 | L228 + D337 | H324 + S383 |
| Q32 + G142 | G7 + Q169 | F113 + L173 | Q172 + N270 | L228 + Q345 | H324 + Q385 |
| Q32 + G149 | G7 + A186 | F113 + A174 | Q172 + G273 | L228 + G346 | H324 + K391 |
| Q32 + T165 | G7 + E190 | F113 + G184 | Q172 + S280 | L228 + G348 | H324 + K393 |
| Q32 + W167 | G7 + A225 | F113 + T193 | Q172 + T285 | L228 + T355 | H324 + Q395 |
| Q32 + R171 | G7 + K242 | F113 + N195 | Q172 + M286 | L228 + S376 | F328 + T334 |
| Q32 + Q172 | G7 + S244 | F113 + G196 | Q172 + F289 | L228 + D377 | F328 + D337 |
| Q32 + L173 | G7 + N260 | F113 + A204 | Q172 + V291 | L228 + D379 | F328 + Q345 |
| Q32 + A174 | G7 + K269 | F113 + V206 | Q172 + Q299 | L228 + Y382 | F328 + G346 |
| Q32 + G184 | G7 + W284 | F113 + P211 | Q172 + S304 | L228 + S383 | F328 + G348 |
| Q32 + T193 | G7 + Y295 | F113 + I214 | Q172 + R320 | L228 + Q385 | F328 + T355 |
| Q32 + N195 | G7 + V326 | F113 + V215 | Q172 + H321 | L228 + K391 | F328 + S376 |
| Q32 + G196 | Q11 + Q169 | F113 + L217 | Q172 + S323 | L228 + K393 | F328 + D377 |
| Q32 + A204 | Q11 + A186 | F113 + L219 | Q172 + H324 | L228 + Q395 | F328 + D379 |
| Q32 + V206 | Q11 + E190 | F113 + L228 | Q172 + F328 | L235 + V238 | F328 + Y382 |
| Q32 + P211 | Q11 + A225 | F113 + L235 | Q172 + T334 | L235 + M246 | F328 + S383 |
| Q32 + I214 | Q11 + K242 | F113 + V238 | Q172 + D337 | L235 + M248 | F328 + Q385 |
| Q32 + V215 | Q11 + S244 | F113 + M246 | Q172 + Q345 | L235 + L250 | F328 + K391 |
| Q32 + L217 | Q11 + N260 | F113 + M248 | Q172 + G346 | L235 + G255 | F328 + K393 |
| Q32 + L219 | Q11 + K269 | F113 + L250 | Q172 + G348 | L235 + Q256 | F328 + Q395 |
| Q32 + L228 | Q11 + W284 | F113 + G255 | Q172 + T355 | L235 + A263 | T334 + D337 |
| Q32 + L235 | Q11 + Y295 | F113 + Q256 | Q172 + S376 | L235 + V264 | T334 + Q345 |
| Q32 + V238 | Q11 + V326 | F113 + A263 | Q172 + D377 | L235 + A265 | T334 + G346 |
| Q32 + M246 | N16 + Q169 | F113 + V264 | Q172 + D379 | L235 + Y267 | T334 + G348 |
| Q32 + M248 | N16 + A186 | F113 + A265 | Q172 + Y382 | L235 + N270 | T334 + T355 |

-continued

| | | | | | |
|---|---|---|---|---|---|
| Q32 + L250 | N16 + E190 | F113 + Y267 | Q172 + S383 | L235 + G273 | T334 + S376 |
| Q32 + G255 | N16 + A225 | F113 + N270 | Q172 + Q385 | L235 + S280 | T334 + D377 |
| Q32 + Q256 | N16 + K242 | F113 + G273 | Q172 + K391 | L235 + T285 | T334 + D379 |
| Q32 + A263 | N16 + S244 | F113 + S280 | Q172 + K393 | L235 + M286 | T334 + Y382 |
| Q32 + V264 | N16 + N260 | F113 + T285 | Q172 + Q395 | L235 + F289 | T334 + S383 |
| Q32 + A265 | N16 + K269 | F113 + M286 | L173 + A174 | L235 + V291 | T334 + Q385 |
| Q32 + Y267 | N16 + W284 | F113 + F289 | L173 + G184 | L235 + Q299 | T334 + K391 |
| Q32 + N270 | N16 + Y295 | F113 + V291 | L173 + T193 | L235 + S304 | T334 + K393 |
| Q32 + G273 | N16 + V326 | F113 + Q299 | L173 + N195 | L235 + R320 | T334 + Q395 |
| Q32 + S280 | V17 + Q169 | F113 + S304 | L173 + G196 | L235 + H321 | D337 + Q345 |
| Q32 + T285 | V17 + A186 | F113 + R320 | L173 + A204 | L235 + S323 | D337 + G346 |
| Q32 + M286 | V17 + E190 | F113 + H321 | L173 + V206 | L235 + H324 | D337 + G348 |
| Q32 + F289 | V17 + A225 | F113 + S323 | L173 + P211 | L235 + F328 | D337 + T355 |
| Q32 + V291 | V17 + K242 | F113 + H324 | L173 + I214 | L235 + T334 | D337 + S376 |
| Q32 + Q299 | V17 + S244 | F113 + F328 | L173 + V215 | L235 + D337 | D337 + D377 |
| Q32 + S304 | V17 + N260 | F113 + T334 | L173 + L217 | L235 + Q345 | D337 + D379 |
| Q32 + R320 | V17 + K269 | F113 + D337 | L173 + L219 | L235 + G346 | D337 + Y382 |
| Q32 + H321 | V17 + W284 | F113 + Q345 | L173 + L228 | L235 + G348 | D337 + S383 |
| Q32 + S323 | V17 + Y295 | F113 + G346 | L173 + L235 | L235 + T355 | D337 + Q385 |
| Q32 + H324 | V17 + V326 | F113 + G348 | L173 + V238 | L235 + S376 | D337 + K391 |
| Q32 + F328 | Q32 + Q169 | F113 + T355 | L173 + M246 | L235 + D377 | D337 + K393 |
| Q32 + T334 | Q32 + A186 | F113 + S376 | L173 + M248 | L235 + D379 | D337 + Q395 |
| Q32 + D337 | Q32 + E190 | F113 + D377 | L173 + L250 | L235 + Y382 | Q345 + G346 |
| Q32 + Q345 | Q32 + A225 | F113 + D379 | L173 + G255 | L235 + S383 | Q345 + G348 |
| Q32 + G346 | Q32 + K242 | F113 + Y382 | L173 + Q256 | L235 + Q385 | Q345 + T355 |
| Q32 + G348 | Q32 + S244 | F113 + S383 | L173 + A263 | L235 + K391 | Q345 + S376 |
| Q32 + T355 | Q32 + N260 | F113 + Q385 | L173 + V264 | L235 + K393 | Q345 + D377 |
| Q32 + S376 | Q32 + K269 | F113 + K391 | L173 + A265 | L235 + Q395 | Q345 + D379 |
| Q32 + D377 | Q32 + W284 | F113 + K393 | L173 + Y267 | V238 + M246 | Q345 + Y382 |
| Q32 + D379 | Q32 + Y295 | F113 + Q395 | L173 + N270 | V238 + M248 | Q345 + S383 |
| Q32 + Y382 | Q32 + V326 | R116 + Q118 | L173 + G273 | V238 + L250 | Q345 + Q385 |
| Q32 + S383 | A37 + Q169 | R116 + Q125 | L173 + S280 | V238 + G255 | Q345 + K391 |
| Q32 + Q385 | A37 + A186 | R116 + G133 | L173 + T285 | V238 + Q256 | Q345 + K393 |
| Q32 + K391 | A37 + E190 | R116 + T134 | L173 + M286 | V238 + A263 | Q345 + Q395 |
| Q32 + K393 | A37 + A225 | R116 + W140 | L173 + F289 | V238 + V264 | G346 + G348 |
| Q32 + Q395 | A37 + K242 | R116 + G142 | L173 + V291 | V238 + A265 | G346 + T355 |
| A37 + T40 | A37 + S244 | R116 + G149 | L173 + Q299 | V238 + Y267 | G346 + S376 |
| A37 + P45 | A37 + N260 | R116 + T165 | L173 + S304 | V238 + N270 | G346 + D377 |
| A37 + W48 | A37 + K269 | R116 + W167 | L173 + R320 | V238 + G273 | G346 + D379 |
| A37 + G50 | A37 + W284 | R116 + R171 | L173 + H321 | V238 + S280 | G346 + Y382 |
| A37 + T51 | A37 + Y295 | R116 + Q172 | L173 + S323 | V238 + T285 | G346 + S383 |
| A37 + N54 | A37 + V326 | R116 + L173 | L173 + H324 | V238 + M286 | G346 + Q385 |
| A37 + V56 | T40 + Q169 | R116 + A174 | L173 + F328 | V238 + F289 | G346 + K391 |
| A37 + A60 | T40 + A186 | R116 + G184 | L173 + T334 | V238 + V291 | G346 + K393 |
| A37 + K72 | T40 + E190 | R116 + T193 | L173 + D337 | V238 + Q299 | G346 + Q395 |
| A37 + R87 | T40 + A225 | R116 + N195 | L173 + Q345 | V238 + S304 | G348 + T355 |
| A37 + Q98 | T40 + K242 | R116 + G196 | L173 + G346 | V238 + R320 | G348 + S376 |
| A37 + M105 | T40 + S244 | R116 + A204 | L173 + G348 | V238 + H321 | G348 + D377 |
| A37 + G109 | T40 + N260 | R116 + V206 | L173 + T355 | V238 + S323 | G348 + D379 |
| A37 + F113 | T40 + K269 | R116 + P211 | L173 + S376 | V238 + H324 | G348 + Y382 |
| A37 + R116 | T40 + W284 | R116 + I214 | L173 + D377 | V238 + F328 | G348 + S383 |
| A37 + Q118 | T40 + Y295 | R116 + V215 | L173 + D379 | V238 + T334 | G348 + Q385 |
| A37 + Q125 | T40 + V326 | R116 + L217 | L173 + Y382 | V238 + D337 | G348 + K391 |
| A37 + G133 | P45 + Q169 | R116 + L219 | L173 + S383 | V238 + Q345 | G348 + K393 |
| A37 + T134 | P45 + A186 | R116 + L228 | L173 + Q385 | V238 + G346 | G348 + Q395 |
| A37 + W140 | P45 + E190 | R116 + L235 | L173 + K391 | V238 + G348 | T355 + S376 |
| A37 + G142 | P45 + A225 | R116 + V238 | L173 + K393 | V238 + T355 | T355 + D377 |
| A37 + G149 | P45 + K242 | R116 + M246 | L173 + Q395 | V238 + S376 | T355 + D379 |
| A37 + T165 | P45 + S244 | R116 + M248 | A174 + G184 | V238 + D377 | T355 + Y382 |
| A37 + W167 | P45 + N260 | R116 + L250 | A174 + T193 | V238 + D379 | T355 + S383 |
| A37 + R171 | P45 + K269 | R116 + G255 | A174 + N195 | V238 + Y382 | T355 + Q385 |
| A37 + Q172 | P45 + W284 | R116 + Q256 | A174 + G196 | V238 + S383 | T355 + K391 |
| A37 + L173 | P45 + Y295 | R116 + A263 | A174 + A204 | V238 + Q385 | T355 + K393 |
| A37 + A174 | P45 + V326 | R116 + V264 | A174 + V206 | V238 + K391 | T355 + Q395 |
| A37 + G184 | W48 + Q169 | R116 + A265 | A174 + P211 | V238 + K393 | S376 + D377 |
| A37 + T193 | W48 + A186 | R116 + Y267 | A174 + I214 | V238 + Q395 | S376 + D379 |
| A37 + N195 | W48 + E190 | R116 + N270 | A174 + V215 | M246 + M248 | S376 + Y382 |
| A37 + G196 | W48 + A225 | R116 + G273 | A174 + L217 | M246 + L250 | S376 + S383 |
| A37 + A204 | W48 + K242 | R116 + S280 | A174 + L219 | M246 + G255 | S376 + Q385 |
| A37 + V206 | W48 + S244 | R116 + T285 | A174 + L228 | M246 + Q256 | S376 + K391 |
| A37 + P211 | W48 + N260 | R116 + M286 | A174 + L235 | M246 + A263 | S376 + K393 |
| A37 + I214 | W48 + K269 | R116 + F289 | A174 + V238 | M246 + V264 | S376 + Q395 |
| A37 + V215 | W48 + W284 | R116 + V291 | A174 + M246 | M246 + A265 | D377 + D379 |
| A37 + L217 | W48 + Y295 | R116 + Q299 | A174 + M248 | M246 + Y267 | D377 + Y382 |
| A37 + L219 | W48 + V326 | R116 + S304 | A174 + L250 | M246 + N270 | D377 + S383 |
| A37 + L228 | G50 + Q169 | R116 + R320 | A174 + G255 | M246 + G273 | D377 + Q385 |
| A37 + L235 | G50 + A186 | R116 + H321 | A174 + Q256 | M246 + S280 | D377 + K391 |
| A37 + V238 | G50 + E190 | R116 + S323 | A174 + A263 | M246 + T285 | D377 + K393 |
| A37 + M246 | G50 + A225 | R116 + H324 | A174 + V264 | M246 + M286 | D377 + Q395 |

-continued

| | | | | | |
|---|---|---|---|---|---|
| A37 + M248 | G50 + K242 | R116 + F328 | A174 + A265 | M246 + F289 | D379 + Y382 |
| A37 + L250 | G50 + S244 | R116 + T334 | A174 + Y267 | M246 + V291 | D379 + S383 |
| A37 + G255 | G50 + N260 | R116 + D337 | A174 + N270 | M246 + Q299 | D379 + Q385 |
| A37 + Q256 | G50 + K269 | R116 + Q345 | A174 + G273 | M246 + S304 | D379 + K391 |
| A37 + A263 | G50 + W284 | R116 + G346 | A174 + S280 | M246 + R320 | D379 + K393 |
| A37 + V264 | G50 + Y295 | R116 + G348 | A174 + T285 | M246 + H321 | D379 + Q395 |
| A37 + A265 | G50 + V326 | R116 + T355 | A174 + M286 | M246 + S323 | Y382 + S383 |
| A37 + Y267 | T51 + Q169 | R116 + S376 | A174 + F289 | M246 + H324 | Y382 + Q385 |
| A37 + N270 | T51 + A186 | R116 + D377 | A174 + V291 | M246 + F328 | Y382 + K391 |
| A37 + G273 | T51 + E190 | R116 + D379 | A174 + Q299 | M246 + T334 | Y382 + K393 |
| A37 + S280 | T51 + A225 | R116 + Y382 | A174 + S304 | M246 + D337 | Y382 + Q395 |
| A37 + T285 | T51 + K242 | R116 + S383 | A174 + R320 | M246 + Q345 | S383 + Q385 |
| A37 + M286 | T51 + S244 | R116 + Q385 | A174 + H321 | M246 + G346 | S383 + K391 |
| A37 + F289 | T51 + N260 | R116 + K391 | A174 + S323 | M246 + G348 | S383 + K393 |
| A37 + V291 | T51 + K269 | R116 + K393 | A174 + H324 | M246 + T355 | S383 + Q395 |
| A37 + Q299 | T51 + W284 | R116 + Q395 | A174 + F328 | M246 + S376 | Q385 + K391 |
| A37 + S304 | T51 + Y295 | Q118 + Q125 | A174 + T334 | M246 + D377 | Q385 + K393 |
| A37 + R320 | T51 + V326 | Q118 + G133 | A174 + D337 | M246 + D379 | Q385 + Q395 |
| A37 + H321 | N54 + Q169 | Q118 + T134 | A174 + Q345 | M246 + Y382 | K391 + K393 |
| A37 + S323 | N54 + A186 | Q118 + W140 | A174 + G346 | M246 + S383 | K391 + Q395 |
| A37 + H324 | N54 + E190 | Q118 + G142 | A174 + G348 | M246 + Q385 | K393 + Q395 |
| A37 + F328 | N54 + A225 | Q118 + G149 | A174 + T355 | M246 + K391 | M248 + F289 |
| A37 + T334 | N54 + K242 | Q118 + T165 | A174 + S376 | M246 + K393 | M248 + V291 |
| A37 + D337 | N54 + S244 | Q118 + W167 | A174 + D377 | M246 + Q395 | G109 + Q169 |
| A37 + Q345 | N54 + N260 | Q118 + R171 | A174 + D379 | M248 + L250 | G109 + A186 |
| A37 + G346 | N54 + K269 | Q118 + Q172 | A174 + Y382 | M248 + G255 | G109 + E190 |
| A37 + G348 | N54 + W284 | Q118 + L173 | A174 + S383 | M248 + Q256 | G109 + A225 |
| A37 + T355 | N54 + Y295 | Q118 + A174 | A174 + Q385 | M248 + A263 | G109 + K242 |
| A37 + S376 | N54 + V326 | Q118 + G184 | A174 + K391 | M248 + V264 | G109 + S244 |
| A37 + D377 | V56 + Q169 | Q118 + T193 | A174 + K393 | M248 + A265 | G109 + N260 |
| A37 + D379 | V56 + A186 | Q118 + N195 | A174 + Q395 | M248 + Y267 | G109 + K269 |
| A37 + Y382 | V56 + E190 | Q118 + G196 | G184 + T193 | M248 + N270 | G109 + W284 |
| A37 + S383 | V56 + A225 | Q118 + A204 | G184 + N195 | M248 + G273 | G109 + Y295 |
| A37 + Q385 | V56 + K242 | Q118 + V206 | G184 + G196 | M248 + S280 | G109 + V326 |
| A37 + K391 | V56 + S244 | Q118 + P211 | G184 + A204 | M248 + T285 | F113 + Q169 |
| A37 + K393 | V56 + N260 | Q118 + I214 | G184 + V206 | M248 + M286 | F113 + A186 |
| A60 + Q169 | V56 + K269 | G133 + Q169 | W167 + Q169 | R171 + A186 | F113 + A225 |
| A60 + A186 | V56 + W284 | G133 + A186 | W167 + A186 | R171 + E190 | F113 + E190 |
| A60 + E190 | V56 + Y295 | G133 + E190 | W167 + E190 | R171 + A225 | F113 + K242 |
| A60 + A225 | V56 + V326 | G133 + A225 | W167 + A225 | R171 + K242 | F113 + S244 |
| A60 + K242 | G184 + A186 | G133 + K242 | W167 + K242 | R171 + S244 | F113 + N260 |
| A60 + S244 | G184 + E190 | G133 + S244 | W167 + S244 | R171 + N260 | F113 + K269 |
| A60 + N260 | G184 + A225 | G133 + N260 | W167 + N260 | R171 + K269 | F113 + W284 |
| A60 + K269 | G184 + K242 | G133 + K269 | W167 + K269 | R171 + W284 | F113 + Y295 |
| A60 + W284 | G184 + S244 | G133 + W284 | W167 + W284 | R171 + Y295 | F113 + V326 |
| A60 + Y295 | G184 + N260 | G133 + Y295 | W167 + Y295 | R171 + V326 | R116 + Q169 |
| A60 + V326 | G184 + K269 | G133 + V326 | W167 + V326 | Q172 + A186 | R116 + A186 |
| K72 + Q169 | G184 + W284 | T134 + Q169 | Q169 + A186 | Q172 + E190 | R116 + E190 |
| K72 + A186 | G184 + Y295 | T134 + A186 | Q169 + E190 | Q172 + A225 | R116 + A225 |
| K72 + E190 | G184 + V326 | T134 + E190 | Q169 + L173 | Q172 + K242 | R116 + K242 |
| K72 + A225 | A186 + E190 | T134 + A225 | Q169 + A174 | Q172 + S244 | R116 + S244 |
| K72 + K242 | A186 + T193 | T134 + K242 | Q169 + G184 | Q172 + N260 | R116 + N260 |
| K72 + S244 | A186 + N195 | T134 + S244 | Q169 + T193 | Q172 + K269 | R116 + K269 |
| K72 + N260 | A186 + G196 | T134 + N260 | Q169 + N195 | Q172 + W284 | R116 + W284 |
| K72 + K269 | A186 + A204 | T134 + K269 | Q169 + G196 | Q172 + Y295 | R116 + Y295 |
| K72 + W284 | A186 + V206 | T134 + W284 | Q169 + A204 | Q172 + V326 | R116 + V326 |
| K72 + Y295 | A186 + P211 | T134 + Y295 | Q169 + V206 | L173 + A186 | Q118 + Q169 |
| K72 + V326 | A186 + I214 | T134 + V326 | Q169 + P211 | L173 + E190 | Q118 + A186 |
| R87 + Q169 | A186 + V215 | W140 + Q169 | Q169 + I214 | L173 + A225 | Q118 + A225 |
| R87 + A186 | A186 + L217 | W140 + A186 | Q169 + V215 | L173 + K242 | Q118 + K242 |
| R87 + E190 | A186 + L219 | W140 + E190 | Q169 + L217 | L173 + S244 | Q118 + S244 |
| R87 + A225 | A186 + A225 | W140 + A225 | Q169 + L219 | L173 + N260 | Q118 + N260 |
| R87 + K242 | A186 + L228 | W140 + K242 | Q169 + A225 | L173 + K269 | Q118 + K269 |
| R87 + S244 | A186 + L235 | W140 + S244 | Q169 + L228 | L173 + W284 | Q118 + W284 |
| R87 + N260 | A186 + V238 | W140 + N260 | Q169 + L235 | L173 + Y295 | Q118 + Y295 |
| R87 + K269 | A186 + K242 | W140 + K269 | Q169 + V238 | L173 + V326 | Q118 + V326 |
| R87 + W284 | A186 + S244 | W140 + W284 | Q169 + K242 | A174 + A186 | Q125 + Q169 |
| R87 + Y295 | A186 + M246 | W140 + Y295 | Q169 + S244 | A174 + E190 | Q125 + A186 |
| R87 + V326 | A186 + M248 | W140 + V326 | Q169 + M246 | A174 + A225 | Q125 + E190 |
| Q98 + Q169 | A186 + L250 | G142 + Q169 | Q169 + M248 | A174 + K242 | Q125 + A225 |
| Q98 + A186 | A186 + G255 | G142 + A186 | Q169 + L250 | A174 + S244 | Q125 + K242 |
| Q98 + E190 | A186 + Q256 | G142 + E190 | Q169 + G255 | A174 + N260 | Q125 + S244 |
| Q98 + A225 | A186 + N260 | G142 + A225 | Q169 + Q256 | A174 + K269 | Q125 + N260 |
| Q98 + K242 | A186 + A263 | G142 + K242 | Q169 + N260 | A174 + W284 | Q125 + K269 |
| Q98 + S244 | A186 + V264 | G142 + S244 | Q169 + A263 | A174 + Y295 | Q125 + W284 |
| Q98 + N260 | A186 + A265 | G142 + N260 | Q169 + V264 | A174 + V326 | Q125 + Y295 |
| Q98 + K269 | A186 + Y267 | G142 + K269 | Q169 + A265 | T193 + A225 | Q125 + V326 |
| Q98 + W284 | A186 + K269 | G142 + W284 | Q169 + Y267 | T193 + K242 | V215 + A225 |
| Q98 + Y295 | A186 + N270 | G142 + Y295 | Q169 + K269 | T193 + S244 | V215 + K242 |

-continued

| | | | | | |
|---|---|---|---|---|---|
| Q98 + V326 | A186 + G273 | G142 + V326 | Q169 + N270 | T193 + N260 | V215 + S244 |
| M105 + Q169 | A186 + S280 | G149 + Q169 | Q169 + G273 | T193 + K269 | V215 + N260 |
| M105 + A186 | A186 + W284 | G149 + A186 | Q169 + S280 | T193 + W284 | V215 + K269 |
| M105 + E190 | A186 + T285 | G149 + E190 | Q169 + W284 | T193 + Y295 | V215 + W284 |
| M105 + A225 | A186 + M286 | G149 + A225 | Q169 + T285 | T193 + V326 | V215 + Y295 |
| M105 + K242 | A186 + F289 | G149 + K242 | Q169 + M286 | N195 + A225 | V215 + V326 |
| M105 + S244 | A186 + V291 | G149 + S244 | Q169 + F289 | N195 + K242 | L217 + A225 |
| M105 + N260 | A186 + Y295 | G149 + N260 | Q169 + V291 | N195 + S244 | L217 + K242 |
| M105 + K269 | A186 + Q299 | G149 + K269 | Q169 + Y295 | N195 + N260 | L217 + S244 |
| M105 + W284 | A186 + S304 | G149 + W284 | Q169 + Q299 | N195 + K269 | L217 + N260 |
| M105 + Y295 | A186 + R320 | G149 + Y295 | Q169 + S304 | N195 + W284 | L217 + K269 |
| M105 + V326 | A186 + H321 | G149 + V326 | Q169 + R320 | N195 + Y295 | L217 + W284 |
| A225 + L228 | A186 + S323 | T165 + Q169 | Q169 + H321 | N195 + V326 | L217 + Y295 |
| A225 + L235 | A186 + H324 | T165 + A186 | Q169 + S323 | G196 + A225 | L217 + V326 |
| A225 + V238 | A186 + V326 | T165 + E190 | Q169 + H324 | G196 + K242 | L219 + A225 |
| A225 + K242 | A186 + F328 | T165 + A225 | Q169 + V326 | G196 + K242 | L219 + K242 |
| A225 + S244 | A186 + T334 | T165 + K242 | Q169 + F328 | G196 + S244 | L219 + S244 |
| A225 + M246 | A186 + D337 | T165 + S244 | Q169 + T334 | G196 + N260 | L219 + N260 |
| A225 + M248 | A186 + Q345 | T165 + N260 | Q169 + D337 | G196 + K269 | L219 + K269 |
| A225 + L250 | A186 + G346 | T165 + K269 | Q169 + Q345 | G196 + W284 | L219 + W284 |
| A225 + G255 | A186 + G348 | T165 + W284 | Q169 + G346 | G196 + Y295 | L219 + Y295 |
| A225 + Q256 | A186 + T355 | T165 + Y295 | Q169 + G348 | G196 + V326 | L219 + V326 |
| A225 + N260 | A186 + S376 | T165 + V326 | Q169 + T355 | A204 + A225 | M246 + N260 |
| A225 + A263 | A186 + D377 | L228 + K242 | Q169 + S376 | A204 + K242 | M246 + K269 |
| A225 + V264 | A186 + D379 | L228 + S244 | Q169 + D377 | A204 + S244 | M246 + W284 |
| A225 + A265 | A186 + Y382 | L228 + N260 | Q169 + D379 | A204 + N260 | M246 + Y295 |
| A225 + Y267 | A186 + S383 | L228 + K269 | Q169 + Y382 | A204 + K269 | M246 + V326 |
| A225 + K269 | A186 + Q385 | L228 + W284 | Q169 + S383 | A204 + W284 | M248 + N260 |
| A225 + N270 | A186 + K391 | L228 + Y295 | Q169 + Q385 | A204 + Y295 | M248 + K269 |
| A225 + G273 | A186 + K393 | L228 + V326 | Q169 + K391 | A204 + V326 | M248 + W284 |
| A225 + S280 | A186 + Q395 | L235 + K242 | Q169 + K393 | V206 + A225 | M248 + Y295 |
| A225 + W284 | E190 + T193 | L235 + S244 | Q169 + Q395 | A206 + K242 | M248 + V326 |
| A225 + T285 | E190 + N195 | L235 + N260 | Q256 + N260 | A206 + S244 | L250 + N260 |
| A225 + M286 | E190 + G196 | L235 + K269 | G256 + K269 | A206 + N260 | L250 + K269 |
| A225 + F289 | E190 + A204 | L235 + W284 | Q256 + W284 | A206 + K269 | L250 + W284 |
| A225 + V291 | E190 + V206 | L235 + Y295 | Q256 + Y295 | A206 + W284 | L250 + Y295 |
| A225 + Y295 | E190 + P211 | L235 + V326 | Q256 + V326 | A206 + Y295 | L250 + V326 |
| A225 + Q299 | E190 + I214 | V238 + K242 | N260 + A263 | A206 + V326 | G255 + N260 |
| A225 + S304 | E190 + V215 | V238 + S244 | N260 + V264 | P211 + A225 | G255 + K269 |
| A225 + R320 | E190 + L217 | V238 + N260 | N260 + A265 | P211 + K242 | G255 + W284 |
| A225 + H321 | E190 + L219 | V238 + K269 | N260 + Y267 | P211 + S244 | G255 + Y295 |
| A225 + S323 | E190 + A225 | V238 + W284 | N260 + K269 | P211 + N206 | G255 + V326 |
| A225 + H324 | E190 + L228 | V238 + Y295 | N260 + N270 | P211 + K269 | N270 + W284 |
| A225 + V326 | E190 + L235 | V238 + V326 | N260 + G273 | P211 + W284 | N270 + Y295 |
| A225 + F328 | E190 + V238 | K242 + S244 | N260 + S280 | P211 + Y295 | N270 + V326 |
| A225 + T334 | E190 + K242 | K242 + M246 | N260 + W284 | P211 + V326 | G273 + W284 |
| A225 + D337 | E190 + S244 | K242 + M248 | N260 + T285 | I214 + A225 | G273 + Y295 |
| A225 + Q345 | E190 + M246 | K242 + L250 | N260 + M286 | I214 + K242 | G273 + V326 |
| A225 + G346 | E190 + M248 | K242 + G255 | N260 + F289 | I214 + S244 | S280 + W284 |
| A225 + G348 | E190 + L250 | K242 + Q256 | N260 + V291 | I214 + N260 | S280 + Y295 |
| A225 + T355 | E190 + G255 | K242 + N260 | N260 + Y295 | I214 + K269 | S280 + V326 |
| A225 + S376 | E190 + Q256 | K242 + A263 | N260 + Q299 | I214 + W284 | W284 + T285 |
| A225 + D377 | E190 + N260 | K242 + V264 | N260 + S304 | I214 + Y295 | W284 + M286 |
| A225 + D379 | E190 + A263 | K242 + A265 | N260 + R320 | I214 + V326 | W284 + F289 |
| A225 + Y382 | E190 + V264 | K242 + Y267 | N260 + H321 | K269 + N270 | W284 + V291 |
| A225 + S383 | E190 + A265 | K242 + K269 | N260 + S323 | K269 + G273 | W284 + Y295 |
| A225 + Q385 | E190 + Y267 | K242 + N270 | N260 + H324 | K269 + S280 | W284 + Q299 |
| A225 + K391 | E190 + K269 | K242 + G273 | N260 + V326 | K269 + W284 | W284 + S304 |
| A225 + K393 | E190 + N270 | K242 + S280 | N260 + F328 | K269 + T285 | W284 + R320 |
| A225 + Q395 | E190 + G273 | K242 + W284 | N260 + T334 | K269 + M286 | W284 + H321 |
| A263 + K269 | E190 + S280 | K242 + T285 | N260 + D337 | K269 + F289 | W284 + S323 |
| A263 + W284 | E190 + W284 | K242 + M286 | N260 + Q345 | K269 + V291 | W284 + H324 |
| A263 + Y295 | E190 + T285 | K242 + F289 | N260 + G346 | K269 + Y295 | W284 + V326 |
| A263 + V326 | E190 + M286 | K242 + V291 | N260 + G348 | K269 + Q299 | W284 + F328 |
| V264 + K269 | E190 + F289 | K242 + Y295 | N260 + T355 | K269 + S304 | W284 + T334 |
| V264 + W284 | E190 + V291 | K242 + Q299 | N260 + S376 | K269 + R320 | W284 + D337 |
| V264 + Y295 | E190 + Y295 | K242 + S304 | N260 + D377 | K269 + H321 | W284 + Q345 |
| V264 + V326 | E190 + Q299 | K242 + R320 | N260 + D379 | K269 + S323 | W284 + G346 |
| A265 + K269 | E190 + S304 | K242 + H321 | N260 + Y382 | K269 + H324 | W284 + G348 |
| A265 + W284 | E190 + R320 | K242 + S323 | N260 + S383 | K269 + V326 | W284 + T355 |
| A265 + Y295 | E190 + H321 | K242 + H324 | N260 + Q385 | K269 + F328 | W284 + S376 |
| A265 + V326 | E190 + S323 | K242 + V326 | N260 + K391 | K269 + T334 | W284 + D377 |
| A265 + K269 | E190 + H324 | K242 + F328 | N260 + K393 | K269 + D337 | W284 + D379 |
| A265 + W284 | E190 + V326 | K242 + T334 | N260 + Q395 | K269 + Q345 | W284 + Y382 |
| A265 + Y295 | E190 + F328 | K242 + D337 | Y295 + S376 | K269 + G346 | W284 + S383 |
| A265 + V326 | E190 + T334 | K242 + Q345 | V326 + S376 | K269 + G348 | W284 + Q385 |
| Y295 + D377 | E190 + D337 | K242 + G346 | V326 + D377 | K269 + T355 | W284 + K391 |
| Y295 + D379 | E190 + Q345 | K242 + G348 | V326 + D379 | K269 + S376 | W284 + K393 |
| Y295 + Y382 | E190 + G346 | K242 + T355 | V326 + Y382 | K269 + D377 | W284 + Q395 |

-continued

| | | | | | |
|---|---|---|---|---|---|
| Y295 + S383 | E190 + G348 | K242 + S376 | V326 + S383 | K269 + D379 | T285 + Y295 |
| Y295 + Q385 | E190 + T355 | K242 + D377 | V326 + Q385 | K269 + Y382 | T285 + V326 |
| Y295 + K391 | E190 + S376 | K242 + D379 | V326 + K391 | K269 + S383 | M286 + Y295 |
| Y295 + K393 | E190 + D377 | K242 + Y382 | V326 + K393 | K269 + Q385 | M286 + V326 |
| Y295 + Q395 | E190 + D379 | K242 + S383 | V326 + Q395 | K269 + K391 | F289 + Y295 |
| Q299 + V326 | E190 + Y382 | K242 + Q385 | S244 + K393 | K269 + K393 | F289 + V326 |
| S304 + V326 | E190 + S383 | K242 + K391 | S244 + Q395 | K269 + Q395 | V291 + Y295 |
| R320 + V326 | E190 + Q385 | K242 + K393 | S244 + Y267 | S244 + R320 | V294 + V326 |
| H321 + V326 | E190 + K391 | K242 + Q395 | S244 + K269 | S244 + H321 | Y295 + Q299 |
| S323 + V326 | E190 + K393 | S244 + M246 | S244 + N270 | S244 + S323 | Y295 + S304 |
| H324 + V326 | E190 + Q395 | S244 + M248 | S244 + G273 | S244 + H324 | Y295 + R320 |
| V326 + F328 | S244 + F289 | S244 + L250 | S244 + S280 | S244 + V326 | Y295 + H321 |
| V326 + T334 | S244 + V291 | S244 + G255 | S244 + W284 | S244 + F328 | Y295 + S323 |
| V326 + D337 | S244 + Y295 | S244 + Q256 | S244 + T285 | S244 + T334 | Y295 + H324 |
| V326 + Q345 | S244 + Q299 | S244 + N260 | S244 + S376 | S244 + D337 | Y295 + V326 |
| V326 + G346 | S244 + S304 | S244 + A263 | S244 + D377 | S244 + Q345 | Y295 + F328 |
| V326 + G348 | S244 + K391 | S244 + V264 | S244 + D379 | S244 + G346 | Y295 + T334 |
| V326 + T355 | S244 + M286 | S244 + A265 | S244 + Y382 | S244 + G348 | Y295 + F328 |
| Y295 + G348 | Y295 + Q345 | | S244 + S383 | S244 + T355 | Y295 + T334 |
| Y295 + T355 | Y295 + G346 | | S244 + Q385 | | Y295 + D337 |

In one particular embodiment, the modifications in one or more positions correspond to the following; H1*, T5K, G7K, G7A, Q11H, N16S, N16H, V17L, Q32S, A37H, A37M, A37V, A37S, A37Y, A37R, A37L, T40D, T40G, T40K, P45A, W48G, W48Y, W48F, G50A, T51K, T51E, T51G, T51A, T51S, T51G, T51D, N54S, V56T, A60V, K72R, K72H, K72S, K72Q, K72E, K72N, K72A, K72M, R87S, Q98S, Q98A, M105F, M105I, M105V, M105L, G109A, G109S, F113W, F113S, F113N, F113Y, F113R, F113L, F113Q, R116Q, R116V, R116K, R116W, R116L, R116A, R116H, R116M, R116E, R116S, R116I, R116G, Q118N, Q118K, Q118G, Q118S, Q118F, Q118R, Q125P, Q125K, Q125A, Q125T, N125D, G133S, F133Q, T134E, W140Y, G142T, G149Q, T165S, T165G, T165V, W167I, W167G, W167F, W167R, W167S, W167H, W167L, W167M, W167Y, Q169E, R171H, Q172G, Q172R, Q172N, Q172D, Q172Y, Q172M, Q172S, Q172T, Q172K, Q172H, Q172E, L173V, L173G, L173H, L173A, L173I, L173P, L173T, L173F, L173M, A174S, A174D, A174P, A174M, A174T, A174H, A174K, A174G, A174Q, A174N, A174V, A174L, G184T, A186D, A186N, A186E, A186Q, A186H, E190P, T193K, N195F, G196R, A204T, A204V, A204S, A204G, V206L, V206S, V206Y, P211D, I214G, I214H, I214S, I214T, I214L, I214E, I214W, V215T, L217T, L217Q, L219V, L219H, A225V, L228I, L235V, L235A, V238A, V238T, V238G, K242Q, S244Q, M246L, M246A, M246I, M246F, M246V, M246S, M248T, L250I, L250V, L250T, L250A, L250F, L250M, G255N, G255A, G255A, Q256A, N260G, A263G, V264I, V264T, A265G, Y267I, Y267M, Y267H, Y267L, K269Q, N270G, N270T, G273R, S280W, S280L, S280T, S280A, S280K, S280Q, W284H, T285L, T285Q, M286F, M286L, A288L, A288V, F289I, F289L, V291G, V291A, V291T, Y295N, Y295F, Q299V, S304N, S304R, R320A, R320V, H321Y, S323N, H324L, V326L, F328L, F328M, F328V, F328I, T334S, D337H, Q345D, G346T, G346D, G346P, G348S, G348P, T355L, T355F, S376H, S376T, S376V, D377H, D377S, D377A, D377Q, D379S, D379G, D379R, D379A, Y382M, Y382I, Y382L, Y382F, S383G, S383A, Q385L, K391A, K391Y, K391V, K391M, K391E, K391D, K391R, K391H, K391W, K391I, K391Q, K391L, K393Y, K393R, K393Q, K393S, and Q395P, wherein said positions correspond to positions of SEQ ID NOs: 7 or 10.

The inventors of the present invention have identified that these specific alterations within the A and B domain (as defined by SEQ ID NO: 10) of the amino acid sequence as set forth in SEQ ID NOs: 7 and 10, are particularly relevant for improving the performance of a variant alpha-amylase having at least 65% sequence identity to the parent polypeptide.

In one embodiment, the variant comprises an alteration in two, three, four, five, six, seven, eight, nine, ten, eleven, twelf, thirteen, fourteen, fifteen, sixteen, or seventeen positions corresponding to the following positions; H1*, T5K, G7K, G7A, Q11H, N16S, N16H, V17L, Q32S, A37H, A37M, A37V, A37S, A37Y, A37R, A37L, T40D, T40G, T40K, P45A, W48G, W48Y, W48F, G50A, T51K, T51E, T51G, T51A, T51S, T51G, T51D, N54S, V56T, A60V, K72R, K72H, K72S, K72Q, K72E, K72N, K72A, K72M, R87S, Q98S, Q98A, M105F, M105I, M105V, M105L, G109A, G109S, F113W, F113S, F113N, F113Y, F113R, F113L, F113Q, R116Q, R116V, R116K, R116W, R116L, R116A, R116H, R116M, R116E, R116S, R116I, R116G, Q118N, Q118K, Q118G, Q118S, Q118F, Q118R, Q125P, Q125K, Q125A, Q125T, N125D, G133S, F133Q, T134E, W140Y, G142T, G149Q, T165S, T165G, T165V, W167I, W167G, W167F, W167R, W167S, W167H, W167L, W167M, W167Y, Q169E, R171H, Q172G, Q172R, Q172N, Q172D, Q172Y, Q172M, Q172S, Q172T, Q172K, Q172H, Q172E, L173V, L173G, L173H, L173A, L173I, L173P, L173T, L173F, L173M, A174S, A174D, A174P, A174M, A174T, A174H, A174K, A174G, A174Q, A174N, A174V, A174L, G184T, A186D, A186N, A186E, A186Q, A186H, E190P, T193K, N195F, G196R, A204T, A204V, A204S, A204G, V206L, V206S, V206Y, P211D, I214G, I214H, I214S, I214T, I214L, I214E, I214W, V215T, L217T, L217Q, L219V, L219H, A225V, L228I, L235V, L235A, V238A, V238T, V238G, K242Q, S244Q, M246L, M246A, M246I, M246F, M246V, M246S, M248T, L250I, L250V, L250T, L250A, L250F, L250M, G255N, G255A, G255S, Q256A, N260G, A263G, V264I, V264T, A265G, Y267I, Y267M, Y267H, Y267L, K269Q, N270G, N270T, G273R, S280W, S280L, S280T, S280A, S280K, S280Q, W284H, T285L, T285Q, M286F, M286L, A288L, A288V, F289I, F289L, V291G, V291A, V291T, Y295N, Y295F, Q299V, S304N, S304R, R320A, R320V, H321Y, S323N, H324L, V326L, F328L, F328M, F328V, F328I, T334S, D337H, Q345D, G346T, G346D, G346P, G348S, G348P, T355L, T355F, S376H, S376T, S376V, D377H, D377S, D377A, D377Q, D379S, D379G, D379R, D379A, Y382M, Y382I, Y382L, Y382F, S383G, S383A, Q385L, K391A, K391Y, K391V, K391M, K391E, K391D, K391R, K391H, K391W, K391I, K391Q, K391L, K393Y, K393R, K393Q, K393S, and Q395P, wherein said positions correspond to positions of SEQ ID NOs: 7 or 10.

The C domain of a variant according to the present invention may also comprise alterations. Thus, in one embodiment, the variant comprises an alteration in one or more amino acid positions corresponding to the amino acid positions of the amino acid sequence set forth in SEQ ID NOs: 11 or 12, or an amino acid sequence having at least 65% sequence identity to an amino acid sequence as set forth in SEQ ID NOs: 11 or 12.

In one particular embodiment, the C domain comprises an alteration in one or more of the following positions corresponding to positions; A420, G423, T444, A445, Q449, T459, P473, C474, G476, G477, and K484 of SEQ ID NO: 13 or I405, A421, A422, A428, R439 G448, W467, D476, and G477 of SEQ ID NO: 14.

In one embodiment, the variant comprises an alteration in two, three, four, five, six, seven, or eight positions corresponding to the following positions; A420, G423, T444, A445, Q449, T459, P473, C474, G476, G477, and K484 of SEQ ID NO: 13 or I405, A421, A422, A428, R439 G448, W467, D476, and G477 of SEQ ID NO: 14.

The inventors of the present invention have identified that specific amino acid substitutions within the C domain of parent polypeptide have an improved effect on performance of the variants. Thus, in a particular embodiment, the alteration in one or more positions correspond to the following T400P, H402R, A420Q, A420S, A420K, A420L, G423H, T444Q, T444S, T444D, T444Y, T444H, T444V, T444R, T444A, A445Q, Q449T, T459N, P473R, P473A, P473G, P473T, P473K, C474V, G476K, G477A, G477Q, K484A, K484G, K484P, K484E, K484Q, and K484S, wherein said positions correspond to positions of SEQ ID NO: 13; or I405L, A421H, A422P, A428T, G448D, D476K, D476G, D476N, D476Y, G477S, G477A, G477T, and G477Q, wherein said positions correspond to positions of SEQ ID NO: 14.

In a particular embodiment, the variant comprises a modification in the following positions;

| | | | | | |
|---|---|---|---|---|---|
| H1 + T5 | T40 + A174 | R87 + N270 | W140 + K393 | V206 + V215 | Y267 + C474 |
| H1 + G7 | T40 + G184 | R87 + G273 | W140 + Q395 | V206 + L217 | Y267 + G476 |
| H1 + Q11 | T40 + T193 | R87 + S280 | W140 + A420 | V206 + L219 | Y267 + G477 |
| H1 + N16 | T40 + N195 | R87 + T285 | W140 + G423 | V206 + L235 | Y267 + K484 |
| H1 + V17 | T40 + A204 | R87 + M286 | W140 + T444 | V206 + V238 | N270 + G273 |
| H1 + Q32 | T40 + V206 | R87 + F289 | W140 + A445 | V206 + M246 | N270 + S280 |
| H1 + A37 | T40 + P211 | R87 + V291 | W140 + Q449 | V206 + M248 | N270 + T285 |
| H1 + T40 | T40 + I214 | R87 + Q299 | W140 + T459 | V206 + L250 | N270 + M286 |
| H1 + P45 | T40 + V215 | R87 + R320 | W140 + P473 | V206 + G255 | N270 + F289 |
| H1 + W48 | T40 + L217 | R87 + H321 | W140 + C474 | V206 + Q256 | N270 + V291 |
| H1 + G50 | T40 + L219 | R87 + S323 | W140 + G476 | V206 + A263 | N270 + Q299 |
| H1 + T51 | T40 + L235 | R87 + H324 | W140 + G477 | V206 + V264 | N270 + R320 |
| H1 + N54 | T40 + V238 | R87 + F328 | W140 + K484 | V206 + Y267 | N270 + H321 |
| H1 + V56 | T40 + M246 | R87 + T334 | G142 + G149 | V206 + N270 | N270 + S323 |
| H1 + K72 | T40 + M248 | R87 + D337 | G142 + T165 | V206 + G273 | N270 + H324 |
| H1 + R87 | T40 + L250 | R87 + Q345 | G142 + W167 | V206 + S280 | N270 + F328 |
| H1 + Q98 | T40 + G255 | R87 + G346 | G142 + R171 | V206 + T285 | N270 + T334 |
| H1 + M105 | T40 + Q256 | R87 + G348 | G142 + Q172 | V206 + M286 | N270 + D337 |
| H1 + G109 | T40 + A263 | R87 + T355 | G142 + L173 | V206 + F289 | N270 + Q345 |
| H1 + F113 | T40 + V264 | R87 + S376 | G142 + A174 | V206 + V291 | N270 + G346 |
| H1 + R116 | T40 + Y267 | R87 + D377 | G142 + G184 | V206 + Q299 | N270 + G348 |
| H1 + Q118 | T40 + N270 | R87 + D379 | G142 + T193 | V206 + R320 | N270 + T355 |
| H1 + Q125 | T40 + G273 | R87 + Y382 | G142 + N195 | V206 + H321 | N270 + S376 |
| H1 + G133 | T40 + S280 | R87 + S383 | G142 + A204 | V206 + S323 | N270 + D377 |
| H1 + T134 | T40 + T285 | R87 + Q385 | G142 + V206 | V206 + H324 | N270 + D379 |
| H1 + W140 | T40 + M286 | R87 + K391 | G142 + P211 | V206 + F328 | N270 + Y382 |
| H1 + G142 | T40 + F289 | R87 + K393 | G142 + I214 | V206 + T334 | N270 + S383 |
| H1 + G149 | T40 + V291 | R87 + Q395 | G142 + V215 | V206 + D337 | N270 + Q385 |
| H1 + T165 | T40 + Q299 | R87 + A420 | G142 + L217 | V206 + Q345 | N270 + K391 |
| H1 + W167 | T40 + R320 | R87 + G423 | G142 + L219 | V206 + G346 | N270 + K393 |
| H1 + R171 | T40 + H321 | R87 + T444 | G142 + L235 | V206 + G348 | N270 + Q395 |
| H1 + Q172 | T40 + S323 | R87 + A445 | G142 + V238 | V206 + T355 | N270 + A420 |
| H1 + L173 | T40 + H324 | R87 + Q449 | G142 + M246 | V206 + S376 | N270 + G423 |
| H1 + A174 | T40 + F328 | R87 + T459 | G142 + M248 | V206 + D377 | N270 + T444 |
| H1 + G184 | T40 + T334 | R87 + P473 | G142 + L250 | V206 + D379 | N270 + A445 |
| H1 + T193 | T40 + D337 | R87 + C474 | G142 + G255 | V206 + Y382 | N270 + Q449 |
| H1 + N195 | T40 + Q345 | R87 + G476 | G142 + Q256 | V206 + S383 | N270 + T459 |
| H1 + A204 | T40 + G346 | R87 + G477 | G142 + A263 | V206 + Q385 | N270 + P473 |
| H1 + V206 | T40 + G348 | R87 + K484 | G142 + V264 | V206 + K391 | N270 + C474 |
| H1 + P211 | T40 + T355 | Q98 + M105 | G142 + Y267 | V206 + K393 | N270 + G476 |
| H1 + I214 | T40 + S376 | Q98 + G109 | G142 + N270 | V206 + Q395 | N270 + G477 |
| H1 + V215 | T40 + D377 | Q98 + F113 | G142 + G273 | V206 + A420 | N270 + K484 |
| H1 + L217 | T40 + D379 | Q98 + R116 | G142 + S280 | V206 + G423 | G273 + S280 |
| H1 + L219 | T40 + Y382 | Q98 + Q118 | G142 + T285 | V206 + T444 | G273 + T285 |
| H1 + L235 | T40 + S383 | Q98 + Q125 | G142 + M286 | V206 + A445 | G273 + M286 |
| H1 + V238 | T40 + Q385 | Q98 + G133 | G142 + F289 | V206 + Q449 | G273 + F289 |
| H1 + M246 | T40 + K391 | Q98 + T134 | G142 + V291 | V206 + T459 | G273 + V291 |
| H1 + M248 | T40 + K393 | Q98 + W140 | G142 + Q299 | V206 + P473 | G273 + Q299 |
| H1 + L250 | T40 + Q395 | Q98 + G142 | G142 + R320 | V206 + C474 | G273 + R320 |
| H1 + G255 | T40 + A420 | Q98 + G149 | G142 + H321 | V206 + G476 | G273 + H321 |
| H1 + Q256 | T40 + G423 | Q98 + T165 | G142 + S323 | V206 + G477 | G273 + S323 |
| H1 + A263 | T40 + T444 | Q98 + W167 | G142 + H324 | V206 + K484 | G273 + H324 |
| H1 + V264 | T40 + A445 | Q98 + R171 | G142 + F328 | P211 + I214 | G273 + F328 |
| H1 + Y267 | T40 + Q449 | Q98 + Q172 | G142 + T334 | P211 + V215 | G273 + T334 |
| H1 + N270 | T40 + T459 | Q98 + L173 | G142 + D337 | P211 + L217 | G273 + D337 |

-continued

| | | | | | |
|---|---|---|---|---|---|
| H1 + G273 | T40 + P473 | Q98 + A174 | G142 + Q345 | P211 + L219 | G273 + Q345 |
| H1 + S280 | T40 + C474 | Q98 + G184 | G142 + G346 | P211 + L235 | G273 + G346 |
| H1 + T285 | T40 + G476 | Q98 + T193 | G142 + G348 | P211 + V238 | G273 + G348 |
| H1 + M286 | T40 + G477 | Q98 + N195 | G142 + T355 | P211 + M246 | G273 + T355 |
| H1 + F289 | T40 + K484 | Q98 + A204 | G142 + S376 | P211 + M248 | G273 + S376 |
| H1 + V291 | P45 + W48 | Q98 + V206 | G142 + D377 | P211 + L250 | G273 + D377 |
| H1 + Q299 | P45 + G50 | Q98 + P211 | G142 + D379 | P211 + G255 | G273 + D379 |
| H1 + R320 | P45 + T51 | Q98 + I214 | G142 + Y382 | P211 + Q256 | G273 + Y382 |
| H1 + H321 | P45 + N54 | Q98 + V215 | G142 + S383 | P211 + A263 | G273 + S383 |
| H1 + S323 | P45 + V56 | Q98 + L217 | G142 + Q385 | P211 + V264 | G273 + Q385 |
| H1 + H324 | P45 + K72 | Q98 + L219 | G142 + K391 | P211 + Y267 | G273 + K391 |
| H1 + F328 | P45 + R87 | Q98 + L235 | G142 + K393 | P211 + N270 | G273 + K393 |
| H1 + T334 | P45 + Q98 | Q98 + V238 | G142 + Q395 | P211 + G273 | G273 + Q395 |
| H1 + D337 | P45 + M105 | Q98 + M246 | G142 + A420 | P211 + S280 | G273 + A420 |
| H1 + Q345 | P45 + G109 | Q98 + M248 | G142 + G423 | P211 + T285 | G273 + G423 |
| H1 + G346 | P45 + F113 | Q98 + L250 | G142 + T444 | P211 + M286 | G273 + T444 |
| H1 + G348 | P45 + R116 | Q98 + G255 | G142 + A445 | P211 + F289 | G273 + A445 |
| H1 + T355 | P45 + Q118 | Q98 + Q256 | G142 + Q449 | P211 + V291 | G273 + Q449 |
| H1 + S376 | P45 + Q125 | Q98 + A263 | G142 + T459 | P211 + Q299 | G273 + T459 |
| H1 + D377 | P45 + G133 | Q98 + V264 | G142 + P473 | P211 + R320 | G273 + P473 |
| H1 + D379 | P45 + T134 | Q98 + Y267 | G142 + C474 | P211 + H321 | G273 + C474 |
| H1 + Y382 | P45 + W140 | Q98 + N270 | G142 + G476 | P211 + S323 | G273 + G476 |
| H1 + S383 | P45 + G142 | Q98 + G273 | G142 + G477 | P211 + H324 | G273 + G477 |
| H1 + Q385 | P45 + G149 | Q98 + S280 | G142 + K484 | P211 + F328 | G273 + K484 |
| H1 + K391 | P45 + T165 | Q98 + T285 | G149 + T165 | P211 + T334 | S280 + T285 |
| H1 + K393 | P45 + W167 | Q98 + M286 | G149 + W167 | P211 + D337 | S280 + M286 |
| H1 + Q395 | P45 + R171 | Q98 + F289 | G149 + R171 | P211 + Q345 | S280 + F289 |
| H1 + A420 | P45 + Q172 | Q98 + V291 | G149 + Q172 | P211 + G346 | S280 + V291 |
| H1 + G423 | P45 + L173 | Q98 + Q299 | G149 + L173 | P211 + G348 | S280 + Q299 |
| H1 + T444 | P45 + A174 | Q98 + R320 | G149 + A174 | P211 + T355 | S280 + R320 |
| H1 + A445 | P45 + G184 | Q98 + H321 | G149 + G184 | P211 + S376 | S280 + H321 |
| H1 + Q449 | P45 + T193 | Q98 + S323 | G149 + T193 | P211 + D377 | S280 + S323 |
| H1 + T459 | P45 + N195 | Q98 + H324 | G149 + N195 | P211 + D379 | S280 + H324 |
| H1 + P473 | P45 + A204 | Q98 + F328 | G149 + A204 | P211 + Y382 | S280 + F328 |
| H1 + C474 | P45 + V206 | Q98 + T334 | G149 + V206 | P211 + S383 | S280 + T334 |
| H1 + G476 | P45 + P211 | Q98 + D337 | G149 + P211 | P211 + Q385 | S280 + D337 |
| H1 + G477 | P45 + I214 | Q98 + Q345 | G149 + I214 | P211 + K391 | S280 + Q345 |
| H1 + K484 | P45 + V215 | Q98 + G346 | G149 + V215 | P211 + K393 | S280 + G346 |
| T5 + G7 | P45 + L217 | Q98 + G348 | G149 + L217 | P211 + Q395 | S280 + G348 |
| T5 + Q11 | P45 + L219 | Q98 + T355 | G149 + L219 | P211 + A420 | S280 + T355 |
| T5 + N16 | P45 + L235 | Q98 + S376 | G149 + L235 | P211 + G423 | S280 + S376 |
| T5 + V17 | P45 + V238 | Q98 + D377 | G149 + V238 | P211 + T444 | S280 + D377 |
| T5 + Q32 | P45 + M246 | Q98 + D379 | G149 + M246 | P211 + A445 | S280 + D379 |
| T5 + A37 | P45 + M248 | Q98 + Y382 | G149 + M248 | P211 + Q449 | S280 + Y382 |
| T5 + T40 | P45 + L250 | Q98 + S383 | G149 + L250 | P211 + T459 | S280 + S383 |
| T5 + P45 | P45 + G255 | Q98 + Q385 | G149 + G255 | P211 + P473 | S280 + Q385 |
| T5 + W48 | P45 + Q256 | Q98 + K391 | G149 + Q256 | P211 + C474 | S280 + K391 |
| T5 + G50 | P45 + A263 | Q98 + K393 | G149 + A263 | P211 + G476 | S280 + K393 |
| T5 + T51 | P45 + V264 | Q98 + Q395 | G149 + V264 | P211 + G477 | S280 + Q395 |
| T5 + N54 | P45 + Y267 | Q98 + A420 | G149 + Y267 | P211 + K484 | S280 + A420 |
| T5 + V56 | P45 + N270 | Q98 + G423 | G149 + N270 | I214 + V215 | S280 + G423 |
| T5 + K72 | P45 + G273 | Q98 + T444 | G149 + G273 | I214 + L217 | S280 + T444 |
| T5 + R87 | P45 + S280 | Q98 + A445 | G149 + S280 | I214 + L219 | S280 + A445 |
| T5 + Q98 | P45 + T285 | Q98 + Q449 | G149 + T285 | I214 + L235 | S280 + Q449 |
| T5 + M105 | P45 + M286 | Q98 + T459 | G149 + M286 | I214 + V238 | S280 + T459 |
| T5 + G109 | P45 + F289 | Q98 + P473 | G149 + F289 | I214 + M246 | S280 + P473 |
| T5 + F113 | P45 + V291 | Q98 + C474 | G149 + V291 | I214 + M248 | S280 + C474 |
| T5 + R116 | P45 + Q299 | Q98 + G476 | G149 + Q299 | I214 + L250 | S280 + G476 |
| T5 + Q118 | P45 + R320 | Q98 + G477 | G149 + R320 | I214 + G255 | S280 + G477 |
| T5 + Q125 | P45 + H321 | Q98 + K484 | G149 + H321 | I214 + Q256 | S280 + K484 |
| T5 + G133 | P45 + S323 | M105 + G109 | G149 + S323 | I214 + A263 | T285 + M286 |
| T5 + T134 | P45 + H324 | M105 + F113 | G149 + H324 | I214 + V264 | T285 + F289 |
| T5 + W140 | P45 + F328 | M105 + R116 | G149 + F328 | I214 + Y267 | T285 + V291 |
| T5 + G142 | P45 + T334 | M105 + Q118 | G149 + T334 | I214 + N270 | T285 + Q299 |
| T5 + G149 | P45 + D337 | M105 + Q125 | G149 + D337 | I214 + G273 | T285 + R320 |
| T5 + T165 | P45 + Q345 | M105 + G133 | G149 + Q345 | I214 + S280 | T285 + H321 |
| T5 + W167 | P45 + G346 | M105 + T134 | G149 + G346 | I214 + T285 | T285 + S323 |
| T5 + R171 | P45 + G348 | M105 + W140 | G149 + G348 | I214 + M286 | T285 + H324 |
| T5 + Q172 | P45 + T355 | M105 + G142 | G149 + T355 | I214 + F289 | T285 + F328 |
| T5 + L173 | P45 + S376 | M105 + G149 | G149 + S376 | I214 + V291 | T285 + T334 |
| T5 + A174 | P45 + D377 | M105 + T165 | G149 + D377 | I214 + Q299 | T285 + D337 |
| T5 + G184 | P45 + D379 | M105 + W167 | G149 + D379 | I214 + R320 | T285 + Q345 |
| T5 + T193 | P45 + Y382 | M105 + R171 | G149 + Y382 | I214 + H321 | T285 + G346 |
| T5 + N195 | P45 + S383 | M105 + Q172 | G149 + S383 | I214 + S323 | T285 + G348 |
| T5 + A204 | P45 + Q385 | M105 + L173 | G149 + Q385 | I214 + H324 | T285 + T355 |
| T5 + V206 | P45 + K391 | M105 + A174 | G149 + K391 | I214 + F328 | T285 + S376 |
| T5 + P211 | P45 + K393 | M105 + G184 | G149 + K393 | I214 + T334 | T285 + D377 |
| T5 + I214 | P45 + Q395 | M105 + T193 | G149 + Q395 | I214 + D337 | T285 + D379 |
| T5 + V215 | P45 + A420 | M105 + N195 | G149 + A420 | I214 + Q345 | T285 + Y382 |

-continued

| | | | | | |
|---|---|---|---|---|---|
| T5 + L217 | P45 + G423 | M105 + A204 | G149 + G423 | I214 + G346 | T285 + S383 |
| T5 + L219 | P45 + T444 | M105 + V206 | G149 + T444 | I214 + G348 | T285 + Q385 |
| T5 + L235 | P45 + A445 | M105 + P211 | G149 + A445 | I214 + T355 | T285 + K391 |
| T5 + V238 | P45 + Q449 | M105 + I214 | G149 + Q449 | I214 + S376 | T285 + K393 |
| T5 + M246 | P45 + T459 | M105 + V215 | G149 + T459 | I214 + D377 | T285 + Q395 |
| T5 + M248 | P45 + P473 | M105 + L217 | G149 + P473 | I214 + D379 | T285 + A420 |
| T5 + L250 | P45 + C474 | M105 + L219 | G149 + C474 | I214 + Y382 | T285 + G423 |
| T5 + G255 | P45 + G476 | M105 + L235 | G149 + G476 | I214 + S383 | T285 + T444 |
| T5 + Q256 | P45 + G477 | M105 + V238 | G149 + G477 | I214 + Q385 | T285 + A445 |
| T5 + A263 | P45 + K484 | M105 + M246 | G149 + K484 | I214 + K391 | T285 + Q449 |
| T5 + V264 | W48 + G50 | M105 + M248 | T165 + W167 | I214 + K393 | T285 + T459 |
| T5 + Y267 | W48 + T51 | M105 + L250 | T165 + R171 | I214 + Q395 | T285 + P473 |
| T5 + N270 | W48 + N54 | M105 + G255 | T165 + Q172 | I214 + A420 | T285 + C474 |
| T5 + G273 | W48 + V56 | M105 + Q256 | T165 + L173 | I214 + G423 | T285 + G476 |
| T5 + S280 | W48 + K72 | M105 + A263 | T165 + A174 | I214 + T444 | T285 + G477 |
| T5 + T285 | W48 + R87 | M105 + V264 | T165 + G184 | I214 + A445 | T285 + K484 |
| T5 + M286 | W48 + Q98 | M105 + Y267 | T165 + T193 | I214 + Q449 | M286 + F289 |
| T5 + F289 | W48 + M105 | M105 + N270 | T165 + N195 | I214 + T459 | M286 + V291 |
| T5 + V291 | W48 + G109 | M105 + G273 | T165 + A204 | I214 + P473 | M286 + Q299 |
| T5 + Q299 | W48 + F113 | M105 + S280 | T165 + V206 | I214 + C474 | M286 + R320 |
| T5 + R320 | W48 + R116 | M105 + T285 | T165 + P211 | I214 + G476 | M286 + H321 |
| T5 + H321 | W48 + Q118 | M105 + M286 | T165 + I214 | I214 + G477 | M286 + S323 |
| T5 + S323 | W48 + Q125 | M105 + F289 | T165 + V215 | I214 + K484 | M286 + H324 |
| T5 + H324 | W48 + G133 | M105 + V291 | T165 + L217 | V215 + L217 | M286 + F328 |
| T5 + F328 | W48 + T134 | M105 + Q299 | T165 + L219 | V215 + L219 | M286 + T334 |
| T5 + T334 | W48 + W140 | M105 + R320 | T165 + L235 | V215 + L235 | M286 + D337 |
| T5 + D337 | W48 + G142 | M105 + H321 | T165 + V238 | V215 + V238 | M286 + Q345 |
| T5 + Q345 | W48 + G149 | M105 + S323 | T165 + M246 | V215 + M246 | M286 + G346 |
| T5 + G346 | W48 + T165 | M105 + H324 | T165 + M248 | V215 + M248 | M286 + G348 |
| T5 + G348 | W48 + W167 | M105 + F328 | T165 + L250 | V215 + L250 | M286 + T355 |
| T5 + T355 | W48 + R171 | M105 + T334 | T165 + G255 | V215 + G255 | M286 + S376 |
| T5 + S376 | W48 + Q172 | M105 + D337 | T165 + Q256 | V215 + Q256 | M286 + D377 |
| T5 + D377 | W48 + L173 | M105 + Q345 | T165 + A263 | V215 + A263 | M286 + D379 |
| T5 + D379 | W48 + A174 | M105 + G346 | T165 + V264 | V215 + V264 | M286 + Y382 |
| T5 + Y382 | W48 + G184 | M105 + G348 | T165 + Y267 | V215 + Y267 | M286 + S383 |
| T5 + S383 | W48 + T193 | M105 + T355 | T165 + N270 | V215 + N270 | M286 + Q385 |
| T5 + Q385 | W48 + N195 | M105 + S376 | T165 + G273 | V215 + G273 | M286 + K391 |
| T5 + K391 | W48 + A204 | M105 + D377 | T165 + S280 | V215 + S280 | M286 + K393 |
| T5 + K393 | W48 + V206 | M105 + D379 | T165 + T285 | V215 + T285 | M286 + Q395 |
| T5 + Q395 | W48 + P211 | M105 + Y382 | T165 + M286 | V215 + M286 | M286 + A420 |
| T5 + A420 | W48 + I214 | M105 + S383 | T165 + F289 | V215 + F289 | M286 + G423 |
| T5 + G423 | W48 + V215 | M105 + Q385 | T165 + V291 | V215 + V291 | M286 + T444 |
| T5 + T444 | W48 + L217 | M105 + K391 | T165 + Q299 | V215 + Q299 | M286 + A445 |
| T5 + A445 | W48 + L219 | M105 + K393 | T165 + R320 | V215 + R320 | M286 + Q449 |
| T5 + Q449 | W48 + L235 | M105 + Q395 | T165 + H321 | V215 + H321 | M286 + T459 |
| T5 + T459 | W48 + V238 | M105 + A420 | T165 + S323 | V215 + S323 | M286 + P473 |
| T5 + P473 | W48 + M246 | M105 + G423 | T165 + H324 | V215 + H324 | M286 + C474 |
| T5 + C474 | W48 + M248 | M105 + T444 | T165 + F328 | V215 + F328 | M286 + G476 |
| T5 + G476 | W48 + L250 | M105 + A445 | T165 + T334 | V215 + T334 | M286 + G477 |
| T5 + G477 | W48 + G255 | M105 + Q449 | T165 + D337 | V215 + D337 | M286 + K484 |
| T5 + K484 | W48 + Q256 | M105 + T459 | T165 + Q345 | V215 + Q345 | F289 + V291 |
| G7 + Q11 | W48 + A263 | M105 + P473 | T165 + G346 | V215 + G346 | F289 + Q299 |
| G7 + N16 | W48 + V264 | M105 + C474 | T165 + G348 | V215 + G348 | F289 + R320 |
| G7 + V17 | W48 + Y267 | M105 + G476 | T165 + T355 | V215 + T355 | F289 + H321 |
| G7 + Q32 | W48 + N270 | M105 + G477 | T165 + S376 | V215 + S376 | F289 + S323 |
| G7 + A37 | W48 + G273 | M105 + K484 | T165 + D377 | V215 + D377 | F289 + H324 |
| G7 + T40 | W48 + S280 | G109 + F113 | T165 + D379 | V215 + D379 | F289 + F328 |
| G7 + P45 | W48 + T285 | G109 + R116 | T165 + Y382 | V215 + Y382 | F289 + T334 |
| G7 + W48 | W48 + M286 | G109 + Q118 | T165 + S383 | V215 + S383 | F289 + D337 |
| G7 + G50 | W48 + F289 | G109 + Q125 | T165 + Q385 | V215 + Q385 | F289 + Q345 |
| G7 + T51 | W48 + V291 | G109 + G133 | T165 + K391 | V215 + K391 | F289 + G346 |
| G7 + N54 | W48 + Q299 | G109 + T134 | T165 + K393 | V215 + K393 | F289 + G348 |
| G7 + V56 | W48 + R320 | G109 + W140 | T165 + Q395 | V215 + Q395 | F289 + T355 |
| G7 + K72 | W48 + H321 | G109 + G142 | T165 + A420 | V215 + A420 | F289 + S376 |
| G7 + R87 | W48 + S323 | G109 + G149 | T165 + G423 | V215 + G423 | F289 + D377 |
| G7 + Q98 | W48 + H324 | G109 + T165 | T165 + T444 | V215 + T444 | F289 + D379 |
| G7 + M105 | W48 + F328 | G109 + W167 | T165 + A445 | V215 + A445 | F289 + Y382 |
| G7 + G109 | W48 + T334 | G109 + R171 | T165 + Q449 | V215 + Q449 | F289 + S383 |
| G7 + F113 | W48 + D337 | G109 + Q172 | T165 + T459 | V215 + T459 | F289 + Q385 |
| G7 + R116 | W48 + Q345 | G109 + L173 | T165 + P473 | V215 + P473 | F289 + K391 |
| G7 + Q118 | W48 + G346 | G109 + A174 | T165 + C474 | V215 + C474 | F289 + K393 |
| G7 + Q125 | W48 + G348 | G109 + G184 | T165 + G476 | V215 + G476 | F289 + Q395 |
| G7 + G133 | W48 + T355 | G109 + T193 | T165 + G477 | V215 + G477 | F289 + A420 |
| G7 + T134 | W48 + S376 | G109 + N195 | T165 + K484 | V215 + K484 | F289 + G423 |
| G7 + W140 | W48 + D377 | G109 + A204 | W167 + R171 | L217 + L219 | F289 + T444 |
| G7 + G142 | W48 + D379 | G109 + V206 | W167 + Q172 | L217 + L235 | F289 + A445 |
| G7 + G149 | W48 + Y382 | G109 + P211 | W167 + L173 | L217 + V238 | F289 + Q449 |
| G7 + T165 | W48 + S383 | G109 + I214 | W167 + A174 | L217 + M246 | F289 + T459 |
| G7 + W167 | W48 + Q385 | G109 + V215 | W167 + G184 | L217 + M248 | F289 + P473 |

-continued

| | | | | | |
|---|---|---|---|---|---|
| G7 + R171 | W48 + K391 | G109 + L217 | W167 + T193 | L217 + L250 | F289 + C474 |
| G7 + Q172 | W48 + K393 | G109 + L219 | W167 + N195 | L217 + G255 | F289 + G476 |
| G7 + L173 | W48 + Q395 | G109 + L235 | W167 + A204 | L217 + Q256 | F289 + G477 |
| G7 + A174 | W48 + A420 | G109 + V238 | W167 + V206 | L217 + A263 | F289 + K484 |
| G7 + G184 | W48 + G423 | G109 + M246 | W167 + P211 | L217 + V264 | V291 + Q299 |
| G7 + T193 | W48 + T444 | G109 + M248 | W167 + I214 | L217 + Y267 | V291 + R320 |
| G7 + N195 | W48 + A445 | G109 + L250 | W167 + V215 | L217 + N270 | V291 + H321 |
| G7 + A204 | W48 + Q449 | G109 + G255 | W167 + L217 | L217 + G273 | V291 + S323 |
| G7 + V206 | W48 + T459 | G109 + Q256 | W167 + L219 | L217 + S280 | V291 + H324 |
| G7 + P211 | W48 + P473 | G109 + A263 | W167 + L235 | L217 + T285 | V291 + F328 |
| G7 + I214 | W48 + C474 | G109 + V264 | W167 + V238 | L217 + M286 | V291 + T334 |
| G7 + V215 | W48 + G476 | G109 + Y267 | W167 + M246 | L217 + F289 | V291 + D337 |
| G7 + L217 | W48 + G477 | G109 + N270 | W167 + M248 | L217 + V291 | V291 + Q345 |
| G7 + L219 | W48 + K484 | G109 + G273 | W167 + L250 | L217 + Q299 | V291 + G346 |
| G7 + L235 | G50 + T51 | G109 + S280 | W167 + G255 | L217 + R320 | V291 + G348 |
| G7 + V238 | G50 + N54 | G109 + T285 | W167 + Q256 | L217 + H321 | V291 + T355 |
| G7 + M246 | G50 + V56 | G109 + M286 | W167 + A263 | L217 + S323 | V291 + S376 |
| G7 + M248 | G50 + K72 | G109 + F289 | W167 + V264 | L217 + H324 | V291 + D377 |
| G7 + L250 | G50 + R87 | G109 + V291 | W167 + Y267 | L217 + F328 | V291 + D379 |
| G7 + G255 | G50 + Q98 | G109 + Q299 | W167 + N270 | L217 + T334 | V291 + Y382 |
| G7 + Q256 | G50 + M105 | G109 + R320 | W167 + G273 | L217 + D337 | V291 + S383 |
| G7 + A263 | G50 + G109 | G109 + H321 | W167 + S280 | L217 + Q345 | V291 + Q385 |
| G7 + V264 | G50 + F113 | G109 + S323 | W167 + T285 | L217 + G346 | V291 + K391 |
| G7 + Y267 | G50 + R116 | G109 + H324 | W167 + M286 | L217 + G348 | V291 + K393 |
| G7 + N270 | G50 + Q118 | G109 + F328 | W167 + F289 | L217 + T355 | V291 + Q395 |
| G7 + G273 | G50 + Q125 | G109 + T334 | W167 + V291 | L217 + S376 | V291 + A420 |
| G7 + S280 | G50 + G133 | G109 + D337 | W167 + Q299 | L217 + D377 | V291 + G423 |
| G7 + T285 | G50 + T134 | G109 + Q345 | W167 + R320 | L217 + D379 | V291 + T444 |
| G7 + M286 | G50 + W140 | G109 + G346 | W167 + H321 | L217 + Y382 | V291 + A445 |
| G7 + F289 | G50 + G142 | G109 + G348 | W167 + S323 | L217 + S383 | V291 + Q449 |
| G7 + V291 | G50 + G149 | G109 + T355 | W167 + H324 | L217 + Q385 | V291 + T459 |
| G7 + Q299 | G50 + T165 | G109 + S376 | W167 + F328 | L217 + K391 | V291 + P473 |
| G7 + R320 | G50 + W167 | G109 + D377 | W167 + T334 | L217 + K393 | V291 + C474 |
| G7 + H321 | G50 + R171 | G109 + D379 | W167 + D337 | L217 + Q395 | V291 + G476 |
| G7 + S323 | G50 + Q172 | G109 + Y382 | W167 + Q345 | L217 + A420 | V291 + G477 |
| G7 + H324 | G50 + L173 | G109 + S383 | W167 + G346 | L217 + G423 | V291 + K484 |
| G7 + F328 | G50 + A174 | G109 + Q385 | W167 + G348 | L217 + T444 | Q299 + R320 |
| G7 + T334 | G50 + G184 | G109 + K391 | W167 + T355 | L217 + A445 | Q299 + H321 |
| G7 + D337 | G50 + T193 | G109 + K393 | W167 + S376 | L217 + Q449 | Q299 + S323 |
| G7 + Q345 | G50 + N195 | G109 + Q395 | W167 + D377 | L217 + T459 | Q299 + H324 |
| G7 + G346 | G50 + A204 | G109 + A420 | W167 + D379 | L217 + P473 | Q299 + F328 |
| G7 + G348 | G50 + V206 | G109 + G423 | W167 + Y382 | L217 + C474 | Q299 + T334 |
| G7 + T355 | G50 + P211 | G109 + T444 | W167 + S383 | L217 + G476 | Q299 + D337 |
| G7 + S376 | G50 + I214 | G109 + A445 | W167 + Q385 | L217 + G477 | Q299 + Q345 |
| G7 + D377 | G50 + V215 | G109 + Q449 | W167 + K391 | L217 + K484 | Q299 + G346 |
| G7 + D379 | G50 + L217 | G109 + T459 | W167 + K393 | L219 + L235 | Q299 + G348 |
| G7 + Y382 | G50 + L219 | G109 + P473 | W167 + Q395 | L219 + V238 | Q299 + T355 |
| G7 + S383 | G50 + L235 | G109 + C474 | W167 + A420 | L219 + M246 | Q299 + S376 |
| G7 + Q385 | G50 + V238 | G109 + G476 | W167 + G423 | L219 + M248 | Q299 + D377 |
| G7 + K391 | G50 + M246 | G109 + G477 | W167 + T444 | L219 + L250 | Q299 + D379 |
| G7 + K393 | G50 + M248 | G109 + K484 | W167 + A445 | L219 + G255 | Q299 + Y382 |
| G7 + Q395 | G50 + L250 | F113 + R116 | W167 + Q449 | L219 + Q256 | Q299 + S383 |
| G7 + A420 | G50 + G255 | F113 + Q118 | W167 + T459 | L219 + A263 | Q299 + Q385 |
| G7 + G423 | G50 + Q256 | F113 + Q125 | W167 + P473 | L219 + V264 | Q299 + K391 |
| G7 + T444 | G50 + A263 | F113 + G133 | W167 + C474 | L219 + Y267 | Q299 + K393 |
| G7 + A445 | G50 + V264 | F113 + T134 | W167 + G476 | L219 + N270 | Q299 + Q395 |
| G7 + Q449 | G50 + Y267 | F113 + W140 | W167 + G477 | L219 + G273 | Q299 + A420 |
| G7 + T459 | G50 + N270 | F113 + G142 | W167 + K484 | L219 + S280 | Q299 + G423 |
| G7 + P473 | G50 + G273 | F113 + G149 | R171 + Q172 | L219 + T285 | Q299 + T444 |
| G7 + C474 | G50 + S280 | F113 + T165 | R171 + L173 | L219 + M286 | Q299 + A445 |
| G7 + G476 | G50 + T285 | F113 + W167 | R171 + A174 | L219 + F289 | Q299 + Q449 |
| G7 + G477 | G50 + M286 | F113 + R171 | R171 + G184 | L219 + V291 | Q299 + T459 |
| G7 + K484 | G50 + F289 | F113 + Q172 | R171 + T193 | L219 + Q299 | Q299 + P473 |
| Q11 + N16 | G50 + V291 | F113 + L173 | R171 + N195 | L219 + R320 | Q299 + C474 |
| Q11 + V17 | G50 + Q299 | F113 + A174 | R171 + A204 | L219 + H321 | Q299 + G476 |
| Q11 + Q32 | G50 + R320 | F113 + G184 | R171 + V206 | L219 + S323 | Q299 + G477 |
| Q11 + A37 | G50 + H321 | F113 + T193 | R171 + P211 | L219 + H324 | Q299 + K484 |
| Q11 + T40 | G50 + S323 | F113 + N195 | R171 + I214 | L219 + F328 | R320 + H321 |
| Q11 + P45 | G50 + H324 | F113 + A204 | R171 + V215 | L219 + T334 | R320 + S323 |
| Q11 + W48 | G50 + F328 | F113 + V206 | R171 + L217 | L219 + D337 | R320 + H324 |
| Q11 + G50 | G50 + T334 | F113 + P211 | R171 + L219 | L219 + Q345 | R320 + F328 |
| Q11 + T51 | G50 + D337 | F113 + I214 | R171 + L235 | L219 + G346 | R320 + T334 |
| Q11 + N54 | G50 + Q345 | F113 + V215 | R171 + V238 | L219 + G348 | R320 + D337 |
| Q11 + V56 | G50 + G346 | F113 + L217 | R171 + M246 | L219 + T355 | R320 + Q345 |
| Q11 + K72 | G50 + G348 | F113 + L219 | R171 + M248 | L219 + S376 | R320 + G346 |
| Q11 + R87 | G50 + T355 | F113 + L235 | R171 + L250 | L219 + D377 | R320 + G348 |
| Q11 + Q98 | G50 + S376 | F113 + V238 | R171 + G255 | L219 + D379 | R320 + T355 |
| Q11 + M105 | G50 + D377 | F113 + M246 | R171 + Q256 | L219 + Y382 | R320 + S376 |
| Q11 + G109 | G50 + D379 | F113 + M248 | R171 + A263 | L219 + S383 | R320 + D377 |

-continued

| | | | | | |
|---|---|---|---|---|---|
| Q11 + F113 | G50 + Y382 | F113 + L250 | R171 + V264 | L219 + Q385 | R320 + D379 |
| Q11 + R116 | G50 + S383 | F113 + G255 | R171 + Y267 | L219 + K391 | R320 + Y382 |
| Q11 + Q118 | G50 + Q385 | F113 + Q256 | R171 + N270 | L219 + K393 | R320 + S383 |
| Q11 + Q125 | G50 + K391 | F113 + A263 | R171 + G273 | L219 + Q395 | R320 + Q385 |
| Q11 + G133 | G50 + K393 | F113 + V264 | R171 + S280 | L219 + A420 | R320 + K391 |
| Q11 + T134 | G50 + Q395 | F113 + Y267 | R171 + T285 | L219 + G423 | R320 + K393 |
| Q11 + W140 | G50 + A420 | F113 + N270 | R171 + M286 | L219 + T444 | R320 + Q395 |
| Q11 + G142 | G50 + G423 | F113 + G273 | R171 + F289 | L219 + A445 | R320 + A420 |
| Q11 + G149 | G50 + T444 | F113 + S280 | R171 + V291 | L219 + Q449 | R320 + G423 |
| Q11 + T165 | G50 + A445 | F113 + T285 | R171 + Q299 | L219 + T459 | R320 + T444 |
| Q11 + W167 | G50 + Q449 | F113 + M286 | R171 + R320 | L219 + P473 | R320 + A445 |
| Q11 + R171 | G50 + T459 | F113 + F289 | R171 + H321 | L219 + C474 | R320 + Q449 |
| Q11 + Q172 | G50 + P473 | F113 + V291 | R171 + S323 | L219 + G476 | R320 + T459 |
| Q11 + L173 | G50 + C474 | F113 + Q299 | R171 + H324 | L219 + G477 | R320 + P473 |
| Q11 + A174 | G50 + G476 | F113 + R320 | R171 + F328 | L219 + K484 | R320 + C474 |
| Q11 + G184 | G50 + G477 | F113 + H321 | R171 + T334 | L235 + V238 | R320 + G476 |
| Q11 + T193 | G50 + K484 | F113 + S323 | R171 + D337 | L235 + M246 | R320 + G477 |
| Q11 + N195 | T51 + N54 | F113 + H324 | R171 + Q345 | L235 + M248 | R320 + K484 |
| Q11 + A204 | T51 + V56 | F113 + F328 | R171 + G346 | L235 + L250 | H321 + S323 |
| Q11 + V206 | T51 + K72 | F113 + T334 | R171 + G348 | L235 + G255 | H321 + H324 |
| Q11 + P211 | T51 + R87 | F113 + D337 | R171 + T355 | L235 + Q256 | H321 + F328 |
| Q11 + I214 | T51 + Q98 | F113 + Q345 | R171 + S376 | L235 + A263 | H321 + T334 |
| Q11 + V215 | T51 + M105 | F113 + G346 | R171 + D377 | L235 + V264 | H321 + D337 |
| Q11 + L217 | T51 + G109 | F113 + G348 | R171 + D379 | L235 + Y267 | H321 + Q345 |
| Q11 + L219 | T51 + F113 | F113 + T355 | R171 + Y382 | L235 + N270 | H321 + G346 |
| Q11 + L235 | T51 + R116 | F113 + S376 | R171 + S383 | L235 + G273 | H321 + G348 |
| Q11 + V238 | T51 + Q118 | F113 + D377 | R171 + Q385 | L235 + S280 | H321 + T355 |
| Q11 + M246 | T51 + Q125 | F113 + D379 | R171 + K391 | L235 + T285 | H321 + S376 |
| Q11 + M248 | T51 + G133 | F113 + Y382 | R171 + K393 | L235 + M286 | H321 + D377 |
| Q11 + L250 | T51 + T134 | F113 + S383 | R171 + Q395 | L235 + F289 | H321 + D379 |
| Q11 + G255 | T51 + W140 | F113 + Q385 | R171 + A420 | L235 + V291 | H321 + Y382 |
| Q11 + Q256 | T51 + G142 | F113 + K391 | R171 + G423 | L235 + Q299 | H321 + S383 |
| Q11 + A263 | T51 + G149 | F113 + K393 | R171 + T444 | L235 + R320 | H321 + Q385 |
| Q11 + V264 | T51 + T165 | F113 + Q395 | R171 + A445 | L235 + H321 | H321 + K391 |
| Q11 + Y267 | T51 + W167 | F113 + A420 | R171 + Q449 | L235 + S323 | H321 + K393 |
| Q11 + N270 | T51 + R171 | F113 + G423 | R171 + T459 | L235 + H324 | H321 + Q395 |
| Q11 + G273 | T51 + Q172 | F113 + T444 | R171 + P473 | L235 + F328 | H321 + A420 |
| Q11 + S280 | T51 + L173 | F113 + A445 | R171 + C474 | L235 + T334 | H321 + G423 |
| Q11 + T285 | T51 + A174 | F113 + Q449 | R171 + G476 | L235 + D337 | H321 + T444 |
| Q11 + M286 | T51 + G184 | F113 + T459 | R171 + G477 | L235 + Q345 | H321 + A445 |
| Q11 + F289 | T51 + T193 | F113 + P473 | R171 + K484 | L235 + G346 | H321 + Q449 |
| Q11 + V291 | T51 + N195 | F113 + C474 | Q172 + L173 | L235 + G348 | H321 + T459 |
| Q11 + Q299 | T51 + A204 | F113 + G476 | Q172 + A174 | L235 + T355 | H321 + P473 |
| Q11 + R320 | T51 + V206 | F113 + G477 | Q172 + G184 | L235 + S376 | H321 + C474 |
| Q11 + H321 | T51 + P211 | F113 + K484 | Q172 + T193 | L235 + D377 | H321 + G476 |
| Q11 + S323 | T51 + I214 | R116 + Q118 | Q172 + N195 | L235 + D379 | H321 + G477 |
| Q11 + H324 | T51 + V215 | R116 + Q125 | Q172 + A204 | L235 + Y382 | H321 + K484 |
| Q11 + F328 | T51 + L217 | R116 + G133 | Q172 + V206 | L235 + S383 | S323 + H324 |
| Q11 + T334 | T51 + L219 | R116 + T134 | Q172 + P211 | L235 + Q385 | S323 + F328 |
| Q11 + D337 | T51 + L235 | R116 + W140 | Q172 + I214 | L235 + K391 | S323 + T334 |
| Q11 + Q345 | T51 + V238 | R116 + G142 | Q172 + V215 | L235 + K393 | S323 + D337 |
| Q11 + G346 | T51 + M246 | R116 + G149 | Q172 + L217 | L235 + Q395 | S323 + Q345 |
| Q11 + G348 | T51 + M248 | R116 + T165 | Q172 + L219 | L235 + A420 | S323 + G346 |
| Q11 + T355 | T51 + L250 | R116 + W167 | Q172 + L235 | L235 + G423 | S323 + G348 |
| Q11 + S376 | T51 + G255 | R116 + R171 | Q172 + V238 | L235 + T444 | S323 + T355 |
| Q11 + D377 | T51 + Q256 | R116 + Q172 | Q172 + M246 | L235 + A445 | S323 + S376 |
| Q11 + D379 | T51 + A263 | R116 + L173 | Q172 + M248 | L235 + Q449 | S323 + D377 |
| Q11 + Y382 | T51 + V264 | R116 + A174 | Q172 + L250 | L235 + T459 | S323 + D379 |
| Q11 + S383 | T51 + Y267 | R116 + G184 | Q172 + G255 | L235 + P473 | S323 + Y382 |
| Q11 + Q385 | T51 + N270 | R116 + T193 | Q172 + Q256 | L235 + C474 | S323 + S383 |
| Q11 + K391 | T51 + G273 | R116 + N195 | Q172 + A263 | L235 + G476 | S323 + Q385 |
| Q11 + K393 | T51 + S280 | R116 + A204 | Q172 + V264 | L235 + G477 | S323 + K391 |
| Q11 + Q395 | T51 + T285 | R116 + V206 | Q172 + Y267 | L235 + K484 | S323 + K393 |
| Q11 + A420 | T51 + M286 | R116 + P211 | Q172 + N270 | V238 + M246 | S323 + Q395 |
| Q11 + G423 | T51 + F289 | R116 + I214 | Q172 + G273 | V238 + M248 | S323 + A420 |
| Q11 + T444 | T51 + V291 | R116 + V215 | Q172 + S280 | V238 + L250 | S323 + G423 |
| Q11 + A445 | T51 + Q299 | R116 + L217 | Q172 + T285 | V238 + G255 | S323 + T444 |
| Q11 + Q449 | T51 + R320 | R116 + L219 | Q172 + M286 | V238 + Q256 | S323 + A445 |
| Q11 + T459 | T51 + H321 | R116 + L235 | Q172 + F289 | V238 + A263 | S323 + Q449 |
| Q11 + P473 | T51 + S323 | R116 + V238 | Q172 + V291 | V238 + V264 | S323 + T459 |
| Q11 + C474 | T51 + H324 | R116 + M246 | Q172 + Q299 | V238 + Y267 | S323 + P473 |
| Q11 + G476 | T51 + F328 | R116 + M248 | Q172 + R320 | V238 + N270 | S323 + C474 |
| Q11 + G477 | T51 + T334 | R116 + L250 | Q172 + H321 | V238 + G273 | S323 + G476 |
| Q11 + K484 | T51 + D337 | R116 + G255 | Q172 + S323 | V238 + S280 | S323 + G477 |
| N16 + V17 | T51 + Q345 | R116 + Q256 | Q172 + H324 | V238 + T285 | S323 + K484 |
| N16 + Q32 | T51 + G346 | R116 + A263 | Q172 + F328 | V238 + M286 | H324 + F328 |
| N16 + A37 | T51 + G348 | R116 + V264 | Q172 + T334 | V238 + F289 | H324 + T334 |
| N16 + T40 | T51 + T355 | R116 + Y267 | Q172 + D337 | V238 + V291 | H324 + D337 |
| N16 + P45 | T51 + S376 | R116 + N270 | Q172 + Q345 | V238 + Q299 | H324 + Q345 |

-continued

| | | | | | |
|---|---|---|---|---|---|
| N16 + W48 | T51 + D377 | R116 + G273 | Q172 + G346 | V238 + R320 | H324 + G346 |
| N16 + G50 | T51 + D379 | R116 + S280 | Q172 + G348 | V238 + H321 | H324 + G348 |
| N16 + T51 | T51 + Y382 | R116 + T285 | Q172 + T355 | V238 + S323 | H324 + T355 |
| N16 + N54 | T51 + S383 | R116 + M286 | Q172 + S376 | V238 + H324 | H324 + S376 |
| N16 + V56 | T51 + Q385 | R116 + F289 | Q172 + D377 | V238 + F328 | H324 + D377 |
| N16 + K72 | T51 + K391 | R116 + V291 | Q172 + D379 | V238 + T334 | H324 + D379 |
| N16 + R87 | T51 + K393 | R116 + Q299 | Q172 + Y382 | V238 + D337 | H324 + Y382 |
| N16 + Q98 | T51 + Q395 | R116 + R320 | Q172 + S383 | V238 + Q345 | H324 + S383 |
| N16 + M105 | T51 + A420 | R116 + H321 | Q172 + Q385 | V238 + G346 | H324 + Q385 |
| N16 + G109 | T51 + G423 | R116 + S323 | Q172 + K391 | V238 + G348 | H324 + K391 |
| N16 + F113 | T51 + T444 | R116 + H324 | Q172 + K393 | V238 + T355 | H324 + K393 |
| N16 + R116 | T51 + A445 | R116 + F328 | Q172 + Q395 | V238 + S376 | H324 + Q395 |
| N16 + Q118 | T51 + Q449 | R116 + T334 | Q172 + A420 | V238 + D377 | H324 + A420 |
| N16 + Q125 | T51 + T459 | R116 + D337 | Q172 + G423 | V238 + D379 | H324 + G423 |
| N16 + G133 | T51 + P473 | R116 + Q345 | Q172 + T444 | V238 + Y382 | H324 + T444 |
| N16 + T134 | T51 + C474 | R116 + G346 | Q172 + A445 | V238 + S383 | H324 + A445 |
| N16 + W140 | T51 + G476 | R116 + G348 | Q172 + Q449 | V238 + Q385 | H324 + Q449 |
| N16 + G142 | T51 + G477 | R116 + T355 | Q172 + T459 | V238 + K391 | H324 + T459 |
| N16 + G149 | T51 + K484 | R116 + S376 | Q172 + P473 | V238 + K393 | H324 + P473 |
| N16 + T165 | N54 + V56 | R116 + D377 | Q172 + C474 | V238 + Q395 | H324 + C474 |
| N16 + W167 | N54 + K72 | R116 + D379 | Q172 + G476 | V238 + A420 | H324 + G476 |
| N16 + R171 | N54 + R87 | R116 + Y382 | Q172 + G477 | V238 + G423 | H324 + G477 |
| N16 + Q172 | N54 + Q98 | R116 + S383 | Q172 + K484 | V238 + T444 | H324 + K484 |
| N16 + L173 | N54 + M105 | R116 + Q385 | L173 + A174 | V238 + A445 | F328 + T334 |
| N16 + A174 | N54 + G109 | R116 + K391 | L173 + G184 | V238 + Q449 | F328 + D337 |
| N16 + G184 | N54 + F113 | R116 + K393 | L173 + T193 | V238 + T459 | F328 + Q345 |
| N16 + T193 | N54 + R116 | R116 + Q395 | L173 + N195 | V238 + P473 | F328 + G346 |
| N16 + N195 | N54 + Q118 | R116 + A420 | L173 + A204 | V238 + C474 | F328 + G348 |
| N16 + A204 | N54 + Q125 | R116 + G423 | L173 + V206 | V238 + G476 | F328 + T355 |
| N16 + V206 | N54 + G133 | R116 + T444 | L173 + P211 | V238 + G477 | F328 + S376 |
| N16 + P211 | N54 + T134 | R116 + A445 | L173 + I214 | V238 + K484 | F328 + D377 |
| N16 + I214 | N54 + W140 | R116 + Q449 | L173 + V215 | M246 + M248 | F328 + D379 |
| N16 + V215 | N54 + G142 | R116 + T459 | L173 + L217 | M246 + L250 | F328 + Y382 |
| N16 + L217 | N54 + G149 | R116 + P473 | L173 + L219 | M246 + G255 | F328 + S383 |
| N16 + L219 | N54 + T165 | R116 + C474 | L173 + L235 | M246 + Q256 | F328 + Q385 |
| N16 + L235 | N54 + W167 | R116 + G476 | L173 + V238 | M246 + A263 | F328 + K391 |
| N16 + V238 | N54 + R171 | R116 + G477 | L173 + M246 | M246 + V264 | F328 + K393 |
| N16 + M246 | N54 + Q172 | R116 + K484 | L173 + M248 | M246 + Y267 | F328 + Q395 |
| N16 + M248 | N54 + L173 | Q118 + Q125 | L173 + L250 | M246 + N270 | F328 + A420 |
| N16 + L250 | N54 + A174 | Q118 + G133 | L173 + G255 | M246 + G273 | F328 + G423 |
| N16 + G255 | N54 + G184 | Q118 + T134 | L173 + Q256 | M246 + S280 | F328 + T444 |
| N16 + Q256 | N54 + T193 | Q118 + W140 | L173 + A263 | M246 + T285 | F328 + A445 |
| N16 + A263 | N54 + N195 | Q118 + G142 | L173 + V264 | M246 + M286 | F328 + Q449 |
| N16 + V264 | N54 + A204 | Q118 + G149 | L173 + Y267 | M246 + F289 | F328 + T459 |
| N16 + Y267 | N54 + V206 | Q118 + T165 | L173 + N270 | M246 + V291 | F328 + P473 |
| N16 + N270 | N54 + P211 | Q118 + W167 | L173 + G273 | M246 + Q299 | F328 + C474 |
| N16 + G273 | N54 + I214 | Q118 + R171 | L173 + S280 | M246 + R320 | F328 + G476 |
| N16 + S280 | N54 + V215 | Q118 + Q172 | L173 + T285 | M246 + H321 | F328 + G477 |
| N16 + T285 | N54 + L217 | Q118 + L173 | L173 + M286 | M246 + S323 | F328 + K484 |
| N16 + M286 | N54 + L219 | Q118 + A174 | L173 + F289 | M246 + H324 | T334 + D337 |
| N16 + F289 | N54 + L235 | Q118 + G184 | L173 + V291 | M246 + F328 | T334 + Q345 |
| N16 + V291 | N54 + V238 | Q118 + T193 | L173 + Q299 | M246 + T334 | T334 + G346 |
| N16 + Q299 | N54 + M246 | Q118 + N195 | L173 + R320 | M246 + D337 | T334 + G348 |
| N16 + R320 | N54 + M248 | Q118 + A204 | L173 + H321 | M246 + Q345 | T334 + T355 |
| N16 + H321 | N54 + L250 | Q118 + V206 | L173 + S323 | M246 + G346 | T334 + S376 |
| N16 + S323 | N54 + G255 | Q118 + P211 | L173 + H324 | M246 + G348 | T334 + D377 |
| N16 + H324 | N54 + Q256 | Q118 + I214 | L173 + F328 | M246 + T355 | T334 + D379 |
| N16 + F328 | N54 + A263 | Q118 + V215 | L173 + T334 | M246 + S376 | T334 + Y382 |
| N16 + T334 | N54 + V264 | Q118 + L217 | L173 + D337 | M246 + D377 | T334 + S383 |
| N16 + D337 | N54 + Y267 | Q118 + L219 | L173 + Q345 | M246 + D379 | T334 + Q385 |
| N16 + Q345 | N54 + N270 | Q118 + L235 | L173 + G346 | M246 + Y382 | T334 + K391 |
| N16 + G346 | N54 + G273 | Q118 + V238 | L173 + G348 | M246 + S383 | T334 + K393 |
| N16 + G348 | N54 + S280 | Q118 + M246 | L173 + T355 | M246 + Q385 | T334 + Q395 |
| N16 + T355 | N54 + T285 | Q118 + M248 | L173 + S376 | M246 + K391 | T334 + A420 |
| N16 + S376 | N54 + M286 | Q118 + L250 | L173 + D377 | M246 + K393 | T334 + G423 |
| N16 + D377 | N54 + F289 | Q118 + G255 | L173 + D379 | M246 + Q395 | T334 + T444 |
| N16 + D379 | N54 + V291 | Q118 + Q256 | L173 + Y382 | M246 + A420 | T334 + A445 |
| N16 + Y382 | N54 + Q299 | Q118 + A263 | L173 + S383 | M246 + G423 | T334 + Q449 |
| N16 + S383 | N54 + R320 | Q118 + V264 | L173 + Q385 | M246 + T444 | T334 + T459 |
| N16 + Q385 | N54 + H321 | Q118 + Y267 | L173 + K391 | M246 + A445 | T334 + P473 |
| N16 + K391 | N54 + S323 | Q118 + N270 | L173 + K393 | M246 + Q449 | T334 + C474 |
| N16 + K393 | N54 + H324 | Q118 + G273 | L173 + Q395 | M246 + T459 | T334 + G476 |
| N16 + Q395 | N54 + F328 | Q118 + S280 | L173 + A420 | M246 + P473 | T334 + G477 |
| N16 + A420 | N54 + T334 | Q118 + T285 | L173 + G423 | M246 + C474 | T334 + K484 |
| N16 + G423 | N54 + D337 | Q118 + M286 | L173 + T444 | M246 + G476 | D337 + Q345 |
| N16 + T444 | N54 + Q345 | Q118 + F289 | L173 + A445 | M246 + G477 | D337 + G346 |
| N16 + A445 | N54 + G346 | Q118 + V291 | L173 + Q449 | M246 + K484 | D337 + G348 |
| N16 + Q449 | N54 + G348 | Q118 + Q299 | L173 + T459 | M248 + L250 | D337 + T355 |
| N16 + T459 | N54 + T355 | Q118 + R320 | L173 + P473 | M248 + G255 | D337 + S376 |

-continued

| | | | | | |
|---|---|---|---|---|---|
| N16 + P473 | N54 + S376 | Q118 + H321 | L173 + C474 | M248 + Q256 | D337 + D377 |
| N16 + C474 | N54 + D377 | Q118 + S323 | L173 + G476 | M248 + A263 | D337 + D379 |
| N16 + G476 | N54 + D379 | Q118 + H324 | L173 + G477 | M248 + V264 | D337 + Y382 |
| N16 + G477 | N54 + Y382 | Q118 + F328 | L173 + K484 | M248 + Y267 | D337 + S383 |
| N16 + K484 | N54 + S383 | Q118 + T334 | A174 + G184 | M248 + N270 | D337 + Q385 |
| V17 + Q32 | N54 + Q385 | Q118 + D337 | A174 + T193 | M248 + G273 | D337 + K391 |
| V17 + A37 | N54 + K391 | Q118 + Q345 | A174 + N195 | M248 + S280 | D337 + K393 |
| V17 + T40 | N54 + K393 | Q118 + G346 | A174 + A204 | M248 + T285 | D337 + Q395 |
| V17 + P45 | N54 + Q395 | Q118 + G348 | A174 + V206 | M248 + M286 | D337 + A420 |
| V17 + W48 | N54 + A420 | Q118 + T355 | A174 + P211 | M248 + F289 | D337 + G423 |
| V17 + G50 | N54 + G423 | Q118 + S376 | A174 + I214 | M248 + V291 | D337 + T444 |
| V17 + T51 | N54 + T444 | Q118 + D377 | A174 + V215 | M248 + Q299 | D337 + A445 |
| V17 + N54 | N54 + A445 | Q118 + D379 | A174 + L217 | M248 + R320 | D337 + Q449 |
| V17 + V56 | N54 + Q449 | Q118 + Y382 | A174 + L219 | M248 + H321 | D337 + T459 |
| V17 + K72 | N54 + T459 | Q118 + S383 | A174 + L235 | M248 + S323 | D337 + P473 |
| V17 + R87 | N54 + P473 | Q118 + Q385 | A174 + V238 | M248 + H324 | D337 + C474 |
| V17 + Q98 | N54 + C474 | Q118 + K391 | A174 + M246 | M248 + F328 | D337 + G476 |
| V17 + M105 | N54 + G476 | Q118 + K393 | A174 + M248 | M248 + T334 | D337 + G477 |
| V17 + G109 | N54 + G477 | Q118 + Q395 | A174 + L250 | M248 + D337 | D337 + K484 |
| V17 + F113 | N54 + K484 | Q118 + A420 | A174 + G255 | M248 + Q345 | Q345 + G346 |
| V17 + R116 | V56 + K72 | Q118 + G423 | A174 + Q256 | M248 + G346 | Q345 + G348 |
| V17 + Q118 | V56 + R87 | Q118 + T444 | A174 + A263 | M248 + G348 | Q345 + T355 |
| V17 + Q125 | V56 + Q98 | Q118 + A445 | A174 + V264 | M248 + T355 | Q345 + S376 |
| V17 + G133 | V56 + M105 | Q118 + Q449 | A174 + Y267 | M248 + S376 | Q345 + D377 |
| V17 + T134 | V56 + G109 | Q118 + T459 | A174 + N270 | M248 + D377 | Q345 + D379 |
| V17 + W140 | V56 + F113 | Q118 + P473 | A174 + G273 | M248 + D379 | Q345 + Y382 |
| V17 + G142 | V56 + R116 | Q118 + C474 | A174 + S280 | M248 + Y382 | Q345 + S383 |
| V17 + G149 | V56 + Q118 | Q118 + G476 | A174 + T285 | M248 + S383 | Q345 + Q385 |
| V17 + T165 | V56 + Q125 | Q118 + G477 | A174 + M286 | M248 + Q385 | Q345 + K391 |
| V17 + W167 | V56 + G133 | Q118 + K484 | A174 + F289 | M248 + K391 | Q345 + K393 |
| V17 + R171 | V56 + T134 | Q125 + G133 | A174 + V291 | M248 + K393 | Q345 + Q395 |
| V17 + Q172 | V56 + W140 | Q125 + T134 | A174 + Q299 | M248 + Q395 | Q345 + A420 |
| V17 + L173 | V56 + G142 | Q125 + W140 | A174 + R320 | M248 + A420 | Q345 + G423 |
| V17 + A174 | V56 + G149 | Q125 + G142 | A174 + H321 | M248 + G423 | Q345 + T444 |
| V17 + G184 | V56 + T165 | Q125 + G149 | A174 + S323 | M248 + T444 | Q345 + A445 |
| V17 + T193 | V56 + W167 | Q125 + T165 | A174 + H324 | M248 + A445 | Q345 + Q449 |
| V17 + N195 | V56 + R171 | Q125 + W167 | A174 + F328 | M248 + Q449 | Q345 + T459 |
| V17 + A204 | V56 + Q172 | Q125 + R171 | A174 + T334 | M248 + T459 | Q345 + P473 |
| V17 + V206 | V56 + L173 | Q125 + Q172 | A174 + D337 | M248 + P473 | Q345 + C474 |
| V17 + P211 | V56 + A174 | Q125 + L173 | A174 + Q345 | M248 + C474 | Q345 + G476 |
| V17 + I214 | V56 + G184 | Q125 + A174 | A174 + G346 | M248 + G476 | Q345 + G477 |
| V17 + V215 | V56 + T193 | Q125 + G184 | A174 + G348 | M248 + G477 | Q345 + K484 |
| V17 + L217 | V56 + N195 | Q125 + T193 | A174 + T355 | M248 + K484 | G346 + G348 |
| V17 + L219 | V56 + A204 | Q125 + N195 | A174 + S376 | L250 + G255 | G346 + T355 |
| V17 + L235 | V56 + V206 | Q125 + A204 | A174 + D377 | L250 + Q256 | G346 + S376 |
| V17 + V238 | V56 + P211 | Q125 + V206 | A174 + D379 | L250 + A263 | G346 + D377 |
| V17 + M246 | V56 + I214 | Q125 + P211 | A174 + Y382 | L250 + V264 | G346 + D379 |
| V17 + M248 | V56 + V215 | Q125 + I214 | A174 + S383 | L250 + Y267 | G346 + Y382 |
| V17 + L250 | V56 + L217 | Q125 + V215 | A174 + Q385 | L250 + N270 | G346 + S383 |
| V17 + G255 | V56 + L219 | Q125 + L217 | A174 + K391 | L250 + G273 | G346 + Q385 |
| V17 + Q256 | V56 + L235 | Q125 + L219 | A174 + K393 | L250 + S280 | G346 + K391 |
| V17 + A263 | V56 + V238 | Q125 + L235 | A174 + Q395 | L250 + T285 | G346 + K393 |
| V17 + V264 | V56 + M246 | Q125 + V238 | A174 + A420 | L250 + M286 | G346 + Q395 |
| V17 + Y267 | V56 + M248 | Q125 + M246 | A174 + G423 | L250 + F289 | G346 + A420 |
| V17 + N270 | V56 + L250 | Q125 + M248 | A174 + T444 | L250 + V291 | G346 + G423 |
| V17 + G273 | V56 + G255 | Q125 + L250 | A174 + A445 | L250 + Q299 | G346 + T444 |
| V17 + S280 | V56 + Q256 | Q125 + G255 | A174 + Q449 | L250 + R320 | G346 + A445 |
| V17 + T285 | V56 + A263 | Q125 + Q256 | A174 + T459 | L250 + H321 | G346 + Q449 |
| V17 + M286 | V56 + V264 | Q125 + A263 | A174 + P473 | L250 + S323 | G346 + T459 |
| V17 + F289 | V56 + Y267 | Q125 + V264 | A174 + C474 | L250 + H324 | G346 + P473 |
| V17 + V291 | V56 + N270 | Q125 + Y267 | A174 + G476 | L250 + F328 | G346 + C474 |
| V17 + Q299 | V56 + G273 | Q125 + N270 | A174 + G477 | L250 + T334 | G346 + G476 |
| V17 + R320 | V56 + S280 | Q125 + G273 | A174 + K484 | L250 + D337 | G346 + G477 |
| V17 + H321 | V56 + T285 | Q125 + S280 | G184 + T193 | L250 + Q345 | G346 + K484 |
| V17 + S323 | V56 + M286 | Q125 + T285 | G184 + N195 | L250 + G346 | G348 + T355 |
| V17 + H324 | V56 + F289 | Q125 + M286 | G184 + A204 | L250 + G348 | G348 + S376 |
| V17 + F328 | V56 + V291 | Q125 + F289 | G184 + V206 | L250 + T355 | G348 + D377 |
| V17 + T334 | V56 + Q299 | Q125 + V291 | G184 + P211 | L250 + S376 | G348 + D379 |
| V17 + D337 | V56 + R320 | Q125 + Q299 | G184 + I214 | L250 + D377 | G348 + Y382 |
| V17 + Q345 | V56 + H321 | Q125 + R320 | G184 + V215 | L250 + D379 | G348 + S383 |
| V17 + G346 | V56 + S323 | Q125 + H321 | G184 + L217 | L250 + Y382 | G348 + Q385 |
| V17 + G348 | V56 + H324 | Q125 + S323 | G184 + L219 | L250 + S383 | G348 + K391 |
| V17 + T355 | V56 + F328 | Q125 + H324 | G184 + L235 | L250 + Q385 | G348 + K393 |
| V17 + S376 | V56 + T334 | Q125 + F328 | G184 + V238 | L250 + K391 | G348 + Q395 |
| V17 + D377 | V56 + D337 | Q125 + T334 | G184 + M246 | L250 + K393 | G348 + A420 |
| V17 + D379 | V56 + Q345 | Q125 + D337 | G184 + M248 | L250 + Q395 | G348 + G423 |
| V17 + Y382 | V56 + G346 | Q125 + Q345 | G184 + L250 | L250 + A420 | G348 + T444 |
| V17 + S383 | V56 + G348 | Q125 + G346 | G184 + G255 | L250 + G423 | G348 + A445 |
| V17 + Q385 | V56 + T355 | Q125 + G348 | G184 + Q256 | L250 + T444 | G348 + Q449 |

-continued

| | | | | | |
|---|---|---|---|---|---|
| V17 + K391 | V56 + S376 | Q125 + T355 | G184 + A263 | L250 + A445 | G348 + T459 |
| V17 + K393 | V56 + D377 | Q125 + S376 | G184 + V264 | L250 + Q449 | G348 + P473 |
| V17 + Q395 | V56 + D379 | Q125 + D377 | G184 + Y267 | L250 + T459 | G348 + C474 |
| V17 + A420 | V56 + Y382 | Q125 + D379 | G184 + N270 | L250 + P473 | G348 + G476 |
| V17 + G423 | V56 + S383 | Q125 + Y382 | G184 + G273 | L250 + C474 | G348 + G477 |
| V17 + T444 | V56 + Q385 | Q125 + S383 | G184 + S280 | L250 + G476 | G348 + K484 |
| V17 + A445 | V56 + K391 | Q125 + Q385 | G184 + T285 | L250 + G477 | T355 + S376 |
| V17 + Q449 | V56 + K393 | Q125 + K391 | G184 + M286 | L250 + K484 | T355 + D377 |
| V17 + T459 | V56 + Q395 | Q125 + K393 | G184 + F289 | G255 + Q256 | T355 + D379 |
| V17 + P473 | V56 + A420 | Q125 + Q395 | G184 + V291 | G255 + A263 | T355 + Y382 |
| V17 + C474 | V56 + G423 | Q125 + A420 | G184 + Q299 | G255 + V264 | T355 + S383 |
| V17 + G476 | V56 + T444 | Q125 + G423 | G184 + R320 | G255 + Y267 | T355 + Q385 |
| V17 + G477 | V56 + A445 | Q125 + T444 | G184 + H321 | G255 + N270 | T355 + K391 |
| V17 + K484 | V56 + Q449 | Q125 + A445 | G184 + S323 | G255 + G273 | T355 + K393 |
| Q32 + A37 | V56 + T459 | Q125 + Q449 | G184 + H324 | G255 + S280 | T355 + Q395 |
| Q32 + T40 | V56 + P473 | Q125 + T459 | G184 + F328 | G255 + T285 | T355 + A420 |
| Q32 + P45 | V56 + C474 | Q125 + P473 | G184 + T334 | G255 + M286 | T355 + G423 |
| Q32 + W48 | V56 + G476 | Q125 + C474 | G184 + D337 | G255 + F289 | T355 + T444 |
| Q32 + G50 | V56 + G477 | Q125 + G476 | G184 + Q345 | G255 + V291 | T355 + A445 |
| Q32 + T51 | V56 + K484 | Q125 + G477 | G184 + G346 | G255 + Q299 | T355 + Q449 |
| Q32 + N54 | K72 + R87 | Q125 + K484 | G184 + G348 | G255 + R320 | T355 + T459 |
| Q32 + V56 | K72 + Q98 | G133 + T134 | G184 + T355 | G255 + H321 | T355 + P473 |
| Q32 + K72 | K72 + M105 | G133 + W140 | G184 + S376 | G255 + S323 | T355 + C474 |
| Q32 + R87 | K72 + G109 | G133 + G142 | G184 + D377 | G255 + H324 | T355 + G476 |
| Q32 + Q98 | K72 + F113 | G133 + G149 | G184 + D379 | G255 + F328 | T355 + G477 |
| Q32 + M105 | K72 + R116 | G133 + T165 | G184 + Y382 | G255 + T334 | T355 + K484 |
| Q32 + G109 | K72 + Q118 | G133 + W167 | G184 + S383 | G255 + D337 | S376 + D377 |
| Q32 + F113 | K72 + Q125 | G133 + R171 | G184 + Q385 | G255 + Q345 | S376 + D379 |
| Q32 + R116 | K72 + G133 | G133 + Q172 | G184 + K391 | G255 + G346 | S376 + Y382 |
| Q32 + Q118 | K72 + T134 | G133 + L173 | G184 + K393 | G255 + G348 | S376 + S383 |
| Q32 + Q125 | K72 + W140 | G133 + A174 | G184 + Q395 | G255 + T355 | S376 + Q385 |
| Q32 + G133 | K72 + G142 | G133 + G184 | G184 + A420 | G255 + S376 | S376 + K391 |
| Q32 + T134 | K72 + G149 | G133 + T193 | G184 + G423 | G255 + D377 | S376 + K393 |
| Q32 + W140 | K72 + T165 | G133 + N195 | G184 + T444 | G255 + D379 | S376 + Q395 |
| Q32 + G142 | K72 + W167 | G133 + A204 | G184 + A445 | G255 + Y382 | S376 + A420 |
| Q32 + G149 | K72 + R171 | G133 + V206 | G184 + Q449 | G255 + S383 | S376 + G423 |
| Q32 + T165 | K72 + Q172 | G133 + P211 | G184 + T459 | G255 + Q385 | S376 + T444 |
| Q32 + W167 | K72 + L173 | G133 + I214 | G184 + P473 | G255 + K391 | S376 + A445 |
| Q32 + R171 | K72 + A174 | G133 + V215 | G184 + C474 | G255 + K393 | S376 + Q449 |
| Q32 + Q172 | K72 + G184 | G133 + L217 | G184 + G476 | G255 + Q395 | S376 + T459 |
| Q32 + L173 | K72 + T193 | G133 + L219 | G184 + G477 | G255 + A420 | S376 + P473 |
| Q32 + A174 | K72 + N195 | G133 + L235 | G184 + K484 | G255 + G423 | S376 + C474 |
| Q32 + G184 | K72 + A204 | G133 + V238 | T193 + N195 | G255 + T444 | S376 + G476 |
| Q32 + T193 | K72 + V206 | G133 + M246 | T193 + A204 | G255 + A445 | S376 + G477 |
| Q32 + N195 | K72 + P211 | G133 + M248 | T193 + V206 | G255 + Q449 | S376 + K484 |
| Q32 + A204 | K72 + I214 | G133 + L250 | T193 + P211 | G255 + T459 | D377 + D379 |
| Q32 + V206 | K72 + V215 | G133 + G255 | T193 + I214 | G255 + P473 | D377 + Y382 |
| Q32 + P211 | K72 + L217 | G133 + Q256 | T193 + V215 | G255 + C474 | D377 + S383 |
| Q32 + I214 | K72 + L219 | G133 + A263 | T193 + L217 | G255 + G476 | D377 + Q385 |
| Q32 + V215 | K72 + L235 | G133 + V264 | T193 + L219 | G255 + G477 | D377 + K391 |
| Q32 + L217 | K72 + V238 | G133 + Y267 | T193 + L235 | G255 + K484 | D377 + K393 |
| Q32 + L219 | K72 + M246 | G133 + N270 | T193 + V238 | Q256 + A263 | D377 + Q395 |
| Q32 + L235 | K72 + M248 | G133 + G273 | T193 + M246 | Q256 + V264 | D377 + A420 |
| Q32 + V238 | K72 + L250 | G133 + S280 | T193 + M248 | Q256 + Y267 | D377 + G423 |
| Q32 + M246 | K72 + G255 | G133 + T285 | T193 + L250 | Q256 + N270 | D377 + T444 |
| Q32 + M248 | K72 + Q256 | G133 + M286 | T193 + G255 | Q256 + G273 | D377 + A445 |
| Q32 + L250 | K72 + A263 | G133 + F289 | T193 + Q256 | Q256 + S280 | D377 + Q449 |
| Q32 + G255 | K72 + V264 | G133 + V291 | T193 + A263 | Q256 + T285 | D377 + T459 |
| Q32 + Q256 | K72 + Y267 | G133 + Q299 | T193 + V264 | Q256 + M286 | D377 + P473 |
| Q32 + A263 | K72 + N270 | G133 + R320 | T193 + Y267 | Q256 + F289 | D377 + C474 |
| Q32 + V264 | K72 + G273 | G133 + H321 | T193 + N270 | Q256 + V291 | D377 + G476 |
| Q32 + Y267 | K72 + S280 | G133 + S323 | T193 + G273 | Q256 + Q299 | D377 + G477 |
| Q32 + N270 | K72 + T285 | G133 + H324 | T193 + S280 | Q256 + R320 | D377 + K484 |
| Q32 + G273 | K72 + M286 | G133 + F328 | T193 + T285 | Q256 + H321 | D379 + Y382 |
| Q32 + S280 | K72 + F289 | G133 + T334 | T193 + M286 | Q256 + S323 | D379 + S383 |
| Q32 + T285 | K72 + V291 | G133 + D337 | T193 + F289 | Q256 + H324 | D379 + Q385 |
| Q32 + M286 | K72 + Q299 | G133 + Q345 | T193 + V291 | Q256 + F328 | D379 + K391 |
| Q32 + F289 | K72 + R320 | G133 + G346 | T193 + Q299 | Q256 + T334 | D379 + K393 |
| Q32 + V291 | K72 + H321 | G133 + G348 | T193 + R320 | Q256 + D337 | D379 + Q395 |
| Q32 + Q299 | K72 + S323 | G133 + T355 | T193 + H321 | Q256 + Q345 | D379 + A420 |
| Q32 + R320 | K72 + H324 | G133 + S376 | T193 + S323 | Q256 + G346 | D379 + G423 |
| Q32 + H321 | K72 + F328 | G133 + D377 | T193 + H324 | Q256 + G348 | D379 + T444 |
| Q32 + S323 | K72 + T334 | G133 + D379 | T193 + F328 | Q256 + T355 | D379 + A445 |
| Q32 + H324 | K72 + D337 | G133 + Y382 | T193 + T334 | Q256 + S376 | D379 + Q449 |
| Q32 + F328 | K72 + Q345 | G133 + S383 | T193 + D337 | Q256 + D377 | D379 + T459 |
| Q32 + T334 | K72 + G346 | G133 + Q385 | T193 + Q345 | Q256 + D379 | D379 + P473 |
| Q32 + D337 | K72 + G348 | G133 + K391 | T193 + G346 | Q256 + Y382 | D379 + C474 |
| Q32 + Q345 | K72 + T355 | G133 + K393 | T193 + G348 | Q256 + S383 | D379 + G476 |
| Q32 + G346 | K72 + S376 | G133 + Q395 | T193 + T355 | Q256 + Q385 | D379 + G477 |

-continued

| | | | | | |
|---|---|---|---|---|---|
| Q32 + G348 | K72 + D377 | G133 + A420 | T193 + S376 | Q256 + K391 | D379 + K484 |
| Q32 + T355 | K72 + D379 | G133 + G423 | T193 + D377 | Q256 + K393 | Y382 + S383 |
| Q32 + S376 | K72 + Y382 | G133 + T444 | T193 + D379 | Q256 + Q395 | Y382 + Q385 |
| Q32 + D377 | K72 + S383 | G133 + A445 | T193 + Y382 | Q256 + A420 | Y382 + K391 |
| Q32 + D379 | K72 + Q385 | G133 + Q449 | T193 + S383 | Q256 + G423 | Y382 + K393 |
| Q32 + Y382 | K72 + K391 | G133 + T459 | T193 + Q385 | Q256 + T444 | Y382 + Q395 |
| Q32 + S383 | K72 + K393 | G133 + P473 | T193 + K391 | Q256 + A445 | Y382 + A420 |
| Q32 + Q385 | K72 + Q395 | G133 + C474 | T193 + K393 | Q256 + Q449 | Y382 + G423 |
| Q32 + K391 | K72 + A420 | G133 + G476 | T193 + Q395 | Q256 + T459 | Y382 + T444 |
| Q32 + K393 | K72 + G423 | G133 + G477 | T193 + A420 | Q256 + P473 | Y382 + A445 |
| Q32 + Q395 | K72 + T444 | G133 + K484 | T193 + G423 | Q256 + C474 | Y382 + Q449 |
| Q32 + A420 | K72 + A445 | T134 + W140 | T193 + T444 | Q256 + G476 | Y382 + T459 |
| Q32 + G423 | K72 + Q449 | T134 + G142 | T193 + A445 | Q256 + G477 | Y382 + P473 |
| Q32 + T444 | K72 + T459 | T134 + G149 | T193 + Q449 | Q256 + K484 | Y382 + C474 |
| Q32 + A445 | K72 + P473 | T134 + T165 | T193 + T459 | A263 + V264 | Y382 + G476 |
| Q32 + Q449 | K72 + C474 | T134 + W167 | T193 + P473 | A263 + Y267 | Y382 + G477 |
| Q32 + T459 | K72 + G476 | T134 + R171 | T193 + C474 | A263 + N270 | Y382 + K484 |
| Q32 + P473 | K72 + G477 | T134 + Q172 | T193 + G476 | A263 + G273 | S383 + Q385 |
| Q32 + C474 | K72 + K484 | T134 + L173 | T193 + G477 | A263 + S280 | S383 + K391 |
| Q32 + G476 | R87 + Q98 | T134 + A174 | T193 + K484 | A263 + T285 | S383 + K393 |
| Q32 + G477 | R87 + M105 | T134 + G184 | N195 + A204 | A263 + M286 | S383 + Q395 |
| Q32 + K484 | R87 + G109 | T134 + T193 | N195 + V206 | A263 + F289 | S383 + A420 |
| A37 + T40 | R87 + F113 | T134 + N195 | N195 + P211 | A263 + V291 | S383 + G423 |
| A37 + P45 | R87 + R116 | T134 + A204 | N195 + I214 | A263 + Q299 | S383 + T444 |
| A37 + W48 | R87 + Q118 | T134 + V206 | N195 + V215 | A263 + R320 | S383 + A445 |
| A37 + G50 | R87 + Q125 | T134 + P211 | N195 + L217 | A263 + H321 | S383 + Q449 |
| A37 + T51 | R87 + G133 | T134 + I214 | N195 + L219 | A263 + S323 | S383 + T459 |
| A37 + N54 | R87 + T134 | T134 + V215 | N195 + L235 | A263 + H324 | S383 + P473 |
| A37 + V56 | R87 + W140 | T134 + L217 | N195 + V238 | A263 + F328 | S383 + C474 |
| A37 + K72 | R87 + G142 | T134 + L219 | N195 + M246 | A263 + T334 | S383 + G476 |
| A37 + R87 | R87 + G149 | T134 + L235 | N195 + M248 | A263 + D337 | S383 + G477 |
| A37 + Q98 | R87 + T165 | T134 + V238 | N195 + L250 | A263 + Q345 | S383 + K484 |
| A37 + M105 | R87 + W167 | T134 + M246 | N195 + G255 | A263 + G346 | Q385 + K391 |
| A37 + G109 | R87 + R171 | T134 + M248 | N195 + Q256 | A263 + G348 | Q385 + K393 |
| A37 + F113 | R87 + Q172 | T134 + L250 | N195 + A263 | A263 + T355 | Q385 + Q395 |
| A37 + R116 | R87 + L173 | T134 + G255 | N195 + V264 | A263 + S376 | Q385 + A420 |
| A37 + Q118 | R87 + A174 | T134 + Q256 | N195 + Y267 | A263 + D377 | Q385 + G423 |
| A37 + Q125 | R87 + G184 | T134 + A263 | N195 + N270 | A263 + D379 | Q385 + T444 |
| A37 + G133 | R87 + T193 | T134 + V264 | N195 + G273 | A263 + Y382 | Q385 + A445 |
| A37 + T134 | R87 + N195 | T134 + Y267 | N195 + S280 | A263 + S383 | Q385 + Q449 |
| A37 + W140 | R87 + A204 | T134 + N270 | N195 + T285 | A263 + Q385 | Q385 + T459 |
| A37 + G142 | R87 + V206 | T134 + G273 | N195 + M286 | A263 + K391 | Q385 + P473 |
| A37 + G149 | R87 + P211 | T134 + S280 | N195 + F289 | A263 + K393 | Q385 + C474 |
| A37 + T165 | R87 + I214 | T134 + T285 | N195 + V291 | A263 + Q395 | Q385 + G476 |
| A37 + W167 | R87 + V215 | T134 + M286 | N195 + Q299 | A263 + A420 | Q385 + G477 |
| A37 + R171 | R87 + L217 | T134 + F289 | N195 + R320 | A263 + G423 | Q385 + K484 |
| A37 + Q172 | R87 + L219 | T134 + V291 | N195 + H321 | A263 + T444 | K391 + K393 |
| A37 + L173 | R87 + L235 | T134 + Q299 | N195 + S323 | A263 + A445 | K391 + Q395 |
| A37 + A174 | R87 + V238 | T134 + R320 | N195 + H324 | A263 + Q449 | K391 + A420 |
| A37 + G184 | R87 + M246 | T134 + H321 | N195 + F328 | A263 + T459 | K391 + G423 |
| A37 + T193 | R87 + M248 | T134 + S323 | N195 + T334 | A263 + P473 | K391 + T444 |
| A37 + N195 | R87 + L250 | T134 + H324 | N195 + D337 | A263 + C474 | K391 + A445 |
| A37 + A204 | R87 + G255 | T134 + F328 | N195 + Q345 | A263 + G476 | K391 + Q449 |
| A37 + V206 | R87 + Q256 | T134 + T334 | N195 + G346 | A263 + G477 | K391 + T459 |
| A37 + P211 | R87 + A263 | T134 + D337 | N195 + G348 | A263 + K484 | K391 + P473 |
| A37 + I214 | R87 + V264 | T134 + Q345 | N195 + T355 | V264 + Y267 | K391 + C474 |
| A37 + V215 | R87 + Y267 | T134 + G346 | N195 + S376 | V264 + N270 | K391 + G476 |
| A37 + L217 | H1 + Q169 | T134 + G348 | N195 + D377 | V264 + G273 | K391 + G477 |
| A37 + L219 | H1 + A186 | T134 + T355 | N195 + D379 | V264 + S280 | K391 + K484 |
| A37 + L235 | H1 + E190 | T134 + S376 | N195 + Y382 | V264 + T285 | K393 + Q395 |
| A37 + V238 | H1 + A225 | T134 + D377 | N195 + S383 | V264 + M286 | K393 + A420 |
| A37 + M246 | H1 + K242 | T134 + D379 | N195 + Q385 | V264 + F289 | K393 + G423 |
| A37 + M248 | H1 + S244 | T134 + Y382 | N195 + K391 | V264 + V291 | K393 + T444 |
| A37 + L250 | H1 + G258 | T134 + S383 | N195 + K393 | V264 + Q299 | K393 + A445 |
| A37 + G255 | H1 + N260 | T134 + Q385 | N195 + Q395 | V264 + R320 | K393 + Q449 |
| A37 + Q256 | H1 + K269 | T134 + K391 | N195 + A420 | V264 + H321 | K393 + T459 |
| A37 + A263 | H1 + W284 | T134 + K393 | N195 + G423 | V264 + S323 | K393 + P473 |
| A37 + V264 | H1 + Y295 | T134 + Q395 | N195 + T444 | V264 + H324 | K393 + C474 |
| A37 + Y267 | H1 + S304 | T134 + A420 | N195 + A445 | V264 + F328 | K393 + G476 |
| A37 + N270 | H1 + V326 | T134 + G423 | N195 + Q449 | V264 + T334 | K393 + G477 |
| A37 + G273 | T5 + Q169 | T134 + T444 | N195 + T459 | V264 + D337 | K393 + K484 |
| A37 + S280 | T5 + A186 | T134 + A445 | N195 + P473 | V264 + Q345 | Q395 + A420 |
| A37 + T285 | T5 + E190 | T134 + Q449 | N195 + C474 | V264 + G346 | Q395 + G423 |
| A37 + M286 | T5 + A225 | T134 + T459 | N195 + G476 | V264 + G348 | Q395 + T444 |
| A37 + F289 | T5 + K242 | T134 + P473 | N195 + G477 | V264 + T355 | Q395 + A445 |
| A37 + V291 | T5 + S244 | T134 + C474 | N195 + K484 | V264 + S376 | Q395 + Q449 |
| A37 + Q299 | T5 + G258 | T134 + G476 | A204 + V206 | V264 + D377 | Q395 + T459 |
| A37 + R320 | T5 + N260 | T134 + G477 | A204 + P211 | V264 + D379 | Q395 + P473 |
| A37 + H321 | T5 + K269 | T134 + K484 | A204 + I214 | V264 + Y382 | Q395 + C474 |

-continued

| | | | | | |
|---|---|---|---|---|---|
| A37 + S323 | T5 + W284 | W140 + G142 | A204 + V215 | V264 + S383 | Q395 + G476 |
| A37 + H324 | T5 + Y295 | W140 + G149 | A204 + L217 | V264 + Q385 | Q395 + G477 |
| A37 + F328 | T5 + S304 | W140 + T165 | A204 + L219 | V264 + K391 | Q395 + K484 |
| A37 + T334 | T5 + V326 | W140 + W167 | A204 + L235 | V264 + K393 | A420 + G423 |
| A37 + D337 | G7 + Q169 | W140 + R171 | A204 + V238 | V264 + Q395 | A420 + T444 |
| A37 + Q345 | G7 + A186 | W140 + Q172 | A204 + M246 | V264 + A420 | A420 + A445 |
| A37 + G346 | G7 + E190 | W140 + L173 | A204 + M248 | V264 + G423 | A420 + Q449 |
| A37 + G348 | G7 + A225 | W140 + A174 | A204 + L250 | V264 + T444 | A420 + T459 |
| A37 + T355 | G7 + K242 | W140 + G184 | A204 + G255 | V264 + A445 | A420 + P473 |
| A37 + S376 | G7 + S244 | W140 + T193 | A204 + Q256 | V264 + Q449 | A420 + C474 |
| A37 + D377 | G7 + G258 | W140 + N195 | A204 + A263 | V264 + T459 | A420 + G476 |
| A37 + D379 | G7 + N260 | W140 + A204 | A204 + V264 | V264 + P473 | A420 + G477 |
| A37 + Y382 | G7 + A265 | W140 + V206 | A204 + Y267 | V264 + C474 | A420 + K484 |
| A37 + S383 | G7 + K269 | W140 + P211 | A204 + N270 | V264 + G476 | G423 + T444 |
| A37 + Q385 | G7 + W284 | W140 + I214 | A204 + G273 | V264 + G477 | G423 + A445 |
| A37 + K391 | G7 + Y295 | W140 + V215 | A204 + S280 | V264 + K484 | G423 + Q449 |
| A37 + K393 | G7 + S304 | W140 + L217 | A204 + T285 | Y267 + N270 | G423 + T459 |
| A37 + Q395 | G7 + V326 | W140 + L219 | A204 + M286 | Y267 + G273 | G423 + P473 |
| A37 + A420 | Q11 + Q169 | W140 + L235 | A204 + F289 | Y267 + S280 | G423 + C474 |
| A37 + G423 | Q11 + A186 | W140 + V238 | A204 + V291 | Y267 + T285 | G423 + G476 |
| A37 + T444 | Q11 + E190 | W140 + M246 | A204 + Q299 | Y267 + M286 | G423 + G477 |
| A37 + A445 | Q11 + A225 | W140 + M248 | A204 + R320 | Y267 + F289 | G423 + K484 |
| A37 + Q449 | Q11 + K242 | W140 + L250 | A204 + H321 | Y267 + V291 | T444 + A445 |
| A37 + T459 | Q11 + S244 | W140 + G255 | A204 + S323 | Y267 + Q299 | T444 + Q449 |
| A37 + P473 | Q11 + G258 | W140 + Q256 | A204 + H324 | Y267 + R320 | T444 + T459 |
| A37 + C474 | Q11 + N260 | W140 + A263 | A204 + F328 | Y267 + H321 | T444 + P473 |
| A37 + G476 | Q11 + K269 | W140 + V264 | A204 + T334 | Y267 + S323 | T444 + C474 |
| A37 + G477 | Q11 + W284 | W140 + Y267 | A204 + D337 | Y267 + H324 | T444 + G476 |
| A37 + K484 | Q11 + Y295 | W140 + N270 | A204 + Q345 | Y267 + F328 | T444 + G477 |
| T40 + P45 | Q11 + S304 | W140 + G273 | A204 + G346 | Y267 + T334 | T444 + K484 |
| T40 + W48 | Q11 + V326 | W140 + S280 | A204 + G348 | Y267 + D337 | A445 + Q449 |
| T40 + G50 | N16 + Q169 | W140 + T285 | A204 + T355 | Y267 + Q345 | A445 + T459 |
| T40 + T51 | N16 + A186 | W140 + M286 | A204 + S376 | Y267 + G346 | A445 + P473 |
| T40 + N54 | N16 + E190 | W140 + F289 | A204 + D377 | Y267 + G348 | A445 + C474 |
| T40 + V56 | N16 + A225 | W140 + V291 | A204 + D379 | Y267 + T355 | A445 + G476 |
| T40 + K72 | N16 + K242 | W140 + Q299 | A204 + Y382 | Y267 + S376 | A445 + G477 |
| T40 + R87 | N16 + S244 | W140 + R320 | A204 + S383 | Y267 + D377 | A445 + K484 |
| T40 + Q98 | N16 + G258 | W140 + H321 | A204 + Q385 | Y267 + D379 | Q449 + T459 |
| T40 + M105 | N16 + N260 | W140 + S323 | A204 + K391 | Y267 + Y382 | Q449 + P473 |
| T40 + G109 | N16 + K269 | W140 + H324 | A204 + K393 | Y267 + S383 | Q449 + C474 |
| T40 + F113 | N16 + W284 | W140 + F328 | A204 + Q395 | Y267 + Q385 | Q449 + G476 |
| T40 + R116 | N16 + Y295 | W140 + T334 | A204 + A420 | Y267 + K391 | Q449 + G477 |
| T40 + Q118 | N16 + S304 | W140 + D337 | A204 + G423 | Y267 + K393 | Q449 + K484 |
| T40 + Q125 | N16 + V326 | W140 + Q345 | A204 + T444 | Y267 + Q395 | T459 + P473 |
| T40 + G133 | V17 + Q169 | W140 + G346 | A204 + A445 | Y267 + A420 | T459 + C474 |
| T40 + T134 | V17 + A186 | W140 + G348 | A204 + Q449 | Y267 + G423 | T459 + G476 |
| T40 + W140 | V17 + E190 | W140 + T355 | A204 + T459 | Y267 + T444 | T459 + G477 |
| T40 + G142 | V17 + A225 | W140 + S376 | A204 + P473 | Y267 + A445 | T459 + K484 |
| T40 + G149 | V17 + K242 | W140 + D377 | A204 + C474 | Y267 + Q449 | P473 + C474 |
| T40 + T165 | V17 + S244 | W140 + D379 | A204 + G476 | Y267 + T459 | P473 + G476 |
| T40 + W167 | V17 + G258 | W140 + Y382 | A204 + G477 | Y267 + P473 | P473 + G477 |
| T40 + R171 | V17 + N260 | W140 + S383 | A204 + K484 | G109 + Q169 | P473 + K484 |
| T40 + Q172 | V17 + K269 | W140 + Q385 | V206 + P211 | G109 + A186 | C474 + G476 |
| T40 + L173 | V17 + W284 | W140 + K391 | V206 + I214 | G109 + E190 | C474 + G477 |
| T40 + Q169 | V17 + Y295 | N54 + Q169 | K72 + Q169 | G109 + A225 | C474 + K484 |
| T40 + A186 | V17 + S304 | N54 + A186 | K72 + A186 | G109 + K242 | G476 + G477 |
| T40 + E190 | V17 + V326 | N54 + E190 | K72 + E190 | G109 + S244 | G476 + K484 |
| T40 + A225 | Q32 + Q169 | N54 + A225 | K72 + A225 | G109 + G258 | G477 + K484 |
| T40 + K242 | Q32 + A186 | N54 + K242 | K72 + K242 | G109 + N260 | G133 + Q169 |
| T40 + S244 | Q32 + E190 | N54 + S244 | K72 + S244 | G109 + K269 | G133 + A186 |
| T40 + G258 | Q32 + A225 | N54 + G258 | K72 + G258 | G109 + W284 | G133 + E190 |
| T40 + N260 | Q32 + K242 | N54 + N260 | K72 + N260 | G109 + Y295 | G133 + A225 |
| T40 + K269 | Q32 + S244 | N54 + K269 | K72 + K269 | G109 + S304 | G133 + K242 |
| T40 + W284 | Q32 + G258 | N54 + W284 | K72 + W284 | G109 + V326 | G133 + S244 |
| T40 + Y295 | Q32 + N260 | N54 + Y295 | K72 + Y295 | F113 + Q169 | G133 + G258 |
| T40 + S304 | Q32 + K269 | N54 + S304 | K72 + S304 | F113 + A186 | G133 + N260 |
| T40 + V326 | Q32 + W284 | N54 + V326 | K72 + V326 | F113 + E190 | G133 + K269 |
| P45 + Q169 | Q32 + Y295 | V56 + Q169 | R87 + Q169 | F113 + A225 | G133 + W284 |
| P45 + A186 | Q32 + S304 | V56 + A186 | R87 + A186 | F113 + K242 | G133 + Y295 |
| P45 + E190 | Q32 + V326 | V56 + E190 | R87 + E190 | F113 + S244 | G133 + S304 |
| P45 + A225 | A37 + Q169 | V56 + A225 | R87 + A225 | F113 + G258 | G133 + V326 |
| P45 + K242 | A37 + A186 | V56 + K242 | R87 + K242 | F113 + N260 | T134 + Q169 |
| P45 + S244 | A37 + E190 | V56 + S244 | R87 + S244 | F113 + K269 | T134 + A186 |
| P45 + G258 | A37 + A225 | V56 + G258 | R87 + G258 | F113 + W284 | T134 + E190 |
| P45 + N260 | A37 + K242 | V56 + N260 | R87 + N260 | F113 + Y295 | T134 + A225 |
| P45 + K269 | A37 + S244 | V56 + K269 | R87 + K269 | F113 + S304 | T134 + K242 |
| P45 + W284 | A37 + G258 | V56 + W284 | R87 + W284 | F113 + V326 | T134 + S244 |
| P45 + Y295 | A37 + N260 | V56 + Y295 | R87 + Y295 | R116 + Q169 | T134 + G258 |
| P45 + S304 | A37 + K269 | V56 + S304 | R87 + S304 | R116 + A186 | T134 + N260 |

-continued

| | | | | | |
|---|---|---|---|---|---|
| P45 + V326 | A37 + W284 | V56 + V326 | R87 + V326 | R116 + E190 | T134 + K269 |
| W48 + Q169 | A37 + Y295 | Q169 + R171 | Q98 + Q169 | R116 + A225 | T134 + W284 |
| W48 + A186 | A37 + S304 | Q169 + Q172 | Q98 + A186 | R116 + K242 | T134 + Y295 |
| W48 + E190 | A37 + V326 | Q169 + L173 | Q98 + E190 | R116 + S244 | T134 + S304 |
| W48 + A225 | G142 + Q169 | Q169 + A174 | Q98 + A225 | R116 + G258 | T134 + V326 |
| W48 + K242 | G142 + A186 | Q169 + G184 | Q98 + K242 | R116 + N260 | W140 + Q169 |
| W48 + S244 | G142 + E190 | Q169 + A186 | Q98 + S244 | R116 + K269 | W140 + A186 |
| W48 + G258 | G142 + A225 | Q169 + E190 | Q98 + G258 | R116 + W284 | W140 + E190 |
| W48 + N260 | G142 + K242 | Q169 + T193 | Q98 + N260 | R116 + Y295 | W140 + A225 |
| W48 + K269 | G142 + S244 | Q169 + N195 | Q98 + K269 | R116 + S304 | W140 + K242 |
| W48 + W284 | G142 + G258 | Q169 + A204 | Q98 + W284 | R116 + V326 | W140 + S244 |
| W48 + Y295 | G142 + N260 | Q169 + V206 | Q98 + Y295 | Q118 + Q169 | W140 + G258 |
| W48 + S304 | G142 + K269 | Q169 + P211 | Q98 + S304 | Q118 + A186 | W140 + N260 |
| W48 + V326 | G142 + W284 | Q169 + I214 | Q98 + V326 | Q118 + E190 | W140 + K269 |
| G50 + Q169 | G142 + Y295 | Q169 + V215 | M105 + Q169 | Q118 + A225 | W140 + W284 |
| G50 + A186 | G142 + S304 | Q169 + L217 | M105 + A186 | Q118 + K242 | W140 + Y295 |
| G50 + E190 | G142 + V326 | Q169 + L219 | M105 + E190 | Q118 + S244 | W140 + S304 |
| G50 + A225 | G149 + Q169 | Q169 + A225 | M105 + A225 | Q118 + G258 | W140 + V326 |
| G50 + K242 | G149 + A186 | Q169 + L235 | M105 + K242 | Q118 + N260 | E190 + L235 |
| G50 + S244 | G149 + E190 | Q169 + V238 | M105 + S244 | Q118 + K269 | A225 + V238 |
| G50 + G258 | G149 + A225 | Q169 + K242 | M105 + G258 | Q118 + W284 | A225 + K242 |
| G50 + N260 | G149 + K242 | Q169 + S244 | M105 + N260 | Q118 + Y295 | A225 + S244 |
| G50 + K269 | G149 + S244 | Q169 + M246 | M105 + K269 | Q118 + S304 | A225 + M246 |
| G50 + W284 | G149 + G258 | Q169 + M248 | M105 + W284 | Q118 + V326 | A225 + M248 |
| G50 + Y295 | G149 + N260 | Q169 + L250 | M105 + Y295 | Q125 + Q169 | A225 + L250 |
| G50 + S304 | G149 + K269 | Q169 + G255 | M105 + S304 | Q125 + A186 | A225 + G255 |
| G50 + V326 | G149 + W284 | Q169 + Q256 | M105 + V326 | Q125 + E190 | A225 + Q256 |
| T51 + Q169 | G149 + Y295 | Q169 + G258 | R171 + A186 | Q125 + A225 | A225 + G258 |
| T51 + A186 | G149 + S304 | Q169 + N260 | R171 + E190 | Q125 + K242 | A225 + N260 |
| T51 + E190 | G149 + V326 | Q169 + A263 | R171 + A225 | Q125 + S244 | A225 + A263 |
| T51 + A225 | T165 + Q169 | Q169 + V264 | R171 + K242 | Q125 + G258 | A225 + V264 |
| T51 + K242 | T165 + A186 | Q169 + Y267 | R171 + S244 | Q125 + N260 | A225 + Y267 |
| T51 + S244 | T165 + E190 | Q169 + K269 | R171 + G258 | Q125 + K269 | A225 + K269 |
| T51 + G258 | T165 + A225 | Q169 + N270 | R171 + N260 | Q125 + W284 | A225 + N270 |
| T51 + N260 | T165 + K242 | Q169 + G273 | R171 + K269 | Q125 + Y295 | A225 + G273 |
| T51 + K269 | T165 + S244 | Q169 + S280 | R171 + W284 | Q125 + S304 | A225 + S280 |
| T51 + W284 | T165 + G258 | Q169 + W284 | R171 + Y295 | Q125 + V326 | A225 + W284 |
| T51 + Y295 | T165 + N260 | Q169 + T285 | R171 + S304 | G184 + A186 | A225 + T285 |
| T51 + S304 | T165 + K269 | Q169 + M286 | R171 + V326 | G184 + E190 | A225 + M286 |
| T51 + V326 | T165 + W284 | Q169 + F289 | Q172 + A186 | G184 + A225 | A225 + F289 |
| A186 + E190 | T165 + Y295 | Q169 + V291 | Q172 + E190 | G184 + K242 | A225 + V291 |
| A186 + T193 | T165 + S304 | Q169 + Y295 | Q172 + A225 | G184 + S244 | A225 + Y295 |
| A186 + N195 | T165 + V326 | Q169 + Q299 | Q172 + K242 | G184 + G258 | A225 + Q299 |
| A186 + A204 | W167 + Q169 | Q169 + S304 | Q172 + S244 | G184 + N260 | A225 + S304 |
| A186 + V206 | W167 + A186 | Q169 + R320 | Q172 + G258 | G184 + K269 | A225 + R320 |
| A186 + P211 | W167 + E190 | Q169 + H321 | Q172 + N260 | G184 + W284 | A225 + H321 |
| A186 + I214 | W167 + A225 | Q169 + S323 | Q172 + K269 | G184 + Y295 | A225 + S323 |
| A186 + V215 | W167 + K242 | Q169 + H324 | Q172 + W284 | G184 + S304 | A225 + H324 |
| A186 + L217 | W167 + S244 | Q169 + V326 | Q172 + Y295 | G184 + V326 | A225 + V326 |
| A186 + L219 | W167 + G258 | Q169 + F328 | Q172 + S304 | L235 + K242 | A225 + F328 |
| A186 + A225 | W167 + N260 | Q169 + T334 | Q172 + V326 | L235 + S244 | A225 + T334 |
| A186 + L235 | W167 + K269 | Q169 + D337 | L173 + A186 | L235 + G258 | A225 + D337 |
| A186 + V238 | W167 + W284 | Q169 + Q345 | L173 + E190 | L235 + N260 | A225 + Q345 |
| A186 + K242 | W167 + Y295 | Q169 + G346 | L173 + A225 | L235 + K269 | A225 + G346 |
| A186 + S244 | W167 + S304 | Q169 + G348 | L173 + K242 | L235 + W284 | A225 + G348 |
| A186 + M246 | W167 + V326 | Q169 + T355 | L173 + S244 | L235 + Y295 | A225 + T355 |
| A186 + M248 | E190 + T193 | Q169 + S376 | L173 + G258 | L235 + S304 | A225 + S376 |
| A186 + L250 | E190 + N195 | Q169 + D377 | L173 + N260 | L235 + V326 | A225 + D377 |
| A186 + G255 | E190 + A204 | Q169 + D379 | L173 + K269 | V238 + K242 | A225 + D379 |
| A186 + Q256 | E190 + V206 | Q169 + Y382 | L173 + W284 | V238 + S244 | A225 + Y382 |
| A186 + G258 | E190 + P211 | Q169 + S383 | L173 + Y295 | V238 + G258 | A225 + S383 |
| A186 + N260 | E190 + I214 | Q169 + Q385 | L173 + S304 | V238 + N260 | A225 + Q385 |
| A186 + A263 | E190 + V215 | Q169 + K391 | L173 + V326 | V238 + K269 | A225 + K391 |
| A186 + V264 | E190 + L217 | Q169 + K393 | A174 + A186 | V238 + W284 | A225 + K393 |
| A186 + Y267 | E190 + L219 | Q169 + Q395 | A174 + E190 | V238 + Y295 | A225 + Q395 |
| A186 + K269 | E190 + A225 | Q169 + A420 | A174 + A225 | V238 + S304 | A225 + A420 |
| A186 + N270 | E190 + L235 | Q169 + G423 | A174 + K242 | V238 + V326 | A225 + G423 |
| A186 + G273 | E190 + V238 | Q169 + T444 | A174 + S244 | K242 + S244 | A225 + T444 |
| A186 + S280 | E190 + K242 | Q169 + A445 | A174 + G258 | K242 + M246 | A225 + A445 |
| A186 + W284 | E190 + S244 | Q169 + Q449 | A174 + N260 | K242 + M248 | A225 + Q449 |
| A186 + T285 | E190 + M246 | Q169 + T459 | A174 + K269 | K242 + L250 | A225 + T459 |
| A186 + M286 | E190 + M248 | Q169 + P473 | A174 + W284 | K242 + G255 | A225 + P473 |
| A186 + F289 | E190 + L250 | Q169 + C474 | A174 + Y295 | K242 + Q256 | A225 + C474 |
| A186 + V291 | E190 + G255 | Q169 + G476 | A174 + S304 | K242 + G258 | A225 + G476 |
| A186 + Y295 | E190 + Q256 | Q169 + G477 | A174 + V326 | K242 + N260 | A225 + G477 |
| A186 + Q299 | E190 + G258 | Q169 + K484 | L217 + A225 | K242 + A263 | A225 + K484 |
| A186 + S304 | E190 + N260 | T193 + A225 | L217 + K242 | K242 + V264 | S244 + M248 |
| A186 + R320 | E190 + A263 | T193 + K242 | L217 + S244 | K242 + Y267 | S244 + L250 |
| A186 + H321 | E190 + V264 | T193 + S244 | L217 + G258 | K242 + K269 | S244 + G255 |

-continued

| | | | | | |
|---|---|---|---|---|---|
| A186 + S323 | E190 + Y267 | T193 + G258 | L217 + N260 | K242 + N270 | S244 + Q256 |
| A186 + H324 | E190 + K269 | T193 + N260 | L217 + K269 | K242 + G273 | S244 + G258 |
| A186 + V326 | E190 + N270 | T193 + K269 | L217 + W284 | K242 + S280 | S244 + N260 |
| A186 + F328 | E190 + G273 | T193 + W284 | L217 + Y295 | K242 + W284 | S244 + A263 |
| A186 + T334 | E190 + S280 | T193 + Y295 | L217 + S304 | K242 + T285 | S244 + V264 |
| A186 + D337 | E190 + W284 | T193 + S304 | L217 + V326 | K242 + M286 | S244 + Y267 |
| A186 + Q345 | E190 + T285 | T193 + V326 | L219 + A225 | K242 + F289 | S244 + K269 |
| A186 + G346 | E190 + M286 | N195 + A225 | L219 + K242 | K242 + V291 | S244 + N270 |
| A186 + G348 | E190 + F289 | N195 + K242 | L219 + S244 | K242 + Y295 | S244 + G273 |
| A186 + T355 | E190 + V291 | N195 + S244 | L219 + G258 | K242 + Q299 | S244 + S280 |
| A186 + S376 | E190 + Y295 | N195 + G258 | L219 + N260 | K242 + S304 | S244 + W284 |
| A186 + D377 | E190 + Q299 | N195 + N260 | L219 + K269 | K242 + R320 | S244 + T285 |
| A186 + D379 | E190 + S304 | N195 + K269 | L219 + W284 | K242 + H321 | S244 + M286 |
| A186 + Y382 | E190 + R320 | N195 + W284 | L219 + Y295 | K242 + S323 | S244 + F289 |
| A186 + S383 | E190 + H321 | N195 + Y295 | L219 + S304 | K242 + H324 | S244 + V291 |
| A186 + Q385 | E190 + S323 | N195 + S304 | L219 + V326 | K242 + V326 | S244 + Y295 |
| A186 + K391 | E190 + H324 | N195 + V326 | M246 + G258 | K242 + F328 | S244 + Q299 |
| A186 + K393 | E190 + V326 | A204 + A225 | M246 + N260 | K242 + T334 | S244 + S304 |
| A186 + Q395 | E190 + F328 | A204 + K242 | M246 + K269 | K242 + D337 | S244 + R320 |
| A186 + A420 | E190 + T334 | A204 + S244 | M246 + W284 | K242 + Q345 | S244 + H321 |
| A186 + G423 | E190 + D337 | A204 + G258 | M246 + Y295 | K242 + G346 | S244 + S323 |
| A186 + T444 | E190 + Q345 | A204 + N260 | M246 + S304 | K242 + G348 | S244 + H324 |
| A186 + A445 | E190 + G346 | A204 + K269 | M246 + V326 | K242 + T355 | S244 + V326 |
| A186 + Q449 | E190 + G348 | A204 + W284 | M248 + G258 | K242 + S376 | S244 + F328 |
| A186 + T459 | E190 + T355 | A204 + Y295 | M248 + N260 | K242 + D377 | S244 + T334 |
| A186 + P473 | E190 + S376 | A204 + S304 | M248 + K269 | K242 + D379 | S244 + D337 |
| A186 + C474 | E190 + D377 | A204 + V326 | M248 + W284 | K242 + Y382 | S244 + Q345 |
| A186 + G476 | E190 + D379 | V206 + A225 | M248 + Y295 | K242 + S383 | S244 + G346 |
| A186 + G477 | E190 + Y382 | V206 + K242 | M248 + S304 | K242 + Q385 | S244 + G348 |
| A186 + K484 | E190 + S383 | V206 + S244 | M248 + V326 | K242 + K391 | S244 + T355 |
| I214 + A225 | E190 + Q385 | V206 + G258 | L250 + G258 | K242 + K393 | S244 + S376 |
| I214 + K242 | E190 + K391 | V206 + N260 | L250 + N260 | K242 + Q395 | S244 + D377 |
| I214 + S244 | E190 + K393 | V206 + K269 | L250 + K269 | K242 + A420 | S244 + D379 |
| I214 + G258 | E190 + Q395 | V206 + W284 | L250 + W284 | K242 + G423 | S244 + Y382 |
| I214 + N260 | E190 + A420 | V206 + Y295 | L250 + Y295 | K242 + T444 | S244 + S383 |
| I214 + K269 | E190 + G423 | V206 + S304 | L250 + S304 | K242 + A445 | S244 + Q385 |
| I214 + W284 | E190 + T444 | V206 + V326 | L250 + V326 | K242 + Q449 | S244 + K391 |
| I214 + Y295 | E190 + A445 | P211 + A225 | G255 + G258 | K242 + T459 | S244 + K393 |
| I214 + S304 | E190 + Q449 | P211 + K242 | G255 + N260 | K242 + P473 | S244 + Q395 |
| I214 + V326 | E190 + T459 | P211 + S244 | G255 + K269 | K242 + C474 | S244 + A420 |
| V215 + A225 | E190 + P473 | P211 + G258 | G255 + W284 | K242 + G476 | S244 + G423 |
| V215 + K242 | E190 + C474 | P211 + N260 | G255 + Y295 | K242 + G477 | S244 + T444 |
| V215 + S244 | E190 + G476 | P211 + K269 | G255 + S304 | K242 + K484 | S244 + A445 |
| V215 + G258 | E190 + G477 | P211 + W284 | G255 + V326 | N260 + A263 | S244 + Q449 |
| V215 + N260 | E190 + K484 | P211 + Y295 | Q256 + G258 | N260 + V264 | S244 + T459 |
| V215 + K269 | G258 + N260 | P211 + S304 | Q256 + N260 | N260 + Y267 | S244 + P473 |
| V215 + W284 | G258 + A263 | P211 + V326 | Q256 + K269 | N260 + K269 | S244 + C474 |
| V215 + Y295 | G258 + V264 | A236 + K269 | Q256 + W284 | N260 + N270 | S244 + G476 |
| V215 + S304 | G258 + Y267 | A236 + W284 | Q256 + Y295 | N260 + G273 | S244 + G477 |
| V215 + V326 | G258 + K269 | A236 + Y295 | Q256 + S304 | N260 + S280 | S244 + K484 |
| N270 + W284 | G258 + N270 | A236 + S304 | Q256 + V326 | N260 + W284 | K269 + N270 |
| N270 + Y295 | G258 + G273 | A236 + V326 | W284 + T285 | N260 + T285 | K269 + G273 |
| N270 + S304 | G258 + S280 | V264 + K269 | W284 + M286 | N260 + M286 | K269 + S280 |
| N270 + V326 | G258 + W284 | V264 + W284 | W284 + F289 | N260 + F289 | K269 + W284 |
| G273 + W284 | G258 + T285 | V264 + Y295 | W284 + V291 | N260 + V291 | K269 + T285 |
| G273 + Y295 | G258 + M286 | V264 + S304 | W284 + Y295 | N260 + Y295 | K269 + M286 |
| G273 + S304 | G258 + F289 | V267 + V326 | W284 + Q299 | N260 + Q299 | K269 + F289 |
| G273 + V326 | G258 + V291 | Y267 + K269 | W284 + S304 | N260 + S304 | K269 + V291 |
| S280 + W284 | G258 + Y295 | Y267 + W284 | W284 + R320 | N260 + R320 | K269 + Y295 |
| S280 + Y295 | G258 + Q299 | Y267 + Y295 | W284 + H321 | N260 + H321 | K269 + Q299 |
| S280 + S304 | G258 + S304 | Y267 + S304 | W284 + S323 | N260 + S323 | K269 + S304 |
| S280 + V326 | G258 + R320 | Y267 + V326 | W284 + H324 | N260 + H324 | K269 + R320 |
| T285 + Y295 | G258 + H321 | A288 + F289 | W284 + V326 | N260 + V326 | K269 + H321 |
| T285 + S304 | G258 + S323 | A288 + V291 | W284 + F328 | N260 + F328 | K269 + S323 |
| T285 + V326 | G258 + H324 | A288 + Y295 | W284 + T334 | N260 + T334 | K269 + H324 |
| M286 + Y295 | G258 + V326 | A288 + Q299 | W284 + D337 | N260 + D337 | K269 + V326 |
| M286 + S304 | G258 + F328 | A288 + S304 | W284 + Q345 | N260 + Q345 | K269 + F328 |
| M286 + V326 | G258 + T334 | A288 + R320 | W284 + G346 | N260 + G346 | K269 + T334 |
| F289 + Y295 | G258 + D337 | A288 + H321 | W284 + G348 | N260 + G348 | K269 + D337 |
| F289 + S304 | G258 + Q345 | A288 + S323 | W284 + T355 | N260 + T355 | K269 + Q345 |
| F289 + V326 | G258 + G346 | A288 + H324 | W284 + S376 | N260 + S376 | K269 + G346 |
| V291 + Y295 | G258 + G348 | A288 + V326 | W284 + D377 | N260 + D377 | K269 + G348 |
| V291 + S304 | G258 + T355 | A288 + F328 | W284 + D379 | N260 + D379 | K269 + T355 |
| V291 + V326 | G258 + S376 | A288 + T334 | W284 + Y382 | N260 + Y382 | K269 + S376 |
| Y295 + Q299 | G258 + D377 | A288 + D337 | W284 + S383 | N260 + S383 | K269 + D377 |
| Y295 + S304 | G258 + D379 | A288 + Q345 | W284 + Q385 | N260 + Q385 | K269 + D379 |
| Y295 + R320 | G258 + Y382 | A288 + G346 | W284 + K391 | N260 + K391 | K269 + Y382 |
| Y295 + H321 | G258 + S383 | A288 + G348 | W284 + K393 | N260 + K393 | K269 + S383 |
| Y295 + S323 | G258 + Q385 | A288 + T355 | W284 + Q395 | N260 + Q395 | K269 + Q385 |

-continued

| | | | | | |
|---|---|---|---|---|---|
| Y295 + H324 | G258 + K391 | A288 + S376 | W284 + A420 | N260 + A420 | K269 + K391 |
| Y295 + V326 | G258 + K393 | A288 + D377 | W284 + G423 | N260 + G423 | K269 + K393 |
| Y295 + F328 | G258 + Q395 | A288 + D379 | W284 + T444 | N260 + T444 | K269 + Q395 |
| Y295 + T334 | G258 + A420 | A288 + Y382 | W284 + A445 | N260 + A445 | K269 + A420 |
| Y295 + D337 | G258 + G423 | A288 + S383 | W284 + Q449 | N260 + Q449 | K269 + G423 |
| Y295 + Q345 | G258 + T444 | A288 + Q385 | W284 + T459 | N260 + T459 | K269 + T444 |
| Y295 + G346 | G258 + A445 | A288 + K391 | W284 + P473 | N260 + P473 | K269 + A445 |
| Y295 + G348 | G258 + Q449 | A288 + K393 | W284 + C474 | N260 + C474 | K269 + Q449 |
| Y295 + T355 | G258 + T459 | A288 + Q395 | W284 + G476 | N260 + G476 | K269 + T459 |
| Y295 + S376 | G258 + P473 | A288 + A420 | W284 + G477 | N260 + G477 | K269 + P473 |
| Y295 + D377 | G258 + C474 | A288 + G423 | W284 + K484 | N260 + K484 | K269 + C474 |
| Y295 + D379 | G258 + G476 | A288 + T444 | S304 + V326 | S304 + K393 | K269 + G476 |
| Y295 + Y382 | G258 + G477 | A288 + A445 | S304 + Y295 | S304 + Q395 | K269 + G477 |
| Y295 + S383 | G258 + K484 | A288 + Q449 | S304 + S304 | S304 + A420 | K269 + K484 |
| Y295 + Q385 | Q299 + S304 | A288 + T459 | S304 + V326 | S304 + G423 | S304 + T355 |
| Y295 + K391 | Q299 + V326 | A288 + P473 | S304 + Q299 | S304 + T444 | S304 + S376 |
| Y295 + K393 | R320 + V326 | A288 + C474 | S304 + S304 | S304 + A445 | S304 + D377 |
| Y295 + Q395 | H321 + V326 | A288 + G476 | S304 + R320 | S304 + Q449 | S304 + D379 |
| Y295 + A420 | S323 + V326 | A288 + G477 | S304 + H321 | S304 + T459 | S304 + Y382 |
| Y295 + G423 | H324 + V326 | A288 + K484 | S304 + S323 | S304 + P473 | S304 + S383 |
| Y295 + T444 | Y295 + P473 | S304 + Q345 | S304 + H324 | S304 + C474 | S304 + Q385 |
| Y295 + A445 | Y295 + C474 | S304 + G346 | S304 + V326 | S304 + G476 | S304 + K391 |
| Y295 + Q449 | Y295 + G476 | S304 + G348 | S304 + F328 | S304 + G477 | S304 + D337 |
| Y295 + T459 | Y295 + G477 | Y295 + K484 | S304 + T334 | S304 + K484 | |

wherein numbering is according to SEQ ID NO: 13; or

| | | | | | |
|---|---|---|---|---|---|
| H1 + A37 | N54 + F113 | K72 + G109 | R116 + A174 | T165 + A174 | N195 + V206 |
| H1 + T40 | N54 + R116 | K72 + F113 | R116 + G184 | T165 + G184 | N195 + L228 |
| H1 + N54 | N54 + N125 | K72 + R116 | R116 + N195 | T165 + N195 | N195 + G255 |
| H1 + V56 | N54 + F133 | K72 + N125 | R116 + G196 | T165 + G196 | N195 + A265 |
| H1 + A60 | N54 + T134 | K72 + F133 | R116 + A204 | T165 + A204 | N195 + S280 |
| H1 + K72 | N54 + T165 | K72 + T134 | R116 + V206 | T165 + V206 | N195 + S304 |
| H1 + G109 | N54 + Q172 | K72 + T165 | R116 + L228 | T165 + L228 | N195 + R320 |
| H1 + F113 | N54 + L173 | K72 + Q172 | R116 + G255 | T165 + G255 | N195 + H321 |
| H1 + R116 | N54 + A174 | K72 + L173 | R116 + A265 | T165 + A265 | N195 + S323 |
| H1 + N125 | N54 + G184 | K72 + A174 | R116 + S280 | T165 + S280 | N195 + K391 |
| H1 + F133 | N54 + N195 | K72 + G184 | R116 + S304 | T165 + S304 | G196 + A204 |
| H1 + T134 | N54 + G196 | K72 + N195 | R116 + R320 | T165 + R320 | G196 + V206 |
| H1 + T165 | N54 + A204 | K72 + G196 | R116 + H321 | T165 + H321 | G196 + L228 |
| H1 + Q172 | N54 + V206 | K72 + A204 | R116 + S323 | T165 + S323 | G196 + G255 |
| H1 + L173 | N54 + L228 | K72 + V206 | R116 + K391 | T165 + K391 | G196 + A265 |
| H1 + A174 | N54 + G255 | K72 + L228 | N125 + F133 | Q172 + L173 | G196 + S280 |
| H1 + G184 | N54 + A265 | K72 + G255 | N125 + T134 | Q172 + A174 | G196 + S304 |
| H1 + N195 | N54 + S280 | K72 + A265 | N125 + T165 | Q172 + G184 | G196 + R320 |
| H1 + G196 | N54 + S304 | K72 + S280 | N125 + Q172 | Q172 + N195 | G196 + H321 |
| H1 + A204 | N54 + R320 | K72 + S304 | N125 + L173 | Q172 + G196 | G196 + S323 |
| H1 + V206 | N54 + H321 | K72 + R320 | N125 + A174 | Q172 + A204 | G196 + K391 |
| H1 + L228 | N54 + S323 | K72 + H321 | N125 + G184 | Q172 + V206 | A204 + V206 |
| H1 + G255 | N54 + K391 | K72 + S323 | N125 + N195 | Q172 + L228 | A204 + L228 |
| H1 + A265 | V56 + A60 | K72 + K391 | N125 + G196 | Q172 + G255 | A204 + G255 |
| H1 + S280 | V56 + K72 | G109 + F113 | N125 + A204 | Q172 + A265 | A204 + A265 |
| H1 + S304 | V56 + G109 | G109 + R116 | N125 + V206 | Q172 + S280 | A204 + S280 |
| H1 + R320 | V56 + F113 | G109 + N125 | N125 + L228 | Q172 + S304 | A204 + S304 |
| H1 + H321 | V56 + R116 | G109 + F133 | N125 + G255 | Q172 + R320 | A204 + R320 |
| H1 + S323 | V56 + N125 | G109 + T134 | N125 + A265 | Q172 + H321 | A204 + H321 |
| H1 + K391 | V56 + F133 | G109 + T165 | N125 + S280 | Q172 + S323 | A204 + S323 |
| A37 + T40 | V56 + T134 | G109 + Q172 | N125 + S304 | Q172 + K391 | A204 + K391 |
| A37 + N54 | V56 + T165 | G109 + L173 | N125 + R320 | L173 + A174 | V206 + L228 |
| A37 + V56 | V56 + Q172 | G109 + A174 | N125 + H321 | L173 + G184 | V206 + G255 |
| A37 + A60 | V56 + L173 | G109 + G184 | N125 + S323 | L173 + N195 | V206 + A265 |
| A37 + K72 | V56 + A174 | G109 + N195 | N125 + K391 | L173 + G196 | V206 + S280 |
| A37 + G109 | V56 + G184 | G109 + G196 | F133 + T134 | L173 + A204 | V206 + S304 |
| A37 + F113 | V56 + N195 | G109 + A204 | F133 + T165 | L173 + V206 | V206 + R320 |
| A37 + R116 | V56 + G196 | G109 + V206 | F133 + Q172 | L173 + L228 | V206 + H321 |
| A37 + N125 | V56 + A204 | G109 + L228 | F133 + L173 | L173 + G255 | V206 + S323 |
| A37 + F133 | V56 + V206 | G109 + G255 | F133 + A174 | L173 + A265 | V206 + K391 |
| A37 + T134 | V56 + L228 | G109 + A265 | F133 + G184 | L173 + S280 | L228 + G255 |
| A37 + T165 | V56 + G255 | G109 + S280 | F133 + N195 | L173 + S304 | L228 + A265 |
| A37 + Q172 | V56 + A265 | G109 + S304 | F133 + G196 | L173 + R320 | L228 + S280 |
| A37 + L173 | V56 + S280 | G109 + R320 | F133 + A204 | L173 + H321 | L228 + S304 |
| A37 + A174 | V56 + S304 | G109 + H321 | F133 + V206 | L173 + S323 | L228 + R320 |
| A37 + G184 | V56 + R320 | G109 + S323 | F133 + L228 | L173 + K391 | L228 + H321 |
| A37 + N195 | V56 + H321 | G109 + K391 | F133 + G255 | A174 + G184 | L228 + S323 |
| A37 + G196 | V56 + S323 | F113 + R116 | F133 + A265 | A174 + N195 | L228 + K391 |
| A37 + A204 | V56 + K391 | F113 + N125 | F133 + S280 | A174 + G196 | G255 + A265 |

-continued

| | | | | | |
|---|---|---|---|---|---|
| A37 + V206 | A60 + K72 | F113 + F133 | F133 + S304 | A174 + A204 | G255 + S280 |
| A37 + L228 | A60 + G109 | F113 + T134 | F133 + R320 | A174 + V206 | G255 + S304 |
| A37 + G255 | A60 + F113 | F113 + T165 | F133 + H321 | A174 + L228 | G255 + R320 |
| A37 + A265 | A60 + R116 | F113 + Q172 | F133 + S323 | A174 + G255 | G255 + H321 |
| A37 + S280 | A60 + N125 | F113 + L173 | F133 + K391 | A174 + A265 | G255 + S323 |
| A37 + S304 | A60 + F133 | F113 + A174 | T134 + T165 | A174 + S280 | G255 + K391 |
| A37 + R320 | A60 + T134 | F113 + G184 | T134 + Q172 | A174 + S304 | A265 + S280 |
| A37 + H321 | A60 + T165 | F113 + N195 | T134 + L173 | A174 + R320 | A265 + S304 |
| A37 + S323 | A60 + Q172 | F113 + G196 | T134 + A174 | A174 + H321 | A265 + R320 |
| A37 + K391 | A60 + L173 | F113 + A204 | T134 + G184 | A174 + S323 | A265 + H321 |
| T40 + N54 | A60 + A174 | F113 + V206 | T134 + N195 | A174 + K391 | A265 + S323 |
| T40 + V56 | A60 + G184 | F113 + L228 | T134 + G196 | G184 + N195 | A265 + K391 |
| T40 + A60 | A60 + N195 | F113 + G255 | T134 + A204 | G184 + G196 | S280 + S304 |
| T40 + K72 | A60 + G196 | F113 + A265 | T134 + V206 | G184 + A204 | S280 + R320 |
| T40 + G109 | A60 + A204 | F113 + S280 | T134 + L228 | G184 + V206 | S280 + H321 |
| T40 + F113 | A60 + V206 | F113 + S304 | T134 + G255 | G184 + L228 | S280 + S323 |
| T40 + R116 | A60 + L228 | F113 + R320 | T134 + A265 | G184 + G255 | S280 + K391 |
| T40 + N125 | A60 + G255 | F113 + H321 | T134 + S280 | G184 + A265 | S304 + R320 |
| T40 + F133 | A60 + A265 | F113 + S323 | T134 + S304 | G184 + S280 | S304 + H321 |
| T40 + T134 | A60 + S280 | F113 + K391 | T134 + R320 | G184 + S304 | S304 + S323 |
| T40 + T165 | A60 + S304 | R116 + N125 | T134 + H321 | G184 + R320 | S304 + K391 |
| T40 + Q172 | A60 + R320 | R116 + F133 | T134 + S323 | G184 + H321 | R320 + H321 |
| T40 + L173 | A60 + H321 | R116 + T134 | T134 + K391 | G184 + S323 | R320 + S323 |
| T40 + A174 | A60 + S323 | R116 + T165 | T165 + Q172 | G184 + K391 | R320 + K391 |
| T40 + G184 | A60 + K391 | R116 + Q172 | T165 + L173 | N195 + G196 | H321 + S323 |
| T40 + N195 | T40 + S323 | R116 + L173 | H1 + Q169 | N195 + A204 | H321 + K391 |
| T40 + G196 | T40 + K391 | T40 + A265 | H1 + A186 | S244 + G255 | S323 + K391 |
| T40 + A204 | N54 + V56 | T40 + S280 | H1 + E190 | S244 + G258 | A265 + K269 |
| T40 + V206 | N54 + A60 | T40 + S304 | H1 + A225 | S244 + N260 | A265 + W284 |
| T40 + L228 | N54 + K72 | T40 + R320 | H1 + K242 | S244 + A265 | A265 + Y295 |
| T40 + G255 | N54 + G109 | T40 + H321 | H1 + S244 | S244 + K269 | A265 + S304 |
| T40 + Q169 | R116 + Q169 | A204 + A225 | H1 + G258 | S244 + S280 | A265 + V326 |
| T40 + A186 | R116 + A186 | A204 + K242 | H1 + N260 | S244 + W284 | K269 + S280 |
| T40 + E190 | R116 + E190 | A204 + S244 | H1 + K269 | S244 + Y295 | K269 + W284 |
| T40 + A225 | R116 + A225 | A204 + G258 | H1 + W284 | S244 + S304 | K269 + Y295 |
| T40 + K242 | R116 + K242 | A204 + N260 | H1 + Y295 | S244 + R320 | K269 + S304 |
| T40 + S244 | R116 + S244 | A204 + K269 | H1 + S304 | S244 + H321 | K269 + R320 |
| T40 + G258 | R116 + G258 | A204 + W284 | H1 + V326 | S244 + S323 | K269 + H321 |
| T40 + N260 | R116 + N260 | A204 + Y295 | A37 + Q169 | S244 + V326 | K269 + S323 |
| T40 + K269 | R116 + K269 | A204 + S304 | A37 + A186 | S244 + K391 | K269 + V326 |
| T40 + W284 | R116 + W284 | V206 + A225 | A37 + E190 | S244 + I405 | K269 + K391 |
| T40 + Y295 | R116 + Y295 | V206 + K242 | A37 + A225 | S244 + A421 | K269 + I405 |
| T40 + S304 | R116 + S304 | V206 + S244 | A37 + K242 | S244 + A422 | K269 + A421 |
| T40 + V326 | N125 + Q169 | V206 + G258 | A37 + S244 | S244 + A428 | K269 + A422 |
| N54 + Q169 | N125 + A186 | V206 + N260 | A37 + G258 | S244 + G448 | K269 + A428 |
| N54 + A186 | N125 + E190 | V206 + K269 | A37 + N260 | S244 + D476 | K269 + G448 |
| N54 + E190 | N125 + A225 | V206 + W284 | A37 + K269 | S244 + G477 | K269 + D476 |
| N54 + A225 | N125 + K242 | V206 + Y295 | A37 + W284 | G255 + G258 | K269 + G477 |
| N54 + K242 | N125 + S244 | V206 + S304 | A37 + Y295 | G255 + N260 | S280 + W284 |
| N54 + S244 | N125 + G258 | V206 + V326 | A37 + S304 | G255 + K269 | S280 + Y295 |
| N54 + G258 | N125 + N260 | A225 + L228 | A37 + V326 | G255 + W284 | S280 + S304 |
| N54 + N260 | N125 + K269 | A225 + K242 | Q172 + A186 | G255 + Y295 | S280 + V326 |
| N54 + K269 | N125 + W284 | A225 + S244 | Q172 + E190 | G255 + S304 | W284 + Y295 |
| N54 + W284 | N125 + Y295 | A225 + G255 | Q172 + A225 | G255 + V326 | W284 + S304 |
| N54 + Y295 | N125 + S304 | A225 + G258 | Q172 + K242 | G258 + N260 | W284 + R320 |
| N54 + S304 | F133 + Q169 | A225 + N260 | Q172 + S244 | G258 + A265 | W284 + H321 |
| N54 + V326 | F133 + A186 | A225 + A265 | Q172 + G258 | G258 + K269 | W284 + S323 |
| V56 + Q169 | F133 + E190 | A225 + K269 | Q172 + N260 | G258 + S280 | W284 + V326 |
| V56 + A186 | F133 + A225 | A225 + S280 | Q172 + K269 | G258 + W284 | W284 + K391 |
| V56 + E190 | F133 + K242 | A225 + W284 | Q172 + W284 | G258 + Y295 | W284 + I405 |
| V56 + A225 | F133 + S244 | A225 + Y295 | Q172 + Y295 | G258 + S304 | W284 + A421 |
| V56 + K242 | F133 + G258 | A225 + S304 | Q172 + S304 | G258 + R320 | W284 + A422 |
| V56 + S244 | F133 + N260 | A225 + R320 | L173 + A186 | G258 + H321 | W284 + A428 |
| V56 + G258 | F133 + K269 | A225 + H321 | L173 + E190 | G258 + S323 | W284 + G448 |
| V56 + N260 | F133 + W284 | A225 + S323 | L173 + A225 | G258 + V326 | W284 + D476 |
| V56 + K269 | F133 + Y295 | A225 + V326 | L173 + K242 | G258 + K391 | W284 + G477 |
| V56 + W284 | F133 + S304 | A225 + K391 | L173 + S244 | G258 + I405 | Y295 + S304 |
| V56 + Y295 | T134 + Q169 | A225 + I405 | L173 + G258 | G258 + A421 | Y295 + R320 |
| V56 + S304 | T134 + A186 | A225 + A421 | L173 + N260 | G258 + A422 | Y295 + H321 |
| V56 + V326 | T134 + E190 | A225 + A422 | L173 + K269 | G258 + A428 | Y295 + S323 |
| A60 + Q169 | T134 + A225 | A225 + A428 | L173 + W284 | G258 + G448 | Y295 + V326 |
| A60 + A186 | T134 + K242 | A225 + G448 | L173 + Y295 | G258 + D476 | Y295 + K391 |
| A60 + E190 | T134 + S244 | A225 + D476 | L173 + S304 | G258 + G477 | Y295 + I405 |
| A60 + A225 | T134 + G258 | A225 + G477 | A174 + A186 | N260 + A265 | Y295 + A421 |
| A60 + K242 | T134 + N260 | L228 + K242 | A174 + E190 | N260 + K269 | Y295 + A422 |
| A60 + S244 | T134 + K269 | L228 + S244 | A174 + A225 | N260 + S280 | Y295 + A428 |
| A60 + G258 | T134 + W284 | L228 + G258 | A174 + K242 | N260 + W284 | Y295 + G448 |
| A60 + N260 | T134 + Y295 | L228 + N260 | A174 + S244 | N260 + Y295 | Y295 + D476 |
| A60 + K269 | T134 + S304 | L228 + K269 | A174 + G258 | N260 + S304 | Y295 + G477 |

-continued

| | | | | | |
|---|---|---|---|---|---|
| A60 + W284 | T134 + V326 | L228 + W284 | A174 + N260 | N260 + R320 | S304 + R320 |
| A60 + Y295 | T165 + Q169 | L228 + Y295 | A174 + K269 | N260 + H321 | S304 + H321 |
| A60 + S304 | T165 + A186 | L228 + S304 | A174 + W284 | N260 + S323 | S304 + S323 |
| A60 + V326 | T165 + E190 | L228 + V326 | A174 + Y295 | N260 + V326 | S304 + V326 |
| K72 + Q169 | T165 + N195 | K242 + S244 | A174 + S304 | N260 + K391 | S304 + K391 |
| K72 + A186 | T165 + A225 | K242 + G255 | G184 + A186 | N260 + I405 | S304 + I405 |
| K72 + E190 | T165 + K242 | K242 + G258 | G184 + E190 | N260 + A421 | S304 + A421 |
| K72 + A225 | T165 + S244 | K242 + N260 | G184 + A225 | N260 + A422 | S304 + A422 |
| K72 + K242 | T165 + G258 | K242 + A265 | G184 + K242 | N260 + A428 | S304 + A428 |
| K72 + S244 | T165 + N260 | K242 + K269 | G184 + S244 | N260 + G448 | S304 + G448 |
| K72 + G258 | T165 + K269 | K242 + S280 | G184 + G258 | N260 + D476 | S304 + D476 |
| K72 + N260 | T165 + W284 | K242 + W284 | G184 + N260 | N260 + G477 | S304 + G477 |
| K72 + K269 | T165 + Y295 | K242 + Y295 | G184 + K269 | N195 + A225 | R320 + H321 |
| K72 + W284 | T165 + S304 | K242 + S304 | G184 + W284 | N195 + K242 | R320 + V326 |
| K72 + Y295 | Q169 + Q172 | K242 + R320 | G184 + Y295 | N195 + S244 | H321 + V326 |
| K72 + S304 | Q169 + L173 | K242 + H321 | G184 + S304 | N195 + G258 | S323 + V326 |
| G109 + Q169 | Q169 + A174 | K242 + S323 | A186 + E190 | N195 + N260 | V326 + K391 |
| G109 + A186 | Q169 + G184 | K242 + V326 | A186 + N195 | N195 + K269 | V326 + I405 |
| G109 + E190 | Q169 + A186 | K242 + K391 | A186 + G196 | N195 + W284 | V326 + A421 |
| G109 + A225 | Q169 + E190 | K242 + I405 | A186 + A204 | N195 + Y295 | V326 + A422 |
| G109 + K242 | Q169 + N195 | K242 + A421 | A186 + V206 | N195 + S304 | V326 + A428 |
| G109 + S244 | Q169 + G196 | K242 + A422 | A186 + A225 | N195 + V326 | V326 + G448 |
| G109 + G258 | Q169 + A204 | K242 + A428 | A186 + L228 | G196 + A225 | V326 + D476 |
| G109 + N260 | Q169 + V206 | K242 + G448 | A186 + K242 | G196 + K242 | V326 + G477 |
| G109 + K269 | Q169 + A225 | K242 + D476 | A186 + S244 | G196 + S244 | E190 + Y295 |
| G109 + W284 | Q169 + L228 | K242 + G477 | A186 + G255 | G196 + G258 | E190 + S304 |
| G109 + Y295 | Q169 + K242 | E190 + A204 | A186 + G258 | G196 + N260 | E190 + R320 |
| G109 + S304 | Q169 + S244 | E190 + V206 | A186 + N260 | G196 + K269 | E190 + H321 |
| G109 + V326 | Q169 + G255 | E190 + A225 | A186 + A265 | G196 + W284 | E190 + S323 |
| F113 + Q169 | Q169 + G258 | E190 + L228 | A186 + K269 | G196 + Y295 | E190 + V326 |
| F113 + A186 | Q169 + N260 | E190 + K242 | A186 + S280 | G196 + S304 | E190 + K391 |
| F113 + E190 | Q169 + A265 | E190 + S244 | A186 + W284 | G196 + V326 | E190 + I405 |
| F113 + A225 | Q169 + K269 | E190 + G255 | A186 + Y295 | A186 + G448 | E190 + A421 |
| F113 + K242 | Q169 + S280 | E190 + G258 | A186 + S304 | A186 + D476 | E190 + A422 |
| F113 + S244 | Q169 + W284 | E190 + N260 | A186 + R320 | A186 + G477 | E190 + A428 |
| F113 + G258 | Q169 + Y295 | E190 + A265 | A186 + H321 | E190 + N195 | E190 + G448 |
| F113 + N260 | Q169 + S304 | E190 + K269 | A186 + S323 | E190 + G196 | E190 + D476 |
| F113 + K269 | Q169 + R320 | E190 + S280 | A186 + V326 | Q169 + A422 | E190 + G477 |
| F113 + W284 | Q169 + H321 | E190 + W284 | A186 + K391 | Q169 + A428 | A186 + A422 |
| F113 + Y295 | Q169 + S323 | Q169 + I405 | A186 + I405 | Q169 + G448 | A186 + A428 |
| F113 + S304 | Q169 + V326 | Q169 + A421 | A186 + A421 | Q169 + D476 | |
| F113 + V326 | Q169 + K391 | | | Q169 + G477 | |

wherein numbering is according to SEQ ID NO: 14.

Stability of a parent polypeptide may be improved by introducing a pairwise deletion within the B domain of parent polypeptide. Thus, in one embodiment, the said variant comprises a) a deletion and/or a substitution at two or more positions corresponding to positions R181, G182, D183, and G184 of the amino acid sequence as set forth in SEQ ID NOs: 7 or 10, and b) an alteration at one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q172, L173, A174, G184, N195, G196, A204, V206, L228, G255, A265, S280, S304, R320, H321, S323, K391, I405, A421, A422, A428, R439, G448, W467, D476, and G477 of SEQ ID NO: 14.

The term "pairwise deletion" as used herein, refers to a deletion of an amino acid in two positions. Said two positions may be adjacent to one another but may also be separated by one, two, three, four, or five amino acids.

In a particular embodiment, the deletion a) is selected from the group consisting of R181+G182, R181+D183, R181+G184, G182+D183, G182+G184, or D183+G184.

In an embodiment, variant comprises one or more of the following alterations; H1*, T5K, G7K, G7A, Q11H, N16S, N16H, V17L, Q32S, A37H, A37M, A37V, A37S, A37Y, A37R, A37L, T40G, T40K, P45A, W48G, W48Y, W48F, G50A, T51K, T51E, T51G, T51A, T51S, T51G, T51D, N54S, V56T, K72R, K72H, K72S, K72Q, K72E, K72N, K72A, K72M, R87S, Q98S, Q98A, M105F, M105I, M105V, M105L, G109A, G109S, F113W, F113S, F113N, F113Y, F113R, F113L, F113Q, R116Q, R116V, R116K, R116W, R116L, R116A, R116H, R116M, R116E, R116S, R116I, R116G, Q118N, Q118K, Q118G, Q118S, Q118F, Q118R, Q125P, Q125K, Q125A, Q125T, G133S, T134E, W140Y, G142T, G149Q, T165S, T165G, T165V, W167I, W167G, W167F, W167R, W167S, W167H, W167L, W167M, W167Y, Q169E, R171H, Q172G, Q172R, Q172N, Q172D, Q172Y, Q172M, Q172S, Q172T, Q172K, Q172H, Q172E, L173V, L173G, L173H, L173A, L173I, L173P, L173T, L173F, L173M, A174S, A174D, A174P, A174M, A174T, A174H, A174K, A174G, A174Q, A174N, A174V, A174L, G184T, A186D, A186N, A186E, A186Q, A186H, E190P, T193K, N195F, A204T, A204V, A204S, A204G, V206L, V206S, V206Y, P211D, I214G, I214H, I214S, I214T, I214L, I214E, I214W, V215T, L217T, L217Q, L219V, L219H, A225V, L235V, L235A, V238A, V238T, V238G, K242Q, S244Q, M246L, M246A, M246I, M246F, M246V, M246S, M248T, L250I, L250V, L250T, L250A, L250F, L250M, G255N, G255A, G255S, Q256A, N260G, A263G, V264I, V264T, Y267I, Y267M, Y267H, Y267L, K269Q, N270G, N270T, G273R, S280W, S280L, S280T, S280A, 5280K, S280Q, W284H, T285L, T285Q, M286F, M286L, A288L, A288V, F289I, F289L, V291G, V291A, V291T, Y295F, Y295N, Q299V, S304R, S304N, R320A, R320V, H321Y, S323N, H324L, V326L, F328L, F328M, F328V, F328I, T334S, D337H, Q345D, G346T, G346D, G346P, G348S, G348P, T355L, T355F, S376H, S376T, S376V, D377H, D377S, D377A, D377Q, D379S, D379G, D379R, D379A, Y382M, Y382I, Y382L, Y382F, S383G, S383A, Q385L, K391A, K391Y, K391V, K391M, K391E, K391D, K391R, K391H, K391W, K391I, K391Q, K391L, K393Y, K393R, K393Q, K393S, Q395P, T400P, H402R, A420Q, A420S, A420K, A420L, G423H, T444Q, T444S, T444D, T444Y, T444H, T444V, T444R, T444A, A445Q, Q449T, T459N, P473R, P473A, P473G, P473T, P473K, C474V, G476K, G477A, G477Q, K484A, K484G, K484P, K484E, K484Q, and K484S of SEQ ID NO: 13; or H1*, G7A, A37H, T40D, W48Y, W48F, N54S, V56T, A60V, K72R, Q98A, G109A, F113Q, R116H, R116V, R116Q, N125D, F133Q, T134E, T165G, Q169E, Q172D, Q172G, Q172N, L173V, A174S, G184T, A186D, A186N, A186E, A186Q, A186H, E190P, N195F, G196R, A204G, V206L, V206Y, A225V, L228I, K242Q, S244Q, G255A, G255S, N260G, A265G, K269Q, N270T, S280Q, W284H, A288L, A288V, F289L, Y295F, Y295N, S304N, S304R, S304N, R320A, H321Y, S323N, V326L, K391A, I405L, A421H, A422P, A428T, G448D, D476K, D476G, D476N, D476Y, G477S, G477A, G477T, and G477Q of SEQ ID NO: 14.

In a particular embodiment, the variant has an IF of >1 when compared to said parent polypeptide, and wherein said variant is selected from G182*+D183*+N195F H1*+N54S+V56T+G109A+A174S+G182*+D183*+N195F+V206L+K391A+G476K H1*+N54S+V56T+R87S+G109A+A174S+G182*+D183*+N195F+V206L+K391A+G476K H1*+T40G+N54S+V56T+G109A+A174S+G182*+D183*+N195F+V206L+K391A+G476K H1*+T51K+N54S+V56T+G109A+A174S+G182*+D183*+N195F+V206L+K391A+G476K H1*+N54S+V56T+K72R+G109A+A174S+G182*+D183*+N195F+V206L+K391A+G476K H1*+N54S+V56T+K72H+G109A+A174S+G182*+D183*+N195F+V206L+K391A+G476K H1*+A37H+N54S+V56T+G109A+A174S+G182*+D183*+N195F+V206L+K391A+G476K H1*+A37M+N54S+V56T+G109A+A174S+G182*+D183*+N195F+V206L+K391A+G476K H1*+A37V+N54S+V56T+G109A+A174S+G182*+D183*+N195F+V206L+K391A+G476K H1*+A37S+N54S+V56T+G109A+A174S+G182*+D183*+N195F+V206L+K391A+G476K H1*+A37Y+N54S+V56T+G109A+A174S+G182*+D183*+N195F+V206L+K391A+G476K H1*+A37R+N54S+V56T+G109A+A174S+G182*+D183*+N195F+V206L+K391A+G476K H1*+N54S+V56T+G109A+F113W+A174S+G182*+D183*+N195F+V206L+K391A+G476K H1*+N54S+V56T+G109A+F113S+A174S+G182*+D183*+N195F+V206L+K391A+G476K H1*+N54S+V56T+G109A+F113N+A174S+G182*+D183*+N195F+V206L+K391A+G476K H1*+N54S+V56T+G109A+F113Y+A174S+G182*+D183*+N195F+V206L+K391A+G476K H1*+N54S+V56T+G109A+F113R+A174S+G182*+D183*+N195F+V206L+K391A+G476K H1*+N54S+V56T+G109A+Q118N+A174S+G182*+D183*+N195F+V206L+K391A+G476K H1*+N54S+V56T+G109A+R116Q+A174S+G182*+D183*+N195F+V206L+K391A+G476K H1*+N54S+V56T+G109A+R116V+A174S+G182*+D183*+N195F+V206L+K391A+G476K H1*+N54S+V56T+G109A+R116K+A174S+G182*+D183*+N195F+V206L+K391A+G476K H1*+N54S+V56T+G109A+R116W+A174S+G182*+D183*+N195F+V206L+K391A+G476K H1*+N54S+V56T+G109A+R116L+A174S+G182*+D183*+N195F+V206L+K391A+G476K H1*+N54S+V56T+G109A+G142T+A174S+G182*+D183*+N195F+V206L+K391A+G476K H1*+N54S+V56T+G109A+Q125P+A174S+G182*+D183*+N195F+V206L+K391A+G476K H1*+N54S+V56T+G109A+Q125K+A174S+G182*+D183*+N195F+V206L+K391A+G476K H1*+N54S+V56T+G109A+A174S+G182*+D183*+N195F+V206L+S381G+K391A+G476K H1*+N54S+V56T+G109A+A174S+G182*+D183*+N195F+V206L+M246T+K391A+G476K H1*+N54S+V56T+G109A+A174S+G182*+D183*+N195F+V206L+V213T+K391A+G476K H1*+A37L+N54S+V56T+G109A+A174S+G182*+D183*+N195F+V206L+K391A+G476K H1*+N54S+V56T+G109A+Q118K+A174S+G182*+D183*+N195F+V206L+K391A+G476K H1*+N54S+V56T+G109A+R116A+A174S+G182*+D183*+N195F+V206L+K391A+G476K H1*+N54S+V56T+G109A+R116H+A174S+G182*+D183*+N195F+V206L+K391A+G476K H1*+N54S+V56T+G109A+Q125A+A174S+G182*+D183*+N195F+V206L+K391A+G476K H1*+N54S+V56T+G109A+Q172G+A174S+G182*+D183*+N195F+V206L+K391A+G476K H1*+N54S+V56T+G109A+Q172R+A174S+G182*+D183*+N195F+V206L+K391A+G476K H1*+N54S+V56T+G109A+A174S+G182*+D183*+N195F+V206L+D377S+K391A+G476K H1*+N54S+V56T+G109A+A174S+G182*+D183*+N195F+V206L+D377G+K391A+G476K H1*+N54S+V56T+G109A+A174S+G182*+D183*+N195F+V206L+D377R+K391A+G476K H1*+N54S+V56T+G109A+A174S+G182*+D183*+N195F+V206L+D377A+K391A+G476K H1*+N54S+V56T+G109A+A174S+G182*+D183*+N195F+V206L+I214G+K391A+G476K H1*+N54S+V56T+G109A+A174S+G182*+D183*+N195F+V206L+S381A+K391A+G476K H1*+N54S+V56T+G109A+W167I+A174S+G182*+D183*+N195F+V206L+K391A+G476K H1*+N54S+V56T+G109A+W167G+A174S+G182*+D183*+N195F+V206L+K391A+G476K H1*+N54S+V56T+G109A+A174S+G182*+D183*+N195F+V206L+G346S+K391A+G476K H1*+N54S+V56T+G109A+A174S+G182*+D183*+N195F+V206L+G346P+K391A+G476K H1*+N54S+V56T+G109A+A174S+G182*+D183*+N195F+V206L+I214H+K391A+G476K H1*+N54S+V56T+G109A+A174S+G182*+D183*+N195F+V206L+I214S+K391A+G476K H1*+N54S+V56T+G109A+A174S+G182*+D183*+N195F+V206L+I214T+K391A+G476K H1*+N54S+V56T+G109A+A174S+G182*+D183*+N195F+V206L+K391A+A420Q+G476K H1*+N54S+V56T+G109A+A174S+G182*+D183*+N195F+V206L+K391A+A420S+G476K H1*+N54S+V56T+G109A+A174S+G182*+D183*+N195F+V206L+K391A+A420K+G476K H1*+N54S+V56T+G109A+A174S+G182*+D183*+N195F+V206L+K391A+A420L+G476K H1*+N54S+V56T+G109A+A174S+G182*+D183*+N195F+V206L+K391A+K391Y+G476K H1*+N54S+V56T+G109A+A174S+G182*+D183*+N195F+V206L+K391A+K391R+G476K H1*+N54S+V56T+G109A+A174S+G182*+D183*+N195F+V206L+K391A+P473R+G476K H1*+N54S+V56T+G109A+A174S+G182*+D183*+N195F+V206L+K391A+P473A+G476K H1*+N54S+V56T+G109A+A174S+G182*+D183*+N195F+V206L+K391A+P473G+

G476K H1*+N54S+V56T+G109A+A174S+G182*+D183*+N195F+V206L+K391A+P473T+G476K H1*+N54S+V56T+G109A+A174S+G182*+D183*+N195F+V206L+K391A+Q395P+G476K H1*+N54S+V56T+G109A+A174S+G182*+D183*+N195F+V206L+K391A+T444Q+G476K H1*+N54S+V56T+G109A+A174S+G182*+D183*+N195F+V206L+K391A+T444S+G476K H1*+N54S+V56T+G109A+A174S+G182*+D183*+N195F+V206L+K391A+T444D+G476K H1*+N54S+V56T+G109A+A174S+G182*+D183*+N195F+V206L+K391A+T444Y+G476K H1*+N54S+V56T+G109A+A174S+G182*+D183*+N195F+V206L+S280W+K391A+G476K H1*+N54S+V56T+G109A+A174S+G182*+D183*+N195F+V206L+S280L+K391A+G476K H1*+N54S+V56T+G109A+A174S+G182*+D183*+N195F+V206L+S280T+K391A+G476K H1*+N54S+V56T+G109A+A174S+G182*+D183*+N195F+V206L+S280A+K391A+G476K H1*+N54S+V56T+G109A+A174S+G182*+D183*+N195F+V206L+G255N+K391A+G476K H1*+N54S+V56T+G109A+A174S+G182*+D183*+N195F+V206L+T285L+K391A+G476K H1*+N54S+V56T+G109A+A174S+G182*+D183*+N195F+V206L+T285Q+K391A+G476K H1*+N54S+V56T+G109A+A174S+G182*+D183*+N195F+V206L+K391A+Q449T+G476K H1*+N54S+V56T+G109A+A174S+G182*+D183*+N195F+V206L+K391A+P473K+G476K H1*+N54S+V56T+K72S+G109A+A174S+G182*+D183*+N195F+V206L+K391A+G476K H1*+T40K+N54S+V56T+G109A+A174S+G182*+D183*+N195F+V206L+G346T+K391A+G476K H1*+G50A+N54S+V56T+G109A++Q172N+A174S+G182*+D183*+N195F+V206L+K391A+G476K H1*+N54S+V56T+G109A+A174S+G182*+D183*+N195F+V206L+K391A+G476K+K484A H1*+N54S+V56T+G109A+A174S+G182*+D183*+N195F+V206L+K391A+G476K+K484G H1*+N54S+V56T+G109A+A174S+G182*+D183*+N195F+V206L+K391A+G476K+K484P H1*+N54S+V56T+G109A+A174S+G182*+D183*+N195F+V206L+K391A+G476K+K484E H1*+N54S+V56T+G109A+A174S+G182*+D183*+N195F+V206L+K391A+G476K+K484Q H1*+N54S+V56T+G109A+A174S+G182*+D183*+N195F+V206L+K391A+G476K+K484S H1*K+G50A+N54S+V56T+G109A+W167F+A174S+G182*+D183*+N195F+V206L+K391A+G476K H1*+N54S+V56T+G109A+L173V+A174S+G182*+D183*+N195F+A204T+V206L+K391A+G476K H1*+N54S+V56T+G109A+W140Y+A174S+G182*+D183*+N195F+V206L+K391A+G476K H1*+N54S+V56T+Q98S+G109A+A174S+G182*+D183*+N195F+V206L+R320A+K391A+G476K H1*+N54S+V56T+G109A+A174S+G182*+D183*+N195F+V206L+H324L+K391A+G476K H1*+N54S+V56T+G109A+G149Q+A174S+G182*+D183*+N195F+V206L+K391A+G476K H1*+N54S+V56T+G109A+A174S+G182*+D183*+N195F+V206L+G346T+K391A+G476K+G477A H1*+N54S+V56T+G109AG255A++A174S+G182*+D183*+N195F+V206L+K391A+G476K H1*+G50A+N54S+V56T+G109A+F113L+R116L+A174S+G182*+D183*+N195F+V206L+K391A+G476K H1*+N54S+V56T+G109A+W167F+A174S+G182*+D183*+N195F+V206L+K391A+G476K H1*+N54S+V56T+G109A+L173V+A174S+G182*+D183*+N195F+V206L+K391A+G476K H1*+N54S+V56T+K72R+G109A+W167F+A174S+G182*+D183*+N195F+V206L+K391A+G476K H1*+N54S+V56T+G109A+A174S+G182*+D183*+N195F+V206L+K391A+G476K+G477Q H1*+N54S+V56T+G109A+A174S+G182*+D183*+N195F+V206L+Q345D+K391A+G476K+G477Q H1*+G50A+N54S+V56T+G109A+Q172D+A174S+G182*+D183*+N195F+V206L+K391A+G476K H1*+N54S+V56T+G109A+A174S+G182*+D183*+N195F+V206L+V264I+K391A+G423H+G476K H1*+N54S+V56T+G109A+A174S+G182*+D183*+N195F+V206L+R320V+K391A+G476Y H1*+T5K+N54S+V56T+G109A+A174S+G182*+D183*+N195F+V206L+K391A+G476K H1*+N54S+V56T+G109A+R116M+A174S+G182*+D183*+N195F+V206L+K391A+G476K H1*+N54S+V56T+G109A+Q172Y+A174S+G182*+D183*+N195F+V206L+K391A+G476K H1*+N54S+V56T+G109A+A174S+G182*+D183*+N195F+V206L+I214L+K391A+G476K H1*+N54S+V56T+G109A+A174S+G182*+D183*+N195F+V206L+L217V+K391A+G476K H1*+N54S+V56T+G109A+A174S+G182*+D183*+N195F+V206L+L217H+K391A+G476K H1*+N54S+V56T+G109A+A174S+G182*+D183*+N195F+V206L+P211D+K391A+G476K H1*+N54S+V56T+G109A+A174S+G182*+D183*+N195F+V206L+K391A+K391Q+G476K H1*+N54S+V56T+G109A+A174S+G182*+D183*+N195F+V206L+K391A+T444H+G476K H1*+N54S+V56T+G109A+A174S+G182*+D183*+N195F+V206L+K391A+T444V+G476K H1*+N54S+V56T+G109A+A174S+G182*+D183*+N195F+V206L+K391A+T444R+G476K H1*+G50A+N54S+V56T+G109A+L173V+A174S+G182*+D183*+N195F+A204V+V206L+K391A+G476K H1*+G50A+N54S+V56T+G109A+F113L+W167F+A174S+G182*+D183*+N195F+V206L+K391A+G476K H1*+G7K+N54S+V56T+G109A+A174S+G182*+D183*+N195F+V206L+R320A+K391A+G476K H1*+N54S+V56T+G109A+Q118G+A174S+G182*+D183*+N195F+V206L+K391A+G476K H1*+N54S+V56T+G109A+A174S+G182*+D183*+N195F+V206L+S280K+K391A+G476K H1*+N54S+V56T+G109A+A174S+G182*+D183*+N195F+V206L+N270G+K391A+G476K H1*+N54S+V56T+G109A+Q172D+A174S+G182*+D183*+N195F+V206L+G346T+K391A+G476K+G477A H1*+N54S+V56T+G109A+Q118S+A174S+G182*+D183*+N195F+V206L+K391A+G476K H1*+N54S+V56T+G109A+A174S+G182*+D183*+N195F+V206L+R320A+K391A+G476K H1*+N54S+V56T+G109A+T134E+A174S+G182*+D183*+N195F+V206L+K391A+G476K H1*+N54S+V56T+G109A+A174S+G182*+D183*+N195F+V206L+G337H+Q385L+K391A+G476K H1*+N54S+V56T+G109A+A174S+G182*+D183*+N195F+V206L+Y382M+K391A+G476K H1*+N54S+V56T+K72R+G109A+A174S+G182*+D183*+N195F+V206L+G255A+D377H+K391A+G476K H1*+N54S+V56T+K72R+G109A+T134E+A174S+G182*+D183*+N195F+V206L+G255A+K391A+G476K H1*+N54S+V56T+K72R+M105F+G109A+A174S+G182*+D183*+N195F+V206L+G255A+K391A+G476K H1*+N54S+V56T+M105F+G109A+T134E+A174S+G182*+D183*+N195F+V206L+K391A+G476K H1*+N54S+V56T+M105F+G109A+Q118F+T134E+A174S+G182*+D183*+N195F+V206L+K391A+G476K H1*+N54S+V56T+G109A+A174S+G182*+D183*+N195F+V206L+R320A+S323N+D377H+K391A+G476K H1*+T51E+N54S+V56T+G109A+A174H+G182*+D183*+N195F+V206L+K391A+G476K H1*+N54S+V56T+G109A+L173A+A174S+G182*+D183*+N195F+V206L+K391A+G476K H1*+N54S+V56T+G109A+A174S+G182*+D183*+N195F+V206L+Q299V+K391A+G476K H1*+N54S+V56T+G109A+L173G+A174S+G182*+D183*+N195F+V206L+K391A+G476K H1*+N54S+V56T+G109A+A174S+G182*+D183*+N195F+V206L+T355L+K391A+G476K H1*+N54S+V56T+G109A+A174S+G182*+D183*+

N195F+V206L+T355F+K391A+G476K H1*+G50A+N54S+V56T+G109A+A174S+G182*+D183*+N195F+A204T+V206L+K391A+G476K H1*+G50A+N54S+V56T+G109A+A174E+G182*+D183*+N195F+A204T+V206L+K391A+G476K H1*+N54S+V56T+K72R+G109A+A174S+G182*+D183*+N195F+V206L+R320A+S323N+K391A+G476K H1*+N54S+V56T+M105I+G109A+A174S+G182*+D183*+N195F+V206L+K391A+G476K H1*+N54S+V56T+G109A+A174S+G182*+D183*+N195F+V206L+M246L+K391A+G476K H1*+T51G+N54S+V56T+G109A+A174N+G182*+D183*+N195F+V206L+K391A+G476K H1*+T51A+N54S+V56T+G109A+A174G+G182*+D183*+N195F+V206L+K391A+G476K H1*+N54S+V56T+G109A+A174D+G182*+D183*+N195F+V206L+K391A+G476K H1*+T51S+N54S+V56T+G109A+A174P+G182*+D183*+N195F+V206L+K391A+G476K H1*+T51G+N54S+V56T+G109A+A174M+G182*+D183*+N195F+V206L+K391A+G476K H1*+N54S+V56T+K72A+G109A+W167S+A174S+G182*+D183*+N195F+V206L+K391A+G476K H1*+N54S+V56T+K72R+G109A+W167R+A174S+G182*+D183*+N195F+V206L+K391A+G476K H1*+N54S+V56T+K72Q+G109A+W167H+A174S+G182*+D183*+N195F+V206L+K391A+G476K H1*+N54S+V56T+G109A+Q118R+T134E+A174S+G182*+D183*+N195F+V206L+D377H+K391A+G476K H1*+Q11H+N54S+V56T+G109A+Q118R+T134E+A174S+G184T+G182*+D183*+N195F+V206L+D377H+K391A+G476K H1*+N54S+V56T+K72R+G109A+T134E+A174S+G182*+D183*+N195F+V206L+K391A+G476K H1*+N54S+V56T+K72R+G109A+T134E+A174S+G182*+D183*+N195F+V206L+D377H+K391A+G476K H1*+N54S+V56T+K72R+G109A+T134E+A174S+G182*+D183*+G184T+N195F+V206L+K391A+G476K H1*+N54S+V56T+G109A+Q118R+T134E+A174S+G182*+D183*+N195F+V206L+G255A+K391A+G476K H1*+N54S+V56T+G109A+Q118R+A174S+G182*+D183*+N195F+V206L+D377H+K391A+G476K H1*+N54S+V56T+G109A+T134E+A174S+G182*+D183*+G184T+N195F+V206L+D377H+K391A+G476K H1*+N54S+V56T+G109A+Q172D+A174Q+G182*+D183*+N195F+V206L+K391A+G476K+G477A H1*+N54S+V56T+K72A+G109A+W167F+A174S+G182*+D183*+N195F+V206L+K391A+G476K H1*+N54S+V56T+G109A+W167S+G182*+D183*+N195F+A174S+V206L+K391A+G476K H1*+N54S+V56T+K72H+G109A+W167S+A174S+G182*+D183*+N195F+V206L+K391A+G476K H1*+N54S+V56T+K72R+G109A+W167T+A174S+G182*+D183*+N195F+V206L+K391A+G476K H1*+N54S+V56T+K72E+G109A+A174S+G182*+D183*+N195F+V206L+K391A+G476K H1*+N54S+V56T+K72R+G109A+W167L+A174S+G182*+D183*+N195F+V206L+K391A+G476K H1*+N54S+V56T+K72R+G109A+W167M+A174S+G182*+D183*+N195F+V206L+K391A+G476K H1*+N54S+V56T+K72R+G109A+W167H+A174S+G182*+D183*+N195F+V206L+K391A+G476K H1*+N54S+V56T+K72R+G109A+A174S+G182*+D183*+G184T+N195F+V206L+G255A+K391A+G476K H1*+N54S+V56T+G109A+A174S+G182*+D183*+G184T+N195F+V206L+D377H+K391A+G476K H1*+N54S+V56T+G109A+A174S+G182*+D183*+N195F+V206L+G255A+D377H+K391A+G476K H1*+N54S+V56T+G109A+Q118R+A174S+G182*+D183*+N195F+V206L+G255A+D377H+K391A+G476K H1*+N54S+V56T+G109A+A174S+G182*+D183*+G184A+T193K+N195F+V206L+K391A+G476K H1*+N54S+V56T+M105F+G109A+A174S+G182*+D183*+G184T+N195F+V206L+K391A+G476K H1*+N54S+V56T+G109A+T134E+A174S+G182*+D183*+N195F+V206L+R320A+S323N+K391A+G476K H1*+N54S+V56T+G109A+A174S+G182*+D183*+N195F+V206L+V291G+D377H+K391A+G476K H1*+N54S+V56T+G109A+A174S+G182*+D183*+N195F+V206L+V291A+F328L+D377H+K391A+G476K H1*+V56T+G109A+A174S+G182*+D183*+N195F+V206L+D377H+K391A+G476K H1*+N54S+V56T+G109A+T134E+A174S+G182*+D183*+G184T+N195F+V206L+K391A+G476K H1*+N54S+V56T+G109A+A174S+G182*+D183*+N195F+V206L+V238A+D377H+K391A+G476K H1*+N54S+V56T+G109A+A174S+G182*+D183*+N195F+V206L+V238T+D377H+K391A+G476K H1*+N54S+V56T+G109A+A174S+G182*+D183*+N195F+V206L+V238G+D377H+K391A+G476K H1*+N54S+V56T+G109A+A174S+G182*+D183*+N195F+V206L+F328M+D377H+K391A+G476K H1*+N54S+V56T+G109A+A174S+G182*+D183*+N195F+V206L+F328L+D377H+K391A+G476K H1*+N54S+V56T+G109A+A174S+G182*+D183*+N195F+V206L+F328V+D377H+K391A+G476K H1*+N54S+V56T+G109A+A174S+G182*+D183*+N195F+V206L+F328I+D377H+K391A+G476K H1*+N54S+V56T+G109A+A174S+G182*+D183*+N195F+V206L+V291T+D377H+K391A+G476K H1*+N54S+V56T+G109A+A174S+G182*+D183*+N195F+V206L+V291A+D377H+K391A+G476K H1*+N54S+V56T+K72R+G109A+T134E+A174S+G182*+D183*+G184T+N195F+V206L+G255A+K391A+G476K H1*+N54S+V56T+G109A+L173H+A174S+G182*+D183*+N195F+V206L+K391A+G476K H1*+N54S+V56T+G109A+Q125T+A174S+G182*+D183*+N195F+V206L+K391A+G476K H1*+N16S+N54S+V56T+G109A+A174S+G182*+D183*+N195F+V206L+K391A+G476K H1*+N54S+V56T+K72N+G109A+A174S+G182*+D183*+N195F+V206L+K391A+G476K H1*+N54S+V56T+K72N+G109A+W167L+A174S+G182*+D183*+N195F+V206L+K391A+G476K H1*+N54S+V56T+K72A+G109A+W167Y+A174S+G182*+D183*+N195F+V206L+K391A+G476K H1*+N54S+V56T+G109A+Q118R+T134E+A174S+G182*+D183*+N195F+V206L+G255A+D377H+K391A+G476K H1*+N54S+V56T+K72R+G109A+A174S+G182*+D183*+N195F+G184T+V206L+K391A+G476K H1*+N54S+V56T+K72R+G109A+Q118R+A174S+G182*+D183*+N195F+V206L+G255A+D377H+K391A+G476K H1*+N54S+V56T+G109A+A174S+G182*+D183*+G184T+N195F+V206L+R320A+S323N+K391A+G476K H1*+N54S+G109A+A174S+G182*+D183*+N195F+V206L+D377H+K391A+G476K H1*+N54S+V56T+A174S+G182*+D183*+N195F+V206L+D377H+K391A+G476K H1*+N54S+V56T+G109A+G182*+D183*+N195F+V206L+D377H+K391A+G476K H1*+N54S+V56T+G109A+A174S+G182*+D183*+N195F+D377H+K391A+G476K H1*+N54S+V56T+G109A+A174S+G182*+D183*+N195F+D377H+K391A+G476K H1*+N54S+V56T+G109A+A174S+G182*+D183*+N195F+V206L+D377H+G476K H1*+N54S+V56T+G109A+A174S+G182*+D183*+N195F+V206L+D377H+K391A H1*+N54S+V56T+G109A+A174S+G182*+D183*+N195F+V206L+D377R+K391A+G476K H1*+N54S+V56T+G109A+A174S+G182*+D183*+N195F+V206L+L217T+K391A+G476K H1*+N54S+V56T+G109A+A174S+G182*+D183*+N195F+V206L+D377S+K391A+G476K H1*+N54S+V56T+G109A+R116E+A174S+G182*+D183*+N195F+V206L+K391A+G476K H1*+N54S+V56T+G109A+A174S+G182*+D183*+N195F+V206L+L217Q+K391A+

G476K H1*+N54S+V56T+G109A+A174S+G182*+D183*+N195F+V206L+G346D+K391A+G476K H1*+N54S+V56T+G109A+A174S+G182*+D183*+N195F+V206L+D377A+K391A+G476K H1*+N54S+V56T+G109A+T134E+A174S+G182*+D183*+N195F+V206L+D377H+K391A+G476K H1*+N54S+V56T+G109A+Q118R+T134E+A174S+G182*+D183*+G184T+N195F+V206L+K391A+G476K H1*+N54S+V56T+K72R+G109A+Q118R+T134E+A174S+G182*+D183*+N195F+V206L+K391A+G476K H1*+N54S+V56T+G109A+A174S+G182*+D183*+N195F+V206L+G346P+K391A+G476K H1*+N54S+V56T+G109A+R116S+A174S+G182*+D183*+N195F+V206L+K391A+G476K H1*+N54S+V56T+G109A+A174S+G182*+D183*+N195F+V206L+D377Q+K391A+G476K H1*+N54S+V56T+G109A+R116I+A174S+G182*+D183*+N195F+V206L+K391A+G476K H1*+N54S+V56T+G109A+A174F+G182*+D183*+N195F+V206L+K391A+G476K H1*+N54S+V56T+G109A+R116G+A174S+G182*+D183*+N195F+V206L+K391A+G476K H1*+N54S+V56T+G109A+A174T+G182*+D183*+N195F+V206L+K391A+G476K H1*+N54S+V56T+G109A+Q118R+T134E+A174S+G182*+D183*+G184T+N195F+V206L+G255A+K391A+G476K H1*+N54S+V56T+K72R+G109A+Q118R+T134E+A174S+G182*+D183*+N195F+V206L+G255A+K391A+G476K H1*+T51G+N54S+V56T+G109A+Q172R+A174S+G182*+D183*+N195F+V206L+K391A+G476K H1*+T51A+N54S+V56T+G109A+Q172D+A174S+G182*+D183*+N195F+V206L+K391A+G476K H1*+T51S+N54S+V56T+G109A+Q172M+A174S+G182*+D183*+N195F+V206L+K391A+G476K H1*+T51A+N54S+V56T+G109A+Q172S+A174S+G182*+D183*+N195F+V206L+K391A+G476K H1*+T51E+N54S+V56T+G109A+Q172T+A174S+G182*+D183*+N195F+V206L+K391A+G476K H1*+T51A+N54S+V56T+G109A+Q172A+A174S+G182*+D183*+N195F+V206L+K391A+G476K H1*+T51S+N54S+V56T+G109A+Q172N+A174S+G182*+D183*+N195F+V206L+K391A+G476K H1*+T51G+N54S+V56T+G109A+Q172K+A174S+G182*+D183*+N195F+V206L+K391A+G476K H1*+T51A+N54S+V56T+G109A+Q172G+A174S+G182*+D183*+N195F+V206L+K391A+G476K H1*+T51E+N54S+V56T+G109A+Q172L+A174S+G182*+D183*+N195F+V206L+K391A+G476K H1*+T51E+N54S+V56T+G109A+Q172R+A174S+G182*+D183*+N195F+V206L+K391A+G476K H1*+N54S+V56T+G109A+Q172K+A174S+G182*+D183*+N195F+V206L+K391A+G476K H1*+T51D+N54S+V56T+G109A+Q172N+A174S+G182*+D183*+N195F+V206L+K391A+G476K H1*+T51A+N54S+V56T+G109A+Q172K+A174S+G182*+D183*+N195F+V206L+K391A+G476K H1*+N54S+V56T+K72R+G109A+Q172S+A174S+G182*+D183*+N195F+V206L+K391A+G476K H1*+N54S+V56T+K72H+G109A+Q172T+A174S+G182*+D183*+N195F+V206L+K391A+G476K H1*+N54S+V56T+K72R+G109A+Q172R+A174S+K179E+G182*+D183*+N195F+V206L+K391A+G476K H1*+N54S+V56T+K72R+G109A+Q172M+A174S+G182*+D183*+N195F+V206L+Y295N+K391A+G476K H1*+N54S+V56T+K72R+G109A+Q172R+A174S+G182*+D183*+N195F+V206L+K391A+G476K H1*+N54S+V56T+K72Q+G109A+Q172R+A174S+G182*+D183*+N195F+V206L+K391A+G476K H1*+N54S+V56T+K72R+G109A+Q172T+A174S+G182*+D183*+N195F+V206L+K391A+G476K H1*+N54S+V56T+K72M+G109A+Q172S+A174S+G182*+D183*+N195F+V206L+K391A+G476K H1*+N54S+V56T+K72Q+G109A+Q172M+A174S+G182*+D183*+N195F+V206L+K391A+G476K H1*+N54S+V56T+G109A+Q172M+A174S+G182*+D183*+N195F+V206L+K391A+G476K H1*+N54S+V56T+K72S+G109A+A174H+G182*+D183*+N195F+V206L+K391A+G476K H1*+N54S+V56T+K72Q+G109A+A174D+G182*+D183*+N195F+V206L+K391A+G476K H1*+N54S+V56T+K72R+G109A+A174D+G182*+D183*+N195F+V206L+K391A+G476K H1*+N54S+V56T+K72Q+G109A+A174K+G182*+D183*+N195F+V206L+K391A+G476K H1*+N54S+V56T+G109A+A174G+G182*+D183*+N195F+V206L+K391A+G476K H1*+N54S+V56T+K72R+G109A+A174Q+G182*+D183*+N195F+V206L+K391A+G476K H1*+N54S+V56T+K72Q+G109A+A174G+G182*+D183*+N195F+V206L+K391A+G476K H1*+N54S+V56T+K72S+G109A+A174N+G182*+D183*+N195F+V206L+K391A+G476K H1*+N54S+V56T+K72R+G109A+A174H+G182*+D183*+N195F+V206L+K391A+G476K H1*+N54S+V56T+G109A+A174S+G182*+D183*+N195F+V206L+K391A+K391S+G476K H1*+N54S+V56T+G109A+A174S+G182*+D183*+N195F+V206L+K391A+T444A+G476K H1*+N54S+V56T+G109A+F113L+W167F+A174S+G182*+D183*+N195F+V206L+K391A+G476K H1*+G50A+N54S+V56T+G109A+A174E+G182*+D183*+N195F+A204T+V206L+S323N+K391A+G476K H1*+N54S+V56T+K72R+G109A+Q118R+A174S+G182*+D183*+G184T+N195F+V206L+G255A+K391A+G476K H1*+N54S+V56T+M105F+G109A+A174S+G182*+D183*+N195F+V206L+D377H+K391A+G476K H1*+N54S+V56T+K72R+G109A+Q118R+A174S+G182*+D183*+N195F+V206L+D377H+K391A+G476K H1*+N54S+V56T+G109A+A174S+G182*+D183*+N195F+A204G+V206L+K391A+G476K H1*+N54S+V56T+G109A+A174S+G182*+D183*+N195F+V206L+A225F+K391A+G476K H1*+N54S+V56T+G109A+A174S+G182*+D183*+N195F+V206L+M246A+K391A+G476K H1*+N54S+V56T+G109A+A174S+G182*+D183*+N195F+V206L+Y382I+K391A+G476K H1*+N54S+V56T+G109A+A174S+G182*+D183*+N195F+V206L+S376H+K391A+G476K H1*+N54S+V56T+G109A+A174S+G182*+D183*+N195F+V206L+I214E+K391A+G476K H1*+N54S+V56T+G109A+A174S+G182*+D183*+N195F+V206L+I214W+K391A+G476K H1*+N54S+V56T+K72R+G109A+Q172K+A174S+G182*+D183*+N195F+V206L+K391A+G476K H1*+N54S+V56T+G109A+A174S+G182*+D183*+N195F+A204T+V206L+D377H+K391A+G476K H1*+N54S+V56T+G109A+A174S+G182*+D183*+N195F+A204S+V206L+D377H+K391A+G476K H1*+N54S+V56T+G109A+T165S+A174S+G182*+D183*+N195F+V206L+D377H+K391A+G476K H1*+N54S+V56T+G109A+A174S+G182*+D183*+N195F+V206L+T334S+D377H+K391A+G476K H1*+N54S+V56T+G109A+A174S+G182*+D183*+N195F+V206L+A263G+D377H+K391A+G476K H1*+N54S+V56T+G109A+A174S+G182*+D183*+N195F+V206L+M286F+D377H+K391A+G476K H1*+N54S+V56T+G109A+A174S+G182*+D183*+N195F+V206L+Y267I+D377H+K391A+G476K H1*+N54S+V56T+G109A+A174S+G182*+D183*+N195F+V206L+L235V+D377H+K391A+G476K H1*+N54S+V56T+G109A+A174S+G182*+D183*+N195F+V206L+L235A+D377H+K391A+G476K H1*+N54S+V56T+M105L+G109A+A174S+G182*+D183*+N195F+V206L+D377H+K391A+G476K H1*+N54S+V56T+M105I+G109A+A174S+G182*+D183*+N195F+V206L+D377H+K391A+G476K H1*+N54S+V56T+M105V+G109A+A174S+G182*+D183*+

N195F+V206L+D377H+K391A+G476K H1*+N54S+V56T+G109A+A174S+G182*+D183*+N195F+V206L+M246I+D377H+K391A+G476K H1*+N54S+V56T+G109A+A174S+G182*+D183*+N195F+V206L+L250I+D377H+K391A+G476K H1*+N54S+V56T+G109A+A174S+G182*+D183*+N195F+V206L+L250V+D377H+K391A+G476K H1*+N54S+V56T+G109A+A174S+G182*+D183*+N195F+V206L+K391Y+G476K H1*+N54S+V56T+G109A+A174S+G182*+D183*+N195F+V206L+K391V+G476K H1*+N54S+V56T+G109A+A174S+G182*+D183*+N195F+V206L+K391M+G476K H1*+N54S+V56T+G109A+A174S+G182*+D183*+N195F+V206L+K391E+G476K H1*+N54S+V56T+G109A+T165G+A174S+G182*+D183*+N195F+V206L+D377H+K391A+G476K H1*+N54R+V56T+G109A+A174S+G182*+D183*+N195F+V206L+K391A+G476K H1*+N54L+V56T+G109A+A174S+G182*+D183*+N195F+V206L+K391A+G476K H1*+N54S+V56T+G109S+A174S+G182*+D183*+N195F+V206L+K391A+G476K H1*+N54S+V56T+G109A+A174V+G182*+D183*+N195F+V206L+K391A+G476K H1*+N54S+V56T+G109A+A174S+G182*+D183*+N195F+V206L+M246F+D377H+K391A+G476K H1*+N54S+V56T+G109A+A174S+G182*+D183*+N195F+V206L+M246V+D377H+K391A+G476K H1*+N54S+V56T+G109A+A174S+G182*+D183*+N195F+V206L+M246S+D377H+K391A+G476K H1*+N54S+V56T+G109A+A174R+G182*+D183*+N195F+V206L+K391A+G476K H1*+N54S+V56T+G109A+A174L+G182*+D183*+N195F+V206L+K391A+G476K H1*+N54S+V56T+G109A+A174S+G182*+D183*+N195F+V206S+K391A+G476K H1*+N54S+V56T+G109A+A174S+G182*+D183*+N195F+V206L+K391D+G476K H1*+N54S+V56T+G109A+A174S+G182*+D183*+N195F+V206L+K391R+G476K H1*+N54S+V56T+G109A+A174S+G182*+D183*+N195F+V206L+K391H+G476K H1*+N54S+V56T+G109A+A174S+G182*+D183*+N195F+V206L+K391W+G476K H1*+N54S+V56T+G109A+A174S+G182*+D183*+N195F+V206L+K391I+G476K H1*+N54S+V56T+G109A+A174S+G182*+D183*+N195F+V206L+L250T+D377H+K391A+G476K H1*+N54S+V56T+G109A+A174S+G182*+D183*+N195F+V206L+L250A+D377H+K391A+G476K H1*+N54S+V56T+G109A+A174S+G182*+D183*+N195F+V206L+L250F+D377H+K391A+G476K H1*+N54S+V56T+G109A+A174S+G182*+D183*+N195F+V206L+L250M+D377H+K391A+G476K H1*+N54S+V56T+G109A+A174S+G182*+D183*+N195F+V206L+K391Q+G476K H1*+N54S+V56T+G109A+Q172H+L173A+A174P+G182*+D183*+N195F+V206L+K391A+G476K H1*+N54S+V56T+G109A+Q172E+L173A+A174R+G182*+D183*+N195F+V206L+K391A+G476K H1*+N54S+V56T+K72Q+G109A+W167R+A174S+G182*+D183*+N195F+V206L+K391A+G476K H1*+N54S+V56T+G109A+A174S+G182*+D183*+G184T+N195F+V206L+G255A+K391A+G476K H1*+N54S+V56T+K72R+G109A+A174S+G182*+D183*+G184T+N195F+V206L+D377H+K391A+G476K H1*+N54S+V56T+G109A+A174S+G182*+D183*+G184T+N195F+V206L+G255A+D377H+K391A+G476K H1*+N54S+V56T+G109A+Q118R+A174S+G182*+D183*+N195F+V206L+K391A+G476K H1*+N54S+V56T+G109A+A174S+G182*+D183*+N195F+V206L+S376T+K391A+G476K H1*+N54S+V56T+G109A+A174S+G182*+D183*+N195F+V206L+S376V+K391A+G476K H1*+N54S+V56T+G109A+Q172E+L173I+A174N+G182*+D183*+N195F+V206L+K391A+G476K H1*+N54S+V56T+G109A+Q172D+L173A+A174T+G182*+D183*+N195F+V206L+K391A+G476K H1*+N54S+V56T+G109A+A174S+G182*+D183*+N195F+V206L+Y267M+D377H+K391A+G476K H1*+N54S+V56T+G109A+A174S+G182*+D183*+N195F+V206L+Y267H+D377H+K391A+G476K H1*+N54S+V56T+G109A+A174S+G182*+D183*+N195F+V206L+V238A+K391A+G476K H1*+N54S+V56T+G109A+A174S+G182*+D183*+N195F+V206L+V238T+K391A+G476K H1*+N54S+V56T+G109A+A174S+G182*+D183*+N195F+V206L+V238G+K391A+G476K H1*+N54S+V56T+M105V+G109A+A174S+G182*+D183*+N195F+V206L+K391A+G476K H1*+N54S+V56T+G109A+A174S+G182*+D183*+N195F+V206L+V264T+K391A+G476K H1*+N54S+V56T+G109A+A174S+G182*+D183*+N195F+V206L+V264I+K391A+G476K H1*+N54S+V56T+G109A+A174S+G182*+D183*+N195F+V206L+L235V+K391A+G476K H1*+N54S+V56T+G109A+W167H+Q172N+L173A+A174S+G182*+D183*+N195F+V206L+K391A+G476K H1*+N54S+V56T+G109A+W167F+Q172E+L173P+A174K+G182*+D183*+N195F+V206L+K391A+G476K H1*+N54S+V56T+G109A+Q172N+L173T+A174S+G182*+D183*+N195F+V206L+K391A+G476K H1*+N54S+V56T+G109A+Q172K+L173V+A174T+G182*+D183*+N195F+V206L+K391A+G476K H1*+N54S+V56T+G109A+Q172E+L173F+A174R+G182*+D183*+N195F+V206L+K391A+G476K H1*+N54S+V56T+G109A+Q172E+L173T+A174R+G182*+D183*+N195F+V206L+K391A+G476K H1*+N54S+V56T+G109A+Q172N+L173V+A174R+G182*+D183*+N195F+V206L+K391A+G476K H1*+N54S+V56T+G109A+L173V+A174R+G182*+D183*+N195F+V206L+K391A+G476K H1*+N54S+V56T+G109A+Q172E+L173M+A174H+G182*+D183*+N195F+V206L+K391A+G476K H1*+N54S+V56T+G109A+Q172E+L173F+A174P+G182*+D183*+N195F+V206L+K391A+G476K H1*+N54S+V56T+G109A+W167Y+Q172E+L173V+A174H+G182*+D183*+N195F+V206L+K391A+G476K H1*+N54S+V56T+G109A+L173A+A174T+G182*+D183*+N195F+V206L+K391A+G476K H1*+N54S+V56T+G109A+A174S+G182*+D183*+N195F+V206L+V291A+F328L+K391A+G476K H1*+N54S+V56T+G109A+A174S+G182*+D183*+N195F+V206L+M246L+K391A+G476K H1*+N54S+V56T+G109A+A174S+G182*+D183*+N195F+V206L+M246S+K391A+G476K H1*+N54S+V56T+G109A+A174S+G182*+D183*+N195F+V206L+L250V+K391A+G476K H1*+N54S+V56T+G109A+A174S+G182*+D183*+N195F+V206L+L250F+K391A+G476K H1*+N54S+V56T+G109A+A174S+G182*+D183*+N195F+V206L+L250M+K391A+G476K H1*+N54S+V56T+G109A+A174S+G182*+D183*+N195F+V206L+K391A+C474V+G476K H1*+N54S+V56T+G109A+A174S+G182*+D183*+N195F+A204S+V206L+K391A+G476K H1*+N54S+V56T+G109A+T165G+A174S+G182*+D183*+N195F+V206L+K391A+G476K H1*+N54S+V56T+G109A+A174S+G182*+D183*+N195F+V206L+T334S+K391A+G476K H1*+N54S+V56T+G109A+A174S+G182*+D183*+N195F+V206L+A263G+M286F+K391A+G476K H1*+N54S+V56T+G109A+A174S+G182*+D183*+N195F+V206L+A263G+M286L+K391A+G476K H1*+N54S+V56T+G109A+A174S+G182*+D183*+N195F+V206L+Y267H+K391A+G476K H1*+N54S+V56T+G109A+A174S+G182*+D183*+N195F+V206L+Y267L+K391A+G476K H1*+N54S+V56T+G109A+A174S+G182*+D183*+N195F+V206L+Y267I+K391A+G476K H1*+T51A+N54S+V56T+G109A+Q172R+A174S+G182*+D183*+N195F+V206L+

K391A+G476K H1*+N54S+V56T+G109A+A174S+G182*+D183*+N195F+V206L+K391L+G476K H1*+N54S+V56T+G109A+F113Q+R116H+Q172G+A174S+G182*+D183*+N195F+V206L+K391A+G476K H1*+N54S+V56T+G109A+F113Q+Q172G+A174S+G182*+D183*+N195F+V206L+K391A+G476K H1*+N54S+V56T+G109S+F113Q+R116Q+A174S+G182*+D183*+N195F+V206L+K391A+G476K H1*+N54S+V56T+G109A+Q172D+A174S+G182*+D183*+N195F+A204G+V206L+K391A+P473R+G476K H1*+N54S+V56T+K72R+G109A+T134E+A174S+G182*+D183*+N195F+A204G+V206L+G255A+K391A+P473R+G476K H1*+N54S+V56T+K72R+G109A+W167F+A174S+G182*+D183*+N195F+A204G+V206L+K391A+G476K H1*+N54S+V56T+K72R+G109A+A174S+G182*+D183*+G184T+N195F+A204G+V206L+K391A+P473R+G476K H1*+N54S+V56T+G109A+W167F+Q172N+A174S+G182*+D183*+N195F+V206L+K391A+P473R+G476K H1*+N54S+V56T+G109A+W167F+Q172G+A174S+G182*+D183*+N195F+V206L+K391A+P473G+G476K H1*+N54S+V56T+G109A+W167F+Q172G+A174S+G182*+D183*+N195F+V206L+K391A+P473R+G476K H1*+N54S+V56T+K72R+G109A+W167F+Q172R+A174S+G182*+D183*+N195F+V206L+K391A+G476K H1*+N54S+V56T+K72R+G109A+R116H+W167F+Q172R+A174S+G182*+D183*+N195F+V206L+K391A+G476K H1*+N54S+V56T+M105F+G109A+A174S+G182*+D183*+N195F+V206L+R320A+S323N+K391A+C474V+G476K H1*+N54S+V56T+K72R+G109A+A174S+G182*+D183*+N195F+V206L+G255A+K391A+C474V+G476K H1*+N54S+V56T+G109A+T134E+A174S+G182*+D183*+N195F+V206L+K391A+C474V+G476K H1*+N54S+V56T+G109A+A174S+G182*+D183*+N195F+V206L+D377H+K391A+C474V+G476K H1*+N54S+V56T+K72R+G109A+A174S+G182*+D183*+N195F+V206L+K391A+C474V+G476K H1*+N54S+V56T+G109A+A174S+G182*+D183*+N195F+V206L+A265G+K391A+T444Q+G476K+G477A H1*+A37V+N54S+V56T+G109A+W167F+Q172G+A174S+G182*+D183*+N195F+V206L+K391A+G346T+G477A+G476K H1*+N54S+V56T+G109A+R116Q+Q172D+A174S+G182*+D183*+N195F+V206L+G346T+K391A+T444Q+G477A+G476K H1*+N54S+V56T+G109A+R116Q+W167F+Q172N+A174S+G182*+D183*+N195F+V206L+G346T+K391A+T444Q+G477A+G476K H1*+N54S+V56T+G109S+W167F+Q172R+A174S+G182*+D183*+N195F+V206L+K391A+G476K H1*+N54S+V56T+G109S+R116Q+W167F+Q172N+A174S+G182*+D183*+N195F+V206L+K391A+G476K H1*+N54S+V56T+G109S+W167F+Q172G+A174S+G182*+D183*+N195F+V206L+K391A+G476K H1*+N54S+V56T+G109A+F113Q+Q172G+A174S+G182*+D183*+N195F+V206L+K391A+T444Q+G476K H1*+N54S+V56T+G109A+F113Q+R116H+Q172G+A174S+G182*+D183*+N195F+V206L+K391A+T444Q+G476K H1*+N54S+V56T+G109A+F113Q+A174S+G182*+D183*+N195F+V206L+K391A+C474V+G476K H1*+N54S+V56T+G109A+Q172N+A174S+G182*+D183*+N195F+V206L+V264I+K391A+C474V+G476K H1*+N54S+V56T+G109A+Q172N+A174S+G182*+D183*+N195F+V206L+K391A+C474V+G476K H1*+N54S+V56T+G109A+A174S+G182*+D183*+N195F+V206L+S280Q+H321Y+K391A+C474V+G476K H1*+N54S+V56T+K72R+G109A+T134E+A174S+G182*+D183*+N195F+V206L+G255A+K391A+C474V+G476K H1*+N54S+V56T+G109A+F113Q+R116H+Q172G+A174S+G182*+D183*+N195F+V206L+K391A+T444Q+P473R+G476K H1*+N54S+V56T+G109A+F113Q+R116Q+Q172G+A174S+G182*+D183*+N195F+V206L+K391A+T444Q+G476K H1*+N54S+V56T+G109A+R116H+W167F+Q172N+A174S+G182*+D183*+N195F+V206L+K391A+G476K H1*+N54S+V56T+G109A+F113Q+R116H+T165G+Q172G+A174S+G182*+D183*+N195F+V206L+K391A+T444Q+G476K H1*+N54S+V56T+G109A+F113Q+R116Q+T165G+Q172G+A174S+G182*+D183*+N195F+V206L+K391A+T444Q+G476K H1*+N54S+V56T+G109A+F113Q+R116H+W167F+Q172R+A174S+G182*+D183*+N195F+V206L+F289I+K391A+G476K H1*+N54S+V56T+G109A+F113Q+Q172N+A174S+G182*+D183*+N195F+V206L+K391A+T444Q+G476K H1*+N54S+V56T+G109A+F113Q+R116H+Q172N+A174S+G182*+D183*+N195F+V206L+K391A+G476K H1*+N54S+V56T+G109A+F113Q+R116Q+Q172M+A174S+G182*+D183*+N195F+V206L+K391A+T444Q+G476K H1*+N54S+V56T+G109A+F113Q+R116H+Q172M+A174S+G182*+D183*+N195F+V206L+K391A+G476K H1*+N54S+V56T+G109A+R116H+Q172M+A174S+G182*+D183*+N195F+V206L+K391A+G476K H1*+N54S+V56T+G109A+F113Q+R116H+T165G+Q172M+A174S+G182*+D183*+N195F+V206L+K391A+Q395P+G476K H1*+N54S+V56T+G109A+F113Q+A174S+G182*+D183*+N195F+V206L+K391A+T444Q+P473R+G476K H1*+N54S+V56T+G109A+R116Q+A174S+G182*+D183*+N195F+V206L+A265G+K391A+T444Q+P473R+G476K H1*+N54S+V56T+G109A+R116Q+A174S+G182*+D183*+N195F+V206L+K391A+T444Q+P473R+G476K H1*+N54S+V56T+K72R+G109A+T134E+T165G+A174S+G182*+D183*+N195F+V206L+G255A+K391A+G476K H1*+N54S+V56T+G109A+F113Q+R116H+W167F+Q172R+A174S+G182*+D183*+N195F+V206L+K391A+G476K H1*+N54S+V56T+G109A+R116Q+W167F+Q172R+A174S+G182*+D183*+N195F+V206L+A265G+K391A+P473R+G476K H1*+N54S+V56T+G109A+F113Q+A174S+G182*+D183*+N195F+V206L+K391A+G476K H1*+N54S+V56T+G109A+Q172N+A174S+G182*+D183*+N195F+V206L+K391A+G476K H1*+T51V+N54S+V56T+G109A+Q172D+A174S+G182*+D183*+N195F+V206L+K391A+G476K H1*+N54S+V56T+G109A+A174S+G182*+D183*+N195F+V206L+S280Q+H321Y+K391A+G476K H1*+N54S+V56T+G109A+F113Q+R116H+Q172N+A174S+G182*+D183*+N195F+V206L+K391A+G476K H1*+N54S+V56T+G109A+F113Q+R116H+Q172G+L173V+A174S+G182*+D183*+N195F+V206L+K391A+T444Q+P473R+G476K H1*+N54S+V56T+G109A+R116Q+W167F+Q172N+L173V+A174S+G182*+D183*+N195F+V206L+K391A+T444Q+G476K H1*+N54S+V56T+G109A+G133Q+W167F+Q172N+A174S+G182*+D183*+N195F+V206L+Q395P+K391A+G476K H1*+N54S+V56T+G109A+F113Q+R116H+W167F+Q172N+L173V+A174S+G182*+D183*+N195F+V206L+K391A+G476K H1*+A37V+N54S+V56T+K72R+G109A+R116H+W167F+Q172R+A174S+G182*+D183*+G184T+N195F+V206L+K391A+P473R+G476K H1*+N54S+V56T+K72R+G109A+F113Q+R116H+W167F+Q172G+L173V+A174S+G182*+D183*+G184T+N195F+V206L+K391A+T444Q+P473R+G476K H1*+N54S+V56T+G109S+R116Q+W167F+Q172R+A174S+G182*+D183*+N195F+V206L+K391A+G476K H1*+N54S+V56T+G109S+R116Q+W167F+Q172G+A174S+G182*+D183*+N195F+V206L+K391A+P473R+G476K H1*+N54S+V56T+G109S+F113Q+W167F+Q172N+A174S+G182*+D183*+N195F+V206L+K391A+G476K H1*+A37V+N54S+V56T+G109S+F113Q+W167F+Q172R+A174S+G182*+

D183*+N195F+V206L+K391A+G476K H1*+N54S+V56T+K72R+G109A+R116H+T134E+W167F+Q172G+L173V+A174S+G182*+D183*+N195F+V206L+G255A+K391A+G476K H1*+N54S+V56T+K72R+G109A+R116H+T134E+W167F+Q172G+L173V+A174S+G182*+D183*+N195F+V206L+G255A+K391A+Q395P+T444Q+P473R+G476K H1*+N54S+V56T+K72R+G109A+F113Q+R116Q+W167F+Q172G+A174S+G182*+D183*+G184T+N195F+V206L+K391A+P473R+G476K H1*+N54S+V56T+K72R+G109A+F113Q+R116Q+T134E+W167F+Q172R+A174S+G182*+D183*+N195F+V206L+G255A+K391A+T444Q+P473R+G476K H1*+N54S+V56T+K72R+G109A+F113Q+T134E+W167F+Q172R+A174S+G182*+D183*+N195F+V206L+G255A+K391A+Q395P+A445Q+P473R+G476K H1*+N54S+V56T+K72R+G109A+F113Q+R116H+T134E+W167F+Q172R+A174S+G182*+D183*+N195F+V206L+G255A+K391A+Q395P+G476K H1*+N54S+V56T+K72R+G109A+T134E+W167F+Q172N+A174S+G182*+D183*+N195F+V206L+G255A+A265G+K391A+T444Q+P473R+G476K H1*+N54S+V56T+K72R+G109A+G133Q+W167F+Q172R+A174S+G182*+D183*+N195F+V206L+K391A+G476K H1*+N54S+V56T+K72R+G109A+F113Q+R116Q+W167F+Q172G+A174S+G182*+D183*+N195F+A204G+V206L+K391A+G476K H1*+N54S+V56T+K72R+G109A+F113Q+R116Q+W167F+Q172N+L173V+A174S+G182*+D183*+G184T+N195F+V206L+K391A+T444Q+P473R+G476K H1*+A37H+N54S+V56T+G109A+F113Q+W167F+Q172N+A174S+G182*+D183*+N195F+V206L+K391A+G476K H1*+A37H+N54S+V56T+G109A+F113Q+A174S+G182*+D183*+N195F+V206L+K391A+G476K H1*+N54S+V56T+G109A+F113Q+W167F+Q172N+A174S+G182*+D183*+N195F+V206L+K391A+T459N+G476K H1*+N54S+V56T+G109A+F113Q+Q172R+L173V+A174S+G182*+D183*+N195F+V206L+K391A+T444Q+G476K H1*+N54S+V56T+G109A+F113Q+R116Q+A174S+G182*+D183*+N195F+V206L+K391A+P473R+G476K H1*+N54S+V56T+A60V+G109A+R116Q+W167F+Q172N+A174S+G182*+D183*+N195F+V206L+K391A+G476K H1*+N54S+V56T+A60V+G109A+R116H+Q172R+L173V+A174S+G182*+D183*+N195F+V206L+K391A+G476K H1*+A37V+N54S+V56T+A60V+G109A+R116Q+T165G+A174S+G182*+D183*+N195F+V206+K391A+G476K H1*+A37H+N54S+V56T+A60V+G109A+R116Q+T165G+A174S+G182*+D183*+N195F+V206+K391A+G476K H1*+N54S+V56T+A60V+G109A+R116Q+W167F+Q172G+L173V+A174S+G182*+D183*+N195F+V206L+K391A+G476K H1*+N54S+V56T+A60V+G109A+R116Q+A174S+G182*+D183*+N195F+V206L+K391A+G476K H1*+A37H+N54S+V56T+A60V+G109A+R116Q+W167F+Q172R+A174S+G182*+D183*+N195F+V206L+K391A+G476K H1*+A37H+N54S+V56T+A60V+G109A+R116Q+W167F+Q172N+A174S+G182*+D183*+N195F+V206L+K391A+G476K H1*+N54S+V56T+A60V+G109A+R116Q+T165G+A174S+G182*+D183*+N195F+V206L+K391A+T444Q+P473R+G476K H1*+N54S+V56T+A60V+G109A+R116Q+A174S+G182*+D183*+N195F+V206L+K391A+T444Q+P473R+G476K H1*+N54S+V56T+A60V+G109A+R116Q+W167F+Q172N+L173V+A174S+G182*+D183*+N195F+V206L+K391A+G476K H1*+N54S+V56T+A60V+G109A+R116Q+W167F+Q172R+A174S+G182*+D183*+N195F+V206L+K391A+G476K H1*+N54S+V56T+G109A+R116A+W167F+Q172R+A174S+G182*+D183*+N195F+A204G+V206L+K391A+P473R+G476K H1*+N54S+V56T+G109A+R116A+A174S+G182*+D183*+N195F+A204G+V206L+K391A+P473R+G476K H1*+N54S+V56T+G109A+R116A+T165G+A174S+G182*+D183*+N195F+V206L+K391A+T444Q+P473R+G476K H1*+N54S+V56T+G109A+G182*+D183*+N195F+K391A+G476K H1*+N54S+V56T+G109A+G182*+D183*+N195F+V206L N54S+V56T+G109A+G182*+D183*+N195F N54S+V56T+G109A+A174S+G182*+D183*+N195F+V206L+K391A+G476K H1*+G109A+A174S+G182*+D183*+N195F+V206L+K391A+G476K H1*+N54S+V56T+G109A+G182*+D183*+N195F+V206L+K391A+G476K H1*+N54S+V56T+G109A+A174S+G182*+D183*+N195F+V206L+K391A H1*+N54S+V56T+G109A+A174S+G182*+D183*+N195F+G476K H1*+N54S+V56T+A174S+G182*+D183*+N195F+V206L+G273R+K391A+G476K H1*+N54S+V56T+G109A+A174S+G182*+D183*+N195F+V206L H1*+W48G+G109A+G182*+D183*+N195F+V206L+K391A+G476K N54S+V56T+G109A+A174S+G182*+D183*+N195F+K391A+G476K H1*+N54S+V56T+G109A+A174S+G182*+D183*+N195F+K391A H1*+N54S+V56T+G109A+F113Q+Q172M+A174S+G182*+D183*+N195F+V206L+K391A+G476K H1*+N54S+V56T+G109A+R116Q+A174S+G182*+D183*+N195F+A204G+V206L+K391A+G476K H1*+N54S+V56T+K72R+G109A+F113Q+T134E+A174S+G182*+D183*+N195F+V206L+G255A+K391A+G476K H1*+N54S+V56T+K72R+G109A+F113Q+T134E+A174S+G182*+D183*+N195F+V206L+G255A+K391A+P473R+G476K H1*+N54S+V56T+K72R+G109A+R116Q+A174S+G182*+D183*+G184T+N195F+V206L+K391A+G476K H1*+A37V+N54S+V56T+G109A+R116A+T165G+A174S+G182*+D183*+N195F+V206L+K391A+G476K H1*+A37V+N54S+V56T+G109A+R116Q+T165G+A174S+G182*+D183*+N195F+V206L+M246F+K391A+G476K H1*+V56A+G109A+A174S+G182*+D183*+N195F+V206L+G476K H1*+N54S+V56T+G109A+G182*+D183*+N195F+V206L+K391A H1*+N54S+V56T+G109A+G182*+D183*+N195F+V206L+G476K G109A+A174S+G182*+D183*+N195F+V206L+K391A+G476K N54S+V56T+G109A+G182*+D183*+N195F+V206L+K391T+G476K H1*+N54S+V56T+K72R+G109A+F113Q+R116H+A174S+G182*+D183*+G184T+N195F+V206L+K391A+T444Q+G476K H1*+N54S+V56T+G109S+F113Q+A174S+G182*+D183*+N195F+V206L+K391A+T444Q+G476K H1*+N54S+V56T+G109A+F113Q+R116H+W167F+Q172G+L173V+A174S+G182*+D183*+N195F+V206L+K391A+P473R+G476K H1*+N54S+V56T+G109A+F113Q+R116Q+Q172N+A174S+G182*+D183*+N195F+V206L+A265G+K391A+P473R+G476K H1*+N54S+V56T+G109A+F113Q+W167F+Q172N+A174S+G182*+D183*+N195F+A204G+V206L+K391A+P473R+G476K H1*+N54S+V56T+G109A+F113Q+R116H+W167F+Q172R+A174S+G182*+D183*+N195F+A204G+V206L+K391A+P473R+G476K H1*+N54S+V56T+G109A+R116A+A174S+G182*+D183*+N195F+V206L+K391A+T444Q+P473R+G476K H1*+N54S+V56T+G109A+R116H+Q172R+A174S+G182*+D183*+N195F+A204G+V206L+K391A+P473R+G476K H1*+A37V+N54S+V56T+G109A+R116Q+T165G+A174S+G182*+D183*+N195F+V206L+K391A+G476K H1*+A37H+N54S+V56T+G109A+R116H+T165G+A174S+G182*+D183*+N195F+V206L+M246F+K391A+G476K H1*+N54S+V56T+G109A+A174S+G182*+D183*+N195F+K391A+G476K H1*+G109A+G182*+D183*+N195F+V206L+K391A+G476K G109A+G182*+D183*+N195F+V206L+G476K H1*+G109A+G182*+D183*+N195F+K391A H1*+N54S+

V56T+G109A+G133S+A174S+G182*+D183*+N195F+K391A+G476H H1*+N54S+V56T+G109A+R116A+Q172N+L173V+A174S+G182*+D183*+N195F+V206L+K391A+G476K H1*+A37V+N54S+V56T+G109A+R116H+T165G+A174S+G182*+D183*+N195F+V206L+K391A+G476K H1*+P45A+N54S+V56T+G109A+A174S+G182*+D183*+N195F+V206L+K391A+C474V+G476K H1*+N54S+V56T+G109A+P124A+A174S+G182*+D183*+N195F+V206L+K391A+C474V+G476K H1*+N54S+V56T+G109A+A174S+G182*+D183*+N195F+V206L+P364A+K391A+C474V+G476K H1*+N54S+V56T+G109A+Q118R+T134E+A174S+G182*+D183*+N195F+V206L+K391A+G476K H1*+N54S+V56T+G109A+A174S+G182*+D183*+G184T+N195F+V206L+K391A+G476K H1*+G50A+T51A+N54S+V56T+G109A+A174S+G182*+D183*+N195F+V206L+K391A+G476K H1*+N54S+V56T+G109A+A174S+G182*+D183*+N195F+V206L+V264F+K391A+G476K H1*+N54S+V56T+G109A+A174S+G182*+D183*+N195F+V206L+Y382L+K391A+G476K H1*+G7K+N54S+V56T+G109A+A174S+G182*+D183*+N195F+V206L+K391A+G476K H1*+N54S+V56T+G109A+A174S+G182*+D183*+N195F+V206L+G255A+Q256A+K391A+G476K H1*+N54S+V56T+G109A+W167Y+A174S+G182*+D183*+N195F+V206L+K391A+G476K H1*+N54S+V56T+G109A+W167H+A174S+G182*+D183*+N195F+V206L+K391A+G476K H1*+N54S+V56T+G109A+T165V+A174S+G182*+D183*+N195F+V206L+K391A+G476K H1*+N54S+V56T+G109A+A174S+G182*+D183*+N195F+V206L+K391A+G476K H1*+N54S+V56T+G109A+A174N+G182*+D183*+N195F+V206L+K391A+G476K H1*+N54S+V56T+G109A+A174Q+G182*+D183*+N195F+V206L+K391A+G476K H1*+N16H+V17L+N54S+V56T+G109A+A174S+G182*+D183*+N195F+V206L+Y382F+K391A+G476K H1*+Q32S+N54S+V56T+G109A+A174S+G182*+D183*+N195F+V206L+Q385L+K391A+G476K H1*+N54S+V56T+R87S+G109A+R171H+A174S+G182*+D183*+N195F+V206L+K391A+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+

Q169E+Q172K+A174*+G182*+D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+G476K, H1*+W48F+N54S+V56T+G109A+A174S+G182*+D183*+N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, H1*+N54S+V56T+G109A+A174S+V206L+G182*+D183*+K391A+G476K, H1*+N54S+V56T+Q169E+Q172K+A174*+G182*+D183*+N195F+V206L+K391A+G476K, H1*+N54S+V56T+G109A+A174S+G182*+D183*+N195F+V206F+K391A+G476K, H1*+N54S+V56T+G109A+G182*+D183*+N195F+V206L+K391A+G476K, H1*+N54S+V56T+G109A+Q172K+A174S+G182*+D183*+N195F+V206L+K391A+G476K, H1*+N54S+V56T+G109A+Q172K+A174*+G182*+D183*+N195F+V206L+K391A+G476K, H1*+N54S+V56T+G109A+A174N+G182*+D183*+N195F+V206L+K391A+G476K, H1*+N54S+V56T+G109A+A174S+A186N+G182*+D183*+N195F+V206L+K391A+G476K, H1*+N54S+V56T+G109A+A174S+G182*+D183*+N195F+V206L+F289L+K391A+G476K, H1*+N54S+V56T+G109A+A174S+G182*+D183*+N195F+V206L+Y295F+K391A+G476K, H1*+N54S+V56T+G109A+A174S+G182*+D183*+N195F+V206L+V291A+K391A+G476K, H1*+N54S+V56T+G109A+A174S+G182*+D183*+N195F+V206L+S244Q+K391A+G476K, G182*+D183*+F328L, G182*+D183*+N195F+A288V, G182*+D183*+A186N+N195F, G182*+D183*+E190P+N195F, W140Y+G182*+D183*+N195F, H1*+N54S+V56T+G109A+A174S+G182*+D183*+N195F+V206L+A225V+K391A+G476K, G182*+D183*+A186D+N195F, H1*+N54S+V56T+G109A+A174S+G182*+D183*+N195F+V206L+K391A+P473R+G476K, H1*+W48Y+N54S+V56T+G109A+A174S+G182*+D183*+N195F+V206L+K391A+G476K, H1*+N54S+V56T+G109A+Q169E+Q172K+A174*+G182*+D183*+N195F+V206L+K391A+G476K, G182*+D183*+N195F+V238A, G182*+D183*+Y295N, Q172G+G182*+D183*, F113Q+G182*+D183*+N195F, H1*+N54S+V56T+Q98A+G109A+A174S+G182*+D183*+N195F+V206L+K391A+G476K, G182*+D183*+N195F+Y295F, G182*+D183*+A186E, H1*+N54S+V56T+G109A+A174S+G182*+D183*+N195F+V206Y+K391A+G476K, G182*+D183*+N195F+W284H, G182*+D183*+A186Q+N195F, K72R+G182*+D183*, D183*+G182*+N195F+V326L, D183*+G182*+A186E+N195F, Q169E+G182*+D183*+N195F, D183*+G182*+N195F+K242Q, G7A+G182*+D183*+N195F, D183*+G182*+N195F+N260G, D183*+G182*+R321A+S323N, D183*+G182*+W284H, H1*+D183*+G182*, D183*+G182*+A186H+N195F, D183*+G182*+F289V, D183*+G182*+K391A, D183*+G182*+S304R, W167F+G182*+D183*+N195F, F113Q+R116H+D183*+G182*, D183*+G182*+N270G, D183*+G182*+S244Q, H1*+N54S+V56T+G109A+A174S+G182*+D183*+G184T+N195F+V206L+K391A+G476K, D183*+G182*+N195F+Y295N, W48F+D183*+G182*, H1*+N54S+V56T+G109A+A174S+G182*+D183*+N195F+V206L+G255A+K391A+G476K, D183*+G182*+A186Q, W140Y+D183*+G182*, D183*+G182*+K242Q, D183*+G182*+V206L, D183*+G182*+N195F+V206F, Q169E+D183*+G182*, D183*+G182*+N195F+R320A, G182*+D183*+G184T+N195F, D183*+G182*+G184T, N54S+V56T+D183*+G182*, D183*+G182*+P473R, W48Y+D183*+G182*, D183*+G182*+R323A, G7A+D183*+G182*, G109A+D183*+G182*, W167F+D183*+G182*, H1*+N54S+V56T+G109A+Q169E+Q172K+A174S+G182*+D183*+N195F+V206L+K391A+G476K, A174S+D183*+G182*, R116Q+D183*+G182*, D183*+G182*+N195F+V291A, Q172K+D183*+G182*, N54S+D183*+G182*, D183*+G182*+N195F+S323N, D183*+G182*+N195F+M246V, W48Y+D183*+G182*+N195F, D183*+G182*+N195F+S304R, V56T+D183*+G182*, wherein numbering is according to SEQ ID NO: 13; and N54S+G182*+D183*+N195F, G109A+G182*+D183*+N195F, G182*+D183*+N195F+K391A, G182*+D183*+N195F+G476K, H1*+G182*+D183*+N195F, N54S+G182*+D183*+N195F, V56T+G182*+D183*+N195F, G182*+D183*+N195F+I405L, H1*+N54S+V56T+G109A+A174S+G182*+D183*+N195F+V206L+I405L+A421H+A422P+A428T+D476K, A174S+G182*+D183*+N195F, H1*+N54S+V56T+G109A+A174S+G182*+D183*+N195F+V206L+I405L+A421H+A422P+A428T, H1*+N54S+V56T+G109A+A174S+D183*+N195F+V206L+K391A+I405L+A421H+A422P+A428T, H1*+N54S+V56T+G109A+A174S+G182*+D183*+N195F+V206L+K391A+I405L+A421H+A422P+A428T+D476K, H1*+N54S+V56T+G109A+A174S+G182*+D183*+N195F+V206L+K391A+I405L+A421H+A422P+A428T+D476G, H1*+N54S+V56T+G109A+A174S+G182*+D183*+N195F+V206L+K391A+I405L+A421H+A422P+A428T+D476K+G477S, H1*+N54S+V56T+G109A+A174S+G182*+D183*+N195F+V206L+K391A+I405L+A421H+A422P+A428T+D476K, H1*+N54S+V56T+K72R+G109A+W167F+A174S+G182*+D183*+N195F+V206L+I405L+A421+A422P+A428T, H1*+N54S+V56T+G109A+A174S+G182*+D183*+N195F+V206L+S304N+I405L+A421H+A422P+A428T+D476K, H1*+N54S+V56T+G109A+A174S+G182*+D183*+N195F+V206L+K391A+I405L+A421H+A422P+A428T+D476K+G477A, H1*+N54S+V56T+G109A+A174S+G182*+D183*+N195F+V206L+K391A+I405L+A421H+A422P+A428T+D476G+G477T, H1*+N54S+V56T+G109A+A174S+G182*+D183*+N195F+V206L+K391A+I405L+A421H+A422P+A428T+G477Q, H1*+N54S+V56T+G109A+A174S+G182*+D183*+N195F+V206L+K391A+I405L+A421H+A422P+A428T+G477A, H1*+N54S+V56T+G109A+A174S+G182*+D183*+N195F+V206L+K391A+I405L+A421H+A422P+A428T+D476K+G477Q, H1*+N54S+V56T+G109A+A174S+G182*+D183*+N195F+V206L+K391A+I405L+A421H+A422P+A428T+D476N, H1*+N54S+V56T+G109A+A174S+G182*+D183*+N195F+V206L+K391A+I405L+A421H+A422P+A428T+D476Y, H1*+N54S+V56T+G109A+A174S+G182*+D183*+N195F+V206I+I405L+A421H+A422P+A428T, H1*+N54S+V56T+G109A+Q172D+A174S+G182*+D183*+N195F+A204G+V206L+I405L+A421H+A422P+A428T, H1*+N54S+V56T+K72R+G109A+T134E+A174S+G182*+D183*+N195F+A204G+V206L+G255A+I405L+A421H+A422P+A428T, H1*+N54S+V56T+G109A+F113Q+R116H+T165G+Q172G+A174S+G182*+D183*+N195F+V206L+I405L+A421H+A422P+A428T, H1*+N54S+V56T+

G109A+F113Q+Q172N+A174S+G182*+D183*+N195F+V206L+I405L+A421H+A422P+A428T, H1*+N54S+V56T+K72R+G109A+T134E+A174S+G182*+D183*+N195F+G196R+V206L+G255A+I405L+A421H+A422P+A428T+N475S, H1*+N54S+V56T+G109A+T134E+A174S+G182*+D183*+N195F+V206L+I405L+A421H+A422P+A428T, H1*+T40D+N54S+V56T+G109A+A174S+G182*+D183*+N195F+V206L+I405L+A421H+A422P+A428T, H1*+N54S+V56T+G109A+F113Q+N125D+A174S+G182*+D183*+N195F+V206L+I405L+A421H+A422P+A428T, H1*+N54S+V56T+A60V+G109A+R116Q+A174S+G182*+D183*+N195F+V206L+I405L+A421H+A422P+A428T, H1*+N54S+V56T+G109A+R116V+A174S+G182*+D183*+N195F+V206L+I405L+A421H+A422P+A428T, H1*+N54S+V56T+G109A+R116Q+G133Q+T165G+Q172G+A174S+G182*+D183*+N195F+V206L+I405L+A421H+A422P+A428T, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116Q+Q172G+A174S+G182*+D183*+N195F+V206L+I405L+A421H+A422P+A428T+G448D, H1*+N54S+V56T+G109A+F113Q+R116H+Q172N+A174S+G182*+D183*+N195F+V206L+I405L+A421H+A422P+A428T, H1*+N54S+V56T+K72R+G109A+T134E+W167F+Q172N+A174S+G182*+D183*+N195F+V206L+G255A+A265G+I405L+A421H+A422P+A428T, H1*+N54S+V56T+K72R+G109A+R116Q+W167F+Q172R+L173V+A174S+G182*+D183*+N195F+V206L+A265G+I405L+A421H+A422P+A428T, H1*+N54S+V56T+K72R+G109A+R116Q+W167F+Q172R+A174S+G182*+D183*+N195F+V206L+I405L+A421H+A422P+A428T, H1*+N54S+V56T+K72R+G109A+F113Q+T134E+W167F+Q172G+A174S+G182*+D183*+N195F+V206L+G255A+I405L+A421H+A422P+A428T, H1*+N54S+V56T+K72R+G109A+F113Q+R116H+W167F+Q172G+L173V+A174S+G182*+D183*+G184T+N195F+V206L+I405L+A421H+A422P+A428T, H1*+N54S+V56T+G109A+F113Q+W167F+Q172G+A174S+G182*+D183*+N195F+V206L+I405L+A421H+A422P+A428T, H1*+N54S+V56T+K72R+G109A+A174S+G182*+D183*+N195F+V206L+G255A+I405L+A421H+A422P+A428T, H1*+N54S+V56T+G109A+F113Q+R116Q+A174S+G182*+D183*+N195F+V206L+I405L+A421H+A422P+A428T, H1*+N54S+V56T+K72R+G109A+F113Q+F116H+W167F+Q172G+L173V+A174S+G182*+D183*+N195F+V206L+I405L+A421H+A422P+A428T, H1*+N54S+V56T+K72R+G109A+F113Q+R116Q+W167F+Q172G+A174S+G182*+D183*+G184T+N195F+V206L+I405L+A421H+A422P+A428T, H1*+N54S+V56T+G109A+F113Q+R116Q+W167F+Q172G+A174S+G182*+D183*+N195F+A204G+V206L+I405L+A421H+A422P+A428T, H1*+N54S+V56T+G109A+F113Q+R116H+W167F+Q172G+A174S+G182*+D183*+N195F+V206L+A265G+I405L+A421H+A422P+A428T, H1*+N54S+V56T+G109A+R116Q+A174S+G182*+D183*+N195F+V206L+I405L+A421H+A422P+A428T, H1*+N54S+V56T+A60V+G109A+R116Q+W167F+Q172N+L173V+A174S+G182*+D183*+N195F+V206L+I405L+A421H+A422P+A428T, H1*+A37H+N54S+V56T+A60V+G109A+R116Q+T165G+A174S+G182*+D183*+N195F+V206L+I405L+A421H+A422P+A428T, H1*+N54S+V56T+G109A+A174S+M105F+G182*+D183*+N195F+V206L+L228I+R320A+S323N+I405L+A421H+A422P+A428T, H1*+N54S+V56T+K72R+G109A+F113Q+T134E+A174S+G182*+D183*+N195F+V206L+G255A+I405L+A421H+A422P+A428T, H1*+N54S+V56T+K72R+G109A+R116Q+V120L+A174S+G182*+D183*+G184T+N195F+V206L+I405L+A421H+A422P+A428T, H1*+N54S+V56T+G109A+F113Q+R116H+W167F+Q172G+L173V+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO:14.

As can be seen from the data obtained in Examples 3 and 4, all tested variants have an Improvement Factor (IF) of at least 1.0, i.e. at least on par with a parent polypeptide having SEQ ID NO: 15, when tested in either (i) a detergent Model A at 15° C. and an enzyme concentration of 0.05 mg/L, (ii) a detergent Model A at 15° C. and an enzyme concentration of 0.2 mg/L, (iii) a detergent Model J at 15° C. and an enzyme concentration of 0.05 mg/L, or (iv) a detergent Model J at 15° C. and an enzyme concentration of 0.2 mg/L. Thus, the variants of the present invention have even in different model detergent compositions, at a low temperature as well as in a low concentrations, a wash performance at least that of the parent polypeptide having SEQ ID NO: 15. Specifications of the model detergents and specific test conditions for the AMSA, can be seen in Examples 3 and 4.

In another embodiment, the variant is selected from the group consisting of; G182*+D183*+N195F+V206F+N260P+L3121+L313I+R320A+T355L+L389I+T400P, H1*+N54S+V56T+G109A+A174S+G182*+D183*+N195F+V206L+K391A+G476K, H1*+G50A+T51A+V56T+G109A+A174S+G182*+D183*+N195F+V206L+G476K, H1*+N54S+V56T+M105F+G109A+A174S+G182*+D183*+N195F+V206L+R320A+S323N+K391A+G476K, H1*+T40K+N54S+V56T+G109A+G149H+A174S+G182*+D183*+N195F+V206L+K391A+G476K, H1*+N54S+V56T+K72R+G109A+A174S+G182*+D183*+N195F+V206L+G255A+K391A+G476K, H1*+N16H+V17L+N54S+V56T+G109A+A174S+G182*+D183*+N195F+V206L+K391A+G476K, H1*+Q22N+N54S+V56T+G109A+A174S+G182*+D183*+N195F+V206L+K391A+G476K, H1*+Q32S+N54S+V56T+G109A+A174S+G182*+D183*+N195F+V206L+K391A+G476K, H1*+H28N+N54S+V56T+G109A+A174S+G182*+D183*+N195F+V206L+K391A+G476K, H1*+N29S+N54S+V56T+G109A+A174S+G182*+D183*+N195F+V206L+K391A+G476K, H1*+H28N+N29S+N54S+V56T+G109A+A174S+G182*+D183*+N195F+V206L+K391A+G476K, H1*+N54S+V56T+G109A+A174S+R176K+G182*+D183*+N195F+V206L+K391A+G476K, H1*+N54S+V56T+G109A+Q169E+Q172K+A174*+R176K+G182*+D183*+N195F+V206L+K391A+G476K, H1*+N54S+V56T+G109A+A174S+N175G+G182*+D183*+N195F+V206L+K391A+G476K, H1*+N54S+V56T+G109A+A174S+G182*+D183*+N195F+V206L+V291A+Y295N+Q299T+K391A+G476K, H1*+N54S+V56T+G109A+A174S+G182*+D183*+N195F+V206L+K269S+A274K+K391A+G476K, H1*+N54S+V56T+G109A+A174S+G182*+D183*+N195F+V206L+L2351+K391A+G476K, H1*+N54S+V56T+G109A+A174S+G182*+D183*+N195F+V206L+L235V+V238A+K391A+G476K, H1*+N54S+V56T+G109A+A174S+G182*+D183*+N195F+V206L+Q365S+K391A+G476K, H1*+N54S+V56T+G109A+A174S+G182*+D183*+N195F+V206L+K391A+H402R+G476K, H1*+N54S+V56T+G109A+A174S+G182*+D183*+N195F+V206L+R320S+H321N+K391A+G476K, H1*+N54S+V56T+G109A+Q169E+Q172K+A174*+G182*+D183*+N195F+

V206L+K391A+G476K, H1*+N54S+V56T+G109A+Q125S+A174S+G182*+D183*+N195F+V206L+K391A+G476K, H1*+N54S+V56T+G109A+A174S+G182*+D183*+N195F+V206L+L235V+K391A+G476K, H1*+N54S+V56T+G109A+A174S+G182*+D183*+N195F+V206L+A265G+K391A+G476K, H1*+T51Q+N54S+V56T+G109A+A174S+G182*+D183*+N195F+Y203F+V206L+K391A+G476K, H1*+N54S+V56T+G109A+Q169E+Q172K+A174*+N175Q+G182*+D183*+N195F+V206L+K391A+G476K, H1*+H28N+N54S+V56T+G109A+A174S+G182*+D183*+N195F+V206L+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+D377H+K391A+G476K, H1*+G50A+T51A+N54S+V56T+G109A+A174S+G182*+D183*+N195F+V206L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+M202V+V206L+K391A+G476K, H1*+N54S+V56T+M105F+G109A+A174S+G182*+D183*+N195F+V206L+M246F+K391A+G476K, H1*+N16H+V17L+N54S+V56T+G109A+A174S+G182*+D183*+N195F+V206L+D377H+K391A+G476K, H1*+T51G+N54S+V56T+G109A+A174S+G182*+D183*+N195F+Y203G+V206L+K391A+G476K, H1*+T51G+N54S+V56T+G109A+G110N+A174S+G182*+D183*+N195F+V206L+K391A+G476K, H1*+N54S+V56T+G109A+Q125S+A174S+N175G+G182*+D183*+N195F+V206L+K391A+G476K, H1*+N54S+V56T+G109A+A174S+G182*+D183*+N195F+V206L+A265G+V291A+F328L+K391A+G476K, H1*+N54S+V56T+G109A+A174S+G182*+D183*+N195F+V206L+M246F+A265G+V291A+F328L+Q365S+K391A+G476K, H1*+N16Y+N54S+V56T+G109A+R116H+A174S+G182*+D183*+N195F+V206L+G337E+D377H+K391A+G476K, H1*+I9L+N54S+V56T+G109A+Q125S+V131T+A174*+G182*+D183*+V206L+Y267F+F289H+Q361E+K391A+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+Q169E+Q172K+A174*+G182*+

D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+G476K, H1*+W48F+N54S+V56T+G109A+A174S+G182*+D183*+N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, H1*+N54S+V56T+G109A+A174S+V206L+G182*+D183*+K391A+G476K, H1*+N54S+V56T+Q169E+Q172K+A174*+G182*+D183*+N195F+V206L+K391A+G476K, H1*+N54S+V56T+G109A+A174S+G182*+D183*+N195F+V206F+K391A+G476K, H1*+N54S+V56T+G109A+G182*+D183*+N195F+V206L+K391A+G476K, H1*+N54S+V56T+G109A+Q172K+A174S+G182*+D183*+N195F+V206L+K391A+G476K, H1*+N54S+V56T+G109A+Q172K+A174*+G182*+D183*+N195F+V206L+K391A+G476K, H1*+N54S+V56T+G109A+A174N+G182*+D183*+N195F+V206L+K391A+G476K, H1*+N54S+V56T+G109A+A174S+A186N+G182*+D183*+N195F+V206L+K391A+G476K, H1*+N54S+V56T+G109A+A174S+G182*+D183*+N195F+V206L+F289L+K391A+G476K, H1*+N54S+V56T+G109A+A174S+G182*+D183*+N195F+V206L+Y295F+K391A+G476K, H1*+N54S+V56T+G109A+A174S+G182*+D183*+N195F+V206L+V291A+K391A+G476K, H1*+N54S+V56T+G109A+A174S+G182*+D183*+N195F+V206L+S244Q+K391A+G476K, G182*+D183*+F328L, G182*+D183*+N195F+A288V, G182*+D183*+A186N+N195F, G182*+D183*+E190P+N195F, W140Y+G182*+D183*+N195F, H1*+N54S+V56T+G109A+A174S+G182*+D183*+N195F+V206L+A225V+K391A+G476K, G182*+D183*+A186D+N195F, H1*+N54S+V56T+G109A+A174S+G182*+D183*+N195F+V206L+K391A+P473R+G476K, H1*+W48Y+N54S+V56T+G109A+A174S+G182*+D183*+N195F+V206L+K391A+G476K, H1*+N54S+V56T+G109A+Q169E+Q172K+A174*+G182*+D183*+N195F+V206L+K391A+G476K, G182*+D183*+N195F+V238A, G182*+D183*+Y295N, Q172G+G182*+D183*, F113Q+G182*+D183*+N195F, H1*+N54S+V56T+Q98A+G109A+A174S+G182*+D183*+N195F+V206L+K391A+G476K, G182*+D183*+N195F+Y295F, G182*+D183*+A186E, H1*+N54S+V56T+G109A+A174S+G182*+D183*+N195F+V206Y+K391A+G476K, G182*+D183*+N195F+W284H, G182*+D183*+A186Q+N195F, K72R+G182*+D183*, D183*+G182*+N195F+V326L, D183*+G182*+A186E+N195F, Q169E+G182*+D183*+N195F, D183*+G182*+N195F+K242Q, G7A+G182*+D183*+N195F, D183*+G182*+N195F+N260G, D183*+G182*+R321A+S323N, D183*+G182*+W284H, H1*+D183*+G182*, D183*+G182*+A186H+N195F, D183*+G182*+F289V, D183*+G182*+K391A, D183*+G182*+S304R, W167F+G182*+D183*+N195F, F113Q+R116H+D183*+G182*, D183*+G182*+N270G, D183*+G182*+S244Q, H1*+N54S+V56T+G109A+A174S+G182*+D183*+G184T+N195F+V206L+K391A+G476K, D183*+G182*+N195F+Y295N, H1*+N54S+V56T+G109A+A174S+G182*+D183*+N195F+V206L+G255A+K391A+G476K, D183*+G182*+A186Q, D183*+G182*+N195F+V206F, D183*+G182*+N195F+R320A, G182*+D183*+G184T+N195F, N54S+V56T+D183*+G182*, W48Y+D183*+G182*, A174S+D183*+G182*, G7A+D183*+G182*, N54S+D183*+G182*, D183*+G182*+N195F+M246V, W48Y+D183*+G182*+N195F, D183*+G182*+N195F+S304R, wherein numbering is according to SEQ ID NO: 13, and wherein the IF is determined by use of Model A detergent.

In one embodiment, the IF is determined by use of Model A detergent at a temperature of 15° C. In a particular embodiment, the variants have an IF of >1 as compared to the parent polypeptide, wherein the IF is determined by use of Model A detergent at a temperature of 15° C. and a concentration of 0.05 mg/L. It can be seen from the Tables in the Examples herein disclosed which such variants may be.

In another embodiment, the variant has an IF of at least 1.0 when compared to the parent polypeptide when tested in Model J detergent, and wherein the variant is selected from the group consisting of: G182*+D183*+N195F, H1*+N54S+V56T+G109A+A174S+G182*+D183*+N195F+V206L+K391A+G476K, H1*+N54S+V56T+R87S+G109A+A174S+G182*+D183*+N195F+V206L+K391A+G476K, H1*+T40G+N54S+V56T+G109A+A174S+G182*+D183*+N195F+V206L+K391A+G476K, H1*+T51K+N54S+V56T+G109A+A174S+G182*+D183*+N195F+V206L+K391A+G476K, H1*+N54S+V56T+K72R+G109A+A174S+G182*+D183*+N195F+V206L+K391A+G476K, H1*+N54S+V56T+K72H+G109A+A174S+G182*+D183*+N195F+V206L+K391A+G476K, H1*+A37H+N54S+V56T+G109A+A174S+G182*+D183*+N195F+V206L+K391A+G476K, H1*+A37M+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+A37S+N54S+V56T+G109A+A174S+G182*+D183*+N195F+V206L+K391A+G476K, H1*+A37Y+N54S+V56T+G109A+A174S+G182*+D183*+N195F+V206L+K391A+G476K, H1*+A37R+N54S+V56T+G109A+A174S+G182*+D183*+N195F+V206L+K391A+G476K, H1*+N54S+V56T+G109A+F113W+A174S+G182*+D183*+N195F+V206L+K391A+G476K, H1*+N54S+V56T+G109A+F113S+A174S+G182*+D183*+N195F+V206L+K391A+G476K, H1*+N54S+V56T+G109A+F113N+A174S+G182*+D183*+N195F+V206L+K391A+G476K, H1*+N54S+V56T+G109A+F113Y+A174S+G182*+D183*+N195F+V206L+K391A+G476K, H1*+N54S+V56T+G109A+F113R+A174S+G182*+D183*+N195F+V206L+K391A+G476K, H1*+N54S+V56T+G109A+Q118N+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+R116V+A174S+G182*+D183*+N195F+V206L+K391A+G476K, H1*+N54S+V56T+G109A+R116K+A174S+G182*+D183*+N195F+V206L+K391A+G476K, H1*+N54S+V56T+G109A+R116W+A174S+G182*+D183*+N195F+V206L+K391A+G476K, H1*+N54S+V56T+G109A+R116L+A174S+G182*+D183*+N195F+V206L+K391A+G476K, H1*+N54S+V56T+G109A+G142T+A174S+G182*+D183*+N195F+V206L+K391A+G476K, H1*+N54S+V56T+G109A+Q125P+A174S+G182*+D183*+N195F+V206L+K391A+G476K, H1*+N54S+V56T+G109A+Q125K+A174S+G182*+D183*+N195F+V206L+

K391A+G476K, H1*+N54S+V56T+G109A+A174S+G182*+D183*+N195F+V206L+S381G+K391A+G476K, H1*+N54S+V56T+G109A+A174S+G182*+D183*+N195F+V206L+M246T+K391A+G476K, H1*+N54S+V56T+G109A+A174S+G182*+D183*+N195F+V206L+V213T+K391A+G476K, H1*+A37L+N54S+V56T+G109A+A174S+G182*+D183*+N195F+V206L+K391A+G476K, H1*+N54S+V56T+G109A+Q118K+A174S+G182*+D183*+N195F+V206L+K391A+G476K, H1*+N54S+V56T+G109A+R116A+A174S+G182*+D183*+N195F+V206L+K391A+G476K, H1*+N54S+V56T+G109A+R116H+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+Q172R+A174S+G182*+D183*+N195F+V206L+K391A+G476K, H1*+N54S+V56T+G109A+A174S+G182*+D183*+N195F+V206L+D377S+K391A+G476K, H1*+N54S+V56T+G109A+A174S+G182*+D183*+N195F+V206L+D377G+K391A+G476K, H1*+N54S+V56T+G109A+A174S+G182*+D183*+N195F+V206L+D377R+K391A+G476K, H1*+N54S+V56T+G109A+A174S+G182*+D183*+N195F+V206L+D377A+K391A+G476K, H1*+N54S+V56T+G109A+A174S+G182*+D183*+N195F+V206L+I214G+K391A+G476K, H1*+N54S+V56T+G109A+A174S+G182*+D183*+N195F+V206L+S381A+K391A+G476K, H1*+N54S+V56T+G109A+W167I+A174S+G182*+D183*+N195F+V206L+K391A+G476K, H1*+N54S+V56T+G109A+W167G+A174S+G182*+D183*+N195F+V206L+K391A+G476K, H1*+N54S+V56T+G109A+A174S+G182*+D183*+N195F+V206L+G346S+K391A+G476K, H1*+N54S+V56T+G109A+A174S+G182*+D183*+N195F+V206L+G346P+K391A+G476K, H1*+N54S+V56T+G109A+A174S+G182*+D183*+N195F+V206L+I214H+K391A+G476K, H1*+N54S+V56T+G109A+A174S+G182*+D183*+N195F+V206L+I214S+K391A+G476K, H1*+N54S+V56T+G109A+A174S+G182*+D183*+N195F+V206L+I214T+K391A+G476K, H1*+N54S+V56T+G109A+A174S+G182*+D183*+N195F+V206L+K391A+A420Q+G476K, H1*+N54S+V56T+G109A+A174S+G182*+D183*+N195F+V206L+K391A+A420S+G476K, H1*+N54S+V56T+G109A+A174S+G182*+D183*+N195F+V206L+K391A+A420K+G476K, H1*+N54S+V56T+G109A+A174S+G182*+D183*+N195F+V206L+K391A+A420L+G476K, H1*+N54S+V56T+G109A+A174S+G182*+D183*+N195F+V206L+K391A+K391Y+G476K, H1*+N54S+V56T+G109A+A174S+G182*+D183*+N195F+V206L+K391A+K391R+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+P473G+G476K, H1*+N54S+V56T+G109A+A174S+G182*+D183*+N195F+V206L+K391A+P473T+G476K, H1*+N54S+V56T+G109A+A174S+G182*+D183*+N195F+V206L+K391A+Q395P+G476K, H1*+N54S+V56T+G109A+A174S+G182*+D183*+N195F+V206L+K391A+T444Q+G476K, H1*+N54S+V56T+G109A+A174S+G182*+D183*+N195F+V206L+K391A+T444S+G476K, H1*+N54S+V56T+G109A+A174S+G182*+D183*+N195F+V206L+K391A+T444D+G476K, H1*+N54S+V56T+G109A+A174S+G182*+D183*+N195F+V206L+K391A+T444Y+G476K, H1*+N54S+V56T+G109A+A174S+G182*+D183*+N195F+V206L+S280W+K391A+G476K, H1*+N54S+V56T+G109A+A174S+G182*+D183*+N195F+V206L+S280L+K391A+G476K, H1*+N54S+V56T+G109A+A174S+G182*+D183*+N195F+V206L+S280T+K391A+G476K, H1*+N54S+V56T+G109A+A174S+G182*+D183*+N195F+V206L+S280A+K391A+G476K, H1*+N54S+V56T+G109A+A174S+G182*+D183*+N195F+V206L+G255N+K391A+G476K, H1*+N54S+V56T+G109A+A174S+G182*+D183*+N195F+V206L+T285L+K391A+G476K, H1*+N54S+V56T+G109A+A174S+G182*+D183*+N195F+V206L+T285Q+K391A+G476K, H1*+N54S+V56T+G109A+A174S+G182*+D183*+N195F+V206L+K391A+Q449T+G476K, H1*+N54S+V56T+G109A+A174S+G182*+D183*+N195F+V206L+K391A+P473K+G476K, H1*+N54S+V56T+K72S+G109A+A174S+G182*+D183*+N195F+V206L+K391A+G476K, H1*+T40K+N54S+V56T+G109A+A174S+G182*+D183*+N195F+V206L+G346T+K391A+G476K, H1*+G50A+N54S+V56T+G109A++Q172N+A174S+G182*+D183*+N195F+V206L+K391A+G476K, H1*+N54S+V56T+G109A+A174S+G182*+D183*+N195F+V206L+K391A+G476K+K484A, H1*+N54S+V56T+G109A+A174S+G182*+D183*+N195F+V206L+K391A+G476K+K484G, H1*+N54S+V56T+G109A+A174S+G182*+D183*+N195F+V206L+K391A+G476K+K484P, H1*+N54S+V56T+G109A+A174S+G182*+D183*+N195F+V206L+K391A+G476K+K484E, H1*+N54S+V56T+G109A+A174S+G182*+D183*+N195F+V206L+K391A+G476K+K484Q, H1*+N54S+V56T+G109A+A174S+G182*+D183*+N195F+V206L+K391A+G476K+K484S, H1*K+G50A+N54S+V56T+G109A+W167F+A174S+G182*+D183*+N195F+V206L+K391A+G476K, H1*+N54S+V56T+G109A+L173V+A174S+G182*+D183*+N195F+A204T+V206L+K391A+G476K, H1*+N54S+V56T+G109A+W140Y+A174S+G182*+D183*+N195F+V206L+K391A+G476K, H1*+N54S+V56T+Q98S+G109A+A174S+G182*+D183*+N195F+V206L+R320A+K391A+G476K, H1*+N54S+V56T+G109A+A174S+G182*+D183*+N195F+V206L+H324L+K391A+G476K, H1*+N54S+V56T+G109A+G149Q+A174S+G182*+D183*+N195F+V206L+K391A+G476K, H1*+N54S+V56T+G109A+A174S+G182*+D183*+N195F+V206L+G346T+K391A+G476K+G477A, H1*+N54S+V56T+G109AG255A++A174S+G182*+D183*+N195F+V206L+K391A+G476K, H1*+G50A+N54S+V56T+G109A+F113L+R116L+A174S+G182*+D183*+N195F+V206L+K391A+G476K, H1*+N54S+V56T+G109A+W167F+A174S+G182*+D183*+N195F+V206L+K391A+G476K, H1*+N54S+V56T+G109A+L173V+A174S+G182*+D183*+N195F+V206L+K391A+G476K, H1*+N54S+V56T+K72R+G109A+W167F+A174S+G182*+D183*+N195F+V206L+K391A+G476K, H1*+N54S+V56T+G109A+A174S+G182*+D183*+N195F+V206L+K391A+G476K+G477Q, H1*+N54S+V56T+G109A+A174S+G182*+D183*+N195F+V206L+Q345D+K391A+G476K+G477Q, H1*+G50A+N54S+V56T+G109A+Q172D+A174S+G182*+D183*+N195F+V206L+K391A+G476K, H1*+N54S+V56T+G109A+A174S+G182*+D183*+N195F+V206L+V264I+K391A+G423H+G476K, H1*+N54S+V56T+G109A+A174S+G182*+D183*+N195F+V206L+R320V+K391A+G476Y, H1*+T5K+N54S+V56T+G109A+A174S+G182*+D183*+N195F+V206L+K391A+G476K, H1*+N54S+V56T+G109A+R116M+A174S+G182*+D183*+N195F+V206L+K391A+G476K, H1*+N54S+V56T+G109A+Q172Y+A174S+G182*+D183*+N195F+V206L+K391A+G476K, H1*+N54S+V56T+G109A+A174S+G182*+D183*+N195F+V206L+I214L+K391A+G476K,

H1*+N54S+V56T+G109A+A174S+G182*+D183*+N195F+V206L+L217V+K391A+G476K, H1*+N54S+V56T+G109A+A174S+G182*+D183*+N195F+V206L+L217H+K391A+G476K, H1*+N54S+V56T+G109A+A174S+G182*+D183*+N195F+V206L+P211D+K391A+G476K, H1*+N54S+V56T+G109A+A174S+G182*+D183*+N195F+V206L+K391A+K391Q+G476K, H1*+N54S+V56T+G109A+A174S+G182*+D183*+N195F+V206L+K391A+T444H+G476K, H1*+N54S+V56T+G109A+A174S+G182*+D183*+N195F+V206L+K391A+T444V+G476K, H1*+N54S+V56T+G109A+A174S+G182*+D183*+N195F+V206L+K391A+T444R+G476K, H1*+G50A+N54S+V56T+G109A+L173V+A174S+G182*+D183*+N195F+A204V+V206L+K391A+G476K, H1*+G50A+N54S+V56T+G109A+F113L+W167F+A174S+G182*+D183*+N195F+V206L+K391A+G476K, H1*°G7K+N54S+V56T+G109A+A174S+G182*+D183*+N195F+V206L+R320A+K391A+G476K, H1*+N54S+V56T+G109A+Q118G+A174S+G182*+D183*+N195F+V206L+K391A+G476K, H1*+N54S+V56T+G109A+A174S+G182*+D183*+N195F+V206L+S280K+K391A+G476K, H1*+N54S+V56T+G109A+A174S+G182*+D183*+N195F+V206L+N270G+K391A+G476K, H1*+N54S+V56T+G109A+Q172D+A174S+G182*+D183*+N195F+V206L+G346T+K391A+G476K+G477A, H1*+N54S+V56T+G109A+Q118S+A174S+G182*+D183*+N195F+V206L+K391A+G476K, H1*+N54S+V56T+G109A+A174S+G182*+D183*+N195F+V206L+R320A+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+G337H+Q385L+K391A+G476K, H1*+N54S+V56T+G109A+A174S+G182*+D183*+N195F+V206L+Y382M+K391A+G476K, H1*+N54S+V56T+K72R+G109A+A174S+G182*+D183*+N195F+V206L+G255A+D377H+K391A+G476K, H1*+N54S+V56T+K72R+G109A+T134E+A174S+G182*+D183*+N195F+V206L+G255A+K391A+G476K, H1*+N54S+V56T+K72R+M105F+G109A+A174S+G182*+D183*+N195F+V206L+G255A+K391A+G476K, H1*+N54S+V56T+M105F+G109A+T134E+A174S+G182*+D183*+N195F+V206L+K391A+G476K, H1*+N54S+V56T+M105F+G109A+Q118F+T134E+A174S+G182*+D183*+N195F+V206L+K391A+G476K, H1*+N54S+V56T+G109A+A174S+G182*+D183*+N195F+V206L+R320A+S323N+D377H+K391A+G476K, H1*+T51E+N54S+V56T+G109A+A174H+G182*+D183*+N195F+V206L+K391A+G476K, H1*+N54S+V56T+G109A+L173A+A174S+G182*+D183*+N195F+V206L+K391A+G476K, H1*+N54S+V56T+G109A+A174S+G182*+D183*+N195F+V206L+Q299V+K391A+G476K, H1*+N54S+V56T+G109A+L173G+A174S+G182*+D183*+N195F+V206L+K391A+G476K, H1*+N54S+V56T+G109A+A174S+G182*+D183*+N195F+V206L+T355L+K391A+G476K, H1*+N54S+V56T+G109A+A174S+G182*+D183*+N195F+V206L+T355F+K391A+G476K, H1*+G50A+N54S+V56T+G109A+A174S+G182*+D183*+N195F+A204T+V206L+K391A+G476K, H1*+G50A+N54S+V56T+G109A+A174E+G182*+D183*+N195F+A204T+V206L+K391A+G476K, H1*+N54S+V56T+K72R+G109A+A174S+G182*+D183*+N195F+V206L+R320A+S323N+K391A+G476K, H1*+N54S+V56T+M105I+G109A+A174S+G182*+D183*+N195F+V206L+K391A+G476K, H1*+N54S+V56T+G109A+A174S+G182*+D183*+N195F+V206L+M246L+K391A+G476K, H1*+T51G+N54S+V56T+G109A+A174N+G182*+D183*+N195F+V206L+K391A+G476K, H1*+T51A+N54S+V56T+G109A+A174G+G182*+D183*+N195F+V206L+K391A+G476K, H1*+N54S+V56T+G109A+A174D+G182*+D183*+N195F+V206L+K391A+G476K, H1*+T51S+N54S+V56T+G109A+A174P+G182*+D183*+N195F+V206L+K391A+G476K, H1*+T51G+N54S+V56T+G109A+A174M+G182*+D183*+N195F+V206L+K391A+G476K, H1*+N54S+V56T+K72Q+G109A+W167H+A174S+G182*+D183*+N195F+V206L+K391A+G476K, H1*+N54S+V56T+G109A+Q118R+T134E+A174S+G182*+D183*+N195F+V206L+D377H+K391A+G476K, H1*+Q11H+N54S+V56T+G109A+Q118R+T134E+A174S+G184T+G182*+D183*+N195F+V206L+D377H+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+Q118R+T134E+A174S+G182*+D183*+N195F+V206L+G255A+K391A+G476K, H1*+N54S+V56T+G109A+Q118R+A174S+G182*+D183*+N195F+V206L+D377H+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+K72A+G109A+W167F+A174S+G182*+D183*+N195F+V206L+K391A+G476K, H1*+N54S+V56T+G109A+W167S+G182*+D183*+N195F+A174S+V206L+K391A+G476K, H1*+N54S+V56T+K72H+G109A+W167S+A174S+G182*+D183*+N195F+V206L+K391A+G476K, H1*+N54S+V56T+K72R+G109A+W167T+A174S+G182*+D183*+N195F+V206L+K391A+G476K, H1*+N54S+V56T+K72E+G109A+A174S+G182*+D183*+N195F+V206L+K391A+G476K, H1*+N54S+V56T+K72R+G109A+W167L+A174S+G182*+D183*+N195F+V206L+K391A+G476K, H1*+N54S+V56T+K72R+G109A+W167M+A174S+G182*+D183*+N195F+V206L+K391A+G476K, H1*+N54S+V56T+K72R+G109A+W167H+A174S+G182*+D183*+N195F+V206L+K391A+G476K, H1*+N54S+V56T+K72R+G109A+A174S+G182*+D183*+G184T+N195F+V206L+G255A+K391A+G476K, H1*+N54S+V56T+G109A+A174S+G182*+D183*+G184T+N195F+V206L+D377H+K391A+G476K, H1*+N54S+V56T+G109A+A174S+G182*+D183*+N195F+V206L+G255A+D377H+K391A+G476K, H1*+N54S+V56T+G109A+Q118R+A174S+G182*+D183*+N195F+V206L+G255A+D377H+K391A+G476K, H1*+N54S+V56T+G109A+A174S+G182*+D183*+G184A+T193K+N195F+V206L+K391A+G476K, H1*+N54S+V56T+M105F+G109A+A174S+G182*+D183*+G184T+N195F+V206L+K391A+G476K, H1*+N54S+V56T+G109A+T134E+A174S+G182*+D183*+N195F+V206L+R320A+S323N+K391A+G476K, H1*+N54S+V56T+G109A+A174S+G182*+D183*+N195F+V206L+V291G+D377H+K391A+G476K, H1*+N54S+V56T+G109A+A174S+G182*+D183*+N195F+V206L+V291A+F328L+D377H+K391A+G476K, H1*+V56T+G109A+A174S+G182*+D183*+N195F+V206L+D377H+K391A+G476K, H1*+N54S+V56T+G109A+T134E+A174S+G182*+D183*+G184T+N195F+V206L+K391A+G476K, H1*+N54S+V56T+G109A+A174S+G182*+D183*+N195F+V206L+V238A+D377H+K391A+G476K, H1*+N54S+V56T+G109A+A174S+G182*+D183*+N195F+V206L+V238T+D377H+K391A+G476K, H1*+N54S+V56T+G109A+A174S+G182*+D183*+N195F+V206L+V238G+D377H+K391A+G476K, H1*+

N54S+V56T+G109A+A174S+G182*+D183*+N195F+V206L+F328M+D377H+K391A+G476K, H1*+N54S+V56T+G109A+A174S+G182*+D183*+N195F+V206L+F328L+D377H+K391A+G476K, H1*+N54S+V56T+G109A+A174S+G182*+D183*+N195F+V206L+F328V+D377H+K391A+G476K, H1*+N54S+V56T+G109A+A174S+G182*+D183*+N195F+V206L+F328I+D377H+K391A+G476K, H1*+N54S+V56T+G109A+A174S+G182*+D183*+N195F+V206L+V291T+D377H+K391A+G476K, H1*+N54S+V56T+G109A+A174S+G182*+D183*+N195F+V206L+V291A+D377H+K391A+G476K, H1*+N54S+V56T+K72R+G109A+T134E+A174S+G182*+D183*+G184T+N195F+V206L+G255A+K391A+G476K, H1*+N54S+V56T+G109A+L173H+A174S+G182*+D183*+N195F+V206L+K391A+G476K, H1*+N54S+V56T+G109A+Q125T+A174S+G182*+D183*+N195F+V206L+K391A+G476K, H1*+N16S+N54S+V56T+G109A+A174S+G182*+D183*+N195F+V206L+K391A+G476K, H1*+N54S+V56T+K72N+G109A+A174S+G182*+D183*+N195F+V206L+K391A+G476K, H1*+N54S+V56T+K72N+G109A+W167L+A174S+G182*+D183*+N195F+V206L+K391A+G476K, H1*+N54S+V56T+K72A+G109A+W167Y+A174S+G182*+D183*+N195F+V206L+K391A+G476K, H1*+N54S+V56T+G109A+Q118R+T134E+A174S+G182*+D183*+N195F+V206L+G255A+D377H+K391A+G476K, H1*+N54S+V56T+K72R+G109A+A174S+G182*+D183*+N195F+G184T+V206L+K391A+G476K, H1*+N54S+V56T+K72R+G109A+Q118R+A174S+G182*+D183*+G184T+N195F+V206L+D377H+K391A+G476K, H1*+N54S+V56T+K72R+G109A+Q118R+A174S+G182*+D183*+N195F+V206L+G255A+D377H+K391A+G476K, H1*+N54S+V56T+G109A+A174S+G182*+D183*+G184T+N195F+V206L+R320A+S323N+K391A+G476K, H1*+N54S+G109A+A174S+G182*+D183*+N195F+V206L+D377H+K391A+G476K, H1*+N54S+V56T+A174S+G182*+D183*+N195F+V206L+D377H+K391A+G476K, H1*+N54S+V56T+G109A+G182*+D183*+N195F+V206L+D377H+K391A+G476K, H1*+N54S+V56T+G109A+A174S+G182*+D183*+N195F+D377H+K391A+G476K, H1*+N54S+V56T+G109A+A174S+G182*+D183*+N195F+D377H+K391A+G476K, H1*+N54S+V56T+G109A+A174S+G182*+D183*+N195F+V206L+D377H+G476K, H1*+N54S+V56T+G109A+A174S+G182*+D183*+N195F+V206L+D377H+K391A, H1*+N54S+V56T+G109A+A174S+G182*+D183*+N195F+V206L+D377R+K391A+G476K, H1*+N54S+V56T+G109A+A174S+G182*+D183*+N195F+V206L+L217T+K391A+G476K, H1*+N54S+V56T+G109A+A174S+G182*+D183*+N195F+V206L+D377S+K391A+G476K, H1*+N54S+V56T+G109A+R116E+A174S+G182*+D183*+N195F+V206L+K391A+G476K, H1*+N54S+V56T+G109A+A174S+G182*+D183*+N195F+V206L+L217Q+K391A+G476K, H1*+N54S+V56T+G109A+A174S+G182*+D183*+N195F+V206L+G346D+K391A+G476K, H1*+N54S+V56T+G109A+A174S+G182*+D183*+N195F+V206L+D377A+K391A+G476K, H1*+N54S+V56T+G109A+T134E+A174S+G182*+D183*+N195F+V206L+D377H+K391A+G476K, H1*+N54S+V56T+G109A+Q118R+T134E+A174S+G182*+D183*+G184T+N195F+V206L+K391A+G476K, H1*+N54S+V56T+K72R+G109A+Q118R+T134E+A174S+G182*+D183*+N195F+V206L+K391A+G476K, H1*+N54S+V56T+G109A+A174S+G182*+D183*+N195F+V206L+G346P+K391A+G476K, H1*+N54S+V56T+G109A+R116S+A174S+G182*+D183*+N195F+V206L+K391A+G476K, H1*+N54S+V56T+G109A+A174S+G182*+D183*+N195F+V206L+D377Q+K391A+G476K, H1*+N54S+V56T+G109A+R116I+A174S+G182*+D183*+N195F+V206L+K391A+G476K, H1*+N54S+V56T+G109A+A174F+G182*+D183*+N195F+V206L+K391A+G476K, H1*+N54S+V56T+G109A+R116G+A174S+G182*+D183*+N195F+V206L+K391A+G476K, H1*+N54S+V56T+G109A+A174T+G182*+D183*+N195F+V206L+K391A+G476K, H1*+N54S+V56T+G109A+Q118R+T134E+A174S+G182*+D183*+G184T+N195F+V206L+G255A+K391A+G476K, H1*+N54S+V56T+K72R+G109A+Q118R+T134E+A174S+G182*+D183*+N195F+V206L+G255A+K391A+G476K, H1*+T51G+N54S+V56T+G109A+Q172R+A174S+G182*+D183*+N195F+V206L+K391A+G476K, H1*+T51A+N54S+V56T+G109A+Q172D+A174S+G182*+D183*+N195F+V206L+K391A+G476K, H1*+T51S+N54S+V56T+G109A+Q172M+A174S+G182*+D183*+N195F+V206L+K391A+G476K, H1*+T51A+N54S+V56T+G109A+Q172S+A174S+G182*+D183*+N195F+V206L+K391A+G476K, H1*+T51E+N54S+V56T+G109A+Q172T+A174S+G182*+D183*+N195F+V206L+K391A+G476K, H1*+T51A+N54S+V56T+G109A+Q172A+A174S+G182*+D183*+N195F+V206L+K391A+G476K, H1*+T51S+N54S+V56T+G109A+Q172N+A174S+G182*+D183*+N195F+V206L+K391A+G476K, H1*+T51G+N54S+V56T+G109A+Q172K+A174S+G182*+D183*+N195F+V206L+K391A+G476K, H1*+T51A+N54S+V56T+G109A+Q172G+A174S+G182*+D183*+N195F+V206L+K391A+G476K, H1*+T51E+N54S+V56T+G109A+Q172L+A174S+G182*+D183*+N195F+V206L+K391A+G476K, H1*+T51E+N54S+V56T+G109A+Q172R+A174S+G182*+D183*+N195F+V206L+K391A+G476K, H1*+N54S+V56T+G109A+Q172K+A174S+G182*+D183*+N195F+V206L+K391A+G476K, H1*+T51D+N54S+V56T+G109A+Q172N+A174S+G182*+D183*+N195F+V206L+K391A+G476K, H1*+T51A+N54S+V56T+G109A+Q172K+A174S+G182*+D183*+N195F+V206L+K391A+G476K, H1*+N54S+V56T+K72R+G109A+Q172S+A174S+G182*+D183*+N195F+V206L+K391A+G476K, H1*+N54S+V56T+K72H+G109A+Q172T+A174S+G182*+D183*+N195F+V206L+K391A+G476K, H1*+N54S+V56T+K72R+G109A+Q172R+A174S+K179E+G182*+D183*+N195F+V206L+K391A+G476K, H1*+N54S+V56T+K72R+G109A+Q172M+A174S+G182*+D183*+N195F+V206L+Y295N+K391A+G476K, H1*+N54S+V56T+K72R+G109A+Q172R+A174S+G182*+D183*+N195F+V206L+K391A+G476K, H1*+N54S+V56T+K72Q+G109A+Q172R+A174S+G182*+D183*+N195F+V206L+K391A+G476K, H1*+N54S+V56T+K72R+G109A+Q172T+A174S+G182*+D183*+N195F+V206L+K391A+G476K, H1*+N54S+V56T+K72M+G109A+Q172S+A174S+G182*+D183*+N195F+V206L+K391A+G476K, H1*+N54S+V56T+K72Q+G109A+Q172M+A174S+G182*+D183*+N195F+V206L+K391A+G476K, H1*+N54S+V56T+G109A+Q172M+A174S+G182*+D183*+N195F+V206L+K391A+G476K, H1*+N54S+V56T+K72S+G109A+A174H+G182*+D183*+N195F+V206L+K391A+G476K, H1*+N54S+V56T+K72Q+G109A+A174D+G182*+D183*+N195F+V206L+K391A+G476K, H1*+N54S+V56T+K72R+G109A+A174D+G182*+D183*+N195F+V206L+K391A+G476K, H1*+N54S+V56T+K72Q+G109A+A174K+G182*+D183*+N195F+V206L+K391A+G476K, H1*+N54S+V56T+G109A+A174G+G182*+D183*+N195F+V206L+K391A+G476K, H1*+N54S+V56T+K72R+G109A+A174Q+G182*+D183*+N195F+V206L+K391A+G476K, H1*+N54S+V56T+

K72Q+G109A+A174G+G182*+D183*+N195F+V206L+K391A+G476K, H1*+N54S+V56T+K72S+G109A+A174N+G182*+D183*+N195F+V206L+K391A+G476K, H1*+N54S+V56T+K72R+G109A+A174H+G182*+D183*+N195F+V206L+K391A+G476K, H1*+N54S+V56T+G109A+A174S+G182*+D183*+N195F+V206L+K391A+K391S+G476K, H1*+N54S+V56T+G109A+A174S+G182*+D183*+N195F+V206L+K391A+T444A+G476K, H1*+N54S+V56T+G109A+F113L+W167F+A174S+G182*+D183*+N195F+V206L+K391A+G476K, H1*+G50A+N54S+V56T+G109A+A174E+G182*+D183*+N195F+A204T+V206L+S323N+K391A+G476K, H1*+N54S+V56T+K72R+G109A+Q118R+A174S+G182*+D183*+G184T+N195F+V206L+G255A+K391A+G476K, H1*+N54S+V56T+M105F+G109A+A174S+G182*+D183*+N195F+V206L+D377H+K391A+G476K, H1*+N54S+V56T+K72R+G109A+Q118R+A174S+G182*+D183*+N195F+V206L+D377H+K391A+G476K, H1*+N54S+V56T+G109A+A174S+G182*+D183*+N195F+A204G+V206L+K391A+G476K, H1*+N54S+V56T+G109A+A174S+G182*+D183*+N195F+V206L+A225F+K391A+G476K, H1*+N54S+V56T+G109A+A174S+G182*+D183*+N195F+V206L+M246A+K391A+G476K, H1*+N54S+V56T+G109A+A174S+G182*+D183*+N195F+V206L+Y382I+K391A+G476K, H1*+N54S+V56T+G109A+A174S+G182*+D183*+N195F+V206L+S376H+K391A+G476K, H1*+N54S+V56T+G109A+A174S+G182*+D183*+N195F+V206L+I214E+K391A+G476K, H1*+N54S+V56T+G109A+A174S+G182*+D183*+N195F+V206L+I214W+K391A+G476K, H1*+N54S+V56T+K72R+G109A+Q172K+A174S+G182*+D183*+N195F+V206L+K391A+G476K, H1*+N54S+V56T+G109A+A174S+G182*+D183*+N195F+A204T+V206L+D377H+K391A+G476K, H1*+N54S+V56T+G109A+A174S+G182*+D183*+N195F+A204S+V206L+D377H+K391A+G476K, H1*+N54S+V56T+G109A+T165S+A174S+G182*+D183*+N195F+V206L+D377H+K391A+G476K, H1*+N54S+V56T+G109A+A174S+G182*+D183*+N195F+V206L+T334S+D377H+K391A+G476K, H1*+N54S+V56T+G109A+A174S+G182*+D183*+N195F+V206L+A263G+D377H+K391A+G476K, H1*+N54S+V56T+G109A+A174S+G182*+D183*+N195F+V206L+M286F+D377H+K391A+G476K, H1*+N54S+V56T+G109A+A174S+G182*+D183*+N195F+V206L+Y267I+D377H+K391A+G476K, H1*+N54S+V56T+G109A+A174S+G182*+D183*+N195F+V206L+L235V+D377H+K391A+G476K, H1*+N54S+V56T+G109A+A174S+G182*+D183*+N195F+V206L+L235A+D377H+K391A+G476K, H1*+N54S+V56T+M105L+G109A+A174S+G182*+D183*+N195F+V206L+D377H+K391A+G476K, H1*+N54S+V56T+M105I+G109A+A174S+G182*+D183*+N195F+V206L+D377H+K391A+G476K, H1*+N54S+V56T+M105V+G109A+A174S+G182*+D183*+N195F+V206L+D377H+K391A+G476K, H1*+N54S+V56T+G109A+A174S+G182*+D183*+N195F+V206L+M246I+D377H+K391A+G476K, H1*+N54S+V56T+G109A+A174S+G182*+D183*+N195F+V206L+L250I+D377H+K391A+G476K, H1*+N54S+V56T+G109A+A174S+G182*+D183*+N195F+V206L+L250V+D377H+K391A+G476K, H1*+N54S+V56T+G109A+A174S+G182*+D183*+N195F+V206L+K391Y+G476K, H1*+N54S+V56T+G109A+A174S+G182*+D183*+N195F+V206L+K391V+G476K, H1*+N54S+V56T+G109A+A174S+G182*+D183*+N195F+V206L+K391M+G476K, H1*+N54S+V56T+G109A+A174S+G182*+D183*+N195F+V206L+K391E+G476K, H1*+N54S+V56T+G109A+T165G+A174S+G182*+D183*+N195F+V206L+D377H+K391A+G476K, H1*+N54R+V56T+G109A+A174S+G182*+D183*+N195F+V206L+K391A+G476K, H1*+N54L+V56T+G109A+A174S+G182*+D183*+N195F+V206L+K391A+G476K, H1*+N54S+V56T+G109S+A174S+G182*+D183*+N195F+V206L+K391A+G476K, H1*+N54S+V56T+G109A+A174V+G182*+D183*+N195F+V206L+K391A+G476K, H1*+N54S+V56T+G109A+A174S+G182*+D183*+N195F+V206L+M246F+D377H+K391A+G476K, H1*+N54S+V56T+G109A+A174S+G182*+D183*+N195F+V206L+M246V+D377H+K391A+G476K, H1*+N54S+V56T+G109A+A174S+G182*+D183*+N195F+V206L+M246S+D377H+K391A+G476K, H1*+N54S+V56T+G109A+A174R+G182*+D183*+N195F+V206L+K391A+G476K, H1*+N54S+V56T+G109A+A174L+G182*+D183*+N195F+V206L+K391A+G476K, H1*+N54S+V56T+G109A+A174S+G182*+D183*+N195F+V206S+K391A+G476K, H1*+N54S+V56T+G109A+A174S+G182*+D183*+N195F+V206L+K391D+G476K, H1*+N54S+V56T+G109A+A174S+G182*+D183*+N195F+V206L+K391R+G476K, H1*+N54S+V56T+G109A+A174S+G182*+D183*+N195F+V206L+K391H+G476K, H1*+N54S+V56T+G109A+A174S+G182*+D183*+N195F+V206L+K391W+G476K, H1*+N54S+V56T+G109A+A174S+G182*+D183*+N195F+V206L+K391I+G476K, H1*+N54S+V56T+G109A+A174S+G182*+D183*+N195F+V206L+L250T+D377H+K391A+G476K, H1*+N54S+V56T+G109A+A174S+G182*+D183*+N195F+V206L+L250A+D377H+K391A+G476K, H1*+N54S+V56T+G109A+A174S+G182*+D183*+N195F+V206L+L250F+D377H+K391A+G476K, H1*+N54S+V56T+G109A+A174S+G182*+D183*+N195F+V206L+L250M+D377H+K391A+G476K, H1*+N54S+V56T+G109A+A174S+G182*+D183*+N195F+V206L+K391Q+G476K, H1*+N54S+V56T+G109A+Q172H+L173A+A174P+G182*+D183*+N195F+V206L+K391A+G476K, H1*+N54S+V56T+G109A+Q172E+L173A+A174R+G182*+D183*+N195F+V206L+K391A+G476K, H1*+N54S+V56T+K72Q+G109A+W167R+A174S+G182*+D183*+N195F+V206L+K391A+G476K, H1*+N54S+V56T+G109A+A174S+G182*+D183*+G184T+N195F+V206L+G255A+K391A+G476K, H1*+N54S+V56T+K72R+G109A+A174S+G182*+D183*+G184T+N195F+V206L+D377H+K391A+G476K, H1*+N54S+V56T+G109A+A174S+G182*+D183*+G184T+N195F+V206L+G255A+D377H+K391A+G476K, H1*+N54S+V56T+G109A+A174S+G182*+D183*+N195F+V206L+S376T+K391A+G476K, H1*+N54S+V56T+G109A+A174S+G182*+D183*+N195F+V206L+S376V+K391A+G476K, H1*+N54S+V56T+G109A+Q172E+L173I+A174N+G182*+D183*+N195F+V206L+K391A+G476K, H1*+N54S+V56T+G109A+Q172D+L173A+A174T+G182*+D183*+N195F+V206L+K391A+G476K, H1*+N54S+V56T+G109A+A174S+G182*+D183*+N195F+V206L+Y267M+D377H+K391A+G476K, H1*+N54S+V56T+G109A+A174S+G182*+D183*+N195F+V206L+Y267H+D377H+K391A+G476K, H1*+N54S+V56T+G109A+A174S+G182*+D183*+N195F+V206L+V238A+K391A+G476K, H1*+N54S+V56T+G109A+A174S+G182*+D183*+N195F+V206L+V238T+K391A+G476K, H1*+N54S+V56T+G109A+A174S+G182*+D183*+N195F+V206L+V238G+K391A+G476K, H1*+N54S+V56T+M105V+G109A+A174S+G182*+D183*+N195F+V206L+K391A+G476K, H1*+N54S+V56T+G109A+A174S+G182*+D183*+N195F+V206L+V264T+K391A+G476K, H1*+N54S+V56T+G109A+A174S+G182*+D183*+N195F+V206L+V264I+K391A+G476K, H1*+

N54S+V56T+G109A+A174S+G182*+D183*+N195F+V206L+L235V+K391A+G476K, H1*+N54S+V56T+G109A+W167H+Q172N+L173A+A174S+G182*+D183*+N195F+V206L+K391A+G476K, H1*+N54S+V56T+G109A+W167F+Q172E+L173P+A174K+G182*+D183*+N195F+V206L+K391A+G476K, H1*+N54S+V56T+G109A+Q172N+L173T+A174S+G182*+D183*+N195F+V206L+K391A+G476K, H1*+N54S+V56T+G109A+Q172K+L173V+A174T+G182*+D183*+N195F+V206L+K391A+G476K, H1*+N54S+V56T+G109A+Q172E+L173F+A174R+G182*+D183*+N195F+V206L+K391A+G476K, H1*+N54S+V56T+G109A+Q172E+L173T+A174R+G182*+D183*+N195F+V206L+K391A+G476K, H1*+N54S+V56T+G109A+Q172N+L173V+A174R+G182*+D183*+N195F+V206L+K391A+G476K, H1*+N54S+V56T+G109A+L173V+A174R+G182*+D183*+N195F+V206L+K391A+G476K, H1*+N54S+V56T+G109A+Q172E+L173M+A174H+G182*+D183*+N195F+V206L+K391A+G476K, H1*+N54S+V56T+G109A+Q172E+L173F+A174P+G182*+D183*+N195F+V206L+K391A+G476K, H1*+N54S+V56T+G109A+W167Y+Q172E+L173V+A174H+G182*+D183*+N195F+V206L+K391A+G476K, H1*+N54S+V56T+G109A+L173A+A174T+G182*+D183*+N195F+V206L+K391A+G476K, H1*+N54S+V56T+G109A+A174S+G182*+D183*+N195F+V206L+V291A+F328L+K391A+G476K, H1*+N54S+V56T+G109A+A174S+G182*+D183*+N195F+V206L+M246L+K391A+G476K, H1*+N54S+V56T+G109A+A174S+G182*+D183*+N195F+V206L+M246S+K391A+G476K, H1*+N54S+V56T+G109A+A174S+G182*+D183*+N195F+V206L+L250V+K391A+G476K, H1*+N54S+V56T+G109A+A174S+G182*+D183*+N195F+V206L+L250F+K391A+G476K, H1*+N54S+V56T+G109A+A174S+G182*+D183*+N195F+V206L+L250M+K391A+G476K, H1*+N54S+V56T+G109A+A174S+G182*+D183*+N195F+V206L+K391A+C474V+G476K, H1*+N54S+V56T+G109A+A174S+G182*+D183*+N195F+A204S+V206L+K391A+G476K, H1*+N54S+V56T+G109A+T165G+A174S+G182*+D183*+N195F+V206L+K391A+G476K, H1*+N54S+V56T+G109A+A174S+G182*+D183*+N195F+V206L+T334S+K391A+G476K, H1*+N54S+V56T+G109A+A174S+G182*+D183*+N195F+V206L+A263G+M286F+K391A+G476K, H1*+N54S+V56T+G109A+A174S+G182*+D183*+N195F+V206L+A263G+M286L+K391A+G476K, H1*+N54S+V56T+G109A+A174S+G182*+D183*+N195F+V206L+Y267H+K391A+G476K, H1*+N54S+V56T+G109A+A174S+G182*+D183*+N195F+V206L+Y267L+K391A+G476K, H1*+N54S+V56T+G109A+A174S+G182*+D183*+N195F+V206L+Y267I+K391A+G476K, H1*+T51A+N54S+V56T+G109A+Q172R+A174S+G182*+D183*+N195F+V206L+K391A+G476K, H1*+N54S+V56T+G109A+A174S+G182*+D183*+N195F+V206L+K391L+G476K, H1*+N54S+V56T+G109A+F113Q+R116H+Q172G+A174S+G182*+D183*+N195F+V206L+K391A+G476K, H1*+N54S+V56T+G109A+F113Q+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+A174S+G182*+D183*+N195F+A204G+V206L+K391A+G476K, H1*+N54S+V56T+K72R+G109A+A174S+G182*+D183*+G184T+N195F+A204G+V206L+K391A+P473R+G476K, H1*+N54S+V56T+G109A+W167F+Q172N+A174S+G182*+D183*+N195F+V206L+K391A+P473R+G476K, H1*+N54S+V56T+G109A+W167F+Q172G+A174S+G182*+D183*+N195F+V206L+K391A+P473G+G476K, H1*+N54S+V56T+G109A+W167F+Q172G+A174S+G182*+D183*+N195F+V206L+K391A+P473R+G476K, H1*+N54S+V56T+K72R+G109A+W167F+Q172R+A174S+G182*+D183*+N195F+V206L+K391A+G476K, H1*+N54S+V56T+K72R+G109A+R116H+W167F+Q172R+A174S+G182*+D183*+N195F+V206L+K391A+G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+A174S+G182*+D183*+N195F+V206L+A265G+K391A+T444Q+G476K+G477A, H1*+A37V+N54S+V56T+G109A+W167F+Q172G+A174S+G182*+D183*+N195F+V206L+K391A+G346T+G477A+G476K, H1*+N54S+V56T+G109A+R116Q+Q172D+A174S+G182*+D183*+N195F+V206L+G346T+K391A+T444Q+G477A+G476K, H1*+N54S+V56T+G109A+R116Q+W167F+Q172N+A174S+G182*+D183*+N195F+V206L+G346T+K391A+T444Q+G477A+G476K, H1*+N54S+V56T+G109S+W167F+Q172R+A174S+G182*+D183*+N195F+V206L+K391A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+G109A+Q172N+A174S+G182*+D183*+N195F+V206L+K391A+C474V+G476K, H1*+N54S+V56T+G109A+A174S+G182*+D183*+N195F+V206L+S280Q+H321Y+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+R116H+W167F+Q172N+A174S+G182*+D183*+N195F+V206L+K391A+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+R116H+W167F+Q172R+A174S+G182*+D183*+N195F+V206L+F289I+K391A+G476K, H1*+N54S+V56T+G109A+F113Q+Q172N+A174S+G182*+D183*+N195F+V206L+K391A+T444Q+G476K, H1*+N54S+V56T+G109A+F113Q+R116H+Q172N+A174S+G182*+D183*+N195F+V206L+K391A+G476K, H1*+N54S+V56T+

G109A+F113Q+R116Q+Q172M+A174S+G182*+D183*+N195F+V206L+K391A+T444Q+G476K, H1*+N54S+V56T+G109A+F113Q+R116H+Q172M+A174S+G182*+D183*+N195F+V206L+K391A+G476K, H1*+N54S+V56T+G109A+R116H+Q172M+A174S+G182*+D183*+N195F+V206L+K391A+G476K, H1*+N54S+V56T+G109A+F113Q+R116H+T165G+Q172M+A174S+G182*+D183*+N195F+V206L+K391A+Q395P+G476K, H1*+N54S+V56T+G109A+F113Q+A174S+G182*+D183*+N195F+V206L+K391A+T444Q+P473R+G476K, H1*+N54S+V56T+G109A+R116Q+A174S+G182*+D183*+N195F+V206L+A265G+K391A+T444Q+P473R+G476K, H1*+N54S+V56T+G109A+R116Q+A174S+G182*+D183*+N195F+V206L+K391A+T444Q+P473R+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+W167F+Q172R+A174S+G182*+D183*+N195F+V206L+K391A+G476K, H1*+N54S+V56T+G109A+R116Q+W167F+Q172R+A174S+G182*+D183*+N195F+V206L+A265G+K391A+P473R+G476K, H1*+N54S+V56T+G109A+F113Q+A174S+G182*+D183*+N195F+V206L+K391A+G476K, H1*+N54S+V56T+G109A+Q172N+A174S+G182*+D183*+N195F+V206L+K391A+G476K, H1*+T51V+N54S+V56T+G109A+Q172D+A174S+G182*+D183*+N195F+V206L+K391A+G476K, H1*+N54S+V56T+G109A+A174S+G182*+D183*+N195F+V206L+S280Q+H321Y+K391A+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172G+L173V+A174S+G182*+D183*+N195F+V206L+K391A+T444Q+P473R+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+N54S+V56T+G109A+F113Q+R116H+W167F+Q172N+L173V+A174S+G182*+D183*+N195F+V206L+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+F113Q+T134E+W167F+Q172R+A174S+G182*+D183*+N195F+V206L+G255A+K391A+Q395P+A445Q+P473R+G476K, H1*+N54S+V56T+K72R+G109A+F113Q+R116H+T134E+W167F+Q172R+A174S+G182*+D183*+N195F+V206L+G255A+K391A+Q395P+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+K72R+G109A+F113Q+R116Q+W167F+Q172N+L173V+A174S+G182*+D183*+G184T+N195F+V206L+K391A+T444Q+P473R+G476K, H1*+A37H+N54S+V56T+G109A+F113Q+W167F+Q172N+A174S+G182*+D183*+N195F+V206L+K391A+G476K, H1*+A37H+N54S+V56T+G109A+F113Q+A174S+G182*+D183*+N195F+V206L+K391A+G476K, H1*+N54S+V56T+G109A+F113Q+W167F+Q172N+A174S+G182*+D183*+N195F+V206L+K391A+T459N+G476K, H1*+N54S+V56T+G109A+F113Q+Q172R+L173V+A174S+G182*+D183*+N195F+V206L+K391A+T444Q+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37V+N54S+V56T+A60V+G109A+R116Q+T165G+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+W167F+Q172G+L173V+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+W167F+Q172R+A174S+G182*+D183*+N195F+A204G+V206L+K391A+P473R+G476K, H1*+N54S+V56T+G109A+R116A+A174S+G182*+D183*+N195F+A204G+V206L+K391A+P473R+G476K, H1*+N54S+V56T+G109A+R116A+T165G+A174S+G182*+D183*+N195F+V206L+K391A+T444Q+P473R+G476K, H1*+N54S+V56T+G109A+G182*+D183*+N195F+K391A+G476K, H1*+N54S+V56T+G109A+G182*+D183*+N195F+V206L, N54S+V56T+G109A+G182*+D183*+N195F, N54S+V56T+G109A+A174S+G182*+D183*+N195F+V206L+K391A+G476K, H1*+G109A+A174S+G182*+D183*+N195F+V206L+K391A+G476K, H1*+N54S+V56T+G109A+G182*+D183*+N195F+V206L+K391A+G476K, H1*+N54S+V56T+G109A+A174S+G182*+D183*+N195F+V206L+K391A, H1*+N54S+V56T+G109A+A174S+G182*+D183*+N195F+G476K, H1*+N54S+V56T+A174S+G182*+D183*+N195F+V206L+G273R+K391A+G476K, H1*+

N54S+V56T+G109A+A174S+G182*+D183*+N195F+V206L, H1*+W48G+G109A+G182*+D183*+N195F+V206L+K391A+G476K, N54S+V56T+G109A+A174S+G182*+D183*+N195F+K391A+G476K, H1*+N54S+V56T+G109A+A174S+G182*+D183*+N195F+K391A, H1*+N54S+V56T+G109A+F113Q+Q172M+A174S+G182*+D183*+N195F+V206L+K391A+G476K, H1*+N54S+V56T+G109A+R116Q+A174S+G182*+D183*+N195F+A204G+V206L+K391A+G476K, H1*+N54S+V56T+K72R+G109A+F113Q+T134E+A174S+G182*+D183*+N195F+V206L+G255A+K391A+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+V56A+G109A+A174S+G182*+D183*+N195F+V206L+G476K, H1*+N54S+V56T+G109A+G182*+D183*+N195F+V206L+K391A, H1*+N54S+V56T+G109A+G182*+D183*+N195F+V206L+G476K, G109A+A174S+G182*+D183*+N195F+V206L+K391A+G476K, N54S+V56T+G109A+G182*+D183*+N195F+V206L+K391T+G476K, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+N54S+V56T+G109A+F113Q+W167F+Q172N+A174S+G182*+D183*+N195F+A204G+V206L+K391A+P473R+G476K, H1*+N54S+V56T+G109A+F113Q+R116H+W167F+Q172R+A174S+G182*+D183*+N195F+A204G+V206L+K391A+P473R+G476K, H1*+N54S+V56T+G109A+R116A+A174S+G182*+D183*+N195F+V206L+K391A+T444Q+P473R+G476K, H1*+N54S+V56T+G109A+R116H+Q172R+A174S+G182*+D183*+N195F+A204G+V206L+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+A174S+G182*+D183*+N195F+K391A+G476K, H1*+G109A+G182*+D183*+N195F+V206L+K391A+G476K, G109A+G182*+D183*+N195F+V206L+G476K, H1*+G109A+G182*+D183*+N195F+K391A, H1*+N54S+V56T+G109A+G133S+A174S+G182*+D183*+N195F+K391A+G476H, H1*+N54S+V56T+G109A+R116A+Q172N+L173V+A174S+G182*+D183*+N195F+V206L+K391A+G476K, H1*+A37V+N54S+V56T+G109A+R116H+T165G+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+P124A+A174S+G182*+D183*+N195F+V206L+K391A+C474V+G476K, H1*+N54S+V56T+G109A+A174S+G182*+D183*+N195F+V206L+P364A+K391A+C474V+G476K, H1*+N54S+V56T+G109A+Q118R+T134E+A174S+G182*+D183*+N195F+V206L+K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+N54S+V56T+G109A+A174S+G182*+D183*+N195F+V206L+Y382L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+W167H+A174S+G182*+D183*+N195F+V206L+K391A+G476K, H1*+N54S+V56T+G109A+T165V+A174S+G182*+D183*+N195F+V206L+K391A+G476K, H1*+N54S+V56T+G109A+A174S+G182*+D183*+N195F+V206L+K391A+G476K, H1*+N54S+V56T+G109A+A174N+G182*+D183*+N195F+V206L+K391A+G476K, H1*+N54S+V56T+G109A+A174Q+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, N54S+G182*+D183*+N195F, G109A+G182*+D183*+N195F, A174S+G182*+D183*+N195F, G182*+D183*+N195F+K391A, G182*+D183*+N195F+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+

G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+Q169E+Q172K+A174*+G182*+D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+G476K, H1*+W48F+N54S+V56T+G109A+A174S+G182*+D183*+N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, H1*+N54S+V56T+G109A+A174S+V206L+G182*+D183*+K391A+G476K, H1*+N54S+V56T+Q169E+Q172K+A174*+G182*+D183*+N195F+V206L+K391A+G476K, H1*+N54S+V56T+G109A+A174S+G182*+D183*+N195F+V206F+K391A+G476K, H1*+N54S+V56T+G109A+G182*+D183*+N195F+V206L+K391A+G476K, H1*+N54S+V56T+G109A+Q172K+A174S+G182*+D183*+N195F+V206L+K391A+G476K, H1*+N54S+V56T+G109A+Q172K+A174*+G182*+D183*+N195F+V206L+K391A+G476K, H1*+N54S+V56T+G109A+A174N+G182*+D183*+N195F+V206L+K391A+G476K, H1*+N54S+V56T+G109A+A174S+A186N+G182*+D183*+N195F+V206L+K391A+G476K, H1*+N54S+V56T+G109A+A174S+G182*+D183*+N195F+V206L+F289L+K391A+G476K, H1*+N54S+V56T+G109A+A174S+G182*+D183*+N195F+V206L+Y295F+K391A+G476K, H1*+N54S+V56T+G109A+A174S+G182*+D183*+N195F+V206L+V291A+K391A+G476K, H1*+N54S+V56T+G109A+A174S+G182*+D183*+N195F+V206L+S244Q+K391A+G476K, G182*+D183*+F328L, G182*+D183*+N195F+A288V, G182*+D183*+A186N+N195F, G182*+D183*+E190P+N195F, W140Y+G182*+D183*+N195F, H1*+N54S+V56T+G109A+A174S+G182*+D183*+N195F+V206L+A225V+K391A+G476K, G182*+D183*+A186D+N195F, H1*+N54S+V56T+G109A+A174S+G182*+D183*+N195F+V206L+K391A+P473R+G476K, H1*+W48Y+N54S+V56T+G109A+A174S+G182*+D183*+N195F+V206L+K391A+G476K, H1*+N54S+V56T+G109A+Q169E+Q172K+A174*+G182*+D183*+N195F+V206L+K391A+G476K, G182*+D183*+N195F+V238A, G182*+D183*+Y295N, Q172G+G182*+D183*, F113Q+G182*+D183*+N195F, H1*+N54S+V56T+Q98A+G109A+A174S+G182*+D183*+N195F+V206L+K391A+G476K, G182*+D183*+N195F+Y295F, G182*+D183*+A186E, H1*+N54S+V56T+G109A+A174S+G182*+D183*+N195F+V206Y+K391A+G476K, G182*+D183*+N195F+W284H, G182*+D183*+A186Q+N195F, K72R+G182*+D183*, D183*+G182*+N195F+V326L, D183*+G182*+A186E+N195F, Q169E+G182*+D183*+N195F, D183*+G182*+N195F+K242Q, G7A+G182*+D183*+N195F, D183*+G182*+N195F+N260G, D183*+G182*+R321A+S323N, D183*+G182*+W284H, H1*+D183*+G182*, D183*+G182*+A186H+N195F, D183*+G182*+F289V, D183*+G182*+K391A, D183*+G182*+S304R, W167F+G182*+D183*+N195F, F113Q+R116H+D183*+G182*, D183*+G182*+N270G, D183*+G182*+S244Q, H1*+N54S+V56T+G109A+A174S+G182*+D183*+G184T+N195F+V206L+K391A+G476K, D183*+G182*+N195F+Y295N, W48F+D183*+G182*, H1*+N54S+V56T+G109A+A174S+G182*+D183*+N195F+V206L+G255A+K391A+G476K, D183*+G182*+A186Q, W140Y+D183*+G182*, D183*+G182*+K242Q, D183*+G182*+V206L, D183*+G182*+N195F+V206F, Q169E+D183*+G182*, D183*+G182*+N195F+R320A, G182*+D183*+G184T+N195F, D183*+G182*+G184T, D183*+G182*+P473R, W48Y+D183*+G182*, D183*+G182*+R323A, G7A+D183*+G182*, H1*+N54S+V56T+G109A+Q169E+Q172K+A174S+G182*+D183*+N195F+V206L+K391A+G476K, A174S+D183*+G182*, D183*+G182*+N195F+

S323N, D183*+G182*+N195F+M246V, W48Y+D183*+G182*+N195F, V56T+D183*+G182*, wherein numbering is according to SEQ ID NO: 13, G182*+D183*+N195F+A428T, G182*+D183*+N195F, H1*+G182*+D183*+N195F, N54S+G182*+D183*+N195F, V56T+G182*+D183*+N195F, G182*+D183*+N195F+I405L, H1*+N54S+V56T+G109A+A174S+G182*+D183*+N195F+V206L+I405L+A421H+A422P+A428T+D476K, H1*+N54S+V56T+G109A+A174S+G182*+D183*+N195F+V206L+I405L+A421H+A422P+A428T, H1*+N54S+V56T+G109A+A174S+D183*+N195F+V206L+K391A+I405L+A421H+A422P+A428T, H1*+N54S+V56T+G109A+A174S+G182*+D183*+N195F+V206L+K391A+I405L+A421H+A422P+A428T+D476K, H1*+N54S+V56T+G109A+A174S+G182*+D183*+N195F+V206L+K391A+I405L+A421H+A422P+A428T+D476G, H1*+N54S+V56T+G109A+A174S+G182*+D183*+N195F+V206L+K391A+I405L+A421H+A422P+A428T+D476K+G477S, H1*+N54S+V56T+G109A+A174S+G182*+D183*+N195F+V206L+K391A+I405L+A421H+A422P+A428T+D476K, H1*+N54S+V56T+K72R+G109A+W167F+A174S+G182*+D183*+N195F+V206L+I405L+A421H+A422P+A428T, H1*+N54S+V56T+G109A+A174S+G182*+D183*+N195F+V206L+S280Q+H321Y+I405L+A421H+A422P+A428T, H1*+N54S+V56T+G109A+A174S+G182*+D183*+N195F+V206L+S304N+I405L+A421H+A422P+A428T+D476K, H1*+N54S+V56T+G109A+A174S+G182*+D183*+N195F+V206L+K391A+I405L+A421H+A422P+A428T+D476K+G477A, H1*+N54S+V56T+G109A+A174S+G182*+D183*+N195F+V206L+K391A+I405L+A421H+A422P+A428T+D476G+G477T, H1*+N54S+V56T+G109A+A174S+G182*+D183*+N195F+V206L+K391A+I405L+A421H+A422P+A428T+G477Q, H1*+N54S+V56T+G109A+A174S+G182*+D183*+N195F+V206L+K391A+I405L+A421H+A422P+A428T+G477A, H1*+N54S+V56T+G109A+A174S+G182*+D183*+N195F+V206L+K391A+I405L+A421H+A422P+A428T+D476K+G477Q, H1*+N54S+V56T+G109A+A174S+G182*+D183*+N195F+V206L+K391A+I405L+A421H+A422P+A428T+D476N, H1*+N54S+V56T+G109A+A174S+G182*+D183*+N195F+V206L+K391A+I405L+A421H+A422P+A428T+D476Y, H1*+N54S+V56T+G109A+A174S+G182*+D183*+N195F+V206I+I405L+A421H+A422P+A428T, H1*+N54S+V56T+G109A+Q172D+A174S+G182*+D183*+N195F+A204G+V206L+I405L+A421H+A422P+A428T, H1*+N54S+V56T+K72R+G109A+T134E+A174S+G182*+D183*+N195F+A204G+V206L+G255A+I405L+A421H+A422P+A428T, H1*+N54S+V56T+G109A+F113Q+R116H+T165G+Q172G+A174S+G182*+D183*+N195F+V206L+I405L+A421H+A422P+A428T, H1*+N54S+V56T+G109A+F113Q+Q172N+A174S+G182*+D183*+N195F+V206L+I405L+A421H+A422P+A428T, H1*+N54S+V56T+K72R+G109A+T134E+A174S+G182*+D183*+N195F+G196R+V206L+G255A+I405L+A421H+A422P+A428T+N475S, H1*+N54S+V56T+G109A+T134E+A174S+G182*+D183*+N195F+V206L+I405L+A421H+A422P+A428T, H1*+T40D+N54S+V56T+G109A+A174S+G182*+D183*+N195F+V206L+I405L+A421H+A422P+A428T, H1*+N54S+V56T+G109A+F113Q+N125D+A174S+G182*+D183*+N195F+V206L+I405L+A421H+A422P+A428T, H1*+N54S+V56T+A60V+G109A+R116Q+A174S+G182*+D183*+N195F+V206L+I405L+A421H+A422P+A428T, H1*+N54S+V56T+G109A+R116V+A174S+G182*+D183*+N195F+V206L+I405L+A421H+A422P+A428T, H1*+N54S+V56T+G109A+R116Q+G133Q+T165G+Q172G+A174S+G182*+D183*+N195F+V206L+I405L+A421H+A422P+A428T, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116Q+Q172G+A174S+G182*+D183*+N195F+V206L+I405L+A421H+A422P+A428T+G448D, H1*+N54S+V56T+G109A+F113Q+R116H+Q172N+A174S+G182*+D183*+N195F+V206L+I405L+A421H+A422P+A428T, H1*+N54S+V56T+K72R+G109A+T134E+W167F+Q172N+A174S+G182*+D183*+N195F+V206L+G255A+A265G+I405L+A421H+A422P+A428T, H1*+N54S+V56T+K72R+G109A+R116Q+W167F+Q172R+L173V+A174S+G182*+D183*+N195F+V206L+A265G+I405L+A421H+A422P+A428T, H1*+N54S+V56T+K72R+G109A+R116Q+W167F+Q172R+A174S+G182*+D183*+N195F+V206L+I405L+A421H+A422P+A428T, H1*+N54S+V56T+K72R+G109A+F113Q+T134E+W167F+Q172G+A174S+G182*+D183*+N195F+V206L+G255A+I405L+A421H+A422P+A428T, H1*+N54S+V56T+K72R+G109A+F113Q+R116H+W167F+Q172G+L173V+A174S+G182*+D183*+G184T+N195F+V206L+I405L+A421H+A422P+A428T, H1*+N54S+V56T+G109A+F113Q+W167F+Q172G+A174S+G182*+D183*+N195F+V206L+I405L+A421H+A422P+A428T, H1*+N54S+V56T+K72R+G109A+A174S+G182*+D183*+N195F+V206L+G255A+I405L+A421H+A422P+A428T, H1*+N54S+V56T+G109A+F113Q+R116Q+A174S+G182*+D183*+N195F+V206L+I405L+A421H+A422P+A428T, H1*+N54S+V56T+K72R+G109A+F113Q+R116Q+W167F+Q172G+A174S+G182*+D183*+G184T+N195F+V206L+I405L+A421H+A422P+A428T, H1*+N54S+V56T+G109A+F113Q+R116Q+W167F+Q172G+A174S+G182*+D183*+N195F+A204G+V206L+I405L+A421H+A422P+A428T, H1*+N54S+V56T+G109A+F113Q+R116H+W167F+Q172G+A174S+G182*+D183*+N195F+V206L+A265G+I405L+A421H+A422P+A428T, H1*+N54S+V56T+G109A+R116Q+A174S+G182*+D183*+N195F+V206L+I405L+A421H+A422P+A428T, H1*+N54S+V56T+A60V+G109A+R116Q+W167F+Q172N+L173V+A174S+G182*+D183*+N195F+V206L+I405L+A421H+A422P+A428T, H1*+A37H+N54S+V56T+A60V+G109A+R116Q+T165G+A174S+G182*+D183*+N195F+V206L+I405L+A421H+A422P+A428T, H1*+N54S+V56T+G109A+A174S+M105F+G182*+D183*+N195F+V206L+L228I+R320A+S323N+I405L+A421H+A422P+A428T, H1*+N54S+V56T+K72R+G109A+F113Q+T134E+A174S+G182*+D183*+N195F+V206L+G255A+I405L+A421H+A422P+A428T, H1*+N54S+V56T+K72R+G109A+R116Q+V120L+A174S+G182*+D183*+G184T+N195F+V206L+I405L+A421H+A422P+A428T, H1*+N54S+V56T+G109A+F113Q+R116H+W167F+Q172G+L173V+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO: 14.

In one embodiment, the IF is determined by use of Model J detergent at a temperature of 15° C. In a particular embodiment, the variants have an IF of >1 as compared to the parent polypeptide, wherein the IF is determined by use of Model J detergent at a temperature of 15° C. and a concentration of 0.05 mg/L. It can be seen from the Tables in the Examples herein disclosed which such variants may be.

In another embodiment, the variant has an IF of at least >1.5 when compared to said parent polypeptide, and wherein said variant is selected from H1*+N54S+V56T+G109A+A174S+G182*+D183*+N195F+V206L+K391A+G476K, H1*+N54S+V56T+R87S+G109A+A174S+G182*+D183*+N195F+V206L+K391A+G476K, H1*+T40G+N54S+V56T+G109A+A174S+G182*+D183*+N195F+V206L+K391A+G476K, H1*+T51K+N54S+V56T+G109A+A174S+G182*+D183*+N195F+V206L+K391A+G476K, H1*+N54S+V56T+K72R+G109A+A174S+G182*+D183*+N195F+V206L+K391A+G476K, H1*+N54S+V56T+K72H+G109A+A174S+G182*+D183*+N195F+V206L+K391A+G476K, H1*+A37H+N54S+V56T+G109A+A174S+G182*+D183*+N195F+V206L+K391A+G476K, H1*+A37M+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+A37S+N54S+V56T+G109A+A174S+G182*+D183*+N195F+V206L+K391A+G476K, H1*+A37Y+N54S+V56T+G109A+A174S+G182*+D183*+N195F+V206L+K391A+G476K, H1*+A37R+N54S+V56T+G109A+A174S+G182*+D183*+N195F+V206L+K391A+G476K, H1*+N54S+V56T+G109A+F113W+A174S+G182*+D183*+N195F+V206L+K391A+G476K, H1*+N54S+V56T+G109A+F113S+A174S+G182*+D183*+N195F+V206L+K391A+G476K, H1*+N54S+V56T+G109A+F113N+A174S+G182*+D183*+N195F+V206L+K391A+G476K, H1*+N54S+V56T+G109A+F113Y+A174S+G182*+D183*+N195F+V206L+K391A+G476K, H1*+N54S+V56T+G109A+Q118N+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+R116V+A174S+G182*+D183*+N195F+V206L+K391A+G476K, H1*+N54S+V56T+G109A+R116K+A174S+G182*+D183*+N195F+V206L+K391A+G476K, H1*+N54S+V56T+G109A+R116W+A174S+G182*+D183*+N195F+V206L+K391A+G476K, H1*+N54S+V56T+G109A+R116L+A174S+G182*+D183*+N195F+V206L+K391A+G476K, H1*+N54S+V56T+G109A+G142T+A174S+G182*+D183*+N195F+V206L+K391A+G476K, H1*+N54S+V56T+G109A+Q125P+A174S+G182*+D183*+N195F+V206L+K391A+G476K, H1*+N54S+V56T+G109A+Q125K+A174S+G182*+D183*+N195F+V206L+K391A+G476K, H1*+N54S+V56T+G109A+A174S+G182*+D183*+N195F+V206L+S381G+K391A+G476K, H1*+N54S+V56T+G109A+A174S+G182*+D183*+N195F+V206L+M246T+K391A+G476K, H1*+N54S+V56T+G109A+A174S+G182*+D183*+N195F+V206L+V213T+K391A+G476K, H1*+A37L+N54S+V56T+G109A+A174S+G182*+D183*+N195F+V206L+K391A+G476K, H1*+N54S+V56T+G109A+Q118K+A174S+G182*+D183*+N195F+V206L+K391A+G476K, H1*+N54S+V56T+G109A+R116A+A174S+G182*+D183*+N195F+V206L+K391A+G476K, H1*+N54S+V56T+G109A+R116H+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+Q172R+A174S+G182*+D183*+N195F+V206L+K391A+G476K, H1*+N54S+V56T+G109A+A174S+G182*+D183*+N195F+V206L+D377S+K391A+G476K, H1*+N54S+V56T+G109A+A174S+G182*+D183*+N195F+V206L+D377G+K391A+G476K, H1*+N54S+V56T+G109A+A174S+G182*+D183*+N195F+V206L+D377R+K391A+G476K, H1*+N54S+V56T+G109A+A174S+G182*+D183*+N195F+V206L+D377A+K391A+G476K, H1*+N54S+V56T+G109A+A174S+G182*+D183*+N195F+V206L+I214G+K391A+G476K, H1*+N54S+V56T+G109A+A174S+G182*+D183*+N195F+V206L+S381A+K391A+G476K, H1*+N54S+V56T+G109A+W167I+A174S+G182*+D183*+N195F+V206L+K391A+G476K, H1*+N54S+V56T+G109A+W167G+A174S+G182*+D183*+N195F+V206L+K391A+G476K, H1*+N54S+V56T+G109A+A174S+G182*+D183*+N195F+V206L+G346S+K391A+G476K, H1*+N54S+V56T+G109A+A174S+G182*+D183*+N195F+V206L+G346P+K391A+G476K, H1*+N54S+V56T+G109A+A174S+G182*+D183*+N195F+V206L+I214H+K391A+G476K, H1*+N54S+V56T+G109A+A174S+G182*+D183*+N195F+V206L+I214S+K391A+G476K, H1*+N54S+V56T+G109A+A174S+G182*+D183*+N195F+V206L+I214T+K391A+G476K, H1*+N54S+V56T+G109A+A174S+G182*+D183*+N195F+V206L+K391A+A420Q+G476K, H1*+N54S+V56T+G109A+A174S+G182*+D183*+N195F+V206L+K391A+A420S+G476K, H1*+N54S+V56T+G109A+A174S+G182*+D183*+N195F+V206L+K391A+A420K+G476K, H1*+N54S+V56T+G109A+A174S+G182*+D183*+N195F+V206L+K391A+A420L+G476K, H1*+N54S+V56T+G109A+A174S+G182*+D183*+N195F+V206L+K391A+K391Y+G476K, H1*+N54S+V56T+G109A+A174S+G182*+D183*+N195F+V206L+K391A+K391R+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+P473G+G476K, H1*+N54S+V56T+G109A+A174S+G182*+D183*+N195F+V206L+K391A+P473T+G476K, H1*+N54S+V56T+G109A+A174S+G182*+D183*+N195F+V206L+K391A+Q395P+G476K, H1*+N54S+V56T+G109A+A174S+G182*+D183*+N195F+V206L+K391A+T444Q+G476K, H1*+N54S+V56T+G109A+A174S+G182*+D183*+N195F+V206L+K391A+T444S+G476K, H1*+N54S+V56T+G109A+A174S+G182*+D183*+N195F+V206L+K391A+T444D+G476K, H1*+N54S+V56T+G109A+A174S+G182*+D183*+N195F+V206L+K391A+T444Y+G476K, H1*+N54S+V56T+G109A+A174S+G182*+D183*+N195F+V206L+S280W+K391A+G476K, H1*+N54S+V56T+G109A+A174S+G182*+D183*+N195F+V206L+S280L+K391A+G476K, H1*+N54S+V56T+G109A+A174S+G182*+D183*+N195F+V206L+S280T+K391A+G476K, H1*+N54S+V56T+G109A+A174S+G182*+D183*+N195F+V206L+S280A+K391A+G476K, H1*+N54S+V56T+G109A+A174S+G182*+D183*+N195F+V206L+G255N+K391A+G476K, H1*+N54S+V56T+G109A+A174S+G182*+D183*+N195F+V206L+T285L+K391A+G476K, H1*+N54S+V56T+G109A+A174S+G182*+D183*+N195F+V206L+T285Q+K391A+G476K, H1*+N54S+V56T+G109A+A174S+G182*+D183*+N195F+V206L+K391A+Q449T+G476K, H1*+N54S+V56T+G109A+A174S+G182*+D183*+N195F+V206L+K391A+P473K+G476K, H1*+N54S+V56T+K72S+G109A+A174S+G182*+D183*+N195F+V206L+K391A+G476K, H1*+T40K+N54S+V56T+G109A+A174S+G182*+D183*+N195F+V206L+G346T+K391A+G476K, H1*+G50A+N54S+V56T+G109A++Q172N+A174S+G182*+D183*+N195F+V206L+K391A+G476K, H1*+N54S+V56T+G109A+A174S+G182*+D183*+N195F+V206L+K391A+G476K+K484A, H1*+N54S+V56T+G109A+A174S+G182*+

D183*+N195F+V206L+K391A+G476K+K484G, H1*+N54S+V56T+G109A+A174S+G182*+D183*+N195F+V206L+K391A+G476K+K484P, H1*+N54S+V56T+G109A+A174S+G182*+D183*+N195F+V206L+K391A+G476K+K484E, H1*+N54S+V56T+G109A+A174S+G182*+D183*+N195F+V206L+K391A+G476K+K484Q, H1*+N54S+V56T+G109A+A174S+G182*+D183*+N195F+V206L+K391A+G476K+K484S, H1*K+G50A+N54S+V56T+G109A+W167F+A174S+G182*+D183*+N195F+V206L+K391A+G476K, H1*+N54S+V56T+G109A+L173V+A174S+G182*+D183*+N195F+A204T+V206L+K391A+G476K, H1*+N54S+V56T+G109A+W140Y+A174S+G182*+D183*+N195F+V206L+K391A+G476K, H1*+N54S+V56T+Q98S+G109A+A174S+G182*+D183*+N195F+V206L+R320A+K391A+G476K, H1*+N54S+V56T+G109A+A174S+G182*+D183*+N195F+V206L+H324L+K391A+G476K, H1*+N54S+V56T+G109A+G149Q+A174S+G182*+D183*+N195F+V206L+K391A+G476K, H1*+N54S+V56T+G109A+A174S+G182*+D183*+N195F+V206L+G346T+K391A+G476K+G477A, H1*+N54S+V56T+G109AG255A++A174S+G182*+D183*+N195F+V206L+K391A+G476K, H1*+G50A+N54S+V56T+G109A+F113L+R116L+A174S+G182*+D183*+N195F+V206L+K391A+G476K, H1*+N54S+V56T+G109A+W167F+A174S+G182*+D183*+N195F+V206L+K391A+G476K, H1*+N54S+V56T+G109A+L173V+A174S+G182*+D183*+N195F+V206L+K391A+G476K, H1*+N54S+V56T+K72R+G109A+W167F+A174S+G182*+D183*+N195F+V206L+K391A+G476K, H1*+N54S+V56T+G109A+A174S+G182*+D183*+N195F+V206L+K391A+G476K+G477Q, H1*+N54S+V56T+G109A+A174S+G182*+D183*+N195F+V206L+Q345D+K391A+G476K+G477Q, H1*+G50A+N54S+V56T+G109A+Q172D+A174S+G182*+D183*+N195F+V206L+K391A+G476K, H1*+N54S+V56T+G109A+A174S+G182*+D183*+N195F+V206L+V264I+K391A+G423H+G476K, H1*+N54S+V56T+G109A+A174S+G182*+D183*+N195F+V206L+R320V+K391A+G476Y, H1*+T5K+N54S+V56T+G109A+A174S+G182*+D183*+N195F+V206L+K391A+G476K, H1*+N54S+V56T+G109A+R116M+A174S+G182*+D183*+N195F+V206L+K391A+G476K, H1*+N54S+V56T+G109A+Q172Y+A174S+G182*+D183*+N195F+V206L+K391A+G476K, H1*+N54S+V56T+G109A+A174S+G182*+D183*+N195F+V206L+I214L+K391A+G476K, H1*+N54S+V56T+G109A+A174S+G182*+D183*+N195F+V206L+L217V+K391A+G476K, H1*+N54S+V56T+G109A+A174S+G182*+D183*+N195F+V206L+L217H+K391A+G476K, H1*+N54S+V56T+G109A+A174S+G182*+D183*+N195F+V206L+P211D+K391A+G476K, H1*+N54S+V56T+G109A+A174S+G182*+D183*+N195F+V206L+K391A+K391Q+G476K, H1*+N54S+V56T+G109A+A174S+G182*+D183*+N195F+V206L+K391A+T444H+G476K, H1*+N54S+V56T+G109A+A174S+G182*+D183*+N195F+V206L+K391A+T444V+G476K, H1*+N54S+V56T+G109A+A174S+G182*+D183*+N195F+V206L+K391A+T444R+G476K, H1*+G50A+N54S+V56T+G109A+L173V+A174S+G182*+D183*+N195F+A204V+V206L+K391A+G476K, H1*+G50A+N54S+V56T+G109A+F113L+W167F+A174S+G182*+D183*+N195F+V206L+K391A+G476K, H1*+G7K+N54S+V56T+G109A+A174S+G182*+D183*+N195F+V206L+R320A+K391A+G476K, H1*+N54S+V56T+G109A+Q118G+A174S+G182*+D183*+N195F+V206L+K391A+G476K, H1*+N54S+V56T+G109A+A174S+G182*+D183*+N195F+V206L+S280K+K391A+G476K, H1*+N54S+V56T+G109A+Q172D+A174S+G182*+D183*+N195F+V206L+G346T+K391A+G476K+G477A, H1*+N54S+V56T+G109A+Q118S+A174S+G182*+D183*+N195F+V206L+K391A+G476K, H1*+N54S+V56T+G109A+A174S+G182*+D183*+N195F+V206L+R320A+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+G337H+Q385L+K391A+G476K, H1*+N54S+V56T+G109A+A174S+G182*+D183*+N195F+V206L+Y382M+K391A+G476K, H1*+N54S+V56T+K72R+G109A+A174S+G182*+D183*+N195F+V206L+G255A+D377H+K391A+G476K, H1*+N54S+V56T+K72R+G109A+T134E+A174S+G182*+D183*+N195F+V206L+G255A+K391A+G476K, H1*+N54S+V56T+K72R+M105F+G109A+A174S+G182*+D183*+N195F+V206L+G255A+K391A+G476K, H1*+N54S+V56T+M105F+G109A+T134E+A174S+G182*+D183*+N195F+V206L+K391A+G476K, H1*+N54S+V56T+M105F+G109A+Q118F+T134E+A174S+G182*+D183*+N195F+V206L+K391A+G476K, H1*+N54S+V56T+G109A+A174S+G182*+D183*+N195F+V206L+R320A+S323N+D377H+K391A+G476K, H1*+T51E+N54S+V56T+G109A+A174H+G182*+D183*+N195F+V206L+K391A+G476K, H1*+N54S+V56T+G109A+L173A+A174S+G182*+D183*+N195F+V206L+K391A+G476K, H1*+N54S+V56T+G109A+A174S+G182*+D183*+N195F+V206L+Q299V+K391A+G476K, H1*+N54S+V56T+G109A+L173G+A174S+G182*+D183*+N195F+V206L+K391A+G476K, H1*+N54S+V56T+G109A+A174S+G182*+D183*+N195F+V206L+T355L+K391A+G476K, H1*+G50A+N54S+V56T+G109A+A174S+G182*+D183*+N195F+A204T+V206L+K391A+G476K, H1*+G50A+N54S+V56T+G109A+A174E+G182*+D183*+N195F+A204T+V206L+K391A+G476K, H1*+N54S+V56T+K72R+G109A+A174S+G182*+D183*+N195F+V206L+R320A+S323N+K391A+G476K, H1*+N54S+V56T+M105I+G109A+A174S+G182*+D183*+N195F+V206L+K391A+G476K, H1*+N54S+V56T+G109A+A174S+G182*+D183*+N195F+V206L+M246L+K391A+G476K, H1*+T51G+N54S+V56T+G109A+A174N+G182*+D183*+N195F+V206L+K391A+G476K, H1*+N54S+V56T+G109A+A174D+G182*+D183*+N195F+V206L+K391A+G476K, H1*+T51S+N54S+V56T+G109A+A174P+G182*+D183*+N195F+V206L+K391A+G476K, H1*+N54S+V56T+K72A+G109A+W167S+A174S+G182*+D183*+N195F+V206L+K391A+G476K, H1*+N54S+V56T+K72Q+G109A+W167H+A174S+G182*+D183*+N195F+V206L+K391A+G476K, H1*+N54S+V56T+G109A+Q118R+T134E+A174S+G182*+D183*+N195F+V206L+D377H+K391A+G476K, H1*+Q11H+N54S+V56T+G109A+Q118R+T134E+A174S+G184T+G182*+D183*+N195F+V206L+D377H+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+Q118R+T134E+A174S+G182*+D183*+N195F+V206L+G255A+K391A+G476K, H1*+N54S+V56T+G109A+Q118R+A174S+G182*+D183*+N195F+V206L+D377H+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+K72R+G109A+W167L+A174S+

G182*+D183*+N195F+V206L+K391A+G476K, H1*+N54S+V56T+K72R+G109A+W167M+A174S+G182*+D183*+N195F+V206L+K391A+G476K, H1*+N54S+V56T+K72R+G109A+A174S+G182*+D183*+G184T+N195F+V206L+G255A+K391A+G476K, H1*+N54S+V56T+G109A+A174S+G182*+D183*+G184T+N195F+V206L+D377H+K391A+G476K, H1*+N54S+V56T+G109A+A174S+G182*+D183*+N195F+V206L+G255A+D377H+K391A+G476K, H1*+N54S+V56T+M105F+G109A+A174S+G182*+D183*+G184T+N195F+V206L+K391A+G476K, H1*+N54S+V56T+G109A+T134E+A174S+G182*+D183*+N195F+V206L+R320A+S323N+K391A+G476K, H1*+N54S+V56T+G109A+A174S+G182*+D183*+N195F+V206L+V291G+D377H+K391A+G476K, H1*+N54S+V56T+G109A+A174S+G182*+D183*+N195F+V206L+V291A+F328L+D377H+K391A+G476K, H1*+N54S+V56T+G109A+T134E+A174S+G182*+D183*+G184T+N195F+V206L+K391A+G476K, H1*+N54S+V56T+G109A+A174S+G182*+D183*+N195F+V206L+V238A+D377H+K391A+G476K, H1*+N54S+V56T+G109A+A174S+G182*+D183*+N195F+V206L+V238T+D377H+K391A+G476K, H1*+N54S+V56T+G109A+A174S+G182*+D183*+N195F+V206L+V238G+D377H+K391A+G476K, H1*+N54S+V56T+G109A+A174S+G182*+D183*+N195F+V206L+F328M+D377H+K391A+G476K, H1*+N54S+V56T+G109A+A174S+G182*+D183*+N195F+V206L+F328L+D377H+K391A+G476K, H1*+N54S+V56T+G109A+A174S+G182*+D183*+N195F+V206L+F328V+D377H+K391A+G476K, H1*+N54S+V56T+G109A+A174S+G182*+D183*+N195F+V206L+F328I+D377H+K391A+G476K, H1*+N54S+V56T+G109A+A174S+G182*+D183*+N195F+V206L+V291T+D377H+K391A+G476K, H1*+N54S+V56T+G109A+A174S+G182*+D183*+N195F+V206L+V291A+D377H+K391A+G476K, H1*+N54S+V56T+K72R+G109A+T134E+A174S+G182*+D183*+G184T+N195F+V206L+G255A+K391A+G476K, H1*+N54S+V56T+G109A+L173H+A174S+G182*+D183*+N195F+V206L+K391A+G476K, H1*+N16S+N54S+V56T+G109A+A174S+G182*+D183*+N195F+V206L+K391A+G476K, H1*+N54S+V56T+K72N+G109A+A174S+G182*+D183*+N195F+V206L+K391A+G476K, H1*+N54S+V56T+K72N+G109A+W167L+A174S+G182*+D183*+N195F+V206L+K391A+G476K, H1*+N54S+V56T+K72A+G109A+W167Y+A174S+G182*+D183*+N195F+V206L+K391A+G476K, H1*+N54S+V56T+G109A+Q118R+T134E+A174S+G182*+D183*+N195F+V206L+G255A+D377H+K391A+G476K, H1*+N54S+V56T+K72R+G109A+A174S+G182*+D183*+N195F+G184T+V206L+K391A+G476K, H1*+N54S+V56T+K72R+G109A+Q118R+A174S+G182*+D183*+N195F+V206L+G255A+D377H+K391A+G476K, H1*+N54S+V56T+G109A+A174S+G182*+D183*+G184T+N195F+V206L+R320A+S323N+K391A+G476K, H1*+N54S+G109A+A174S+G182*+D183*+N195F+V206L+D377H+K391A+G476K, H1*+N54S+V56T+A174S+G182*+D183*+N195F+V206L+D377H+K391A+G476K, H1*+N54S+V56T+G109A+G182*+D183*+N195F+V206L+D377H+K391A+G476K, H1*+N54S+V56T+G109A+A174S+G182*+D183*+N195F+D377H+K391A+G476K, H1*+N54S+V56T+G109A+A174S+G182*+D183*+N195F+D377H+K391A+G476K, H1*+N54S+V56T+G109A+A174S+G182*+D183*+N195F+V206L+D377H+G476K, H1*+N54S+V56T+G109A+A174S+G182*+D183*+N195F+V206L+D377H+K391A, H1*+N54S+V56T+G109A+A174S+G182*+D183*+N195F+V206L+L217T+K391A+G476K, H1*+N54S+V56T+G109A+A174S+G182*+D183*+N195F+V206L+D377S+K391A+G476K, H1*+N54S+V56T+G109A+R116E+A174S+G182*+D183*+N195F+V206L+K391A+G476K, H1*+N54S+V56T+G109A+A174S+G182*+D183*+N195F+V206L+L217Q+K391A+G476K, H1*+N54S+V56T+G109A+A174S+G182*+D183*+N195F+V206L+D377A+K391A+G476K, H1*+N54S+V56T+G109A+T134E+A174S+G182*+D183*+N195F+V206L+D377H+K391A+G476K, H1*+N54S+V56T+G109A+Q118R+T134E+A174S+G182*+D183*+G184T+N195F+V206L+K391A+G476K, H1*+N54S+V56T+K72R+G109A+Q118R+T134E+A174S+G182*+D183*+N195F+V206L+K391A+G476K, H1*+N54S+V56T+G109A+A174S+G182*+D183*+N195F+V206L+G346P+K391A+G476K, H1*+N54S+V56T+G109A+R116S+A174S+G182*+D183*+N195F+V206L+K391A+G476K, H1*+N54S+V56T+G109A+A174S+G182*+D183*+N195F+V206L+D377Q+K391A+G476K, H1*+N54S+V56T+G109A+R116G+A174S+G182*+D183*+N195F+V206L+K391A+G476K, H1*+N54S+V56T+G109A+A174F+G182*+D183*+N195F+V206L+K391A+G476K, H1*+N54S+V56T+G109A+R116G+A174S+G182*+D183*+N195F+V206L+K391A+G476K, H1*+N54S+V56T+G109A+A174T+G182*+D183*+N195F+V206L+K391A+G476K, H1*+N54S+V56T+G109A+Q118R+T134E+A174S+G182*+D183*+G184T+N195F+V206L+G255A+K391A+G476K, H1*+N54S+V56T+K72R+G109A+Q118R+T134E+A174S+G182*+D183*+N195F+V206L+G255A+K391A+G476K, H1*+T51A+N54S+V56T+G109A+Q172D+A174S+G182*+D183*+N195F+V206L+K391A+G476K, H1*+T51S+N54S+V56T+G109A+Q172M+A174S+G182*+D183*+N195F+V206L+K391A+G476K, H1*+T51A+N54S+V56T+G109A+Q172S+A174S+G182*+D183*+N195F+V206L+K391A+G476K, H1*+T51E+N54S+V56T+G109A+Q172T+A174S+G182*+D183*+N195F+V206L+K391A+G476K, H1*+T51A+N54S+V56T+G109A+Q172A+A174S+G182*+D183*+N195F+V206L+K391A+G476K, H1*+T51S+N54S+V56T+G109A+Q172N+A174S+G182*+D183*+N195F+V206L+K391A+G476K, H1*+T51A+N54S+V56T+G109A+Q172G+A174S+G182*+D183*+N195F+V206L+K391A+G476K, H1*+T51E+N54S+V56T+G109A+Q172L+A174S+G182*+D183*+N195F+V206L+K391A+G476K, H1*+T51E+N54S+V56T+G109A+Q172R+A174S+G182*+D183*+N195F+V206L+K391A+G476K, H1*+N54S+V56T+G109A+Q172K+A174S+G182*+D183*+N195F+V206L+K391A+G476K, H1*+T51D+N54S+V56T+G109A+Q172N+A174S+G182*+D183*+N195F+V206L+K391A+G476K, H1*+T51A+N54S+V56T+G109A+Q172K+A174S+G182*+D183*+N195F+V206L+K391A+G476K, H1*+N54S+V56T+K72R+G109A+Q172S+A174S+G182*+D183*+N195F+V206L+K391A+G476K, H1*+N54S+V56T+K72H+G109A+Q172T+A174S+G182*+D183*+N195F+V206L+K391A+G476K, H1*+N54S+V56T+K72R+G109A+Q172R+A174S+K179E+G182*+D183*+N195F+V206L+K391A+G476K, H1*+N54S+V56T+K72R+G109A+Q172M+A174S+G182*+D183*+N195F+V206L+Y295N+K391A+G476K, H1*+N54S+V56T+K72Q+G109A+Q172R+A174S+G182*+D183*+N195F+V206L+K391A+G476K, H1*+N54S+V56T+K72R+G109A+Q172T+A174S+G182*+D183*+N195F+V206L+K391A+G476K, H1*+N54S+V56T+K72M+G109A+Q172S+A174S+G182*+D183*+N195F+V206L+K391A+G476K, H1*+N54S+V56T+K72Q+G109A+Q172M+A174S+G182*+D183*+N195F+V206L+K391A+G476K, H1*+N54S+V56T+G109A+Q172M+A174S+G182*+D183*+N195F+V206L+

K391A+G476K, H1*+N54S+V56T+K72S+G109A+A174H+G182*+D183*+N195F+V206L+K391A+G476K, H1*+N54S+V56T+K72Q+G109A+A174D+G182*+D183*+N195F+V206L+K391A+G476K, H1*+N54S+V56T+K72R+G109A+A174D+G182*+D183*+N195F+V206L+K391A+G476K, H1*+N54S+V56T+K72Q+G109A+A174K+G182*+D183*+N195F+V206L+K391A+G476K, H1*+N54S+V56T+G109A+A174G+G182*+D183*+N195F+V206L+K391A+G476K, H1*+N54S+V56T+K72R+G109A+A174Q+G182*+D183*+N195F+V206L+K391A+G476K, H1*+N54S+V56T+K72Q+G109A+A174G+G182*+D183*+N195F+V206L+K391A+G476K, H1*+N54S+V56T+K72S+G109A+A174N+G182*+D183*+N195F+V206L+K391A+G476K, H1*+N54S+V56T+K72R+G109A+A174H+G182*+D183*+N195F+V206L+K391A+G476K, H1*+N54S+V56T+G109A+A174S+G182*+D183*+N195F+V206L+K391A+K391S+G476K, H1*+N54S+V56T+G109A+A174S+G182*+D183*+N195F+V206L+K391A+T444A+G476K, H1*+N54S+V56T+G109A+F113L+W167F+A174S+G182*+D183*+N195F+V206L+K391A+G476K, H1*+G50A+N54S+V56T+G109A+A174E+G182*+D183*+N195F+A204T+V206L+S323N+K391A+G476K, H1*+N54S+V56T+K72R+G109A+Q118R+A174S+G182*+D183*+G184T+N195F+V206L+G255A+K391A+G476K, H1*+N54S+V56T+M105F+G109A+A174S+G182*+D183*+N195F+V206L+D377H+K391A+G476K, H1*+N54S+V56T+K72R+G109A+Q118R+A174S+G182*+D183*+N195F+V206L+D377H+K391A+G476K, H1*+N54S+V56T+G109A+A174S+G182*+D183*+N195F+A204G+V206L+K391A+G476K, H1*+N54S+V56T+G109A+A174S+G182*+D183*+N195F+V206L+A225F+K391A+G476K, H1*+N54S+V56T+G109A+A174S+G182*+D183*+N195F+V206L+M246A+K391A+G476K, H1*+N54S+V56T+G109A+A174S+G182*+D183*+N195F+V206L+Y382I+K391A+G476K, H1*+N54S+V56T+G109A+A174S+G182*+D183*+N195F+V206L+S376H+K391A+G476K, H1*+N54S+V56T+G109A+A174S+G182*+D183*+N195F+V206L+I214E+K391A+G476K, H1*+N54S+V56T+G109A+A174S+G182*+D183*+N195F+V206L+I214W+K391A+G476K, H1*+N54S+V56T+K72R+G109A+Q172K+A174S+G182*+D183*+N195F+V206L+K391A+G476K, H1*+N54S+V56T+G109A+A174S+G182*+D183*+N195F+A204T+V206L+D377H+K391A+G476K, H1*+N54S+V56T+G109A+A174S+G182*+D183*+N195F+A204S+V206L+D377H+K391A+G476K, H1*+N54S+V56T+G109A+T165S+A174S+G182*+D183*+N195F+V206L+D377H+K391A+G476K, H1*+N54S+V56T+G109A+A174S+G182*+D183*+N195F+V206L+T334S+D377H+K391A+G476K, H1*+N54S+V56T+G109A+A174S+G182*+D183*+N195F+V206L+A263G+D377H+K391A+G476K, H1*+N54S+V56T+G109A+A174S+G182*+D183*+N195F+V206L+M286F+D377H+K391A+G476K, H1*+N54S+V56T+G109A+A174S+G182*+D183*+N195F+V206L+Y267I+D377H+K391A+G476K, H1*+N54S+V56T+G109A+A174S+G182*+D183*+N195F+V206L+L235V+D377H+K391A+G476K, H1*+N54S+V56T+G109A+A174S+G182*+D183*+N195F+V206L+L235A+D377H+K391A+G476K, H1*+N54S+V56T+M105L+G109A+A174S+G182*+D183*+N195F+V206L+D377H+K391A+G476K, H1*+N54S+V56T+M105I+G109A+A174S+G182*+D183*+N195F+V206L+D377H+K391A+G476K, H1*+N54S+V56T+M105V+G109A+A174S+G182*+D183*+N195F+V206L+D377H+K391A+G476K, H1*+N54S+V56T+G109A+A174S+G182*+D183*+N195F+V206L+M246I+D377H+K391A+G476K, H1*+N54S+V56T+G109A+A174S+G182*+D183*+N195F+V206L+L250I+D377H+K391A+G476K, H1*+N54S+V56T+G109A+A174S+G182*+D183*+N195F+V206L+L250V+D377H+K391A+G476K, H1*+N54S+V56T+G109A+A174S+G182*+D183*+N195F+V206L+K391Y+G476K, H1*+N54S+V56T+G109A+A174S+G182*+D183*+N195F+V206L+K391V+G476K, H1*+N54S+V56T+G109A+A174S+G182*+D183*+N195F+V206L+K391M+G476K, H1*+N54S+V56T+G109A+A174S+G182*+D183*+N195F+V206L+K391E+G476K, H1*+N54S+V56T+G109A+T165G+A174S+G182*+D183*+N195F+V206L+D377H+K391A+G476K, H1*+N54L+V56T+G109A+A174S+G182*+D183*+N195F+V206L+K391A+G476K, H1*+N54S+V56T+G109S+A174S+G182*+D183*+N195F+V206L+K391A+G476K, H1*+N54S+V56T+G109A+A174V+G182*+D183*+N195F+V206L+K391A+G476K, H1*+N54S+V56T+G109A+A174S+G182*+D183*+N195F+V206L+M246F+D377H+K391A+G476K, H1*+N54S+V56T+G109A+A174S+G182*+D183*+N195F+V206L+M246V+D377H+K391A+G476K, H1*+N54S+V56T+G109A+A174S+G182*+D183*+N195F+V206L+M246S+D377H+K391A+G476K, H1*+N54S+V56T+G109A+A174R+G182*+D183*+N195F+V206L+K391A+G476K, H1*+N54S+V56T+G109A+A174L+G182*+D183*+N195F+V206L+K391A+G476K, H1*+N54S+V56T+G109A+A174S+G182*+D183*+N195F+V206S+K391A+G476K, H1*+N54S+V56T+G109A+A174S+G182*+D183*+N195F+V206L+K391D+G476K, H1*+N54S+V56T+G109A+A174S+G182*+D183*+N195F+V206L+K391R+G476K, H1*+N54S+V56T+G109A+A174S+G182*+D183*+N195F+V206L+K391H+G476K, H1*+N54S+V56T+G109A+A174S+G182*+D183*+N195F+V206L+K391W+G476K, H1*+N54S+V56T+G109A+A174S+G182*+D183*+N195F+V206L+K391I+G476K, H1*+N54S+V56T+G109A+A174S+G182*+D183*+N195F+V206L+L250T+D377H+K391A+G476K, H1*+N54S+V56T+G109A+A174S+G182*+D183*+N195F+V206L+L250A+D377H+K391A+G476K, H1*+N54S+V56T+G109A+A174S+G182*+D183*+N195F+V206L+L250F+D377H+K391A+G476K, H1*+N54S+V56T+G109A+A174S+G182*+D183*+N195F+V206L+L250M+D377H+K391A+G476K, H1*+N54S+V56T+G109A+A174S+G182*+D183*+N195F+V206L+K391A+G476K, H1*+N54S+V56T+G109A+Q172H+L173A+A174P+G182*+D183*+N195F+V206L+K391A+G476K, H1*+N54S+V56T+K72Q+G109A+W167R+A174S+G182*+D183*+N195F+V206L+K391A+G476K, H1*+N54S+V56T+G109A+A174S+G182*+D183*+G184T+N195F+V206L+G255A+K391A+G476K, H1*+N54S+V56T+K72R+G109A+A174S+G182*+D183*+G184T+N195F+V206L+D377H+K391A+G476K, H1*+N54S+V56T+G109A+A174S+G182*+D183*+G184T+N195F+V206L+G255A+D377H+K391A+G476K, H1*+N54S+V56T+G109A+Q118R+A174S+G182*+D183*+N195F+V206L+K391A+G476K, H1*+N54S+V56T+G109A+A174S+G182*+D183*+N195F+V206L+S376T+K391A+G476K, H1*+N54S+V56T+G109A+A174S+G182*+D183*+N195F+V206L+S376V+K391A+G476K, H1*+N54S+V56T+G109A+Q172E+L173I+A174N+G182*+D183*+N195F+V206L+K391A+G476K, H1*+N54S+V56T+G109A+Q172D+L173A+A174T+G182*+D183*+N195F+V206L+K391A+G476K, H1*+N54S+V56T+G109A+A174S+G182*+D183*+N195F+V206L+Y267M+D377H+K391A+G476K, H1*+N54S+V56T+G109A+A174S+G182*+D183*+N195F+V206L+Y267H+D377H+K391A+G476K, H1*+N54S+V56T+G109A+A174S+G182*+D183*+N195F+V206L+

V238A+K391A+G476K, H1*+N54S+V56T+G109A+A174S+G182*+D183*+N195F+V206L+V238T+K391A+G476K, H1*+N54S+V56T+G109A+A174S+G182*+D183*+N195F+V206L+V238G+K391A+G476K, H1*+N54S+V56T+M105V+G109A+A174S+G182*+D183*+N195F+V206L+K391A+G476K, H1*+N54S+V56T+G109A+A174S+G182*+D183*+N195F+V206L+V264T+K391A+G476K, H1*+N54S+V56T+G109A+A174S+G182*+D183*+N195F+V206L+V264I+K391A+G476K, H1*+N54S+V56T+G109A+A174S+G182*+D183*+N195F+V206L+L235V+K391A+G476K, H1*+N54S+V56T+G109A+W167H+Q172N+L173A+A174S+G182*+D183*+N195F+V206L+K391A+G476K, H1*+N54S+V56T+G109A+W167F+Q172E+L173P+A174K+G182*+D183*+N195F+V206L+K391A+G476K, H1*+N54S+V56T+G109A+Q172N+L173T+A174S+G182*+D183*+N195F+V206L+K391A+G476K, H1*+N54S+V56T+G109A+Q172K+L173V+A174T+G182*+D183*+N195F+V206L+K391A+G476K, H1*+N54S+V56T+G109A+Q172E+L173F+A174R+G182*+D183*+N195F+V206L+K391A+G476K, H1*+N54S+V56T+G109A+Q172E+L173T+A174R+G182*+D183*+N195F+V206L+K391A+G476K, H1*+N54S+V56T+G109A+Q172N+L173V+A174R+G182*+D183*+N195F+V206L+K391A+G476K, H1*+N54S+V56T+G109A+L173V+A174R+G182*+D183*+N195F+V206L+K391A+G476K, H1*+N54S+V56T+G109A+Q172E+L173M+A174H+G182*+D183*+N195F+V206L+K391A+G476K, H1*+N54S+V56T+G109A+Q172E+L173F+A174P+G182*+D183*+N195F+V206L+K391A+G476K, H1*+N54S+V56T+G109A+W167Y+Q172E+L173V+A174H+G182*+D183*+N195F+V206L+K391A+G476K, H1*+N54S+V56T+G109A+L173A+A174T+G182*+D183*+N195F+V206L+K391A+G476K, H1*+N54S+V56T+G109A+A174S+G182*+D183*+N195F+V206L+V291A+F328L+K391A+G476K, H1*+N54S+V56T+G109A+A174S+G182*+D183*+N195F+V206L+M246L+K391A+G476K, H1*+N54S+V56T+G109A+A174S+G182*+D183*+N195F+V206L+M246S+K391A+G476K, H1*+N54S+V56T+G109A+A174S+G182*+D183*+N195F+V206L+L250V+K391A+G476K, H1*+N54S+V56T+G109A+A174S+G182*+D183*+N195F+V206L+L250+K391A+G476K, H1*+N54S+V56T+G109A+A174S+G182*+D183*+N195F+V206L+L250M+K391A+G476K, H1*+N54S+V56T+G109A+A174S+G182*+D183*+N195F+V206L+K391A+C474V+G476K, H1*+N54S+V56T+G109A+A174S+G182*+D183*+N195F+A204S+V206L+K391A+G476K, H1*+N54S+V56T+G109A+T165G+A174S+G182*+D183*+N195F+V206L+K391A+G476K, H1*+N54S+V56T+G109A+A174S+G182*+D183*+N195F+V206L+T334S+K391A+G476K, H1*+N54S+V56T+G109A+A174S+G182*+D183*+N195F+V206L+A263G+M286L+K391A+G476K, H1*+N54S+V56T+G109A+A174S+G182*+D183*+N195F+V206L+Y267H+K391A+G476K, H1*+N54S+V56T+G109A+A174S+G182*+D183*+N195F+V206L+Y267L+K391A+G476K, H1*+T51A+N54S+V56T+G109A+Q172R+A174S+G182*+D183*+N195F+V206L+K391A+G476K, H1*+N54S+V56T+G109A+A174S+G182*+D183*+N195F+V206L+K391L+G476K, H1*+N54S+V56T+G109A+F113Q+R116H+Q172G+A174S+G182*+D183*+N195F+V206L+K391A+G476K, H1*+N54S+V56T+G109A+F113Q+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+A174S+G182*+D183*+N195F+A204G+V206L+K391A+G476K, H1*+N54S+V56T+K72R+G109A+A174S+G182*+D183*+G184T+N195F+A204G+V206L+K391A+P473R+G476K, H1*+N54S+V56T+G109A+W167F+Q172N+A174S+G182*+D183*+N195F+V206L+K391A+P473R+G476K, H1*+N54S+V56T+G109A+W167F+Q172G+A174S+G182*+D183*+N195F+V206L+K391A+P473G+G476K, H1*+N54S+V56T+G109A+W167F+Q172G+A174S+G182*+D183*+N195F+V206L+K391A+P473R+G476K, H1*+N54S+V56T+K72R+G109A+W167F+Q172R+A174S+G182*+D183*+N195F+V206L+K391A+G476K, H1*+N54S+V56T+K72R+G109A+R116H+W167F+Q172R+A174S+G182*+D183*+N195F+V206L+K391A+G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+A174S+G182*+D183*+N195F+V206L+A265G+K391A+T444Q+G476K+G477A, H1*+A37V+N54S+V56T+G109A+W167F+Q172G+A174S+G182*+D183*+N195F+V206L+K391A+G346T+G477A+G476K, H1*+N54S+V56T+G109A+R116Q+Q172D+A174S+G182*+D183*+N195F+V206L+G346T+K391A+T444Q+G477A+G476K, H1*+N54S+V56T+G109A+R116Q+W167F+Q172N+A174S+G182*+D183*+N195F+V206L+G346T+K391A+T444Q+G477A+G476K, H1*+N54S+V56T+G109S+W167F+Q172R+A174S+G182*+D183*+N195F+V206L+K391A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+G109A+Q172N+A174S+G182*+D183*+N195F+V206L+K391A+C474V+G476K, H1*+N54S+V56T+G109A+A174S+G182*+D183*+N195F+V206L+S280Q+H321Y+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+R116H+W167F+Q172N+A174S+G182*+D183*+N195F+V206L+K391A+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+R116H+W167F+Q172R+

A174S+G182*+D183*+N195F+V206L+F289I+K391A+G476K, H1*+N54S+V56T+G109A+F113Q+Q172N+A174S+G182*+D183*+N195F+V206L+K391A+T444Q+G476K, H1*+N54S+V56T+G109A+F113Q+R116H+Q172N+A174S+G182*+D183*+N195F+V206L+K391A+G476K, H1*+N54S+V56T+G109A+F113Q+R116Q+Q172M+A174S+G182*+D183*+N195F+V206L+K391A+T444Q+G476K, H1*+N54S+V56T+G109A+F113Q+R116H+Q172M+A174S+G182*+D183*+N195F+V206L+K391A+G476K, H1*+N54S+V56T+G109A+R116H+Q172M+A174S+G182*+D183*+N195F+V206L+K391A+G476K, H1*+N54S+V56T+G109A+F113Q+R116H+T165G+Q172M+A174S+G182*+D183*+N195F+V206L+K391A+Q395P+G476K, H1*+N54S+V56T+G109A+F113Q+A174S+G182*+D183*+N195F+V206L+K391A+T444Q+P473R+G476K, H1*+N54S+V56T+G109A+R116Q+A174S+G182*+D183*+N195F+V206L+A265G+K391A+T444Q+P473R+G476K, H1*+N54S+V56T+G109A+R116Q+A174S+G182*+D183*+N195F+V206L+K391A+T444Q+P473R+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+W167F+Q172R+A174S+G182*+D183*+N195F+V206L+K391A+G476K, H1*+N54S+V56T+G109A+R116Q+W167F+Q172R+A174S+G182*+D183*+N195F+V206L+A265G+K391A+P473R+G476K, H1*+N54S+V56T+G109A+F113Q+A174S+G182*+D183*+N195F+V206L+K391A+G476K, H1*+N54S+V56T+G109A+Q172N+A174S+G182*+D183*+N195F+V206L+K391A+G476K, H1*+T51V+N54S+V56T+G109A+Q172D+A174S+G182*+D183*+N195F+V206L+K391A+G476K, H1*+N54S+V56T+G109A+A174S+G182*+D183*+N195F+V206L+S280Q+H321Y+K391A+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172G+L173V+A174S+G182*+D183*+N195F+V206L+K391A+T444Q+P473R+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+N54S+V56T+G109A+F113Q+R116H+W167F+Q172N+L173V+A174S+G182*+D183*+N195F+V206L+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+F113Q+T134E+W167F+Q172R+A174S+G182*+D183*+N195F+V206L+G255A+K391A+Q395P+A445Q+P473R+G476K, H1*+N54S+V56T+K72R+G109A+F113Q+R116H+T134E+W167F+Q172R+A174S+G182*+D183*+N195F+V206L+G255A+K391A+Q395P+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+K72R+G109A+F113Q+R116Q+W167F+Q172N+L173V+A174S+G182*+D183*+G184T+N195F+V206L+K391A+T444Q+P473R+G476K, H1*+A37H+N54S+V56T+G109A+F113Q+W167F+Q172N+A174S+G182*+D183*+N195F+V206L+K391A+G476K, H1*+A37H+N54S+V56T+G109A+F113Q+A174S+G182*+D183*+N195F+V206L+K391A+G476K, H1*+N54S+V56T+G109A+F113Q+W167F+Q172N+A174S+G182*+D183*+N195F+V206L+K391A+T459N+G476K, H1*+N54S+V56T+G109A+F113Q+Q172R+L173V+A174S+G182*+D183*+N195F+V206L+K391A+T444Q+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37V+N54S+V56T+A60V+G109A+R116Q+T165G+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+W167F+Q172G+L173V+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+W167F+Q172R+A174S+G182*+D183*+N195F+A204G+V206L+K391A+P473R+G476K, H1*+N54S+V56T+G109A+R116A+A174S+G182*+D183*+N195F+A204G+V206L+K391A+P473R+G476K, H1*+N54S+V56T+G109A+R116A+T165G+A174S+G182*+D183*+N195F+V206L+K391A+T444Q+P473R+G476K, H1*+N54S+V56T+G109A+G182*+D183*+N195F+K391A+G476K, H1*+N54S+V56T+G109A+G182*+D183*+N195F+V206L, N54S+V56T+G109A+G182*+D183*+N195F, N54S+V56T+G109A+A174S+G182*+D183*+N195F+V206L+K391A+G476K, H1*+G109A+A174S+G182*+D183*+N195F+V206L+K391A+G476K, H1*+N54S+

V56T+G109A+G182*+D183*+N195F+V206L+K391A+G476K, H1*+N54S+V56T+G109A+A174S+G182*+D183*+N195F+V206L+K391A, H1*+N54S+V56T+G109A+A174S+G182*+D183*+N195F+G476K, H1*+N54S+V56T+A174S+G182*+D183*+N195F+V206L+G273R+K391A+G476K, H1*+N54S+V56T+G109A+A174S+G182*+D183*+N195F+V206L, H1*+W48G+G109A+G182*+D183*+N195F+V206L+K391A+G476K, N54S+V56T+G109A+A174S+G182*+D183*+N195F+K391A+G476K, H1*+N54S+V56T+G109A+F113Q+Q172M+A174S+G182*+D183*+N195F+V206L+K391A+G476K, H1*+N54S+V56T+G109A+R116Q+A174S+G182*+D183*+N195F+A204G+V206L+K391A+G476K, H1*+N54S+V56T+K72R+G109A+F113Q+T134E+A174S+G182*+D183*+N195F+V206L+G255A+K391A+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+V56A+G109A+A174S+G182*+D183*+N195F+V206L+G476K, H1*+N54S+V56T+G109A+G182*+D183*+N195F+V206L+K391A, H1*+N54S+V56T+G109A+G182*+D183*+N195F+V206L+G476K, G109A+A174S+G182*+D183*+N195F+V206L+K391A+G476K, N54S+V56T+G109A+G182*+D183*+N195F+V206L+K391T+G476K, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+N54S+V56T+G109A+F113Q+W167F+Q172N+A174S+G182*+D183*+N195F+A204G+V206L+K391A+P473R+G476K, H1*+N54S+V56T+G109A+F113Q+R116H+W167F+Q172R+A174S+G182*+D183*+N195F+A204G+V206L+K391A+P473R+G476K, H1*+N54S+V56T+G109A+R116A+A174S+G182*+D183*+N195F+V206L+K391A+T444Q+P473R+G476K, H1*+N54S+V56T+G109A+R116H+Q172R+A174S+G182*+D183*+N195F+A204G+V206L+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+A174S+G182*+D183*+N195F+K391A+G476K, H1*+G109A+G182*+D183*+N195F+V206L+K391A+G476K, G109A+G182*+D183*+N195F+V206L+G476K, H1*+G109A+G182*+D183*+N195F+K391A, H1*+N54S+V56T+G109A+G133S+A174S+G182*+D183*+N195F+K391A+G476H, H1*+N54S+V56T+G109A+R116A+Q172N+L173V+A174S+G182*+D183*+N195F+V206L+K391A+G476K, H1*+A37V+N54S+V56T+G109A+R116H+T165G+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+P124A+A174S+G182*+D183*+N195F+V206L+K391A+C474V+G476K, H1*+N54S+V56T+G109A+A174S+G182*+D183*+N195F+V206L+P364A+K391A+C474V+G476K, H1*+N54S+V56T+G109A+Q118R+T134E+A174S+G182*+D183*+N195F+V206L+K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+N54S+V56T+G109A+A174S+G182*+D183*+N195F+V206L+Y382L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+W167H+A174S+G182*+D183*+N195F+V206L+K391A+G476K, H1*+N54S+V56T+G109A+T165V+A174S+G182*+D183*+N195F+V206L+K391A+G476K, H1*+N54S+V56T+G109A+A174S+G182*+D183*+N195F+V206L+K391A+G476K, H1*+N54S+V56T+G109A+A174N+G182*+D183*+N195F+V206L+K391A+G476K, H1*+N54S+V56T+G109A+A174Q+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, G109A+G182*+D183*+N195F, G182*+D183*+N195F+K391A, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+

D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+Q169E+Q172K+A174*+G182*+D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+

G476K, H1*+W48F+N54S+V56T+G109A+A174S+G182*+D183*+N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, H1*+N54S+V56T+G109A+A174S+V206L+G182*+D183*+K391A+G476K, H1*+N54S+V56T+Q169E+Q172K+A174*+G182*+D183*+N195F+V206L+K391A+G476K, H1*+N54S+V56T+G109A+A174S+G182*+D183*+N195F+V206F+K391A+G476K, H1*+N54S+V56T+G109A+G182*+D183*+N195F+V206L+K391A+G476K, H1*+N54S+V56T+G109A+Q172K+A174S+G182*+D183*+N195F+V206L+K391A+G476K, H1*+N54S+V56T+G109A+Q172K+A174*+G182*+D183*+N195F+V206L+K391A+G476K, H1*+N54S+V56T+G109A+A174N+G182*+D183*+N195F+V206L+K391A+G476K, H1*+N54S+V56T+G109A+A174S+A186N+G182*+D183*+N195F+V206L+K391A+G476K, H1*+N54S+V56T+G109A+A174S+G182*+D183*+N195F+V206L+F289L+K391A+G476K, H1*+N54S+V56T+G109A+A174S+G182*+D183*+N195F+V206L+Y295F+K391A+G476K, H1*+N54S+V56T+G109A+A174S+G182*+D183*+N195F+V206L+V291A+K391A+G476K, G182*+D183*+A186N+N195F, G182*+D183*+A186D+N195F, G182*+D183*+N195F+W284H, D183*+G182*+N195F+V326L, wherein numbering is according to SEQ ID NO: 13, and H1*+N54S+V56T+G109A+A174S+G182*+D183*+N195F+V206L+K391A+I405L+A421H+A422P+A428T+D476G+G477T, H1*+N54S+V56T+G109A+A174S+G182*+D183*+N195F+V206L+K391A+I405L+A421H+A422P+A428T+G477Q, H1*+N54S+V56T+G109A+A174S+G182*+D183*+N195F+V206L+K391A+I405L+A421H+A422P+A428T+G477A, H1*+N54S+V56T+G109A+A174S+G182*+D183*+N195F+V206L+K391A+I405L+A421H+A422P+A428T+D476N, H1*+N54S+V56T+G109A+A174S+G182*+D183*+N195F+V206L+K391A+I405L+A421H+A422P+A428T+D476Y, H1*+N54S+V56T+G109A+A1745+G182*+D183*+N195F+V206I+I405L+A421H+A422P+A428T, H1*+N54S+V56T+G109A+T134E+A174S+G182*+D183*+N195F+V206L+I405L+A421H+A422P+A428T, H1*+T40D+N54S+V56T+G109A+A174S+G182*+D183*+N195F+V206L+I405L+A421H+A422P+A428T, H1*+N54S+V56T+G109A+F113Q+N125D+A174S+G182*+D183*+N195F+V206L+I405L+A421H+A422P+A428T, H1*+N54S+V56T+A60V+G109A+R116Q+A174S+G182*+D183*+N195F+V206L+I405L+A421H+A422P+A428T, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116H+Q172N+A174S+G182*+D183*+N195F+V206L+I405L+A421H+A422P+A428T, H1*+N54S+V56T+K72R+G109A+T134E+W167F+Q172N+A174S+G182*+D183*+N195F+V206L+G255A+A265G+I405L+A421H+A422P+A428T, H1*+N54S+V56T+K72R+G109A+R116Q+W167F+Q172R+L173V+A174S+G182*+D183*+N195F+V206L+A265G+I405L+A421H+A422P+A428T, H1*+N54S+V56T+K72R+G109A+R116Q+W167F+Q172R+A174S+G182*+D183*+N195F+V206L+I405L+A421H+A422P+A428T, H1*+N54S+V56T+K72R+G109A+F113Q+T134E+W167F+Q172G+A174S+G182*+D183*+N195F+V206L+G255A+I405L+A421H+A422P+A428T, H1*+N54S+V56T+K72R+G109A+F113Q+R116H+W167F+Q172G+L173V+A174S+G182*+D183*+G184T+N195F+V206L+I405L+A421H+A422P+A428T, H1*+N54S+V56T+K72R+G109A+A174S+G182*+D183*+N195F+V206L+G255A+I405L+A421H+A422P+A428T, H1*+N54S+V56T+G109A+F113Q+R116Q+A174S+G182*+D183*+N195F+V206L+I405L+A421H+A422P+A428T, H1*+N54S+V56T+K72R+G109A+F113Q+F116H+W167F+Q172G+L173V+A174S+G182*+D183*+N195F+V206L+I405L+A421H+A422P+A428T, H1*+N54S+V56T+K72R+G109A+F113Q+R116Q+W167F+Q172G+A174S+G182*+D183*+G184T+N195F+V206L+I405L+A421H+A422P+A428T, H1*+N54S+V56T+G109A+F113Q+R116Q+W167F+Q172G+A174S+G182*+D183*+N195F+A204G+V206L+I405L+A421H+A422P+A428T, H1*+N54S+V56T+G109A+F113Q+R116H+W167F+Q172G+A174S+G182*+D183*+N195F+V206L+A265G+I405L+A421H+A422P+A428T, H1*+N54S+V56T+G109A+R116Q+A174S+G182*+D183*+N195F+V206L+I405L+A421H+A422P+A428T, H1*+A37H+N54S+V56T+A60V+G109A+R116Q+T165G+A174S+G182*+D183*+N195F+V206L+I405L+A421H+A422P+A428T, H1*+N54S+V56T+K72R+G109A+F113Q+T134E+A174S+G182*+D183*+N195F+V206L+G255A+I405L+A421H+A422P+A428T, H1*+N54S+V56T+K72R+G109A+R116Q+V120L+A174S+G182*+D183*+G184T+N195F+V206L+I405L+A421H+A422P+A428T, H1*+N54S+V56T+G109A+F113Q+R116H+W167F+Q172G+L173V+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO: 14, and wherein the IF is determined by use of Model A detergent.

In one embodiment, the IF is determined by use of Model A detergent at a temperature of 15° C. In a particular embodiment, the variants have an IF of >1.5 as compared to the parent polypeptide, wherein the IF is determined by use of Model A detergent at a temperature of 15° C. and a concentration of 0.05 mg/L. It can be seen from the Tables in the Examples herein disclosed which such variants may be.

In another embodiment, the variant has an IF of at least 1.5 when compared to the parent polypeptide and when determined by use of Model J detergent, wherein the variant is selected from the group consisting of: G182*+D183*+N195F, H1*+N54S+V56T+G109A+A174S+G182*+D183*+N195F+V206L+K391A+G476K, H1*+N54S+V56T+R87S+G109A+A174S+G182*+D183*+N195F+V206L+K391A+G476K, H1*+T40G+N54S+V56T+G109A+A174S+G182*+D183*+N195F+V206L+K391A+G476K, H1*+T51K+N54S+V56T+G109A+A174S+G182*+D183*+N195F+V206L+K391A+G476K, H1*+N54S+V56T+K72R+G109A+A174S+G182*+D183*+N195F+V206L+K391A+G476K, H1*+N54S+V56T+K72H+G109A+A174S+G182*+D183*+N195F+V206L+K391A+G476K, H1*+A37H+N54S+V56T+G109A+A174S+G182*+D183*+N195F+V206L+K391A+G476K, H1*+A37M+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+A37S+N54S+V56T+G109A+A174S+G182*+D183*+N195F+V206L+K391A+G476K, H1*+A37Y+N54S+V56T+G109A+A174S+G182*+D183*+N195F+V206L+K391A+G476K, H1*+A37R+N54S+V56T+G109A+A174S+G182*+D183*+N195F+V206L+K391A+G476K, H1*+N54S+V56T+G109A+F113W+A174S+G182*+D183*+N195F+V206L+K391A+G476K, H1*+N54S+V56T+G109A+F113S+A174S+G182*+D183*+N195F+V206L+K391A+G476K, H1*+N54S+V56T+G109A+F113N+A174S+G182*+D183*+N195F+V206L+K391A+G476K, H1*+N54S+V56T+G109A+F113Y+A174S+G182*+D183*+N195F+V206L+K391A+G476K, H1*+N54S+V56T+G109A+F113R+A174S+G182*+D183*+N195F+V206L+K391A+G476K, H1*+N54S+V56T+G109A+Q118N+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+R116V+A174S+G182*+D183*+N195F+V206L+K391A+G476K, H1*+N54S+V56T+G109A+R116K+A174S+G182*+D183*+N195F+V206L+K391A+G476K, H1*+N54S+V56T+G109A+R116L+A174S+G182*+D183*+N195F+V206L+K391A+G476K, H1*+N54S+V56T+G109A+G142T+A174S+G182*+D183*+N195F+V206L+K391A+G476K, H1*+N54S+V56T+G109A+Q125P+A174S+G182*+D183*+N195F+V206L+K391A+G476K, H1*+N54S+V56T+G109A+Q125K+A174S+G182*+D183*+N195F+V206L+K391A+G476K, H1*+N54S+V56T+G109A+A174S+G182*+D183*+N195F+V206L+S381G+K391A+G476K, H1*+N54S+V56T+G109A+A174S+G182*+D183*+N195F+V206L+M246T+K391A+G476K, H1*+N54S+V56T+G109A+A174S+G182*+D183*+N195F+V206L+V213T+K391A+G476K, H1*+A37L+N54S+V56T+G109A+A174S+G182*+D183*+N195F+V206L+K391A+G476K, H1*+N54S+V56T+G109A+Q118K+A174S+G182*+D183*+N195F+V206L+K391A+G476K, H1*+N54S+V56T+G109A+R116A+A174S+G182*+D183*+N195F+V206L+K391A+G476K, H1*+N54S+V56T+G109A+R116H+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+Q172R+A174S+G182*+D183*+N195F+V206L+K391A+G476K, H1*+N54S+V56T+G109A+A174S+G182*+D183*+N195F+V206L+D377S+K391A+G476K, H1*+N54S+V56T+G109A+A174S+G182*+D183*+N195F+V206L+D377G+K391A+G476K, H1*+N54S+V56T+G109A+A174S+G182*+D183*+N195F+V206L+D377R+K391A+G476K, H1*+N54S+V56T+G109A+A174S+G182*+D183*+N195F+V206L+D377A+K391A+G476K, H1*+N54S+V56T+G109A+A174S+G182*+D183*+N195F+V206L+I214G+K391A+G476K, H1*+N54S+V56T+G109A+A174S+G182*+D183*+N195F+V206L+S381A+K391A+G476K, H1*+N54S+V56T+G109A+W167I+A174S+G182*+D183*+N195F+V206L+K391A+G476K, H1*+N54S+V56T+G109A+W167G+A174S+G182*+D183*+N195F+V206L+K391A+G476K, H1*+N54S+V56T+G109A+A174S+G182*+D183*+N195F+V206L+G346S+K391A+G476K, H1*+N54S+V56T+G109A+A174S+G182*+D183*+N195F+V206L+G346P+K391A+G476K, H1*+N54S+V56T+G109A+A174S+G182*+D183*+N195F+V206L+I214H+K391A+G476K, H1*+N54S+V56T+G109A+A174S+G182*+D183*+N195F+V206L+I214S+K391A+G476K, H1*+N54S+V56T+G109A+A174S+G182*+D183*+N195F+V206L+I214T+K391A+G476K, H1*+N54S+V56T+G109A+A174S+G182*+D183*+N195F+V206L+K391A+A420Q+G476K, H1*+N54S+V56T+G109A+A174S+G182*+D183*+

N195F+V206L+K391A+A420S+G476K, H1*+N54S+V56T+G109A+A174S+G182*+D183*+N195F+V206L+K391A+A420K+G476K, H1*+N54S+V56T+G109A+A174S+G182*+D183*+N195F+V206L+K391A+A420L+G476K, H1*+N54S+V56T+G109A+A174S+G182*+D183*+N195F+V206L+K391A+K391Y+G476K, H1*+N54S+V56T+G109A+A174S+G182*+D183*+N195F+V206L+K391A+K391R+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+P473G+G476K, H1*+N54S+V56T+G109A+A174S+G182*+D183*+N195F+V206L+K391A+P473T+G476K, H1*+N54S+V56T+G109A+A174S+G182*+D183*+N195F+V206L+K391A+Q395P+G476K, H1*+N54S+V56T+G109A+A174S+G182*+D183*+N195F+V206L+K391A+T444Q+G476K, H1*+N54S+V56T+G109A+A174S+G182*+D183*+N195F+V206L+K391A+T444S+G476K, H1*+N54S+V56T+G109A+A174S+G182*+D183*+N195F+V206L+K391A+T444D+G476K, H1*+N54S+V56T+G109A+A174S+G182*+D183*+N195F+V206L+K391A+T444Y+G476K, H1*+N54S+V56T+G109A+A174S+G182*+D183*+N195F+V206L+S280W+K391A+G476K, H1*+N54S+V56T+G109A+A174S+G182*+D183*+N195F+V206L+S280L+K391A+G476K, H1*+N54S+V56T+G109A+A174S+G182*+D183*+N195F+V206L+S280T+K391A+G476K, H1*+N54S+V56T+G109A+A174S+G182*+D183*+N195F+V206L+S280A+K391A+G476K, H1*+N54S+V56T+G109A+A174S+G182*+D183*+N195F+V206L+G255N+K391A+G476K, H1*+N54S+V56T+G109A+A174S+G182*+D183*+N195F+V206L+T285L+K391A+G476K, H1*+N54S+V56T+G109A+A174S+G182*+D183*+N195F+V206L+T285Q+K391A+G476K, H1*+N54S+V56T+G109A+A174S+G182*+D183*+N195F+V206L+K391A+Q449T+G476K, H1*+N54S+V56T+G109A+A174S+G182*+D183*+N195F+V206L+K391A+P473K+G476K, H1*+N54S+V56T+K72S+G109A+A174S+G182*+D183*+N195F+V206L+K391A+G476K, H1*+T40K+N54S+V56T+G109A+A174S+G182*+D183*+N195F+V206L+G346T+K391A+G476K, H1*+G50A+N54S+V56T+G109A++Q172N+A174S+G182*+D183*+N195F+V206L+K391A+G476K, H1*+N54S+V56T+G109A+A174S+G182*+D183*+N195F+V206L+K391A+G476K+K484A, H1*+N54S+V56T+G109A+A174S+G182*+D183*+N195F+V206L+K391A+G476K+K484G, H1*+N54S+V56T+G109A+A174S+G182*+D183*+N195F+V206L+K391A+G476K+K484P, H1*+N54S+V56T+G109A+A174S+G182*+D183*+N195F+V206L+K391A+G476K+K484E, H1*+N54S+V56T+G109A+A174S+G182*+D183*+N195F+V206L+K391A+G476K+K484Q, H1*+N54S+V56T+G109A+A174S+G182*+D183*+N195F+V206L+K391A+G476K+K484S, H1*K+G50A+N54S+V56T+G109A+W167F+A174S+G182*+D183*+N195F+V206L+K391A+G476K, H1*+N54S+V56T+G109A+L173V+A174S+G182*+D183*+N195F+A204T+V206L+K391A+G476K, H1*+N54S+V56T+G109A+W140Y+A174S+G182*+D183*+N195F+V206L+K391A+G476K, H1*+N54S+V56T+Q98S+G109A+A174S+G182*+D183*+N195F+V206L+R320A+K391A+G476K, H1*+N54S+V56T+G109A+A174S+G182*+D183*+N195F+V206L+H324L+K391A+G476K, H1*+N54S+V56T+G109A+G149Q+A174S+G182*+D183*+N195F+V206L+K391A+G476K, H1*+N54S+V56T+G109A+A174S+G182*+D183*+N195F+V206L+G346T+K391A+G476K+G477A, H1*+N54S+V56T+G109AG255A++A174S+G182*+D183*+N195F+V206L+K391A+G476K, H1*+G50A+N54S+V56T+G109A+F113L+R116L+A174S+G182*+D183*+N195F+V206L+K391A+G476K, H1*+N54S+V56T+G109A+W167F+A174S+G182*+D183*+N195F+V206L+K391A+G476K, H1*+N54S+V56T+G109A+L173V+A174S+G182*+D183*+N195F+V206L+K391A+G476K, H1*+N54S+V56T+K72R+G109A+W167F+A174S+G182*+D183*+N195F+V206L+K391A+G476K, H1*+N54S+V56T+G109A+A174S+G182*+D183*+N195F+V206L+K391A+G476K+G477Q, H1*+N54S+V56T+G109A+A174S+G182*+D183*+N195F+V206L+Q345D+K391A+G476K+G477Q, H1*+G50A+N54S+V56T+G109A+Q172D+A174S+G182*+D183*+N195F+V206L+K391A+G476K, H1*+N54S+V56T+G109A+A174S+G182*+D183*+N195F+V206L+V264I+K391A+G423H+G476K, H1*+N54S+V56T+G109A+A174S+G182*+D183*+N195F+V206L+R320V+K391A+G476Y, H1*+T5K+N54S+V56T+G109A+A174S+G182*+D183*+N195F+V206L+K391A+G476K, H1*+N54S+V56T+G109A+R116M+A174S+G182*+D183*+N195F+V206L+K391A+G476K, H1*+N54S+V56T+G109A+Q172Y+A174S+G182*+D183*+N195F+V206L+K391A+G476K, H1*+N54S+V56T+G109A+A174S+G182*+D183*+N195F+V206L+I214L+K391A+G476K, H1*+N54S+V56T+G109A+A174S+G182*+D183*+N195F+V206L+L217V+K391A+G476K, H1*+N54S+V56T+G109A+A174S+G182*+D183*+N195F+V206L+L217H+K391A+G476K, H1*+N54S+V56T+G109A+A174S+G182*+D183*+N195F+V206L+P211D+K391A+G476K, H1*+N54S+V56T+G109A+A174S+G182*+D183*+N195F+V206L+K391A+K391Q+G476K, H1*+N54S+V56T+G109A+A174S+G182*+D183*+N195F+V206L+K391A+T444H+G476K, H1*+N54S+V56T+G109A+A174S+G182*+D183*+N195F+V206L+K391A+T444V+G476K, H1*+N54S+V56T+G109A+A174S+G182*+D183*+N195F+V206L+K391A+T444R+G476K, H1*+G50A+N54S+V56T+G109A+L173V+A174S+G182*+D183*+N195F+A204V+V206L+K391A+G476K, H1*+G50A+N54S+V56T+G109A+F113L+W167F+A174S+G182*+D183*+N195F+V206L+K391A+G476K, H1*+G7K+N54S+V56T+G109A+A174S+G182*+D183*+N195F+V206L+R320A+K391A+G476K, H1*+N54S+V56T+G109A+Q118G+A174S+G182*+D183*+N195F+V206L+K391A+G476K, H1*+N54S+V56T+G109A+A174S+G182*+D183*+N195F+V206L+S280K+K391A+G476K, H1*+N54S+V56T+G109A+A174S+G182*+D183*+N195F+V206L+N270G+K391A+G476K, H1*+N54S+V56T+G109A+Q172D+A174S+G182*+D183*+N195F+V206L+G346T+K391A+G476K+G477A, H1*+N54S+V56T+G109A+Q118S+A174S+G182*+D183*+N195F+V206L+K391A+G476K, H1*+N54S+V56T+G109A+A174S+G182*+D183*+N195F+V206L+R320A+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+G337H+Q385L+K391A+G476K, H1*+N54S+V56T+G109A+A174S+G182*+D183*+N195F+V206L+Y382M+K391A+G476K, H1*+N54S+V56T+K72R+G109A+A174S+G182*+D183*+N195F+V206L+G255A+D377H+K391A+G476K, H1*+N54S+V56T+K72R+G109A+T134E+A174S+G182*+D183*+N195F+V206L+G255A+K391A+G476K, H1*+N54S+V56T+K72R+M105F+G109A+A174S+G182*+D183*+N195F+V206L+G255A+K391A+G476K, H1*+N54S+V56T+M105F+G109A+T134E+A174S+G182*+D183*+N195F+V206L+K391A+G476K, H1*+N54S+V56T+M105F+G109A+Q118F+

T134E+A174S+G182*+D183*+N195F+V206L+K391A+G476K, H1*+N54S+V56T+G109A+A174S+G182*+D183*+N195F+V206L+R320A+S323N+D377H+K391A+G476K, H1*+T51E+N54S+V56T+G109A+A174H+G182*+D183*+N195F+V206L+K391A+G476K, H1*+N54S+V56T+G109A+L173A+A174S+G182*+D183*+N195F+V206L+K391A+G476K, H1*+N54S+V56T+G109A+A174S+G182*+D183*+N195F+V206L+Q299V+K391A+G476K, H1*+N54S+V56T+G109A+L173G+A174S+G182*+D183*+N195F+V206L+K391A+G476K, H1*+N54S+V56T+G109A+A174S+G182*+D183*+N195F+V206L+T355L+K391A+G476K, H1*+N54S+V56T+G109A+A174S+G182*+D183*+N195F+V206L+T355F+K391A+G476K, H1*+G50A+N54S+V56T+G109A+A174S+G182*+D183*+N195F+A204T+V206L+K391A+G476K, H1*+G50A+N54S+V56T+G109A+A174E+G182*+D183*+N195F+A204T+V206L+K391A+G476K, H1*+N54S+V56T+K72R+G109A+A174S+G182*+D183*+N195F+V206L+R320A+S323N+K391A+G476K, H1*+N54S+V56T+M105I+G109A+A174S+G182*+D183*+N195F+V206L+K391A+G476K, H1*+N54S+V56T+G109A+A174S+G182*+D183*+N195F+V206L+M246L+K391A+G476K, H1*+T51G+N54S+V56T+G109A+A174N+G182*+D183*+N195F+V206L+K391A+G476K, H1*+T51A+N54S+V56T+G109A+A174G+G182*+D183*+N195F+V206L+K391A+G476K, H1*+N54S+V56T+G109A+A174D+G182*+D183*+N195F+V206L+K391A+G476K, H1*+T51G+N54S+V56T+G109A+A174M+G182*+D183*+N195F+V206L+K391A+G476K, H1*+N54S+V56T+K72Q+G109A+W167H+A174S+G182*+D183*+N195F+V206L+K391A+G476K, H1*+N54S+V56T+G109A+Q118R+T134E+A174S+G182*+D183*+N195F+V206L+D377H+K391A+G476K, H1*+Q11H+N54S+V56T+G109A+Q118R+T134E+A174S+G184T+G182*+D183*+N195F+V206L+D377H+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+Q118R+T134E+A174S+G182*+D183*+N195F+V206L+G255A+K391A+G476K, H1*+N54S+V56T+G109A+Q118R+A174S+G182*+D183*+N195F+V206L+D377H+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+K72A+G109A+W167F+A174S+G182*+D183*+N195F+V206L+K391A+G476K, H1*+N54S+V56T+G109A+W167S+G182*+D183*+N195F+A174S+V206L+K391A+G476K, H1*+N54S+V56T+K72R+G109A+W167L+A174S+G182*+D183*+N195F+V206L+K391A+G476K, H1*+N54S+V56T+K72R+G109A+W167M+A174S+G182*+D183*+N195F+V206L+K391A+G476K, H1*+N54S+V56T+K72R+G109A+W167H+A174S+G182*+D183*+N195F+V206L+K391A+G476K, H1*+N54S+V56T+K72R+G109A+A174S+G182*+D183*+G184T+N195F+V206L+G255A+K391A+G476K, H1*+N54S+V56T+G109A+A174S+G182*+D183*+G184T+N195F+V206L+D377H+K391A+G476K, H1*+N54S+V56T+G109A+A174S+G182*+D183*+N195F+V206L+G255A+D377H+K391A+G476K, H1*+N54S+V56T+G109A+Q118R+A174S+G182*+D183*+N195F+V206L+G255A+D377H+K391A+G476K, H1*+N54S+V56T+M105F+G109A+A174S+G182*+D183*+G184T+N195F+V206L+K391A+G476K, H1*+N54S+V56T+G109A+T134E+A174S+G182*+D183*+N195F+V206L+R320A+S323N+K391A+G476K, H1*+N54S+V56T+G109A+A174S+G182*+D183*+N195F+V206L+V291G+D377H+K391A+G476K, H1*+N54S+V56T+G109A+A174S+G182*+D183*+N195F+V206L+V291A+F328L+D377H+K391A+G476K, H1*+V56T+G109A+A174S+G182*+D183*+N195F+V206L+D377H+K391A+G476K, H1*+N54S+V56T+G109A+T134E+A174S+G182*+D183*+G184T+N195F+V206L+K391A+G476K, H1*+N54S+V56T+G109A+A174S+G182*+D183*+N195F+V206L+V238A+D377H+K391A+G476K, H1*+N54S+V56T+G109A+A174S+G182*+D183*+N195F+V206L+V238T+D377H+K391A+G476K, H1*+N54S+V56T+G109A+A174S+G182*+D183*+N195F+V206L+V238G+D377H+K391A+G476K, H1*+N54S+V56T+G109A+A174S+G182*+D183*+N195F+V206L+F328M+D377H+K391A+G476K, H1*+N54S+V56T+G109A+A174S+G182*+D183*+N195F+V206L+F328L+D377H+K391A+G476K, H1*+N54S+V56T+G109A+A174S+G182*+D183*+N195F+V206L+F328V+D377H+K391A+G476K, H1*+N54S+V56T+G109A+A174S+G182*+D183*+N195F+V206L+F328I+D377H+K391A+G476K, H1*+N54S+V56T+G109A+A174S+G182*+D183*+N195F+V206L+V291T+D377H+K391A+G476K, H1*+N54S+V56T+G109A+A174S+G182*+D183*+N195F+V206L+V291A+D377H+K391A+G476K, H1*+N54S+V56T+K72R+G109A+T134E+A174S+G182*+D183*+G184T+N195F+V206L+G255A+K391A+G476K, H1*+N54S+V56T+G109A+L173H+A174S+G182*+D183*+N195F+V206L+K391A+G476K, H1*+N54S+V56T+G109A+Q125T+A174S+G182*+D183*+N195F+V206L+K391A+G476K, H1*+N16S+N54S+V56T+G109A+A174S+G182*+D183*+N195F+V206L+K391A+G476K, H1*+N54S+V56T+K72N+G109A+A174S+G182*+D183*+N195F+V206L+K391A+G476K, H1*+N54S+V56T+K72N+G109A+W167L+A174S+G182*+D183*+N195F+V206L+K391A+G476K, H1*+N54S+V56T+K72A+G109A+W167Y+A174S+G182*+D183*+N195F+V206L+K391A+G476K, H1*+N54S+V56T+G109A+Q118R+T134E+A174S+G182*+D183*+N195F+V206L+G255A+D377H+K391A+G476K, H1*+N54S+V56T+K72R+G109A+A174S+G182*+D183*+N195F+G184T+V206L+K391A+G476K, H1*+N54S+V56T+K72R+G109A+Q118R+A174S+G182*+D183*+N195F+V206L+G255A+D377H+K391A+G476K, H1*+N54S+V56T+G109A+A174S+G182*+D183*+G184T+N195F+V206L+R320A+S323N+K391A+G476K, H1*+N54S+G109A+A174S+G182*+D183*+N195F+V206L+D377H+K391A+G476K, H1*+N54S+V56T+A174S+G182*+D183*+N195F+V206L+D377H+K391A+G476K, H1*+N54S+V56T+G109A+G182*+D183*+N195F+V206L+D377H+K391A+G476K, H1*+N54S+V56T+G109A+A174S+G182*+D183*+N195F+D377H+K391A+G476K, H1*+N54S+V56T+G109A+A174S+G182*+D183*+N195F+D377H+K391A+G476K, H1*+N54S+V56T+G109A+A174S+G182*+D183*+N195F+V206L+D377H+G476K, H1*+N54S+V56T+G109A+A174S+G182*+D183*+N195F+V206L+D377H+K391A, H1*+N54S+V56T+G109A+A174S+G182*+D183*+N195F+V206L+D377R+K391A+G476K, H1*+N54S+V56T+G109A+A174S+G182*+D183*+N195F+V206L+L217T+K391A+G476K, H1*+N54S+V56T+G109A+A174S+G182*+D183*+N195F+V206L+D377S+K391A+G476K, H1*+N54S+V56T+G109A+R116E+A174S+G182*+D183*+N195F+V206L+K391A+G476K, H1*+N54S+V56T+G109A+A174S+G182*+D183*+N195F+V206L+L217Q+K391A+

G476K, H1*+N54S+V56T+G109A+A174S+G182*+D183*+N195F+V206L+G346D+K391A+G476K, H1*+N54S+V56T+G109A+A174S+G182*+D183*+N195F+V206L+D377A+K391A+G476K, H1*+N54S+V56T+G109A+T134E+A174S+G182*+D183*+N195F+V206L+D377H+K391A+G476K, H1*+N54S+V56T+G109A+Q118R+T134E+A174S+G182*+D183*+G184T+N195F+V206L+K391A+G476K, H1*+N54S+V56T+K72R+G109A+Q118R+T134E+A174S+G182*+D183*+N195F+V206L+K391A+G476K, H1*+N54S+V56T+G109A+A174S+G182*+D183*+N195F+V206L+G346P+K391A+G476K, H1*+N54S+V56T+G109A+R116S+A174S+G182*+D183*+N195F+V206L+K391A+G476K, H1*+N54S+V56T+G109A+A174S+G182*+D183*+N195F+V206L+D377Q+K391A+G476K, H1*+N54S+V56T+G109A+R116G+A174S+G182*+D183*+N195F+V206L+K391A+G476K, H1*+N54S+V56T+G109A+A174F+G182*+D183*+N195F+V206L+K391A+G476K, H1*+N54S+V56T+G109A+R116G+A174S+G182*+D183*+N195F+V206L+K391A+G476K, H1*+N54S+V56T+G109A+A174T+G182*+D183*+N195F+V206L+K391A+G476K, H1*+N54S+V56T+G109A+Q118R+T134E+A174S+G182*+D183*+G184T+N195F+V206L+G255A+K391A+G476K, H1*+N54S+V56T+K72R+G109A+Q118R+T134E+A174S+G182*+D183*+N195F+V206L+G255A+K391A+G476K, H1*+T51G+N54S+V56T+G109A+Q172R+A174S+G182*+D183*+N195F+V206L+K391A+G476K, H1*+T51A+N54S+V56T+G109A+Q172D+A174S+G182*+D183*+N195F+V206L+K391A+G476K, H1*+T51S+N54S+V56T+G109A+Q172M+A174S+G182*+D183*+N195F+V206L+K391A+G476K, H1*+T51A+N54S+V56T+G109A+Q172S+A174S+G182*+D183*+N195F+V206L+K391A+G476K, H1*+T51E+N54S+V56T+G109A+Q172T+A174S+G182*+D183*+N195F+V206L+K391A+G476K, H1*+T51A+N54S+V56T+G109A+Q172A+A174S+G182*+D183*+N195F+V206L+K391A+G476K, H1*+T51S+N54S+V56T+G109A+Q172N+A174S+G182*+D183*+N195F+V206L+K391A+G476K, H1*+T51G+N54S+V56T+G109A+Q172K+A174S+G182*+D183*+N195F+V206L+K391A+G476K, H1*+T51A+N54S+V56T+G109A+Q172G+A174S+G182*+D183*+N195F+V206L+K391A+G476K, H1*+T51E+N54S+V56T+G109A+Q172L+A174S+G182*+D183*+N195F+V206L+K391A+G476K, H1*+T51E+N54S+V56T+G109A+Q172R+A174S+G182*+D183*+N195F+V206L+K391A+G476K, H1*+N54S+V56T+G109A+Q172K+A174S+G182*+D183*+N195F+V206L+K391A+G476K, H1*+T51D+N54S+V56T+G109A+Q172N+A174S+G182*+D183*+N195F+V206L+K391A+G476K, H1*+T51A+N54S+V56T+G109A+Q172K+A174S+G182*+D183*+N195F+V206L+K391A+G476K, H1*+N54S+V56T+K72R+G109A+Q172S+A174S+G182*+D183*+N195F+V206L+K391A+G476K, H1*+N54S+V56T+K72H+G109A+Q172T+A174S+G182*+D183*+N195F+V206L+K391A+G476K, H1*+N54S+V56T+K72R+G109A+Q172M+A174S+G182*+D183*+N195F+V206L+Y295N+K391A+G476K, H1*+N54S+V56T+K72R+G109A+Q172R+A174S+G182*+D183*+N195F+V206L+K391A+G476K, H1*+N54S+V56T+K72Q+G109A+Q172R+A174S+G182*+D183*+N195F+V206L+K391A+G476K, H1*+N54S+V56T+K72R+G109A+Q172T+A174S+G182*+D183*+N195F+V206L+K391A+G476K, H1*+N54S+V56T+K72M+G109A+Q172S+A174S+G182*+D183*+N195F+V206L+K391A+G476K, H1*+N54S+V56T+K72Q+G109A+Q172M+A174S+G182*+D183*+N195F+V206L+K391A+G476K, H1*+N54S+V56T+G109A+Q172M+

A174S+G182*+D183*+N195F+V206L+K391A+G476K, H1*+N54S+V56T+K72S+G109A+A174H+G182*+D183*+N195F+V206L+K391A+G476K, H1*+N54S+V56T+K72Q+G109A+A174D+G182*+D183*+N195F+V206L+K391A+G476K, H1*+N54S+V56T+K72R+G109A+A174D+G182*+D183*+N195F+V206L+K391A+G476K, H1*+N54S+V56T+K72Q+G109A+A174K+G182*+D183*+N195F+V206L+K391A+G476K, H1*+N54S+V56T+G109A+A174G+G182*+D183*+N195F+V206L+K391A+G476K, H1*+N54S+V56T+K72R+G109A+A174Q+G182*+D183*+N195F+V206L+K391A+G476K, H1*+N54S+V56T+K72Q+G109A+A174G+G182*+D183*+N195F+V206L+K391A+G476K, H1*+N54S+V56T+K72S+G109A+A174N+G182*+D183*+N195F+V206L+K391A+G476K, H1*+N54S+V56T+K72R+G109A+A174H+G182*+D183*+N195F+V206L+K391A+G476K, H1*+N54S+V56T+G109A+A174S+G182*+D183*+N195F+V206L+K391A+K391S+G476K, H1*+N54S+V56T+G109A+A174S+G182*+D183*+N195F+V206L+K391A+T444A+G476K, H1*+N54S+V56T+G109A+F113L+W167F+A174S+G182*+D183*+N195F+V206L+K391A+G476K, H1*+G50A+N54S+V56T+G109A+A174E+G182*+D183*+N195F+A204T+V206L+S323N+K391A+G476K, H1*+N54S+V56T+M105F+G109A+A174S+G182*+D183*+N195F+V206L+D377H+K391A+G476K, H1*+N54S+V56T+G109A+A174S+G182*+D183*+N195F+A204G+V206L+K391A+G476K, H1*+N54S+V56T+G109A+A174S+G182*+D183*+N195F+V206L+A225F+K391A+G476K, H1*+N54S+V56T+G109A+A174S+G182*+D183*+N195F+V206L+M246A+K391A+G476K, H1*+N54S+V56T+G109A+A174S+G182*+D183*+N195F+V206L+Y382I+K391A+G476K, H1*+N54S+V56T+G109A+A174S+G182*+D183*+N195F+V206L+S376H+K391A+G476K, H1*+N54S+V56T+G109A+A174S+G182*+D183*+N195F+V206L+I214E+K391A+G476K, H1*+N54S+V56T+G109A+A174S+G182*+D183*+N195F+V206L+I214W+K391A+G476K, H1*+N54S+V56T+K72R+G109A+Q172K+A174S+G182*+D183*+N195F+V206L+K391A+G476K, H1*+N54S+V56T+G109A+A174S+G182*+D183*+N195F+A204T+V206L+D377H+K391A+G476K, H1*+N54S+V56T+G109A+A174S+G182*+D183*+N195F+A204S+V206L+D377H+K391A+G476K, H1*+N54S+V56T+G109A+T165S+A174S+G182*+D183*+N195F+V206L+D377H+K391A+G476K, H1*+N54S+V56T+G109A+A174S+G182*+D183*+N195F+V206L+T334S+D377H+K391A+G476K, H1*+N54S+V56T+G109A+A174S+G182*+D183*+N195F+V206L+A263G+D377H+K391A+G476K, H1*+N54S+V56T+G109A+A174S+G182*+D183*+N195F+V206L+M286F+D377H+K391A+G476K, H1*+N54S+V56T+G109A+A174S+G182*+D183*+N195F+V206L+Y267I+D377H+K391A+G476K, H1*+N54S+V56T+G109A+A174S+G182*+D183*+N195F+V206L+L235V+D377H+K391A+G476K, H1*+N54S+V56T+G109A+A174S+G182*+D183*+N195F+V206L+L235A+D377H+K391A+G476K, H1*+N54S+V56T+M105L+G109A+A174S+G182*+D183*+N195F+V206L+D377H+K391A+G476K, H1*+N54S+V56T+M105I+G109A+A174S+G182*+D183*+N195F+V206L+D377H+K391A+G476K, H1*+N54S+V56T+M105V+G109A+A174S+G182*+D183*+N195F+V206L+D377H+K391A+G476K, H1*+N54S+V56T+G109A+A174S+G182*+D183*+N195F+V206L+M246I+D377H+K391A+G476K, H1*+N54S+V56T+G109A+A174S+G182*+D183*+N195F+V206L+L250I+D377H+K391A+G476K, H1*+N54S+V56T+G109A+A174S+G182*+D183*+N195F+V206L+L250V+D377H+K391A+

G476K, H1*+N54S+V56T+G109A+A174S+G182*+D183*+N195F+V206L+K391Y+G476K, H1*+N54S+V56T+G109A+A174S+G182*+D183*+N195F+V206L+K391V+G476K, H1*+N54S+V56T+G109A+A174S+G182*+D183*+N195F+V206L+K391M+G476K, H1*+N54S+V56T+G109A+A174S+G182*+D183*+N195F+V206L+K391E+G476K, H1*+N54S+V56T+G109A+T165G+A174S+G182*+D183*+N195F+V206L+D377H+K391A+G476K, H1*+N54S+V56T+G109S+A174S+G182*+D183*+N195F+V206L+K391A+G476K, H1*+N54S+V56T+G109A+A174V+G182*+D183*+N195F+V206L+K391A+G476K, H1*+N54S+V56T+G109A+A174S+G182*+D183*+N195F+V206L+M246F+D377H+K391A+G476K, H1*+N54S+V56T+G109A+A174S+G182*+D183*+N195F+V206L+M246V+D377H+K391A+G476K, H1*+N54S+V56T+G109A+A174S+G182*+D183*+N195F+V206L+M246S+D377H+K391A+G476K, H1*+N54S+V56T+G109A+A174R+G182*+D183*+N195F+V206L+K391A+G476K, H1*+N54S+V56T+G109A+A174L+G182*+D183*+N195F+V206L+K391A+G476K, H1*+N54S+V56T+G109A+A174S+G182*+D183*+N195F+V206S+K391A+G476K, H1*+N54S+V56T+G109A+A174S+G182*+D183*+N195F+V206L+K391D+G476K, H1*+N54S+V56T+G109A+A174S+G182*+D183*+N195F+V206L+K391R+G476K, H1*+N54S+V56T+G109A+A174S+G182*+D183*+N195F+V206L+K391H+G476K, H1*+N54S+V56T+G109A+A174S+G182*+D183*+N195F+V206L+K391W+G476K, H1*+N54S+V56T+G109A+A174S+G182*+D183*+N195F+V206L+K391I+G476K, H1*+N54S+V56T+G109A+A174S+G182*+D183*+N195F+V206L+L250T+D377H+K391A+G476K, H1*+N54S+V56T+G109A+A174S+G182*+D183*+N195F+V206L+L250A+D377H+K391A+G476K, H1*+N54S+V56T+G109A+A174S+G182*+D183*+N195F+V206L+L250F+D377H+K391A+G476K, H1*+N54S+V56T+G109A+A174S+G182*+D183*+N195F+V206L+L250M+D377H+K391A+G476K, H1*+N54S+V56T+G109A+A174S+G182*+D183*+N195F+V206L+K391Q+G476K, H1*+N54S+V56T+G109A+Q172H+L173A+A174P+G182*+D183*+N195F+V206L+K391A+G476K, H1*+N54S+V56T+G109A+Q172E+L173A+A174R+G182*+D183*+N195F+V206L+K391A+G476K, H1*+N54S+V56T+K72Q+G109A+W167R+A174S+G182*+D183*+N195F+V206L+K391A+G476K, H1*+N54S+V56T+G109A+A174S+G182*+D183*+G184T+N195F+V206L+G255A+K391A+G476K, H1*+N54S+V56T+K72R+G109A+A174S+G182*+D183*+G184T+N195F+V206L+D377H+K391A+G476K, H1*+N54S+V56T+G109A+A174S+G182*+D183*+G184T+N195F+V206L+G255A+D377H+K391A+G476K, H1*+N54S+V56T+G109A+A174S+G182*+D183*+N195F+V206L+S376T+K391A+G476K, H1*+N54S+V56T+G109A+A174S+G182*+D183*+N195F+V206L+S376V+K391A+G476K, H1*+N54S+V56T+G109A+Q172E+L173I+A174N+G182*+D183*+N195F+V206L+K391A+G476K, H1*+N54S+V56T+G109A+Q172D+L173A+A174T+G182*+D183*+N195F+V206L+K391A+G476K, H1*+N54S+V56T+G109A+A174S+G182*+D183*+N195F+V206L+Y267M+D377H+K391A+G476K, H1*+N54S+V56T+G109A+A174S+G182*+D183*+N195F+V206L+Y267H+D377H+K391A+G476K, H1*+N54S+V56T+G109A+A174S+G182*+D183*+N195F+V206L+V238A+K391A+G476K, H1*+N54S+V56T+G109A+A174S+G182*+D183*+N195F+V206L+V238T+K391A+G476K, H1*+N54S+V56T+G109A+A174S+G182*+D183*+N195F+V206L+V238G+K391A+G476K, H1*+N54S+V56T+M105V+G109A+A174S+G182*+D183*+N195F+V206L+K391A+G476K, H1*+N54S+V56T+G109A+A174S+G182*+D183*+N195F+V206L+V264T+K391A+G476K, H1*+N54S+V56T+G109A+A174S+G182*+D183*+N195F+V206L+V264I+K391A+G476K, H1*+N54S+V56T+G109A+A174S+G182*+D183*+N195F+V206L+L235V+K391A+G476K, H1*+N54S+V56T+G109A+W167H+Q172N+L173A+A174S+G182*+D183*+N195F+V206L+K391A+G476K, H1*+N54S+V56T+G109A+W167F+Q172E+L173P+A174K+G182*+D183*+N195F+V206L+K391A+G476K, H1*+N54S+V56T+G109A+Q172N+L173T+A174S+G182*+D183*+N195F+V206L+K391A+G476K, H1*+N54S+V56T+G109A+Q172K+L173V+A174T+G182*+D183*+N195F+V206L+K391A+G476K, H1*+N54S+V56T+G109A+Q172E+L173F+A174R+G182*+D183*+N195F+V206L+K391A+G476K, H1*+N54S+V56T+G109A+Q172E+L173T+A174R+G182*+D183*+N195F+V206L+K391A+G476K, H1*+N54S+V56T+G109A+Q172N+L173V+A174R+G182*+D183*+N195F+V206L+K391A+G476K, H1*+N54S+V56T+G109A+L173V+A174R+G182*+D183*+N195F+V206L+K391A+G476K, H1*+N54S+V56T+G109A+Q172E+L173M+A174H+G182*+D183*+N195F+V206L+K391A+G476K, H1*+N54S+V56T+G109A+Q172E+L173F+A174P+G182*+D183*+N195F+V206L+K391A+G476K, H1*+N54S+V56T+G109A+W167Y+Q172E+L173V+A174H+G182*+D183*+N195F+V206L+K391A+G476K, H1*+N54S+V56T+G109A+L173A+A174T+G182*+D183*+N195F+V206L+K391A+G476K, H1*+N54S+V56T+G109A+A174S+G182*+D183*+N195F+V206L+V291A+F328L+K391A+G476K, H1*+N54S+V56T+G109A+A174S+G182*+D183*+N195F+V206L+M246L+K391A+G476K, H1*+N54S+V56T+G109A+A174S+G182*+D183*+N195F+V206L+M246S+K391A+G476K, H1*+N54S+V56T+G109A+A174S+G182*+D183*+N195F+V206L+L250V+K391A+G476K, H1*+N54S+V56T+G109A+A174S+G182*+D183*+N195F+V206L+L250F+K391A+G476K, H1*+N54S+V56T+G109A+A174S+G182*+D183*+N195F+V206L+L250M+K391A+G476K, H1*+N54S+V56T+G109A+A174S+G182*+D183*+N195F+V206L+K391A+C474V+G476K, H1*+N54S+V56T+G109A+A174S+G182*+D183*+N195F+A204S+V206L+K391A+G476K, H1*+N54S+V56T+G109A+T165G+A174S+G182*+D183*+N195F+V206L+K391A+G476K, H1*+N54S+V56T+G109A+A174S+G182*+D183*+N195F+V206L+T334S+K391A+G476K, H1*+N54S+V56T+G109A+A174S+G182*+D183*+N195F+V206L+A263G+M286L+K391A+G476K, H1*+N54S+V56T+G109A+A174S+G182*+D183*+N195F+V206L+Y267H+K391A+G476K, H1*+N54S+V56T+G109A+A174S+G182*+D183*+N195F+V206L+Y267L+K391A+G476K, H1*+N54S+V56T+G109A+A174S+G182*+D183*+N195F+V206L+Y267I+K391A+G476K, H1*+T51A+N54S+V56T+G109A+Q172R+A174S+G182*+D183*+N195F+V206L+K391A+G476K, H1*+N54S+V56T+G109A+A174S+G182*+D183*+N195F+V206L+K391L+G476K, H1*+N54S+V56T+G109A+F113Q+R116H+Q172G+A174S+G182*+D183*+N195F+V206L+K391A+G476K, H1*+N54S+V56T+G109A+F113Q+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+

A174S+G182*+D183*+N195F+A204G+V206L+K391A+G476K, H1*+N54S+V56T+K72R+G109A+A174S+G182*+D183*+G184T+N195F+A204G+V206L+K391A+P473R+G476K, H1*+N54S+V56T+G109A+W167F+Q172N+A174S+G182*+D183*+N195F+V206L+K391A+P473R+G476K, H1*+N54S+V56T+G109A+W167F+Q172G+A174S+G182*+D183*+N195F+V206L+K391A+P473G+G476K, H1*+N54S+V56T+G109A+W167F+Q172G+A174S+G182*+D183*+N195F+V206L+K391A+P473R+G476K, H1*+N54S+V56T+K72R+G109A+W167F+Q172R+A174S+G182*+D183*+N195F+V206L+K391A+G476K, H1*+N54S+V56T+K72R+G109A+R116H+W167F+Q172R+A174S+G182*+D183*+N195F+V206L+K391A+G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+A174S+G182*+D183*+N195F+V206L+A265G+K391A+T444Q+G476K+G477A, H1*+A37V+N54S+V56T+G109A+W167F+Q172G+A174S+G182*+D183*+N195F+V206L+K391A+G346T+G477A+G476K, H1*+N54S+V56T+G109A+R116Q+Q172D+A174S+G182*+D183*+N195F+V206L+G346T+K391A+T444Q+G477A+G476K, H1*+N54S+V56T+G109A+R116Q+W167F+Q172N+A174S+G182*+D183*+N195F+V206L+G346T+K391A+T444Q+G477A+G476K, H1*+N54S+V56T+G109S+W167F+Q172R+A174S+G182*+D183*+N195F+V206L+K391A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+G109A+Q172N+A174S+G182*+D183*+N195F+V206L+K391A+C474V+G476K, H1*+N54S+V56T+G109A+A174S+G182*+D183*+N195F+V206L+S280Q+H321Y+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+R116H+W167F+Q172N+A174S+G182*+D183*+N195F+V206L+K391A+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+R116H+W167F+Q172R+A174S+G182*+D183*+N195F+V206L+F289I+K391A+G476K, H1*+N54S+V56T+G109A+F113Q+Q172N+A174S+G182*+D183*+N195F+V206L+K391A+T444Q+G476K, H1*+N54S+V56T+G109A+F113Q+R116H+Q172N+A174S+G182*+D183*+N195F+V206L+K391A+G476K, H1*+N54S+V56T+G109A+F113Q+R116Q+Q172M+A174S+G182*+D183*+N195F+V206L+K391A+T444Q+G476K, H1*+N54S+V56T+G109A+F113Q+R116H+Q172M+A174S+G182*+D183*+N195F+V206L+K391A+G476K, H1*+N54S+V56T+G109A+R116H+Q172M+A174S+G182*+D183*+N195F+V206L+K391A+G476K, H1*+N54S+V56T+G109A+F113Q+R116H+T165G+Q172M+A174S+G182*+D183*+N195F+V206L+K391A+Q395P+G476K, H1*+N54S+V56T+G109A+F113Q+A174S+G182*+D183*+N195F+V206L+K391A+T444Q+P473R+G476K, H1*+N54S+V56T+G109A+R116Q+A174S+G182*+D183*+N195F+V206L+A265G+K391A+T444Q+P473R+G476K, H1*+N54S+V56T+G109A+R116Q+A174S+G182*+D183*+N195F+V206L+K391A+T444Q+P473R+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+W167F+Q172R+A174S+G182*+D183*+N195F+V206L+K391A+G476K, H1*+N54S+V56T+G109A+R116Q+W167F+Q172R+A174S+G182*+D183*+N195F+V206L+A265G+K391A+P473R+G476K, H1*+N54S+V56T+G109A+F113Q+A174S+G182*+D183*+N195F+V206L+K391A+G476K, H1*+N54S+V56T+G109A+Q172N+A174S+G182*+D183*+N195F+V206L+K391A+G476K, H1*+T51V+N54S+V56T+G109A+Q172D+A174S+G182*+D183*+N195F+V206L+K391A+G476K, H1*+N54S+V56T+G109A+A174S+G182*+D183*+N195F+V206L+S280Q+H321Y+K391A+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172G+L173V+A174S+G182*+D183*+N195F+V206L+K391A+T444Q+P473R+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+N54S+V56T+G109A+F113Q+R116H+W167F+Q172N+L173V+A174S+G182*+D183*+N195F+V206L+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+F113Q+

T134E+W167F+Q172R+A174S+G182*+D183*+N195F+V206L+G255A+K391A+Q395P+A445Q+P473R+G476K, H1*+N54S+V56T+K72R+G109A+F113Q+R116H+T134E+W167F+Q172R+A174S+G182*+D183*+N195F+V206L+G255A+K391A+Q395P+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+K72R+G109A+F113Q+R116Q+W167F+Q172N+L173V+A174S+G182*+D183*+G184T+N195F+V206L+K391A+T444Q+P473R+G476K, H1*+A37H+N54S+V56T+G109A+F113Q+W167F+Q172N+A174S+G182*+D183*+N195F+V206L+K391A+G476K, H1*+A37H+N54S+V56T+G109A+F113Q+A174S+G182*+D183*+N195F+V206L+K391A+G476K, H1*+N54S+V56T+G109A+F113Q+W167F+Q172N+A174S+G182*+D183*+N195F+V206L+K391A+T459N+G476K, H1*+N54S+V56T+G109A+F113Q+Q172R+L173V+A174S+G182*+D183*+N195F+V206L+K391A+T444Q+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37V+N54S+V56T+A60V+G109A+R116Q+T165G+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+W167F+Q172G+L173V+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+W167F+Q172R+A174S+G182*+D183*+N195F+A204G+V206L+K391A+P473R+G476K, H1*+N54S+V56T+G109A+R116A+A174S+G182*+D183*+N195F+A204G+V206L+K391A+P473R+G476K, H1*+N54S+V56T+G109A+R116A+T165G+A174S+G182*+D183*+N195F+V206L+K391A+T444Q+P473R+G476K, H1*+N54S+V56T+G109A+G182*+D183*+N195F+K391A+G476K, H1*+N54S+V56T+G109A+G182*+D183*+N195F+V206L, N54S+V56T+G109A+G182*+D183*+N195F, N54S+V56T+G109A+A174S+G182*+D183*+N195F+V206L+K391A+G476K, H1*+G109A+A174S+G182*+D183*+N195F+V206L+K391A+G476K, H1*+N54S+V56T+G109A+G182*+D183*+N195F+V206L+K391A+G476K, H1*+N54S+V56T+G109A+A174S+G182*+D183*+N195F+V206L+K391A, H1*+N54S+V56T+G109A+A174S+G182*+D183*+N195F+G476K, H1*+N54S+V56T+A174S+G182*+D183*+N195F+V206L+G273R+K391A+G476K, H1*+N54S+V56T+G109A+A174S+G182*+D183*+N195F+V206L, H1*+W48G+G109A+G182*+D183*+N195F+V206L+K391A+G476K, N54S+V56T+G109A+A174S+G182*+D183*+N195F+K391A+G476K, H1*+N54S+V56T+G109A+A174S+G182*+D183*+N195F+K391A, H1*+N54S+V56T+G109A+F113Q+Q172M+A174S+G182*+D183*+N195F+V206L+K391A+G476K, H1*+N54S+V56T+G109A+R116Q+A174S+G182*+D183*+N195F+A204G+V206L+K391A+G476K, H1*+N54S+V56T+K72R+G109A+F113Q+T134E+A174S+G182*+D183*+N195F+V206L+G255A+K391A+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+V56A+G109A+A174S+G182*+D183*+N195F+V206L+G476K, H1*+N54S+V56T+G109A+G182*+D183*+N195F+V206L+K391A, H1*+N54S+V56T+G109A+G182*+D183*+N195F+V206L+G476K, G109A+A174S+G182*+D183*+N195F+V206L+K391A+G476K, N54S+V56T+G109A+G182*+D183*+N195F+V206L+K391T+G476K, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+N54S+V56T+G109A+F113Q+W167F+Q172N+A174S+G182*+D183*+N195F+A204G+V206L+K391A+P473R+G476K, H1*+N54S+V56T+G109A+F113Q+R116H+W167F+Q172R+A174S+G182*+D183*+N195F+A204G+V206L+K391A+P473R+G476K, H1*+N54S+V56T+G109A+R116A+A174S+G182*+D183*+N195F+V206L+K391A+T444Q+P473R+G476K, H1*+N54S+V56T+G109A+R116H+Q172R+A174S+G182*+D183*+N195F+A204G+V206L+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+A174S+G182*+D183*+N195F+K391A+G476K, H1*+G109A+G182*+D183*+N195F+V206L+K391A+G476K, G109A+G182*+D183*+N195F+V206L+G476K, H1*+G109A+G182*+D183*+N195F+K391A, H1*+N54S+V56T+G109A+G133S+A174S+G182*+D183*+N195F+K391A+G476H, H1*+N54S+V56T+G109A+R116A+Q172N+L173V+A174S+G182*+D183*+N195F+V206L+K391A+G476K, H1*+A37V+N54S+V56T+G109A+R116H+T165G+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+P124A+A174S+G182*+D183*+N195F+V206L+K391A+C474V+G476K, H1*+N54S+V56T+G109A+A174S+G182*+D183*+N195F+V206L+P364A+K391A+C474V+G476K, H1*+N54S+V56T+G109A+Q118R+T134E+A174S+G182*+D183*+N195F+V206L+

K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+N54S+V56T+G109A+A174S+G182*+D183*+N195F+V206L+Y382L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+W167H+A174S+G182*+D183*+N195F+V206L+K391A+G476K, H1*+N54S+V56T+G109A+T165V+A174S+G182*+D183*+N195F+V206L+K391A+G476K, H1*+N54S+V56T+G109A+A174S+G182*+D183*+N195F+V206L+K391A+G476K, H1*+N54S+V56T+G109A+A174N+G182*+D183*+N195F+V206L+K391A+G476K, H1*+N54S+V56T+G109A+A174Q+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, N54S+G182*+D183*+N195F, G109A+G182*+D183*+N195F, G182*+D183*+N195F+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+Q169E+Q172K+A174*+G182*+D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+G476K, H1*+W48F+N54S+V56T+G109A+A174S+G182*+D183*+

N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, H1*+N54S+V56T+G109A+A174S+V206L+G182*+D183*+K391A+G476K, H1*+N54S+V56T+Q169E+Q172K+A174*+G182*+D183*+N195F+V206L+K391A+G476K, H1*+N54S+V56T+G109A+A174S+G182*+D183*+N195F+V206F+K391A+G476K, H1*+N54S+V56T+G109A+G182*+D183*+N195F+V206L+K391A+G476K, H1*+N54S+V56T+G109A+Q172K+A174S+G182*+D183*+N195F+V206L+K391A+G476K, H1*+N54S+V56T+G109A+Q172K+A174*+G182*+D183*+N195F+V206L+K391A+G476K, H1*+N54S+V56T+G109A+A174N+G182*+D183*+N195F+V206L+K391A+G476K, H1*+N54S+V56T+G109A+A174S+A186N+G182*+D183*+N195F+V206L+K391A+G476K, H1*+N54S+V56T+G109A+A174S+G182*+D183*+N195F+V206L+F289L+K391A+G476K, H1*+N54S+V56T+G109A+A174S+G182*+D183*+N195F+V206L+Y295F+K391A+G476K, H1*+N54S+V56T+G109A+A174S+G182*+D183*+N195F+V206L+V291A+K391A+G476K, H1*+N54S+V56T+G109A+A174S+G182*+D183*+N195F+V206L+S244Q+K391A+G476K, G182*+D183*+F328L, G182*+D183*+N195F+A288V, G182*+D183*+A186N+N195F, G182*+D183*+E190P+N195F, W140Y+G182*+D183*+N195F, H1*+N54S+V56T+G109A+A174S+G182*+D183*+N195F+V206L+A225V+K391A+G476K, G182*+D183*+A186D+N195F, H1*+N54S+V56T+G109A+A174S+G182*+D183*+N195F+V206L+K391A+P473R+G476K, H1*+W48Y+N54S+V56T+G109A+A174S+G182*+D183*+N195F+V206L+K391A+G476K, H1*+N54S+V56T+G109A+Q169E+Q172K+A174*+G182*+D183*+N195F+V206L+K391A+G476K, G182*+D183*+N195F+V238A, G182*+D183*+Y295N, Q172G+G182*+D183*, F113Q+G182*+D183*+N195F, H1*+N54S+V56T+Q98A+G109A+A174S+G182*+D183*+N195F+V206L+K391A+G476K, G182*+D183*+N195F+Y295F, G182*+D183*+A186E, H1*+N54S+V56T+G109A+A174S+G182*+D183*+N195F+V206Y+K391A+G476K, G182*+D183*+N195F+W284H, G182*+D183*+A186Q+N195F, K72R+G182*+D183*, D183*+G182*+N195F+V326L, D183*+G182*+A186E+N195F, Q169E+G182*+D183*+N195F, D183*+G182*+N195F+K242Q, G7A+G182*+D183*+N195F, D183*+G182*+N195F+N260G, D183*+G182*+R321A+S323N, D183*+G182*+W284H, D183*+G182*+A186H+N195F, D183*+G182*+K391A, wherein numbering is according to SEQ ID NO: 13, V56T+G182*+D183*+N195F, H1*+N54S+V56T+G109A+A174S+G182*+D183*+N195F+V206L+I405L+A421H+A422P+A428T, H1*+N54S+V56T+G109A+A174S+D183*+N195F+V206L+K391A+I405L+A421H+A422P+A428T, H1*+N54S+V56T+G109A+A174S+G182*+D183*+N195F+V206L+K391A+I405L+A421H+A422P+A428T+D476K+G477S, H1*+N54S+V56T+G109A+A174S+G182*+D183*+N195F+V206L+K391A+I405L+A421H+A422P+A428T+D476K, H1*+N54S+V56T+G109A+A174S+G182*+D183*+N195F+V206L+K391A+I405L+A421H+A422P+A428T+D476G+G477T, H1*+N54S+V56T+G109A+A174S+G182*+D183*+N195F+V206L+K391A+I405L+A421H+A422P+A428T+G477Q, H1*+N54S+V56T+G109A+A174S+G182*+D183*+N195F+V206L+K391A+I405L+A421H+A422P+A428T+G477A, H1*+N54S+V56T+G109A+A174S+G182*+D183*+N195F+V206L+K391A+I405L+A421H+A422P+A428T+D476K+G477Q, H1*+N54S+V56T+G109A+A174S+G182*+D183*+N195F+V206L+K391A+I405L+A421H+A422P+A428T+D476N, H1*+N54S+V56T+G109A+A174S+G182*+D183*+N195F+V206L+K391A+I405L+A421H+A422P+A428T+D476Y, H1*+N54S+V56T+G109A+A174S+G182*+D183*+N195F+V206I+I405L+A421H+A422P+A428T, H1*+N54S+V56T+G109A+Q172D+A174S+G182*+D183*+N195F+A204G+V206L+I405L+A421H+A422P+A428T, H1*+N54S+V56T+K72R+G109A+T134E+A174S+G182*+D183*+N195F+A204G+V206L+G255A+I405L+A421H+A422P+A428T, H1*+N54S+V56T+G109A+F113Q+R116H+T165G+Q172G+A174S+G182*+D183*+N195F+V206L+I405L+A421H+A422P+A428T, H1*+N54S+V56T+G109A+F113Q+Q172N+A174S+G182*+D183*+N195F+V206L+I405L+A421H+A422P+A428T, H1*+N54S+V56T+K72R+G109A+T134E+A174S+G182*+D183*+N195F+G196R+V206L+G255A+I405L+A421H+A422P+A428T+N475S, H1*+N54S+V56T+G109A+T134E+A174S+G182*+D183*+N195F+V206L+I405L+A421H+A422P+A428T, H1*+T40D+N54S+V56T+G109A+A174S+G182*+D183*+N195F+V206L+I405L+A421H+A422P+A428T, H1*+N54S+V56T+G109A+F113Q+N125D+A174S+G182*+D183*+N195F+V206L+I405L+A421H+A422P+A428T, H1*+N54S+V56T+A60V+G109A+R116Q+A174S+G182*+D183*+N195F+V206L+I405L+A421H+A422P+A428T, H1*+N54S+V56T+G109A+R116V+A174S+G182*+D183*+N195F+V206L+I405L+A421H+A422P+A428T, H1*+N54S+V56T+G109A+R116Q+G133Q+T165G+Q172G+A174S+G182*+D183*+N195F+V206L+I405L+A421H+A422P+A428T, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116Q+Q172G+A174S+G182*+D183*+N195F+V206L+I405L+A421H+A422P+A428T+G448D, H1*+N54S+V56T+G109A+F113Q+R116H+Q172N+A174S+G182*+D183*+N195F+V206L+I405L+A421H+A422P+A428T, H1*+N54S+V56T+K72R+G109A+T134E+W167F+Q172N+A174S+G182*+D183*+N195F+V206L+G255A+A265G+I405L+A421H+A422P+A428T, H1*+N54S+V56T+K72R+G109A+R116Q+W167F+Q172R+L173V+A174S+G182*+D183*+N195F+V206L+A265G+I405L+A421H+A422P+A428T, H1*+N54S+V56T+K72R+G109A+R116Q+W167F+Q172R+A174S+G182*+D183*+N195F+V206L+I405L+A421H+A422P+A428T, H1*+N54S+V56T+K72R+G109A+F113Q+T134E+W167F+Q172G+A174S+G182*+D183*+N195F+V206L+G255A+I405L+A421H+A422P+A428T, H1*+N54S+V56T+K72R+G109A+F113Q+R116H+W167F+Q172G+L173V+A174S+G182*+D183*+G184T+N195F+V206L+I405L+A421H+A422P+A428T, H1*+N54S+V56T+G109A+F113Q+W167F+Q172G+A174S+G182*+D183*+N195F+V206L+I405L+A421H+A422P+A428T, H1*+N54S+V56T+K72R+G109A+A174S+G182*+D183*+N195F+V206L+G255A+I405L+A421H+A422P+A428T, H1*+N54S+V56T+K72R+G109A+F113Q+R116Q+W167F+Q172G+A174S+G182*+D183*+G184T+N195F+V206L+I405L+A421H+A422P+A428T, H1*+N54S+V56T+G109A+F113Q+R116Q+W167F+Q172G+A174S+G182*+D183*+N195F+A204G+V206L+I405L+A421H+A422P+A428T, H1*+N54S+V56T+G109A+R116Q+A174S+G182*+D183*+N195F+V206L+I405L+A421H+A422P+A428T, H1*+A37H+N54S+V56T+A60V+G109A+R116Q+T165G+A174S+

G182*+D183*+N195F+V206L+I405L+A421H+A422P+A428T, H1*+N54S+V56T+G109A+A174S+M105F+G182*+D183*+N195F+V206L+L228I+R320A+S323N+I405L+A421H+A422P+A428T, H1*+N54S+V56T+K72R+G109A+F113Q+T134E+A174S+G182*+D183*+N195F+V206L+G255A+I405L+A421H+A422P+A428T, H1*+N54S+V56T+K72R+G109A+R116Q+V120L+A174S+G182*+D183*+G184T+N195F+V206L+I405L+A421H+A422P+A428T, H1*+N54S+V56T+G109A+F113Q+R116H+W167F+Q172G+L173V+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO: 14.

In one embodiment, the IF is determined by use of Model J detergent at a temperature of 15° C. In a particular embodiment, the variants have an IF of >1.5 as compared to the parent polypeptide, wherein the IF is determined by use of Model J detergent at a temperature of 15° C. and a concentration of 0.05 mg/L. It can be seen from the Tables in the Examples herein disclosed which such variants may be.

Some variants according to the invention have an even further improved wash performance indicated by an IF of at least 2.0 when compared the a parent polypeptide having an amino acid sequence set forth in SEQ ID NO: 15, and wherein the IF is determined by use of Model A detergent at a temperature of 15° C.

Thus, in one embodiment, the variant has an IF of at least >2.0 when compared to said parent polypeptide, and wherein said variant is selected from H1*+N54S+V56T+G109A+A174S+G182*+D183*+N195F+V206L+K391A+G476K, H1*+N54S+V56T+R87S+G109A+A174S+G182*+D183*+N195F+V206L+K391A+G476K, H1*+T40G+N54S+V56T+G109A+A174S+G182*+D183*+N195F+V206L+K391A+G476K, H1*+T51K+N54S+V56T+G109A+A174S+G182*+D183*+N195F+V206L+K391A+G476K, H1*+N54S+V56T+K72R+G109A+A174S+G182*+D183*+N195F+V206L+K391A+G476K, H1*+N54S+V56T+K72H+G109A+A174S+G182*+D183*+N195F+V206L+K391A+G476K, H1*+A37H+N54S+V56T+G109A+A174S+G182*+D183*+N195F+V206L+K391A+G476K, H1*+A37M+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+A37S+N54S+V56T+G109A+A174S+G182*+D183*+N195F+V206L+K391A+G476K, H1*+A37Y+N54S+V56T+G109A+A174S+G182*+D183*+N195F+V206L+K391A+G476K, H1*+A37R+N54S+V56T+G109A+A174S+G182*+D183*+N195F+V206L+K391A+G476K, H1*+N54S+V56T+G109A+F113W+A174S+G182*+D183*+N195F+V206L+K391A+G476K, H1*+N54S+V56T+G109A+F113S+A174S+G182*+D183*+N195F+V206L+K391A+G476K, H1*+N54S+V56T+G109A+F113N+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+R116V+A174S+G182*+D183*+N195F+V206L+K391A+G476K, H1*+N54S+V56T+G109A+R116K+A174S+G182*+D183*+N195F+V206L+K391A+G476K, H1*+N54S+V56T+G109A+Q125P+A174S+G182*+D183*+N195F+V206L+K391A+G476K, H1*+N54S+V56T+G109A+A174S+G182*+D183*+N195F+V206L+S381G+K391A+G476K, H1*+N54S+V56T+G109A+A174S+G182*+D183*+N195F+V206L+M246T+K391A+G476K, H1*+A37L+N54S+V56T+G109A+A174S+G182*+D183*+N195F+V206L+K391A+G476K, H1*+N54S+V56T+G109A+R116A+A174S+G182*+D183*+N195F+V206L+K391A+G476K, H1*+N54S+V56T+G109A+R116H+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+Q172R+A174S+G182*+D183*+N195F+V206L+K391A+G476K, H1*+N54S+V56T+G109A+A174S+G182*+D183*+N195F+V206L+D377S+K391A+G476K, H1*+N54S+V56T+G109A+A174S+G182*+D183*+N195F+V206L+D377A+K391A+G476K, H1*+N54S+V56T+G109A+A174S+G182*+D183*+N195F+V206L+S381A+K391A+G476K, H1*+N54S+V56T+G109A+A174S+G182*+D183*+N195F+V206L+G346P+K391A+G476K, H1*+N54S+V56T+G109A+A174S+G182*+D183*+N195F+V206L+I214H+K391A+G476K, H1*+N54S+V56T+G109A+A174S+G182*+D183*+N195F+V206L+I214S+K391A+G476K, H1*+N54S+V56T+G109A+A174S+G182*+D183*+N195F+V206L+K391A+A420Q+G476K, H1*+N54S+V56T+G109A+A174S+G182*+D183*+N195F+V206L+K391A+A420S+G476K, H1*+N54S+V56T+G109A+A174S+G182*+D183*+N195F+V206L+K391A+A420K+G476K, H1*+N54S+V56T+G109A+A174S+G182*+D183*+N195F+V206L+K391A+A420L+G476K, H1*+N54S+V56T+G109A+A174S+G182*+D183*+N195F+V206L+K391A+K391Y+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+P473G+G476K, H1*+N54S+V56T+G109A+A174S+G182*+D183*+N195F+V206L+K391A+T444D+G476K, H1*+N54S+V56T+G109A+A174S+G182*+D183*+N195F+V206L+K391A+T444Y+G476K, H1*+N54S+V56T+G109A+A174S+G182*+D183*+N195F+V206L+S280W+K391A+G476K, H1*+N54S+V56T+G109A+A174S+G182*+D183*+N195F+V206L+S280L+K391A+G476K, H1*+N54S+V56T+K72S+G109A+A174S+G182*+D183*+N195F+V206L+K391A+G476K, H1*+T40K+N54S+V56T+G109A+A174S+G182*+D183*+N195F+V206L+G346T+K391A+G476K, H1*+G50A+N54S+V56T+G109A++Q172N+A174S+G182*+D183*+N195F+V206L+K391A+G476K, H1*+N54S+V56T+G109A+A174S+G182*+D183*+N195F+V206L+K391A+G476K+K484S, H1*K+G50A+N54S+V56T+G109A+W167F+A174S+G182*+D183*+N195F+V206L+K391A+G476K, H1*+N54S+V56T+G109A+L173V+A174S+G182*+D183*+N195F+A204T+V206L+K391A+G476K, H1*+N54S+V56T+G109A+W140Y+A174S+G182*+D183*+N195F+V206L+K391A+G476K, H1*+N54S+V56T+G109A+A174S+G182*+D183*+N195F+V206L+G346T+K391A+G476K+G477A, H1*+N54S+V56T+G109AG255A++A174S+G182*+D183*+N195F+V206L+K391A+G476K, H1*+G50A+N54S+V56T+G109A+F113L+R116L+A174S+G182*+D183*+N195F+V206L+K391A+G476K, H1*+N54S+V56T+G109A+W167F+A174S+G182*+D183*+N195F+V206L+K391A+G476K, H1*+N54S+V56T+K72R+G109A+W167F+A174S+G182*+D183*+N195F+V206L+K391A+G476K, H1*+N54S+V56T+G109A+A174S+G182*+D183*+N195F+V206L+R320V+K391A+G476Y, H1*+N54S+V56T+G109A+R116M+A174S+G182*+D183*+N195F+V206L+K391A+G476K, H1*+N54S+V56T+G109A+Q172Y+A174S+G182*+D183*+N195F+V206L+K391A+G476K, H1*+N54S+V56T+G109A+A174S+G182*+D183*+N195F+V206L+I214L+K391A+G476K, H1*+N54S+V56T+G109A+A174S+G182*+D183*+N195F+V206L+L217V+K391A+G476K, H1*+N54S+V56T+G109A+A174S+G182*+D183*+N195F+V206L+L217H+K391A+G476K, H1*+N54S+V56T+G109A+A174S+G182*+D183*+N195F+V206L+P211D+K391A+G476K, H1*+N54S+V56T+G109A+A174S+G182*+D183*+N195F+V206L+K391A+K391Q+G476K, H1*+N54S+V56T+G109A+A174S+G182*+D183*+N195F+V206L+K391A+T444H+G476K, H1*+N54S+V56T+G109A+A174S+G182*+D183*+N195F+V206L+K391A+T444V+G476K, H1*+N54S+V56T+G109A+A174S+G182*+D183*+N195F+V206L+K391A+T444R+G476K, H1*+G50A+N54S+V56T+G109A+L173V+A174S+G182*+D183*+N195F+A204V+V206L+K391A+G476K, H1*+G7K+N54S+V56T+G109A+A174S+G182*+D183*+N195F+V206L+R320A+K391A+G476K, H1*+N54S+V56T+G109A+Q172D+A174S+G182*+D183*+N195F+V206L+G346T+K391A+G476K+G477A, H1*+N54S+V56T+G109A+Q118S+A174S+G182*+D183*+N195F+V206L+K391A+G476K, H1*+N54S+V56T+G109A+A174S+G182*+D183*+N195F+V206L+R320A+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+Y382M+K391A+G476K, H1*+N54S+V56T+K72R+G109A+T134E+A174S+G182*+D183*+N195F+V206L+G255A+K391A+G476K, H1*+N54S+V56T+K72R+M105F+G109A+A174S+G182*+D183*+N195F+V206L+G255A+K391A+G476K, H1*+N54S+V56T+M105F+G109A+T134E+A174S+G182*+D183*+N195F+V206L+K391A+G476K, H1*+N54S+V56T+G109A+A174S+G182*+D183*+N195F+V206L+R320A+S323N+D377H+K391A+G476K, H1*+T51E+N54S+V56T+G109A+A174H+G182*+D183*+N195F+V206L+K391A+G476K, H1*+N54S+V56T+G109A+L173A+A174S+G182*+D183*+N195F+V206L+K391A+G476K, H1*+N54S+V56T+G109A+A174S+G182*+D183*+N195F+V206L+Q299V+K391A+G476K, H1*+N54S+V56T+G109A+L173G+A174S+G182*+D183*+N195F+V206L+K391A+G476K, H1*+N54S+V56T+G109A+A174S+G182*+D183*+N195F+V206L+T355L+K391A+G476K, H1*+G50A+N54S+V56T+G109A+A174S+G182*+D183*+N195F+A204T+V206L+K391A+G476K, H1*+N54S+V56T+K72R+G109A+A174S+G182*+D183*+N195F+V206L+R320A+S323N+K391A+G476K, H1*+N54S+V56T+G109A+A174S+G182*+D183*+N195F+V206L+M246L+K391A+G476K, H1*+N54S+V56T+K72Q+G109A+W167H+A174S+G182*+D183*+N195F+V206L+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+Q118R+T134E+A174S+G182*+D183*+N195F+V206L+G255A+K391A+G476K, H1*+N54S+V56T+G109A+Q118R+A174S+G182*+D183*+N195F+V206L+D377H+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+K72R+G109A+A174S+G182*+D183*+G184T+N195F+V206L+G255A+K391A+G476K, H1*+N54S+V56T+G109A+A174S+G182*+D183*+G184T+N195F+V206L+D377H+K391A+G476K, H1*+N54S+V56T+G109A+A174S+G182*+D183*+N195F+V206L+G255A+D377H+K391A+G476K, H1*+N54S+V56T+G109A+T134E+A174S+G182*+D183*+G184T+N195F+V206L+K391A+G476K, H1*+N54S+V56T+G109A+A174S+G182*+D183*+N195F+V206L+V238T+D377H+K391A+G476K, H1*+N54S+V56T+G109A+A174S+G182*+D183*+N195F+V206L+V291A+D377H+K391A+G476K, H1*+N54S+V56T+K72R+G109A+T134E+A174S+G182*+D183*+G184T+N195F+V206L+G255A+K391A+G476K, H1*+N54S+V56T+G109A+L173H+A174S+G182*+D183*+N195F+V206L+K391A+G476K, H1*+N54S+V56T+K72N+G109A+A174S+G182*+D183*+N195F+V206L+K391A+G476K, H1*+N54S+V56T+K72N+G109A+W167L+A174S+G182*+D183*+N195F+V206L+K391A+G476K, H1*+N54S+V56T+G109A+Q118R+T134E+A174S+G182*+D183*+N195F+V206L+G255A+D377H+K391A+G476K, H1*+N54S+V56T+K72R+G109A+A174S+G182*+D183*+N195F+G184T+V206L+K391A+G476K, H1*+N54S+V56T+K72R+G109A+Q118R+A174S+G182*+D183*+N195F+V206L+G255A+D377H+K391A+G476K, H1*+N54S+V56T+G109A+G182*+D183*+N195F+V206L+D377H+K391A+G476K, H1*+N54S+V56T+G109A+A174S+G182*+D183*+N195F+D377H+K391A+G476K, H1*+N54S+V56T+G109A+A174S+G182*+D183*+N195F+V206L+D377H+G476K, H1*+N54S+V56T+G109A+A174S+G182*+D183*+N195F+V206L+D377H+K391A, H1*+N54S+V56T+G109A+A174S+G182*+D183*+N195F+V206L+D377S+K391A+G476K, H1*+N54S+V56T+G109A+R116E+A174S+G182*+D183*+N195F+V206L+K391A+G476K, H1*+N54S+V56T+G109A+T134E+A174S+G182*+D183*+N195F+V206L+D377H+K391A+G476K, H1*+N54S+V56T+G109A+R116S+A174S+G182*+D183*+N195F+V206L+K391A+G476K, H1*+N54S+V56T+G109A+R116G+A174S+G182*+D183*+N195F+V206L+K391A+G476K, H1*+N54S+V56T+G109A+R116G+A174S+G182*+D183*+N195F+V206L+K391A+G476K, H1*+T51A+N54S+V56T+G109A+Q172S+A174S+G182*+D183*+N195F+V206L+K391A+G476K, H1*+T51E+N54S+V56T+G109A+Q172T+A174S+G182*+D183*+N195F+V206L+K391A+G476K, H1*+T51S+N54S+V56T+G109A+Q172N+A174S+G182*+D183*+N195F+V206L+K391A+G476K, H1*+T51E+N54S+V56T+G109A+Q172L+A174S+G182*+D183*+N195F+V206L+K391A+G476K, H1*+T51E+N54S+V56T+G109A+Q172R+A174S+G182*+D183*+N195F+V206L+K391A+G476K, H1*+N54S+V56T+G109A+Q172K+A174S+G182*+D183*+N195F+V206L+K391A+G476K, H1*+N54S+V56T+K72R+G109A+Q172S+A174S+G182*+D183*+N195F+V206L+K391A+G476K, H1*+N54S+V56T+K72H+G109A+Q172T+A174S+G182*+D183*+N195F+V206L+K391A+G476K, H1*+N54S+V56T+K72Q+G109A+Q172R+A174S+G182*+D183*+N195F+V206L+K391A+G476K, H1*+N54S+V56T+K72R+G109A+Q172T+A174S+G182*+D183*+N195F+V206L+K391A+G476K, H1*+N54S+V56T+K72M+G109A+Q172S+A174S+G182*+D183*+N195F+V206L+K391A+G476K, H1*+N54S+V56T+K72Q+G109A+Q172M+A174S+G182*+D183*+N195F+V206L+K391A+G476K, H1*+N54S+V56T+K72S+G109A+A174H+G182*+D183*+N195F+V206L+K391A+G476K, H1*+N54S+V56T+K72Q+G109A+A174D+G182*+D183*+N195F+V206L+

K391A+G476K, H1*+N54S+V56T+K72R+G109A+A174D+G182*+D183*+N195F+V206L+K391A+G476K, H1*+N54S+V56T+K72Q+G109A+A174K+G182*+D183*+N195F+V206L+K391A+G476K, H1*+N54S+V56T+G109A+A174G+G182*+D183*+N195F+V206L+K391A+G476K, H1*+N54S+V56T+K72R+G109A+A174Q+G182*+D183*+N195F+V206L+K391A+G476K, H1*+N54S+V56T+K72Q+G109A+A174G+G182*+D183*+N195F+V206L+K391A+G476K, H1*+N54S+V56T+K72S+G109A+A174N+G182*+D183*+N195F+V206L+K391A+G476K, H1*+N54S+V56T+K72R+G109A+A174H+G182*+D183*+N195F+V206L+K391A+G476K, H1*+G50A+N54S+V56T+G109A+A174E+G182*+D183*+N195F+A204T+V206L+S323N+K391A+G476K, H1*+N54S+V56T+G109A+A174S+G182*+D183*+N195F+A204G+V206L+K391A+G476K, H1*+N54S+V56T+G109A+A174S+G182*+D183*+N195F+V206L+Y382I+K391A+G476K, H1*+N54S+V56T+G109A+A174S+G182*+D183*+N195F+V206L+I214W+K391A+G476K, H1*+N54S+V56T+G109A+A174S+G182*+D183*+N195F+A204S+V206L+D377H+K391A+G476K, H1*+N54S+V56T+G109A+A174S+G182*+D183*+N195F+V206L+T334S+D377H+K391A+G476K, H1*+N54S+V56T+G109A+A174S+G182*+D183*+N195F+V206L+A263G+D377H+K391A+G476K, H1*+N54S+V56T+G109A+A174S+G182*+D183*+N195F+V206L+M286F+D377H+K391A+G476K, H1*+N54S+V56T+G109A+A174S+G182*+D183*+N195F+V206L+L235V+D377H+K391A+G476K, H1*+N54S+V56T+M105L+G109A+A174S+G182*+D183*+N195F+V206L+D377H+K391A+G476K, H1*+N54S+V56T+M105I+G109A+A174S+G182*+D183*+N195F+V206L+D377H+K391A+G476K, H1*+N54S+V56T+M105V+G109A+A174S+G182*+D183*+N195F+V206L+D377H+K391A+G476K, H1*+N54S+V56T+G109A+A174S+G182*+D183*+N195F+V206L+M246I+D377H+K391A+G476K, H1*+N54S+V56T+G109A+A174S+G182*+D183*+N195F+V206L+L250I+D377H+K391A+G476K, H1*+N54S+V56T+G109A+A174S+G182*+D183*+N195F+V206L+L250V+D377H+K391A+G476K, H1*+N54S+V56T+G109A+A174S+G182*+D183*+N195F+V206L+K391Y+G476K, H1*+N54S+V56T+G109A+A174S+G182*+D183*+N195F+V206L+K391V+G476K, H1*+N54S+V56T+G109A+A174S+G182*+D183*+N195F+V206L+K391M+G476K, H1*+N54S+V56T+G109A+T165G+A174S+G182*+D183*+N195F+V206L+D377H+K391A+G476K, H1*+N54S+V56T+G109S+A174S+G182*+D183*+N195F+V206L+K391A+G476K, H1*+N54S+V56T+G109A+A174V+G182*+D183*+N195F+V206L+K391A+G476K, H1*+N54S+V56T+G109A+A174S+G182*+D183*+N195F+V206L+M246F+D377H+K391A+G476K, H1*+N54S+V56T+G109A+A174S+G182*+D183*+N195F+V206L+M246V+D377H+K391A+G476K, H1*+N54S+V56T+G109A+A174S+G182*+D183*+N195F+V206L+M246S+D377H+K391A+G476K, H1*+N54S+V56T+G109A+A174S+G182*+D183*+N195F+V206L+K391R+G476K, H1*+N54S+V56T+G109A+A174S+G182*+D183*+N195F+V206L+K391H+G476K, H1*+N54S+V56T+G109A+A174S+G182*+D183*+N195F+V206L+K391W+G476K, H1*+N54S+V56T+G109A+A174S+G182*+D183*+N195F+V206L+K391I+G476K, H1*+N54S+V56T+G109A+A174S+G182*+D183*+N195F+V206L+L250T+D377H+K391A+G476K, H1*+N54S+V56T+G109A+A174S+G182*+D183*+N195F+V206L+L250A+D377H+K391A+G476K, H1*+N54S+V56T+G109A+A174S+G182*+D183*+N195F+V206L+L250F+D377H+K391A+G476K, H1*+N54S+V56T+G109A+A174S+G182*+D183*+N195F+V206L+L250M+D377H+K391A+G476K, H1*+N54S+V56T+G109A+Q172H+L173A+A174P+G182*+D183*+N195F+V206L+K391A+G476K, H1*+N54S+V56T+G109A+A174S+G182*+D183*+G184T+N195F+V206L+G255A+D377H+K391A+G476K, H1*+N54S+V56T+G109A+A174S+G182*+D183*+N195F+V206L+S376T+K391A+G476K, H1*+N54S+V56T+G109A+A174S+G182*+D183*+N195F+V206L+S376V+K391A+G476K, H1*+N54S+V56T+G109A+Q172E+L173I+A174N+G182*+D183*+N195F+V206L+K391A+G476K, H1*+N54S+V56T+G109A+Q172D+L173A+A174T+G182*+D183*+N195F+V206L+K391A+G476K, H1*+N54S+V56T+G109A+A174S+G182*+D183*+N195F+V206L+Y267M+D377H+K391A+G476K, H1*+N54S+V56T+G109A+A174S+G182*+D183*+N195F+V206L+V238G+K391A+G476K, H1*+N54S+V56T+M105V+G109A+A174S+G182*+D183*+N195F+V206L+K391A+G476K, H1*+N54S+V56T+G109A+A174S+G182*+D183*+N195F+V206L+V264T+K391A+G476K, H1*+N54S+V56T+G109A+A174S+G182*+D183*+N195F+V206L+V264I+K391A+G476K, H1*+N54S+V56T+G109A+W167H+Q172N+L173A+A174S+G182*+D183*+N195F+V206L+K391A+G476K, H1*+N54S+V56T+G109A+Q172N+L173T+A174S+G182*+D183*+N195F+V206L+K391A+G476K, H1*+N54S+V56T+G109A+Q172E+L173M+A174H+G182*+D183*+N195F+V206L+K391A+G476K, H1*+N54S+V56T+G109A+W167Y+Q172E+L173V+A174H+G182*+D183*+N195F+V206L+K391A+G476K, H1*+N54S+V56T+G109A+L173A+A174T+G182*+D183*+N195F+V206L+K391A+G476K, H1*+N54S+V56T+G109A+A174S+G182*+D183*+N195F+V206L+V291A+F328L+K391A+G476K, H1*+N54S+V56T+G109A+A174S+G182*+D183*+N195F+V206L+M246L+K391A+G476K, H1*+N54S+V56T+G109A+A174S+G182*+D183*+N195F+V206L+L250V+K391A+G476K, H1*+N54S+V56T+G109A+A174S+G182*+D183*+N195F+V206L+L250F+K391A+G476K, H1*+N54S+V56T+G109A+A174S+G182*+D183*+N195F+V206L+L250M+K391A+G476K, H1*+N54S+V56T+G109A+T165G+A174S+G182*+D183*+N195F+V206L+K391A+G476K, H1*+T51A+N54S+V56T+G109A+Q172R+A174S+G182*+D183*+N195F+V206L+K391A+G476K, H1*+N54S+V56T+G109A+A174S+G182*+D183*+N195F+V206L+K391L+G476K, H1*+N54S+V56T+G109A+F113Q+R116H+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+A174S+G182*+D183*+N195F+A204G+V206L+K391A+G476K, H1*+N54S+V56T+K72R+G109A+A174S+G182*+D183*+G184T+N195F+A204G+V206L+K391A+P473R+G476K, H1*+N54S+V56T+G109A+W167F+Q172N+A174S+G182*+D183*+N195F+V206L+K391A+P473R+G476K, H1*+N54S+V56T+G109A+W167F+Q172G+A174S+G182*+D183*+N195F+V206L+K391A+P473G+G476K, H1*+N54S+V56T+G109A+W167F+Q172G+A174S+G182*+D183*+N195F+V206L+K391A+P473R+G476K, H1*+N54S+V56T+K72R+G109A+W167F+Q172R+A174S+G182*+D183*+N195F+V206L+K391A+G476K, H1*+N54S+V56T+K72R+G109A+R116H+W167F+Q172R+A174S+G182*+D183*+N195F+V206L+K391A+

G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+A174S+G182*+D183*+N195F+V206L+A265G+K391A+T444Q+G476K+G477A, H1*+A37V+N54S+V56T+G109A+W167F+Q172G+A174S+G182*+D183*+N195F+V206L+K391A+G346T+G477A+G476K, H1*+N54S+V56T+G109A+R116Q+Q172D+A174S+G182*+D183*+N195F+V206L+G346T+K391A+T444Q+G477A+G476K, H1*+N54S+V56T+G109A+R116Q+W167F+Q172N+A174S+G182*+D183*+N195F+V206L+G346T+K391A+T444Q+G477A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+G109A+Q172N+A174S+G182*+D183*+N195F+V206L+K391A+C474V+G476K, H1*+N54S+V56T+G109A+A174S+G182*+D183*+N195F+V206L+S280Q+H321Y+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+R116H+W167F+Q172N+A174S+G182*+D183*+N195F+V206L+K391A+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+R116H+W167F+Q172R+A174S+G182*+D183*+N195F+V206L+F289I+K391A+G476K, H1*+N54S+V56T+G109A+F113Q+Q172N+A174S+G182*+D183*+N195F+V206L+K391A+T444Q+G476K, H1*+N54S+V56T+G109A+F113Q+R116H+Q172N+A174S+G182*+D183*+N195F+V206L+K391A+G476K, H1*+N54S+V56T+G109A+F113Q+R116Q+Q172M+A174S+G182*+D183*+N195F+V206L+K391A+T444Q+G476K, H1*+N54S+V56T+G109A+F113Q+R116H+Q172M+A174S+G182*+D183*+N195F+V206L+K391A+G476K, H1*+N54S+V56T+G109A+R116H+Q172M+A174S+G182*+D183*+N195F+V206L+K391A+G476K, H1*+N54S+V56T+G109A+R116Q+A174S+G182*+D183*+N195F+V206L+A265G+K391A+T444Q+P473R+G476K, H1*+N54S+V56T+G109A+R116Q+A174S+G182*+D183*+N195F+V206L+K391A+T444Q+P473R+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+W167F+Q172R+A174S+G182*+D183*+N195F+V206L+K391A+G476K, H1*+N54S+V56T+G109A+R116Q+W167F+Q172R+A174S+G182*+D183*+N195F+V206L+A265G+K391A+P473R+G476K, H1*+N54S+V56T+G109A+F113Q+A174S+G182*+D183*+N195F+V206L+K391A+G476K, H1*+N54S+V56T+G109A+Q172N+A174S+G182*+D183*+N195F+V206L+K391A+G476K, H1*+T51V+N54S+V56T+G109A+Q172D+A174S+G182*+D183*+N195F+V206L+K391A+G476K, H1*+N54S+V56T+G109A+A174S+G182*+D183*+N195F+V206L+S280Q+H321Y+K391A+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172G+L173V+A174S+G182*+D183*+N195F+V206L+K391A+T444Q+P473R+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+N54S+V56T+G109A+F113Q+R116H+W167F+Q172N+L173V+A174S+G182*+D183*+N195F+V206L+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+F113Q+R116H+T134E+W167F+Q172R+A174S+G182*+D183*+N195F+V206L+G255A+K391A+Q395P+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+K72R+G109A+F113Q+R116Q+W167F+Q172N+L173V+A174S+G182*+D183*+G184T+N195F+V206L+K391A+T444Q+P473R+G476K, H1*+A37H+N54S+V56T+G109A+F113Q+W167F+Q172N+A174S+G182*+D183*+N195F+V206L+K391A+G476K, H1*+N54S+V56T+G109A+F113Q+W167F+Q172N+A174S+G182*+D183*+N195F+V206L+K391A+T459N+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+

A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37V+N54S+V56T+A60V+G109A+R116Q+T165G+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+W167F+Q172G+L173V+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+W167F+Q172R+A174S+G182*+D183*+N195F+A204G+V206L+K391A+P473R+G476K, H1*+N54S+V56T+G109A+R116A+A174S+G182*+D183*+N195F+A204G+V206L+K391A+P473R+G476K, H1*+N54S+V56T+G109A+R116A+T165G+A174S+G182*+D183*+N195F+V206L+K391A+T444Q+P473R+G476K, H1*+N54S+V56T+G109A+G182*+D183*+N195F+K391A+G476K, H1*+N54S+V56T+G109A+G182*+D183*+N195F+V206L, N54S+V56T+G109A+G182*+D183*+N195F, N54S+V56T+G109A+A174S+G182*+D183*+N195F+V206L+K391A+G476K, H1*+N54S+V56T+G109A+G182*+D183*+N195F+V206L+K391A+G476K, H1*+N54S+V56T+G109A+A174S+G182*+D183*+N195F+V206L+K391A, H1*+N54S+V56T+G109A+A174S+G182*+D183*+N195F+G476K, H1*+N54S+V56T+A174S+G182*+D183*+N195F+V206L+G273R+K391A+G476K, H1*+N54S+V56T+G109A+A174S+G182*+D183*+N195F+V206L, N54S+V56T+G109A+A174S+G182*+D183*+N195F+K391A+G476K, H1*+N54S+V56T+G109A+F113Q+Q172M+A174S+G182*+D183*+N195F+V206L+K391A+G476K, H1*+N54S+V56T+K72R+G109A+F113Q+T134E+A174S+G182*+D183*+N195F+V206L+G255A+K391A+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+V56A+G109A+A174S+G182*+D183*+N195F+V206L+G476K, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+N54S+V56T+G109A+F113Q+W167F+Q172N+A174S+G182*+D183*+N195F+A204G+V206L+K391A+P473R+G476K, H1*+N54S+V56T+G109A+F113Q+R116H+W167F+Q172R+A174S+G182*+D183*+N195F+A204G+V206L+K391A+P473R+G476K, H1*+N54S+V56T+G109A+R116A+A174S+G182*+D183*+N195F+V206L+K391A+T444Q+P473R+G476K, H1*+N54S+V56T+G109A+R116H+Q172R+A174S+G182*+D183*+N195F+A204G+V206L+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+A174S+G182*+D183*+N195F+K391A+G476K, H1*+N54S+V56T+G109A+G133S+A174S+G182*+D183*+N195F+K391A+G476H, H1*+N54S+V56T+G109A+R116A+Q172N+L173V+A174S+G182*+D183*+N195F+V206L+K391A+G476K, H1*+A37V+N54S+V56T+G109A+R116H+T165G+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+A174S+G182*+D183*+N195F+V206L+P364A+K391A+C474V+G476K, H1*+N54S+V56T+G109A+Q118R+T134E+A174S+G182*+D183*+N195F+V206L+K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+N54S+V56T+G109A+A174S+G182*+D183*+N195F+V206L+Y382L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+W167H+A174S+G182*+D183*+N195F+V206L+K391A+G476K, H1*+N54S+V56T+G109A+T165V+A174S+G182*+D183*+N195F+V206L+K391A+G476K, H1*+N54S+V56T+G109A+A174S+G182*+D183*+N195F+V206L+K391A+G476K, H1*+N54S+V56T+G109A+A174N+G182*+D183*+N195F+V206L+K391A+G476K, H1*+N54S+V56T+G109A+A174Q+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+

A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, wherein numbering is according to SEQ ID NO: 13, and H1*+T40D+N54S+V56T+G109A+A174S+G182*+D183*+N195F+V206L+I405L+A421H+A422P+A428T H1*+N54S+V56T+G109A+F113Q+N125D+A174S+G182*+D183*+N195F+V206L+I405L+A421H+A422P+A428T H1*+N54S+V56T+G109A+F113Q+R116H+Q172N+A174S+G182*+D183*+N195F+V206L+I405L+A421H+A422P+A428T H1*+N54S+V56T+K72R+G109A+T134E+W167F+Q172N+A174S+G182*+D183*+N195F+V206L+G255A+A265G+I405L+A421H+A422P+A428T H1*+N54S+V56T+K72R+G109A+R116Q+W167F+Q172R+L173V+A174S+G182*+D183*+N195F+V206L+A265G+I405L+A421H+A422P+A428T H1*+N54S+V56T+K72R+G109A+R116Q+W167F+Q172R+A174S+G182*+D183*+N195F+V206L+I405L+A421H+A422P+A428T H1*+N54S+V56T+K72R+G109A+F113Q+T134E+W167F+Q172G+A174S+G182*+D183*+N195F+V206L+G255A+I405L+A421H+A422P+A428T H1*+N54S+V56T+G109A+F113Q+R116Q+W167F+Q172G+A174S+G182*+D183*+N195F+A204G+V206L+I405L+A421H+A422P+A428T H1*+N54S+V56T+K72R+G109A+R116Q+V120L+A174S+G182*+D183*+G184T+N195F+V206L+I405L+A421H+A422P+A428T H1*+N54S+V56T+G109A+F113Q+R116H+W167F+Q172G+L173V+A174S+G182*+D183*+N195F+V206L+I405L+A421H+A422P+A428T H1*+N54S+V56T+G109A+F113Q+R116Q+Q172N+A174S+G182*+D183*+N195F+V206L+A265G+I405L+A421H+A422P+A428T H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO: 14, and wherein the IF is determined by use of Model A detergent.

In one embodiment, the variant has an IF of at least 2.0 when compared to the parent polypeptide, wherein the IF is determined by use of Model A detergent at a temperature of 15° C. and a concentration of 0.05 mg enzyme/L.

In one embodiment, the variant has an IF of at least 2.0 when compared to the parent polypeptide and when determined by use of Model J detergent, and wherein the variant is selected from the group consisting of: H1*+N54S+V56T+G109A+A174S+G182*+D183*+N195F+V206L+K391A+G476K, H1*+N54S+V56T+R87S+G109A+A174S+G182*+D183*+N195F+V206L+K391A+G476K, H1*+T40G+N54S+V56T+G109A+A174S+G182*+D183*+N195F+V206L+K391A+G476K, H1*+T51K+N54S+V56T+G109A+A174S+G182*+D183*+N195F+V206L+K391A+G476K, H1*+N54S+V56T+K72R+G109A+A174S+G182*+D183*+N195F+V206L+K391A+G476K, H1*+N54S+V56T+K72H+G109A+A174S+G182*+D183*+N195F+V206L+K391A+G476K, H1*+A37H+N54S+V56T+G109A+A174S+G182*+D183*+N195F+V206L+K391A+G476K, H1*+A37M+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+A37S+N54S+V56T+G109A+A174S+G182*+D183*+N195F+V206L+K391A+G476K, H1*+A37Y+N54S+V56T+G109A+A174S+G182*+D183*+N195F+V206L+K391A+G476K, H1*+A37R+N54S+V56T+G109A+A174S+G182*+D183*+N195F+V206L+K391A+G476K, H1*+N54S+V56T+G109A+F113W+A174S+G182*+D183*+N195F+V206L+K391A+G476K, H1*+N54S+V56T+G109A+F113S+A174S+G182*+D183*+N195F+V206L+K391A+G476K, H1*+N54S+V56T+G109A+F113N+A174S+G182*+D183*+N195F+V206L+K391A+G476K, H1*+N54S+V56T+G109A+F113Y+A174S+G182*+D183*+N195F+V206L+K391A+G476K, H1*+N54S+V56T+G109A+F113R+A174S+G182*+D183*+N195F+V206L+K391A+G476K, H1*+N54S+V56T+G109A+Q118N+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+R116V+A174S+G182*+D183*+N195F+V206L+K391A+G476K, H1*+N54S+V56T+G109A+R116K+A174S+G182*+D183*+N195F+V206L+K391A+G476K, H1*+N54S+V56T+G109A+Q125P+A174S+G182*+D183*+N195F+V206L+K391A+G476K, H1*+N54S+V56T+G109A+Q125K+A174S+G182*+D183*+N195F+V206L+K391A+G476K, H1*+N54S+V56T+G109A+A174S+G182*+D183*+N195F+

V206L+S381G+K391A+G476K, H1*+N54S+V56T+G109A+A174S+G182*+D183*+N195F+V206L+M246T+K391A+G476K, H1*+N54S+V56T+G109A+A174S+G182*+D183*+N195F+V206L+V213T+K391A+G476K, H1*+A37L+N54S+V56T+G109A+A174S+G182*+D183*+N195F+V206L+K391A+G476K, H1*+N54S+V56T+G109A+R116A+A174S+G182*+D183*+N195F+V206L+K391A+G476K, H1*+N54S+V56T+G109A+R116H+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+Q172R+A174S+G182*+D183*+N195F+V206L+K391A+G476K, H1*+N54S+V56T+G109A+A174S+G182*+D183*+N195F+V206L+D377S+K391A+G476K, H1*+N54S+V56T+G109A+A174S+G182*+D183*+N195F+V206L+D377G+K391A+G476K, H1*+N54S+V56T+G109A+A174S+G182*+D183*+N195F+V206L+D377R+K391A+G476K, H1*+N54S+V56T+G109A+A174S+G182*+D183*+N195F+V206L+D377A+K391A+G476K, H1*+N54S+V56T+G109A+A174S+G182*+D183*+N195F+V206L+I214G+K391A+G476K, H1*+N54S+V56T+G109A+A174S+G182*+D183*+N195F+V206L+S381A+K391A+G476K, H1*+N54S+V56T+G109A+W167I+A174S+G182*+D183*+N195F+V206L+K391A+G476K, H1*+N54S+V56T+G109A+W167G+A174S+G182*+D183*+N195F+V206L+K391A+G476K, H1*+N54S+V56T+G109A+A174S+G182*+D183*+N195F+V206L+G346S+K391A+G476K, H1*+N54S+V56T+G109A+A174S+G182*+D183*+N195F+V206L+G346P+K391A+G476K, H1*+N54S+V56T+G109A+A174S+G182*+D183*+N195F+V206L+I214H+K391A+G476K, H1*+N54S+V56T+G109A+A174S+G182*+D183*+N195F+V206L+I214S+K391A+G476K, H1*+N54S+V56T+G109A+A174S+G182*+D183*+N195F+V206L+I214T+K391A+G476K, H1*+N54S+V56T+G109A+A174S+G182*+D183*+N195F+V206L+K391A+A420S+G476K, H1*+N54S+V56T+G109A+A174S+G182*+D183*+N195F+V206L+K391A+A420K+G476K, H1*+N54S+V56T+G109A+A174S+G182*+D183*+N195F+V206L+K391A+A420L+G476K, H1*+N54S+V56T+G109A+A174S+G182*+D183*+N195F+V206L+K391A+K391Y+G476K, H1*+N54S+V56T+G109A+A174S+G182*+D183*+N195F+V206L+K391A+K391R+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+P473G+G476K, H1*+N54S+V56T+G109A+A174S+G182*+D183*+N195F+V206L+K391A+P473T+G476K, H1*+N54S+V56T+G109A+A174S+G182*+D183*+N195F+V206L+K391A+Q395P+G476K, H1*+N54S+V56T+G109A+A174S+G182*+D183*+N195F+V206L+K391A+T444Q+G476K, H1*+N54S+V56T+G109A+A174S+G182*+D183*+N195F+V206L+K391A+T444S+G476K, H1*+N54S+V56T+G109A+A174S+G182*+D183*+N195F+V206L+K391A+T444D+G476K, H1*+N54S+V56T+G109A+A174S+G182*+D183*+N195F+V206L+K391A+T444Y+G476K, H1*+N54S+V56T+G109A+A174S+G182*+D183*+N195F+V206L+S280W+K391A+G476K, H1*+N54S+V56T+G109A+A174S+G182*+D183*+N195F+V206L+S280L+K391A+G476K, H1*+N54S+V56T+G109A+A174S+G182*+D183*+N195F+V206L+S280T+K391A+G476K, H1*+N54S+V56T+G109A+A174S+G182*+D183*+N195F+V206L+S280A+K391A+G476K, H1*+N54S+V56T+G109A+A174S+G182*+D183*+N195F+V206L+G255N+K391A+G476K, H1*+N54S+V56T+G109A+A174S+G182*+D183*+N195F+V206L+T285L+K391A+G476K, H1*+N54S+V56T+G109A+A174S+G182*+D183*+N195F+V206L+T285Q+K391A+G476K, H1*+N54S+V56T+G109A+A174S+G182*+D183*+N195F+V206L+K391A+P473K+G476K, H1*+N54S+V56T+K72S+G109A+A174S+G182*+D183*+N195F+V206L+K391A+G476K, H1*+T40K+N54S+V56T+G109A+A174S+G182*+D183*+N195F+V206L+G346T+K391A+G476K, H1*+G50A+N54S+V56T+G109A++Q172N+A174S+G182*+D183*+N195F+V206L+K391A+G476K, H1*+N54S+V56T+G109A+A174S+G182*+D183*+N195F+V206L+K391A+G476K+K484A, H1*+N54S+V56T+G109A+A174S+G182*+D183*+N195F+V206L+K391A+G476K+K484G, H1*+N54S+V56T+G109A+A174S+G182*+D183*+N195F+V206L+K391A+G476K+K484P, H1*+N54S+V56T+G109A+A174S+G182*+D183*+N195F+V206L+K391A+G476K+K484E, H1*+N54S+V56T+G109A+A174S+G182*+D183*+N195F+V206L+K391A+G476K+K484Q, H1*+N54S+V56T+G109A+A174S+G182*+D183*+N195F+V206L+K391A+G476K+K484S, H1*K+G50A+N54S+V56T+G109A+W167F+A174S+G182*+D183*+N195F+V206L+K391A+G476K, H1*+N54S+V56T+G109A+L173V+A174S+G182*+D183*+N195F+A204T+V206L+K391A+G476K, H1*+N54S+V56T+G109A+W140Y+A174S+G182*+D183*+N195F+V206L+K391A+G476K, H1*+N54S+V56T+Q98S+G109A+A174S+G182*+D183*+N195F+V206L+R320A+K391A+G476K, H1*+N54S+V56T+G109A+A174S+G182*+D183*+N195F+V206L+H324L+K391A+G476K, H1*+N54S+V56T+G109A+A174S+G182*+D183*+N195F+V206L+G346T+K391A+G476K+G477A, H1*+N54S+V56T+G109AG255A++A174S+G182*+D183*+N195F+V206L+K391A+G476K, H1*+G50A+N54S+V56T+G109A+F113L+R116L+A174S+G182*+D183*+N195F+V206L+K391A+G476K, H1*+N54S+V56T+G109A+W167F+A174S+G182*+D183*+N195F+V206L+K391A+G476K, H1*+N54S+V56T+G109A+L173V+A174S+G182*+D183*+N195F+V206L+K391A+G476K, H1*+N54S+V56T+K72R+G109A+W167F+A174S+G182*+D183*+N195F+V206L+K391A+G476K, H1*+N54S+V56T+G109A+A174S+G182*+D183*+N195F+V206L+K391A+G476K+G477Q, H1*+N54S+V56T+G109A+A174S+G182*+D183*+N195F+V206L+Q345D+K391A+G476K+G477Q, H1*+G50A+N54S+V56T+G109A+Q172D+A174S+G182*+D183*+N195F+V206L+K391A+G476K, H1*+N54S+V56T+G109A+A174S+G182*+D183*+N195F+V206L+V264I+K391A+G423H+G476K, H1*+N54S+V56T+G109A+A174S+G182*+D183*+N195F+V206L+R320V+K391A+G476Y, H1*+N54S+V56T+G109A+R116M+A174S+G182*+D183*+N195F+V206L+K391A+G476K, H1*+N54S+V56T+G109A+A174S+G182*+D183*+N195F+V206L+L217V+K391A+G476K, H1*+N54S+V56T+G109A+A174S+G182*+D183*+N195F+V206L+L217H+K391A+G476K, H1*+N54S+V56T+G109A+A174S+G182*+D183*+N195F+V206L+P211D+K391A+G476K, H1*+N54S+V56T+G109A+A174S+G182*+D183*+N195F+V206L+K391A+K391Q+G476K, H1*+N54S+V56T+G109A+A174S+G182*+D183*+N195F+V206L+K391A+T444H+G476K, H1*+N54S+V56T+G109A+A174S+G182*+D183*+N195F+V206L+K391A+T444V+G476K, H1*+G50A+N54S+V56T+G109A+L173V+A174S+G182*+D183*+N195F+A204V+V206L+K391A+G476K, H1*+G50A+N54S+V56T+G109A+F113L+W167F+A174S+

G182*+D183*+N195F+V206L+K391A+G476K, H1*+G7K+N54S+V56T+G109A+A174S+G182*+D183*+N195F+V206L+R320A+K391A+G476K H1*+N54S+V56T+G109A+Q118G+A174S+G182*+D183*+N195F+V206L+K391A+G476K, H1*+N54S+V56T+G109A+Q172D+A174S+G182*+D183*+N195F+V206L+G346T+K391A+G476K+G477A, H1*+N54S+V56T+G109A+A174S+G182*+D183*+N195F+V206L+R320A+K391A+G476K, H1*+N54S+V56T+G109A+T134E+A174S+G182*+D183*+N195F+V206L+K391A+G476K, H1*+N54S+V56T+G109A+A174S+G182*+D183*+N195F+V206L+Y382M+K391A+G476K, H1*+N54S+V56T+K72R+G109A+A174S+G182*+D183*+N195F+V206L+G255A+D377H+K391A+G476K, H1*+N54S+V56T+K72R+G109A+T134E+A174S+G182*+D183*+N195F+V206L+G255A+K391A+G476K, H1*+N54S+V56T+K72R+M105F+G109A+A174S+G182*+D183*+N195F+V206L+G255A+K391A+G476K, H1*+N54S+V56T+M105F+G109A+T134E+A174S+G182*+D183*+N195F+V206L+K391A+G476K, H1*+N54S+V56T+G109A+A174S+G182*+D183*+N195F+V206L+R320A+S323N+D377H+K391A+G476K, H1*+T51E+N54S+V56T+G109A+A174H+G182*+D183*+N195F+V206L+K391A+G476K, H1*+N54S+V56T+G109A+L173A+A174S+G182*+D183*+N195F+V206L+K391A+G476K, H1*+N54S+V56T+G109A+A174S+G182*+D183*+N195F+V206L+Q299V+K391A+G476K, H1*+N54S+V56T+G109A+L173G+A174S+G182*+D183*+N195F+V206L+K391A+G476K, H1*+N54S+V56T+G109A+A174S+G182*+D183*+N195F+V206L+T355L+K391A+G476K, H1*+G50A+N54S+V56T+G109A+A174S+G182*+D183*+N195F+A204T+V206L+K391A+G476K, H1*+G50A+N54S+V56T+G109A+A174E+G182*+D183*+N195F+A204T+V206L+K391A+G476K, H1*+N54S+V56T+K72R+G109A+A174S+G182*+D183*+N195F+V206L+R320A+S323N+K391A+G476K, H1*+T51G+N54S+V56T+G109A+A174N+G182*+D183*+N195F+V206L+K391A+G476K, H1*+N54S+V56T+G109A+Q118R+T134E+A174S+G182*+D183*+N195F+V206L+D377H+K391A+G476K, H1*+Q11H+N54S+V56T+G109A+Q118R+T134E+A174S+G184T+G182*+D183*+N195F+V206L+D377H+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+Q118R+T134E+A174S+G182*+D183*+N195F+V206L+G255A+K391A+G476K, H1*+N54S+V56T+G109A+Q118R+A174S+G182*+D183*+N195F+V206L+D377H+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+K72R+G109A+W167L+A174S+G182*+D183*+N195F+V206L+K391A+G476K, H1*+N54S+V56T+K72R+G109A+A174S+G182*+D183*+G184T+N195F+V206L+G255A+K391A+G476K, H1*+N54S+V56T+G109A+A174S+G182*+D183*+G184T+N195F+V206L+D377H+K391A+G476K, H1*+N54S+V56T+G109A+A174S+G182*+D183*+N195F+V206L+G255A+D377H+K391A+G476K, H1*+N54S+V56T+M105F+G109A+A174S+G182*+D183*+G184T+N195F+V206L+K391A+G476K, H1*+N54S+V56T+G109A+T134E+A174S+G182*+D183*+N195F+V206L+R320A+S323N+K391A+G476K, H1*+N54S+V56T+G109A+A174S+G182*+D183*+N195F+V206L+V291G+D377H+K391A+G476K, H1*+N54S+V56T+G109A+A174S+G182*+D183*+N195F+V206L+V291A+F328L+D377H+K391A+G476K, H1*+N54S+V56T+G109A+T134E+A174S+G182*+D183*+G184T+N195F+V206L+K391A+G476K, H1*+N54S+V56T+G109A+A174S+G182*+D183*+N195F+V206L+V238A+D377H+K391A+G476K, H1*+N54S+V56T+G109A+A174S+G182*+D183*+N195F+V206L+V238T+D377H+K391A+G476K H1*+N54S+V56T+G109A+A174S+G182*+D183*+N195F+V206L+V238G+D377H+K391A+G476K, H1*+N54S+V56T+G109A+A174S+G182*+D183*+N195F+V206L+F328M+D377H+K391A+G476K, H1*+N54S+V56T+G109A+A174S+G182*+D183*+N195F+V206L+F328I+D377H+K391A+G476K, H1*+N54S+V56T+G109A+A174S+G182*+D183*+N195F+V206L+V291T+D377H+K391A+G476K, H1*+N54S+V56T+G109A+A174S+G182*+D183*+N195F+V206L+V291A+D377H+K391A+G476K, H1*+N54S+V56T+K72R+G109A+T134E+A174S+G182*+D183*+G184T+N195F+V206L+G255A+K391A+G476K, H1*+N54S+V56T+G109A+L173H+A174S+G182*+D183*+N195F+V206L+K391A+G476K, H1*+N54S+V56T+G109A+Q125T+A174S+G182*+D183*+N195F+V206L+K391A+G476K, H1*+N16S+N54S+V56T+G109A+A174S+G182*+D183*+N195F+V206L+K391A+G476K, H1*+N54S+V56T+K72N+G109A+A174S+G182*+D183*+N195F+V206L+K391A+G476K, H1*+N54S+V56T+G109A+Q118R+T134E+A174S+G182*+D183*+N195F+V206L+G255A+D377H+K391A+G476K, H1*+N54S+V56T+K72R+G109A+A174S+G182*+D183*+N195F+G184T+V206L+K391A+G476K, H1*+N54S+V56T+K72R+G109A+Q118R+A174S+G182*+D183*+N195F+V206L+G255A+D377H+K391A+G476K, H1*+N54S+V56T+G109A+A174S+G182*+D183*+G184T+N195F+V206L+R320A+S323N+K391A+G476K, H1*+N54S+G109A+A174S+G182*+D183*+N195F+V206L+D377H+K391A+G476K, H1*+N54S+V56T+A174S+G182*+D183*+N195F+V206L+D377H+K391A+G476K, H1*+N54S+V56T+G109A+G182*+D183*+N195F+V206L+D377H+K391A+G476K, H1*+N54S+V56T+G109A+A174S+G182*+D183*+N195F+D377H+K391A+G476K, H1*+N54S+V56T+G109A+A174S+G182*+D183*+N195F+D377H+K391A+G476K, H1*+N54S+V56T+G109A+A174S+G182*+D183*+N195F+V206L+D377H+G476K, H1*+N54S+V56T+G109A+A174S+G182*+D183*+N195F+V206L+D377H+K391A, H1*+N54S+V56T+G109A+A174S+G182*+D183*+N195F+V206L+L217T+K391A+G476K, H1*+N54S+V56T+G109A+A174S+G182*+D183*+N195F+V206L+D377S+K391A+G476K, H1*+N54S+V56T+G109A+R116E+A174S+G182*+D183*+N195F+V206L+K391A+G476K, H1*+N54S+V56T+G109A+A174S+G182*+D183*+N195F+V206L+D377A+K391A+G476K, H1*+N54S+V56T+G109A+T134E+A174S+G182*+D183*+N195F+V206L+D377H+K391A+G476K, H1*+N54S+V56T+G109A+Q118R+T134E+A174S+G182*+D183*+G184T+N195F+V206L+K391A+G476K, H1*+N54S+V56T+K72R+G109A+Q118R+T134E+A174S+G182*+D183*+N195F+V206L+K391A+G476K, H1*+N54S+V56T+G109A+A174S+G182*+D183*+N195F+V206L+G346P+K391A+G476K, H1*+N54S+V56T+G109A+R116S+A174S+G182*+D183*+N195F+V206L+K391A+G476K, H1*+N54S+V56T+G109A+A174S+G182*+D183*+N195F+V206L+D377Q+K391A+G476K, H1*+N54S+V56T+G109A+R116G+A174S+G182*+D183*+N195F+V206L+K391A+G476K, H1*+N54S+V56T+G109A+R116G+A174S+

G182*+D183*+N195F+V206L+K391A+G476K, H1*+N54S+V56T+K72R+G109A+Q118R+T134E+A174S+G182*+D183*+N195F+V206L+G255A+K391A+G476K, H1*+T51A+N54S+V56T+G109A+Q172D+A174S+G182*+D183*+N195F+V206L+K391A+G476K, H1*+T51S+N54S+V56T+G109A+Q172M+A174S+G182*+D183*+N195F+V206L+K391A+G476K, H1*-+T51A+N54S+V56T+G109A+Q172S+A174S+G182*+D183*+N195F+V206L+K391A+G476K, H1*+T51E+N54S+V56T+G109A+Q172T+A174S+G182*+D183*+N195F+V206L+K391A+G476K, H1*+T51A+N54S+V56T+G109A+Q172A+A174S+G182*+D183*+N195F+V206L+K391A+G476K, H1*+T51S+N54S+V56T+G109A+Q172N+A174S+G182*+D183*+N195F+V206L+K391A+G476K, H1*+T51A+N54S+V56T+G109A+Q172G+A174S+G182*+D183*+N195F+V206L+K391A+G476K, H1*+T51E+N54S+V56T+G109A+Q172L+A174S+G182*+D183*+N195F+V206L+K391A+G476K, H1*+N54S+V56T+G109A+Q172K+A174S+G182*+D183*+N195F+V206L+K391A+G476K, H1*+N54S+V56T+K72R+G109A+Q172S+A174S+G182*+D183*+N195F+V206L+K391A+G476K, H1*+N54S+V56T+K72H+G109A+Q172T+A174S+G182*+D183*+N195F+V206L+K391A+G476K, H1*+N54S+V56T+K72R+G109A+Q172M+A174S+G182*+D183*+N195F+V206L+Y295N+K391A+G476K, H1*+N54S+V56T+K72Q+G109A+Q172R+A174S+G182*+D183*+N195F+V206L+K391A+G476K, H1*+N54S+V56T+K72R+G109A+Q172T+A174S+G182*+D183*+N195F+V206L+K391A+G476K, H1*+N54S+V56T+K72M+G109A+Q172S+A174S+G182*+D183*+N195F+V206L+K391A+G476K, H1*+N54S+V56T+K72Q+G109A+Q172M+A174S+G182*+D183*+N195F+V206L+K391A+G476K, H1*+N54S+V56T+G109A+Q172M+A174S+G182*+D183*+N195F+V206L+K391A+G476K, H1*+N54S+V56T+K72S+G109A+A174H+G182*+D183*+N195F+V206L+K391A+G476K, H1*+N54S+V56T+K72Q+G109A+A174D+G182*+D183*+N195F+V206L+K391A+G476K, H1*+N54S+V56T+K72R+G109A+A174D+G182*+D183*+N195F+V206L+K391A+G476K, H1*+N54S+V56T+K72Q+G109A+A174K+G182*+D183*+N195F+V206L+K391A+G476K, H1*+N54S+V56T+G109A+A174G+G182*+D183*+N195F+V206L+K391A+G476K, H1*+N54S+V56T+K72R+G109A+A174Q+G182*+D183*+N195F+V206L+K391A+G476K, H1*+N54S+V56T+K72Q+G109A+A174G+G182*+D183*+N195F+V206L+K391A+G476K, H1*+N54S+V56T+K72S+G109A+A174N+G182*+D183*+N195F+V206L+K391A+G476K, H1*+N54S+V56T+K72R+G109A+A174H+G182*+D183*+N195F+V206L+K391A+G476K, H1*+N54S+V56T+G109A+A174S+G182*+D183*+N195F+V206L+K391A+T444A+G476K, H1*+N54S+V56T+G109A+F113L+W167F+A174S+G182*+D183*+N195F+V206L+K391A+G476K, H1*+N54S+V56T+M105F+G109A+A174S+G182*+D183*+N195F+V206L+D377H+K391A+G476K, H1*+N54S+V56T+G109A+A174S+G182*+D183*+N195F+A204G+V206L+K391A+G476K, H1*+N54S+V56T+G109A+A174S+G182*+D183*+N195F+V206L+S376H+K391A+G476K, H1*+N54S+V56T+G109A+A174S+G182*+D183*+N195F+V206L+I214E+K391A+G476K, H1*+N54S+V56T+G109A+A174S+G182*+D183*+N195F+V206L+I214W+K391A+G476K, H1*+N54S+V56T+K72R+G109A+Q172K+A174S+G182*+D183*+N195F+V206L+K391A+G476K, H1*+N54S+V56T+G109A+A174S+G182*+D183*+N195F+A204T+V206L+D377H+K391A+G476K, H1*+N54S+V56T+G109A+A174S+G182*+D183*+N195F+A204S+V206L+D377H+K391A+G476K, H1*+N54S+V56T+G109A+T165S+A174S+G182*+D183*+N195F+V206L+D377H+K391A+G476K, H1*+N54S+V56T+G109A+A174S+G182*+D183*+N195F+V206L+T334S+D377H+K391A+G476K, H1*+N54S+V56T+G109A+A174S+G182*+D183*+N195F+V206L+A263G+D377H+K391A+G476K, H1*+N54S+V56T+G109A+A174S+G182*+D183*+N195F+V206L+M286F+D377H+K391A+G476K, H1*+N54S+V56T+G109A+A174S+G182*+D183*+N195F+V206L+L235V+D377H+K391A+G476K, H1*+N54S+V56T+G109A+A174S+G182*+D183*+N195F+V206L+L235A+D377H+K391A+G476K, H1*+N54S+V56T+M105L+G109A+A174S+G182*+D183*+N195F+V206L+D377H+K391A+G476K, H1*+N54S+V56T+M105I+G109A+A174S+G182*+D183*+N195F+V206L+D377H+K391A+G476K, H1*+N54S+V56T+M105V+G109A+A174S+G182*+D183*+N195F+V206L+D377H+K391A+G476K, H1*+N54S+V56T+G109A+A174S+G182*+D183*+N195F+V206L+M246I+D377H+K391A+G476K, H1*+N54S+V56T+G109A+A174S+G182*+D183*+N195F+V206L+L250I+D377H+K391A+G476K, H1*+N54S+V56T+G109A+A174S+G182*+D183*+N195F+V206L+L250V+D377H+K391A+G476K, H1*+N54S+V56T+G109A+A174S+G182*+D183*+N195F+V206L+K391Y+G476K, H1*+N54S+V56T+G109A+A174S+G182*+D183*+N195F+V206L+K391V+G476K, H1*+N54S+V56T+G109A+A174S+G182*+D183*+N195F+V206L+K391M+G476K, H1*+N54S+V56T+G109A+A174S+G182*+D183*+N195F+V206L+K391E+G476K, H1*+N54S+V56T+G109A+T165G+A174S+G182*+D183*+N195F+V206L+D377H+K391A+G476K, H1*+N54S+V56T+G109S+A174S+G182*+D183*+N195F+V206L+K391A+G476K, H1*+N54S+V56T+G109A+A174V+G182*+D183*+N195F+V206L+K391A+G476K, H1*+N54S+V56T+G109A+A174S+G182*+D183*+N195F+V206L+M246F+D377H+K391A+G476K, H1*+N54S+V56T+G109A+A174L+G182*+D183*+N195F+V206L+K391A+G476K, H1*+N54S+V56T+G109A+A174S+G182*+D183*+N195F+V206S+K391A+G476K, H1*+N54S+V56T+G109A+A174S+G182*+D183*+N195F+V206L+K391D+G476K, H1*+N54S+V56T+G109A+A174S+G182*+D183*+N195F+V206L+K391R+G476K, H1*+N54S+V56T+G109A+A174S+G182*+D183*+N195F+V206L+K391H+G476K, H1*+N54S+V56T+G109A+A174S+G182*+D183*+N195F+V206L+K391W+G476K, H1*+N54S+V56T+G109A+A174S+G182*+D183*+N195F+V206L+K391I+G476K, H1*+N54S+V56T+G109A+A174S+G182*+D183*+N195F+V206L+L250T+D377H+K391A+G476K, H1*+N54S+V56T+G109A+A174S+G182*+D183*+N195F+V206L+L250A+D377H+K391A+G476K, H1*+N54S+V56T+G109A+A174S+G182*+D183*+N195F+V206L+L250F+D377H+K391A+G476K, H1*+N54S+V56T+G109A+A174S+G182*+D183*+N195F+V206L+L250M+D377H+K391A+G476K, H1*+N54S+V56T+G109A+Q172H+L173A+A174P+G182*+D183*+N195F+V206L+K391A+G476K, H1*+N54S+V56T+G109A+A174S+G182*+D183*+G184T+N195F+V206L+G255A+K391A+G476K, H1*+N54S+V56T+G109A+A174S+G182*+D183*+G184T+N195F+V206L+G255A+D377H+K391A+G476K, H1*+N54S+V56T+G109A+A174S+G182*+D183*+N195F+V206L+S376T+K391A+G476K, H1*+N54S+V56T+G109A+A174S+G182*+D183*+N195F+V206L+S376V+K391A+G476K, H1*+N54S+V56T+G109A+Q172E+L173I+A174N+G182*+D183*+N195F+V206L+K391A+G476K, H1*+N54S+V56T+G109A+Q172D+L173A+A174T+G182*+D183*+N195F+V206L+

K391A+G476K, H1*+N54S+V56T+G109A+A174S+G182*+D183*+N195F+V206L+Y267M+D377H+K391A+G476K, H1*+N54S+V56T+G109A+A174S+G182*+D183*+N195F+V206L+Y267H+D377H+K391A+G476K, H1*+N54S+V56T+G109A+A174S+G182*+D183*+N195F+V206L+V238A+K391A+G476K, H1*+N54S+V56T+G109A+A174S+G182*+D183*+N195F+V206L+V238G+K391A+G476K, H1*+N54S+V56T+M105V+G109A+A174S+G182*+D183*+N195F+V206L+K391A+G476K, H1*+N54S+V56T+G109A+A174S+G182*+D183*+N195F+V206L+V264T+K391A+G476K, H1*+N54S+V56T+G109A+A174S+G182*+D183*+N195F+V206L+V264I+K391A+G476K, H1*+N54S+V56T+G109A+A174S+G182*+D183*+N195F+V206L+L235V+K391A+G476K, H1*+N54S+V56T+G109A+W167H+Q172N+L173A+A174S+G182*+D183*+N195F+V206L+K391A+G476K, H1*+N54S+V56T+G109A+W167F+Q172E+L173P+A174K+G182*+D183*+N195F+V206L+K391A+G476K, H1*+N54S+V56T+G109A+Q172N+L173T+A174S+G182*+D183*+N195F+V206L+K391A+G476K, H1*+N54S+V56T+G109A+Q172E+L173F+A174R+G182*+D183*+N195F+V206L+K391A+G476K, H1*+N54S+V56T+G109A+Q172E+L173T+A174R+G182*+D183*+N195F+V206L+K391A+G476K, H1*+N54S+V56T+G109A+Q172N+L173V+A174R+G182*+D183*+N195F+V206L+K391A+G476K, H1*+N54S+V56T+G109A+Q172E+L173M+A174H+G182*+D183*+N195F+V206L+K391A+G476K, H1*+N54S+V56T+G109A+Q172E+L173F+A174P+G182*+D183*+N195F+V206L+K391A+G476K, H1*+N54S+V56T+G109A+W167Y+Q172E+L173V+A174H+G182*+D183*+N195F+V206L+K391A+G476K, H1*+N54S+V56T+G109A+L173A+A174T+G182*+D183*+N195F+V206L+K391A+G476K, H1*+N54S+V56T+G109A+A174S+G182*+D183*+N195F+V206L+V291A+F328L+K391A+G476K, H1*+N54S+V56T+G109A+A174S+G182*+D183*+N195F+V206L+M246L+K391A+G476K, H1*+N54S+V56T+G109A+A174S+G182*+D183*+N195F+V206L+M246S+K391A+G476K, H1*+N54S+V56T+G109A+A174S+G182*+D183*+N195F+V206L+L250V+K391A+G476K, H1*+N54S+V56T+G109A+A174S+G182*+D183*+N195F+V206L+L250F+K391A+G476K, H1*+N54S+V56T+G109A+A174S+G182*+D183*+N195F+V206L+L250M+K391A+G476K, H1*+N54S+V56T+G109A+A174S+G182*+D183*+N195F+V206L+K391A+C474V+G476K, H1*+N54S+V56T+G109A+T165G+A174S+G182*+D183*+N195F+V206L+K391A+G476K, H1*+N54S+V56T+G109A+A174S+G182*+D183*+N195F+V206L+T334S+K391A+G476K, H1*+N54S+V56T+G109A+A174S+G182*+D183*+N195F+V206L+A263G+M286L+K391A+G476K, H1*+N54S+V56T+G109A+A174S+G182*+D183*+N195F+V206L+Y267H+K391A+G476K, H1*+N54S+V56T+G109A+A174S+G182*+D183*+N195F+V206L+Y267L+K391A+G476K, H1*+N54S+V56T+G109A+A174S+G182*+D183*+N195F+V206L+K391L+G476K, H1*+N54S+V56T+G109A+F113Q+R116H+Q172G+A174S+G182*+D183*+N195F+V206L+K391A+G476K, H1*+N54S+V56T+G109A+F113Q+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+A174S+G182*+D183*+N195F+A204G+V206L+K391A+G476K, H1*+N54S+V56T+K72R+G109A+A174S+G182*+D183*+G184T+N195F+A204G+V206L+K391A+P473R+G476K, H1*+N54S+V56T+G109A+W167F+Q172N+A174S+G182*+D183*+N195F+V206L+K391A+P473R+G476K, H1*+N54S+V56T+G109A+W167F+Q172G+A174S+G182*+D183*+N195F+V206L+K391A+P473G+G476K, H1*+N54S+V56T+G109A+W167F+Q172G+A174S+G182*+D183*+N195F+V206L+K391A+P473R+G476K, H1*+N54S+V56T+K72R+G109A+W167F+Q172R+A174S+G182*+D183*+N195F+V206L+K391A+G476K, H1*+N54S+V56T+K72R+G109A+R116H+W167F+Q172R+A174S+G182*+D183*+N195F+V206L+K391A+G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+A174S+G182*+D183*+N195F+V206L+A265G+K391A+T444Q+G476K+G477A, H1*+A37V+N54S+V56T+G109A+W167F+Q172G+A174S+G182*+D183*+N195F+V206L+K391A+G346T+G477A+G476K, H1*+N54S+V56T+G109A+R116Q+Q172D+A174S+G182*+D183*+N195F+V206L+G346T+K391A+T444Q+G477A+G476K, H1*+N54S+V56T+G109A+R116Q+W167F+Q172N+A174S+G182*+D183*+N195F+V206L+G346T+K391A+T444Q+G477A+G476K, H1*+N54S+V56T+G109S+W167F+Q172R+A174S+G182*+D183*+N195F+V206L+K391A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+G109A+Q172N+A174S+G182*+D183*+N195F+V206L+K391A+C474V+G476K, H1*+N54S+V56T+G109A+A174S+G182*+D183*+N195F+V206L+S280Q+H321Y+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+R116H+W167F+Q172N+A174S+G182*+D183*+N195F+V206L+K391A+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+R116H+W167F+Q172R+A174S+G182*+D183*+N195F+V206L+F289I+K391A+G476K, H1*+N54S+V56T+G109A+F113Q+Q172N+A174S+G182*+D183*+N195F+V206L+K391A+T444Q+G476K, H1*+N54S+V56T+

G109A+F113Q+R116H+Q172N+A174S+G182*+D183*+N195F+V206L+K391A+G476K, H1*+N54S+V56T+G109A+F113Q+R116Q+Q172M+A174S+G182*+D183*+N195F+V206L+K391A+T444Q+G476K, H1*+N54S+V56T+G109A+F113Q+R116H+Q172M+A174S+G182*+D183*+N195F+V206L+K391A+G476K, H1*+N54S+V56T+G109A+R116H+Q172M+A174S+G182*+D183*+N195F+V206L+K391A+G476K, H1*+N54S+V56T+G109A+F113Q+R116H+T165G+Q172M+A174S+G182*+D183*+N195F+V206L+K391A+Q395P+G476K, H1*+N54S+V56T+G109A+R116Q+A174S+G182*+D183*+N195F+V206L+A265G+K391A+T444Q+P473R+G476K, H1*+N54S+V56T+G109A+R116Q+A174S+G182*+D183*+N195F+V206L+K391A+T444Q+P473R+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+W167F+Q172R+A174S+G182*+D183*+N195F+V206L+K391A+G476K, H1*+N54S+V56T+G109A+R116Q+W167F+Q172R+A174S+G182*+D183*+N195F+V206L+A265G+K391A+P473R+G476K, H1*+N54S+V56T+G109A+F113Q+A174S+G182*+D183*+N195F+V206L+K391A+G476K, H1*+N54S+V56T+G109A+Q172N+A174S+G182*+D183*+N195F+V206L+K391A+G476K, H1*+T51V+N54S+V56T+G109A+Q172D+A174S+G182*+D183*+N195F+V206L+K391A+G476K, H1*+N54S+V56T+G109A+A174S+G182*+D183*+N195F+V206L+S280Q+H321Y+K391A+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172G+L173V+A174S+G182*+D183*+N195F+V206L+K391A+T444Q+P473R+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+N54S+V56T+G109A+F113Q+R116H+W167F+Q172N+L173V+A174S+G182*+D183*+N195F+V206L+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+F113Q+T134E+W167F+Q172R+A174S+G182*+D183*+N195F+V206L+G255A+K391A+Q395P+A445Q+P473R+G476K, H1*+N54S+V56T+K72R+

G109A+F113Q+R116H+T134E+W167F+Q172R+A174S+G182*+D183*+N195F+V206L+G255A+K391A+Q395P+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+K72R+G109A+F113Q+R116Q+W167F+Q172N+L173V+A174S+G182*+D183*+G184T+N195F+V206L+K391A+T444Q+P473R+G476K, H1*+A37H+N54S+V56T+G109A+F113Q+W167F+Q172N+A174S+G182*+D183*+N195F+V206L+K391A+G476K, H1*+A37H+N54S+V56T+G109A+F113Q+A174S+G182*+D183*+N195F+V206L+K391A+G476K, H1*+N54S+V56T+G109A+F113Q+W167F+Q172N+A174S+G182*+D183*+N195F+V206L+K391A+T459N+G476K, H1*+N54S+V56T+G109A+F113Q+Q172R+L173V+A174S+G182*+D183*+N195F+V206L+K391A+T444Q+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37V+N54S+V56T+A60V+G109A+R116Q+T165G+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+W167F+Q172G+L173V+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+W167F+Q172R+A174S+G182*+D183*+N195F+A204G+V206L+K391A+P473R+G476K, H1*+N54S+V56T+G109A+R116A+A174S+G182*+D183*+N195F+A204G+V206L+K391A+P473R+G476K, H1*+N54S+V56T+G109A+R116A+T165G+A174S+G182*+D183*+N195F+V206L+K391A+T444Q+P473R+G476K, H1*+N54S+V56T+G109A+G182*+D183*+N195F+K391A+G476K, H1*+N54S+V56T+G109A+G182*+D183*+N195F+V206L, N54S+V56T+G109A+G182*+D183*+N195F, N54S+V56T+G109A+A174S+G182*+D183*+N195F+V206L+K391A+G476K, H1*+G109A+A174S+G182*+D183*+N195F+V206L+K391A+G476K, H1*+N54S+V56T+G109A+G182*+D183*+N195F+V206L+K391A+G476K, H1*+N54S+V56T+G109A+A174S+G182*+D183*+N195F+V206L+K391A, H1*+N54S+V56T+G109A+A174S+G182*+D183*+N195F+G476K, H1*+N54S+V56T+A174S+G182*+D183*+N195F+V206L+G273R+K391A+G476K, H1*+

N54S+V56T+G109A+A174S+G182*+D183*+N195F+V206L, H1*+W48G+G109A+G182*+D183*+N195F+V206L+K391A+G476K, N54S+V56T+G109A+A174S+G182*+D183*+N195F+K391A+G476K, H1*+N54S+V56T+G109A+A174S+G182*+D183*+N195F+K391A, H1*+N54S+V56T+G109A+F113Q+Q172M+A174S+G182*+D183*+N195F+V206L+K391A+G476K, H1*+N54S+V56T+K72R+G109A+F113Q+T134E+A174S+G182*+D183*+N195F+V206L+G255A+K391A+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+V56A+G109A+A174S+G182*+D183*+N195F+V206L+G476K, H1*+N54S+V56T+G109A+G182*+D183*+N195F+V206L+K391A, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+N54S+V56T+G109A+F113Q+W167F+Q172N+A174S+G182*+D183*+N195F+A204G+V206L+K391A+P473R+G476K, H1*+N54S+V56T+G109A+F113Q+R116H+W167F+Q172R+A174S+G182*+D183*+N195F+A204G+V206L+K391A+P473R+G476K, H1*+N54S+V56T+G109A+R116A+A174S+G182*+D183*+N195F+V206L+K391A+T444Q+P473R+G476K, H1*+N54S+V56T+G109A+R116H+Q172R+A174S+G182*+D183*+N195F+A204G+V206L+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+A174S+G182*+D183*+N195F+K391A+G476K, G109A+G182*+D183*+N195F+V206L+G476K, H1*+N54S+V56T+G109A+G133S+A174S+G182*+D183*+N195F+K391A+G476H, H1*+N54S+V56T+G109A+R116A+Q172N+L173V+A174S+G182*+D183*+N195F+V206L+K391A+G476K, H1*+A37V+N54S+V56T+G109A+R116H+T165G+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+P124A+A174S+G182*+D183*+N195F+V206L+K391A+C474V+G476K, H1*+N54S+V56T+G109A+A174S+G182*+D183*+N195F+V206L+P364A+K391A+C474V+G476K, H1*+N54S+V56T+G109A+Q118R+T134E+A174S+G182*+D183*+N195F+V206L+K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+N54S+V56T+G109A+A174S+G182*+D183*+N195F+V206L+Y382L+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+W167H+A174S+G182*+D183*+N195F+V206L+K391A+G476K, H1*+N54S+V56T+G109A+T165V+A174S+G182*+D183*+N195F+V206L+K391A+G476K, H1*+N54S+V56T+G109A+A174S+G182*+D183*+N195F+V206L+K391A+G476K, H1*+N54S+V56T+G109A+A174N+G182*+D183*+N195F+V206L+K391A+G476K, H1*+N54S+V56T+G109A+A174Q+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+G182*+D183*+N195F+V206L+G476K, H1*+N54S+V56T+G109A+

Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, H1*+N54S+V56T+G109A+Q172G+A174S+G182*+D183*+N195F+V206L+K391A+G476K, H1*+N54S+V56T+G109A+A174S+A186D+G182*+D183*+N195F+V206L+K391A+G476K, H1*+N54S+V56T+G109A+Q169E+Q172K+A174*+G182*+D183*+N195F+V206L+A225V+K391A+G476K, H1*+G109A+Q169E+Q172K+A174*+G182*+D183*+N195F+V206L+K391A+G476K, H1*+N54S+V56T+G109A+Q169E+Q172K+A174*+G182*+D183*+N195F+V206L+G255S+K391A+G476K, H1*+N54S+V56T+G109A+Q169E+Q172K+A174*+G182*+D183*+N195F+V206L+K269Q+K391A+G476K, H1*+N54S+V56T+G109A+A174S+G182*+D183*+N195F+V206L+G255S+K391A+G476K, H1*+N54S+V56T+G109A+Q169E+Q172K+A174S+G182*+D183*+N195F+V206L+K391A+G476K, G182*+D183*+N195F, H1*+N54S+V56T+G109A+Q169E+A174S+G182*+D183*+N195F+V206L+K391A+G476K, H1*+N54S+V56T+G109A+Q169E+Q172K+A174*+G182*+D183*+N195F+V206L+W284H+K391A+G476K, H1*+N54S+G109A+A174S+G182*+D183*+N195F+V206L+K391A+G476K, H1*+N54S+V56T+G109A+Q169E+Q172K+A174*+G182*+D183*+N195F+V206L+S304R+K391A+G476K, H1*+N54S+V56T+K72R+G109A+F113Q+R116Q+W167F+Q172G+A174S+G182*+D183*+G184T+N195F+V206L+K391A+P473R, H1*+N54S+V56T+G109A+A174S+G182*+D183*+N195F+V206L+M246V+K391A+G476K, H1*+N54S+V56T+G109A+Q169E+Q172K+A174*+G182*+D183*+N195F+V206L+K391A, H1*+N54S+V56T+G109A+Q169E+Q172K+A174*+G182*+D183*+N195F+V206L+N270G+K391A+G476K, H1*+N54S+V56T+G109A+Q169E+Q172K+A174*+G182*+D183*+N195F+V206L+Y295F+K391A+G476K, H1*+N54S+V56T+G109A+A174S+G182*+D183*+N195F+V206L+R320A+K391A+G476K, H1*+N54S+V56T+G109A+Q169E+Q172K+A174T+G182*+D183*+N195F+V206L+K391A+G476K, H1*+N54S+V56T+G109A+Q169E+Q172K+G182*+D183*+N195F+V206L+K391A+G476K, H1*+N54S+V56T+G109A+W140Y+Q169E+Q172K+A174*+G182*+D183*+N195F+V206L+K391A+G476K, H1*+N54S+V56T+G109A+A174S+G182*+D183*+N195F+V206L+K391A, H1*+N54S+V56T+G109A+Q169E+Q172K+A174*+G182*+D183*+N195F+V206L+F328L+K391A+G476K, H1*+N54S+V56T+G109A+A174S+G182*+D183*+N195F+V206L+G476K, F113Q+R116H+D183*+G182*+N195F, H1*+N54S+V56T+G109A+A174S+G182*+D183*+N195F+V206L+A288L+K391A+G476K, H1*+N54S+V56T+G109A+A174S+G182*+D183*+N195F+V206L+N270G+K391A+G476K, Q169E+Q172K+A174*+D183*+G182*+N195F, H1*+N54S+V56T+G109A+A174S+G182*+D183*+N195F+V206L+K269Q+K391A+G476K, H1*+W48F+N54S+V56T+G109A+A174S+G182*+D183*+N195F+V206L+K391A+G476K, F113Q+R116Q+D183*+G182*+N195F, N54S+V56T+D183*+G182*+N195F, H1*+N54S+V56T+G109A+A174T+G182*+D183*+N195F+V206L+K391A+G476K, H1*+N54S+V56T+G109A+R116W+A174S+G182*+D183*+N195F+V206L+K391A+G476K, Q169E+Q172K+G182*+D183*+N195F, G182*+D183*+A186D, H1*+N54S+V56T+G109A+A174S+G182*+D183*+N195F+V206L+V238A+K391A+G476K, G182*+D183*+A186N, wherein numbering is according to SEQ ID NO: 13, H1*+N54S+V56T+G109A+A1745+G182*+D183*+N195F+V206I+I405L+A421H+A422P+A428T, H1*+N54S+V56T+G109A+Q172D+A174S+G182*+D183*+N195F+A204G+V206L+I405L+A421H+A422P+A428T, H1*+N54S+V56T+K72R+G109A+T134E+A174S+G182*+D183*+N195F+A204G+V206L+G255A+I405L+A421H+A422P+A428T, H1*+N54S+V56T+G109A+F113Q+R116H+T165G+Q172G+A174S+G182*+D183*+N195F+V206L+I405L+A421H+A422P+A428T, H1*+N54S+V56T+K72R+G109A+T134E+A174S+G182*+D183*+N195F+G196R+V206L+G255A+I405L+A421H+A422P+A428T+N475S, H1*+N54S+V56T+G109A+T134E+A174S+G182*+D183*+N195F+V206L+I405L+A421H+A422P+A428T, H1*+N54S+V56T+G109A+F113Q+N125D+A174S+G182*+D183*+N195F+V206L+I405L+A421H+A422P+A428T, H1*+N54S+V56T+G109A+R116V+A174S+G182*+D183*+N195F+V206L+I405L+A421H+A422P+A428T, H1*+N54S+V56T+G109A+R116Q+G133Q+T165G+Q172G+A174S+G182*+D183*+N195F+V206L+I405L+A421H+A422P+A428T, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116Q+Q172G+A174S+G182*+D183*+N195F+V206L+I405L+A421H+A422P+A428T+G448D, H1*+N54S+V56T+G109A+F113Q+R116H+Q172N+A174S+G182*+D183*+N195F+V206L+I405L+A421H+A422P+A428T, H1*+N54S+V56T+K72R+G109A+T134E+W167F+Q172N+A174S+G182*+D183*+N195F+V206L+G255A+A265G+I405L+A421H+A422P+A428T, H1*+N54S+V56T+K72R+G109A+R116Q+W167F+Q172R+L173V+A174S+G182*+D183*+N195F+V206L+A265G+I405L+A421H+A422P+A428T, H1*+N54S+V56T+K72R+G109A+R116Q+W167F+Q172R+A174S+G182*+D183*+N195F+V206L+I405L+A421H+A422P+A428T, H1*+N54S+V56T+K72R+G109A+F113Q+T134E+W167F+Q172G+A174S+G182*+D183*+N195F+V206L+G255A+I405L+A421H+A422P+A428T, H1*+N54S+V56T+G109A+F113Q+W167F+Q172G+A174S+G182*+D183*+N195F+V206L+I405L+A421H+A422P+A428T, H1*+N54S+V56T+K72R+G109A+A174S+G182*+D183*+N195F+V206L+G255A+I405L+A421H+A422P+A428T, H1*+N54S+V56T+K72R+G109A+R116Q+V120L+A174S+G182*+D183*+G184T+N195F+V206L+I405L+A421H+A422P+A428T, H1*+N54S+V56T+G109A+F113Q+R116H+W167F+Q172G+L173V+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, H1*+A37H+N54S+V56T+A60V+G109A+R116Q+W167F+Q172R+A174S+G182*+D183*+N195F+V206L+I405L+A421H+A422P+A428T, wherein numbering is according to SEQ ID NO: 14.

In one embodiment, the variant has an IF of at least 2.0 when compared to the parent polypeptide, wherein the IF is determined by use of Model J detergent at a temperature of 15° C. and an enzymes concentration of 0.05 mg/L.

Other variants according to the invention have an IF of at least 3.0, indicating that at least these variants have a significantly improved wash performance when compared the a parent polypeptide having an amino acid sequence set forth in SEQ ID NO: 15.

In a particular embodiment, the variant is selected from a group consisting of: H1*+N54S+V56T+G109A+A174S+G182*+D183*+N195F+V206L+K391A+G476K, H1*+N54S+V56T+G109A+Q169E+Q172K+A174*+N195F+V206L+K391A+G476K, H1*+N54S+V56T+G109A+R116H+A174S+G182*+D183*+N195F+V206L+K391A+G476K, H1*+N54S+V56T+K72R+G109A+F113Q+

R116Q+W167F+Q172G+A174S+G182*+D183*+G184T+N195F+V206L+K391A+P473R+G476K, H1*+N54S+V56T+G109A+R116Q+W167F+A174S+G182*+D183*+G184T+N195F+V206L+K391A+G476K, H1*+N54S+V56T+K72R+G109A+F113Q+R116Q+W167F+Q172G+A174S+G182*+D183*+N195F+V206L+K391A+G476K, H1*+N54S+V56T+G109A+F113Q+R116Q+Q172N+A174S+G182*+D183*+N195F+V206L+A265G+K391A+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+R116H+T134E+W167F+Q172G+L173V+A174S+G182*+D183*+N195F+V206L+G255A+K391A+G476K, and H1*+N54S+V56T+K72R+G109A+R116H+T134E+W167F+Q172G+L173V+A174S+G182*+D183*+N195F+V206L+G255A+K391A+Q395P+T444Q+P473R+G476K, wherein numbering is according to SEQ ID NO: 13.

In another embodiment, the variant has an IF of at least 3.0 when compared to the parent polypeptide and determined by use of Model J detergent, and wherein the variant is selected from the group consisting of: H1*+T51K+N54S+V56T+G109A+A174S+G182*+D183*+N195F+V206L+K391A+G476K, H1*+A37V+N54S+V56T+G109A+A174S+G182*+D183*+N195F+V206L+K391A+G476K, H1*+N54S+V56T+G109A+F113Y+A174S+G182*+D183*+N195F+V206L+K391A+G476K, H1*+N54S+V56T+G109A+R116Q+A174S+G182*+D183*+N195F+V206L+K391A+G476K, H1*+N54S+V56T+G109A+Q125A+A174S+G182*+D183*+N195F+V206L+K391A+G476K, H1*+N54S+V56T+G109A+A174S+G182*+D183*+N195F+V206L+K391A+P473R+G476K, H1*+N54S+V56T+G109A+A174S+G182*+D183*+N195F+V206L+K391A+P473A+G476K, H1*+N54S+V56T+G109A+A174S+G182*+D183*+N195F+V206L+K391A+T444D+G476K, H1*+N54S+V56T+K72S+G109A+A174S+G182*+D183*+N195F+V206L+K391A+G476K, H1*+G50A+N54S+V56T+G109A+L173V+A174S+G182*+D183*+N195F+A204V+V206L+K391A+G476K, H1*+N54S+V56T+G109A+Q172D+A174S+G182*+D183*+N195F+V206L+G346T+K391A+G476K+G477A, H1*+N54S+V56T+K72R+G109A+T134E+A174S+G182*+D183*+N195F+V206L+G255A+K391A+G476K, H1*+N54S+V56T+K72R+G109A+T134E+A174S+G182*+D183*+N195F+V206L+K391A+G476K, H1*+N54S+V56T+K72R+G109A+T134E+A174S+G182*+D183*+N195F+V206L+D377H+K391A+G476K, H1*+N54S+V56T+K72R+G109A+T134E+A174S+G182*+D183*+G184T+N195F+V206L+K391A+G476K, H1*+N54S+V56T+G109A+T134E+A174S+G182*+D183*+G184T+N195F+V206L+D377H+K391A+G476K, H1*+N54S+V56T+G109A+Q172D+A174Q+G182*+D183*+N195F+V206L+K391A+G476K+G477A, H1*+N54S+V56T+G109A+T134E+A174S+G182*+D183*+G184T+N195F+V206L+K391A+G476K, H1*+N54S+V56T+K72R+G109A+A174S+G182*+D183*+N195F+G184T+V206L+K391A+G476K, H1*+N54S+V56T+G109A+A174S+G182*+D183*+N195F+V206L+V238G+K391A+G476K, H1*+N54S+V56T+G109A+W167F+Q172E+L173P+A174K+G182*+D183*+N195F+V206L+K391A+G476K, H1*+N54S+V56T+G109A+A174S+G182*+D183*+N195F+V206L+L250M+K391A+G476K, H1*+N54S+V56T+G109A+F113Q+R116H+Q172G+A174S+G182*+D183*+N195F+V206L+K391A+G476K, H1*+N54S+V56T+G109S+F113Q+R116Q+A174S+G182*+D183*+N195F+V206L+K391A+G476K, H1*+N54S+V56T+G109A+Q172D+A174S+G182*+D183*+N195F+A204G+V206L+K391A+P473R+G476K, H1*+N54S+V56T+K72R+G109A+T134E+A174S+G182*+D183*+N195F+A204G+V206L+G255A+K391A+P473R+G476K, H1*+N54S+V56T+K72R+G109A+W167F+A174S+G182*+D183*+N195F+A204G+V206L+K391A+G476K, H1*+N54S+V56T+M105F+G109A+A174S+G182*+D183*+N195F+V206L+R320A+S323N+K391A+C474V+G476K, H1*+N54S+V56T+K72R+G109A+A174S+G182*+D183*+N195F+V206L+G255A+K391A+C474V+G476K, H1*+N54S+V56T+G109A+T134E+A174S+G182*+D183*+N195F+V206L+K391A+C474V+G476K, H1*+N54S+V56T+G109A+A174S+G182*+D183*+N195F+V206L+D377H+K391A+C474V+G476K, H1*+N54S+V56T+K72R+G109A+A174S+G182*+D183*+N195F+V206L+K391A+C474V+G476K, H1*+N54S+V56T+G109A+R116Q+Q172D+A174S+G182*+D183*+N195F+V206L+G346T+K391A+T444Q+G477A+G476K, H1*+N54S+V56T+G109S+R116Q+W167F+Q172N+A174S+G182*+D183*+N195F+V206L+K391A+G476K, H1*+N54S+V56T+G109S+W167F+Q172G+A174S+G182*+D183*+N195F+V206L+K391A+G476K, H1*+N54S+V56T+G109A+F113Q+Q172G+A174S+G182*+D183*+N195F+V206L+K391A+T444Q+G476K, H1*+N54S+V56T+G109A+F113Q+R116H+Q172G+A174S+G182*+D183*+N195F+V206L+K391A+T444Q+G476K, H1*+N54S+V56T+G109A+F113Q+A174S+G182*+D183*+N195F+V206L+K391A+C474V+G476K, H1*+N54S+V56T+G109A+Q172N+A174S+G182*+D183*+N195F+V206L+V264I+K391A+C474V+G476K, H1*+N54S+V56T+K72R+G109A+T134E+A174S+G182*+D183*+N195F+V206L+G255A+K391A+C474V+G476K, H1*+N54S+V56T+G109A+F113Q+R116H+Q172G+A174S+G182*+D183*+N195F+V206L+K391A+T444Q+P473R+G476K, H1*+N54S+V56T+G109A+F113Q+R116Q+Q172G+A174S+G182*+D183*+N195F+V206L+K391A+T444Q+G476K, H1*+N54S+V56T+G109A+F113Q+R116H+T165G+Q172G+A174S+G182*+D183*+N195F+V206L+K391A+T444Q+G476K, H1*+N54S+V56T+G109A+F113Q+R116Q+T165G+Q172G+A174S+G182*+D183*+N195F+V206L+K391A+T444Q+G476K, H1*+N54S+V56T+G109A+F113Q+Q172N+A174S+G182*+D183*+N195F+V206L+K391A+T444Q+G476K, H1*+N54S+V56T+G109A+F113Q+R116H+Q172N+A174S+G182*+D183*+N195F+V206L+K391A+G476K, H1*+N54S+V56T+G109A+F113Q+R116H+Q172M+A174S+G182*+D183*+N195F+V206L+K391A+G476K, H1*+N54S+V56T+K72R+G109A+T134E+T165G+A174S+G182*+D183*+N195F+V206L+G255A+K391A+G476K, H1*+N54S+V56T+G109A+F113Q+R116H+Q172N+A174S+G182*+D183*+N195F+V206L+K391A+G476K, H1*+N54S+V56T+G109A+R116Q+W167F+Q172N+L173V+A174S+G182*+D183*+N195F+V206L+K391A+T444Q+G476K, H1*+N54S+V56T+G109A+G133Q+W167F+Q172N+A174S+G182*+D183*+N195F+V206L+Q395P+K391A+G476K, H1*+A37V+N54S+V56T+K72R+G109A+R116H+W167F+Q172R+A174S+G182*+D183*+G184T+N195F+V206L+K391A+P473R+G476K, H1*+N54S+V56T+K72R+G109A+F113Q+R116H+W167F+Q172G+L173V+A174S+G182*+D183*+G184T+N195F+V206L+K391A+T444Q+P473R+G476K, H1*+N54S+V56T+G109S+R116Q+W167F+Q172R+A174S+G182*+D183*+N195F+V206L+K391A+G476K, H1*+N54S+V56T+G109S+R116Q+W167F+Q172G+A174S+G182*+D183*+N195F+V206L+K391A+P473R+G476K, H1*+N54S+V56T+G109S+F113Q+W167F+Q172N+A174S+G182*+D183*+N195F+V206L+K391A+G476K, H1*+A37V+N54S+V56T+G109S+F113Q+W167F+Q172R+A174S+G182*+D183*+N195F+V206L+

K391A+G476K, H1*+N54S+V56T+K72R+G109A+R116H+T134E+W167F+Q172G+L173V+A174S+G182*+D183*+N195F+V206L+G255A+K391A+Q395P+T444Q+P473R+G476K, H1*+N54S+V56T+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+T134E+W167F+Q172R+A174S+G182*+D183*+N195F+V206L+G255A+K391A+T444Q+P473R+G476K, H1*+N54S+V56T+K72R+G109A+T134E+W167F+Q172N+A174S+G182*+D183*+N195F+V206L+G255A+A265G+K391A+T444Q+P473R+G476K, H1*+N54S+V56T+K72R+G109A+G133Q+W167F+Q172R+A174S+G182*+D183*+N195F+V206L+K391A+G476K, H1*+N54S+V56T+K72R+G109A+F113Q+R116Q+W167F+Q172G+A174S+G182*+D183*+N195F+A204G+V206L+K391A+G476K, H1*+N54S+V56T+G109A+F113Q+R116Q+A174S+G182*+D183*+N195F+V206L+K391A+P473R+G476K, H1*+N54S+V56T+A60V+G109A+R116Q+W167F+Q172N+A174S+G182*+D183*+N195F+V206L+K391A+G476K, H1*+N54S+V56T+A60V+G109A+R116H+Q172R+L173V+A174S+G182*+D183*+N195F+V206L+K391A+G476K, H1*+A37H+N54S+V56T+A60V+G109A+R116Q+T165G+A174S+G182*+D183*+N195F+V206L+K391A+G476K, H1*+N54S+V56T+A60V+G109A+R116Q+A174S+G182*+D183*+N195F+V206L+K391A+G476K, H1*+A37H+N54S+V56T+A60V+G109A+R116Q+W167F+Q172R+A174S+G182*+D183*+N195F+V206L+K391A+G476K, H1*+A37H+N54S+V56T+A60V+G109A+R116Q+W167F+Q172N+A174S+G182*+D183*+N195F+V206L+K391A+G476K, H1*+N54S+V56T+A60V+G109A+R116Q+T165G+A174S+G182*+D183*+N195F+V206L+K391A+T444Q+P473R+G476K, H1*+N54S+V56T+A60V+G109A+R116Q+W167F+Q172N+L173V+A174S+G182*+D183*+N195F+V206L+K391A+G476K, H1*+N54S+V56T+A60V+G109A+R116Q+W167F+Q172R+A174S+G182*+D183*+N195F+V206L+K391A+G476K, H1*+N54S+V56T+G109A+R116A+A174S+G182*+D183*+N195F+A204G+V206L+K391A+P473R+G476K, H1*+N54S+V56T+K72R+G109A+F113Q+T134E+A174S+G182*+D183*+N195F+V206L+G255A+K391A+P473R+G476K, H1*+N54S+V56T+K72R+G109A+R116Q+A174S+G182*+D183*+G184T+N195F+V206L+K391A+G476K, H1*+A37V+N54S+V56T+G109A+R116A+T165G+A174S+G182*+D183*+N195F+V206L+K391A+G476K, H1*+A37V+N54S+V56T+G109A+R116Q+T165G+A174S+G182*+D183*+N195F+V206L+M246F+K391A+G476K, H1*+N54S+V56T+K72R+G109A+F113Q+R116H+A174S+G182*+D183*+G184T+N195F+V206L+K391A+T444Q+G476K, H1*+N54S+V56T+G109S+F113Q+A174S+G182*+D183*+N195F+V206L+K391A+T444Q+G476K, H1*+N54S+V56T+G109A+F113Q+R116H+W167F+Q172G+L173V+A174S+G182*+D183*+N195F+V206L+K391A+P473R+G476K, H1*+N54S+V56T+G109A+F113Q+R116Q+Q172N+A174S+G182*+D183*+N195F+V206L+A265G+K391A+P473R+G476K, H1*+A37V+N54S+V56T+G109A+R116Q+T165G+A174S+G182*+D183*+N195F+V206L+K391A+G476K, H1*+A37H+N54S+V56T+G109A+R116H+T165G+A174S+G182*+D183*+N195F+V206L+M246F+K391A+G476K, H1*+N54S+V56T+G109A+R116A+Q172N+L173V+A174S+G182*+D183*+N195F+V206L+K391A+G476K, H1*+P45A+N54S+V56T+G109A+A174S+G182*+D183*+N195F+V206L+K391A+C474V+G476K, H1*+N54S+V56T+G109A+Q118R+T134E+A174S+G182*+D183*+N195F+V206L+K391A+G476K, H1*+N54S+V56T+G109A+A174S+G182*+D183*+G184T+N195F+V206L+K391A+G476K, H1*+G50A+T51A+N54S+V56T+G109A+A174S+G182*+D183*+N195F+V206L+K391A+G476K, H1*+N54S+V56T+G109A+A174S+G182*+D183*+N195F+V206L+V264F+K391A+G476K, H1*+G7K+N54S+V56T+G109A+A174S+G182*+D183*+N195F+V206L+K391A+G476K, H1*+N54S+V56T+G109A+A174S+G182*+D183*+N195F+V206L+G255A+Q256A+K391A+G476K, H1*+N54S+V56T+G109A+W167Y+A174S+G182*+D183*+N195F+V206L+K391A+G476K, H1*+N54S+V56T+G109A+A174S+G182*+D183*+N195F+V206L+K391A+G476K, H1*+N16H+V17L+N54S+V56T+G109A+A174S+G182*+D183*+N195F+V206L+Y382F+K391A+G476K, H1*+Q32S+N54S+V56T+G109A+A174S+G182*+D183*+N195F+V206L+Q385L+K391A+G476K, H1*+N54S+V56T+R87S+G109A+R171H+A174S+G182*+D183*+N195F+V206L+K391A+G476K, H1*+N54S+V56T+G109A+R116H+Q169E+Q172K+A174*+G182*+D183*+N195F+V206L+K391A+G476K, H1*+N54S+V56T+G109A+A174*+G182*+D183*+N195F+V206L+K391A+G476K, H1*+K72R+G109A+F113Q+R116Q+W167F+Q172G+A174S+G182*+D183*+G184T+N195F+V206L+K391A+P473R+G476K, H1*+N54S+V56T+K72R+G109A+F113Q+R116Q+W167F+Q172G+A174S+G182*+D183*+G184T+N195F+V206L+P473R+G476K, H1*+N54S+V56T+G109A+Q169E+Q172G+A174*+G182*+D183*+N195F+V206L+K391A+G476K, H1*+N54S+V56T+K72R+G109A+F113Q+R116Q+W167F+Q172G+A174S+G182*+D183*+G184T+N195F+K391A+P473R+G476K, H1*+N54S+V56T+G109A+R116W+Q169E+Q172K+A174*+G182*+D183*+N195F+V206L+K391A+G476K, H1*+N54S+V56T+G109A+Q169E+Q172K+A174*+G182*+D183*+N195F+V206F+K391A+G476K, H1*+V56T+G109A+A174S+G182*+D183*+N195F+V206L+K391A+G476K, H1*+N54S+V56T+G109A+A174S+G182*+D183*+N195F+V206L+N260G+K391A+G476K, H1*+N54S+V56T+K72R+G109A+A174S+G182*+D183*+N195F+V206L+K391A+G476K, H1*+N54S+V56T+G109A+Q169E+Q172K+A174*+G182*+D183*+G184T+N195F+V206L+K391A+G476K, H1*+N54S+V56T+G109A+Q169E+Q172K+A174*+G182*+D183*+N195F+V206L+Y295N+K391A+G476K, H1*+N54S+V56T+G109A+W167F+A174S+G182*+D183*+N195F+V206L+K391A+G476K, H1*+N54S+V56T+G109A+Q169E+Q172K+A174*+G182*+D183*+A186N+N195F+V206L+K391A+G476K, H1*+N54S+V56T+G109A+Q169E+Q172K+A174*+G182*+D183*+N195F+V206L+A288V+K391A+G476K, H1*+N54S+V56T+G109A+Q169E+Q172K+A174*+G182*+D183*+N195F+V206L+G255A+K391A+G476K, H1*+N54S+G109A+Q169E+Q172K+A174*+G182*+D183*+N195F+V206L+K391A+G476K, H1*+W48F+N54S+V56T+G109A+Q169E+Q172K+A174*+G182*+D183*+N195F+V206L+K391A+G476K, H1*+N54S+V56T+G109A+Q169E+Q172K+A174*+G182*+D183*+N195F+V206L+V291A+K391A+G476K, H1*+N54S+V56T+G109A+F113Q+A174S+G182*+D183*+N195F+V206L+K391A+G476K, H1*+N54S+V56T+G109A+Q169E+Q172K+A174*+G182*+D183*+N195F+V206L+R320A+S323N+K391A+G476K, H1*+V56T+G109A+Q169E+Q172K+A174*+G182*+D183*+N195F+V206L+K391A+G476K, H1*+N54S+V56T+K72R+G109A+F113Q+R116H+W167F+Q172G+A174S+G182*+D183*+G184T+N195F+V206L+K391A+P473R+G476K, H1*+N54S+V56T+G109A+A174S+G182*+D183*+N195F+V206L+N270T+K391A+G476K, H1*+N54S+V56T+G109A+Q169E+Q172K+A174*+

G182*+D183*+N195F+V206L+G476K, H1*+N54S+V56T+G109A+Q169E+Q172K+A174*+G182*+D183*+N195F+V206L+N260G+K391A+G476K, H1*+N54S+V56T+G109A+F113Q+R116H+A174S+G182*+D183*+N195F+V206L+K391A+G476K, wherein numbering is according to SEQ ID NO: 13, H1*+N54S+V56T+G109A+F113Q+R116H+Q172G+A174S+G182*+D183*+N195F+V206L+I405L+A421H+A422P+A428T, H1*+N54S+V56T+G109A+F113Q+R116Q+Q172N+A174S+G182*+D183*+N195F+V206L+A265G+I405L+A421H+A422P+A428T, wherein numbering is according to SEQ ID NO: 14.

The variants according to the present invention may further comprise one or more additional alterations than those described above at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide may be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants according to the present invention may consist of 400 to 485 amino acids, e.g., 410 to 485, 425 to 485, and 440 to 485 amino acids.

Polynucleotides

The present invention also relates to polynucleotides encoding a variant of the present invention. Thus, in particular, the present invention relates to a polynucleotide encoding a variant comprising an alteration in one or more positions corresponding to the H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, S304, R320, H321, S323, V326, K391, I405, A421, A422, A428, G448, D476, and G477 of SEQ ID NO: 14.

The term "polynucleotides encoding" as used herein, refers to a polynucleotide that encodes a mature polypeptide having alpha-amylase having alpha-amylase activity. In one aspect, the polypeptide coding sequence is the nucleotide sequence set forth in SEQ ID NO: 1, 2, or 3.

In one embodiment, the polynucleotide encoding a variant according to the present invention as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99% but less than 100% sequence identity to the polynucleotide of SEQ ID NOs: 1, 2 and 3.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in particular, the present invention relates to a nucleic acid construct comprising a polynucleotide encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, wherein the polynucleotide is operately linked to one or more control sequences.

The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" as used herein, refers to a configuration in which a control sequence is placed at an appropriate position relative to the coding sequence of a polynucleotide such that the control sequence directs expression of the coding sequence.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter comprises transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Expression Vectors

The present invention also relates to recombinant expression vectors comprising a polynucleotide encoding a variant of the present invention, a promoter, and transcriptional and translational stop signals. Thus, the present invention relates to an expression vector, optionally recombinant, comprising a polynucleotide encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, a promotor, and transcriptional and translational stop signals.

The term "expression vector" as used herein, refers to a linear or circular DNA molecule that comprises a polynucleotide encoding a variant and is operably linked to control sequences that provide for its expression.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

The skilled person would know which expression vector is the most suitable for specific expression systems. Thus, the present invention is not limited to any specific expression vector, but any expression vector comprising the polynucleotide encoding a variant according to the invention is considered part of the present invention.

Host Cells

The present invention also relates to recombinant host cells, comprising a polynucleotide encoding a variant of the present invention operably linked to one or more control sequences that direct the production of a variant of the present invention. Thus, the present invention relates to a host cell, optionally a recombinant host cell, comprising a polynucleotide encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, operably linked to one or more control sequences that direct the production of the variant.

The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

A construct or vector comprising a polynucleotide is introduced into a host cell so that the construct or vector is maintained as a chromosomal integrant or as a self-replicating extrachromosomal vector as described earlier. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

Methods According to the Invention

The present invention also relates to methods of producing a variant, comprising: (a) cultivating a host cell of the present invention under conditions suitable for expression of the variant; and (b) recovering the variant. Thus, the present invention relates to a method of producing a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, wherein the method comprises the steps of a) cultivating a host cell according to the invention under conditions suitable for expression of the variant, and b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the polypeptides having alpha amylase activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Furthermore, the present invention relates to methods for obtaining a variant, comprising introducing into a parent alpha-amylase having at least 80% sequence identity to the polypeptide of SEQ ID NO: 4

(a) a substitution and/or deletion of two or more positions in the parent alpha-amylase said positions corresponding to positions 181, 182, 183, and 184 of the mature polypeptide of SEQ ID NO: 4; and (b) an alteration at one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, I405, A421, A422, A428, R439, G448, W467, D476, and G477 of SEQ ID NO: 14, wherein the resulting variant has at least 80%, such as at least 85%, such as at least 90%, such as at least 95%, such as at least 97%, but less than 100% sequence identity with the mature polypeptide of SEQ ID NO: 4, wherein said variant has alpha-amylase activity;

(c) recovering said variant.

The variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent polypeptide and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure may be used in the present invention. There are many commercial kits available that can be used to prepare variants. The skilled person in the art is well-aware of such commercial kits and how to use them.

Synthetic gene construction entails in vitro synthesis of a designed polynucleotide molecule to encode a polypeptide of interest. Gene synthesis may be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions may be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that may be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods may be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides may be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The present invention also relates to a method of improving wash performance of a parent polypeptide having the amino acid sequence of SEQ ID NO: 13 or 14, or having at least 80% sequence identity thereto, said method comprising the steps of:

a) a substitution and/or deletion of two, three or four positions in the parent alpha-amylase said positions corresponding to positions 181, G182, D183, and G184 of the mature polypeptide of SEQ ID NO: 4; and b) an alteration at one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, I405, A421, A422, A428, R439, G448, W467, D476, and G477 of SEQ ID NO: 14, wherein the variant has at least 80%, at least 85%, at least 90%, at least 95%, at least 97%, at least 98%, at least 99%, but less than 100% sequence identity with the polypeptide of SEQ ID NO: 4 or 7, and wherein the variant has alpha-amylase activity and improved wash performance compared to the parent polypeptide.

In one embodiment, the variant has at least 50%, such as at least 60%, or at least 70%, or at least 80%, or at least 90%, or at least 100% of the activity of the parent polypeptide having the amino acid sequence of SEQ ID NO: 7.

In one embodiment, the activity is determined according to a Phadebas assay.

The alpha-amylase activity may be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The variant sample to be analyzed is diluted in activity buffer with the desired pH. Two substrate tablets are suspended in 5 mL activity buffer and mixed on magnetic stirrer. During mixing of substrate transfer 150 μl to microtiter plate (MTP) or PCR-MTP. Add 30 μl diluted amylase sample to 150 μl substrate and mix. Incubate for 15 minutes at 37° C. The reaction is stopped by adding 30 μl M NaOH and mix. Centrifuge MTP for 5 minutes at 4000×g. Transfer 100 μl to new MTP and measure absorbance at 620 nm.

The alpha-amylase sample should be diluted so that the absorbance at 620 nm is between 0 and 2.2, and is within the linear range of the activity assay.

Thus, in one embodiment, the activity is determined by a method comprising the steps of;

a) incubating an alpha-amylase variant according to the invention with a dyed amylose substrate for 15 minute at 37° C.; and b) measuring the absorption at OD 620 nm.

In a further embodiment, the activity is determined by a method comprising the steps of;

a) incubating an alpha-amylase variant according to the invention with a dyed amylose substrate for 15 minute at 37° C.; and b) centrifuging the sample;

c) transferring the supernatant to reader plate, and measuring the absorption at OD 620 nm.

Fermentation Broth Formulations or Cell Compositions

The present invention also relates to a fermentation broth formulation or a cell composition comprising a polypeptide of the present invention. Thus, in one embodiment, the fermentation broth formulation or the cell composition comprises a polynucleotide encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, 1214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, a nucleic acid construct encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, or an expression vector encoding a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q269, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, I405, A421, A422, A428, R439, G448, W467, D476, and G477 of SEQ ID NO: 14. The fermentation broth product may further comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a particular embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one embodiment, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may comprise the unfractionated contents of the fermentation materials derived at the end of the fermentation. Typically, the cell-killed whole broth or composition comprises the spent culture medium and cell debris present after the microbial cells (e.g., filamentous fungal cells) are grown to saturation, incubated under carbon-limiting conditions to allow protein synthesis. In some embodiments, the cell-killed whole broth or composition comprises the spent cell culture medium, extracellular enzymes, and killed filamentous fungal cells. In some embodiments, the microbial cells present in the cell-killed whole broth or composition may be permeabilized and/or lysed using methods known in the art.

A whole broth or cell composition as described herein is typically a liquid, but may comprise insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a variant according to the invention. Thus, the invention relates to a composition comprising a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, I405, A421, A422, A428, R439, G448, W467, D476, and G477 of SEQ ID NO: 14.

In one embodiment, the composition comprises a variant comprising a) a deletion and/or a substitution at two or more positions corresponding to positions R181, G182, D183, and G184 of the amino acid sequence as set forth in SEQ ID NOs: 7 or 10, and b) an alteration at one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, T173, A174, A186, E190, T193, N195, A204, V206, P211, V213, 1214, L217, A225, L235, V238, K242, S244, M246, L250, G255, Q256, N260, A263, V264, Y267, K269, N270, G273, S280, W284, T285, M286, F289, V291, Y295, Q299, R320, H321, S323, H324, V326, F328, T334, G337, Q345, G346, T355, S376, D377, S381, Y382, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14. Preferably, the compositions are enriched in such a variant. The term "enriched" as used herein, refers to that the alpha-amylase activity of the composition has been increased, e.g., with an enrichment factor of at least 1.1.

The compositions may comprise a variant of the present invention as the major enzymatic component, e.g., a mono-component composition. In another embodiment, the composition further comprises at least one further active component.

The term "active component" as used herein, refers to any biological or non-biological molecule which in itself is active. For example, an active component is an enzyme.

Thus, in one embodiment, the further active component is an enzyme, such as a protease, lipase, cellulose, pectate lyase and mannanase. Thus, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In one embodiment, the composition is a liquid laundry or liquid dish wash composition, such as an Automatic Dish Wash (ADW) liquid detergent composition, or a powder laundry, such as a soap bar, or powder dish wash composition, such as an ADW unit dose detergent composition and such as a Hand Dish Wash (HDW) detergent composition.

The choice of additional components is within the skills of the skilled person in the art and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment of the present invention, the variant of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor. The term "protein" in this context is contemplated to be understood to include a variant according to the present invention.

A composition for use in automatic dish wash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The variants of the invention as well as the further active components, such as additional enzymes, may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO092/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

A variant of the present invention may also be incorporated in the detergent formulations disclosed in WO97/07202, which is hereby incorporated by reference.

Examples are given herein of preferred uses of the compositions of the present invention. The dosage of the composition and other conditions under which the composition is used may be determined on the basis of methods known in the art.

In particular, a composition according to the present invention further comprises a chelator.

The term "chelator" as used herein, refers to chemicals which form molecules with certain metal ions, inactivating the ions so that they cannot react with other elements. Thus, a chelator may be defined as a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium (Ca2+) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation. Chelating agent may be present in the composition in an amount from 0.0001 wt % to 20 wt %, preferably from 0.01 to 10 wt %, more preferably from 0.1 to 5 wt %.

Non-limiting examples of chelating agents are; EDTA, DTMPA, HEDP, and citrate. Thus, in one embodiment, the composition comprises a variant according to the invention and a chelating agent, such as EDTA, DTMPA, HEDP or citrate.

The term "EDTA" as used herein, refers to ethylenediamine-tetra-acetic acid which falls under the definition of "strong chelating agents".

The term "DTMPA" as used herein, refers to diethylenetriamine penta(methylene phosphonic acid). DTMPA can inhibit the scale formation of carbonate, sulfate and phosphate.

The term "HEDP" as used herein, refers to hydroxyethane diphosphonic acid, which falls under the definition of "strong chelating agents".

The chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In an assay the chelating agents may be characterized by their ability to reduce the concentration of free calcium ions (Ca2+) from 2.0 mM to 0.10 mM or less at pH 8.0, e.g. by using a test based on the method described by M. K. Nagarajan et al., JAOCS, Vol. 61, no. 9 (September 1984), pp. 1475-1478.

For reference, a chelator having the same ability to reduce the concentration of free calcium ions (Ca2+) from 2.0 mM to 0.10 mM at pH as EDTA at equal concentrations of the chelator are said to be strong chelators.

The composition of the present invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components may be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Another form of composition is in the form of a soap bar, such as a laundry soap bar, and may be used for hand washing laundry, fabrics and/or textiles. The term "soap bar" as used herein, refers to includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term "solid" as used herein, refers to a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The soap bar may also comprise complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the soap bars by any single method. The premix of the invention may be added to the soap at different stages of the process. For example, the premix comprising a soap, an enzyme, optionally one or more additional enzymes, a protease inhibitor, and a salt of a monovalent cation and an organic anion may be prepared and the mixture may then plodded. The enzyme and optional additional enzymes may be added at the same time as an enzyme inhibitor, e.g. a protease inhibitor, for example in liquid form. Besides the mixing step and the plodding step, the process may further comprise the steps of milling, extruding, cutting, stamping, cooling and/or wrapping.

Uses

The present invention further relates to the use of a variant according to the present invention in a cleaning process such as laundry or hard surface cleaning including automated dish wash and industrial cleaning. The soils and stains that are important for cleaning are composed of many different substances, and a range of different enzymes, all with different substrate specificities, have been developed for use in detergents both in relation to laundry and hard surface cleaning, such as dishwashing. These enzymes are considered to provide an enzyme detergency benefit, since they specifically improve stain removal in the cleaning process that they are used in, compared to the same process without enzymes. Stain removing enzymes that are known in the art include enzymes such as proteases, amylases, lipases, cutinases, cellulases, endoglucanases, xyloglucanases, pectinases, pectin lyases, xanthanases, peroxidaes, haloperoxygenases, catalases and mannanases.

In one embodiment, the invention relates the use of variants of the present invention in detergent compositions, for use in cleaning hard-surfaces, such as dish wash, or in laundering or for stain removal. In another embodiment, the invention relates to the use of an alpha-amylase variant according to the invention in a cleaning process such as laundry or hard surface cleaning including, but not limited to, dish wash and industrial cleaning. Thus, in one embodiment, the invention relates to the use of a variant comprising an alteration in one or more positions corresponding to the positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, I405, A421, A422, A428, R439, G448, W467, D476, and G477 of SEQ ID NO: 14 in a cleaning process such as laundry or hard surface cleaning including dish wash and industrial cleaning.

In a particular embodiment, the invention relates to the use of a variant comprising a) a substitution and/or deletion of two, three or four positions in the parent alpha-amylase said positions corresponding to positions 181, G182, D183, and G184 of the mature polypeptide of SEQ ID NO: 4; and b) an alteration at one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, W140, G142, G149, T165, W167, Q169, R171, Q172, L173, A174, G184, A186, E190, T193, N195, A204, V206, P211, I214, V215, L217, L219, A225, L235, V238, K242, S244, M246, M248, L250, G255, Q256, N260, A263, V264, Y267, K269, N270, G273, S280, W284, T285, M286, F289, V291, Y295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, G476, G477, and K484 of SEQ ID NO: 13; or H1, A37, T40, N54, V56, A60, K72, G109, F113, R116, N125, F133, T134, T165, Q169, Q172, L173, A174, G184, A186, E190, N195, G196, A204, V206, A225, L228, K242, S244, G255, N260, A265, K269, S280, W284, Y295, S304, R320, H321, S323, V326, K391, 1405, A421, A422, A428, R439, G448, W467, D476, and G477 of SEQ ID NO: 14, in a cleaning process such as laundry or hard surface cleaning including dish wash and industrial cleaning.

In one embodiment of the invention relates the use of a composition according to the invention comprising a variant of the present invention together with one or more surfactants and optionally one or more detergent components, selected from the list comprising of hydrotropes, builders and co-builders, bleaching systems, polymers, fabric hueing agents and adjunct materials, or any mixture thereof in detergent compositions and in detergent applications.

A further embodiment is the use of the composition according to the invention comprising a variant of the present invention together with one or more surfactants, and one or more additional enzymes selected from the group comprising of proteases, lipases, cutinases, cellulases, endoglucanases, xyloglucanases, pectinases, pectin lyases, xanthanases, peroxidaes, haloperoxygenases, catalases and mannanases, or any mixture thereof in detergent compositions and in detergent applications.

In another aspect, the invention relates to a laundering process which may be for household laundering as well as industrial laundering. Furthermore, the invention relates to a process for the laundering of textiles (e.g. fabrics, garments, cloths etc.) where the process comprises treating the textile with a washing solution containing a detergent composition and an alpha-amylase of the present invention. The laundering can for example be carried out using a household or an industrial washing machine or be carried out by hand using a detergent composition containing a glucoamylase of the invention.

In another aspect, the invention relates to a dish wash process which may be for household dish wash as well as industrial dish wash. The term “dish wash” as used herein, refers to both manual dish wash and automated dish wash. Furthermore, the invention relates to a process for the washing of hard surfaces (e.g. cutlery such as knives, forks, spoons; crockery such as plates, glasses, bowls; and pans) where the process comprises treating the hard surface with a washing solution containing a detergent composition and an alpha-amylase variant of the present invention. The hard surface washing can for example be carried out using a household or an industrial dishwasher or be carried out by hand using a detergent composition containing an alpha-amylase of the invention, optionally together with one or more further enzymes selected from the group comprising of proteases, amylases, lipases, cutinases, cellulases, endoglucanases, xyloglucanases, pectinases, pectin lyases, xanthanases, peroxidaes, haloperoxygenases, catalases, mannanases, or any mixture thereof.

In a further aspect, the invention relates to a method for removing a stain from a surface comprising contacting the surface with a composition comprising an alpha-amylase of the present invention together with one or more surfactants and optionally one or more detergent components selected from the list comprising of hydrotropes, builders and co-builders, bleaching systems, polymers, fabric hueing agents and adjunct materials, or any mixture thereof in detergent compositions and in detergent applications. A further aspect is a method for removing a stain from a surface comprising contacting the surface with a composition comprising an alpha-amylase variant of the present invention together with one or more surfactants, one or more additional enzymes selected from the group comprising of proteases, lipases, cutinases, cellulases, endoglucanases, xyloglucanases, pectinases, pectin lyases, xanthanases, peroxidaes, haloperoxygenases, catalases and mannanases, or any mixture thereof in detergent compositions and in detergent applications.

The present invention is further described by the following examples that should not be construed as limiting the scope of the invention.

EXAMPLES

Example 1a: Construction of the Parent Polypeptide as Set Forth in SEQ ID NO: 13

Construction of a hybrid between the A and B domain from a polypeptide having the amino acid sequence set forth SEQ ID NO: 10 (the first parent polypeptide) and the C domain from a polypeptide having the amino acid sequence set forth SEQ ID NO: 11 (the second parent polypeptide).

Based on 3D structural alignment of the two amylases, amino acid no 1 to amino acid no 397 of the first parent polypeptide are defined as domain A and B, and amino acid 398 to amino acid no. 485 of the second parent polypeptide are defined as the C domain. Synthetic DNA fragments coding for part of the A domain from the first parent polypeptide and the C domain from the second parent polypeptide were designed and purchased from an external vendor. In addition to combining fragments of the two different amylases, the following stabilizing substitutions were designed into the synthetic amylase gene: G182* and D183*.

The new gene consisting of a gene fragment encoding the A and B domain of the first parent polypeptide and the C domain of the second parent polypeptide coded by the synthetic gene fragments was constructed by triple SOE (splicing by overlap extension) PCR method. The two fragments were assembled by splicing by overlap extension polymerase chain reaction and transformed into a competent *B. subtilis* host for overexpression. The resulting amylase consisting of the A and B domain from the first parent polypeptide and the C domain from the second parent polypeptide, and having the deletions of G182* and D183* is the polypeptide as set forth in SEQ ID NO: 13.

Example 1b: Construction of the Parent Polypeptide as Set Forth in SEQ ID NO: 14

Construction of a hybrid between the A and B domain from a polypeptide having the amino acid sequence set forth SEQ ID NO: 10 (the first parent polypeptide) and the C domain from a polypeptide having the amino acid sequence set forth SEQ ID NO: 12 (the third parent polypeptide).

Based on 3D structural alignment of the two amylases, amino acid no 1 to amino acid no 397 of the first parent polypeptide are defined as domain A and B, and amino acid 398 to amino acid no. 485 of the third parent polypeptide are defined as the C domain. Synthetic DNA fragments coding for part of the A domain from the first parent polypeptide and the C domain from the second parent polypeptide were designed and purchased from an external vendor. In addition to combining fragments of the two different amylases, the following stabilizing substitutions were designed into the synthetic amylase gene: G182* and D183*.

The new gene consisting of a gene fragment encoding the A and B domain of the first parent polypeptide and the C domain of the second parent polypeptide coded by the synthetic gene fragments was constructed by triple SOE (splicing by overlap extension) PCR method. A DNA fragment was amplified from an expression clone of the first amylase. The fragments were finally assembled by triple SOE and the derived PCR fragment was transformed into a suitable *B. subtilis* host and the gene integrated into the *B. subtilis* chromosome by homologous recombination into the pectate lyase (pel) locus. The gene coding for chloramphenicol acetyltransferase was used as maker (as described in (Diderichsen et al., 1993, Plasmid 30: 312-315). Chloramphenicol resistant clones were analyzed by DNA sequencing to verify the correct DNA sequence of the construct. The resulting amylase consisting of the A and B domain from the first parent polypeptide and the C domain from the second parent polypeptide, and having the deletions of G182* and D183* is the polypeptide as set forth in SEQ ID NO: 14.

Example 2: Generation of Variants According to the Invention

The variants of the present invention have been generated by site-directed mutagenesis. Genomic DNA prepared from the organism containing amylase gene at the Pel locus was used as template for generating the site-directed mutants.

Mutagenic forward primer and PnMi4490 (CAATCCAAGAGAACCCTGATACGGATG—SEQ ID NO: 16) reverse primer was used to generate a ~3.8 kb fragment. This fragment was used as a megaprimer along with PnMi4491 (CGGAACGCCTGGCTGACAACACG—SEQ ID NO: 17) forward primer to get 6 kb insertion cassette. To enable integration in the Pel locus by double cross-over upon transformation, along with the amylase and cat genes, the cassette contained upstream and downstream Pel sequences at the ends. Selection was done on LB Agar containing chloramphenicol and the mutation was confirmed by DNA sequencing of amylase gene.

A library of variants were generated where different combinations of alterations in the following positions were made; H1, T5, G7, Q11, N16, V17, Q32, A37, T40, P45, W48, G50, T51, N54, V56, A60, K72, R87, Q98, M105, G109, F113, R116, Q118, Q125, G133, T134, W140, G142, G149, T165, W167, Q169, R171, Q172, L173, A174, G184, A186, E190, T193, N195, G196, A204, V206, P211, V213, I214, L217, A225, L228, L235, V238, K242, S244, M246, L2502, G255, N260, A263, V264, A265, Y267, K269, N270, G273, S280, W284, T285, M286, F289, V291, Y295, Q299, S304, R320, H321, S323, H324, V326, F328, T334, G337, Q345, G346, T355, S376, D377, D381, Y382, Q385, K391, and Q395 of SEQ ID NOs: 7 or 10; A420, G423, T444, A445, Q449, T459, P473, C474, G476, G477, and K484 of SEQ ID NO: 13; and I405, A421, A422, A428, G448, D476, and G477 of SEQ ID NO: 14.

The generated variants are listed in the following examples.

Example 3: Wash Performance of Generated Variants Using Automatic Mechanical Stress Assay (AMSA)

In order to assess the wash performance of the variants of the present invention in a detergent base composition, washing experiments may be performed using Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid were vigorously shaken to bring the test solution in contact with the textile and apply mechanical stress in a regular, periodic oscillating manner. For further description see WO 02/42740, especially the paragraph "Special method embodiments" at page 23-24.

General Wash Performance Description

A test solution comprising water (6° dH), 0.79 g/L detergent, e.g. Model detergent J as described below, and the enzyme of the invention at concentration of 0, 0.05 or 0.2 mg enzyme protein/L, is prepared. Fabrics stained with starch (CS-28 from Center For Test materials BV, P.O. Box 120, 3133 KT, Vlaardingen, The Netherlands) was added and washed for 20 minutes at 15° C. and 30° C., or alternatively 20 minutes at 15° C. and 40° C. as specified below. After thorough rinse under running tap water and drying in the dark, the light intensity values of the stained fabrics were subsequently measured as a measure for wash performance. The test with 0 mg enzyme protein/L was used as a blank and corresponded to the contribution from the detergent. Preferably mechanical action is applied during the wash step, e.g. in the form of shaking, rotating or stirring the wash solution with the fabrics. The AMSA wash performance experiments was conducted under the experimental conditions specified below:

TABLE A

| Experimental condition | |
|---|---|
| Detergent | Liquid Model detergent J (see Table B) |
| Detergent dosage | 0.79 g/L |
| Test solution volume | 160 micro L |
| pH | As is |
| Wash time | 20 minutes |
| Temperature | 15° C. or 30° C. |
| Water hardness | 6° dH |
| Enzyme concentration in test | 0.2 mg enzyme protein/L and 0.05 mg enzyme protein/L |
| Test material | CS-28 (Rice starch cotton) |

TABLE B

Model detergent J

| Compound | Content of compound (% w/w) | % active component (% w/w) |
|---|---|---|
| LAS linear alkylbenzene sulfonates | 5.15 | 5.00 |
| AS alkylbenzene sulfonates | 5.00 | 4.50 |
| AEOS alkyl ethoxy sulfate | 14.18 | 10.00 |
| Coco fatty acid | 1.00 | 1.00 |
| AEO alkyl ethoxylate | 5.00 | 5.00 |
| MEA monoethanolamine | 0.30 | 0.30 |
| MPG monopropylene glycol | 3.00 | 3.00 |
| Ethanol | 1.50 | 1.35 |
| DTPA (as Na5 salt) pentasodium diethylenetriaminepenta-acetic acid | 0.25 | 0.10 |
| Sodium citrate | 4.00 | 4.00 |
| Sodium formate | 1.00 | 1.00 |
| Sodium hydroxide | 0.66 | 0.66 |
| $H_2O$, ion exchanged | 58.95 | 58.95 |

Water hardness was adjusted to 6° dH by addition of $CaCl_2$, $MgCl_2$, and $NaHCO_3$ ($Ca^{2+}$:$Mg^{2+}$:$HCO_3^-$=2:1:4.5) to the test system. After washing the textiles were flushed in tap water and dried.

TABLE C

| Experimental condition | |
|---|---|
| Detergent | Liquid Model detergent A (see Table D) |
| Detergent dosage | 3.33 g/L |
| Test solution volume | 160 micro L |
| pH | As is |
| Wash time | 20 minutes |
| Temperature | 15° C. or 40° C. |
| Water hardness | 15° dH |
| Enzyme concentration in test | 0.2 mg enzyme protein/L, 0.05 mg enzyme protein/L |
| Test material | CS-28 (Rice starch cotton) |

TABLE D

| Model detergent A | | |
|---|---|---|
| Compound | Content of compound (% w/w) | % active component (% w/w) |
| LAS (linear alkylbenzene sulfonates) | 12.00 | 11.60 |
| AEOS (alkyl ethoxy sulfate), SLES (sodium lauryl ether sulfate) | 17.63 | 4.90 |
| Soy fatty acid | 2.75 | 2.48 |
| Coco fatty acid | 2.75 | 2.80 |
| AEO (alkyl ethoxylate) | 11.00 | 11.00 |
| Sodium hydroxide | 1.75 | 1.80 |
| Ethanol/Propan-2-ol | 3.00 | 2.70/0.30 |
| MPG monopropylene glycol | 6.00 | 6.00 |
| Glycerol | 1.71 | 1.70 |
| TEA (triethanolamine) | 3.33 | 3.30 |
| Sodium formate | 1.00 | 1.00 |
| Sodium citrate | 2.00 | 2.00 |
| DTMPA (diethylenetriaminepenta-acetic acid) | 0.48 | 0.20 |
| PCA polycarboxylic acid type polymer | 0.46 | 0.18 |
| Phenoxy ethanol | 0.50 | 0.50 |
| $H_2O$, ion exchanged | 33.64 | 33.64 |

Water hardness was adjusted to 15° dH by addition of $CaCl_2$, $MgCl_2$, and $NaHCO_3$ ($Ca^{2+}$:$Mg^{2+}$:$HCO_3^-$=4:1:7.5) to the test system. After washing the textiles were flushed in tap water and dried.

The wash performance was measured as the brightness expressed as the intensity of the light reflected from the sample when illuminated with white light. When the sample was stained the intensity of the reflected light was lower, than that of a clean sample. Therefore the intensity of the reflected light can be used to measure wash performance.

Color measurements were made with a professional flatbed scanner (EPSON Expression 10000XL, EPSON) used to capture an image of the washed textile.

To extract a value for the light intensity from the scanned images, 48→24 Bit Color pixel values from the image were converted into values for red, green and blue (RGB). The intensity value (Int) is calculated by adding the RGB values together as vectors and then taking the length of the resulting vector:

$$Int=\sqrt{r^2+g^2+b^2}$$

The term "improved wash performance" of the present experiment is defined as displaying an alteration of the wash performance of a variant of the present invention relative to the wash performance of the polypeptide having an amino acid sequence as set forth in SEQ ID NO: 15, The alteration may e.g. be seen as increased stain removal. Improved wash performance was determined as described above. The wash performance was considered to be improved if the Improvement Factor (IF) is at least 1.0, preferably at least 1.05 in one or more of the conditions listed above; i.e. either in Model detergent A at 15° C. or 40° C., where the variant concentration was 0.05 or 0.2 mg/L or in Model detergent J at 15° C. or 30° C., where the variant concentration was 0.05 or 0.2 mg/L. The wash conditions were as described above in Tables A and C.

The terms "Delta intensity" or "Delta intensity value" as used herein refers to the result of an intensity measurement of a test material, e.g. a swatch CS-28 (Center For Testmaterials BV, P.O. Box 120, 3133 KT Vlaardingen, the Netherlands). The swatch was measured with a portion of the swatch, washed under identical conditions, as background. The delta intensity is the intensity value of the test material washed with amylase subtracting the intensity value of the test material washed without amylase.

The wash performance of the variants according to the invention obtained by AMSA are the following;

| Modifications in SEQ ID NO: 13 | A-15-0.05 mg/L | A-15-0.2 mg/L | A-40-0.05 mg/L | A-40-0.2 mg/L | J-15-0.05 mg/L | J-15-0.2 mg/L | J-30-0.05 mg/L | J-30-0.2 mg/L |
|---|---|---|---|---|---|---|---|---|
| Reference | 1.0 | 1.0 | 1.0 | 1.0 | 1.0 | 1.0 | 1.0 | 1.0 |
| G182* + D183* + N195F | 1.0 | 1.3 | 1.1 | 1.0 | 1.5 | 1.3 | 1.0 | 1.0 |
| H1* + N54S + V56T + G109A + A174S + G182* + D183* + N195F + V206L + K391A + G476K | 2.1 | 1.9 | 1.2 | 1.2 | 2.6 | 2.0 | 1.5 | 1.3 |
| H1* + N54S + V56T + R87S + G109A + A174S + G182* + D183* + N195F + V206L + K391A + G476K | 2.8 | 2.2 | 1.3 | 1.1 | 2.6 | 2.4 | 1.9 | 1.5 |
| H1* + T40G + N54S + V56T + G109A + A174S + G182* + D183* + N195F + V206L + K391A + G476K | 2.2 | 1.7 | 1.3 | 1.1 | 2.5 | 2.2 | 1.9 | 1.6 |
| H1* + T51K + N54S + V56T + G109A + A174S + G182* + D183* + N195F + V206L + K391A + G476K | 2.7 | 2.1 | 1.3 | 1.1 | 3.2 | 2.3 | 2.0 | 1.5 |
| H1* + N54S + V56T + K72R + G109A + A174S + G182* + D183* + N195F + V206L + K391A + G476K | 2.6 | 2.2 | 1.2 | 1.0 | 2.6 | 2.5 | 1.7 | 1.5 |
| H1* + N54S + V56T + K72H + G109A + A174S + G182* + D183* + N195F + V206L + K391A + G476K | 2.5 | 2.4 | 1.4 | 1.1 | 2.6 | 2.3 | 1.7 | 1.6 |
| H1* + A37H + N54S + V56T + G109A + A174S + G182* + D183* + N195F + V206L + K391A + G476K | 2.8 | 2.7 | 1.4 | 1.2 | 2.8 | 2.8 | 1.9 | 1.6 |
| H1* + A37M + N54S + V56T + G109A + A174S + G182* + D183* + N195F + V206L + K391A + G476K | 2.0 | 2.3 | 1.4 | 1.2 | 2.7 | 2.5 | 2.1 | 1.6 |

-continued

| | | | | | | | | |
|---|---|---|---|---|---|---|---|---|
| H1* + A37V + N54S + V56T + G109A + A174S + G182* + D183* + N195F + V206L + K391A + G476K | 3.0 | 2.6 | 1.4 | 1.2 | 3.1 | 2.5 | 2.2 | 1.7 |
| H1* + A37S + N54S + V56T + G109A + A174S + G182* + D183* + N195F + V206L + K391A + G476K | 2.9 | 2.5 | 1.2 | 1.2 | 2.9 | 2.3 | 1.5 | 1.3 |
| H1* + A37Y + N54S + V56T + G109A + A174S + G182* + D183* + N195F + V206L + K391A + G476K | 2.6 | 2.0 | 1.3 | 1.2 | 2.5 | 2.1 | 1.5 | 1.3 |
| H1* + A37R + N54S + V56T + G109A + A174S + G182* + D183* + N195F + V206L + K391A + G476K | 2.2 | 1.9 | 1.3 | 1.2 | 2.5 | 2.1 | 1.4 | 1.3 |
| H1* + N54S + V56T + G109A + F113W + A174S + G182* + D183* + N195F + V206L + K391A + G476K | 2.8 | 2.2 | 1.3 | 1.2 | 2.7 | 2.1 | 1.5 | 1.2 |
| H1* + N54S + V56T + G109A + F113S + A174S + G182* + D183* + N195F + V206L + K391A + G476K | 2.3 | 1.9 | 1.3 | 1.1 | 2.4 | 1.7 | 1.3 | 1.2 |
| H1* + N54S + V56T + G109A + F113N + A174S + G182* + D183* + N195F + V206L + K391A + G476K | 2.0 | 1.9 | 1.2 | 1.2 | 2.3 | 2.1 | 1.4 | 1.2 |
| H1* + N54S + V56T + G109A + F113Y + A174S + G182* + D183* + N195F + V206L + K391A + G476K | 1.9 | 2.1 | 1.2 | 1.2 | 3.1 | 2.3 | 1.5 | 1.3 |
| H1* + N54S + V56T + G109A + F113R + A174S + G182* + D183* + N195F + V206L + K391A + G476K | 1.0 | 1.4 | 1.2 | 1.2 | 2.0 | 1.8 | 1.4 | 1.3 |
| H1* + N54S + V56T + G109A + Q118N + A174S + G182* + D183* + N195F + V206L + K391A + G476K | 1.9 | 1.8 | 1.3 | 1.2 | 2.9 | 2.3 | 1.5 | 1.3 |
| H1* + N54S + V56T + G109A + R116Q + A174S + G182* + D183* + N195F + V206L + K391A + G476K | 2.6 | 2.0 | 1.2 | 1.2 | 3.5 | 2.6 | 1.7 | 1.4 |
| H1* + N54S + V56T + G109A + R116V + A174S + G182* + D183* + N195F + V206L + K391A + G476K | 2.1 | 2.0 | 1.1 | 1.1 | 2.7 | 2.3 | 1.6 | 1.3 |
| H1* + N54S + V56T + G109A + R116K + A174S + G182* + D183* + N195F + V206L + K391A + G476K | 2.2 | 2.1 | 1.2 | 1.1 | 2.4 | 2.2 | 1.4 | 1.3 |
| H1* + N54S + V56T + G109A + R116W + A174S + G182* + D183* + N195F + V206L + K391A + G476K | 1.8 | 2.0 | 0.7 | 0.9 | 1.1 | 1.9 | 1.0 | 1.2 |
| H1* + N54S + V56T + G109A + R116L + A174S + G182* + D183* + N195F + V206L + K391A + G476K | 1.8 | 1.8 | 1.2 | 1.1 | 1.9 | 2.0 | 1.3 | 1.2 |
| H1* + N54S + V56T + G109A + G142T + A174S + G182* + D183* + N195F + V206L + K391A + G476K | 1.6 | 1.7 | 1.2 | 1.1 | 1.9 | 2.0 | 1.3 | 1.1 |
| H1* + N54S + V56T + G109A + Q125P + A174S + G182* + D183* + N195F + V206L + K391A + G476K | 2.1 | 2.1 | 1.2 | 1.1 | 2.4 | 2.0 | 1.4 | 1.3 |
| H1* + N54S + V56T + G109A + Q125K + A174S + G182* + D183* + N195F + V206L + K391A + G476K | 1.9 | 1.8 | 1.3 | 1.1 | 2.6 | 1.9 | 1.5 | 1.2 |
| H1* + N54S + V56T + G109A + A174S + G182* + D183* + N195F + V206L + S381G + K391A + G476K | 2.3 | 2.1 | 1.0 | 1.0 | 2.5 | 2.2 | 1.4 | 1.2 |
| H1* + N54S + V56T + G109A + A174S + G182* + D183* + N195F + V206L + M246T + K391A + G476K | 2.0 | 1.9 | 1.1 | 1.0 | 2.6 | 1.8 | 1.5 | 1.2 |
| H1* + N54S + V56T + G109A + A174S + G182* + D183* + N195F + V206L + V213T + K391A + G476K | 1.9 | 1.9 | 1.1 | 1.1 | 2.8 | 2.1 | 1.5 | 1.3 |
| H1* + A37L + N54S + V56T + G109A + A174S + G182* + D183* + N195F + V206L + K391A + G476K | 2.5 | 2.2 | 1.2 | 1.1 | 2.5 | 2.2 | 1.8 | 1.4 |
| H1* + N54S + V56T + G109A + Q118K + A174S + G182* + D183* + N195F + V206L + K391A + G476K | 1.8 | 2.0 | 1.2 | 1.1 | 1.5 | 1.6 | 1.4 | 1.2 |
| H1* + N54S + V56T + G109A + R116A + A174S + G182* + D183* + N195F + V206L + K391A + G476K | 2.7 | 2.3 | 1.2 | 1.1 | 2.4 | 2.1 | 1.6 | 1.3 |
| H1* + N54S + V56T + G109A + R116H + A174S + G182* + D183* + N195F + V206L + K391A + G476K | 2.9 | 2.4 | 1.3 | 1.2 | 2.4 | 2.3 | 1.9 | 1.5 |
| H1* + N54S + V56T + G109A + Q125A + A174S + G182* + D183* + N195F + V206L + K391A + G476K | 2.1 | 2.0 | 1.1 | 1.2 | 3.1 | 2.1 | 1.5 | 1.2 |
| H1* + N54S + V56T + G109A + Q172G + A174S + G182* + D183* + N195F + V206L + K391A + G476K | 2.6 | 2.1 | 1.4 | 1.2 | 2.7 | 2.2 | 2.1 | 1.5 |
| H1* + N54S + V56T + G109A + Q172R + A174S + G182* + D183* + N195F + V206L + K391A + G476K | 2.6 | 2.2 | 1.4 | 1.2 | 2.7 | 2.4 | 2.0 | 1.5 |
| H1* + N54S + V56T + G109A + A174S + G182* + D183* + N195F + V206L + D377S + K391A + G476K | 2.4 | 1.7 | 1.3 | 1.2 | 2.8 | 1.8 | 1.7 | 1.3 |
| H1* + N54S + V56T + G109A + A174S + G182* + D183* + N195F + V206L + D377G + K391A + G476K | 1.7 | 1.7 | 1.2 | 1.1 | 2.3 | 1.5 | 1.7 | 1.3 |
| H1* + N54S + V56T + G109A + A174S + G182* + D183* + N195F + V206L + D377R + K391A + G476K | 1.9 | 1.5 | 1.1 | 1.1 | 2.6 | 1.6 | 1.4 | 1.2 |
| H1* + N54S + V56T + G109A + A174S + G182* + D183* + N195F + V206L + D377A + K391A + G476K | 2.0 | 1.9 | 1.2 | 1.0 | 2.8 | 1.9 | 1.5 | 1.2 |
| H1* + N54S + V56T + G109A + A174S + G182* + D183* + N195F + V206L + I214G + K391A + G476K | 1.6 | 1.6 | 1.3 | 1.1 | 2.9 | 1.7 | 1.5 | 1.1 |
| H1* + N54S + V56T + G109A + A174S + G182* + D183* + N195F + V206L + S381A + K391A + G476K | 2.3 | 1.6 | 1.4 | 1.2 | 2.8 | 1.9 | 1.6 | 1.4 |
| H1* + N54S + V56T + G109A + W167I + A174S + G182* + D183* + N195F + V206L + K391A + G476K | 1.7 | 1.9 | 1.3 | 1.2 | 2.8 | 1.8 | 1.6 | 1.3 |
| H1* + N54S + V56T + G109A + W167G + A174S + G182* + D183* + N195F + V206L + K391A + G476K | 1.5 | 1.8 | 1.2 | 1.1 | 2.5 | 1.8 | 1.5 | 1.3 |
| H1* + N54S + V56T + G109A + A174S + G182* + D183* + N195F + V206L + G346S + K391A + G476K | 1.7 | 1.8 | 1.3 | 1.2 | 2.8 | 2.0 | 1.6 | 1.3 |
| H1* + N54S + V56T + G109A + A174S + G182* + D183* + N195F + V206L + G346P + K391A + G476K | 2.1 | 1.9 | 1.3 | 1.1 | 2.9 | 2.1 | 1.6 | 1.3 |
| H1* + N54S + V56T + G109A + A174S + G182* + D183* + N195F + V206L + I214H + K391A + G476K | 2.2 | 1.7 | 1.3 | 1.1 | 2.2 | 2.1 | 1.7 | 1.3 |

-continued

| | | | | | | | | |
|---|---|---|---|---|---|---|---|---|
| H1* + N54S + V56T + G109A + A174S + G182* + D183* + N195F + V206L + I214S + K391A + G476K | 2.3 | 1.8 | 1.3 | 1.1 | 2.9 | 2.0 | 1.5 | 1.3 |
| H1* + N54S + V56T + G109A + A174S + G182* + D183* + N195F + V206L + I214T + K391A + G476K | 1.9 | 1.7 | 1.3 | 1.2 | 2.4 | 1.7 | 1.6 | 1.3 |
| H1* + N54S + V56T + G109A + A174S + G182* + D183* + N195F + V206L + K391A + A420Q + G476K | 2.0 | 1.7 | 1.2 | 1.1 | 1.9 | 1.7 | 1.3 | 1.1 |
| H1* + N54S + V56T + G109A + A174S + G182* + D183* + N195F + V206L + K391A + A420S + G476K | 2.0 | 1.8 | 1.2 | 1.1 | 2.6 | 1.8 | 1.5 | 1.3 |
| H1* + N54S + V56T + G109A + A174S + G182* + D183* + N195F + V206L + K391A + A420K + G476K | 2.2 | 1.9 | 1.3 | 1.2 | 2.3 | 1.8 | 1.7 | 1.4 |
| H1* + N54S + V56T + G109A + A174S + G182* + D183* + N195F + V206L + K391A + A420L + G476K | 2.2 | 2.0 | 1.3 | 1.2 | 2.4 | 1.9 | 1.2 | 1.3 |
| H1* + N54S + V56T + G109A + A174S + G182* + D183* + N195F + V206L + K391A + K391Y + G476K | 2.0 | 1.9 | 1.3 | 1.2 | 2.9 | 1.9 | 1.1 | 1.3 |
| H1* + N54S + V56T + G109A + A174S + G182* + D183* + N195F + V206L + K391A + K391R + G476K | 1.9 | 1.9 | 1.3 | 1.2 | 2.5 | 1.7 | 1.4 | 1.4 |
| H1* + N54S + V56T + G109A + A174S + G182* + D183* + N195F + V206L + K391A + P473R + G476K | 2.2 | 1.9 | 1.2 | 1.2 | 3.4 | 2.0 | 2.1 | 1.3 |
| H1* + N54S + V56T + G109A + A174S + G182* + D183* + N195F + V206L + K391A + P473A + G476K | 2.5 | 1.8 | 1.5 | 1.1 | 3.4 | 1.9 | 1.9 | 1.4 |
| H1* + N54S + V56T + G109A + A174S + G182* + D183* + N195F + V206L + K391A + P473G + G476K | 2.5 | 1.9 | 1.3 | 1.2 | 2.8 | 1.9 | 1.5 | 1.3 |
| H1* + N54S + V56T + G109A + A174S + G182* + D183* + N195F + V206L + K391A + P473T + G476K | 1.9 | 1.7 | 1.3 | 1.2 | 2.5 | 1.9 | 1.5 | 1.2 |
| H1* + N54S + V56T + G109A + A174S + G182* + D183* + N195F + V206L + K391A + Q395P + G476K | 1.8 | 1.6 | 1.3 | 1.1 | 2.3 | 1.8 | 1.8 | 1.4 |
| H1* + N54S + V56T + G109A + A174S + G182* + D183* + N195F + V206L + K391A + T444Q + G476K | 1.7 | 1.8 | 1.3 | 1.2 | 2.8 | 2.0 | 1.4 | 1.3 |
| H1* + N54S + V56T + G109A + A174S + G182* + D183* + N195F + V206L + K391A + T444S + G476K | 1.7 | 1.8 | 1.3 | 1.2 | 2.8 | 2.0 | 1.5 | 1.4 |
| H1* + N54S + V56T + G109A + A174S + G182* + D183* + N195F + V206L + K391A + T444D + G476K | 2.3 | 1.8 | 1.3 | 1.3 | 3.0 | 2.3 | 1.7 | 1.4 |
| H1* + N54S + V56T + G109A + A174S + G182* + D183* + N195F + V206L + K391A + T444Y + G476K | 2.0 | 1.7 | 1.5 | 1.2 | 2.0 | 2.1 | 1.8 | 1.5 |
| H1* + N54S + V56T + G109A + A174S + G182* + D183* + N195F + V206L + S280W + K391A + G476K | 2.3 | 1.7 | 1.3 | 1.1 | 2.5 | 2.0 | 1.5 | 1.3 |
| H1* + N54S + V56T + G109A + A174S + G182* + D183* + N195F + V206L + S280L + K391A + G476K | 2.1 | 1.7 | 1.2 | 1.1 | 2.5 | 1.8 | 1.4 | 1.3 |
| H1* + N54S + V56T + G109A + A174S + G182* + D183* + N195F + V206L + S280T + K391A + G476K | 1.7 | 1.6 | 1.1 | 1.1 | 2.4 | 1.6 | 1.3 | 1.2 |
| H1* + N54S + V56T + G109A + A174S + G182* + D183* + N195F + V206L + S280A + K391A + G476K | 1.9 | 1.4 | 1.2 | 1.0 | 2.3 | 1.8 | 1.3 | 1.1 |
| H1* + N54S + V56T + G109A + A174S + G182* + D183* + N195F + V206L + G255N + K391A + G476K | 1.9 | 1.7 | 1.2 | 1.2 | 2.6 | 2.1 | 1.5 | 1.4 |
| H1* + N54S + V56T + G109A + A174S + G182* + D183* + N195F + V206L + T285L + K391A + G476K | 1.9 | 1.8 | 1.3 | 1.2 | 2.3 | 2.2 | 1.5 | 1.3 |
| H1* + N54S + V56T + G109A + A174S + G182* + D183* + N195F + V206L + T285Q + K391A + G476K | 1.6 | 1.7 | 1.2 | 1.2 | 2.2 | 2.1 | 1.6 | 1.3 |
| H1* + N54S + V56T + G109A + A174S + G182* + D183* + N195F + V206L + K391A + Q449T + G476K | 1.8 | 1.6 | 1.1 | 1.1 | 1.8 | 1.6 | 1.2 | 1.2 |
| H1* + N54S + V56T + G109A + A174S + G182* + D183* + N195F + V206L + K391A + P473K + G476K | 1.8 | 1.7 | 1.3 | 1.1 | 2.2 | 2.0 | 1.3 | 1.2 |
| H1* + N54S + V56T + K72S + G109A + A174S + G182* + D183* + N195F + V206L + K391A + G476K | 2.5 | 2.3 | 1.2 | 1.1 | 3.7 | 2.2 | 1.5 | 1.4 |
| H1* + T40K + N54S + V56T + G109A + A174S + G182* + D183* + N195F + V206L + G346T + K391A + G476K | 2.3 | 2.1 | 1.2 | 1.1 | 2.0 | 1.7 | 1.5 | 1.3 |
| H1* + G50A + N54S + V56T + G109A ++ Q172N + A174S + G182* + D183* + N195F + V206L + K391A + G476K | 2.4 | 2.1 | 1.2 | 1.2 | 2.0 | 1.9 | 1.4 | 1.3 |
| H1* + N54S + V56T + G109A + A174S + G182* + D183* + N195F + V206L + K391A + G476K + K484A | 1.9 | 1.7 | 1.3 | 1.0 | 2.4 | 1.6 | 1.5 | 1.3 |
| H1* + N54S + V56T + G109A + A174S + G182* + D183* + N195F + V206L + K391A + G476K + K484G | 1.8 | 1.8 | 1.2 | 1.0 | 2.2 | 1.8 | 1.4 | 1.2 |
| H1* + N54S + V56T + G109A + A174S + G182* + D183* + N195F + V206L + K391A + G476K + K484P | 1.8 | 1.7 | 1.1 | 1.0 | 2.4 | 2.0 | 1.4 | 1.3 |
| H1* + N54S + V56T + G109A + A174S + G182* + D183* + N195F + V206L + K391A + G476K + K484E | 1.9 | 1.4 | 1.2 | 1.1 | 2.5 | 1.7 | 1.3 | 1.2 |
| H1* + N54S + V56T + G109A + A174S + G182* + D183* + N195F + V206L + K391A + G476K + K484Q | 1.7 | 1.5 | 1.1 | 1.0 | 2.0 | 1.3 | 1.3 | 1.2 |
| H1* + N54S + V56T + G109A + A174S + G182* + D183* + N195F + V206L + K391A + G476K + K484S | 2.3 | 2.0 | 1.2 | 1.2 | 2.7 | 1.7 | 1.6 | 1.4 |
| H1*K + G50A + N54S + V56T + G109A + W167F + A174S + G182* + D183* + N195F + V206L + K391A + G476K | 2.1 | 1.9 | 1.1 | 1.1 | 2.2 | 1.7 | 1.3 | 1.2 |
| H1* + N54S + V56T + G109A + L173V + A174S + G182* + D183* + N195F + A204T + V206L + K391A + G476K | 2.2 | 1.8 | 1.1 | 1.1 | 2.2 | 1.7 | 1.1 | 1.1 |
| H1* + N54S + V56T + G109A + W140Y + A174S + G182* + D183* + N195F + V206L + K391A + G476K | 2.2 | 1.9 | 1.2 | 1.1 | 2.5 | 1.9 | 1.3 | 1.3 |
| H1* + N54S + V56T + Q98S + G109A + A174S + G182* + D183* + N195F + V206L + R320A + K391A + G476K | 1.9 | 1.8 | 1.2 | 1.1 | 2.1 | 1.8 | 1.1 | 1.1 |

-continued

| | | | | | | | | |
|---|---|---|---|---|---|---|---|---|
| H1* + N54S + V56T + G109A + A174S + G182* + D183* + N195F + V206L + H324L + K391A + G476K | 1.9 | 1.7 | 1.1 | 1.1 | 2.1 | 1.5 | 1.2 | 1.1 |
| H1* + N54S + V56T + G109A + G149Q + A174S + G182* + D183* + N195F + V206L + K391A + G476K | 1.7 | 1.9 | 1.2 | 1.2 | 1.6 | 1.4 | 1.0 | 1.2 |
| H1* + N54S + V56T + G109A + A174S + G182* + D183* + N195F + V206L + G346T + K391A + G476K + G477A | 2.1 | 2.0 | 1.2 | 1.2 | 2.3 | 1.7 | 1.2 | 1.2 |
| H1* + N54S + V56T + G109AG255A ++ A174S + G182* + D183* + N195F + V206L + K391A + G476K | 2.1 | 2.0 | 1.2 | 1.2 | 2.3 | 1.8 | 1.2 | 1.2 |
| H1* + G50A + N54S + V56T + G109A + F113L + R116L + A174S + G182* + D183* + N195F + V206L + K391A + G476K | 2.3 | 2.2 | 1.2 | 1.1 | 2.6 | 2.2 | 1.3 | 1.2 |
| H1* + N54S + V56T + G109A + W167F + A174S + G182* + D183* + N195F + V206L + K391A + G476K | 2.0 | 1.9 | 1.1 | 1.0 | 2.3 | 2.0 | 1.4 | 1.2 |
| H1* + N54S + V56T + G109A + L173V + A174S + G182* + D183* + N195F + V206L + K391A + G476K | 1.8 | 1.9 | 1.0 | 1.0 | 2.2 | 1.8 | 1.4 | 1.3 |
| H1* + N54S + V56T + K72R + G109A + W167F + A174S + G182* + D183* + N195F + V206L + K391A + G476K | 2.1 | 1.7 | 1.1 | 1.1 | 2.9 | 2.0 | 1.4 | 1.3 |
| H1* + N54S + V56T + G109A + A174S + G182* + D183* + N195F + V206L + K391A + G476K + G477Q | 1.8 | 1.4 | 1.0 | 1.1 | 2.4 | 1.9 | 1.4 | 1.3 |
| H1* + N54S + V56T + G109A + A174S + G182* + D183* + N195F + V206L + Q345D + K391A + G476K + G477Q | 1.6 | 1.5 | 1.0 | 1.0 | 2.2 | 1.7 | 1.3 | 1.2 |
| H1* + G50A + N54S + V56T + G109A + Q172D + A174S + G182* + D183* + N195F + V206L + K391A + G476K | 1.9 | 1.9 | 0.9 | 1.1 | 2.1 | 1.9 | 1.6 | 1.3 |
| H1* + N54S + V56T + G109A + A174S + G182* + D183* + N195F + V206L + V264I + K391A + G423H + G476K | 1.9 | 1.9 | 0.7 | 1.0 | 2.2 | 2.0 | 1.4 | 1.3 |
| H1* + N54S + V56T + G109A + A174S + G182* + D183* + N195F + V206L + R320V + K391A + G476Y | 2.1 | 2.0 | 0.8 | 1.0 | 2.1 | 2.1 | 1.5 | 1.3 |
| H1* + T5K + N54S + V56T + G109A + A174S + G182* + D183* + N195F + V206L + K391A + G476K | 1.7 | 1.8 | 0.9 | 1.0 | 1.8 | 1.7 | 1.4 | 1.2 |
| H1* + N54S + V56T + G109A + R116M + A174S + G182* + D183* + N195F + V206L + K391A + G476K | 2.9 | 2.2 | 1.2 | 1.1 | 2.8 | 2.1 | 1.2 | 1.1 |
| H1* + N54S + V56T + G109A + Q172Y + A174S + G182* + D183* + N195F + V206L + K391A + G476K | 2.1 | 1.8 | 1.1 | 1.1 | 1.9 | 1.8 | 1.4 | 1.1 |
| H1* + N54S + V56T + G109A + A174S + G182* + D183* + N195F + V206L + I214L + K391A + G476K | 2.0 | 1.7 | 1.1 | 1.1 | 1.9 | 1.7 | 1.3 | 1.2 |
| H1* + N54S + V56T + G109A + A174S + G182* + D183* + N195F + V206L + L217V + K391A + G476K | 2.2 | 1.9 | 1.2 | 1.2 | 2.2 | 2.2 | 1.3 | 1.2 |
| H1* + N54S + V56T + G109A + A174S + G182* + D183* + N195F + V206L + L217H + K391A + G476K | 2.2 | 1.7 | 1.2 | 1.2 | 2.3 | 2.1 | 1.4 | 1.2 |
| H1* + N54S + V56T + G109A + A174S + G182* + D183* + N195F + V206L + P211D + K391A + G476K | 2.1 | 2.0 | 1.1 | 1.1 | 2.3 | 2.1 | 1.2 | 1.2 |
| H1* + N54S + V56T + G109A + A174S + G182* + D183* + N195F + V206L + K391A + K391Q + G476K | 2.1 | 1.9 | 1.1 | 1.2 | 2.3 | 1.9 | 1.3 | 1.3 |
| H1* + N54S + V56T + G109A + A174S + G182* + D183* + N195F + V206L + K391A + T444H + G476K | 2.0 | 1.9 | 1.1 | 1.1 | 2.3 | 1.9 | 1.4 | 1.2 |
| H1* + N54S + V56T + G109A + A174S + G182* + D183* + N195F + V206L + K391A + T444V + G476K | 2.2 | 1.7 | 1.1 | 1.0 | 2.3 | 1.8 | 1.2 | 1.2 |
| H1* + N54S + V56T + G109A + A174S + G182* + D183* + N195F + V206L + K391A + T444R + G476K | 2.0 | 1.6 | 1.2 | 1.1 | 1.9 | 1.8 | 1.3 | 1.2 |
| H1* + G50A + N54S + V56T + G109A + L173V + A174S + G182* + D183* + N195F + A204V + V206L + K391A + G476K | 2.4 | 2.1 | 1.2 | 1.2 | 3.2 | 2.2 | 1.6 | 1.4 |
| H1* + G50A + N54S + V56T + G109A + F113L + W167F + A174S + G182* + D183* + N195F + V206L + K391A + G476K | 1.9 | 1.7 | 1.0 | 1.1 | 2.1 | 1.8 | 1.2 | 1.2 |
| H1* + G7K + N54S + V56T + G109A + A174S + G182* + D183* + N195F + V206L + R320A + K391A + G476K | 2.0 | 1.8 | 1.1 | 1.1 | 2.7 | 2.1 | 1.6 | 1.2 |
| H1* + N54S + V56T + G109A + Q118G + A174S + G182* + D183* + N195F + V206L + K391A + G476K | 1.7 | 1.8 | 1.1 | 1.1 | 2.4 | 1.6 | 1.5 | 1.2 |
| H1* + N54S + V56T + G109A + A174S + G182* + D183* + N195F + V206L + S280K + K391A + G476K | 1.6 | 1.6 | 1.0 | 1.1 | 1.6 | 1.6 | 1.3 | 1.2 |
| H1* + N54S + V56T + G109A + A174S + G182* + D183* + N195F + V206L + N270G + K391A + G476K | 1.4 | 1.6 | 1.1 | 1.1 | 1.8 | 1.6 | 1.4 | 1.2 |
| H1* + N54S + V56T + G109A + Q172D + A174S + G182* + D183* + N195F + V206L + G346T + K391A + G476K + G477A | 2.1 | 1.9 | 1.2 | 1.1 | 3.1 | 2.3 | 1.6 | 1.4 |
| H1* + N54S + V56T + G109A + Q118S + A174S + G182* + D183* + N195F + V206L + K391A + G476K | 2.1 | 1.9 | 1.1 | 1.1 | 1.8 | 1.5 | 1.4 | 1.2 |
| H1* + N54S + V56T + G109A + A174S + G182* + D183* + N195F + V206L + R320A + K391A + G476K | 2.0 | 1.9 | 1.2 | 1.2 | 2.3 | 1.7 | 1.5 | 1.3 |
| H1* + N54S + V56T + G109A + T134E + A174S + G182* + D183* + N195F + V206L + K391A + G476K | 2.4 | 2.1 | 1.2 | 1.1 | 2.8 | 2.4 | 1.4 | 1.4 |
| H1* + N54S + V56T + G109A + A174S + G182* + D183* + N195F + V206L + G337H + Q385L + K391A + G476K | 1.7 | 1.8 | 1.0 | 1.0 | 1.8 | 1.8 | 1.2 | 1.2 |
| H1* + N54S + V56T + G109A + A174S + G182* + D183* + N195F + V206L + Y382M + K391A + G476K | 2.0 | 1.8 | 1.1 | 1.1 | 2.2 | 1.9 | 1.3 | 1.2 |
| H1* + N54S + V56T + K72R + G109A + A174S + G182* + D183* + N195F + V206L + G255A + D377H + K391A + G476K | 1.9 | 1.9 | 1.1 | 1.1 | 2.7 | 2.2 | 1.4 | 1.3 |
| H1* + N54S + V56T + K72R + G109A + T134E + A174S + G182* + D183* + N195F + V206L + G255A + K391A + G476K | 2.4 | 2.0 | 1.2 | 1.1 | 3.0 | 2.3 | 1.4 | 1.3 |
| H1* + N54S + V56T + K72R + M105F + G109A + A174S + G182* + D183* + N195F + V206L + G255A + K391A + G476K | 2.0 | 1.7 | 1.2 | 1.1 | 2.5 | 2.0 | 1.4 | 1.2 |

-continued

| | | | | | | | | |
|---|---|---|---|---|---|---|---|---|
| H1* + N54S + V56T + M105F + G109A + T134E + A174S + G182* + D183* + N195F + V206L + K391A + G476K | 2.0 | 1.9 | 1.0 | 1.0 | 2.3 | 2.1 | 1.2 | 1.1 |
| H1* + N54S + V56T + M105F + G109A + Q118F + T134E + A174S + G182* + D183* + N195F + V206L + K391A + G476K | 1.9 | 1.7 | 1.1 | 1.1 | 1.7 | 1.9 | 1.3 | 1.2 |
| H1* + N54S + V56T + G109A + A174S + G182* + D183* + N195F + V206L + R320A + S323N + D377H + K391A + G476K | 2.0 | 1.9 | 1.1 | 1.0 | 2.3 | 2.0 | 1.4 | 1.3 |
| H1* + T51E + N54S + V56T + G109A + A174H + G182* + D183* + N195F + V206L + K391A + G476K | 2.3 | 1.9 | 1.2 | 1.1 | 2.6 | 2.2 | 1.6 | 1.4 |
| H1* + N54S + V56T + G109A + L173A + A174S + G182* + D183* + N195F + V206L + K391A + G476K | 2.4 | 2.0 | 1.3 | 1.2 | 2.4 | 2.0 | 1.6 | 1.4 |
| H1* + N54S + V56T + G109A + A174S + G182* + D183* + N195F + V206L + Q299V + K391A + G476K | 2.5 | 2.0 | 1.3 | 1.2 | 2.4 | 1.6 | 1.6 | 1.4 |
| H1* + N54S + V56T + G109A + L173G + A174S + G182* + D183* + N195F + V206L + K391A + G476K | 2.2 | 2.0 | 1.3 | 1.2 | 2.3 | 1.9 | 1.7 | 1.4 |
| H1* + N54S + V56T + G109A + A174S + G182* + D183* + N195F + V206L + T355L + K391A + G476K | 2.1 | 2.0 | 1.3 | 1.2 | 2.4 | 2.0 | 1.5 | 1.3 |
| H1* + N54S + V56T + G109A + A174S + G182* + D183* + N195F + V206L + T355F + K391A + G476K | 1.3 | 1.7 | 1.0 | 1.0 | 1.9 | 1.6 | 1.2 | 1.1 |
| H1* + G50A + N54S + V56T + G109A + A174S + G182* + D183* + N195F + A204T + V206L + K391A + G476K | 2.3 | 2.0 | 1.2 | 1.1 | 2.1 | 1.8 | 1.4 | 1.3 |
| H1* + G50A + N54S + V56T + G109A + A174E + G182* + D183* + N195F + A204T + V206L + K391A + G476K | 1.8 | 1.6 | 1.1 | 1.1 | 2.1 | 1.8 | 1.2 | 1.2 |
| H1* + N54S + V56T + K72R + G109A + A174S + G182* + D183* + N195F + V206L + R320A + S323N + K391A + G476K | 2.2 | 1.8 | 1.2 | 1.1 | 2.7 | 2.1 | 1.4 | 1.2 |
| H1* + N54S + V56T + M105I + G109A + A174S + G182* + D183* + N195F + V206L + K391A + G476K | 1.8 | 1.8 | 1.1 | 1.1 | 1.5 | 1.5 | 1.3 | 1.2 |
| H1* + N54S + V56T + G109A + A174S + G182* + D183* + N195F + V206L + M246L + K391A + G476K | 2.0 | 1.8 | 1.1 | 1.0 | 1.8 | 1.6 | 1.3 | 1.2 |
| H1* + T51G + N54S + V56T + G109A + A174N + G182* + D183* + N195F + V206L + K391A + G476K | 1.6 | 1.5 | 1.0 | 1.0 | 2.1 | 1.7 | 1.3 | 1.1 |
| H1* + T51A + N54S + V56T + G109A + A174G + G182* + D183* + N195F + V206L + K391A + G476K | 1.4 | 1.5 | 0.9 | 0.9 | 1.6 | 1.5 | 1.3 | 1.0 |
| H1* + N54S + V56T + G109A + A174D + G182* + D183* + N195F + V206L + K391A + G476K | 1.9 | 1.5 | 1.0 | 1.0 | 1.5 | 1.5 | 1.1 | 1.0 |
| H1* + T51S + N54S + V56T + G109A + A174P + G182* + D183* + N195F + V206L + K391A + G476K | 1.7 | 1.7 | 0.9 | 1.0 | 1.1 | 1.2 | 0.8 | 0.9 |
| H1* + T51G + N54S + V56T + G109A + A174M + G182* + D183* + N195F + V206L + K391A + G476K | 1.3 | 1.5 | 1.0 | 1.0 | 1.6 | 1.5 | 0.9 | 1.1 |
| H1* + N54S + V56T + G109A + K72A + W167R + A174S + G182* + D183* + N195F + V206L + K391A + G476K | 0.9 | 1.2 | 0.5 | 0.7 | 0.7 | 0.8 | 0.4 | 0.7 |
| H1* + N54S + V56T + K72A + G109A + W167S + A174S + G182* + D183* + N195F + V206L + K391A + G476K | 1.6 | 1.8 | 0.4 | 0.8 | 0.7 | 1.2 | 0.6 | 0.8 |
| H1* + N54S + V56T + K72R + G109A + W167R + A174S + G182* + D183* + N195F + V206L + K391A + G476K | 1.1 | 1.1 | 0.8 | 0.8 | 0.7 | 0.8 | 0.7 | 0.7 |
| H1* + N54S + V56T + K72Q + G109A + W167H + A174S + G182* + D183* + N195F + V206L + K391A + G476K | 2.4 | 2.2 | 0.9 | 1.0 | 1.8 | 1.7 | 1.0 | 1.1 |
| H1* + N54S + V56T + G109A + Q118R + T134E + A174S + G182* + D183* + N195F + V206L + D377H + K391A + G476K | 1.8 | 1.7 | 1.1 | 1.0 | 2.1 | 1.7 | 1.2 | 1.1 |
| H1* + Q11H + N54S + V56T + G109A + Q118R + T134E + A174S + G184T + G182* + D183* + N195F + V206L + D377H + K391A + G476K | 1.9 | 1.6 | 1.1 | 1.0 | 2.2 | 1.6 | 1.3 | 1.3 |
| H1* + N54S + V56T + K72R + G109A + T134E + A174S + G182* + D183* + N195F + V206L + K391A + G476K | 2.3 | 2.1 | 1.2 | 1.1 | 3.2 | 1.9 | 1.3 | 1.3 |
| H1* + N54S + V56T + K72R + G109A + T134E + A174S + G182* + D183* + N195F + V206L + D377H + K391A + G476K | 2.2 | 2.0 | 1.1 | 1.0 | 3.8 | 1.9 | 1.3 | 1.2 |
| H1* + N54S + V56T + K72R + G109A + T134E + A174S + G182* + D183* + G184T + N195F + V206L + K391A + G476K | 2.2 | 2.0 | 1.2 | 1.1 | 3.9 | 2.4 | 1.4 | 1.3 |
| H1* + N54S + V56T + G109A + Q118R + T134E + A174S + G182* + D183* + N195F + V206L + G255A + K391A + G476K | 2.0 | 1.9 | 1.0 | 1.2 | 2.5 | 2.0 | 1.2 | 1.1 |
| H1* + N54S + V56T + G109A + Q118R + A174S + G182* + D183* + N195F + V206L + D377H + K391A + G476K | 2.2 | 1.9 | 1.1 | 1.1 | 2.8 | 1.8 | 1.2 | 1.2 |
| H1* + N54S + V56T + G109A + T134E + A174S + G182* + D183* + G184T + N195F + V206L + D377H + K391A + G476K | 2.1 | 2.1 | 1.0 | 1.1 | 3.4 | 2.3 | 1.3 | 1.3 |
| H1* + N54S + V56T + G109A + Q172D + A174Q + G182* + D183* + N195F + V206L + K391A + G476K + G477A | 2.0 | 1.9 | 1.2 | 1.1 | 3.0 | 2.2 | 1.1 | 1.2 |
| H1* + N54S + V56T + K72A + G109A + W167F + A174S + G182* + D183* + N195F + V206L + K391A + G476K | 1.1 | 1.4 | 0.6 | 0.8 | 1.5 | 1.3 | 1.0 | 0.8 |
| H1* + N54S + V56T + G109A + W167S + G182* + D183* + N195F + A174S + V206L + K391A + G476K | 1.4 | 1.3 | 0.8 | 1.0 | 1.5 | 1.6 | 1.3 | 1.1 |
| H1* + N54S + V56T + K72H + G109A + W167S + A174S + G182* + D183* + N195F + V206L + K391A + G476K | 1.4 | 1.4 | 0.5 | 1.0 | 1.0 | 1.4 | 0.8 | 1.1 |
| H1* + N54S + V56T + K72R + G109A + W167T + A174S + G182* + D183* + N195F + V206L + K391A + G476K | 1.3 | 1.2 | 0.8 | 0.8 | 1.2 | 1.0 | 1.1 | 1.0 |
| H1* + N54S + V56T + K72E + G109A + A174S + G182* + D183* + N195F + V206L + K391A + G476K | 1.3 | 1.4 | 0.8 | 0.9 | 1.4 | 1.3 | 0.9 | 0.9 |
| H1* + N54S + V56T + K72R + G109A + W167L + A174S + G182* + D183* + N195F + V206L + K391A + G476K | 1.6 | 1.6 | 1.1 | 1.1 | 2.0 | 1.5 | 1.4 | 1.2 |
| H1* + N54S + V56T + K72R + G109A + W167M + A174S + G182* + D183* + N195F + V206L + K391A + G476K | 1.5 | 1.6 | 0.8 | 1.0 | 1.5 | 1.3 | 1.2 | 1.2 |

-continued

| | | | | | | | | |
|---|---|---|---|---|---|---|---|---|
| H1* + N54S + V56T + K72R + G109A + W167H + A174S + G182* + D183* + N195F + V206L + K391A + G476K | 1.3 | 1.4 | 0.6 | 1.0 | 1.6 | 1.3 | 0.9 | 1.1 |
| H1* + N54S + V56T + K72R + G109A + A174S + G182* + D183* + G184T + N195F + V206L + G255A + K391A + G476K | 2.0 | 1.9 | 1.2 | 1.1 | 2.5 | 2.0 | 1.4 | 1.3 |
| H1* + N54S + V56T + G109A + A174S + G182* + D183* + G184T + N195F + V206L + D377H + K391A + G476K | 2.2 | 1.9 | 1.1 | 1.1 | 2.3 | 1.9 | 1.5 | 1.4 |
| H1* + N54S + V56T + G109A + A174S + G182* + D183* + N195F + V206L + G255A + D377H + K391A + G476K | 2.1 | 2.0 | 1.2 | 1.0 | 2.1 | 1.7 | 1.3 | 1.3 |
| H1* + N54S + V56T + G109A + Q118R + A174S + G182* + D183* + N195F + V206L + G255A + D377H + K391A + G476K | 1.2 | 1.5 | 1.0 | 1.0 | 1.8 | 1.2 | 1.0 | 1.0 |
| H1* + N54S + V56T + G109A + A174S + G182* + D183* + G184A + T193K + N195F + V206L + K391A + G476K | 1.2 | 1.3 | 0.9 | 1.0 | 1.3 | 1.3 | 1.0 | 1.0 |
| H1* + N54S + V56T + M105F + G109A + A174S + G182* + D183* + G184T + N195F + V206L + K391A + G476K | 1.9 | 2.0 | 1.1 | 1.2 | 2.1 | 1.9 | 1.4 | 1.3 |
| H1* + N54S + V56T + G109A + T134E + A174S + G182* + D183* + N195F + V206L + R320A + S323N + K391A + G476K | 1.7 | 2.1 | 1.1 | 1.1 | 2.1 | 2.0 | 1.3 | 1.3 |
| H1* + N54S + V56T + G109A + A174S + G182* + D183* + N195F + V206L + V291G + D377H + K391A + G476K | 1.7 | 1.8 | 1.2 | 1.1 | 2.1 | 1.9 | 1.4 | 1.3 |
| H1* + N54S + V56T + G109A + A174S + G182* + D183* + N195F + V206L + V291A + F328L + D377H + K391A + G476K | 1.7 | 1.9 | 1.1 | 1.1 | 2.1 | 1.9 | 1.3 | 1.3 |
| H1* + V56T + G109A + A174S + G182* + D183* + N195F + V206L + D377H + K391A + G476K | 1.3 | 1.8 | 1.1 | 1.1 | 1.5 | 1.5 | 1.3 | 1.2 |
| H1* + N54S + V56T + G109A + T134E + A174S + G182* + D183* + G184T + N195F + V206L + K391A + G476K | 2.4 | 2.2 | 1.1 | 1.1 | 3.0 | 2.4 | 1.5 | 1.3 |
| H1* + N54S + V56T + G109A + A174S + G182* + D183* + N195F + V206L + V238A + D377H + K391A + G476K | 1.7 | 1.8 | 1.2 | 1.1 | 2.1 | 1.9 | 1.4 | 1.2 |
| H1* + N54S + V56T + G109A + A174S + G182* + D183* + N195F + V206L + V238T + D377H + K391A + G476K | 2.0 | 1.8 | 1.1 | 1.1 | 2.5 | 1.9 | 1.3 | 1.2 |
| H1* + N54S + V56T + G109A + A174S + G182* + D183* + N195F + V206L + V238G + D377H + K391A + G476K | 1.9 | 1.6 | 1.1 | 1.1 | 2.3 | 1.8 | 1.2 | 1.2 |
| H1* + N54S + V56T + G109A + A174S + G182* + D183* + N195F + V206L + F328M + D377H + K391A + G476K | 1.6 | 1.8 | 1.0 | 1.0 | 2.1 | 1.8 | 1.2 | 1.2 |
| H1* + N54S + V56T + G109A + A174S + G182* + D183* + N195F + V206L + F328L + D377H + K391A + G476K | 1.6 | 1.7 | 0.9 | 1.0 | 1.7 | 1.5 | 1.0 | 1.1 |
| H1* + N54S + V56T + G109A + A174S + G182* + D183* + N195F + V206L + F328V + D377H + K391A + G476K | 1.6 | 1.6 | 0.8 | 1.0 | 1.8 | 1.7 | 1.0 | 1.1 |
| H1* + N54S + V56T + G109A + A174S + G182* + D183* + N195F + V206L + F328I + D377H + K391A + G476K | 1.6 | 1.6 | 0.9 | 1.1 | 2.0 | 1.6 | 1.1 | 1.0 |
| H1* + N54S + V56T + G109A + A174S + G182* + D183* + N195F + V206L + V291T + D377H + K391A + G476K | 1.9 | 1.8 | 1.2 | 1.1 | 2.4 | 1.9 | 1.3 | 1.2 |
| H1* + N54S + V56T + G109A + A174S + G182* + D183* + N195F + V206L + V291A + D377H + K391A + G476K | 2.4 | 1.9 | 1.2 | 1.2 | 2.9 | 2.1 | 1.5 | 1.3 |
| H1* + N54S + V56T + K72R + G109A + T134E + A174S + G182* + D183* + G184T + N195F + V206L + G255A + K391A + G476K | 2.1 | 1.9 | 1.0 | 1.1 | 2.1 | 2.0 | 1.4 | 1.2 |
| H1* + N54S + V56T + G109A + L173H + A174S + G182* + D183* + N195F + V206L + K391A + G476K | 2.0 | 1.8 | 1.2 | 1.1 | 2.6 | 2.0 | 1.4 | 1.2 |
| H1* + N54S + V56T + G109A + Q125T + A174S + G182* + D183* + N195F + V206L + K391A + G476K | 1.4 | 1.7 | 0.9 | 1.0 | 2.0 | 1.8 | 1.2 | 1.0 |
| H1* + N16S + N54S + V56T + G109A + A174S + G182* + D183* + N195F + V206L + K391A + G476K | 1.9 | 1.6 | 1.0 | 1.0 | 2.1 | 1.9 | 1.3 | 1.2 |
| H1* + N54S + V56T + K72N + G109A + A174S + G182* + D183* + N195F + V206L + K391A + G476K | 2.1 | 1.6 | 1.0 | 1.0 | 2.1 | 2.2 | 1.3 | 1.3 |
| H1* + N54S + V56T + K72N + G109A + W167L + A174S + G182* + D183* + N195F + V206L + K391A + G476K | 2.2 | 1.9 | 0.9 | 1.2 | 1.9 | 2.1 | 1.2 | 1.2 |
| H1* + N54S + V56T + K72A + G109A + W167Y + A174S + G182* + D183* + N195F + V206L + K391A + G476K | 1.7 | 1.8 | 0.8 | 1.1 | 1.6 | 2.0 | 1.1 | 1.2 |
| H1* + N54S + V56T + G109A + Q118R + T134E + A174S + G182* + D183* + N195F + V206L + G255A + D377H + K391A + G476K | 2.0 | 1.9 | 1.0 | 1.1 | 2.0 | 2.0 | 1.2 | 1.2 |
| H1* + N54S + V56T + K72R + G109A + A174S + G182* + D183* + N195F + G184T + V206L + K391A + G476K | 2.2 | 2.1 | 1.1 | 1.1 | 3.3 | 2.5 | 1.5 | 1.3 |
| H1* + N54S + V56T + K72R + G109A + Q118R + A174S + G182* + D183* + G184T + N195F + V206L + D377H + K391A + G476K | 0.9 | 1.3 | 0.8 | 0.9 | 1.3 | 1.5 | 1.0 | 1.1 |
| H1* + N54S + V56T + K72R + G109A + Q118R + A174S + G182* + D183* + N195F + V206L + G255A + D377H + K391A + G476K | 2.4 | 2.1 | 1.2 | 1.2 | 2.8 | 2.2 | 1.5 | 1.3 |
| H1* + N54S + V56T + G109A + A174S + G182* + D183* + G184T + N195F + V206L + R320A + S323N + K391A + G476K | 1.9 | 1.8 | 1.2 | 1.1 | 2.5 | 2.0 | 1.5 | 1.4 |
| H1* + N54S + G109A + A174S + G182* + D183* + N195F + V206L + D377H + K391A + G476K | 1.5 | 1.7 | 1.1 | 1.1 | 2.3 | 1.8 | 1.4 | 1.3 |
| H1* + N54S + V56T + A174S + G182* + D183* + N195F + V206L + D377H + K391A + G476K | 1.8 | 1.7 | 1.1 | 0.9 | 2.1 | 1.7 | 1.4 | 1.2 |
| H1* + N54S + V56T + G109A + G182* + D183* + N195F + V206L + D377H + K391A + G476K | 2.0 | 1.8 | 1.2 | 1.2 | 2.6 | 1.7 | 1.3 | 1.2 |
| H1* + N54S + V56T + G109A + A174S + G182* + D183* + N195F + D377H + K391A + G476K | 1.6 | 1.6 | 1.3 | 1.1 | 2.8 | 2.1 | 1.5 | 1.2 |

-continued

| | | | | | | | | |
|---|---|---|---|---|---|---|---|---|
| H1* + N54S + V56T + G109A + A174S + G182* + D183* + N195F + D377H + K391A + G476K | 2.0 | 1.6 | 1.1 | 1.1 | 2.6 | 2.0 | 1.3 | 1.1 |
| H1* + N54S + V56T + G109A + A174S + G182* + D183* + N195F + V206L + D377H + G476K | 2.2 | 2.0 | 1.2 | 1.1 | 2.6 | 1.9 | 1.5 | 1.4 |
| H1* + N54S + V56T + G109A + A174S + G182* + D183* + N195F + V206L + D377H + K391A | 2.0 | 1.9 | 1.2 | 1.1 | 2.5 | 1.8 | 1.6 | 1.4 |
| H1* + N54S + V56T + G109A + A174S + G182* + D183* + N195F + V206L + D377R + K391A + G476K | 1.4 | 1.6 | 1.1 | 1.0 | 1.5 | 1.7 | 1.3 | 1.0 |
| H1* + N54S + V56T + G109A + A174S + G182* + D183* + N195F + V206L + L217T + K391A + G476K | 1.5 | 1.7 | 1.1 | 1.0 | 2.3 | 1.2 | 1.4 | 1.2 |
| H1* + N54S + V56T + G109A + A174S + G182* + D183* + N195F + V206L + D377S + K391A + G476K | 2.0 | 1.8 | 1.3 | 1.2 | 2.4 | 1.8 | 1.5 | 1.4 |
| H1* + N54S + V56T + G109A + R116E + A174S + G182* + D183* + N195F + V206L + K391A + G476K | 2.0 | 1.9 | 1.2 | 1.1 | 2.3 | 2.0 | 1.5 | 1.3 |
| H1* + N54S + V56T + G109A + A174S + G182* + D183* + N195F + V206L + L217Q + K391A + G476K | 1.5 | 1.7 | 1.0 | 1.1 | 1.7 | 1.4 | 1.2 | 1.2 |
| H1* + N54S + V56T + G109A + A174S + G182* + D183* + N195F + V206L + G346D + K391A + G476K | 1.3 | 1.5 | 1.0 | 1.0 | 1.7 | 1.6 | 1.2 | 1.2 |
| H1* + N54S + V56T + G109A + A174S + G182* + D183* + N195F + V206L + D377A + K391A + G476K | 1.9 | 1.7 | 1.1 | 1.2 | 2.5 | 1.7 | 1.4 | 1.3 |
| H1* + N54S + V56T + G109A + T134E + A174S + G182* + D183* + N195F + V206L + D377H + K391A + G476K | 2.2 | 2.1 | 1.2 | 1.1 | 2.3 | 2.1 | 1.1 | 1.2 |
| H1* + N54S + V56T + G109A + Q118R + T134E + A174S + G182* + D183* + G184T + N195F + V206L + K391A + G476K | 1.9 | 1.7 | 1.3 | 1.2 | 2.0 | 1.7 | 1.2 | 1.2 |
| H1* + N54S + V56T + K72R + G109A + Q118R + T134E + A174S + G182* + D183* + N195F + V206L + K391A + G476K | 1.9 | 1.7 | 1.1 | 1.1 | 2.1 | 1.9 | 1.0 | 1.1 |
| H1* + N54S + V56T + G109A + A174S + G182* + D183* + N195F + V206L + G346P + K391A + G476K | 1.7 | 1.6 | 1.2 | 1.1 | 2.3 | 1.9 | 1.2 | 1.1 |
| H1* + N54S + V56T + G109A + R116S + A174S + G182* + D183* + N195F + V206L + K391A + G476K | 2.0 | 1.8 | 1.2 | 1.1 | 2.1 | 1.9 | 1.1 | 1.2 |
| H1* + N54S + V56T + G109A + A174S + G182* + D183* + N195F + V206L + D377Q + K391A + G476K | 1.7 | 1.8 | 1.2 | 1.1 | 2.0 | 2.0 | 1.2 | 1.2 |
| H1* + N54S + V56T + G109A + R116I + A174S + G182* + D183* + N195F + V206L + K391A + G476K | 2.2 | 1.8 | 1.2 | 1.1 | 2.1 | 2.0 | 1.3 | 1.3 |
| H1* + N54S + V56T + G109A + A174F + G182* + D183* + N195F + V206L + K391A + G476K | 1.7 | 1.5 | 1.1 | 1.0 | 1.5 | 1.6 | 1.3 | 1.2 |
| H1* + N54S + V56T + G109A + R116G + A174S + G182* + D183* + N195F + V206L + K391A + G476K | 2.0 | 1.9 | 1.2 | 1.2 | 2.1 | 2.0 | 1.0 | 1.2 |
| H1* + N54S + V56T + G109A + A174T + G182* + D183* + N195F + V206L + K391A + G476K | 1.9 | 1.8 | 1.2 | 1.2 | 1.9 | 2.0 | 1.1 | 1.2 |
| H1* + N54S + V56T + G109A + Q118R + T134E + A174S + G182* + D183* + G184T + N195F + V206L + G255A + K391A + G476K | 1.5 | 1.8 | 1.1 | 1.0 | 1.9 | 1.9 | 1.4 | 1.2 |
| H1* + N54S + V56T + K72R + G109A + Q118R + T134E + A174S + G182* + D183* + N195F + V206L + G255A + K391A + G476K | 1.7 | 1.8 | 1.1 | 1.0 | 2.2 | 1.8 | 1.5 | 1.2 |
| H1* + T51G + N54S + V56T + G109A + Q172R + A174S + G182* + D183* + N195F + V206L + K391A + G476K | 1.2 | 1.6 | 1.0 | 1.0 | 1.6 | 1.4 | 1.3 | 1.1 |
| H1* + T51A + N54S + V56T + G109A + Q172D + A174S + G182* + D183* + N195F + V206L + K391A + G476K | 1.5 | 1.7 | 1.0 | 1.0 | 2.3 | 1.9 | 1.4 | 1.2 |
| H1* + T51S + N54S + V56T + G109A + Q172M + A174S + G182* + D183* + N195F + V206L + K391A + G476K | 1.7 | 1.6 | 1.0 | 1.0 | 2.0 | 1.8 | 1.2 | 1.2 |
| H1* + T51A + N54S + V56T + G109A + Q172S + A174S + G182* + D183* + N195F + V206L + K391A + G476K | 2.4 | 1.8 | 1.3 | 1.1 | 2.8 | 2.1 | 1.7 | 1.3 |
| H1* + T51E + N54S + V56T + G109A + Q172T + A174S + G182* + D183* + N195F + V206L + K391A + G476K | 2.0 | 1.8 | 0.9 | 1.0 | 2.6 | 1.9 | 1.6 | 1.3 |
| H1* + T51A + N54S + V56T + G109A + Q172A + A174S + G182* + D183* + N195F + V206L + K391A + G476K | 1.9 | 1.8 | 1.0 | 1.1 | 2.3 | 1.9 | 1.6 | 1.3 |
| H1* + T51S + N54S + V56T + G109A + Q172N + A174S + G182* + D183* + N195F + V206L + K391A + G476K | 2.2 | 1.9 | 1.1 | 1.1 | 2.4 | 1.9 | 1.5 | 1.3 |
| H1* + T51G + N54S + V56T + G109A + Q172K + A174S + G182* + D183* + N195F + V206L + K391A + G476K | 1.4 | 1.3 | 1.0 | 0.9 | 1.7 | 1.5 | 1.2 | 1.1 |
| H1* + T51A + N54S + V56T + G109A + Q172G + A174S + G182* + D183* + N195F + V206L + K391A + G476K | 1.7 | 1.7 | 1.2 | 1.0 | 2.2 | 1.9 | 1.4 | 1.2 |
| H1* + T51E + N54S + V56T + G109A + Q172L + A174S + G182* + D183* + N195F + V206L + K391A + G476K | 2.0 | 1.9 | 1.0 | 1.1 | 2.2 | 1.8 | 1.2 | 1.1 |
| H1* + T51E + N54S + V56T + G109A + Q172R + A174S + G182* + D183* + N195F + V206L + K391A + G476K | 2.0 | 1.9 | 1.1 | 1.1 | 1.8 | 1.7 | 1.4 | 1.1 |
| H1* + N54S + V56T + G109A + Q172K + A174S + G182* + D183* + N195F + V206L + K391A + G476K | 2.1 | 1.8 | 1.0 | 1.1 | 2.0 | 1.6 | 1.3 | 1.2 |
| H1* + T51D + N54S + V56T + G109A + Q172N + A174S + G182* + D183* + N195F + V206L + K391A + G476K | 1.8 | 1.7 | 1.0 | 1.0 | 1.9 | 1.6 | 1.3 | 1.1 |
| H1* + T51A + N54S + V56T + G109A + Q172K + A174S + G182* + D183* + N195F + V206L + K391A + G476K | 1.7 | 1.7 | 1.2 | 1.1 | 1.8 | 1.4 | 1.3 | 1.2 |
| H1* + N54S + V56T + K72R + G109A + Q172S + A174S + G182* + D183* + N195F + V206L + K391A + G476K | 2.0 | 1.8 | 1.3 | 1.1 | 2.6 | 1.8 | 1.4 | 1.3 |
| H1* + N54S + V56T + K72H + G109A + Q172T + A174S + G182* + D183* + N195F + V206L + K391A + G476K | 2.0 | 1.8 | 1.2 | 1.1 | 2.0 | 1.9 | 1.3 | 1.2 |

-continued

| | | | | | | | | |
|---|---|---|---|---|---|---|---|---|
| H1* + N54S + V56T + K72R + G109A + Q172R + A174S + K179E + G182* + D183* + N195F + V206L + K391A + G476K | 1.8 | 1.6 | 1.1 | 1.1 | 1.4 | 1.5 | 1.1 | 1.1 |
| H1* + N54S + V56T + K72R + G109A + Q172M + A174S + G182* + D183* + N195F + V206L + Y295N + K391A + G476K | 1.9 | 1.8 | 1.2 | 1.1 | 2.1 | 1.7 | 1.3 | 1.2 |
| H1* + N54S + V56T + K72R + G109A + Q172R + A174S + G182* + D183* + N195F + V206L + K391A + G476K | 1.4 | 1.4 | 1.0 | 1.0 | 1.5 | 1.4 | 1.2 | 0.9 |
| H1* + N54S + V56T + K72Q + G109A + Q172R + A174S + G182* + D183* + N195F + V206L + K391A + G476K | 2.0 | 2.0 | 1.0 | 1.0 | 2.6 | 2.1 | 1.3 | 1.2 |
| H1* + N54S + V56T + K72R + G109A + Q172T + A174S + G182* + D183* + N195F + V206L + K391A + G476K | 2.1 | 2.1 | 1.3 | 1.1 | 2.3 | 2.0 | 1.4 | 1.2 |
| H1* + N54S + V56T + K72M + G109A + Q172S + A174S + G182* + D183* + N195F + V206L + K391A + G476K | 2.3 | 1.9 | 1.2 | 1.1 | 2.4 | 2.0 | 1.2 | 1.2 |
| H1* + N54S + V56T + K72Q + G109A + Q172M + A174S + G182* + D183* + N195F + V206L + K391A + G476K | 2.1 | 2.1 | 1.3 | 1.1 | 2.8 | 2.2 | 1.5 | 1.3 |
| H1* + N54S + V56T + G109A + Q172M + A174S + G182* + D183* + N195F + V206L + K391A + G476K | 1.9 | 2.0 | 1.2 | 1.1 | 2.4 | 1.7 | 1.4 | 1.3 |
| H1* + N54S + V56T + K72S + G109A + A174H + G182* + D183* + N195F + V206L + K391A + G476K | 2.3 | 2.0 | 1.2 | 1.1 | 2.2 | 2.1 | 1.4 | 1.4 |
| H1* + N54S + V56T + K72Q + G109A + A174D + G182* + D183* + N195F + V206L + K391A + G476K | 2.3 | 2.1 | 1.1 | 1.1 | 2.2 | 1.9 | 1.4 | 1.3 |
| H1* + N54S + V56T + K72R + G109A + A174D + G182* + D183* + N195F + V206L + K391A + G476K | 2.5 | 2.0 | 1.1 | 1.1 | 2.3 | 2.1 | 1.4 | 1.3 |
| H1* + N54S + V56T + K72Q + G109A + A174K + G182* + D183* + N195F + V206L + K391A + G476K | 2.2 | 1.9 | 1.2 | 1.1 | 2.6 | 2.0 | 1.5 | 1.3 |
| H1* + N54S + V56T + G109A + A174G + G182* + D183* + N195F + V206L + K391A + G476K | 2.3 | 1.9 | 1.2 | 1.1 | 2.6 | 2.2 | 1.5 | 1.4 |
| H1* + N54S + V56T + K72R + G109A + A174Q + G182* + D183* + N195F + V206L + K391A + G476K | 2.5 | 2.1 | 1.2 | 1.2 | 2.3 | 2.1 | 1.5 | 1.4 |
| H1* + N54S + V56T + K72Q + G109A + A174G + G182* + D183* + N195F + V206L + K391A + G476K | 2.3 | 2.1 | 1.1 | 1.1 | 2.6 | 2.2 | 1.4 | 1.4 |
| H1* + N54S + V56T + K72S + G109A + A174N + G182* + D183* + N195F + V206L + K391A + G476K | 2.6 | 2.1 | 1.3 | 1.1 | 2.6 | 2.3 | 1.5 | 1.4 |
| H1* + N54S + V56T + K72R + G109A + A174H + G182* + D183* + N195F + V206L + K391A + G476K | 2.1 | 1.9 | 1.3 | 1.2 | 2.5 | 2.2 | 1.5 | 1.4 |
| H1* + N54S + V56T + G109A + A174S + G182* + D183* + N195F + V206L + K391A + K391S + G476K | 1.7 | 1.7 | 1.1 | 1.1 | 1.9 | 1.6 | 1.4 | 1.2 |
| H1* + N54S + V56T + G109A + A174S + G182* + D183* + N195F + V206L + K391A + T444A + G476K | 1.7 | 1.6 | 1.2 | 1.1 | 2.2 | 1.6 | 1.4 | 1.2 |
| H1* + N54S + V56T + G109A + F113L + W167F + A174S + G182* + D183* + N195F + V206L + K391A + G476K | 1.7 | 1.6 | 1.0 | 1.0 | 2.1 | 1.7 | 1.2 | 1.2 |
| H1* + G50A + N54S + V56T + G109A + A174E + G182* + D183* + N195F + A204T + V206L + S323N + K391A + G476K | 2.0 | 1.8 | 1.0 | 1.1 | 1.5 | 1.7 | 1.3 | 1.2 |
| H1* + N54S + V56T + K72R + G109A + Q118R + A174S + G182* + D183* + G184T + N195F + V206L + G255A + K391A + G476K | 1.6 | 1.6 | 1.1 | 1.0 | 1.2 | 1.3 | 1.2 | 1.2 |
| H1* + N54S + V56T + M105F + G109A + A174S + G182* + D183* + N195F + V206L + D377H + K391A + G476K | 1.8 | 1.9 | 1.2 | 1.1 | 2.6 | 1.9 | 1.5 | 1.3 |
| H1* + N54S + V56T + K72R + G109A + Q118R + A174S + G182* + D183* + N195F + V206L + D377H + K391A + G476K | 1.5 | 1.6 | 1.1 | 1.1 | 1.4 | 1.3 | 1.3 | 1.2 |
| H1* + N54S + V56T + G109A + A174S + G182* + D183* + N195F + A204G + V206L + K391A + G476K | 2.7 | 2.1 | 1.2 | 1.2 | 2.9 | 2.6 | 1.6 | 1.4 |
| H1* + N54S + V56T + G109A + A174S + G182* + D183* + N195F + V206L + A225F + K391A + G476K | 1.8 | 1.8 | 1.0 | 0.9 | 1.8 | 1.7 | 1.4 | 1.2 |
| H1* + N54S + V56T + G109A + A174S + G182* + D183* + N195F + V206L + M246A + K391A + G476K | 1.8 | 1.6 | 0.9 | 0.9 | 1.7 | 1.8 | 1.2 | 1.2 |
| H1* + N54S + V56T + G109A + A174S + G182* + D183* + N195F + V206L + Y382I + K391A + G476K | 2.1 | 1.7 | 0.9 | 0.9 | 1.8 | 1.5 | 1.3 | 1.1 |
| H1* + N54S + V56T + G109A + A174S + G182* + D183* + N195F + V206L + S376H + K391A + G476K | 1.8 | 1.7 | 1.1 | 0.9 | 2.1 | 2.0 | 1.3 | 1.1 |
| H1* + N54S + V56T + G109A + A174S + G182* + D183* + N195F + V206L + I214E + K391A + G476K | 1.7 | 1.5 | 1.1 | 0.9 | 2.1 | 2.1 | 1.2 | 1.3 |
| H1* + N54S + V56T + G109A + A174S + G182* + D183* + N195F + V206L + I214W + K391A + G476K | 2.2 | 1.9 | 1.1 | 1.1 | 2.4 | 2.0 | 1.4 | 1.3 |
| H1* + N54S + V56T + K72R + G109A + Q172K + A174S + G182* + D183* + N195F + V206L + K391A + G476K | 1.7 | 1.4 | 0.9 | 1.0 | 2.1 | 1.7 | 1.2 | 1.1 |
| H1* + N54S + V56T + G109A + A174S + G182* + D183* + N195F + A204T + V206L + D377H + K391A + G476K | 1.9 | 1.9 | 1.1 | 1.1 | 2.7 | 2.1 | 1.5 | 1.3 |
| H1* + N54S + V56T + G109A + A174S + G182* + D183* + N195F + A204S + V206L + D377H + K391A + G476K | 2.1 | 1.6 | 1.2 | 1.1 | 2.2 | 1.8 | 1.3 | 1.3 |
| H1* + N54S + V56T + G109A + T165S + A174S + G182* + D183* + N195F + V206L + D377H + K391A + G476K | 1.9 | 1.8 | 1.1 | 1.1 | 2.3 | 2.0 | 1.4 | 1.2 |
| H1* + N54S + V56T + G109A + A174S + G182* + D183* + N195F + V206L + T334S + D377H + K391A + G476K | 2.0 | 1.6 | 1.0 | 1.0 | 2.3 | 1.7 | 1.5 | 1.3 |
| H1* + N54S + V56T + G109A + A174S + G182* + D183* + N195F + V206L + A263G + D377H + K391A + G476K | 2.0 | 1.6 | 1.0 | 1.0 | 2.1 | 1.6 | 1.4 | 1.1 |
| H1* + N54S + V56T + G109A + A174S + G182* + D183* + N195F + V206L + M286F + D377H + K391A + G476K | 2.0 | 1.6 | 1.1 | 1.0 | 2.3 | 1.7 | 1.3 | 1.1 |
| H1* + N54S + V56T + G109A + A174S + G182* + D183* + N195F + V206L + Y267I + D377H + K391A + G476K | 1.9 | 1.6 | 1.0 | 1.0 | 1.8 | 1.7 | 1.3 | 1.2 |

-continued

| | | | | | | | | |
|---|---|---|---|---|---|---|---|---|
| H1* + N54S + V56T + G109A + A174S + G182* + D183* + N195F + V206L + L235V + D377H + K391A + G476K | 2.1 | 1.8 | 1.1 | 1.0 | 2.5 | 2.1 | 1.5 | 1.3 |
| H1* + N54S + V56T + G109A + A174S + G182* + D183* + N195F + V206L + L235A + D377H + K391A + G476K | 1.6 | 1.6 | 0.8 | 0.9 | 2.3 | 1.9 | 1.3 | 1.2 |
| H1* + N54S + V56T + M105L + G109A + A174S + G182* + D183* + N195F + V206L + D377H + K391A + G476K | 2.1 | 1.9 | 1.1 | 1.1 | 2.9 | 2.1 | 1.5 | 1.3 |
| H1* + N54S + V56T + M105I + G109A + A174S + G182* + D183* + N195F + V206L + D377H + K391A + G476K | 2.2 | 2.0 | 1.1 | 1.1 | 2.3 | 2.0 | 1.6 | 1.4 |
| H1* + N54S + V56T + M105V + G109A + A174S + G182* + D183* + N195F + V206L + D377H + K391A + G476K | 2.3 | 2.1 | 1.2 | 1.1 | 2.6 | 2.1 | 1.5 | 1.4 |
| H1* + N54S + V56T + G109A + A174S + G182* + D183* + N195F + V206L + M246I + D377H + K391A + G476K | 2.2 | 1.9 | 1.3 | 1.1 | 2.6 | 2.0 | 1.7 | 1.3 |
| H1* + N54S + V56T + G109A + A174S + G182* + D183* + N195F + V206L + L250I + D377H + K391A + G476K | 2.3 | 2.0 | 1.3 | 1.1 | 2.3 | 1.9 | 1.6 | 1.3 |
| H1* + N54S + V56T + G109A + A174S + G182* + D183* + N195F + V206L + L250V + D377H + K391A + G476K | 2.2 | 1.9 | 1.3 | 1.2 | 2.5 | 2.0 | 1.6 | 1.3 |
| H1* + N54S + V56T + G109A + A174S + G182* + D183* + N195F + V206L + K391Y + G476K | 2.2 | 1.9 | 1.2 | 1.1 | 2.1 | 1.9 | 1.6 | 1.4 |
| H1* + N54S + V56T + G109A + A174S + G182* + D183* + N195F + V206L + K391V + G476K | 2.1 | 1.9 | 1.0 | 1.0 | 2.1 | 1.8 | 1.4 | 1.3 |
| H1* + N54S + V56T + G109A + A174S + G182* + D183* + N195F + V206L + K391M + G476K | 2.2 | 1.8 | 1.3 | 1.1 | 2.6 | 2.1 | 1.5 | 1.3 |
| H1* + N54S + V56T + G109A + A174S + G182* + D183* + N195F + V206L + K391E + G476K | 1.8 | 1.6 | 1.2 | 1.0 | 2.1 | 1.9 | 1.3 | 1.1 |
| H1* + N54S + V56T + G109A + T165G + A174S + G182* + D183* + N195F + V206L + D377H + K391A + G476K | 2.3 | 2.0 | 1.3 | 1.1 | 2.9 | 2.0 | 1.7 | 1.3 |
| H1* + N54R + V56T + G109A + A174S + G182* + D183* + N195F + V206L + K391A + G476K | 1.3 | 1.4 | 1.1 | 1.1 | 1.1 | 1.1 | 1.1 | 0.8 |
| H1* + N54L + V56T + G109A + A174S + G182* + D183* + N195F + V206L + K391A + G476K | 1.6 | 1.4 | 1.1 | 1.0 | 1.3 | 1.6 | 1.3 | 1.2 |
| H1* + N54S + V56T + G109S + A174S + G182* + D183* + N195F + V206L + K391A + G476K | 2.4 | 2.4 | 1.4 | 1.2 | 2.3 | 2.0 | 1.4 | 1.3 |
| H1* + N54S + V56T + G109A + A174V + G182* + D183* + N195F + V206L + K391A + G476K | 2.2 | 2.2 | 1.3 | 1.3 | 2.3 | 2.0 | 1.5 | 1.4 |
| H1* + N54S + V56T + G109A + A174S + G182* + D183* + N195F + V206L + M246F + D377H + K391A + G476K | 2.6 | 2.3 | 1.3 | 1.1 | 2.5 | 2.0 | 1.6 | 1.2 |
| H1* + N54S + V56T + G109A + A174S + G182* + D183* + N195F + V206L + M246V + D377H + K391A + G476K | 2.2 | 1.8 | 1.3 | 1.2 | 1.9 | 1.8 | 1.4 | 1.3 |
| H1* + N54S + V56T + G109A + A174S + G182* + D183* + N195F + V206L + M246S + D377H + K391A + G476K | 2.3 | 1.9 | 1.2 | 1.2 | 1.8 | 1.6 | 1.4 | 1.1 |
| H1* + N54S + V56T + G109A + A174R + G182* + D183* + N195F + V206L + K391A + G476K | 1.7 | 1.6 | 1.2 | 1.1 | 1.7 | 1.6 | 1.4 | 1.2 |
| H1* + N54S + V56T + G109A + A174L + G182* + D183* + N195F + V206L + K391A + G476K | 1.9 | 1.7 | 1.2 | 1.2 | 2.2 | 1.7 | 1.3 | 1.2 |
| H1* + N54S + V56T + G109A + A174S + G182* + D183* + N195F + V206S + K391A + G476K | 1.8 | 1.6 | 1.0 | 1.1 | 2.0 | 1.7 | 1.3 | 1.3 |
| H1* + N54S + V56T + G109A + A174S + G182* + D183* + N195F + V206L + K391D + G476K | 1.9 | 2.0 | 1.3 | 1.2 | 2.2 | 2.0 | 1.5 | 1.4 |
| H1* + N54S + V56T + G109A + A174S + G182* + D183* + N195F + V206L + K391R + G476K | 2.3 | 1.8 | 1.3 | 1.2 | 2.5 | 1.9 | 1.4 | 1.3 |
| H1* + N54S + V56T + G109A + A174S + G182* + D183* + N195F + V206L + K391H + G476K | 2.2 | 1.9 | 1.2 | 1.2 | 2.3 | 2.0 | 1.5 | 1.3 |
| H1* + N54S + V56T + G109A + A174S + G182* + D183* + N195F + V206L + K391W + G476K | 2.2 | 1.6 | 1.3 | 1.2 | 2.5 | 2.0 | 1.4 | 1.3 |
| H1* + N54S + V56T + G109A + A174S + G182* + D183* + N195F + V206L + K391I + G476K | 2.1 | 1.8 | 1.2 | 1.2 | 2.0 | 1.8 | 1.3 | 1.3 |
| H1* + N54S + V56T + G109A + A174S + G182* + D183* + N195F + V206L + L250T + D377H + K391A + G476K | 2.0 | 1.6 | 1.1 | 1.1 | 2.6 | 2.0 | 1.4 | 1.3 |
| H1* + N54S + V56T + G109A + A174S + G182* + D183* + N195F + V206L + L250A + D377H + K391A + G476K | 2.1 | 1.8 | 1.0 | 1.0 | 2.6 | 2.0 | 1.5 | 1.3 |
| H1* + N54S + V56T + G109A + A174S + G182* + D183* + N195F + V206L + L250F + D377H + K391A + G476K | 2.2 | 1.7 | 1.1 | 1.1 | 2.4 | 2.0 | 1.6 | 1.2 |
| H1* + N54S + V56T + G109A + A174S + G182* + D183* + N195F + V206L + L250M + D377H + K391A + G476K | 2.2 | 1.7 | 1.1 | 1.1 | 2.0 | 1.9 | 1.4 | 1.3 |
| H1* + N54S + V56T + G109A + A174S + G182* + D183* + N195F + V206L + K391Q + G476K | 1.8 | 1.4 | 1.1 | 1.0 | 1.5 | 1.7 | 1.2 | 1.2 |
| H1* + N54S + V56T + G109A + Q172H + L173A + A174P + G182* + D183* + N195F + V206L + K391A + G476K | 2.5 | 1.8 | 1.3 | 1.2 | 2.3 | 2.1 | 1.6 | 1.4 |
| H1* + N54S + V56T + G109A + Q172E + L173A + A174R + G182* + D183* + N195F + V206L + K391A + G476K | 1.1 | 1.4 | 0.7 | 1.0 | 1.8 | 1.7 | 1.2 | 1.2 |
| H1* + N54S + V56T + K72Q + G109A + W167R + A174S + G182* + D183* + N195F + V206L + K391A + G476K | 1.9 | 1.7 | 1.2 | 1.1 | 1.6 | 1.6 | 1.0 | 1.1 |
| H1* + N54S + V56T + G109A + A174S + G182* + D183* + G184T + N195F + V206L + G255A + K391A + G476K | 1.8 | 1.7 | 1.1 | 1.0 | 2.0 | 1.7 | 1.3 | 1.2 |
| H1* + N54S + V56T + K72R + G109A + A174S + G182* + D183* + G184T + N195F + V206L + D377H + K391A + G476K | 1.7 | 1.6 | 1.1 | 1.1 | 1.9 | 1.6 | 1.1 | 1.0 |
| H1* + N54S + V56T + G109A + A174S + G182* + D183* + G184T + N195F + V206L + G255A + D377H + K391A + G476K | 2.4 | 2.1 | 1.3 | 1.2 | 2.3 | 2.0 | 1.4 | 1.2 |

-continued

| | | | | | | | | |
|---|---|---|---|---|---|---|---|---|
| H1* + N54S + V56T + G109A + Q118R + A174S + G182* + D183* + N195F + V206L + K391A + G476K | 1.6 | 1.5 | 1.1 | 1.2 | 0.7 | 1.1 | 0.8 | 1.0 |
| H1* + N54S + V56T + G109A + A174S + G182* + D183* + N195F + V206L + S376T + K391A + G476K | 2.2 | 2.0 | 1.3 | 1.2 | 2.3 | 1.8 | 1.3 | 1.3 |
| H1* + N54S + V56T + G109A + A174S + G182* + D183* + N195F + V206L + S376V + K391A + G476K | 2.0 | 1.8 | 1.2 | 1.2 | 2.1 | 1.8 | 1.4 | 1.3 |
| H1* + N54S + V56T + G109A + Q172E + L173I + A174N + G182* + D183* + N195F + V206L + K391A + G476K | 2.3 | 1.9 | 1.1 | 1.1 | 2.1 | 1.9 | 1.1 | 1.2 |
| H1* + N54S + V56T + G109A + Q172D + L173A + A174T + G182* + D183* + N195F + V206L + K391A + G476K | 2.3 | 2.0 | 1.1 | 1.1 | 2.2 | 2.0 | 1.1 | 1.2 |
| H1* + N54S + V56T + G109A + A174S + G182* + D183* + N195F + V206L + Y267M + D377H + K391A + G476K | 2.1 | 2.0 | 1.2 | 1.2 | 2.6 | 2.0 | 1.5 | 1.3 |
| H1* + N54S + V56T + G109A + A174S + G182* + D183* + N195F + V206L + Y267H + D377H + K391A + G476K | 1.7 | 1.6 | 1.1 | 1.0 | 2.5 | 1.9 | 1.2 | 1.2 |
| H1* + N54S + V56T + G109A + A174S + G182* + D183* + N195F + V206L + V238A + K391A + G476K | 1.6 | 1.5 | 1.1 | 1.0 | 2.3 | 1.7 | 1.2 | 1.1 |
| H1* + N54S + V56T + G109A + A174S + G182* + D183* + N195F + V206L + V238T + K391A + G476K | 1.5 | 1.3 | 1.1 | 0.9 | 1.7 | 1.5 | 1.2 | 1.1 |
| H1* + N54S + V56T + G109A + A174S + G182* + D183* + N195F + V206L + V238G + K391A + G476K | 2.3 | 1.7 | 1.2 | 1.1 | 3.0 | 2.1 | 1.4 | 1.3 |
| H1* + N54S + V56T + M105V + G109A + A174S + G182* + D183* + N195F + V206L + K391A + G476K | 2.0 | 1.7 | 1.2 | 1.1 | 2.3 | 2.1 | 1.5 | 1.4 |
| H1* + N54S + V56T + G109A + A174S + G182* + D183* + N195F + V206L + V264T + K391A + G476K | 2.2 | 2.1 | 1.2 | 1.0 | 2.9 | 1.9 | 1.4 | 1.3 |
| H1* + N54S + V56T + G109A + A174S + G182* + D183* + N195F + V206L + V264I + K391A + G476K | 2.4 | 1.8 | 1.3 | 1.1 | 2.9 | 2.3 | 1.5 | 1.4 |
| H1* + N54S + V56T + G109A + A174S + G182* + D183* + N195F + V206L + L235V + K391A + G476K | 1.9 | 1.7 | 1.1 | 1.0 | 2.4 | 1.9 | 1.3 | 1.3 |
| H1* + N54S + V56T + G109A + W167H + Q172N + L173A + A174S + G182* + D183* + N195F + V206L + K391A + G476K | 2.0 | 1.7 | 1.2 | 1.1 | 2.9 | 2.1 | 1.4 | 1.3 |
| H1* + N54S + V56T + G109A + W167F + Q172E + L173P + A174K + G182* + D183* + N195F + V206L + K391A + G476K | 1.7 | 1.9 | 1.2 | 1.1 | 3.3 | 2.2 | 1.5 | 1.3 |
| H1* + N54S + V56T + G109A + Q172N + L173T + A174S + G182* + D183* + N195F + V206L + K391A + G476K | 2.0 | 1.7 | 1.2 | 1.1 | 2.8 | 2.0 | 1.4 | 1.4 |
| H1* + N54S + V56T + G109A + Q172K + L173V + A174T + G182* + D183* + N195F + V206L + K391A + G476K | 1.6 | 1.4 | 1.0 | 1.1 | 1.6 | 1.6 | 1.0 | 1.0 |
| H1* + N54S + V56T + G109A + Q172E + L173F + A174R + G182* + D183* + N195F + V206L + K391A + G476K | 1.9 | 1.6 | 1.1 | 1.0 | 2.0 | 1.9 | 1.3 | 1.1 |
| H1* + N54S + V56T + G109A + Q172E + L173T + A174R + G182* + D183* + N195F + V206L + K391A + G476K | 1.9 | 1.8 | 1.2 | 1.2 | 2.5 | 2.1 | 0.9 | 1.3 |
| H1* + N54S + V56T + G109A + Q172N + L173V + A174R + G182* + D183* + N195F + V206L + K391A + G476K | 1.9 | 1.7 | 1.3 | 1.2 | 2.2 | 1.8 | 0.9 | 1.2 |
| H1* + N54S + V56T + G109A + L173V + A174R + G182* + D183* + N195F + V206L + K391A + G476K | 1.7 | 1.8 | 1.3 | 1.2 | 1.7 | 1.6 | 0.8 | 1.1 |
| H1* + N54S + V56T + G109A + Q172E + L173M + A174H + G182* + D183* + N195F + V206L + K391A + G476K | 2.1 | 2.1 | 1.3 | 1.2 | 2.8 | 2.1 | 1.3 | 1.3 |
| H1* + N54S + V56T + G109A + Q172E + L173F + A174P + G182* + D183* + N195F + V206L + K391A + G476K | 1.9 | 1.9 | 1.2 | 1.2 | 2.7 | 2.3 | 0.8 | 1.3 |
| H1* + N54S + V56T + G109A + W167Y + Q172E + L173V + A174H + G182* + D183* + N195F + V206L + K391A + G476K | 2.0 | 1.8 | 1.1 | 1.0 | 2.8 | 2.0 | 1.4 | 1.3 |
| H1* + N54S + V56T + G109A + L173A + A174T + G182* + D183* + N195F + V206L + K391A + G476K | 2.0 | 1.8 | 1.0 | 1.0 | 2.4 | 1.8 | 1.4 | 1.3 |
| H1* + N54S + V56T + G109A + A174S + G182* + D183* + N195F + V206L + V291A + F328L + K391A + G476K | 2.0 | 1.6 | 1.1 | 1.0 | 2.9 | 1.7 | 1.4 | 1.2 |
| H1* + N54S + V56T + G109A + A174S + G182* + D183* + N195F + V206L + M246L + K391A + G476K | 2.2 | 1.7 | 1.0 | 1.0 | 2.8 | 1.7 | 1.2 | 1.2 |
| H1* + N54S + V56T + G109A + A174S + G182* + D183* + N195F + V206L + M246S + K391A + G476K | 1.8 | 1.8 | 1.2 | 1.1 | 2.9 | 2.0 | 1.5 | 1.4 |
| H1* + N54S + V56T + G109A + A174S + G182* + D183* + N195F + V206L + L250V + K391A + G476K | 2.0 | 1.9 | 1.3 | 1.2 | 2.8 | 2.0 | 1.6 | 1.4 |
| H1* + N54S + V56T + G109A + A174S + G182* + D183* + N195F + V206L + L250F + K391A + G476K | 2.0 | 1.8 | 1.1 | 1.0 | 2.9 | 2.1 | 1.5 | 1.3 |
| H1* + N54S + V56T + G109A + A174S + G182* + D183* + N195F + V206L + L250M + K391A + G476K | 2.3 | 1.7 | 1.2 | 1.1 | 3.0 | 2.1 | 1.5 | 1.4 |
| H1* + N54S + V56T + G109A + A174S + G182* + D183* + N195F + V206L + K391A + C474V + G476K | 1.9 | 1.8 | 1.3 | 1.0 | 2.8 | 2.0 | 1.3 | 1.3 |
| H1* + N54S + V56T + G109A + A174S + G182* + D183* + N195F + A204S + V206L + K391A + G476K | 1.7 | 1.6 | 1.0 | 1.0 | 1.7 | 1.8 | 1.4 | 1.3 |
| H1* + N54S + V56T + G109A + T165G + A174S + G182* + D183* + N195F + V206L + K391A + G476K | 2.3 | 1.9 | 1.2 | 1.1 | 2.9 | 2.2 | 1.3 | 1.3 |
| H1* + N54S + V56T + G109A + A174S + G182* + D183* + N195F + V206L + T334S + K391A + G476K | 1.9 | 1.7 | 1.0 | 1.0 | 2.6 | 2.0 | 1.4 | 1.3 |
| H1* + N54S + V56T + G109A + A174S + G182* + D183* + N195F + V206L + A263G + M286F + K391A + G476K | 1.1 | 1.3 | 1.0 | 0.9 | 1.4 | 1.3 | 1.1 | 1.1 |
| H1* + N54S + V56T + G109A + A174S + G182* + D183* + N195F + V206L + A263G + M286L + K391A + G476K | 1.7 | 1.5 | 1.1 | 1.0 | 2.2 | 1.9 | 1.3 | 1.1 |
| H1* + N54S + V56T + G109A + A174S + G182* + D183* + N195F + V206L + Y267H + K391A + G476K | 1.9 | 1.9 | 1.2 | 1.2 | 2.7 | 2.2 | 1.5 | 1.4 |

-continued

| | | | | | | | | |
|---|---|---|---|---|---|---|---|---|
| H1* + N54S + V56T + G109A + A174S + G182* + D183* + N195F + V206L + Y267L + K391A + G476K | 1.9 | 1.8 | 1.0 | 1.1 | 2.4 | 2.2 | 1.5 | 1.4 |
| H1* + N54S + V56T + G109A + A174S + G182* + D183* + N195F + V206L + Y267I + K391A + G476K | 1.2 | 1.5 | 0.7 | 0.9 | 1.7 | 1.9 | 1.3 | 1.3 |
| H1* + T51A + N54S + V56T + G109A + Q172R + A174S + G182* + D183* + N195F + V206L + K391A + G476K | 2.1 | 1.5 | 1.1 | 1.0 | 1.5 | 1.6 | 1.4 | 1.1 |
| H1* + N54S + V56T + G109A + A174S + G182* + D183* + N195F + V206L + K391L + G476K | 2.4 | 1.9 | 1.1 | 1.1 | 2.5 | 1.9 | 1.4 | 1.2 |
| H1* + N54S + V56T + G109A + F113Q + R116H + Q172G + A174S + G182* + D183* + N195F + V206L + K391A + G476K | 2.6 | 2.1 | 1.1 | 1.0 | 3.1 | 2.1 | 1.4 | 1.2 |
| H1* + N54S + V56T + G109A + F113Q + Q172G + A174S + G182* + D183* + N195F + V206L + K391A + G476K | 1.9 | 1.8 | 0.9 | 0.9 | 2.7 | 1.9 | 1.2 | 1.1 |
| H1* + N54S + V56T + G109S + F113Q + R116Q + A174S + G182* + D183* + N195F + V206L + K391A + G476K | 2.9 | 2.2 | 1.2 | 1.1 | 3.3 | 2.6 | 1.5 | 1.3 |
| H1* + N54S + V56T + G109A + Q172D + A174S + G182* + D183* + N195F + A204G + V206L + K391A + P473R + G476K | 2.7 | 2.2 | 1.2 | 1.1 | 3.1 | 2.1 | 1.5 | 1.3 |
| H1* + N54S + V56T + K72R + G109A + T134E + A174S + G182* + D183* + N195F + A204G + V206L + G255A + K391A + P473R + G476K | 2.8 | 2.3 | 1.2 | 1.1 | 3.4 | 2.4 | 1.7 | 1.3 |
| H1* + N54S + V56T + K72R + G109A + W167F + A174S + G182* + D183* + N195F + A204G + V206L + K391A + G476K | 2.7 | 2.2 | 1.2 | 1.1 | 3.1 | 2.2 | 1.6 | 1.3 |
| H1* + N54S + V56T + K72R + G109A + A174S + G182* + D183* + G184T + N195F + A204G + V206L + K391A + P473R + G476K | 2.3 | 2.1 | 1.2 | 1.1 | 2.7 | 2.0 | 1.4 | 1.3 |
| H1* + N54S + V56T + G109A + W167F + Q172N + A174S + G182* + D183* + N195F + V206L + K391A + P473R + G476K | 2.5 | 1.8 | 1.3 | 1.2 | 2.6 | 1.8 | 1.6 | 1.2 |
| H1* + N54S + V56T + G109A + W167F + Q172G + A174S + G182* + D183* + N195F + V206L + K391A + P473G + G476K | 2.4 | 2.0 | 1.3 | 1.2 | 2.8 | 2.0 | 1.6 | 1.2 |
| H1* + N54S + V56T + G109A + W167F + Q172G + A174S + G182* + D183* + N195F + V206L + K391A + P473R + G476K | 2.1 | 1.8 | 1.3 | 1.1 | 2.3 | 1.8 | 1.5 | 1.2 |
| H1* + N54S + V56T + K72R + G109A + W167F + Q172R + A174S + G182* + D183* + N195F + V206L + K391A + G476K | 2.2 | 1.9 | 1.1 | 1.1 | 2.0 | 1.8 | 1.2 | 1.1 |
| H1* + N54S + V56T + K72R + G109A + R116H + W167F + Q172R + A174S + G182* + D183* + N195F + V206L + K391A + G476K | 2.4 | 1.8 | 1.2 | 1.1 | 2.4 | 1.9 | 1.5 | 1.2 |
| H1* + N54S + V56T + M105F + G109A + A174S + G182* + D183* + N195F + V206L + R320A + S323N + K391A + C474V + G476K | 2.6 | 2.2 | 1.3 | 1.3 | 3.4 | 2.4 | 1.5 | 1.4 |
| H1* + N54S + V56T + K72R + G109A + A174S + G182* + D183* + N195F + V206L + G255A + K391A + C474V + G476K | 2.4 | 2.1 | 1.4 | 1.3 | 3.2 | 2.2 | 1.7 | 1.3 |
| H1* + N54S + V56T + G109A + T134E + A174S + G182* + D183* + N195F + V206L + K391A + C474V + G476K | 2.8 | 2.3 | 1.3 | 1.2 | 3.7 | 2.3 | 1.6 | 1.4 |
| H1* + N54S + V56T + G109A + A174S + G182* + D183* + N195F + V206L + D377H + K391A + C474V + G476K | 2.6 | 2.0 | 1.3 | 1.2 | 3.0 | 2.1 | 1.5 | 1.3 |
| H1* + N54S + V56T + K72R + G109A + A174S + G182* + D183* + N195F + V206L + K391A + C474V + G476K | 2.8 | 2.1 | 1.3 | 1.2 | 3.3 | 2.4 | 1.5 | 1.4 |
| H1* + N54S + V56T + G109A + A174S + G182* + D183* + N195F + V206L + A265G + K391A + T444Q + G476K + G477A | 2.1 | 1.9 | 1.0 | 1.1 | 2.6 | 2.0 | 1.5 | 1.3 |
| H1* + A37V + N54S + V56T + G109A + W167F + Q172G + A174S + G182* + D183* + N195F + V206L + K391A + G346T + G477A + G476K | 2.3 | 2.0 | 1.2 | 1.2 | 2.8 | 2.2 | 1.5 | 1.3 |
| H1* + N54S + V56T + G109A + R116Q + Q172D + A174S + G182* + D183* + N195F + V206L + G346T + K391A + T444Q + G477A + G476K | 2.3 | 2.1 | 0.9 | 1.1 | 3.1 | 2.4 | 1.4 | 1.3 |
| H1* + N54S + V56T + G109A + R116Q + W167F + Q172N + A174S + G182* + D183* + N195F + V206L + G346T + K391A + T444Q + G477A + G476K | 2.2 | 2.2 | 1.1 | 1.2 | 2.7 | 2.4 | 1.3 | 1.3 |
| H1* + N54S + V56T + G109S + W167F + Q172R + A174S + G182* + D183* + N195F + V206L + K391A + G476K | 1.9 | 1.4 | 1.2 | 1.1 | 2.1 | 1.6 | 1.3 | 1.2 |
| H1* + N54S + V56T + G109S + R116Q + W167F + Q172N + A174S + G182* + D183* + N195F + V206L + K391A + G476K | 2.8 | 2.2 | 1.4 | 1.2 | 3.2 | 3.0 | 1.5 | 1.5 |
| H1* + N54S + V56T + G109S + W167F + Q172G + A174S + G182* + D183* + N195F + V206L + K391A + G476K | 2.6 | 1.9 | 1.4 | 1.1 | 3.2 | 2.2 | 1.6 | 1.5 |
| H1* + N54S + V56T + G109A + F113Q + Q172G + A174S + G182* + D183* + N195F + V206L + K391A + T444Q + G476K | 2.5 | 2.0 | 1.5 | 1.2 | 3.2 | 2.2 | 1.5 | 1.4 |
| H1* + N54S + V56T + G109A + F113Q + R116H + Q172G + A174S + G182* + D183* + N195F + V206L + K391A + T444Q + G476K | 2.6 | 2.2 | 1.3 | 1.1 | 3.5 | 2.6 | 1.7 | 1.4 |
| H1* + N54S + V56T + G109A + F113Q + A174S + G182* + D183* + N195F + V206L + K391A + C474V + G476K | 2.5 | 2.0 | 1.3 | 1.1 | 3.1 | 2.6 | 1.6 | 1.5 |
| H1* + N54S + V56T + G109A + Q172N + A174S + G182* + D183* + N195F + V206L + V264I + K391A + C474V + G476K | 2.4 | 1.7 | 1.4 | 1.1 | 3.2 | 2.4 | 1.5 | 1.4 |
| H1* + N54S + V56T + G109A + Q172N + A174S + G182* + D183* + N195F + V206L + K391A + C474V + G476K | 2.5 | 1.7 | 1.3 | 1.1 | 2.0 | 2.1 | 1.3 | 1.3 |
| H1* + N54S + V56T + G109A + A174S + G182* + D183* + N195F + V206L + S280Q + H321Y + K391A + C474V + G476K | 2.1 | 1.8 | 1.2 | 1.1 | 2.9 | 2.1 | 1.5 | 1.4 |
| H1* + N54S + V56T + K72R + G109A + T134E + A174S + G182* + D183* + N195F + V206L + G255A + K391A + C474V + G476K | 2.1 | 1.8 | 1.2 | 1.0 | 3.3 | 2.3 | 1.6 | 1.4 |

-continued

| | | | | | | | | |
|---|---|---|---|---|---|---|---|---|
| H1* + N54S + V56T + G109A + F113Q + R116H + Q172G + A174S + G182* + D183* + N195F + V206L + K391A + T444Q + P473R + G476K | 2.4 | 2.0 | 1.2 | 1.1 | 3.3 | 2.3 | 1.7 | 1.3 |
| H1* + N54S + V56T + G109A + F113Q + R116Q + Q172G + A174S + G182* + D183* + N195F + V206L + K391A + T444Q + G476K | 2.8 | 2.1 | 1.3 | 1.1 | 3.1 | 2.3 | 1.5 | 1.3 |
| H1* + N54S + V56T + G109A + R116H + W167F + Q172N + A174S + G182* + D183* + N195F + V206L + K391A + G476K | 2.4 | 2.0 | 1.2 | 1.1 | 2.8 | 2.2 | 1.5 | 1.3 |
| H1* + N54S + V56T + G109A + F113Q + R116H + T165G + Q172G + A174S + G182* + D183* + N195F + V206L + K391A + T444Q + G476K | 2.4 | 2.0 | 1.2 | 1.1 | 3.1 | 2.2 | 1.6 | 1.2 |
| H1* + N54S + V56T + G109A + F113Q + R116Q + T165G + Q172G + A174S + G182* + D183* + N195F + V206L + K391A + T444Q + G476K | 2.5 | 2.1 | 1.3 | 1.2 | 3.4 | 2.3 | 1.7 | 1.4 |
| H1* + N54S + V56T + G109A + F113Q + R116H + W167F + Q172R + A174S + G182* + D183* + N195F + V206L + F289I + K391A + G476K | 2.3 | 1.8 | 1.2 | 1.1 | 2.6 | 2.0 | 1.4 | 1.3 |
| H1* + N54S + V56T + G109A + F113Q + Q172N + A174S + G182* + D183* + N195F + V206L + K391A + T444Q + G476K | 2.6 | 2.2 | 1.3 | 1.2 | 3.3 | 2.3 | 1.6 | 1.3 |
| H1* + N54S + V56T + G109A + F113Q + R116H + Q172N + A174S + G182* + D183* + N195F + V206L + K391A + G476K | 2.6 | 2.0 | 1.3 | 1.2 | 3.2 | 2.2 | 1.7 | 1.4 |
| H1* + N54S + V56T + G109A + F113Q + R116Q + Q172M + A174S + G182* + D183* + N195F + V206L + K391A + T444Q + G476K | 2.2 | 2.0 | 1.2 | 1.1 | 2.8 | 2.2 | 1.3 | 1.3 |
| H1* + N54S + V56T + G109A + F113Q + R116H + Q172M + A174S + G182* + D183* + N195F + V206L + K391A + G476K | 2.2 | 1.9 | 1.2 | 1.0 | 3.0 | 2.4 | 1.5 | 1.3 |
| H1* + N54S + V56T + G109A + R116H + Q172M + A174S + G182* + D183* + N195F + V206L + K391A + G476K | 2.3 | 2.1 | 1.1 | 1.0 | 2.7 | 2.1 | 1.5 | 1.3 |
| H1* + N54S + V56T + G109A + F113Q + R116H + T165G + Q172M + A174S + G182* + D183* + N195F + V206L + K391A + Q395P + G476K | 1.9 | 1.7 | 1.2 | 1.1 | 2.6 | 1.8 | 1.5 | 1.3 |
| H1* + N54S + V56T + G109A + F113Q + A174S + G182* + D183* + N195F + V206L + K391A + T444Q + P473R + G476K | 1.7 | 1.3 | 0.9 | 1.0 | 1.9 | 1.6 | 0.9 | 1.0 |
| H1* + N54S + V56T + G109A + R116Q + A174S + G182* + D183* + N195F + V206L + A265G + K391A + T444Q + P473R + G476K | 2.4 | 2.2 | 1.3 | 1.2 | 2.7 | 2.4 | 1.5 | 1.4 |
| H1* + N54S + V56T + G109A + R116Q + A174S + G182* + D183* + N195F + V206L + K391A + T444Q + P473R + G476K | 2.4 | 2.1 | 1.3 | 1.1 | 2.9 | 2.3 | 1.3 | 1.3 |
| H1* + N54S + V56T + K72R + G109A + T134E + T165G + A174S + G182* + D183* + N195F + V206L + G255A + K391A + G476K | 2.5 | 2.1 | 1.2 | 1.1 | 3.0 | 2.3 | 1.4 | 1.3 |
| H1* + N54S + V56T + G109A + F113Q + R116H + W167F + Q172R + A174S + G182* + D183* + N195F + V206L + K391A + G476K | 2.1 | 2.0 | 1.2 | 1.2 | 2.9 | 2.3 | 1.5 | 1.3 |
| H1* + N54S + V56T + G109A + R116Q + W167F + Q172R + A174S + G182* + D183* + N195F + V206L + A265G + K391A + P473R + G476K | 2.0 | 1.8 | 1.2 | 1.1 | 2.2 | 2.0 | 1.3 | 1.3 |
| H1* + N54S + V56T + G109A + F113Q + A174S + G182* + D183* + N195F + V206L + K391A + G476K | 2.1 | 1.9 | 1.0 | 1.0 | 2.6 | 2.0 | 1.4 | 1.2 |
| H1* + N54S + V56T + G109A + Q172N + A174S + G182* + D183* + N195F + V206L + K391A + G476K | 2.0 | 1.7 | 1.2 | 1.1 | 2.5 | 1.9 | 1.5 | 1.1 |
| H1* + T51V + N54S + V56T + G109A + Q172D + A174S + G182* + D183* + N195F + V206L + K391A + G476K | 2.4 | 1.9 | 1.2 | 1.1 | 2.6 | 1.9 | 1.6 | 1.2 |
| H1* + N54S + V56T + G109A + A174S + G182* + D183* + N195F + V206L + S280Q + H321Y + K391A + G476K | 2.3 | 1.9 | 1.2 | 1.1 | 2.5 | 1.8 | 1.5 | 1.2 |
| H1* + N54S + V56T + G109A + F113Q + R116H + Q172N + A174S + G182* + D183* + N195F + V206L + K391A + G476K | 2.6 | 2.3 | 1.3 | 1.2 | 3.1 | 2.4 | 1.7 | 1.4 |
| H1* + N54S + V56T + G109A + F113Q + R116H + Q172G + L173V + A174S + G182* + D183* + N195F + V206L + K391A + T444Q + P473R + G476K | 2.3 | 2.0 | 1.3 | 1.2 | 2.9 | 2.3 | 1.6 | 1.3 |
| H1* + N54S + V56T + G109A + R116Q + W167F + Q172N + L173V + A174S + G182* + D183* + N195F + V206L + K391A + T444Q + G476K | 2.6 | 2.2 | 1.3 | 1.1 | 3.3 | 2.5 | 1.8 | 1.3 |
| H1* + N54S + V56T + G109A + G133Q + W167F + Q172N + A174S + G182* + D183* + N195F + V206L + Q395P + K391A + G476K | 2.5 | 2.3 | 1.3 | 1.2 | 3.3 | 2.4 | 1.8 | 1.4 |
| H1* + N54S + V56T + G109A + F113Q + R116H + W167F + Q172N + L173V + A174S + G182* + D183* + N195F + V206L + K391A + G476K | 2.3 | 2.0 | 1.2 | 1.2 | 2.8 | 2.3 | 1.6 | 1.3 |
| H1* + A37V + N54S + V56T + K72R + G109A + R116H + W167F + Q172R + A174S + G182* + D183* + G184T + N195F + V206L + K391A + P473R + G476K | 2.5 | 2.2 | 1.3 | 1.1 | 3.3 | 2.5 | 1.7 | 1.2 |
| H1* + N54S + V56T + K72R + G109A + F113Q + R116H + W167F + Q172G + L173V + A174S + G182* + D183* + G184T + N195F + V206L + K391A + T444Q + P473R + G476K | 2.2 | 2.2 | 1.2 | 1.1 | 3.1 | 2.4 | 1.7 | 1.3 |
| H1* + N54S + V56T + G109S + R116Q + W167F + Q172R + A174S + G182* + D183* + N195F + V206L + K391A + G476K | 2.5 | 2.2 | 1.2 | 1.0 | 3.1 | 2.5 | 1.6 | 1.3 |

-continued

| | | | | | | | | |
|---|---|---|---|---|---|---|---|---|
| H1* + N54S + V56T + G109S + R116Q + W167F + Q172G + A174S + G182* + D183* + N195F + V206L + K391A + P473R + G476K | 2.5 | 2.1 | 1.2 | 1.1 | 3.0 | 2.3 | 1.6 | 1.2 |
| H1* + N54S + V56T + G109S + F113Q + W167F + Q172N + A174S + G182* + D183* + N195F + V206L + K391A + G476K | 2.7 | 2.4 | 1.4 | 1.3 | 3.1 | 2.5 | 1.7 | 1.4 |
| H1* + A37V + N54S + V56T + G109S + F113Q + W167F + Q172R + A174S + G182* + D183* + N195F + V206L + K391A + G476K | 2.8 | 2.4 | 1.3 | 1.2 | 3.5 | 2.5 | 1.7 | 1.3 |
| H1* + N54S + V56T + K72R + G109A + R116H + T134E + W167F + Q172G + L173V + A174S + G182* + D183* + N195F + V206L + G255A + K391A + G476K | 2.2 | 1.9 | 1.2 | 1.1 | 2.7 | 2.4 | 1.6 | 1.3 |
| H1* + N54S + V56T + K72R + G109A + R116H + T134E + W167F + Q172G + L173V + A174S + G182* + D183* + N195F + V206L + G255A + K391A + Q395P + T444Q + P473R + G476K | 2.5 | 2.0 | 1.2 | 1.1 | 3.5 | 2.5 | 1.6 | 1.3 |
| H1* + N54S + V56T + K72R + G109A + F113Q + R116Q + W167F + Q172G + A174S + G182* + D183* + G184T + N195F + V206L + K391A + P473R + G476K | 2.5 | 2.1 | 1.3 | 1.1 | 3.4 | 2.5 | 1.6 | 1.3 |
| H1* + N54S + V56T + K72R + G109A + F113Q + R116Q + T134E + W167F + Q172R + A174S + G182* + D183* + N195F + V206L + G255A + K391A + T444Q + P473R + G476K | 2.3 | 2.0 | 1.1 | 1.1 | 3.1 | 2.6 | 1.5 | 1.3 |
| H1* + N54S + V56T + K72R + G109A + F113Q + T134E + W167F + Q172R + A174S + G182* + D183* + N195F + V206L + G255A + K391A + Q395P + A445Q + P473R + G476K | 1.9 | 1.9 | 1.1 | 1.1 | 2.7 | 2.1 | 1.6 | 1.3 |
| H1* + N54S + V56T + K72R + G109A + F113Q + R116H + T134E + W167F + Q172R + A174S + G182* + D183* + N195F + V206L + G255A + K391A + Q395P + G476K | 2.1 | 2.2 | 1.3 | 1.2 | 2.9 | 2.4 | 1.6 | 1.4 |
| H1* + N54S + V56T + K72R + G109A + T134E + W167F + Q172N + A174S + G182* + D183* + N195F + V206L + G255A + A265G + K391A + T444Q + P473R + G476K | 2.6 | 2.4 | 1.3 | 1.2 | 3.2 | 2.5 | 1.7 | 1.4 |
| H1* + N54S + V56T + K72R + G109A + G133Q + W167F + Q172R + A174S + G182* + D183* + N195F + V206L + K391A + G476K | 2.4 | 2.2 | 1.3 | 1.2 | 3.2 | 2.4 | 1.6 | 1.4 |
| H1* + N54S + V56T + K72R + G109A + F113Q + R116Q + W167F + Q172G + A174S + G182* + D183* + N195F + A204G + V206L + K391A + G476K | 2.9 | 2.3 | 1.3 | 1.2 | 3.7 | 2.8 | 1.8 | 1.4 |
| H1* + N54S + V56T + K72R + G109A + F113Q + R116Q + W167F + Q172N + L173V + A174S + G182* + D183* + G184T + N195F + V206L + K391A + T444Q + P473R + G476K | 2.0 | 2.0 | 1.3 | 1.2 | 2.7 | 2.1 | 1.5 | 1.3 |
| H1* + A37H + N54S + V56T + G109A + F113Q + W167F + Q172N + A174S + G182* + D183* + N195F + V206L + K391A + G476K | 2.5 | 1.9 | 1.2 | 1.1 | 2.6 | 1.8 | 1.6 | 1.3 |
| H1* + A37H + N54S + V56T + G109A + F113Q + A174S + G182* + D183* + N195F + V206L + K391A + G476K | 1.9 | 1.7 | 1.3 | 1.2 | 2.8 | 2.0 | 1.3 | 1.3 |
| H1* + N54S + V56T + G109A + F113Q + W167F + Q172N + A174S + G182* + D183* + N195F + V206L + K391A + T459N + G476K | 2.3 | 1.6 | 1.3 | 1.2 | 2.8 | 1.8 | 1.5 | 1.2 |
| H1* + N54S + V56T + G109A + F113Q + Q172R + L173V + A174S + G182* + D183* + N195F + V206L + K391A + T444Q + G476K | 1.9 | 1.5 | 1.1 | 1.0 | 2.6 | 1.5 | 1.3 | 1.1 |
| H1* + N54S + V56T + G109A + F113Q + R116Q + A174S + G182* + D183* + N195F + V206L + K391A + P473R + G476K | 2.3 | 2.2 | 1.1 | 1.1 | 3.2 | 2.3 | 1.4 | 1.2 |
| H1* + N54S + V56T + A60V + G109A + R116Q + W167F + Q172N + A174S + G182* + D183* + N195F + V206L + K391A + G476K | 2.4 | 2.2 | 1.2 | 1.2 | 3.3 | 2.4 | 1.3 | 1.4 |
| H1* + N54S + V56T + A60V + G109A + R116H + Q172R + L173V + A174S + G182* + D183* + N195F + V206L + K391A + G476K | 2.7 | 2.0 | 1.4 | 1.2 | 3.2 | 2.5 | 1.3 | 1.4 |
| H1* + A37V + N54S + V56T + A60V + G109A + R116Q + T165G + A174S + G182* + D183* + N195F + V206L + K391A + G476K | 2.5 | 1.9 | 1.1 | 1.2 | 2.9 | 2.1 | 1.1 | 1.3 |
| H1* + A37H + N54S + V56T + A60V + G109A + R116Q + T165G + A174S + G182* + D183* + N195F + V206L + K391A + G476K | 2.7 | 2.2 | 1.2 | 1.2 | 3.6 | 2.5 | 1.7 | 1.4 |
| H1* + N54S + V56T + A60V + G109A + R116Q + W167F + Q172G + L173V + A174S + G182* + D183* + N195F + V206L + K391A + G476K | 2.3 | 2.3 | 1.0 | 1.2 | 2.5 | 2.3 | 1.2 | 1.3 |
| H1* + N54S + V56T + A60V + G109A + R116Q + A174S + G182* + D183* + N195F + V206L + K391A + G476K | 2.3 | 2.1 | 0.9 | 1.1 | 3.1 | 2.4 | 1.4 | 1.3 |
| H1* + A37H + N54S + V56T + A60V + G109A + R116Q + W167F + Q172R + A174S + G182* + D183* + N195F + V206L + K391A + G476K | 3.0 | 2.4 | 1.2 | 1.1 | 3.6 | 2.4 | 1.7 | 1.3 |
| H1* + A37H + N54S + V56T + A60V + G109A + R116Q + W167F + Q172N + A174S + G182* + D183* + N195F + V206L + K391A + G476K | 2.7 | 2.7 | 1.1 | 1.1 | 3.0 | 2.4 | 1.4 | 1.3 |
| H1* + N54S + V56T + A60V + G109A + R116Q + T165G + A174S + G182* + D183* + N195F + V206L + K391A + T444Q + P473R + G476K | 2.4 | 2.2 | 1.2 | 1.2 | 3.0 | 2.2 | 1.3 | 1.2 |

-continued

| | | | | | | | | |
|---|---|---|---|---|---|---|---|---|
| H1* + N54S + V56T + A60V + G109A + R116Q + A174S + G182* + D183* + N195F + V206L + K391A + T444Q + P473R + G476K | 2.5 | 1.8 | 0.9 | 1.0 | 2.2 | 2.0 | 1.1 | 1.2 |
| H1* + N54S + V56T + A60V + G109A + R116Q + W167F + Q172N + L173V + A174S + G182* + D183* + N195F + V206L + K391A + G476K | 2.7 | 2.8 | 1.0 | 1.1 | 3.3 | 2.7 | 1.6 | 1.4 |
| H1* + N54S + V56T + A60V + G109A + R116Q + W167F + Q172R + A174S + G182* + D183* + N195F + V206L + K391A + G476K | 2.8 | 2.5 | 1.3 | 1.2 | 3.6 | 2.7 | 1.7 | 1.4 |
| H1* + N54S + V56T + G109A + R116A + W167F + Q172R + A174S + G182* + D183* + N195F + A204G + V206L + K391A + P473R + G476K | 2.3 | 2.0 | 1.1 | 1.1 | 2.5 | 2.0 | 1.6 | 1.3 |
| H1* + N54S + V56T + G109A + R116A + A174S + G182* + D183* + N195F + A204G + V206L + K391A + P473R + G476K | 2.8 | 2.5 | 1.3 | 1.2 | 3.4 | 2.3 | 1.6 | 1.5 |
| H1* + N54S + V56T + G109A + R116A + T165G + A174S + G182* + D183* + N195F + V206L + K391A + T444Q + P473R + G476K | 2.5 | 2.1 | 1.2 | 1.1 | 2.8 | 2.0 | 1.6 | 1.3 |
| H1* + N54S + V56T + G109A + G182* + D183* + N195F + K391A + G476K | 2.2 | 2.2 | 1.2 | 1.1 | 2.3 | 2.1 | 1.5 | 1.5 |
| H1* + N54S + V56T + G109A + G182* + D183* + N195F + V206L | 2.2 | 2.0 | 1.3 | 1.2 | 2.4 | 1.9 | 1.5 | 1.4 |
| N54S + V56T + G109A + G182* + D183* + N195F | 2.2 | 2.0 | 1.3 | 1.2 | 2.3 | 2.0 | 1.5 | 1.4 |
| N54S + V56T + G109A + A174S + G182* + D183* + N195F + V206L + K391A + G476K | 2.4 | 2.0 | 1.3 | 1.2 | 2.5 | 2.0 | 1.5 | 1.4 |
| H1* + G109A + A174S + G182* + D183* + N195F + V206L + K391A + G476K | 1.9 | 1.9 | 1.3 | 1.2 | 2.4 | 2.0 | 1.5 | 1.3 |
| H1* + N54S + V56T + G109A + G182* + D183* + N195F + V206L + K391A + G476K | 2.2 | 1.9 | 1.2 | 1.1 | 2.5 | 1.7 | 1.3 | 1.3 |
| H1* + N54S + V56T + G109A + A174S + G182* + D183* + N195F + V206L + K391A | 2.0 | 1.9 | 1.2 | 1.1 | 2.2 | 1.8 | 1.5 | 1.3 |
| H1* + N54S + V56T + G109A + A174S + G182* + D183* + N195F + G476K | 2.0 | 1.9 | 1.2 | 1.1 | 2.5 | 1.9 | 1.4 | 1.3 |
| H1* + N54S + V56T + A174S + G182* + D183* + N195F + V206L + G273R + K391A + G476K | 2.3 | 2.0 | 1.2 | 1.1 | 2.6 | 2.1 | 1.4 | 1.4 |
| H1* + N54S + V56T + G109A + A174S + G182* + D183* + N195F + V206L | 2.4 | 2.1 | 1.3 | 1.1 | 2.7 | 2.1 | 1.6 | 1.4 |
| H1* + W48G + G109A + G182* + D183* + N195F + V206L + K391A + G476K | 1.7 | 1.6 | 1.2 | 1.1 | 2.2 | 1.7 | 1.3 | 1.2 |
| N54S + V56T + G109A + A174S + G182* + D183* + N195F + K391A + G476K | 2.0 | 1.7 | 1.2 | 1.2 | 2.9 | 2.2 | 1.5 | 1.3 |
| H1* + N54S + V56T + G109A + A174S + G182* + D183* + N195F + K391A | 1.4 | 1.5 | 1.1 | 1.1 | 2.3 | 1.8 | 1.3 | 1.3 |
| H1* + N54S + V56T + G109A + F113Q + Q172M + A174S + G182* + D183* + N195F + V206L + K391A + G476K | 2.0 | 1.9 | 1.2 | 1.1 | 2.9 | 2.2 | 1.3 | 1.2 |
| H1* + N54S + V56T + G109A + R116Q + A174S + G182* + D183* + N195F + A204G + V206L + K391A + G476K | 1.8 | 1.6 | 0.9 | 1.0 | 1.7 | 1.8 | 1.0 | 1.1 |
| H1* + N54S + V56T + K72R + G109A + F113Q + T134E + A174S + G182* + D183* + N195F + V206L + G255A + K391A + G476K | 2.5 | 2.2 | 1.2 | 1.2 | 2.9 | 2.5 | 1.4 | 1.4 |
| H1* + N54S + V56T + K72R + G109A + F113Q + T134E + A174S + G182* + D183* + N195F + V206L + G255A + K391A + P473R + G476K | 2.7 | 2.3 | 1.3 | 1.2 | 3.3 | 2.5 | 1.7 | 1.4 |
| H1* + N54S + V56T + K72R + G109A + R116Q + A174S + G182* + D183* + G184T + N195F + V206L + K391A + G476K | 2.7 | 2.2 | 1.2 | 1.2 | 3.4 | 2.4 | 1.6 | 1.3 |
| H1* + A37V + N54S + V56T + G109A + R116A + T165G + A174S + G182* + D183* + N195F + V206L + K391A + G476K | 2.4 | 2.2 | 1.2 | 1.2 | 3.1 | 2.5 | 1.5 | 1.3 |
| H1* + A37V + N54S + V56T + G109A + R116Q + T165G + A174S + G182* + D183* + N195F + V206L + M246F + K391A + G476K | 2.5 | 2.2 | 1.2 | 1.2 | 3.0 | 2.3 | 1.5 | 1.3 |
| H1* + V56A + G109A + A174S + G182* + D183* + N195F + V206L + G476K | 2.0 | 2.0 | 1.1 | 1.1 | 2.5 | 2.1 | 1.5 | 1.3 |
| H1* + N54S + V56T + G109A + G182* + D183* + N195F + V206L + K391A | 1.8 | 2.0 | 1.2 | 1.0 | 2.2 | 1.9 | 1.6 | 1.4 |
| H1* + N54S + V56T + G109A + G182* + D183* + N195F + V206L + G476K | 1.8 | 1.7 | 1.0 | 1.1 | 1.9 | 1.9 | 1.4 | 1.3 |
| G109A + A174S + G182* + D183* + N195F + V206L + K391A + G476K | 1.5 | 1.6 | 1.0 | 1.0 | 1.7 | 1.7 | 1.2 | 1.2 |
| N54S + V56T + G109A + G182* + D183* + N195F + V206L + K391T + G476K | 1.7 | 1.7 | 1.2 | 1.0 | 1.6 | 1.7 | 1.4 | 1.3 |
| H1* + N54S + V56T + K72R + G109A + F113Q + R116H + A174S + G182* + D183* + G184T + N195F + V206L + K391A + T444Q + G476K | 2.4 | 2.2 | 1.2 | 1.2 | 3.4 | 2.3 | 1.4 | 1.4 |
| H1* + N54S + V56T + G109S + F113Q + A174S + G182* + D183* + N195F + V206L + K391A + T444Q + G476K | 2.4 | 2.0 | 1.3 | 1.2 | 3.1 | 2.2 | 1.6 | 1.3 |

-continued

| | | | | | | | | |
|---|---|---|---|---|---|---|---|---|
| H1* + N54S + V56T + G109A + F113Q + R116H + W167F + Q172G + L173V + A174S + G182* + D183* + N195F + V206L + K391A + P473R + G476K | 2.9 | 2.3 | 1.3 | 1.2 | 3.8 | 2.6 | 1.8 | 1.4 |
| H1* + N54S + V56T + G109A + F113Q + R116Q + Q172N + A174S + G182* + D183* + N195F + V206L + A265G + K391A + P473R + G476K | 2.8 | 2.3 | 1.2 | 1.2 | 3.5 | 2.6 | 1.7 | 1.5 |
| H1* + N54S + V56T + G109A + F113Q + W167F + Q172N + A174S + G182* + D183* + N195F + A204G + V206L + K391A + P473R + G476K | 2.5 | 2.0 | 1.2 | 1.2 | 2.9 | 2.2 | 1.7 | 1.4 |
| H1* + N54S + V56T + G109A + F113Q + R116H + W167F + Q172R + A174S + G182* + D183* + N195F + A204G + V206L + K391A + P473R + G476K | 2.1 | 1.9 | 1.2 | 1.1 | 2.3 | 1.8 | 1.3 | 1.3 |
| H1* + N54S + V56T + G109A + R116A + A174S + G182* + D183* + N195F + V206L + K391A + T444Q + P473R + G476K | 2.1 | 1.9 | 1.1 | 1.1 | 2.7 | 2.2 | 1.5 | 1.3 |
| H1* + N54S + V56T + G109A + R116H + Q172R + A174S + G182* + D183* + N195F + A204G + V206L + K391A + P473R + G476K | 2.2 | 1.6 | 1.2 | 1.1 | 2.5 | 1.8 | 1.5 | 1.2 |
| H1* + A37V + N54S + V56T + G109A + R116Q + T165G + A174S + G182* + D183* + N195F + V206L + K391A + G476K | 2.3 | 2.0 | 1.2 | 1.1 | 3.0 | 2.1 | 1.5 | 1.4 |
| H1* + A37H + N54S + V56T + G109A + R116H + T165G + A174S + G182* + D183* + N195F + V206L + M246F + K391A + G476K | 2.3 | 2.0 | 1.3 | 1.1 | 3.2 | 2.2 | 1.5 | 1.4 |
| H1* + N54S + V56T + G109A + A174S + G182* + D183* + N195F + K391A + G476K | 2.0 | 1.9 | 1.1 | 1.1 | 2.1 | 1.9 | 1.2 | 1.2 |
| H1* + G109A + G182* + D183* + N195F + V206L + K391A + G476K | 1.7 | 1.6 | 1.1 | 1.1 | 1.8 | 1.5 | 1.3 | 1.2 |
| G109A + G182* + D183* + N195F + V206L + G476K | 1.9 | 1.7 | 1.2 | 1.1 | 2.1 | 1.5 | 1.2 | 1.1 |
| H1* + G109A + G182* + D183* + N195F + K391A | 1.9 | 1.9 | 1.2 | 1.2 | 1.6 | 1.7 | 1.3 | 1.3 |
| H1* + N54S + V56T + G109A + G133S + A174S + G182* + D183* + N195F + K391A + G476H | 2.2 | 1.9 | 1.2 | 1.1 | 2.4 | 2.0 | 1.3 | 1.3 |
| H1* + N54S + V56T + G109A + R116A + Q172N + L173V + A174S + G182* + D183* + N195F + V206L + K391A + G476K | 2.5 | 2.3 | 1.2 | 1.2 | 3.2 | 2.5 | 1.6 | 1.4 |
| H1* + A37V + N54S + V56T + G109A + R116H + T165G + A174S + G182* + D183* + N195F + V206L + K391A + G476K | 2.5 | 2.1 | 1.1 | 1.2 | 2.6 | 2.3 | 1.4 | 1.3 |
| H1* + P45A + N54S + V56T + G109A + A174S + G182* + D183* + N195F + V206L + K391A + C474V + G476K | 2.3 | 2.1 | 1.3 | 1.2 | 3.1 | 2.1 | 1.5 | 1.4 |
| H1* + N54S + V56T + G109A + P124A + A174S + G182* + D183* + N195F + V206L + K391A + C474V + G476K | 1.9 | 2.2 | 1.3 | 1.2 | 2.8 | 2.2 | 1.4 | 1.3 |
| H1* + N54S + V56T + G109A + A174S + G182* + D183* + N195F + V206L + P364A + K391A + C474V + G476K | 2.0 | 2.0 | 1.3 | 1.2 | 2.4 | 2.1 | 1.5 | 1.4 |
| H1* + N54S + V56T + G109A + Q118R + T134E + A174S + G182* + D183* + N195F + V206L + K391A + G476K | 3.7 | 2.5 | 1.6 | 1.2 | 3.2 | 2.6 | 1.5 | 1.6 |
| H1* + N54S + V56T + G109A + A174S + G182* + D183* + G184T + N195F + V206L + K391A + G476K | 3.4 | 2.4 | 1.6 | 1.3 | 3.9 | 2.7 | 1.6 | 1.7 |
| H1* + G50A + T51A + N54S + V56T + G109A + A174S + G182* + D183* + N195F + V206L + K391A + G476K | 3.2 | 2.2 | 1.5 | 1.2 | 3.1 | 2.4 | 1.8 | 1.5 |
| H1* + N54S + V56T + G109A + A174S + G182* + D183* + N195F + V206L + V264F + K391A + G476K | 3.2 | 2.3 | 1.6 | 1.3 | 3.4 | 2.3 | 1.7 | 1.5 |
| H1* + N54S + V56T + G109A + A174S + G182* + D183* + N195F + V206L + Y382L + K391A + G476K | 3.0 | 2.2 | 1.6 | 1.2 | 2.9 | 2.4 | 1.4 | 1.4 |
| H1* + G7K + N54S + V56T + G109A + A174S + G182* + D183* + N195F + V206L + K391A + G476K | 3.7 | 2.2 | 1.5 | 1.1 | 3.7 | 2.6 | 1.7 | 1.3 |
| H1* + N54S + V56T + G109A + A174S + G182* + D183* + N195F + V206L + G255A + Q256A + K391A + G476K | 3.0 | 2.2 | 1.5 | 1.2 | 3.2 | 2.6 | 1.7 | 1.5 |
| H1* + N54S + V56T + G109A + W167Y + A174S + G182* + D183* + N195F + V206L + K391A + G476K | 3.4 | 2.3 | 1.4 | 1.3 | 3.0 | 2.4 | 1.8 | 1.5 |
| H1* + N54S + V56T + G109A + W167H + A174S + G182* + D183* + N195F + V206L + K391A + G476K | 2.9 | 2.0 | 1.4 | 1.1 | 2.5 | 2.1 | 1.8 | 1.5 |
| H1* + N54S + V56T + G109A + T165V + A174S + G182* + D183* + N195F + V206L + K391A + G476K | 2.6 | 2.0 | 1.4 | 1.2 | 2.5 | 2.2 | 1.6 | 1.5 |
| H1* + N54S + V56T + G109A + A174S + G182* + D183* + N195F + V206L + K391A + G476K | 3.2 | 2.4 | 1.3 | 1.2 | 3.0 | 2.1 | 1.9 | 1.5 |
| H1* + N54S + V56T + G109A + A174N + G182* + D183* + N195F + V206L + K391A + G476K | 2.8 | 2.2 | 1.4 | 1.2 | 2.7 | 1.8 | 1.4 | 1.4 |
| H1* + N54S + V56T + G109A + A174Q + G182* + D183* + N195F + V206L + K391A + G476K | 3.5 | 2.0 | 1.6 | 1.2 | 2.4 | 2.1 | 1.8 | 1.5 |
| H1* + N16H + V17L + N54S + V56T + G109A + A174S + G182* + D183* + N195F + V206L + Y382F + K391A + G476K | 2.7 | 1.9 | 1.3 | 1.2 | 4.6 | 2.3 | 1.6 | 1.4 |
| H1* + Q32S + N54S + V56T + G109A + A174S + G182* + D183* + N195F + V206L + Q385L + K391A + G476K | 2.7 | 1.8 | 1.3 | 1.1 | 3.5 | 2.2 | 1.4 | 1.3 |
| H1* + N54S + V56T + R87S + G109A + R171H + A174S + G182* + D183* + N195F + V206L + K391A + G476K | 2.5 | 1.9 | 1.1 | 1.1 | 3.4 | 2.1 | 1.4 | 1.4 |
| N54S + G182* + D183* + N195F | 1.1 | 1.1 | 1.1 | 1.0 | 1.6 | 1.5 | 1.0 | 1.0 |
| G109A + G182* + D183* + N195F | 1.6 | 1.4 | 1.3 | 1.0 | 1.8 | 1.4 | 1.0 | 1.1 |

-continued

| | | | | | | | | |
|---|---|---|---|---|---|---|---|---|
| A174S + G182* + D183* + N195F | 0.8 | 1.1 | 1.3 | 0.9 | 1.2 | 1.2 | 0.9 | 1.0 |
| G182* + D183* + N195F + V206L | 0.7 | 0.7 | 1.0 | 1.0 | 0.9 | 1.3 | 0.8 | 1.0 |
| G182* + D183* + N195F + K391A | 1.6 | 1.4 | 1.3 | 1.0 | 1.4 | 1.5 | 1.0 | 1.1 |
| G182* + D183* + N195F + G476K | 1.3 | 1.4 | 1.3 | 1.0 | 1.8 | 1.5 | 1.1 | 1.0 |
| H1* + N54S + V56T + G109A + R116H + Q169E + Q172K + A174* + G182* + D183* + N195F + V206L + K391A + G476K | 3.5 | 1.9 | 1.2 | 1.1 | 3.4 | 2.2 | 1.6 | 1.2 |
| H1* + N54S + V56T + G109A + A174* + G182* + D183* + N195F + V206L + K391A + G476K | 3.4 | 2.1 | 1.3 | 1.1 | 3.2 | 2.1 | 1.5 | 1.1 |
| H1* + K72R + G109A + F113Q + R116Q + W167F + Q172G + A174S + G182* + D183* + G184T + N195F + V206L + K391A + P473R + G476K | 3.1 | 2.0 | 1.1 | 1.0 | 3.0 | 2.1 | 1.7 | 1.4 |
| H1* + N54S + V56T + K72R + G109A + F113Q + R116Q + W167F + Q172G + A174S + G182* + D183* + G184T + N195F + V206L + P473R + G476K | 3.1 | 1.9 | 1.2 | 1.0 | 3.0 | 1.9 | 1.6 | 1.3 |
| H1* + N54S + V56T + G109A + Q169E + Q172G + A174* + G182* + D183* + N195F + V206L + K391A + G476K | 3.0 | 1.9 | 1.1 | 1.0 | 2.7 | 2.0 | 1.3 | 1.2 |
| H1* + N54S + V56T + K72R + G109A + F113Q + R116Q + W167F + Q172G + A174S + G182* + D183* + G184T + N195F + K391A + P473R + G476K | 2.9 | 1.8 | 1.1 | 1.0 | 2.9 | 1.9 | 1.4 | 1.1 |
| H1* + N54S + V56T + G109A + R116W + Q169E + Q172K + A174* + G182* + D183* + N195F + V206L + K391A + G476K | 2.8 | 1.9 | 1.1 | 1.0 | 3.2 | 2.1 | 1.5 | 1.1 |
| H1* + N54S + V56T + G109A + Q169E + Q172K + A174* + G182* + D183* + N195F + V206F + K391A + G476K | 2.7 | 1.8 | 1.3 | 1.0 | 3.3 | 2.0 | 1.7 | 1.2 |
| H1* + V56T + G109A + A174S + G182* + D183* + N195F + V206L + K391A + G476K | 2.6 | 1.6 | 1.2 | 1.1 | 2.4 | 1.6 | 1.4 | 1.1 |
| H1* + N54S + V56T + G109A + A174S + G182* + D183* + N195F + V206L + N260G + K391A + G476K | 2.6 | 1.7 | 1.2 | 1.0 | 3.4 | 2.2 | 1.4 | 1.1 |
| H1* + N54S + V56T + K72R + G109A + A174S + G182* + D183* + N195F + V206L + K391A + G476K | 2.6 | 1.5 | 1.2 | 1.0 | 3.1 | 1.8 | 1.6 | 1.2 |
| H1* + N54S + V56T + G109A + Q169E + Q172K + A174* + G182* + D183* + G184T + N195F + V206L + K391A + G476K | 2.5 | 1.8 | 1.2 | 1.0 | 2.2 | 1.7 | 1.6 | 1.2 |
| H1* + N54S + V56T + G109A + Q169E + Q172K + A174* + G182* + D183* + N195F + V206L + Y295N + K391A + G476K | 2.4 | 1.6 | 1.1 | 1.0 | 2.6 | 1.9 | 1.5 | 1.2 |
| H1* + N54S + V56T + G109A + W167F + A174S + G182* + D183* + N195F + V206L + K391A + G476K | 2.4 | 1.7 | 1.2 | 1.0 | 2.5 | 1.9 | 1.7 | 1.3 |
| H1* + N54S + V56T + G109A + Q169E + Q172K + A174* + G182* + D183* + A186N + N195F + V206L + K391A + G476K | 2.4 | 1.6 | 1.4 | 1.0 | 4.9 | 1.8 | 1.8 | 1.2 |
| H1* + N54S + V56T + G109A + Q169E + Q172K + A174* + G182* + D183* + N195F + V206L + A288V + K391A + G476K | 2.4 | 1.6 | 1.1 | 1.0 | 2.4 | 1.6 | 1.3 | 1.1 |
| H1* + N54S + V56T + G109A + Q169E + Q172K + A174* + G182* + D183* + N195F + V206L + G255A + K391A + G476K | 2.4 | 1.9 | 1.2 | 1.0 | 3.2 | 2.2 | 2.0 | 1.3 |
| H1* + N54S + G109A + Q169E + Q172K + A174* + G182* + D183* + N195F + V206L + K391A + G476K | 2.3 | 1.7 | 1.1 | 1.1 | 3.2 | 2.2 | 1.5 | 1.2 |
| H1* + W48F + N54S + V56T + G109A + Q169E + Q172K + A174* + G182* + D183* + N195F + V206L + K391A + G476K | 2.3 | 1.6 | 1.1 | 1.0 | 2.3 | 1.6 | 1.4 | 1.2 |
| H1* + N54S + V56T + G109A + Q169E + Q172K + A174* + G182* + D183* + N195F + V206L + V291A + K391A + G476K | 2.3 | 1.8 | 1.2 | 1.1 | 1.8 | 1.8 | 1.6 | 1.2 |
| H1* + N54S + V56T + G109A + F113Q + A174S + G182* + D183* + N195F + V206L + K391A + G476K | 2.3 | 1.7 | 1.3 | 1.0 | 2.3 | 2.0 | 1.7 | 1.3 |
| H1* + N54S + V56T + G109A + Q169E + Q172K + A174* + G182* + D183* + N195F + V206L + R320A + S323N + K391A + G476K | 2.3 | 1.6 | 1.2 | 1.0 | 3.3 | 2.0 | 1.6 | 1.2 |
| H1* + V56T + G109A + Q169E + Q172K + A174* + G182* + D183* + N195F + V206L + K391A + G476K | 2.3 | 1.6 | 1.2 | 0.9 | 2.0 | 1.7 | 1.6 | 1.1 |
| H1* + N54S + V56T + K72R + G109A + F113Q + R116H + W167F + Q172G + A174S + G182* + D183* + G184T + N195F + V206L + K391A + P473R + G476K | 2.3 | 1.7 | 1.1 | 1.0 | 2.0 | 1.7 | 1.7 | 1.2 |
| H1* + N54S + V56T + G109A + A174S + G182* + D183* + N195F + V206L + N270T + K391A + G476K | 2.2 | 1.7 | 1.1 | 1.0 | 2.6 | 2.1 | 1.8 | 1.4 |
| H1* + N54S + V56T + G109A + Q169E + Q172K + A174* + G182* + D183* + N195F + V206L + G476K | 2.2 | 1.6 | 1.2 | 1.1 | 2.4 | 1.6 | 1.3 | 1.2 |
| H1* + N54S + V56T + G109A + Q169E + Q172K + A174* + G182* + D183* + N195F + V206L + N260G + K391A + G476K | 2.2 | 1.6 | 1.1 | 1.0 | 3.2 | 2.0 | 1.7 | 1.2 |
| H1* + N54S + V56T + G109A + F113Q + R116H + A174S + G182* + D183* + N195F + V206L + K391A + G476K | 2.2 | 1.7 | 1.1 | 1.1 | 3.4 | 2.1 | 1.4 | 1.2 |
| H1* + N54S + V56T + G109A + Q172G + A174S + G182* + D183* + N195F + V206L + K391A + G476K | 2.2 | 1.8 | 1.2 | 1.1 | 2.3 | 1.9 | 1.6 | 1.3 |
| H1* + N54S + V56T + G109A + A174S + A186D + G182* + D183* + N195F + V206L + K391A + G476K | 2.1 | 1.7 | 1.2 | 1.0 | 2.2 | 1.7 | 1.5 | 1.2 |

-continued

| | | | | | | | | |
|---|---|---|---|---|---|---|---|---|
| H1* + N54S + V56T + G109A + Q169E + Q172K + A174* + G182* + D183* + N195F + V206L + A225V + K391A + G476K | 2.1 | 1.8 | 1.0 | 0.9 | 2.0 | 2.0 | 1.9 | 1.3 |
| H1* + G109A + Q169E + Q172K + A174* + G182* + D183* + N195F + V206L + K391A + G476K | 2.1 | 1.5 | 1.1 | 0.9 | 1.8 | 1.4 | 1.3 | 1.1 |
| H1* + N54S + V56T + G109A + Q169E + Q172K + A174* + G182* + D183* + N195F + V206L + G255S + K391A + G476K | 2.1 | 1.6 | 1.2 | 1.0 | 3.3 | 2.1 | 1.6 | 1.2 |
| H1* + N54S + V56T + G109A + Q169E + Q172K + A174* + G182* + D183* + N195F + V206L + K269Q + K391A + G476K | 2.1 | 1.7 | 1.0 | 1.1 | 2.0 | 1.8 | 1.4 | 1.3 |
| H1* + N54S + V56T + G109A + A174S + G182* + D183* + N195F + V206L + G255S + K391A + G476K | 2.1 | 1.5 | 1.1 | 1.0 | 2.0 | 1.5 | 1.2 | 1.0 |
| H1* + N54S + V56T + G109A + Q169E + Q172K + A174S + G182* + D183* + N195F + V206L + K391A + G476K | 2.1 | 1.6 | 1.1 | 1.1 | 2.9 | 2.1 | 1.5 | 1.3 |
| G182* + D183* + N195F | 2.0 | 1.7 | 1.2 | 0.9 | 2.9 | 1.8 | 1.8 | 1.2 |
| H1* + N54S + V56T + G109A + Q169E + A174S + G182* + D183* + N195F + V206L + K391A + G476K | 2.0 | 1.6 | 1.1 | 1.1 | 2.0 | 1.8 | 1.6 | 1.3 |
| H1* + N54S + V56T + G109A + Q169E + Q172K + A174* + G182* + D183* + N195F + V206L + W284H + K391A + G476K | 2.0 | 1.5 | 1.1 | 1.0 | 2.8 | 1.9 | 1.4 | 1.2 |
| H1* + N54S + G109A + A174S + G182* + D183* + N195F + V206L + K391A + G476K | 2.0 | 1.5 | 1.1 | 1.0 | 2.3 | 1.8 | 1.4 | 1.2 |
| H1* + N54S + V56T + G109A + Q169E + Q172K + A174* + G182* + D183* + N195F + V206L + S304R + K391A + G476K | 2.0 | 1.5 | 1.4 | 1.0 | 5.8 | 1.7 | 1.9 | 1.3 |
| H1* + N54S + V56T + K72R + G109A + F113Q + R116Q + W167F + Q172G + A174S + G182* + D183* + G184T + N195F + V206L + K391A + P473R | 2.0 | 1.6 | 1.2 | 1.1 | 2.0 | 1.6 | 1.3 | 1.1 |
| H1* + N54S + V56T + G109A + A174S + G182* + D183* + N195F + V206L + M246V + K391A + G476K | 2.0 | 1.7 | 1.2 | 1.1 | 1.9 | 1.9 | 1.5 | 1.3 |
| H1* + N54S + V56T + G109A + Q169E + Q172K + A174* + G182* + D183* + N195F + V206L + K391A | 1.9 | 1.4 | 1.2 | 1.1 | 2.7 | 2.0 | 1.4 | 1.2 |
| H1* + N54S + V56T + G109A + Q169E + Q172K + A174* + G182* + D183* + N195F + V206L + N270G + K391A + G476K | 1.9 | 1.5 | 1.1 | 1.0 | 2.2 | 1.7 | 1.4 | 1.1 |
| H1* + N54S + V56T + G109A + Q169E + Q172K + A174* + G182* + D183* + N195F + V206L + Y295F + K391A + G476K | 1.9 | 1.6 | 1.2 | 1.0 | 2.7 | 1.8 | 1.4 | 1.2 |
| H1* + N54S + V56T + G109A + A174S + G182* + D183* + N195F + V206L + R320A + K391A + G476K | 1.9 | 1.5 | 1.2 | 1.1 | 2.9 | 1.8 | 1.3 | 1.3 |
| H1* + N54S + V56T + G109A + Q169E + Q172K + A174T + G182* + D183* + N195F + V206L + K391A + G476K | 1.9 | 1.9 | 1.2 | 1.0 | 2.4 | 2.1 | 1.6 | 1.4 |
| H1* + N54S + V56T + G109A + Q169E + Q172K + G182* + D183* + N195F + V206L + K391A + G476K | 1.9 | 1.7 | 1.1 | 1.0 | 2.6 | 1.7 | 1.8 | 1.2 |
| H1* + N54S + V56T + G109A + W140Y + Q169E + Q172K + A174* + G182* + D183* + N195F + V206L + K391A + G476K | 1.9 | 1.4 | 1.1 | 1.0 | 2.1 | 1.8 | 1.5 | 1.4 |
| H1* + N54S + V56T + G109A + A174S + G182* + D183* + N195F + V206L + K391A | 1.9 | 1.6 | 1.1 | 1.1 | 2.2 | 1.9 | 1.7 | 1.4 |
| H1* + N54S + V56T + G109A + Q169E + Q172K + A174* + G182* + D183* + N195F + V206L + F328L + K391A + G476K | 1.8 | 1.6 | 1.1 | 1.0 | 1.7 | 1.4 | 1.5 | 1.1 |
| H1* + N54S + V56T + G109A + A174S + G182* + D183* + N195F + V206L + G476K | 1.8 | 2.0 | 1.5 | 1.1 | 5.2 | 2.0 | 1.8 | 1.5 |
| F113Q + R116H + D183* + G182* + N195F | 1.8 | 1.7 | 1.1 | 1.0 | 1.9 | 1.9 | 1.7 | 1.3 |
| H1* + N54S + V56T + G109A + A174S + G182* + D183* + N195F + V206L + A288L + K391A + G476K | 1.8 | 1.3 | 1.1 | 1.0 | 2.6 | 1.8 | 1.5 | 1.2 |
| H1* + N54S + V56T + G109A + A174S + G182* + D183* + N195F + V206L + N270G + K391A + G476K | 1.8 | 1.6 | 1.2 | 1.1 | 1.9 | 1.8 | 1.6 | 1.2 |
| Q169E + Q172K + A174* + D183* + G182* + N195F | 1.8 | 1.2 | 1.2 | 1.0 | 3.3 | 1.4 | 1.5 | 1.3 |
| H1* + N54S + V56T + G109A + A174S + G182* + D183* + N195F + V206L + K269Q + K391A + G476K | 1.8 | 1.0 | 1.1 | 0.9 | 1.8 | 1.4 | 1.5 | 1.1 |
| H1* + W48F + N54S + V56T + G109A + A174S + G182* + D183* + N195F + V206L + K391A + G476K | 1.8 | 1.4 | 1.1 | 1.0 | 2.2 | 1.7 | 1.5 | 1.2 |
| F113Q + R116Q + D183* + G182* + N195F | 1.8 | 1.7 | 1.1 | 1.0 | 2.1 | 1.7 | 1.7 | 1.4 |
| N54S + V56T + D183* + G182* + N195F | 1.8 | 1.2 | 0.8 | 0.9 | 1.3 | 1.3 | 1.0 | 1.0 |
| H1* + N54S + V56T + G109A + A174T + G182* + D183* + N195F + V206L + K391A + G476K | 1.7 | 1.7 | 1.2 | 1.1 | 2.4 | 1.9 | 1.8 | 1.3 |
| H1* + N54S + V56T + G109A + R116W + A174S + G182* + D183* + N195F + V206L + K391A + G476K | 1.7 | 1.6 | 1.2 | 1.1 | 1.8 | 1.8 | 1.6 | 1.2 |
| Q169E + Q172K + G182* + D183* + N195F | 1.7 | 1.4 | 1.3 | 1.0 | 4.9 | 1.6 | 1.8 | 1.3 |
| G182* + D183* + A186D | 1.7 | 1.6 | 1.0 | 1.0 | 1.6 | 1.7 | 1.3 | 1.1 |
| H1* + N54S + V56T + G109A + A174S + G182* + D183* + N195F + V206L + V238A + K391A + G476K | 1.7 | 1.5 | 1.1 | 1.0 | 1.8 | 1.6 | 1.4 | 1.1 |
| G182* + D183* + A186N | 1.7 | 1.8 | 1.2 | 1.1 | 3.8 | 1.8 | 1.6 | 1.5 |
| H1* + N54S + V56T + G109A + A174S + V206L + G182* + D183* + K391A + G476K | 1.7 | 1.1 | 1.1 | 1.0 | 3.3 | 1.1 | 1.3 | 1.1 |

-continued

| | | | | | | | | |
|---|---|---|---|---|---|---|---|---|
| H1* + N54S + V56T + Q169E + Q172K + A174* + G182* + D183* + N195F + V206L + K391A + G476K | 1.7 | 1.4 | 1.3 | 1.0 | 3.6 | 1.4 | 1.8 | 1.2 |
| H1* + N54S + V56T + G109A + A174S + G182* + D183* + N195F + V206F + K391A + G476K | 1.7 | 1.7 | 1.2 | 1.0 | 1.7 | 1.7 | 1.6 | 1.3 |
| H1* + N54S + V56T + G109A + G182* + D183* + N195F + V206L + K391A + G476K | 1.7 | 1.4 | 1.1 | 1.0 | 1.9 | 1.6 | 1.2 | 1.0 |
| H1* + N54S + V56T + G109A + Q172K + A174S + G182* + D183* + N195F + V206L + K391A + G476K | 1.7 | 1.5 | 1.1 | 1.1 | 3.6 | 1.6 | 1.5 | 1.3 |
| H1* + N54S + V56T + G109A + Q172K + A174* + G182* + D183* + N195F + V206L + K391A + G476K | 1.6 | 1.4 | 1.1 | 1.1 | 1.6 | 1.4 | 1.3 | 1.1 |
| H1* + N54S + V56T + G109A + A174N + G182* + D183* + N195F + V206L + K391A + G476K | 1.6 | 1.8 | 1.2 | 1.2 | 4.6 | 2.0 | 2.0 | 1.7 |
| H1* + N54S + V56T + G109A + A174S + A186N + G182* + D183* + N195F + V206L + K391A + G476K | 1.6 | 1.8 | 1.1 | 1.0 | 1.5 | 1.9 | 1.7 | 1.3 |
| H1* + N54S + V56T + G109A + A174S + G182* + D183* + N195F + V206L + F289L + K391A + G476K | 1.6 | 1.5 | 1.0 | 1.0 | 1.7 | 1.7 | 1.4 | 1.2 |
| H1* + N54S + V56T + G109A + A174S + G182* + D183* + N195F + V206L + Y295F + K391A + G476K | 1.6 | 1.2 | 1.0 | 0.8 | 1.2 | 1.2 | 1.3 | 1.1 |
| H1* + N54S + V56T + G109A + A174S + G182* + D183* + N195F + V206L + V291A + K391A + G476K | 1.6 | 1.2 | 1.1 | 1.0 | 1.2 | 1.0 | 1.2 | 1.0 |
| H1* + N54S + V56T + G109A + A174S + G182* + D183* + N195F + V206L + S244Q + K391A + G476K | 1.5 | 1.4 | 1.1 | 1.0 | 2.1 | 1.5 | 1.3 | 1.1 |
| G182* + D183* + F328L | 1.5 | 1.5 | 1.1 | 1.1 | 1.8 | 1.8 | 1.6 | 1.3 |
| G182* + D183* + N195F + A288V | 1.5 | 1.3 | 1.2 | 1.0 | 1.8 | 1.6 | 1.5 | 1.1 |
| G182* + D183* + A186N + N195F | 1.5 | 1.6 | 0.9 | 0.9 | 2.4 | 1.7 | 1.5 | 1.2 |
| G182* + D183* + E190P + N195F | 1.5 | 1.4 | 0.9 | 1.0 | 2.1 | 1.7 | 1.1 | 1.1 |
| W140Y + G182* + D183* + N195F | 1.5 | 1.4 | 1.1 | 1.1 | 1.4 | 1.7 | 1.5 | 1.3 |
| H1* + N54S + V56T + G109A + A174S + G182* + D183* + N195F + V206L + A225V + K391A + G476K | 1.5 | 1.0 | 1.1 | 0.9 | 1.5 | 1.0 | 1.5 | 1.0 |
| G182* + D183* + A186D + N195F | 1.5 | 1.7 | 1.4 | 1.1 | 3.3 | 2.0 | 1.8 | 1.6 |
| H1* + N54S + V56T + G109A + A174S + G182* + D183* + N195F + V206L + K391A + P473R + G476K | 1.5 | 1.2 | 1.1 | 1.0 | 1.5 | 1.2 | 1.3 | 1.2 |
| H1* + W48Y + N54S + V56T + G109A + A174S + G182* + D183* + N195F + V206L + K391A + G476K | 1.5 | 1.3 | 1.0 | 1.1 | 1.2 | 1.4 | 1.3 | 1.2 |
| H1* + N54S + V56T + G109A + Q169E + Q172K + A174* + G182* + D183* + N195F + V206L + K391A + G476K | 1.5 | 1.3 | 1.4 | 1.1 | 3.8 | 1.4 | 1.5 | 1.3 |
| G182* + D183* + N195F + V238A | 1.5 | 1.5 | 1.0 | 1.1 | 1.9 | 1.4 | 1.1 | 1.0 |
| G182* + D183* + Y295N | 1.4 | 1.1 | 1.3 | 1.0 | 2.5 | 1.2 | 1.6 | 1.2 |
| Q172G + G182* + D183* | 1.4 | 1.4 | 1.1 | 1.0 | 1.4 | 1.3 | 1.5 | 1.3 |
| F113Q + G182* + D183* + N195F | 1.4 | 0.8 | 1.0 | 0.8 | 1.0 | 1.0 | 1.3 | 1.0 |
| H1* + N54S + V56T + Q98A + G109A + A174S + G182* + D183* + N195F + V206L + K391A + G476K | 1.4 | 1.3 | 1.2 | 1.0 | 2.7 | 1.1 | 1.5 | 1.2 |
| G182* + D183* + N195F + Y295F | 1.3 | 1.3 | 1.2 | 1.1 | 1.3 | 1.2 | 1.4 | 1.1 |
| G182* + D183* + A186E | 1.3 | 1.2 | 1.2 | 1.0 | 2.0 | 1.4 | 1.4 | 1.2 |
| H1* + N54S + V56T + G109A + A174S + G182* + D183* + N195F + V206Y + K391A + G476K | 1.3 | 1.1 | 1.2 | 1.1 | 2.8 | 1.2 | 1.3 | 1.2 |
| G182* + D183* + N195F + W284H | 1.3 | 1.6 | 1.1 | 1.2 | 3.3 | 1.8 | 1.6 | 1.6 |
| G182* + D183* + A186Q + N195F | 1.3 | 1.2 | 1.1 | 1.0 | 2.0 | 1.7 | 1.5 | 1.1 |
| K72R + G182* + D183* | 1.3 | 1.3 | 1.0 | 1.0 | 1.4 | 1.5 | 1.3 | 1.1 |
| D183* + G182* + N195F + V326L | 1.3 | 1.6 | 1.2 | 1.2 | 3.5 | 1.8 | 1.5 | 1.6 |
| D183* + G182* + A186E + N195F | 1.3 | 1.3 | 1.1 | 1.0 | 1.7 | 1.4 | 1.5 | 1.2 |
| Q169E + G182* + D183* + N195F | 1.2 | 1.0 | 1.1 | 1.0 | 1.7 | 0.8 | 1.4 | 1.2 |
| D183* + G182* + N195F + K242Q | 1.2 | 0.8 | 0.9 | 0.9 | 2.0 | 1.2 | 0.9 | 1.0 |
| G7A + G182* + D183* + N195F | 1.2 | 1.2 | 1.1 | 1.0 | 1.5 | 1.6 | 1.4 | 1.1 |
| D183* + G182* + N195F + N260G | 1.2 | 1.4 | 1.0 | 0.9 | 1.6 | 1.2 | 1.3 | 1.1 |
| D183* + G182* + R321A + S323N | 1.2 | 1.3 | 1.1 | 1.1 | 1.2 | 1.1 | 1.5 | 1.2 |
| D183* + G182* + W284H | 1.2 | 0.9 | 1.2 | 1.0 | 0.9 | 1.0 | 1.1 | 1.1 |
| H1* + D183* + G182* | 1.2 | 1.5 | 1.0 | 1.0 | 3.6 | 1.7 | 1.6 | 1.3 |
| D183* + G182* + A186H + N195F | 1.1 | 1.3 | 1.1 | 1.0 | 2.0 | 1.2 | 1.4 | 1.0 |
| D183* + G182* + F289V | 1.1 | 1.3 | 1.0 | 1.0 | 2.2 | 1.3 | 1.7 | 1.4 |
| D183* + G182* + K391A | 1.1 | 0.7 | 1.0 | 0.8 | 0.7 | 0.7 | 1.0 | 0.8 |
| D183* + G182* + S304R | 1.1 | 1.2 | 0.9 | 0.9 | 0.6 | 0.9 | 1.0 | 1.0 |
| W167F + G182* + D183* + N195F | 1.1 | 1.0 | 1.0 | 0.9 | 3.3 | 1.1 | 1.3 | 1.1 |
| F113Q + R116H + D183* + G182* | 1.1 | 0.7 | 1.0 | 0.8 | 1.2 | 0.8 | 1.3 | 0.9 |
| D183* + G182* + N270G | 1.1 | 1.0 | 0.9 | 0.9 | 1.0 | 1.3 | 1.0 | 1.0 |
| D183* + G182* + S244Q | 1.0 | 1.1 | 1.1 | 0.9 | 1.8 | 1.6 | 1.5 | 1.0 |
| H1* + N54S + V56T + G109A + A174S + G182* + D183* + G184T + N195F + V206L + K391A + G476K | 1.0 | 1.0 | 1.1 | 1.0 | 0.6 | 0.6 | 0.9 | 0.9 |
| D183* + G182* + N195F + Y295N | 1.0 | 1.1 | 1.0 | 1.0 | 1.6 | 0.9 | 1.2 | 1.3 |
| W48F + D183* + G182* | 1.0 | 0.9 | 1.0 | 0.9 | 1.8 | 1.0 | 1.3 | 1.0 |
| H1* + N54S + V56T + G109A + A174S + G182* + D183* + N195F + V206L + G255A + K391A + G476K | 1.0 | 1.2 | 1.0 | 1.0 | 1.8 | 1.1 | 1.2 | 1.1 |
| D183* + G182* + A186Q | 1.0 | 0.7 | 1.1 | 0.9 | 0.4 | 0.5 | 1.0 | 0.9 |
| W140Y + D183* + G182* | 0.9 | 0.6 | 0.9 | 0.9 | 0.5 | 0.9 | 1.1 | 1.0 |
| D183* + G182* + K242Q | 0.9 | 0.8 | 1.0 | 0.9 | 0.8 | 0.9 | 1.0 | 1.1 |
| D183* + G182* + V206L | 0.9 | 0.8 | 0.9 | 0.9 | 1.1 | 0.9 | 0.9 | 0.9 |
| D183* + G182* + N195F + V206F | 0.9 | 0.9 | 0.9 | 1.1 | 0.5 | 0.8 | 1.1 | 1.0 |
| Q169E + D183* + G182* | 0.9 | 0.8 | 1.0 | 0.9 | 1.1 | 0.8 | 0.9 | 0.9 |
| D183* + G182* + N195F + R320A | 0.8 | 0.9 | 1.1 | 1.0 | 0.8 | 0.9 | 1.0 | 1.0 |

-continued

| | | | | | | | | |
|---|---|---|---|---|---|---|---|---|
| G182* + D183* + G184T + N195F | 0.8 | 1.1 | 0.9 | 1.0 | 0.9 | 1.0 | 1.2 | 1.0 |
| D183* + G182* + G184T | 0.8 | 0.9 | 1.0 | 0.9 | 0.7 | 0.8 | 1.0 | 1.1 |
| N54S + V56T + D183* + G182* | 0.8 | 0.8 | 1.1 | 1.0 | 0.9 | 0.7 | 1.1 | 0.9 |
| D183* + G182* + P473R | 0.8 | 0.9 | 1.0 | 1.0 | 1.1 | 0.8 | 1.0 | 1.0 |
| W48Y + D183* + G182* | 0.8 | 0.9 | 1.1 | 1.1 | 1.0 | 0.6 | 1.0 | 0.9 |
| D183* + G182* + R323A | 0.8 | 0.8 | 0.9 | 1.0 | 1.1 | 0.8 | 1.1 | 0.8 |
| G7A + D183* + G182* | 0.8 | 0.8 | 1.1 | 0.9 | 1.3 | 1.1 | 1.2 | 1.0 |
| G109A + D183* + G182* | 0.8 | 0.8 | 0.8 | 0.8 | 0.0 | 0.6 | 1.0 | 1.1 |
| W167F + D183* + G182* | 0.7 | 0.7 | 1.0 | 0.9 | 1.4 | 0.9 | 1.1 | 1.0 |
| H1* + N54S + V56T + G109A + Q169E + Q172K + A174S + G182* + D183* + N195F + V206L + K391A + G476K | 0.7 | 0.7 | 0.8 | 0.9 | 1.1 | 0.5 | 0.8 | 0.8 |
| A174S + D183* + G182* | 0.7 | 1.2 | 0.8 | 0.9 | 2.2 | 0.9 | 1.1 | 1.3 |
| R116Q + D183* + G182* | 0.7 | 0.7 | 0.9 | 0.9 | 0.7 | 0.6 | 1.1 | 0.9 |
| D183* + G182* + N195F + V291A | 0.7 | 0.9 | 1.0 | 1.1 | 0.6 | 0.9 | 0.9 | 1.0 |
| Q172K + D183* + G182* | 0.7 | 0.9 | 0.9 | 1.0 | 0.4 | 0.5 | 1.1 | 0.9 |
| N54S + D183* + G182* | 0.7 | 1.2 | 1.0 | 1.1 | 1.7 | 1.1 | 1.0 | 1.3 |
| D183* + G182* + N195F + S323N | 0.7 | 0.9 | 0.8 | 0.9 | 1.8 | 1.0 | 1.0 | 1.0 |
| D183* + G182* + N195F + M246V | 0.7 | 0.8 | 1.1 | 1.0 | 0.6 | 0.5 | 0.9 | 0.9 |
| W48Y + D183* + G182* + N195F | 0.6 | 1.2 | 1.1 | 1.1 | 2.0 | 1.5 | 1.2 | 1.4 |
| D183* + G182* + N195F + S304R | 0.6 | 1.1 | 0.7 | 1.0 | 1.6 | 0.7 | 1.0 | 1.2 |
| V56T + D183* + G182* | 0.3 | 0.8 | 0.2 | 0.6 | 1.9 | 0.6 | 0.3 | 0.7 |

| Modifications in SEQ ID NO: 14 | A-15-0.05 mg/L | A-15-0.2 mg/L | A-40-0.05 mg/L | A-40-0.2 mg/L | J-15-0.05 mg/L | J-15-0.2 mg/L | J-30-0.05 mg/L | J-30-0.2 mg/L |
|---|---|---|---|---|---|---|---|---|
| Reference | 1.0 | 1.0 | 1.0 | 1.0 | 1.0 | 1.0 | 1.0 | 1.0 |
| G182* + D183* + N195F | 1.4 | 1.2 | 1.0 | 1.0 | 1.2 | 1.3 | 1.1 | 1.1 |
| H1* + G182* + D183* + N195F | 1.1 | 1.0 | 1.0 | 1.1 | 1.1 | 1.0 | 1.1 | 1.1 |
| N54S + G182* + D183* + N195F | 1.2 | 1.1 | 0.9 | 1.1 | 1.3 | 1.1 | 1.1 | 1.1 |
| V56T + G182* + D183* + N195F | 1.4 | 1.1 | 1.0 | 1.0 | 1.5 | 1.2 | 1.1 | 1.1 |
| G182* + D183* + N195F + I405L | 1.1 | 1.1 | 1.0 | 1.0 | 1.1 | 1.1 | 1.0 | 1.0 |
| H1* + N54S + V56T + G109A + A174S + G182* + D183* + N195F + V206L + I405L + A421H + A422P + A428T + D476K | 1.0 | 1.1 | 0.9 | 0.9 | 1.4 | 1.0 | 1.1 | 0.9 |
| A174S + G182* + D183* + N195F | 1.2 | 1.0 | 1.0 | 0.9 | 0.9 | 0.9 | 1.0 | 1.0 |
| H1* + N54S + V56T + G109A + A174S + G182* + D183* + N195F + V206L + I405L + A421H + A422P + A428T | 1.4 | 1.3 | 1.1 | 1.0 | 1.6 | 1.3 | 1.3 | 1.1 |
| H1* + N54S + V56T + G109A + A174S + D183* + N195F + V206L + K391A + I405L + A421H + A422P + A428T | 1.2 | 1.3 | 1.0 | 1.0 | 1.6 | 1.3 | 1.2 | 1.1 |
| H1* + N54S + V56T + G109A + A174S + G182* + D183* + N195F + V206L + K391A + I405L + A421H + A422P + A428T + D476K | 1.3 | 1.3 | 1.1 | 1.0 | 1.4 | 1.3 | 1.1 | 1.0 |
| H1* + N54S + V56T + G109A + A174S + G182* + D183* + N195F + V206L + K391A + I405L + A421H + A422P + A428T + D476G | 1.2 | 1.1 | 1.1 | 1.0 | 1.4 | 1.2 | 1.2 | 1.1 |
| H1* + N54S + V56T + G109A + A174S + G182* + D183* + N195F + V206L + K391A + I405L + A421H + A422P + A428T + D476K + G477S | 1.3 | 1.3 | 1.0 | 1.0 | 1.5 | 1.2 | 1.1 | 1.0 |
| H1* + N54S + V56T + G109A + A174S + G182* + D183* + N195F + V206L + K391A + I405L + A421H + A422P + A428T + D476K | 1.3 | 1.2 | 1.0 | 1.0 | 1.5 | 1.2 | 1.2 | 1.0 |
| H1* + N54S + V56T + K72R + G109A + W167F + A174S + G182* + D183* + N195F + V206L + I405L + A421H + A422P + A428T | 1.1 | 1.2 | 1.0 | 1.1 | 1.4 | 1.4 | 1.3 | 1.1 |
| H1* + N54S + V56T + G109A + A174S + G182* + D183* + N195F + V206L + S280Q + H321Y + I405L + A421H + A422P + A428T | 0.9 | 1.2 | 1.1 | 0.9 | 1.3 | 1.2 | 1.3 | 1.0 |
| H1* + N54S + V56T + G109A + A174S + G182* + D183* + N195F + V206L + S304N + I405L + A421H + A422P + A428T + D476K | 1.1 | 1.2 | 1.0 | 1.0 | 1.2 | 1.1 | 1.1 | 1.0 |
| H1* + N54S + V56T + G109A + A174S + G182* + D183* + N195F + V206L + K391A + I405L + A421H + A422P + A428T + D476K + G477A | 1.2 | 1.2 | 1.0 | 1.0 | 1.2 | 1.0 | 1.0 | 0.9 |
| H1* + N54S + V56T + G109A + A174S + G182* + D183* + N195F + V206L + K391A + I405L + A421H + A422P + A428T + D476G + G477T | 1.6 | 1.4 | 1.1 | 1.1 | 1.9 | 1.4 | 1.3 | 1.2 |
| H1* + N54S + V56T + G109A + F113Q + R116Q + Q172N + A174S + G182* + D183* + N195F + V206L + I405L + A421H + A422P + A428T | 0.9 | 1.2 | 0.8 | 1.1 | 0.8 | 1.7 | 0.9 | 1.1 |
| H1* + N54S + V56T + G109A + A174S + G182* + D183* + N195F + V206L + K391A + I405L + A421H + A422P + A428T + G477Q | 1.7 | 1.3 | 1.1 | 1.0 | 1.9 | 1.4 | 1.3 | 1.1 |
| H1* + N54S + V56T + G109A + A174S + G182* + D183* + N195F + V206L + K391A + I405L + A421H + A422P + A428T + G477A | 1.5 | 1.4 | 1.1 | 1.0 | 1.9 | 1.4 | 1.3 | 1.1 |
| H1* + N54S + V56T + G109A + A174S + G182* + D183* + N195F + V206L + K391A + I405L + A421H + A422P + A428T + D476K + G477Q | 1.3 | 1.3 | 1.0 | 1.0 | 1.7 | 1.2 | 1.1 | 1.0 |

-continued

| | | | | | | | | |
|---|---|---|---|---|---|---|---|---|
| H1* + N54S + V56T + G109A + A174S + G182* + D183* + N195F + V206L + K391A + I405L + A421H + A422P + A428T + D476N | 1.5 | 1.3 | 1.1 | 1.1 | 1.7 | 1.4 | 1.3 | 1.2 |
| H1* + N54S + V56T + G109A + A174S + G182* + D183* + N195F + V206L + K391A + I405L + A421H + A422P + A428T + D476Y | 1.5 | 1.3 | 1.1 | 1.0 | 1.7 | 1.3 | 1.3 | 1.2 |
| H1* + N54S + V56T + G109A + A174S + G182* + D183* + N195F + V206I + I405L + A421H + A422P + A428T | 1.5 | 1.2 | 1.1 | 1.1 | 2.2 | 1.4 | 1.4 | 1.1 |
| H1* + N54S + V56T + G109A + Q172D + A174S + G182* + D183* + N195F + A204G + V206L + I405L + A421H + A422P + A428T | 1.4 | 1.3 | 1.1 | 1.0 | 2.8 | 2.0 | 1.4 | 1.2 |
| H1* + N54S + V56T + K72R + G109A + T134E + A174S + G182* + D183* + N195F + A204G + V206L + G255A + I405L + A421H + A422P + A428T | 1.3 | 1.1 | 1.0 | 1.0 | 2.1 | 2.1 | 1.3 | 1.0 |
| H1* + N54S + V56T + G109A + F113Q + R116H + T165G + Q172G + A174S + G182* + D183* + N195F + V206L + I405L + A421H + A422P + A428T | 1.3 | 1.3 | 1.0 | 1.0 | 2.9 | 1.9 | 1.3 | 1.1 |
| H1* + N54S + V56T + G109A + F113Q + Q172N + A174S + G182* + D183* + N195F + V206L + I405L + A421H + A422P + A428T | 1.3 | 1.3 | 1.1 | 1.1 | 1.9 | 2.2 | 1.5 | 1.3 |
| H1* + N54S + V56T + K72R + G109A + T134E + A174S + G182* + D183* + N195F + G196R + V206L + G255A + I405L + A421H + A422P + A428T + N475S | 1.4 | 1.3 | 1.1 | 1.1 | 2.5 | 2.3 | 1.5 | 1.3 |
| H1* + N54S + V56T + G109A + T134E + A174S + G182* + D183* + N195F + V206L + I405L + A421H + A422P + A428T | 1.8 | 1.5 | 1.2 | 1.0 | 2.3 | 1.8 | 1.5 | 1.2 |
| H1* + T40D + N54S + V56T + G109A + A174S + G182* + D183* + N195F + V206L + I405L + A421H + A422P + A428T | 2.0 | 1.5 | 1.2 | 1.1 | 1.8 | 1.6 | 1.5 | 1.3 |
| H1* + N54S + V56T + G109A + F113Q + N125D + A174S + G182* + D183* + N195F + V206L + I405L + A421H + A422P + A428T | 2.1 | 1.6 | 1.3 | 1.0 | 2.2 | 1.7 | 1.5 | 1.2 |
| H1* + N54S + V56T + A60V + G109A + R116Q + A174S + G182* + D183* + N195F + V206L + I405L + A421H + A422P + A428T | 1.6 | 1.6 | 1.1 | 1.0 | 1.9 | 1.6 | 1.4 | 1.2 |
| H1* + N54S + V56T + G109A + R116V + A174S + G182* + D183* + N195F + V206L + I405L + A421H + A422P + A428T | 1.4 | 1.4 | 1.0 | 1.0 | 2.1 | 1.4 | 1.4 | 1.2 |
| H1* + N54S + V56T + G109A + R116Q + G133Q + T165G + Q172G + A174S + G182* + D183* + N195F + V206L + I405L + A421H + A422P + A428T | 1.1 | 1.4 | 1.0 | 1.1 | 2.0 | 2.3 | 1.5 | 1.3 |
| H1* + N54S + V56T + G109A + F113Q + R116H + Q172G + A174S + G182* + D183* + N195F + V206L + I405L + A421H + A422P + A428T | 1.7 | 1.6 | 1.2 | 1.1 | 3.0 | 1.9 | 1.5 | 1.2 |
| H1* + N54S + V56T + G109A + F113Q + R116Q + Q172G + A174S + G182* + D183* + N195F + V206L + I405L + A421H + A422P + A428T + G448D | 1.4 | 1.5 | 1.1 | 1.1 | 2.1 | 1.8 | 1.3 | 1.2 |
| H1* + N54S + V56T + G109A + F113Q + R116H + Q172N + A174S + G182* + D183* + N195F + V206L + I405L + A421H + A422P + A428T | 2.2 | 1.6 | 1.3 | 1.2 | 2.5 | 1.6 | 1.6 | 1.3 |
| H1* + N54S + V56T + K72R + G109A + T134E + W167F + Q172N + A174S + G182* + D183* + N195F + V206L + G255A + A265G + I405L + A421H + A422P + A428T | 2.2 | 1.6 | 1.3 | 1.2 | 2.4 | 1.6 | 1.7 | 1.2 |
| H1* + N54S + V56T + K72R + G109A + R116Q + W167F + Q172R + L173V + A174S + G182* + D183* + N195F + V206L + A265G + I405L + A421H + A422P + A428T | 2.0 | 1.6 | 1.2 | 1.2 | 2.3 | 1.6 | 1.7 | 1.2 |
| H1* + N54S + V56T + K72R + G109A + R116Q + W167F + Q172R + A174S + G182* + D183* + N195F + V206L + I405L + A421H + A422P + A428T | 2.1 | 1.4 | 1.3 | 1.2 | 2.3 | 1.6 | 1.7 | 1.2 |
| H1* + N54S + V56T + K72R + G109A + F113Q + T134E + W167F + Q172G + A174S + G182* + D183* + N195F + V206L + G255A + I405L + A421H + A422P + A428T | 2.0 | 1.5 | 1.1 | 1.1 | 2.6 | 1.9 | 1.4 | 1.2 |
| H1* + N54S + V56T + K72R + G109A + F113Q + R116H + W167F + Q172G + L173V + A174S + G182* + D183* + G184T + N195F + V206L + I405L + A421H + A422P + A428T | 1.7 | 1.6 | 1.0 | 0.9 | 1.8 | 1.5 | 1.1 | 1.1 |
| H1* + N54S + V56T + G109A + F113Q + W167F + Q172G + A174S + G182* + D183* + N195F + V206L + I405L + A421H + A422P + A428T | 1.2 | 1.2 | 1.0 | 0.9 | 2.2 | 1.3 | 1.2 | 1.1 |
| H1* + N54S + V56T + K72R + G109A + A174S + G182* + D183* + N195F + V206L + G255A + I405L + A421H + A422P + A428T | 1.5 | 1.2 | 1.2 | 1.0 | 2.2 | 1.1 | 1.5 | 1.1 |
| H1* + N54S + V56T + G109A + F113Q + R116Q + A174S + G182* + D183* + N195F + V206L + I405L + A421H + A422P + A428T | 1.6 | 1.3 | 1.1 | 1.0 | 1.4 | 1.2 | 1.3 | 1.1 |
| H1* + N54S + V56T + K72R + G109A + F113Q + F116H + W167F + Q172G + L173V + A174S + G182* + D183* + N195F + V206L + I405L + A421H + A422P + A428T | 1.8 | 1.6 | 1.0 | 1.0 | 0.9 | 1.4 | 0.9 | 1.1 |

-continued

| | | | | | | | | |
|---|---|---|---|---|---|---|---|---|
| H1* + N54S + V56T + K72R + G109A + F113Q + R116Q + W167F + Q172G + A174S + G182* + D183* + G184T + N195F + V206L + I405L + A421H + A422P + A428T | 1.8 | 1.5 | 1.1 | 1.0 | 1.9 | 1.5 | 1.3 | 1.1 |
| H1* + N54S + V56T + G109A + F113Q + R116Q + W167F + Q172G + A174S + G182* + D183* + N195F + A204G + V206L + I405L + A421H + A422P + A428T | 2.0 | 1.5 | 1.0 | 1.0 | 1.8 | 1.5 | 1.2 | 1.0 |
| H1* + N54S + V56T + G109A + F113Q + R116H + W167F + Q172G + A174S + G182* + D183* + N195F + V206L + A265G + I405L + A421H + A422P + A428T | 1.5 | 1.3 | 0.9 | 0.9 | 1.4 | 1.3 | 1.2 | 1.1 |
| H1* + N54S + V56T + G109A + R116Q + A174S + G182* + D183* + N195F + V206L + I405L + A421H + A422P + A428T | 1.8 | 1.6 | 1.0 | 0.9 | 1.6 | 1.3 | 1.4 | 1.1 |
| H1* + N54S + V56T + A60V + G109A + R116Q + W167F + Q172N + L173V + A174S + G182* + D183* + N195F + V206L + I405L + A421H + A422P + A428T | 1.4 | 1.4 | 0.7 | 0.9 | 1.1 | 1.3 | 0.8 | 1.0 |
| H1* + A37H + N54S + V56T + A60V + G109A + R116Q + T165G + A174S + G182* + D183* + N195F + V206L + I405L + A421H + A422P + A428T | 1.9 | 1.6 | 1.1 | 1.1 | 1.7 | 1.6 | 1.4 | 1.2 |
| H1* + N54S + V56T + G109A + A174S + M105F + G182* + D183* + N195F + V206L + L228I + R320A + S323N + I405L + A421H + A422P + A428T | 1.4 | 1.2 | 1.0 | 1.0 | 1.5 | 1.2 | 1.2 | 1.0 |
| H1* + N54S + V56T + K72R + G109A + F113Q + T134E + A174S + G182* + D183* + N195F + V206L + G255A + I405L + A421H + A422P + A428T | 1.8 | 1.5 | 1.1 | 1.0 | 1.7 | 2.1 | 1.4 | 1.2 |
| H1* + N54S + V56T + K72R + G109A + R116Q + V120L + A174S + G182* + D183* + G184T + N195F + V206L + I405L + A421H + A422P + A428T | 2.1 | 1.8 | 1.2 | 1.1 | 2.8 | 2.5 | 1.6 | 1.3 |
| H1* + N54S + V56T + G109A + F113Q + R116H + W167F + Q172G + L173V + A174S + G182* + D183* + N195F + V206L + I405L + A421H + A422P + A428T | 2.6 | 1.9 | 1.2 | 1.1 | 2.8 | 2.6 | 1.6 | 1.3 |
| H1* + N54S + V56T + G109A + F113Q + R116Q + Q172N + A174S + G182* + D183* + N195F + V206L + A265G + I405L + A421H + A422P + A428T | 2.3 | 1.6 | 1.1 | 1.1 | 3.0 | 2.1 | 1.5 | 1.3 |
| H1* + A37H + N54S + V56T + A60V + G109A + R116Q + W167F + Q172R + A174S + G182* + D183* + N195F + V206L + I405L + A421H + A422P + A428T | 2.1 | 1.7 | 1.2 | 1.1 | 2.5 | 2.1 | 1.5 | 1.2 |

Example 4: Wash Performance of a Subset of Variants According to the Invention (AMSA)

The following variants have been tested as described above. The color measurements were done by use of a professional flatbed scanner (Kodak iQsmart, Kodak) used to capture an image of the washed textile and with a controlled digital imaging system (DigiEye) for capture an image of the washed melamine plates.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

The results obtained were the following;

| Modifications in SEQ ID NO: 13 | A-15-0.05 mg/L | A-15-0.2 mg/L | A-40-0.05 mg/L | A-40-0.2 mg/L | J-15-0.05 mg/L | J-15-0.2 mg/L | J-30-0.05 mg/L | J-30-0.2 mg/L |
|---|---|---|---|---|---|---|---|---|
| Reference | 1.0 | 1.0 | 1.0 | 1.0 | 1.0 | 1.0 | 1.0 | 1.0 |
| G182* + D183* + N195F + V206F + N260P + L312I + L313I + R320A + T355L + L389I + T400P | 0.7 | 1.0 | 0.6 | 0.7 | 1.3 | 0.9 | 0.8 | 1.0 |
| G182* + D183* + N195F | 0.1 | 0.7 | 1.0 | 1.0 | 1.0 | 0.8 | 1.0 | 1.0 |
| H1* + N54S + V56T + G109A + A174S + G182* + D183* + N195F + V206L + K391A + G476K | 1.7 | 1.9 | 1.7 | 1.3 | 2.5 | 1.9 | 1.2 | 1.2 |
| H1* + G50A + T51A + V56T + G109A + A174S + G182* + D183* + N195F + V206L + G476K | 1.5 | 1.6 | 1.5 | 1.4 | 2.5 | 1.6 | 1.3 | 1.2 |
| H1* + N54S + V56T + M105F + G109A + A174S + G182* + D183* + N195F + V206L + R320A + S323N + K391A + G476K | 2.5 | 2.2 | 1.6 | 1.4 | 3.8 | 1.9 | 1.2 | 1.1 |
| H1* + T40K + N54S + V56T + G109A + G149H + A174S + G182* + D183* + N195F + V206L + K391A + G476K | 0.9 | 1.2 | 1.0 | 1.0 | 0.8 | 1.2 | 0.9 | 1.0 |
| H1* + N54S + V56T + K72R + G109A + A174S + G182* + D183* + N195F + V206L + G255A + K391A + G476K | 1.9 | 1.7 | 1.4 | 1.4 | 2.8 | 1.5 | 1.2 | 1.1 |
| H1* + N16H + V17L + N54S + V56T + G109A + A174S + G182* + D183* + N195F + V206L + K391A + G476K | 2.6 | 1.8 | 1.7 | 1.4 | 3.6 | 1.8 | 1.3 | 1.1 |
| H1* + Q22N + N54S + V56T + G109A + A174S + G182* + D183* + N195F + V206L + K391A + G476K | 2.5 | 1.9 | 1.8 | 1.4 | 3.8 | 2.1 | 1.3 | 1.1 |
| H1* + Q32S + N54S + V56T + G109A + A174S + G182* + D183* + N195F + V206L + K391A + G476K | 2.3 | 1.9 | 1.9 | 1.5 | 3.3 | 2.0 | 1.2 | 1.2 |
| H1* + H28N + N54S + V56T + G109A + A174S + G182* + D183* + N195F + V206L + K391A + G476K | 2.7 | 1.7 | 1.6 | 1.5 | 4.2 | 2.0 | 1.3 | 1.1 |
| H1* + N29S + N54S + V56T + G109A + A174S + G182* + D183* + N195F + V206L + K391A + G476K | 1.6 | 1.3 | 1.3 | 1.4 | 2.6 | 1.6 | 1.2 | 1.0 |

-continued

| Modifications in SEQ ID NO: 13 | A-15-0.05 mg/L | A-15-0.2 mg/L | A-40-0.05 mg/L | A-40-0.2 mg/L | J-15-0.05 mg/L | J-15-0.2 mg/L | J-30-0.05 mg/L | J-30-0.2 mg/L |
|---|---|---|---|---|---|---|---|---|
| H1* + H28N + N29S + N54S + V56T + G109A + A174S + G182* + D183* + N195F + V206L + K391A + G476K | 1.8 | 1.9 | 1.8 | 1.4 | 3.1 | 1.8 | 1.2 | 1.1 |
| H1* + N54S + V56T + G109A + A174S + R176K + N195F + V206L + K391A + G476K | 2.3 | 2.0 | 1.7 | 1.5 | 5.1 | 1.9 | 1.3 | 1.2 |
| H1* + N54S + V56T + G109A + Q169E + Q172K + A174* + R176K + N195F + V206L + K391A + G476K | 3.8 | 2.4 | 2.1 | 1.7 | 5.6 | 2.8 | 1.4 | 1.2 |
| H1* + N54S + V56T + G109A + A174S + N175G + N195F + V206L + K391A + G476K | 2.6 | 1.8 | 1.8 | 1.4 | 4.9 | 2.0 | 1.3 | 1.2 |
| H1* + N54S + V56T + G109A + A174S + N195F + V206L + V291A + Y295N + Q299T + K391A + G476K | 1.7 | 1.4 | 1.4 | 1.3 | 2.7 | 1.6 | 1.0 | 1.1 |
| H1* + N54S + V56T + G109A + A174S + N195F + V206L + K269S + A274K + K391A + G476K | 1.7 | 1.4 | 1.6 | 1.2 | 1.4 | 1.8 | 1.0 | 1.0 |
| H1* + N54S + V56T + G109A + A174S + N195F + V206L + L235I + K391A + G476K | 2.6 | 1.5 | 2.0 | 1.3 | 1.3 | 2.1 | 1.0 | 1.1 |
| H1* + N54S + V56T + G109A + A174S + N195F + V206L + L235V + V238A + K391A + G476K | 2.8 | 1.4 | 1.7 | 1.2 | 0.6 | 2.2 | 1.1 | 1.0 |
| H1* + N54S + V56T + G109A + A174S + N195F + V206L + Q365S + K391A + G476K | 1.9 | 1.5 | 1.9 | 1.3 | 2.0 | 1.7 | 1.2 | 1.0 |
| H1* + N54S + V56T + G109A + A174S + N195F + V206L + K391A + H402R + G476K | 2.2 | 1.4 | 2.0 | 1.2 | 0.6 | 1.2 | 1.1 | 1.1 |
| H1* + N54S + V56T + G109A + A174S + N195F + V206L + R320S + H321N + K391A + G476K | 5.6 | 2.7 | 2.5 | 1.6 | 4.2 | 2.9 | 1.2 | 1.2 |
| H1* + N54S + V56T + G109A + Q169E + Q172K + A174* + N195F + V206L + K391A + G476K | 3.8 | 2.6 | 3.0 | 1.7 | 3.6 | 2.8 | 1.3 | 1.2 |
| H1* + N54S + V56T + G109A + Q125S + A174S + N195F + V206L + K391A + G476K | 3.1 | 2.2 | 2.4 | 1.4 | 2.0 | 2.3 | 1.3 | 1.1 |
| H1* + N54S + V56T + G109A + A174S + N195F + V206L + L235V + K391A + G476K | 4.2 | 1.9 | 1.9 | 1.5 | 1.8 | 2.4 | 1.0 | 1.0 |
| H1* + N54S + V56T + G109A + A174S + N195F + V206L + A265G + K391A + G476K | 4.2 | 1.5 | 2.2 | 1.4 | 1.2 | 2.6 | 1.1 | 1.1 |
| H1* + T51Q + N54S + V56T + G109A + A174S + N195F + Y203F + V206L + K391A + G476K | 3.7 | 2.1 | 2.6 | 1.6 | 3.6 | 2.7 | 1.3 | 1.1 |
| H1* + N54S + V56T + G109A + Q169E + Q172K + A174* + N175Q + N195F + V206L + K391A + G476K | 4.0 | 2.0 | 2.7 | 1.5 | 3.3 | 2.8 | 1.2 | 1.2 |
| H1* + H28N + N54S + V56T + G109A + A174S + G182* + D183* + N195F + V206L + K391A + G476K | 4.5 | 2.3 | 2.5 | 1.6 | 3.1 | 2.7 | 1.2 | 1.1 |
| H1* + N54S + V56T + G109A + T134E + A174S + G182* + D183* + N195F + V206L + K391A + G476K | 3.9 | 2.1 | 2.6 | 1.6 | 3.3 | 3.0 | 1.4 | 1.1 |
| H1* + N54S + V56T + G109A + A174S + G182* + D183* + N195F + V206L + D377H + K391A + G476K | 5.3 | 2.9 | 3.0 | 1.7 | 3.8 | 2.9 | 1.3 | 1.2 |
| H1* + G50A + T51A + N54S + V56T + G109A + A174S + G182* + D183* + N195F + V206L + K391A + G476K | 4.4 | 2.1 | 2.3 | 1.4 | 2.6 | 2.3 | 1.3 | 1.2 |
| H1* + G7K + N54S + V56T + G109A + A174S + G182* + D183* + N195F + V206L + K391A + G476K | 4.1 | 2.3 | 2.7 | 1.6 | 2.4 | 2.5 | 1.3 | 1.2 |
| H1* + N54S + V56T + G109A + A174S + G182* + D183* + N195F + M202V + V206L + K391A + G476K | 2.7 | 1.9 | 1.4 | 1.4 | 1.9 | 2.2 | 0.9 | 1.0 |
| H1* + N54S + V56T + M105F + G109A + A174S + N195F + V206L + M246F + K391A + G476K | 3.7 | 2.1 | 2.4 | 1.5 | 2.7 | 2.5 | 1.2 | 1.1 |
| H1* + N16H + V17L + N54S + V56T + G109A + A174S + G182* + D183* + N195F + V206L + D377H + K391A + G476K | 4.5 | 2.7 | 1.8 | 1.4 | 4.3 | 2.2 | 1.5 | 1.3 |
| H1* + N54S + V56T + G109A + A174S + N195F + V206L | 1.1 | 1.9 | 1.3 | 1.1 | 3.0 | 1.9 | 1.3 | 1.1 |
| H1* + T51G + N54S + V56T + G109A + A174S + N195F + Y203G + V206L + K391A + G476K | 2.2 | 1.8 | 1.1 | 1.0 | 2.7 | 2.0 | 0.9 | 1.1 |
| H1* + T51G + N54S + V56T + G109A + G110N + A174S + N195F + V206L + K391A + G476K | 1.6 | 2.1 | 1.0 | 1.1 | 1.9 | 1.9 | 1.1 | 1.1 |
| H1* + N54S + V56T + G109A + Q125S + A174S + N175G + N195F + V206L + K391A + G476K | 2.0 | 2.3 | 1.5 | 1.2 | 2.6 | 1.8 | 1.3 | 1.2 |
| H1* + N54S + V56T + G109A + A174S + N195F + V206L + A265G + V291A + F328L + K391A + G476K | 0.7 | 2.1 | 1.1 | 1.0 | 1.8 | 1.7 | 1.0 | 1.1 |
| H1* + N54S + V56T + G109A + A174S + N195F + V206L + M246F + A265G + V291A + F328L + Q365S + K391A + G476K | 3.9 | 2.6 | 1.9 | 1.4 | 4.0 | 2.1 | 1.5 | 1.2 |
| H1* + N16Y + N54S + V56T + G109A + R116H + A174S + N195F + V206L + G337E + D377H + K391A + G476K | 4.8 | 3.5 | 2.0 | 1.5 | 4.9 | 2.7 | 1.5 | 1.3 |
| H1* + I9L + N54S + V56T + G109A + Q125S + V131T + A174* + V206L + Y267F + F289H + Q361E + K391A + G476K | 3.1 | 2.9 | 1.4 | 1.2 | 2.5 | 2.0 | 1.2 | 1.1 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of improving wash performance of a parent alpha-amylase polypeptide, said method comprising the steps of:

a) substituting and/or deleting two, three or four positions in the parent alpha-amylase having the amino acid sequence of SEQ ID NO: 13 or SEQ ID NO: 14, or having at least 80% sequence identity thereto, wherein said positions correspond to positions R181, G182, D183, and G184 of SEQ ID NO: 13 or SEQ ID NO: 14; and b) mutating one or more positions corresponding to positions H1, T5, G7, Q11, N16, V17, Q32, A37, T40, P45, W48, G50, T51, N54, V56, K72, R87, Q98, M105, G109, F113, R116, Q118, Q125, G133, T134, G142, G149, T165, R171, Q172, L173, A174, G184, A186, E190, T193, N195, A204, V206, P211, I214, V215, L217, L219, A225, L235, V238, K242, S244, M246, M248, L250, G255, Q256, A263, V264, Y267, K269, N270, G273, S280, T285, M286, V291, N295, Q299, R320, H321, S323, H324, V326, F328, T334, D337, Q345, G346, G348, T355, S376, D377, D379, Y382, S383, Q385, K391, K393, Q395, A420, G423, T444, A445, Q449, T459, P473, C474, and K484 of SEQ ID NO: 13; or H1, A37, T40, N54, V56, A60, K72, G109, F113, R116, N125, F133, T134, T165, Q172, L173, A174, G184, A186, E190, N195, G196, A204, V206, A225, L228, K242, S244, G255, A265, K269, S280, N295, R320, H321, S323, V326, K391, I405, A421, A422, A428, and G448 of SEQ ID NO: 14, wherein the resulting alpha-amylase variant has at least 85%, but less than 100% sequence identity with the polypeptide of SEQ ID NO: 4 or SEQ ID NO: 7, and wherein said variant has alpha-amylase activity and improved wash performance compared to said parent polypeptide.

2. The method according to claim 1, wherein said variant has improved alpha-amylase activity compared to that of said parent alpha-amylase polypeptide.

3. The method according to claim 1, wherein said activity is determined according to a Phadebas assay.

4. The method according to claim 1, wherein said variant has at least 90%, but less than 100% sequence identity with the polypeptide of SEQ ID NO: 4.

5. The method according to claim 1, wherein said variant has at least 95%, but less than 100% sequence identity with the polypeptide of SEQ ID NO: 4.

6. The method according to claim 1, wherein said variant has at least 97%, but less than 100% sequence identity with the polypeptide of SEQ ID NO: 4.

7. The method according to claim 1, wherein said variant has at least 98%, but less than 100% sequence identity with the polypeptide of SEQ ID NO: 4.

8. The method according to claim 1, wherein said variant has at least 99%, but less than 100% sequence identity with the polypeptide of SEQ ID NO: 4.

9. The method according to claim 1, wherein said variant has at least 90%, but less than 100% sequence identity with the polypeptide of SEQ ID NO: 7.

10. The method according to claim 1, wherein said variant has at least 95%, but less than 100% sequence identity with the polypeptide of SEQ ID NO: 7.

11. The method according to claim 1, wherein said variant has at least 97%, but less than 100% sequence identity with the polypeptide of SEQ ID NO: 7.

12. The method according to claim 1, wherein said variant has at least 98%, but less than 100% sequence identity with the polypeptide of SEQ ID NO: 7.

13. The method according to claim 1, wherein said variant has at least 99%, but less than 100% sequence identity with the polypeptide of SEQ ID NO: 7.

* * * * *